US012616733B2

(12) United States Patent
Bae et al.

(10) Patent No.: US 12,616,733 B2
(45) Date of Patent: May 5, 2026

(54) XBP1, CD138, AND CS1 PEPTIDES, PHARMACEUTICAL COMPOSITIONS THAT INCLUDE THE PEPTIDES, AND METHODS OF USING SUCH PEPTIDES AND COMPOSITIONS

(71) Applicant: DANA-FARBER CANCER INSTITUTE, INC., Boston, MA (US)

(72) Inventors: Jooeun Bae, West Roxbury, MA (US); Nikhil Munshi, Needham, MA (US); Kenneth Anderson, Wellesley, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 920 days.

(21) Appl. No.: 17/172,805

(22) Filed: Feb. 10, 2021

(65) Prior Publication Data

US 2021/0170004 A1 Jun. 10, 2021

Related U.S. Application Data

(63) Continuation of application No. 15/689,159, filed on Aug. 29, 2017, now abandoned, which is a continuation of application No. 14/440,442, filed as application No. PCT/US2013/068582 on Nov. 5, 2013, now Pat. No. 9,950,047.

(60) Provisional application No. 61/790,780, filed on Mar. 15, 2013, provisional application No. 61/722,446, filed on Nov. 5, 2012.

(51) Int. Cl.
| | |
|---|---|
| *A61K 39/00* | (2006.01) |
| *A61K 38/17* | (2006.01) |
| *A61K 38/19* | (2006.01) |
| *A61K 39/39* | (2006.01) |
| *A61K 39/395* | (2006.01) |
| *A61K 45/06* | (2006.01) |

(52) U.S. Cl.
CPC ...... *A61K 38/1774* (2013.01); *A61K 38/1709* (2013.01); *A61K 38/193* (2013.01); *A61K 39/0011* (2013.01); *A61K 39/001152* (2018.08); *A61K 39/39* (2013.01); *A61K 39/39558* (2013.01); *A61K 45/06* (2013.01); *A61K 2039/505* (2013.01); *A61K 2039/55511* (2013.01)

(58) Field of Classification Search
CPC .... A61K 38/08; A61K 38/10; A61K 38/1709; A61K 38/04; A61K 38/16; A61K 39/0011; A61K 39/001152; A61K 39/001102
See application file for complete search history.

(56) References Cited

U.S. PATENT DOCUMENTS

| | | | |
|---|---|---|---|
| 9,950,047 B2 * | 4/2018 | Bae ......................... A61P 15/00 |
| 2003/0113332 A1 | 6/2003 | Mathew et al. | |
| 2007/0065888 A1 | 3/2007 | Ring et al. | |
| 2008/0020979 A1 | 1/2008 | Rapraeger et al. | |
| 2011/0159021 A1 | 6/2011 | Munshi et al. | |
| 2016/0008444 A1 | 1/2016 | Munshi et al. | |

FOREIGN PATENT DOCUMENTS

| | | |
|---|---|---|
| CN | 102112147 A | 6/2011 |
| JP | 2007503465 A | 2/2007 |
| JP | 2007530675 A | 11/2007 |
| JP | 2009-509910 A | 3/2009 |
| JP | 2010514791 A | 5/2010 |
| JP | 2011523560 A | 8/2011 |
| WO | 200168848 A2 | 9/2001 |
| WO | 2005037855 A2 | 4/2005 |
| WO | 2008019376 A2 | 2/2008 |
| WO | 2008019378 A1 | 2/2008 |
| WO | 2009149021 A2 | 12/2009 |
| WO | 2010132867 | 11/2010 |
| WO | 2012027379 A2 | 3/2012 |
| WO | 2014/071402 A1 | 5/2014 |

OTHER PUBLICATIONS

Carrasco et al (Cancer Cell, 2007, vol. 11, pp. 349-360) (Year: 2007).*
Rajkumar (Hematology, Am Soc Hematol Educ Program, 2005, pp. 340-345). (Year: 2005).*
Bertucci et al (Human Molecular Genetics, 2000, vol. 9, pp. 2981-2991) (Year: 2000).*
O'Brien, Immunome Research, 2008, vol. 4, No. 6, 7 pages (Year: 2008).*
Zhu et al. "Identification of HLA-A *0201-restricted Cytotoxic T Lymphocye Epitope from TRAG-3 Antigen", Clinical Cancer Research. vol. 9, 1850-1857, May 2003.
Fujimoto et al., Upregulation and Overexpression of Human X-box Binding Protein 1 (hXBP-1) Gene in Primary Breast Cancers, Breast Cancer, 10(4):301-306, 2003.
Shimada et al., "Syndecan-1, a new target molecule invloved in progression of androgen-independent prostate cancer" Cancer Science, 2009, vol. 100, No. 7, pp. 1248-1254.
(Continued)

*Primary Examiner* — Karen A. Canella
(74) *Attorney, Agent, or Firm* — Mueting Raasch Group

(57) ABSTRACT

The disclosure features, inter alia, immunogenic XBP1-, CD138-, and CS1-derived peptides (and pharmaceutical compositions thereof). The peptides can be used in a variety of methods such as methods for inducing an immune response, methods for producing an antibody, and methods for treating a cancer (e.g., breast cancer, colon cancer, pancreatic cancer, a blood cancer, e.g., leukemia or a plasma cell disorder such as multiple myeloma or Waldenstrom's macroglobulinemia). The peptides (and pharmaceutical compositions comprising the peptides) can be used, e.g., in a method of treating a precancerous condition such as smoldering multiple myeloma. The peptides can also be included in MHC molecule multimer compositions and used in, e.g., methods for detecting a T cell in a population of cells.

16 Claims, 106 Drawing Sheets

Specification includes a Sequence Listing.

(56)                    References Cited

OTHER PUBLICATIONS

Patel et al., "Sipuleucel-T: A vaccine for metastatic, asymptomatic, androgen-independent prostate cancer" The Annals of Pharmacotherapy, 2008, vol. 42, pp. 91-98.
Cuperlovic-Culf et al., "Multi-gene biomarker panel for reference free prostate cancer diagnosis: determination and independent validation" Biomarkers, 2010, vol. 15, No. 8, pp. 693-706.
Bennett et al., "Androgens modulate autophagy and cell death via regulation of the endoplasmic reticulum chaperone glucose-regulated protein 78/BiP in prostate cancer cells" Cell Death and Disease, 2010, vol. 1, e72, 12 pages.
A_Geneseq Ace No. AAU29119, 2007.
Akiyama Y et al. Identification of novel MAGE-A6- and MAGE-A12-derived HLA-A24-restricted cytotoxic T lymphocyte epitopes using an in silico peptide-docking assay. Cancer Immunol Immunother Dec. 2012;61(12):2311-9. doi: 10.1007/s00262-012-1298-1. Epub Jun. 16, 2012.
Appendix, Trial record I of I for: PVX-410, Phase 112a Study of Cancer Vaccine to Treat Smoldering Multiple Myeloma.
Bae et al. Novel heteroclitic XBP1 peptides induce antigen-specific memory CD3+CD8+ T cells expressing critical T cell markers and transcription regulators. Abstract 2894.
Bae et al., "identification of novel myeloma-specific XBP1 peptides able to generate cytotoxic T lymphocytes: a potential therapeutic application in multiple myeloma", Leukemia 2011, pp. 1610-1619.
Bae et al., Identification of CD19 and CD20 Peptides for Induction of Antigen-Specific CTLs against B-Cell Malignancies, Clin. Cancer Res., Amer. Assoc. Cancer Res., 11:1629-1638 (Feb. 15, 2005).
Bae et al., XBP-1 a Selective and Specific Target for Immunotherapy in Myeloma, Blood, (ASH Annual Meeting Abstracts) 2005 106: Abstract 1594.
Bae et al: "Induction of T Cell Immunity Using a Multipeptide Cocktail Containing XBP1, CD138 and CS1 Peptides in Smoldering Multiple Myeloma", Blood, vol. 120, No. 21, Nov. 2012, p. 5039. Abstract.
Bae et al: "Myeloma-Specific Multiple Peptides Able to Generate Cytotoxic T Lymphocytes: A Potential Therapeutic Application in Multiple Myeloma and Other Plasma Cell Disorders", Clinical Cancer Research, vol. 18, No. 17, Sep. 1, 2012, pp. 4850-4860.
Bae J. et al. J Clin Oncol. 2013; 31. Novel heteroclitic XBP1 peptides evoking antigen-specific cytotoxic T lymphocytes targeting various solid tumors.
Bae J. et al. Leukemia. May 14, 2014. [epub ahead of print] a multiepitope of XBP1, CD138 and CS1 peptides induces myeloma-specific cytotoxic T lymphocytes in T cells of cmoldering myeloma patients.
Blood. 2014; 124. Initial Results of a Phase 1/2a, Dose Escalation Study of PVX-410 Multi-Peptide Cancer Vaccine in Patients with Smoldering Multiple Myeloma (SMM). Wang M, Nooka AK, Yee AJ, Thomas SK, O'Donnell EK, Shah J, Weber DM, Kaufman JL, Lonial S, Avigan D, Raje No. (ASH Annual Meeting Abstract #4737).
Blood. 2015; 126 Updated Results of a Phase 1/2a, Dose Escalation Study of Pvx-410 Multi-Peptide Cancer Vaccine in Patients with Smoldering Multiple Myeloma (SMM) Nooka AK, Wang M, Yee AJ, Thomas SK, O'Donnell EK, Shah JJ, Kaufman JL, Lonial S, Richardson PG, Raje NS. (ASH Annual Meeting Abstract #4246).
Bouchon et al., Cutting Edge: Activation of NK Cell-Mediated Cytotoxicity by a SAP Independent Receptor of the CD2 Family, J. Immunol., 167(10):5517-5521 (2001).
Br J Haematol. Nov. 2011;155(3):349-61. doi: 10.1111/j.1365-2141. 2011.08850.x. Epub Sep. 9, 2011. Novel epitope evoking CD138 antigen-specific cytotoxic T lymphocytes targeting multiple myeloma and other plasma cell disorders. Bae J, Tai YT, Anderson KC, Munshi NC.
Br J Haematol. Jun. 2012; 157(6):687-701. Epub Apr. 26, 2012. A novel immunogenic CS1-specific peptide inducing antigen-specific cytotoxic T lymphocytes targeting multiple myeloma. Bae J, Song W, Smith R, Daley J, Tai YT, Anderson KC, Munshi NC.

Celis et al., "Induction of Anti-Tumor Cytotoxic T. Lymphocytes in Normal Humans Using Primary Cultures and Synthetic Peptide Epitopes", Proceedings of the National Academy of Sciences, vol. 91, pp. 2105-2109, Mar. 1994.
Cerny et al (J. Clin. Invest. 1995, 95: 521-530).
Development of Novel CD138 Antigen-Specific Peptide Capable of Eliciting Myeloma-Specific Cytotoxic T Lymphocytes Response, Bae et al., Blood: 2005; 106 (ASH Annual Meeting Abstracts) Abstract 3465.
Diefenbach et al., Safety and Immunogenicity Study of NY-ESO-1b Peptide and Montanide SA-51 Vacination of Patients with Epithelial Ovarian Cancer in High-Risk First Remission, Clin Cancer Res;14:2740-2748 (2008).
Dredge et al., "Adjuvants and the promotion of Th1-type cytokines in tumour immunotherapy", Cancer Immunology Immunotherapy, vol. 51, pp. 521-531, 2002.
Fournier and Schirrmacher (Expert. Rev. Vaccines 8(1 ); 51-66, 2009).
Gomez et al., "Human X-Box binding protein-1 confers both estrogen independence and antiestrogen resistance in breast cancer cell lines", FASEB Journal, vol. 21, pp. 4013-4027, 2007.
Horiguchi et al., "Screening of HLA-A24-restricted Epitope Peptides from Prostate-specific Membrane Antigen That Induce Specific Antitumor Cytotoxic T Lymphocytes", (Clin. Canc. Res. 2002, 8: 3885-3892).
Hundemer et al., Identification of a new HLA-A2 restricted T-cell epitope within HMI.24 as immunotherapy target for multiple myeloma, Experimental Hematology, 34 (4): 486-496 (Apr. 1, 2006).
Identification of CS 1 Peptides for Induction of Antigen-Specific CTLs in Multiple Myeloma, Song et al., Blood (ASH Annual Meeting Abstracts) 2007 110: Abstract 1611.
International Search Report and Written Opinion from corresponding International Application No. PCT/US2009/045866 dated May 25, 2010.
International Search Report and Written Opinion from corresponding International Application No. PCT/US2013/068582 dated Mar. 11, 2014.
Jain et al., Synthetic Tumor-Specific Breakpoint Peptide Vaccine in Patients With Chronic Myeloid Leukemia and Minimal Residual Disease, Cancer, 3924-3934, (Sep. 1, 2009) vol. 115.
Jalili, Induction of HM1.24 peptide-specific cytotoxic T lymphocytes by using peripheral-blood stem-cell harvests in patients with multiple myeloma, Blood, 106(10): 3538-3545 (Nov. 15, 2005).
Janeway CA jr, Travers P, Walport M, et al. "The generation of T-cell receptor ligands", Immunobiology: The Immune System in Health and Disease. 5th edition. New York: Garland Science; 2001.
Kawashima et al., "The Multi-Epitope Approach for Immunotherapy for Cancer: Identification of Several CTL Epitopes from Various tumor-Associated Antigens Expressed on Solid Epithelial Tumors", Human Immunology, New York, NY, US, vol. 1 • 59, No. 1, Jan. 1, 1998 (Jan. 1, 1998), pp. 1-14.
Keilholz et al., A clinical and immunologic phase 2 trial of Wilms tumor gene product 1 (WTJ) peptide vaccination in patients with AML and MDS, Blood, 113(26):6541-6548 (Jun. 25, 2009).
Kirkwood et al., Immunogenicity and Antitumor Effects of Vaccination with Peptide Vaccine +/− Granulocyte-Monocyte Colony-Stimulating Factor and/or IFN-a.2b in Advanced Metastatic Melanoma: Eastern Cooperative Oncology Group Phase II Trial EI696, Clin Cancer Res, 15:1443-1451 (2009).
Klebanoff et al., Therapeutic cancer vaccines: are we there yet?, Immunol Rev., 239(1): 27-44 (Jan. 2011).
Lenalidomide treatment enhances the anti-tumor activities of XBP1 specific cytotoxic T lymphocytes by increasing the frequency and tumor specific response of central memory CD3+CD8+ T cells. J. Bae et al. Abstract.
Levine et al., "Initial Clinical Trials in Cancer Patients of Polyriboinosinic-Polyribocytidylic Acid Stabilized with Poly-L-lysine, in Carboxymethylcellulose [Poly(ICLC)], a Highly Effective Interferon Inducer", Cancer Research, vol. 39, pp. 1645-1650, 1979.
Lotz et al., Targeting positive regulatory domain I-binding factor 1 and X box-binding protein 1 transcription factors by multiple myeloma-reactive CTL, J. Immunol., 175(2):1301-1309, 2005.

(56)                    References Cited

OTHER PUBLICATIONS

Lotz, Tolerance and Immunity to Human Tumor-Associated Antigens. Dissertation Johannes Gutenberg-Universitat in Mainz 2003 [Online] p. 40 table 2 and p. 46 para 2, p. 43 para 2 (100 pages).

Maslak et al., Vaccination with synthetic analog pep tides derived from WTJ oncoprotein induces T-cell responses in patients with complete remission from acute myeloid leukemia, Blood, 116(2):171-179.

Munshi, Nikhil C., "Novel immunotherapy approaches in multiple myeloma, 2007", (Power Point Presentation; 38 pages).

Parker et al. Scheme for ranking potential HLA-A2 binding peptides based on independent binding of individual peptide side-chains. J. immunol1994, 152(1):163-175.

Perez et al., A New Era in Anticancer Peptide Vaccines, Cancer, 2071-2080 (May 1, 2010).

Rock L. Kenneth et al. "Protein Degradation and the Generation of MHC class I-Presented Peptides", Advances in Immunology vol. 80 p. 1-70, 2002. Department of Pathology, University of Massachusetts Medical School.

Rousseau et al., "Syndecan-1 antigen, a promising new target for triple-negative breast cancer immuno-PET and radioimmunotherapy. A preclinical study on MDA-MB-468 xenograft tumors", EJNMMI Research, vol. 1, No. 20, 11 pages, 2011.

Schrieber et al (Seminar. Immunol. 22: 105-112, 2010).

Supplementary European Search Report dated Sep. 17, 2011 for EP Application No. 09 75 9182.

Toyoshima T et al. Cancer Lett. Sep. 1, 2012;322(1):86-91. doi: 10.1016/j.canlet.2012.02.016. Epub Feb. 22, 2012. In vitro induction of specific CD8+ T lymphocytes by tumor-associated antigenic peptides in patients with oral squamous cell carcinoma.

Tsuruma et al., Clinical and immunological evaluation of anti-apoptosis protein, survivin-derived peptide vaccine in phase I clinical study for patients with advanced or recurrent breast cancer, J Translational Medicine, 6(24): 1-11, (2008).

Vacchelli et al., Trial watch- Peptide vaccines in cancer therapy, OncoImmunology 1(9):1557-1576 (Dec. 2012).

* cited by examiner

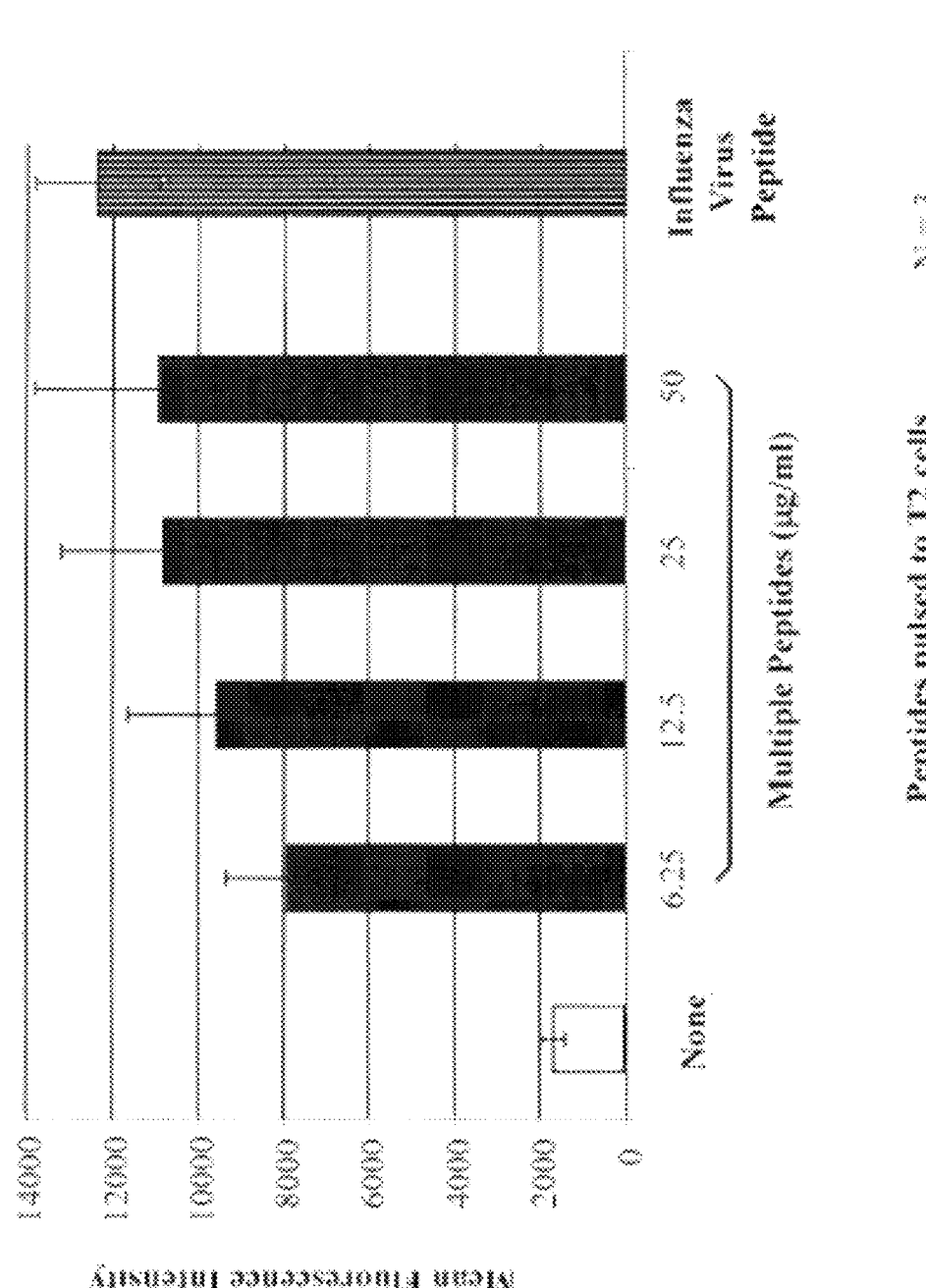
Fig. 1a  HLA-A2 binding capacity of multipeptide cocktail

Fig. 1b HLA-A2 stability of multipeptide cocktail
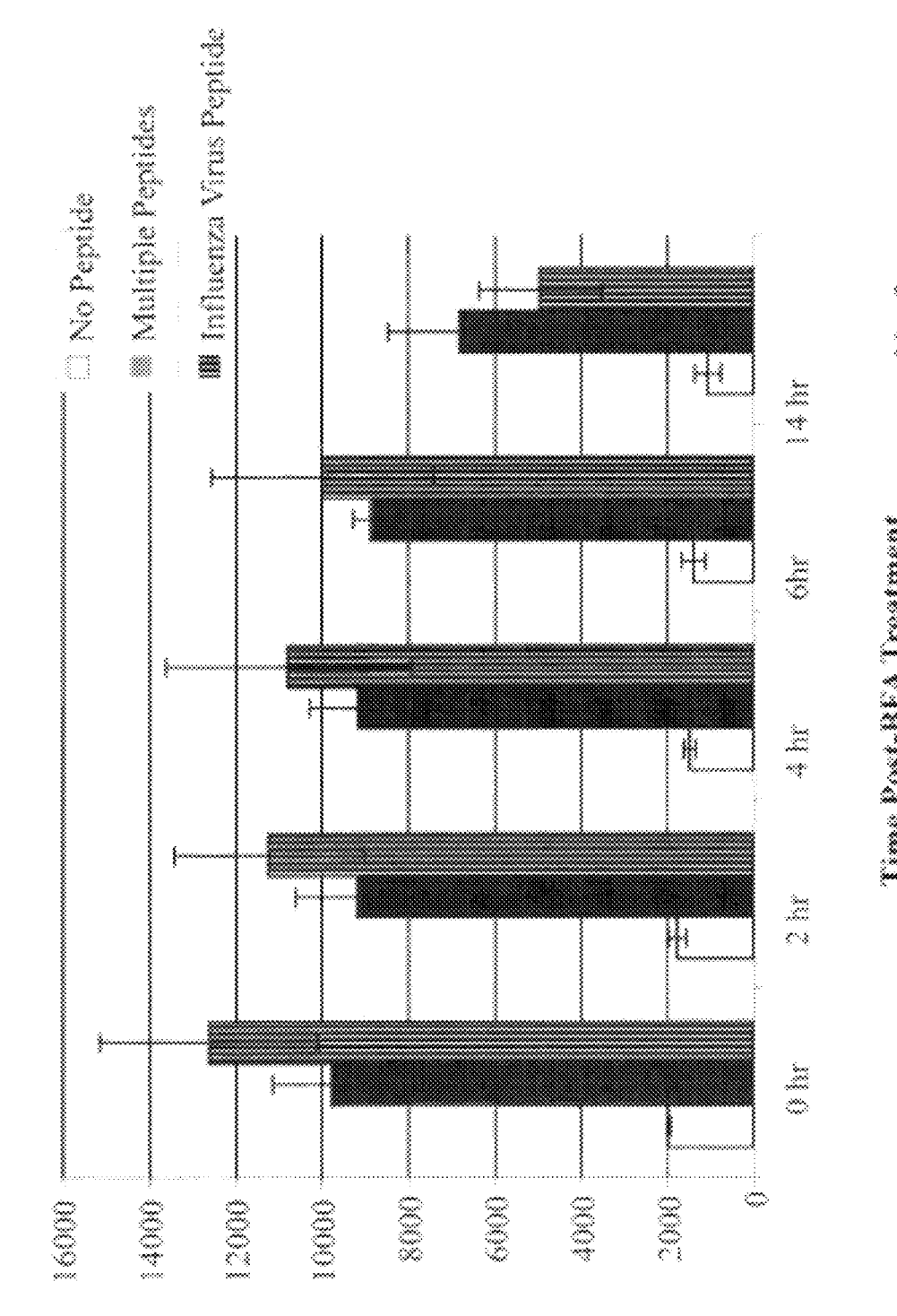

Fig. 2 Distinct phenotype of multipeptide-specific CTL
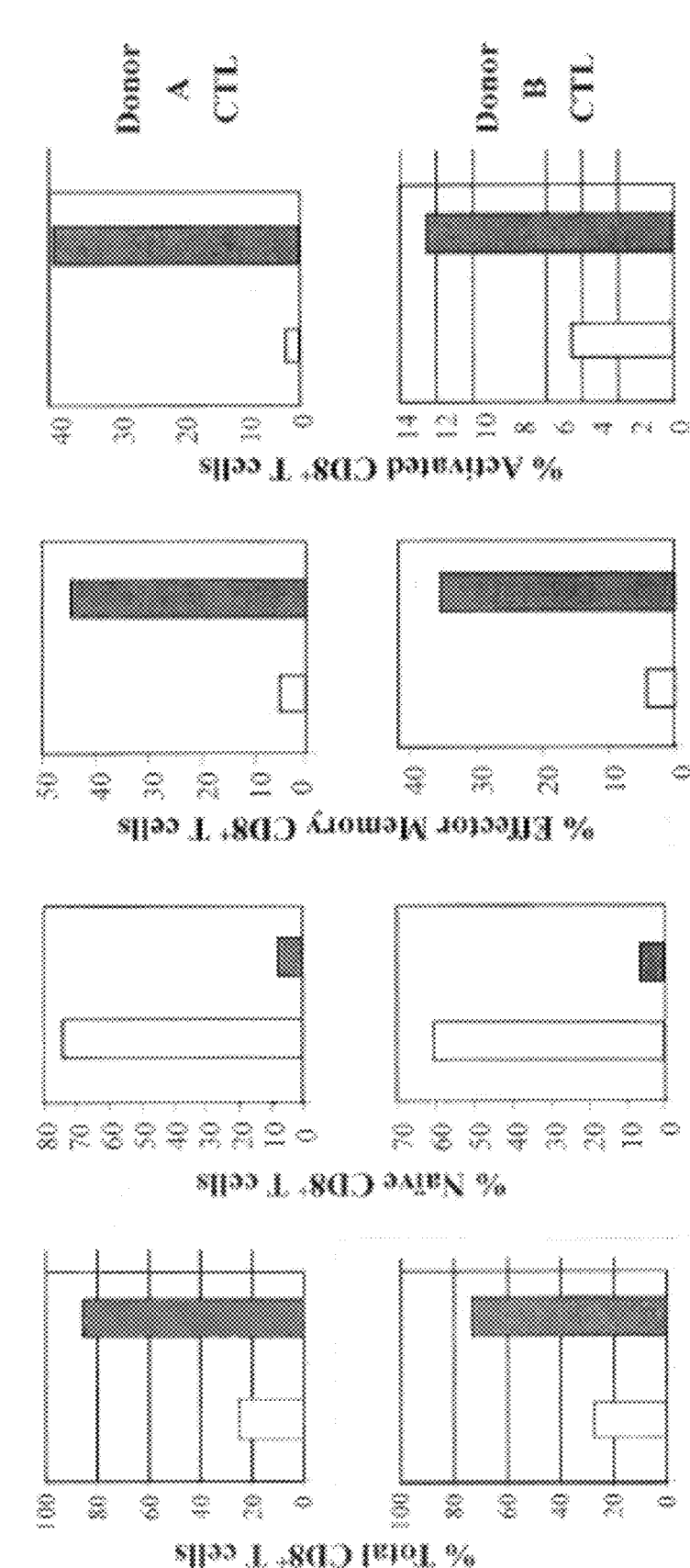

Fig. 3 IFN-γ production by multipeptide-specific CTL
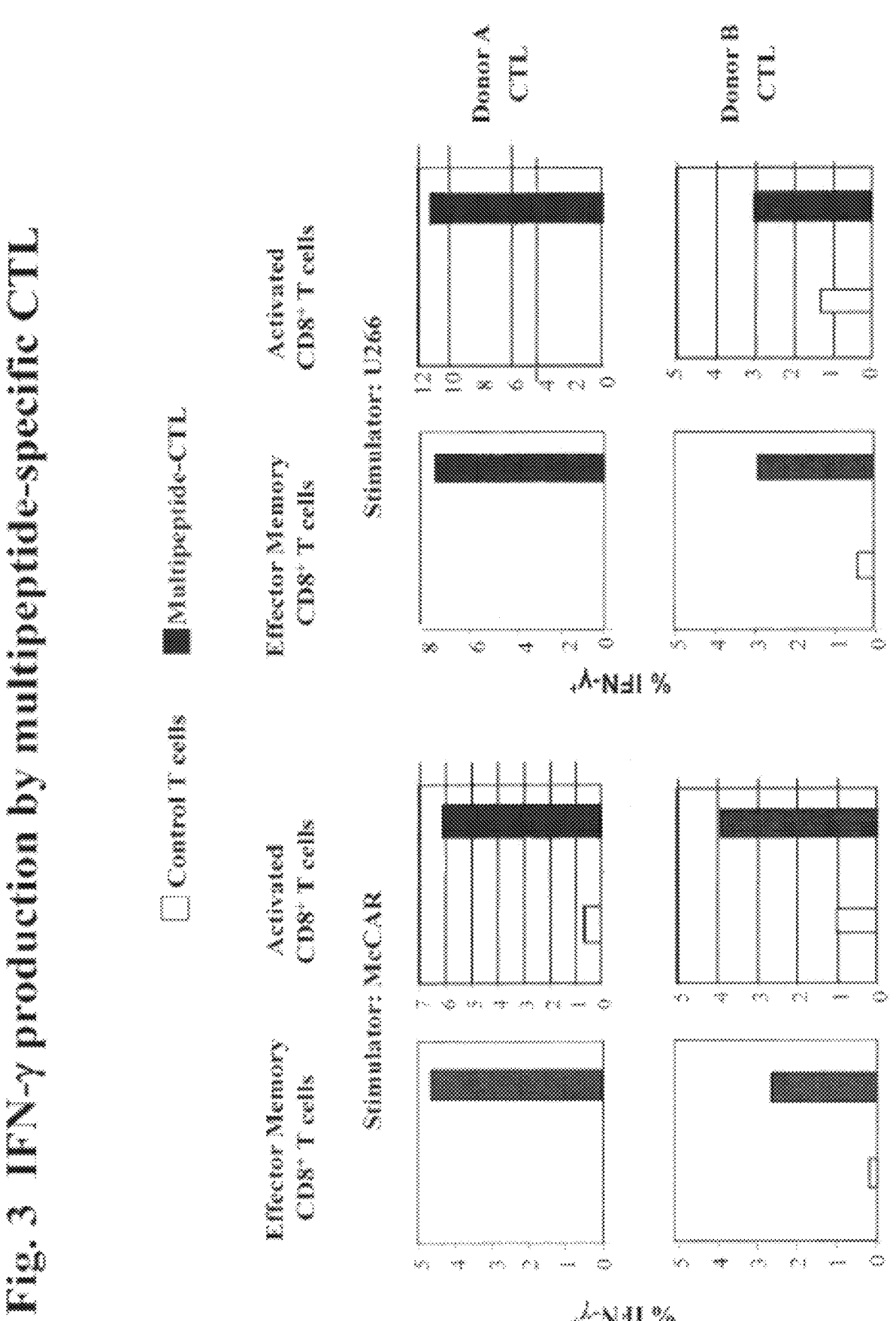

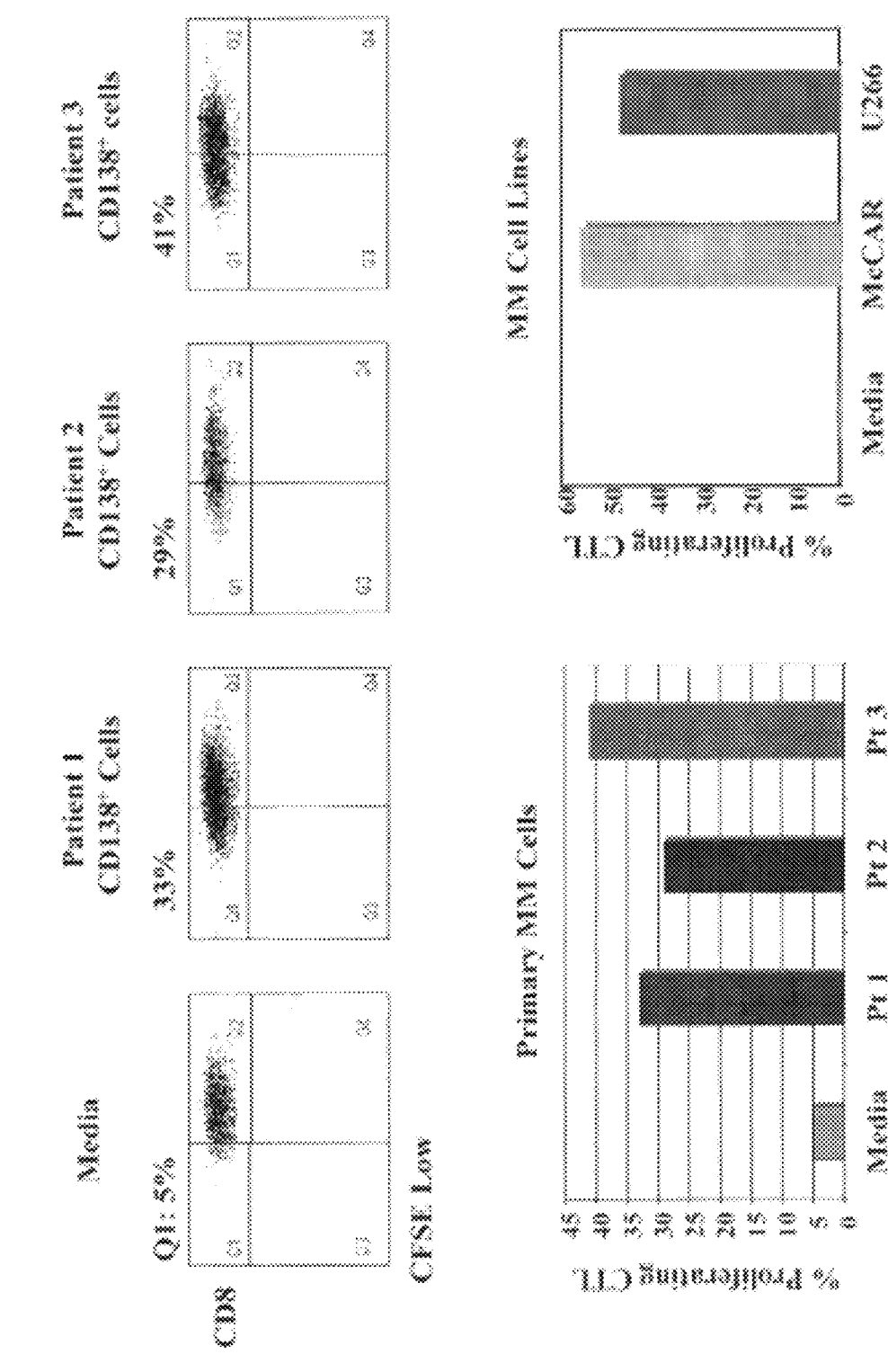
Fig. 4 Induction of multipeptide-specific CTL proliferation by HLA-A2⁺ MM cells including primary cells and cell lines

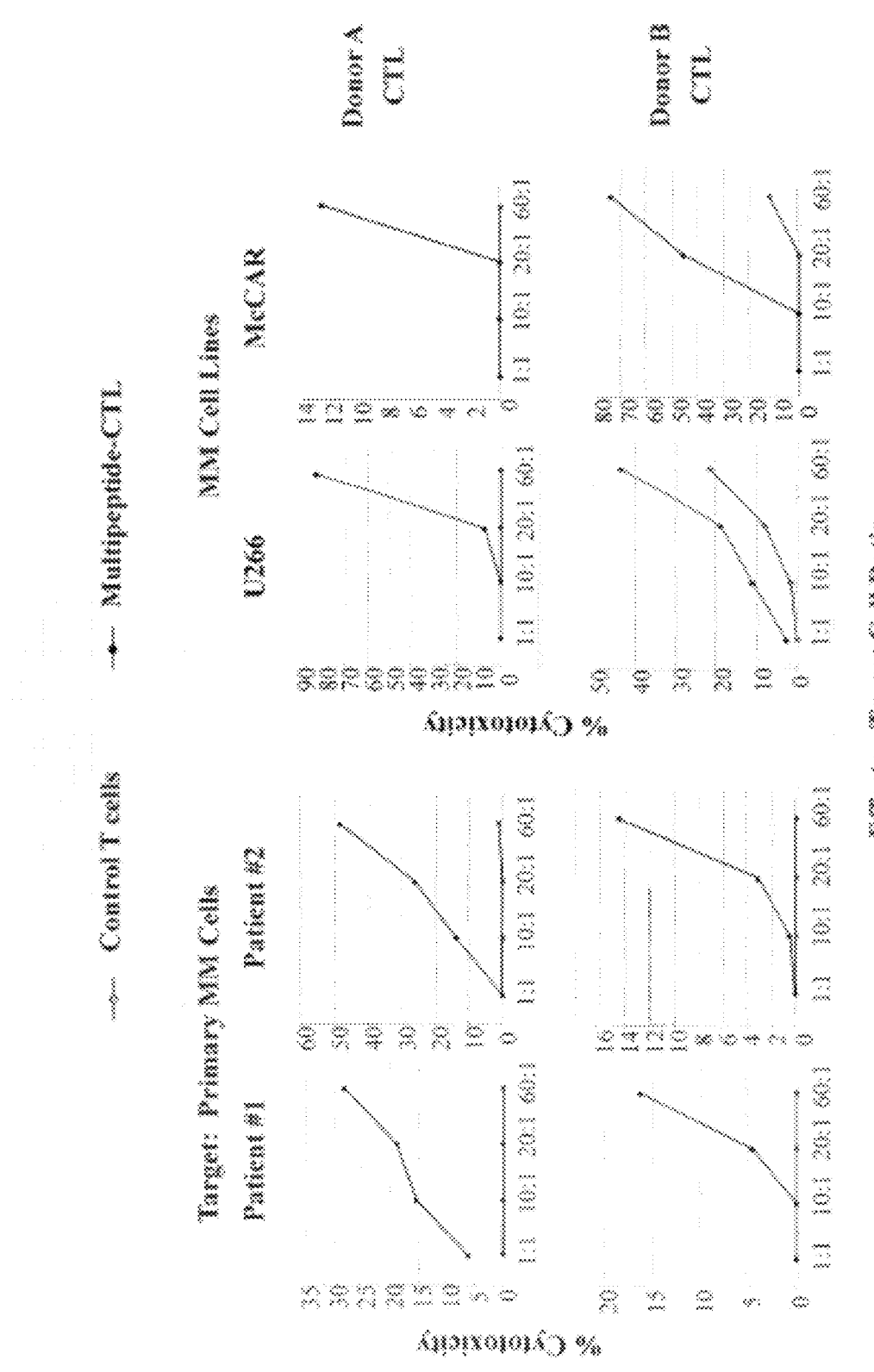
Fig. 5 Cytotoxic activity of multipeptide-CTL against HLA-A2⁺ MM primary cells and MM cell lines

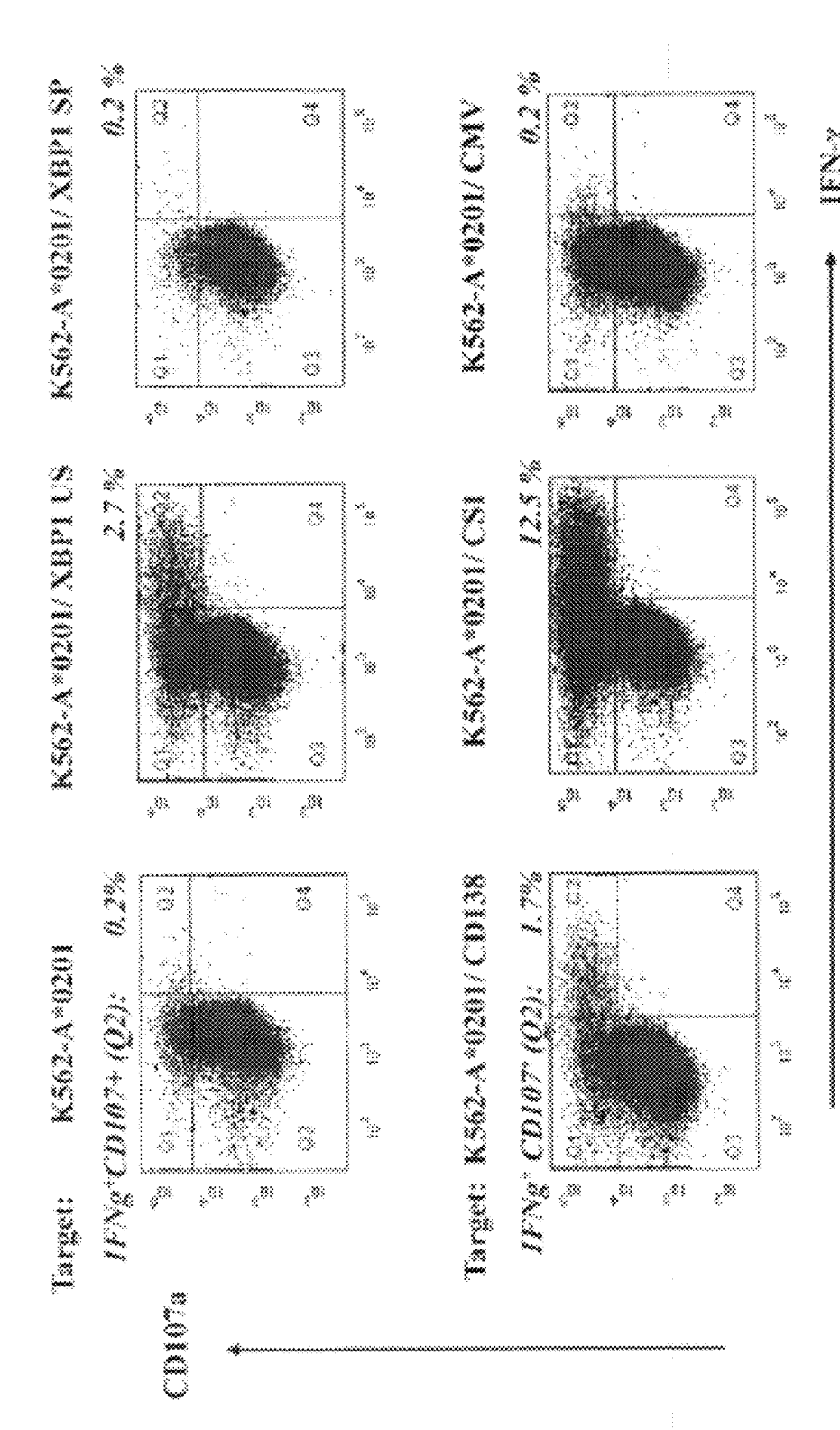
Fig. 6a Peptide-specific response of multipeptide-CTL detected by CD107a degranulation and IFN-γ production (Donor A)

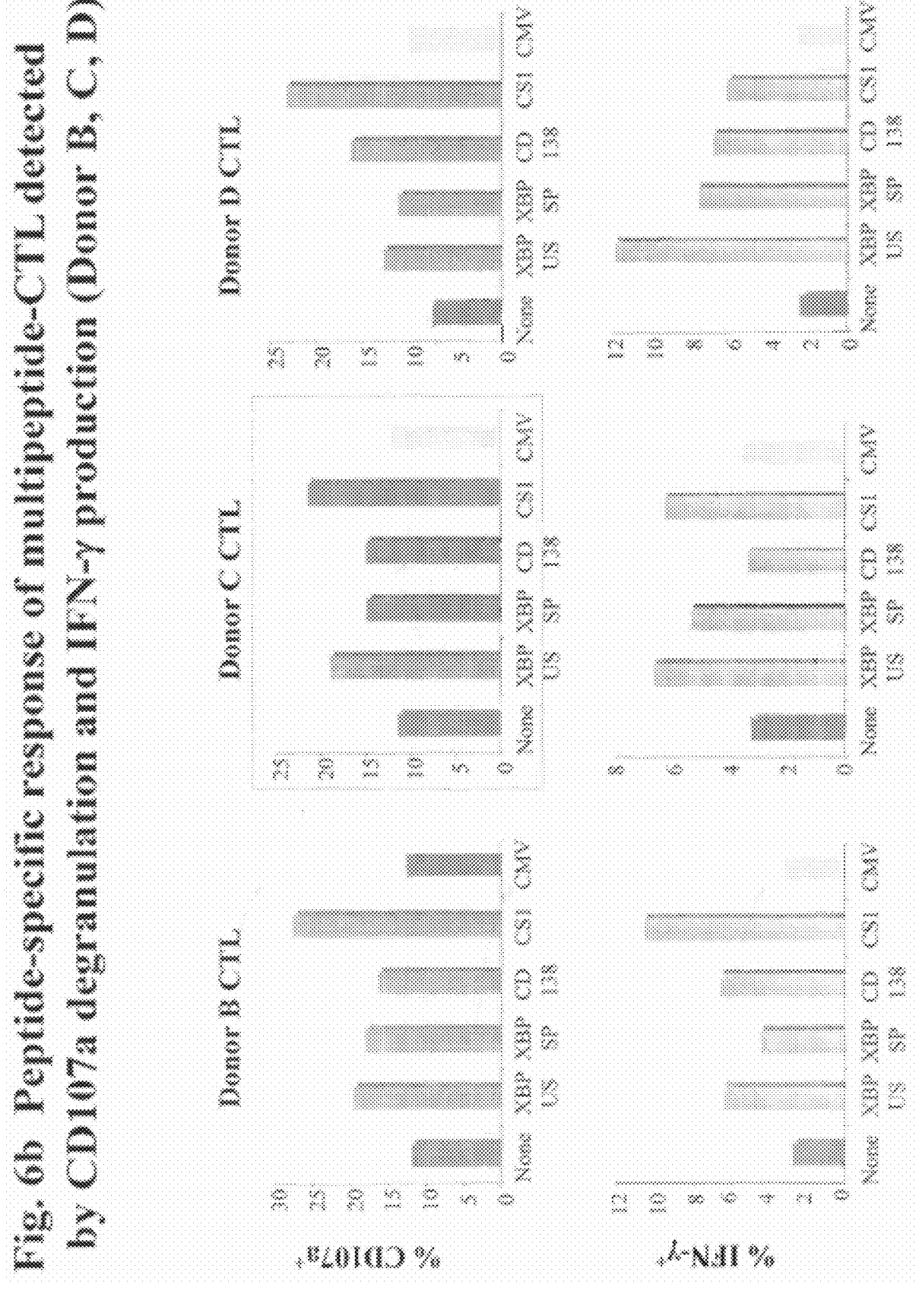
Fig. 6b Peptide-specific response of multipeptide-CTL detected by CD107a degranulation and IFN-γ production (Donor B, C, D)

Fig. 7 Relative XBP1 Expression Level on Cancer Cell Lines

| Cancer Type | Cell Line | XBP1 Unspliced | | XBP1 Spliced | |
|---|---|---|---|---|---|
| Prostate Cancer | LnCap | - | 0 | - | 0 |
| | Vcap | - | 0 | - | 0 |
| Multiple Myeloma | MM1S | ++ | 2 | ++ | 2 |
| | U266 | ++ | 3 | +++ | 4 |
| | McCAR | + | 1 | ++ | 3 |
| Breast Cancer | MB231 | ++ | 2 | +++ | 5 |
| | MCF7 | +++ | 3 | +++ | 5 |
| | BT474 | ++ | 3 | +++ | 5 |
| Colon Cancer | LS180 | +++ | 4 | +++ | 5 |
| | SW480 | ++ | 2 | ++ | 4 |
| | WiDr | + | 1 | +++ | 5 |

| Cancer Type | Cell Line | XBP1 Unspliced | | XBP1 Spliced | |
|---|---|---|---|---|---|
| Pancreatic Cancer | 8978XL | ++++ | 4 | ++++ | 5 |
| | MiaPaca | ++ | 3 | +++ | 6 |
| | Panc1 | ++ | 3 | +++ | 4 |
| | 8902 | ++ | 2 | +++ | 3 |
| | PL45 | + | 1 | +++ | 4 |
| | BxPanc96 | + | 1 | + | 2 |
| AML | OCI | + | 1 | ++ | 2 |
| | U937 | + | 1 | ++ | 3 |
| | HEL | ++ | 2 | +++ | 3 |
| | UT7 | +++ | 3 | +++ | 5 |
| | Namo1 | + | 1 | ++ | 2 |
| CML | K562-A2 | ++ | 3 | ++ | 3 |

Measured by Flow Cytometry

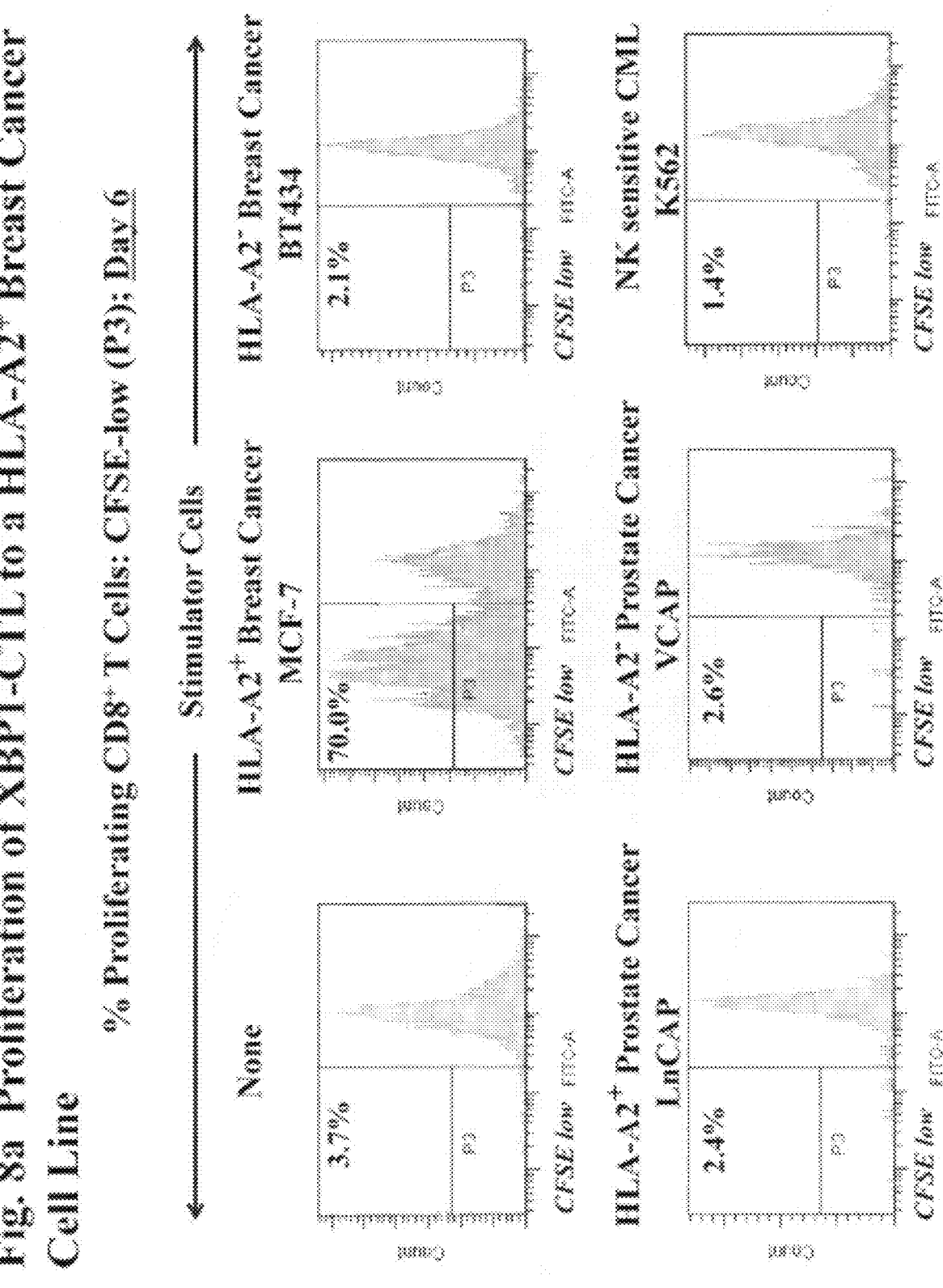
Fig. 8a Proliferation of XBP1-CTL to a HLA-A2⁺ Breast Cancer Cell Line

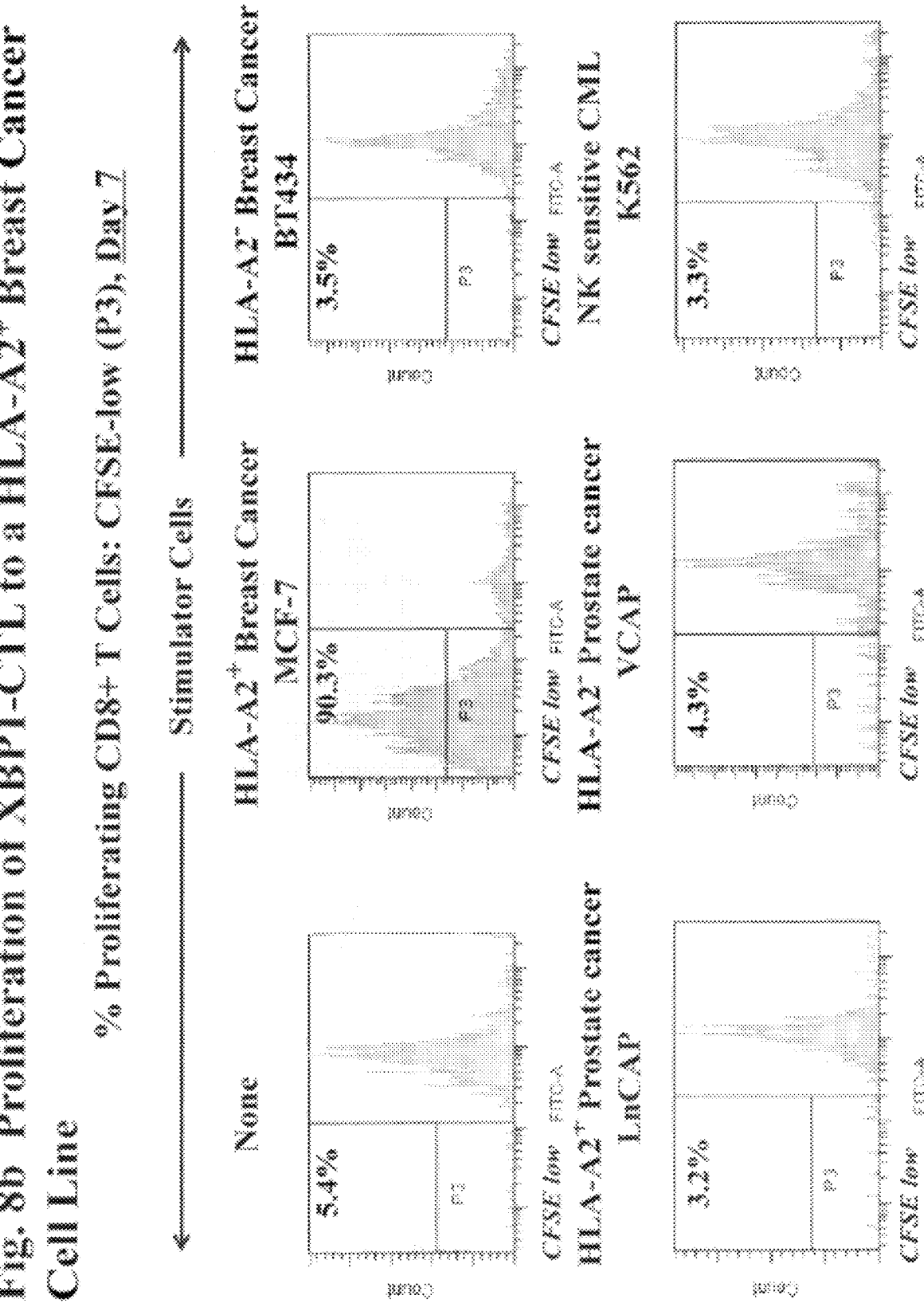
Fig. 8b Proliferation of XBP1-CTL to a HLA-A2⁺ Breast Cancer Cell Line

Fig. 9 IFN-γ Production and Cell Activation of XBP1-CTL to HLA-A2⁺ Breast Cancer Cell Lines
% IFN-γ⁺/CD69⁺ (Q2) : Gated on CD8⁺ T cells
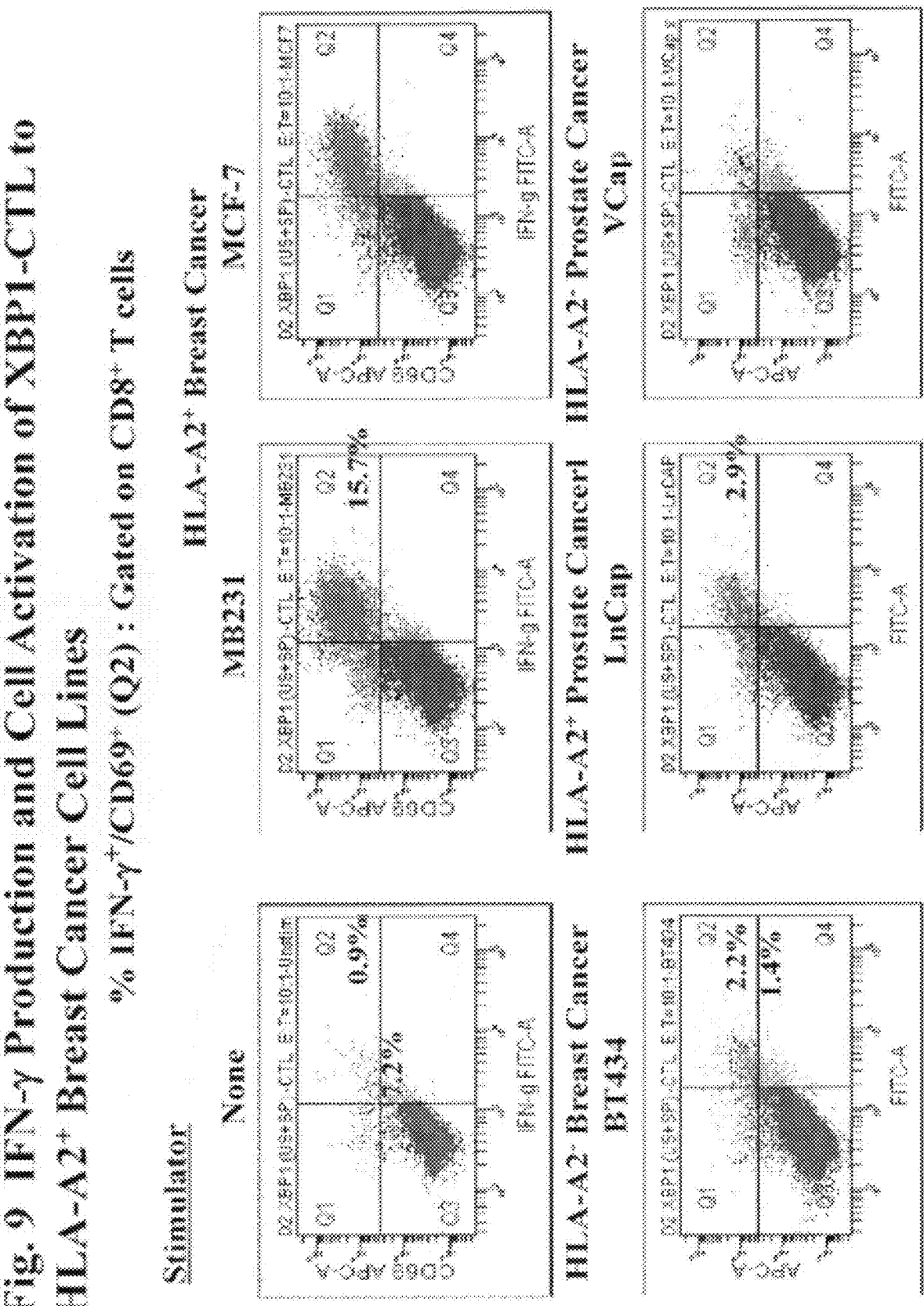

Fig. 10 CD107a Degranulation of XBP1-CTL to HLA-A2⁺ Breast Cancer Cell Lines
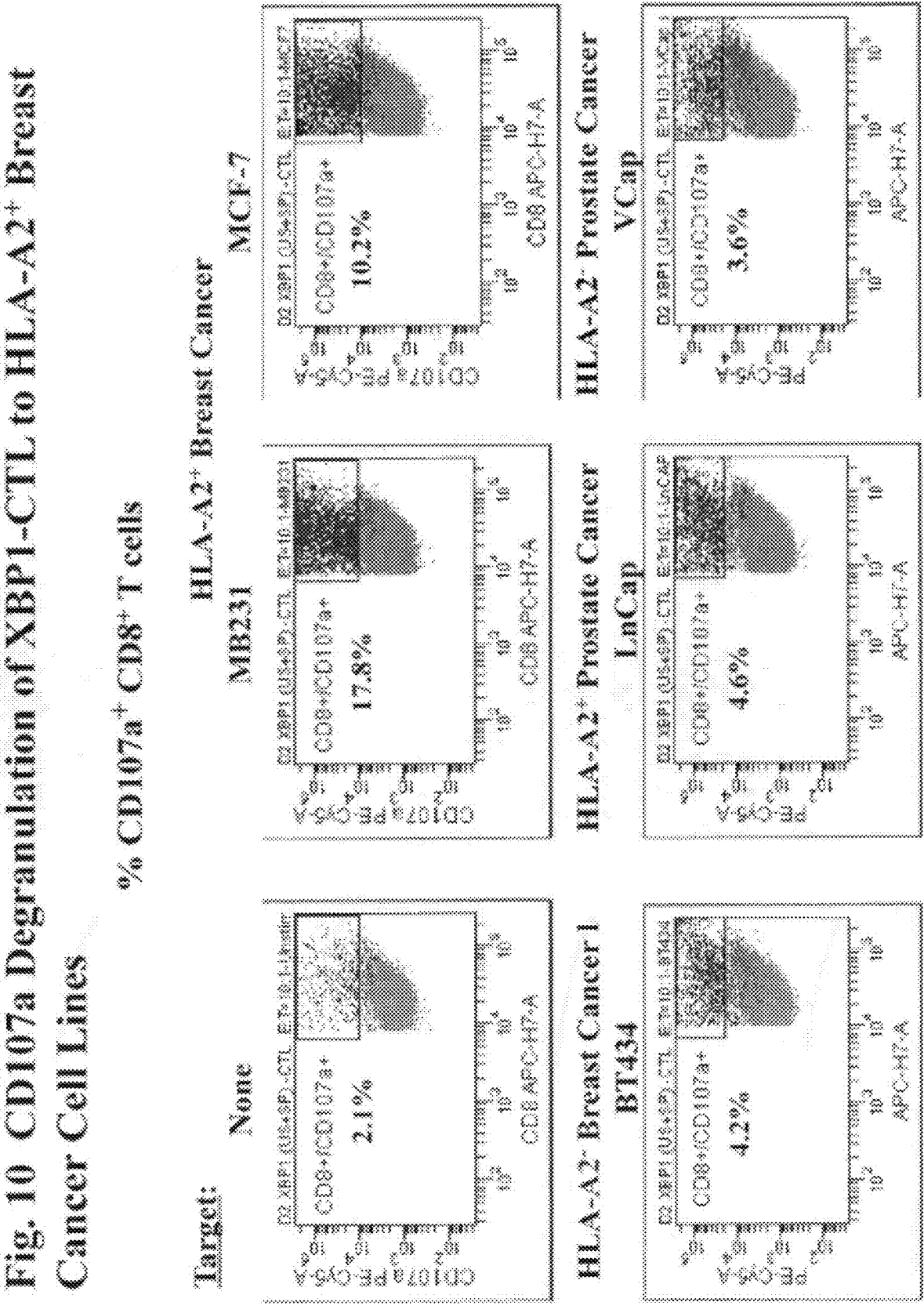

Fig. 11 Proliferation of XBP1-CTL to HLA-A2⁺ Pancreatic and Colon Cancer Cell Lines % Proliferating (CFSE low) CD8⁺ T cells

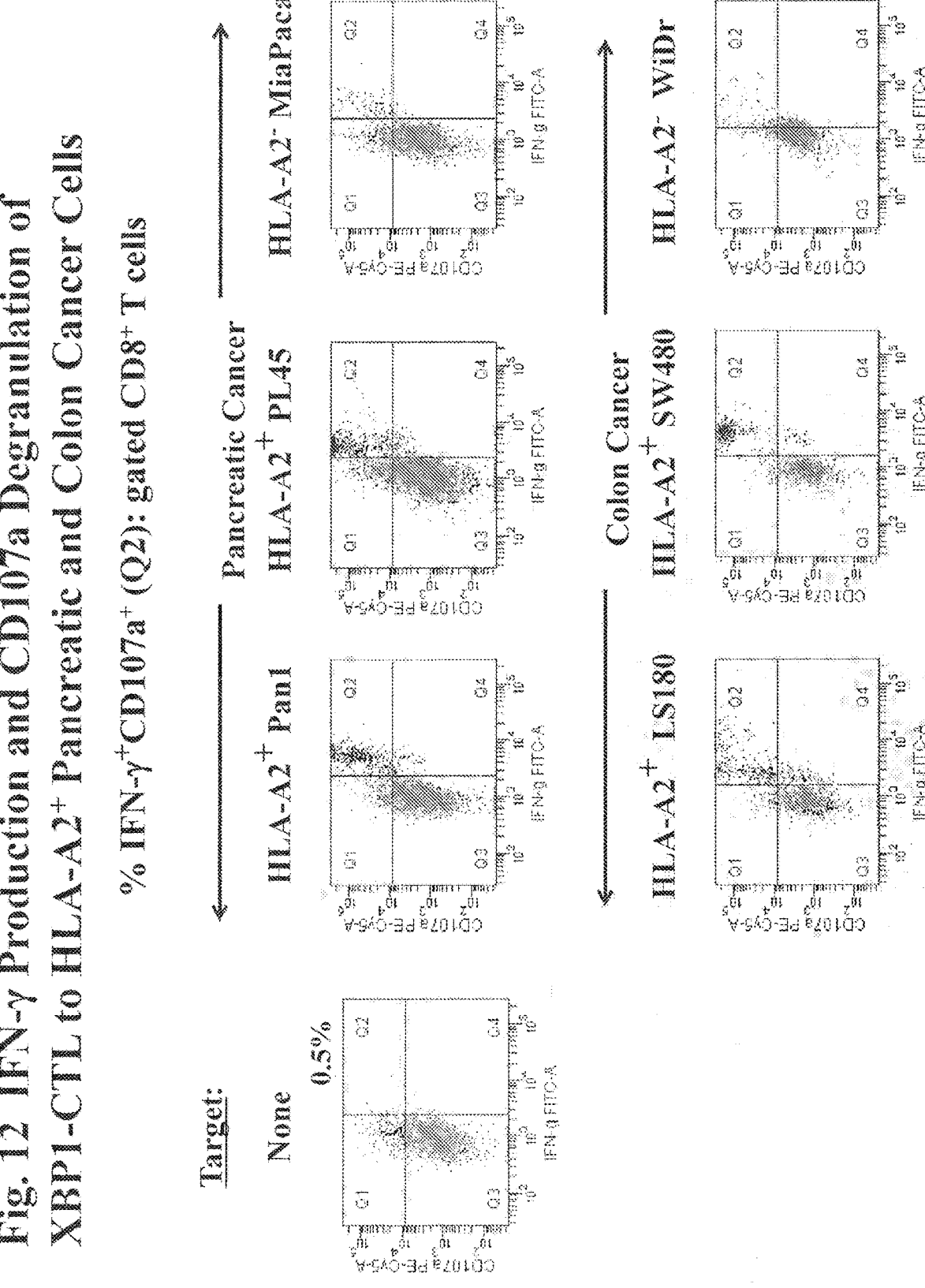
Fig. 12 IFN-γ Production and CD107a Degranulation of XBP1-CTL to HLA-A2+ Pancreatic and Colon Cancer Cells

Fig. 13 Relative CD138 Expression on Cancer Cell Lines

| Cancer Type | Cell Line | CD138 | |
|---|---|---|---|
| Multiple Myeloma | MM1S | ++ | 2 |
| | U266 | ++ | 2 |
| | RPMI | +++++ | 5 |
| | INA6 | ++ | 2 |
| Breast Cancer | MB231 | +++++ | 5 |
| | MCF7 | +++++ | 5 |
| | BT474 | +++++ | 5 |
| Prostate Cancer | LnCap | ++++ | 4 |
| | Vcap | +++++ | 5 |
| Colon Cancer | LS180 | +++++ | 5 |
| | SW480 | + | 1 |
| | WiDr | +++++ | 4 |

| Cancer Type | Cell Line | CD138 | |
|---|---|---|---|
| Pancreatic Cancer | 897881 | ++ | 2 |
| | MiaPaca | +++ | 3 |
| | Panc1 | +++ | 3 |
| | 8902 | ++ | 2 |
| | PL45 | +++++ | 5 |
| | mPanc96 | +++++ | 5 |
| AML | OCI | + | 1 |
| | U937 | - | 0 |
| | HEL | + | 1 |
| | UT7 | - | 0 |
| | HL60 | ++ | 2 |
| | Nomo1 | - | 0 |
| | THP1 | + | 1 |

Measured by Flow Cytometry

Fig. 14 Relative CS-1 Expression on Cancer Cell Lines

| Cancer Type | Cell Line | CS-1 | |
|---|---|---|---|
| Multiple Myeloma | MM1S | +++ | 3 |
| | U266 | + | 1 |
| | RPMI | + | 1 |
| Breast Cancer | MB231 | + | 1 |
| | MCF7 | + | 1 |
| | BT474 | ++ | 2 |
| Prostate Cancer | LnCap | - | 0 |
| | Vcap | + | 1 |
| Colon Cancer | LS180 | + | 1 |
| | SW480 | - | 0 |
| | WiDr | - | 0 |

| Cancer Type | Cell Line | CS-1 | |
|---|---|---|---|
| AML | OCI | +++++ | 5 |
| | U937 | +++++ | 5 |
| | HEL | - | 0 |
| | UT7 | - | 0 |
| | HL60 | ++ | 2 |
| | Nomo1 | +++++ | 5 |
| | THP1 | +++ | 3 |

Measured by Flow Cytometry

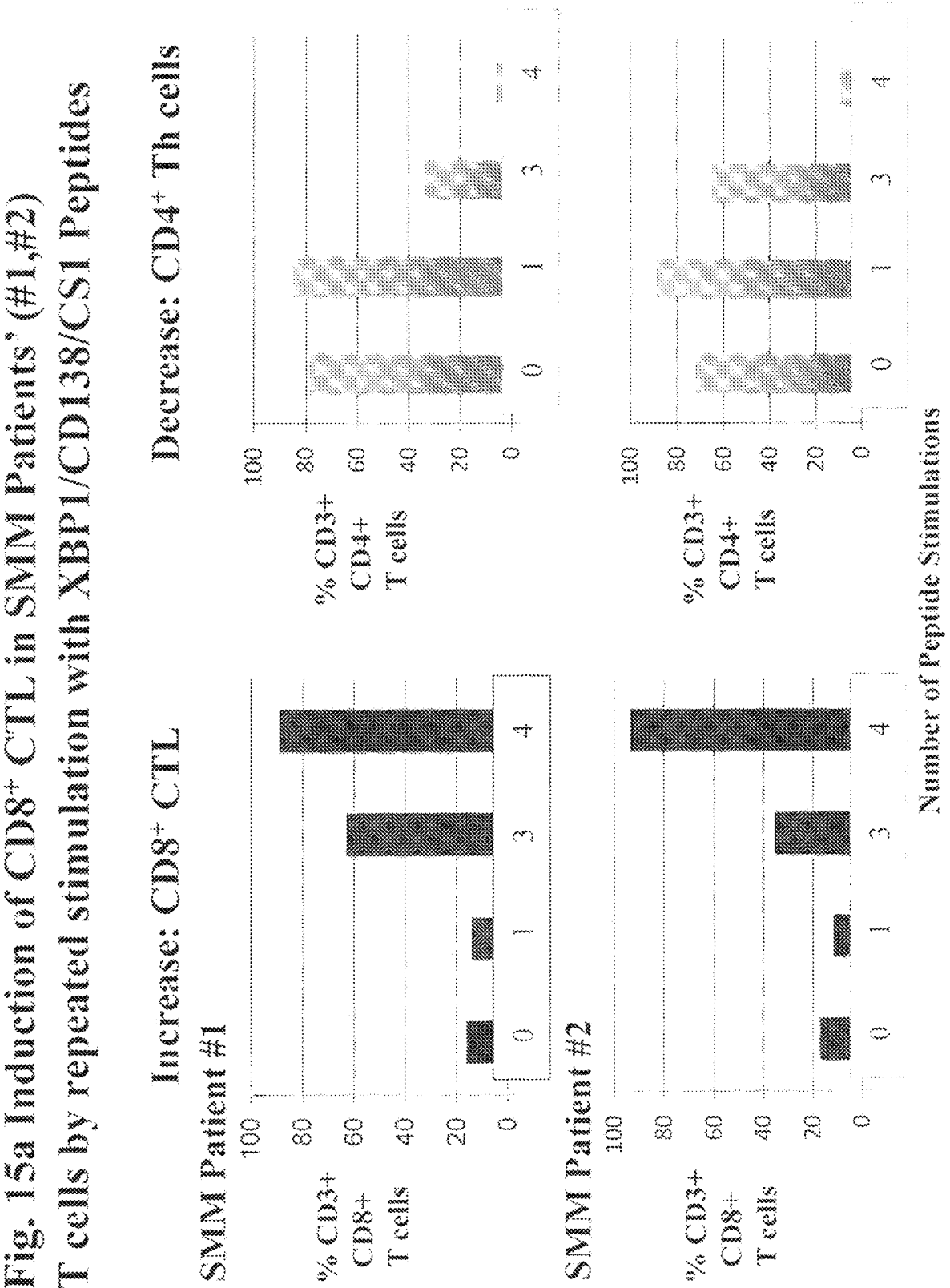
Fig. 15a Induction of CD8+ CTL in SMM Patients' (#1,#2) T cells by repeated stimulation with XBP1/CD138/CS1 Peptides Fig. 15b Induction of CD8+ CTL in SMM Patients' (#3,#4) T cells by repeated stimulation with XBP1/CD138/CS1 Peptides
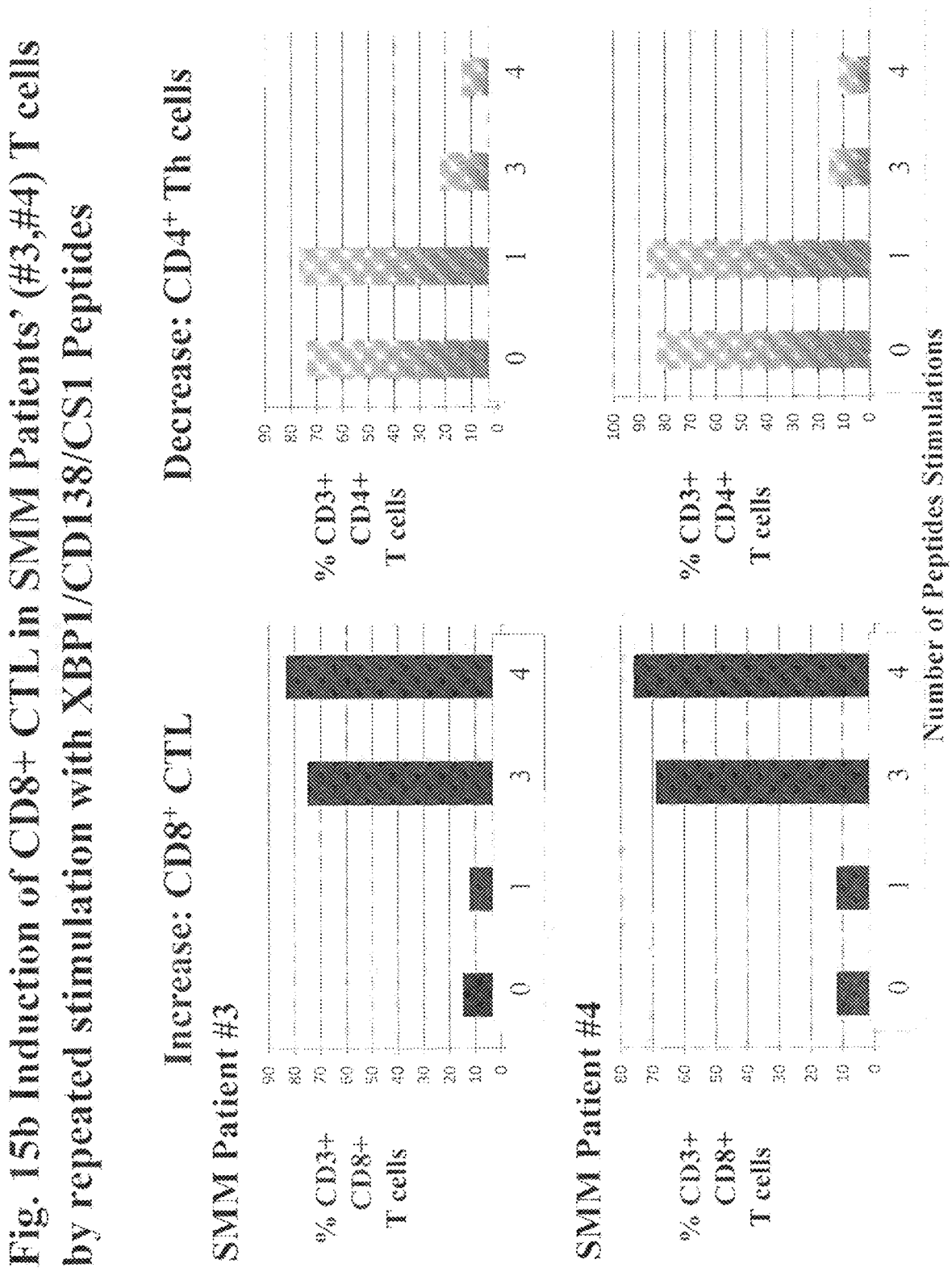

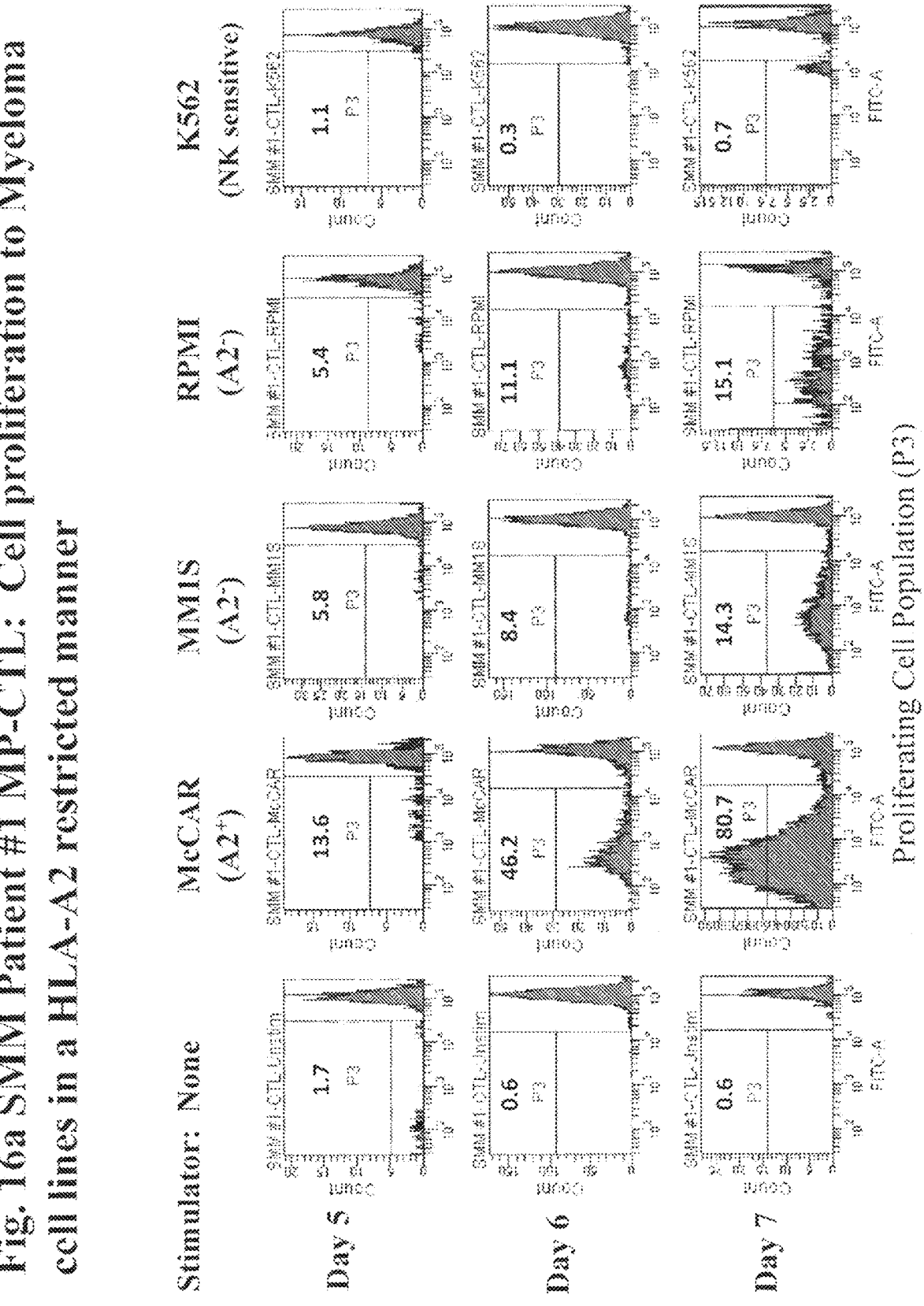
Fig. 16a SMM Patient #1 MP~CTL: Cell proliferation to Myeloma cell lines in a HLA-A2 restricted manner

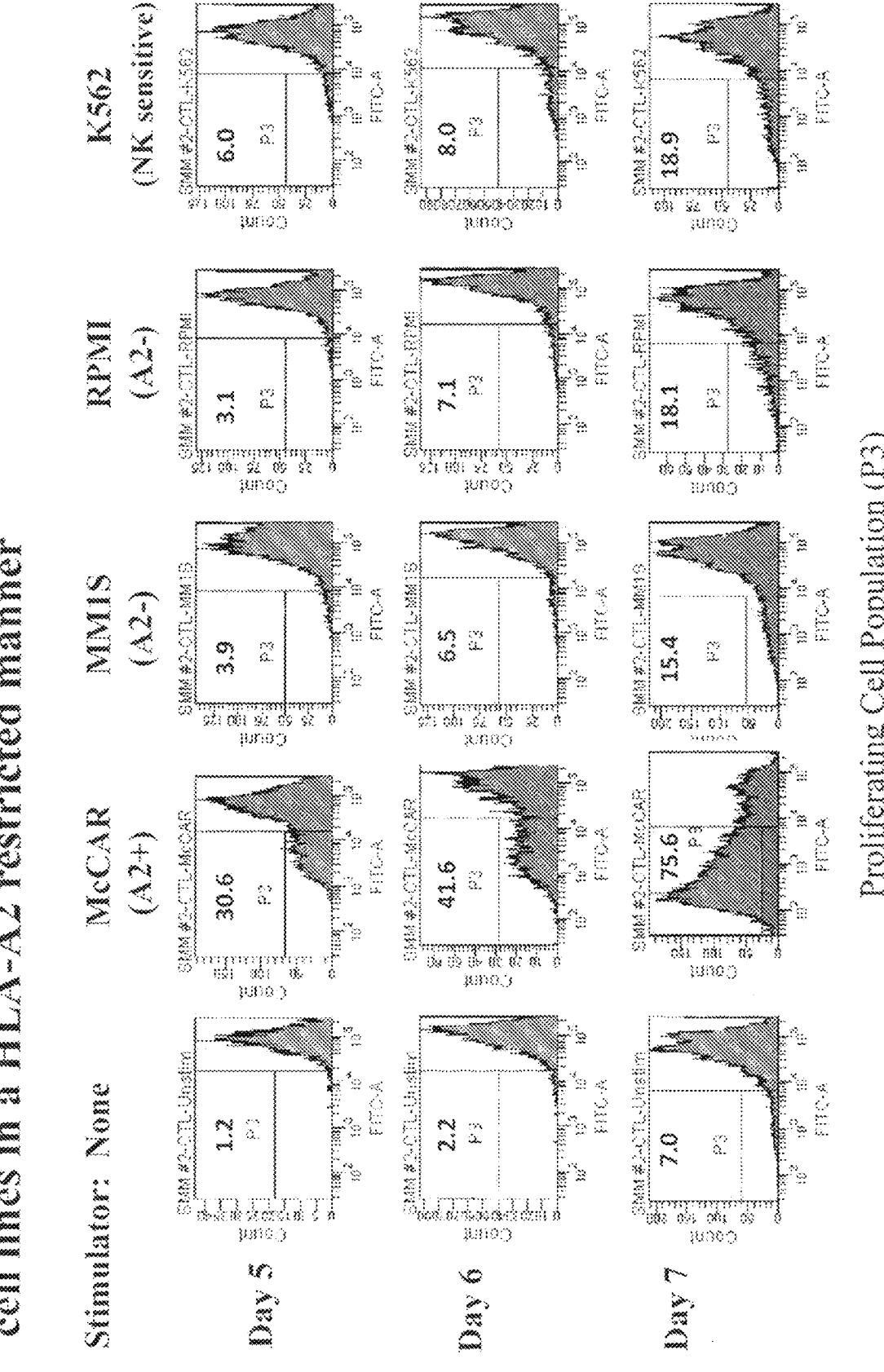
Fig. 16b SMM Patient #2 MP-CTL: Cell proliferation to Myeloma cell lines in a HLA-A2 restricted manner Fig. 17a IFN-γ production by SMM MP-CTL to Myeloma cell lines in a HLA-A2 restricted manner
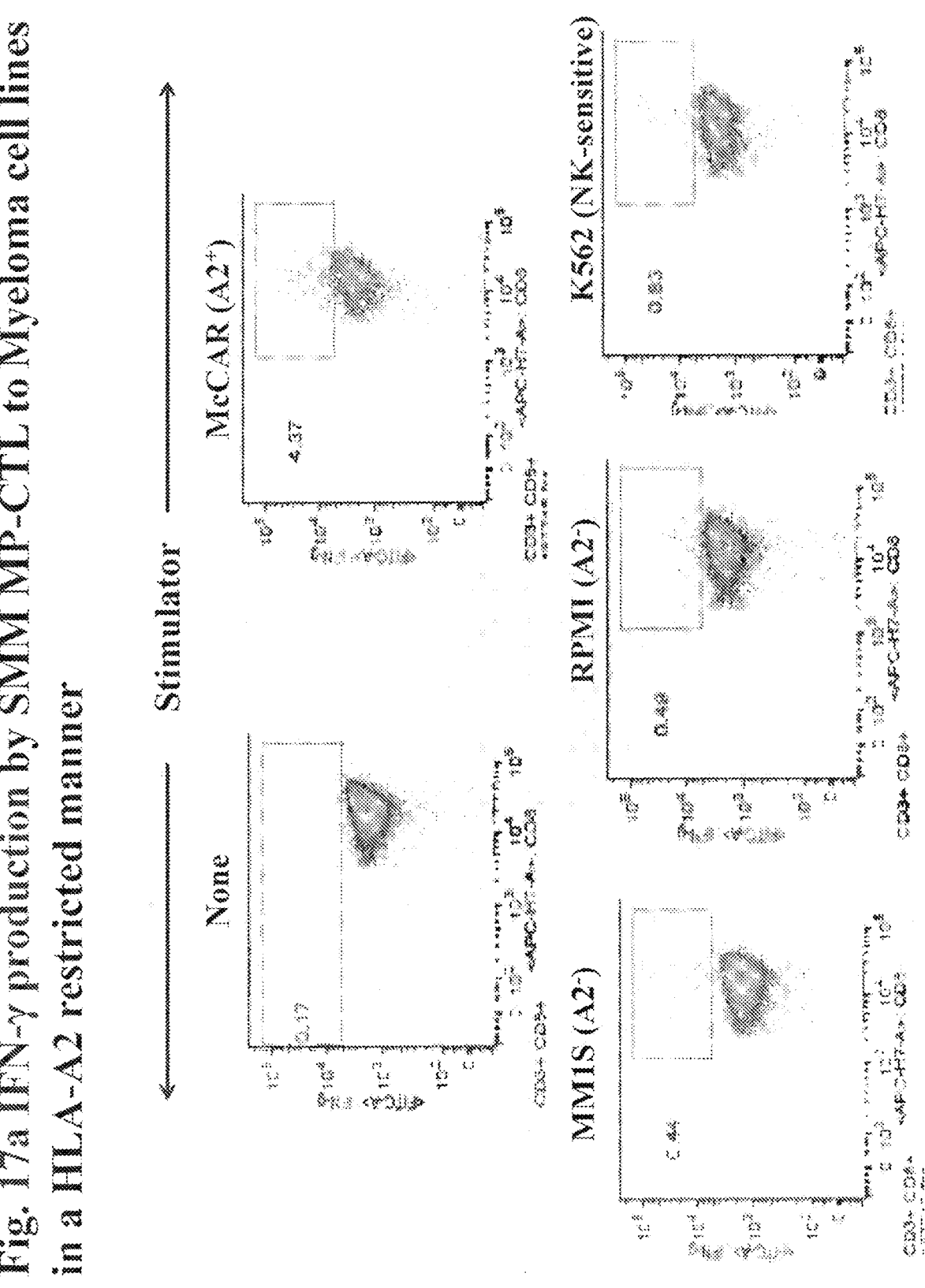

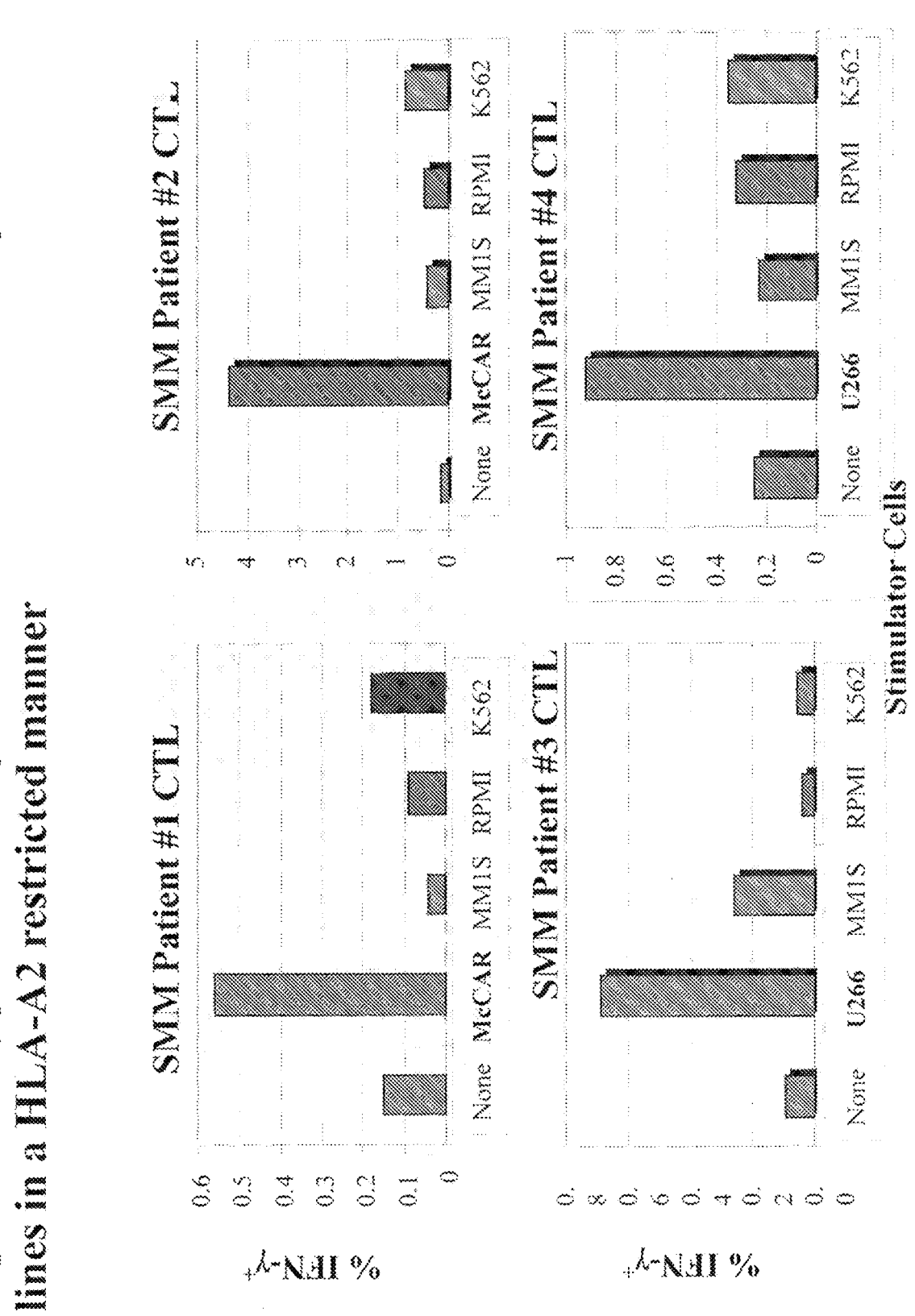
Fig. 17b IFN-γ production by four SMM MP-CTL to Myeloma cell lines in a HLA-A2 restricted manner Fig. 18a CD107a degranulation by SMM MP–CTL to Myeloma cells in a HLA–A2 restricted manner
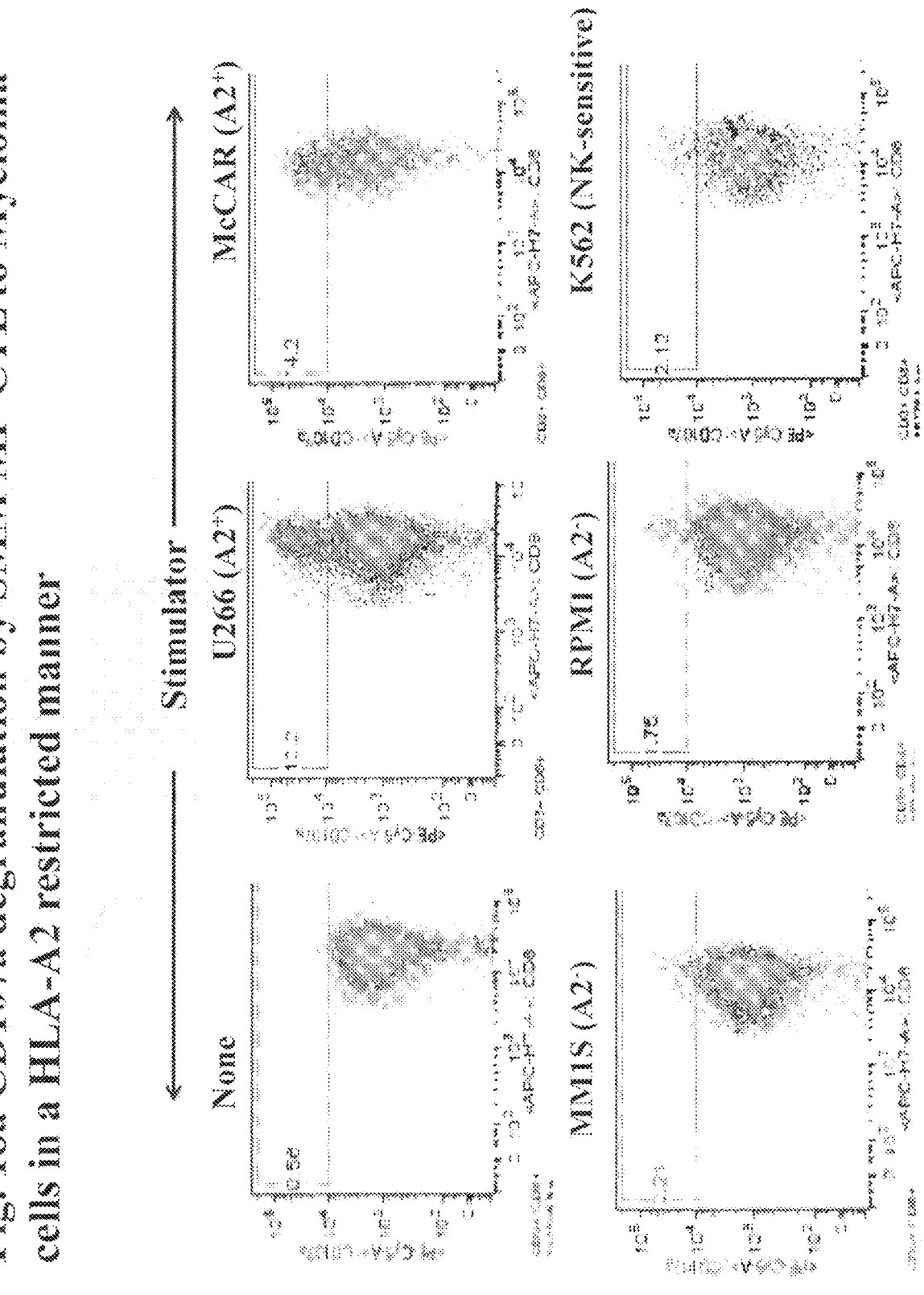

Fig. 18b CD107a degranulation by four SMM MP-CTL to Myeloma cells in a HLA-A2 restricted manner
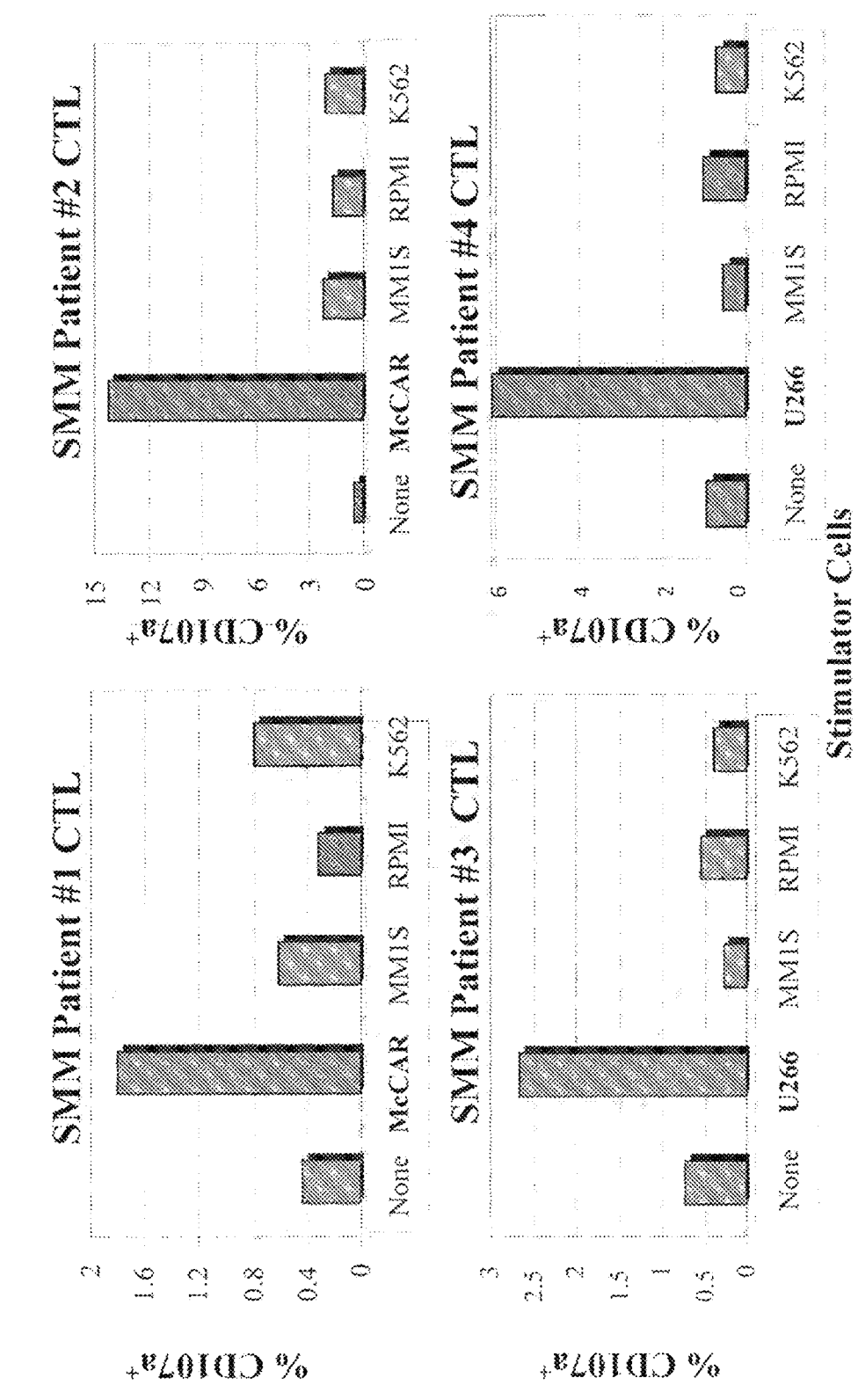

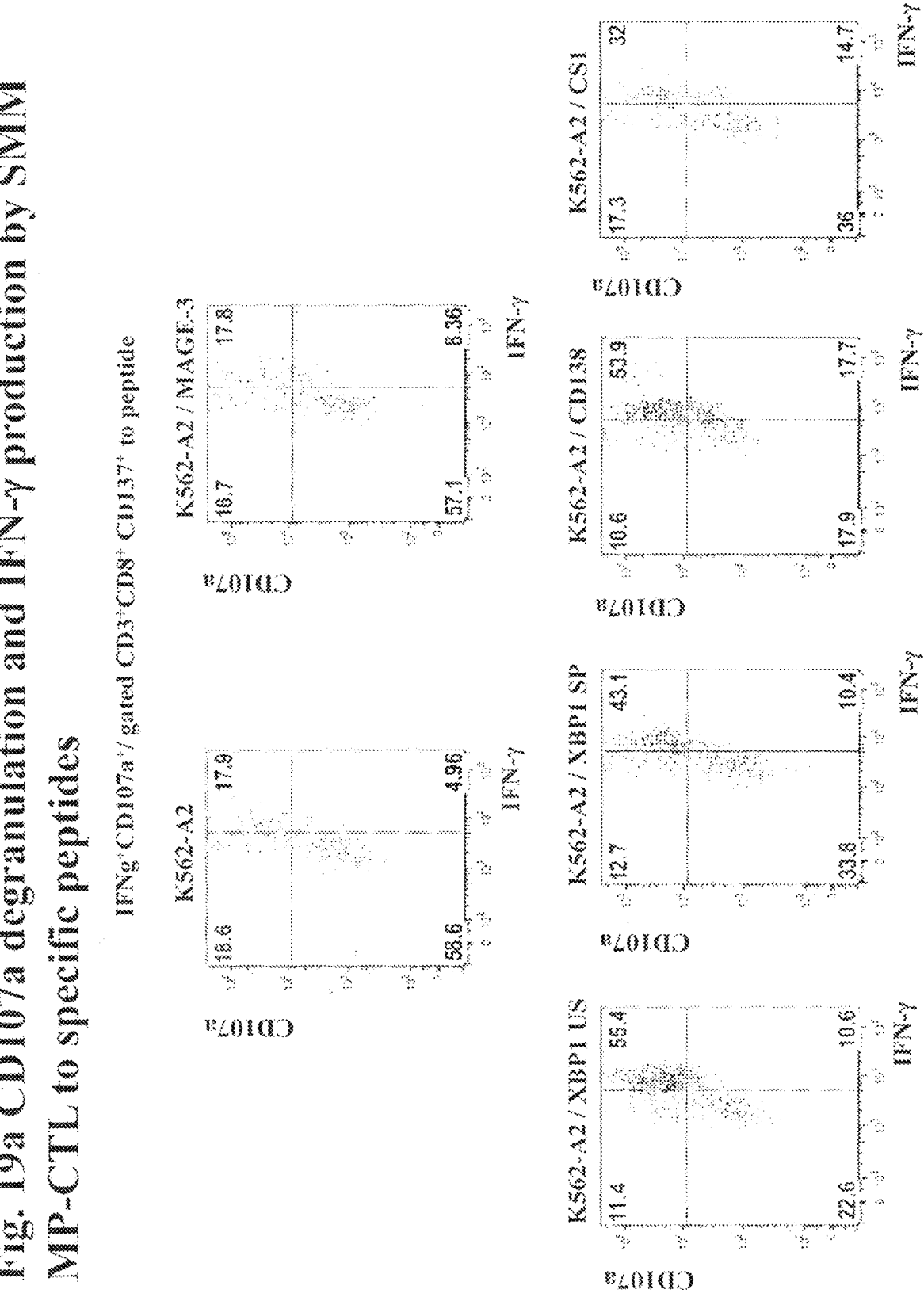
Fig. 19a CD107a degranulation and IFN-γ production by SMM MP-CTL to specific peptides

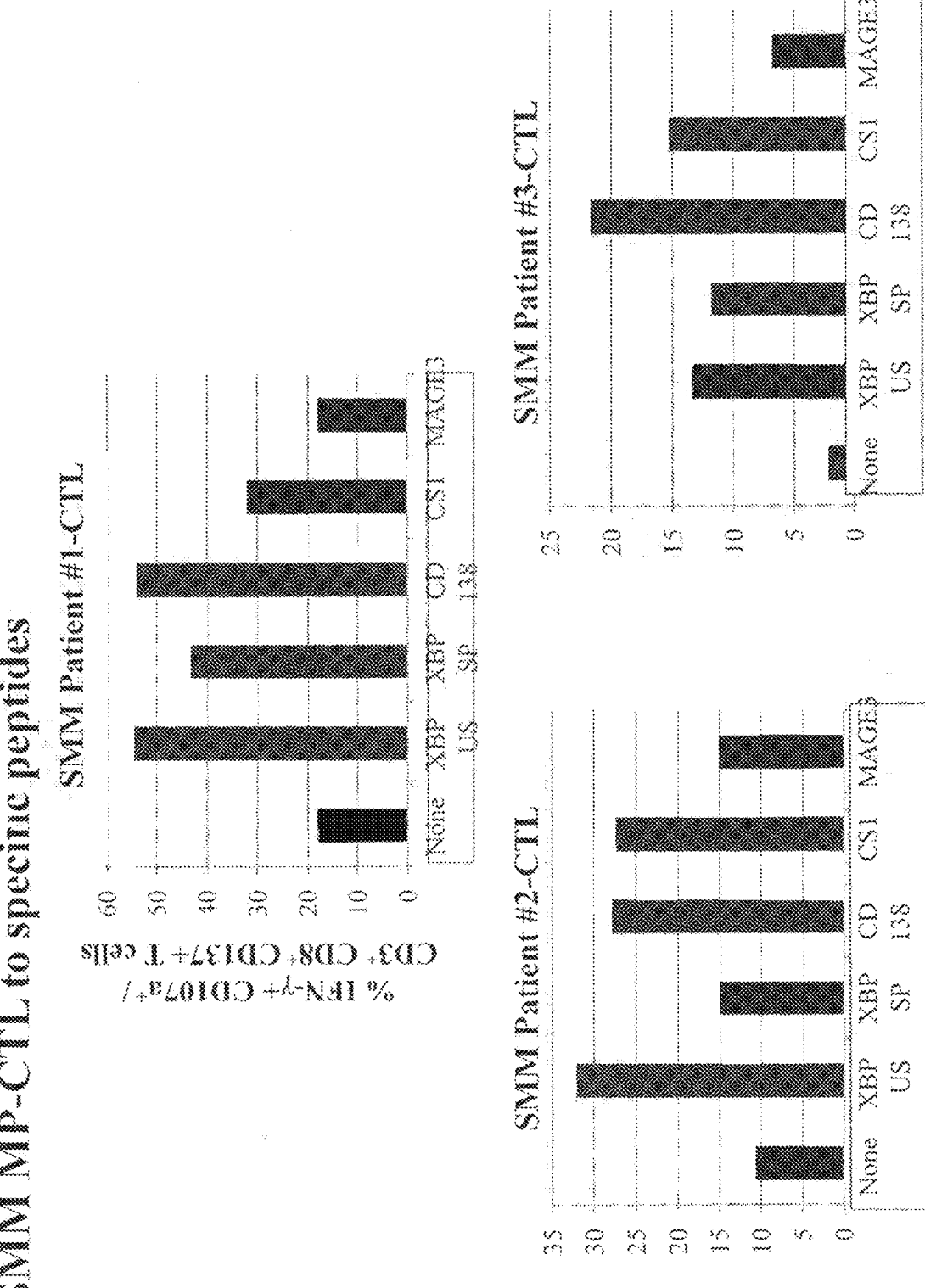
Fig. 19b CD107a degranulation and IFN-γ production by three SMM MP-CTL to specific peptides

Fig. 19c Summary of total CD107a degranulation and total IFN-γ production by three SMM MP-CTL

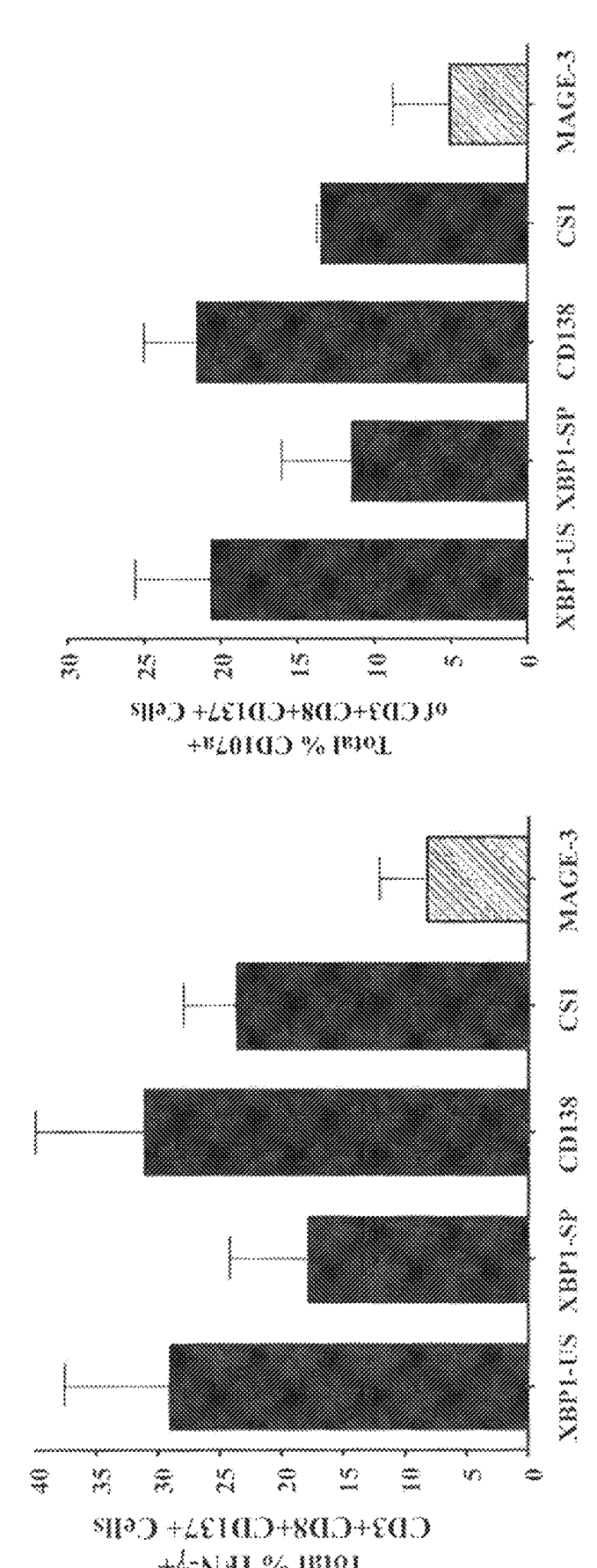
Fig. 19d Summary of total CD107a degranulation or total IFN-γ production by three SMM MP-CTL

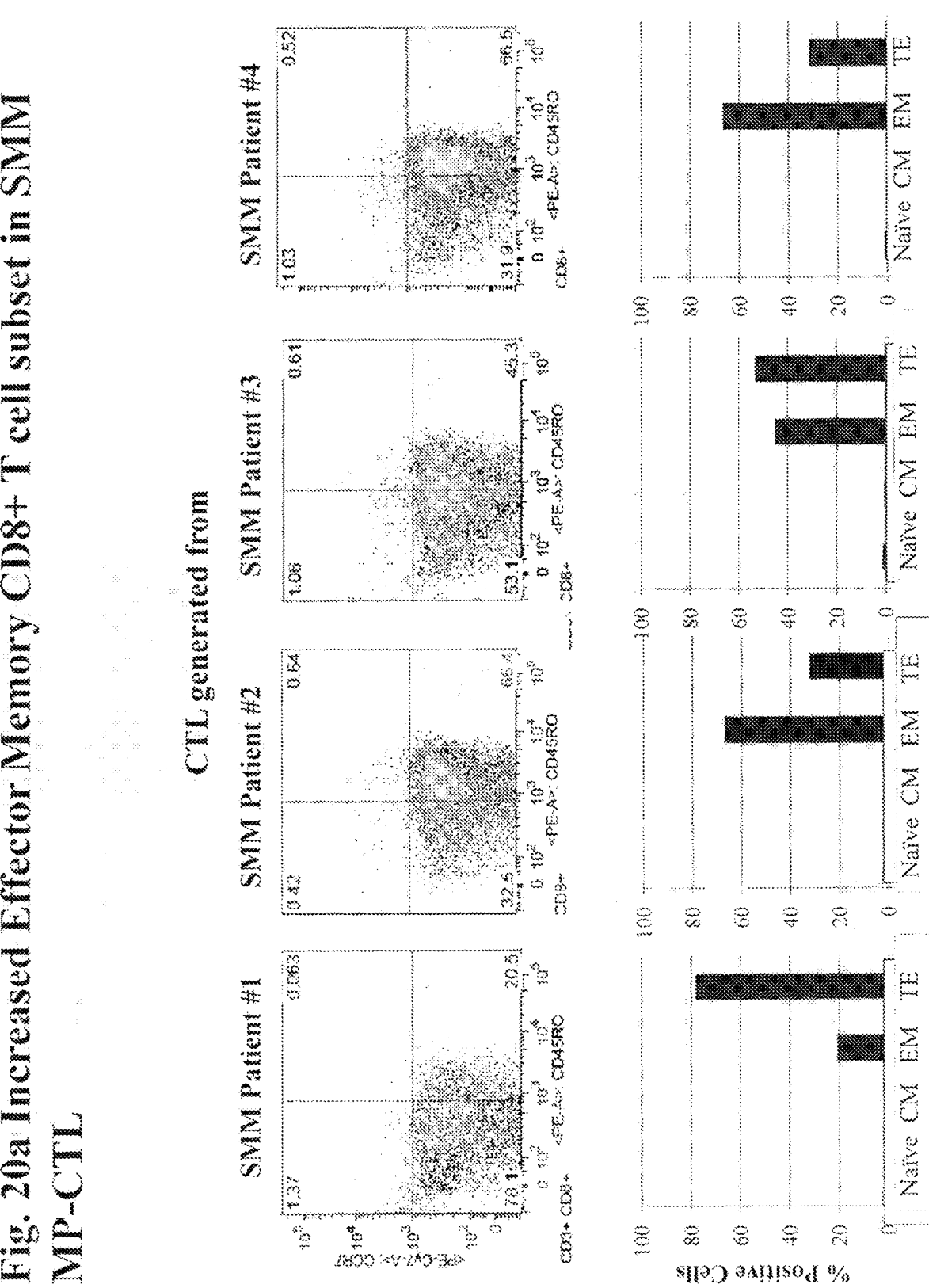
Fig. 20a Increased Effector Memory CD8+ T cell subset in SMM MP-CTL

Fig. 20b Expansion of Effector Memory CD8+ T cells with more number of peptides stimulation in SMM MP-CTL
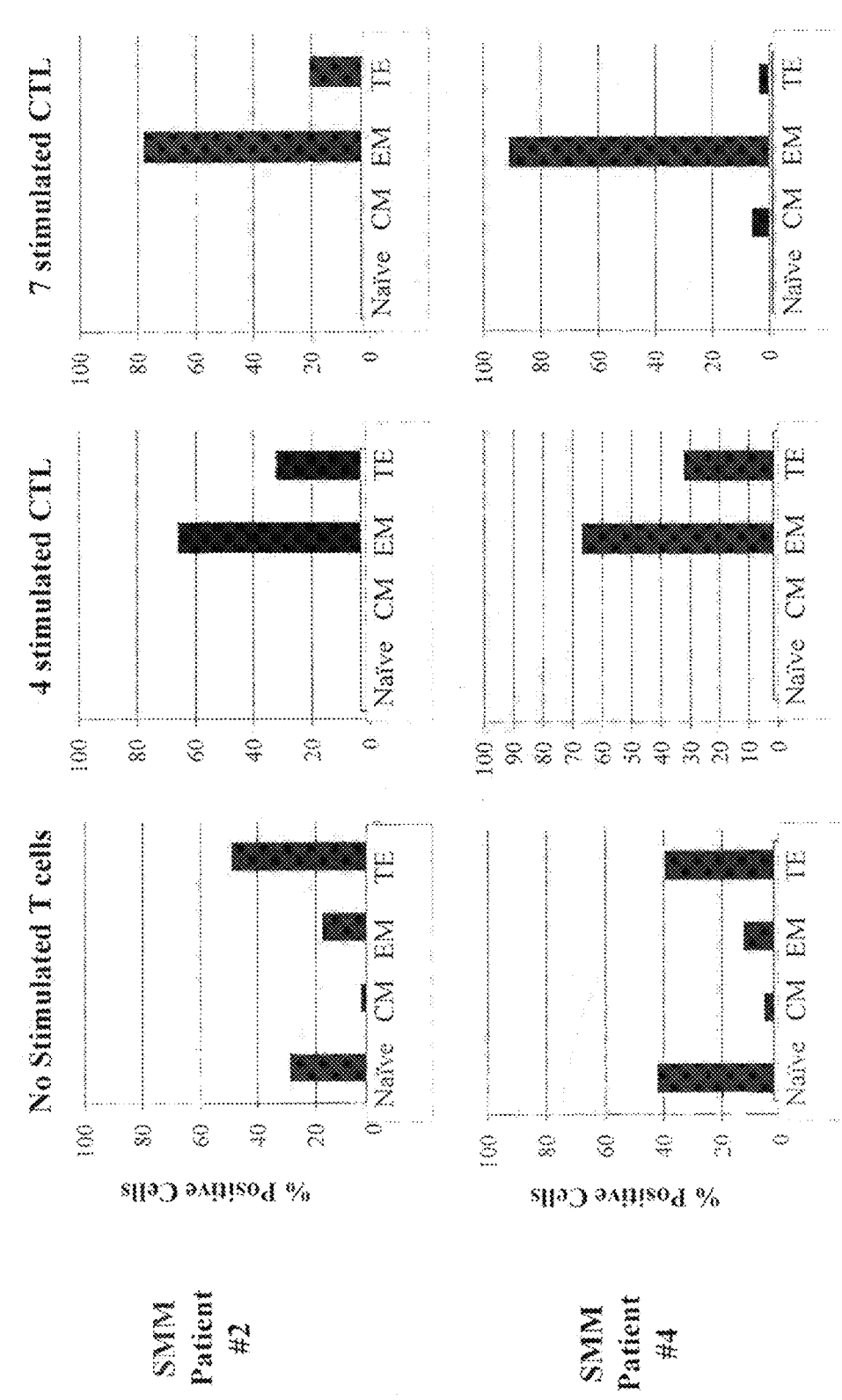

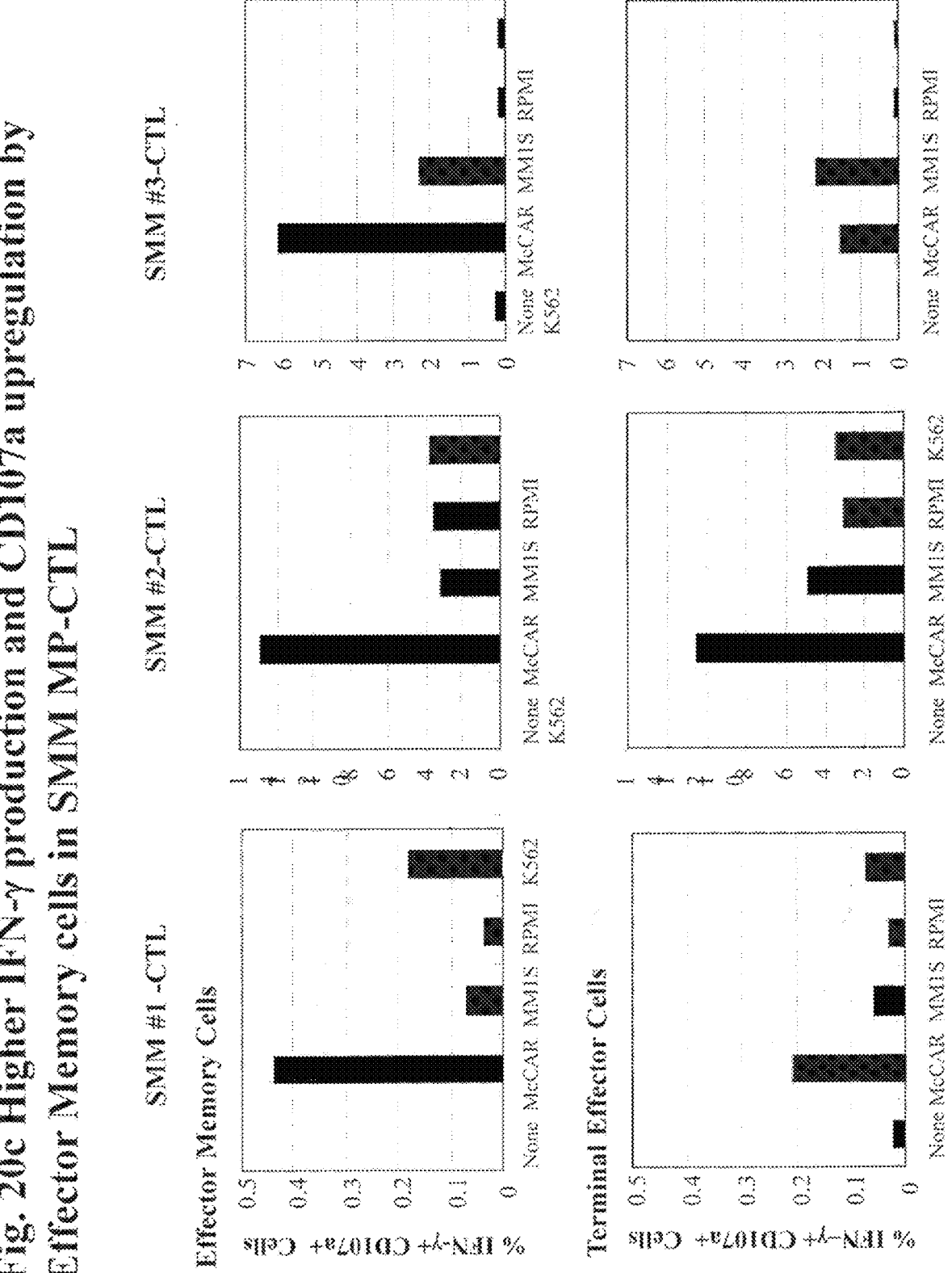
Fig. 20c Higher IFN-γ production and CD107a upregulation by Effector Memory cells in SMM MP-CTL

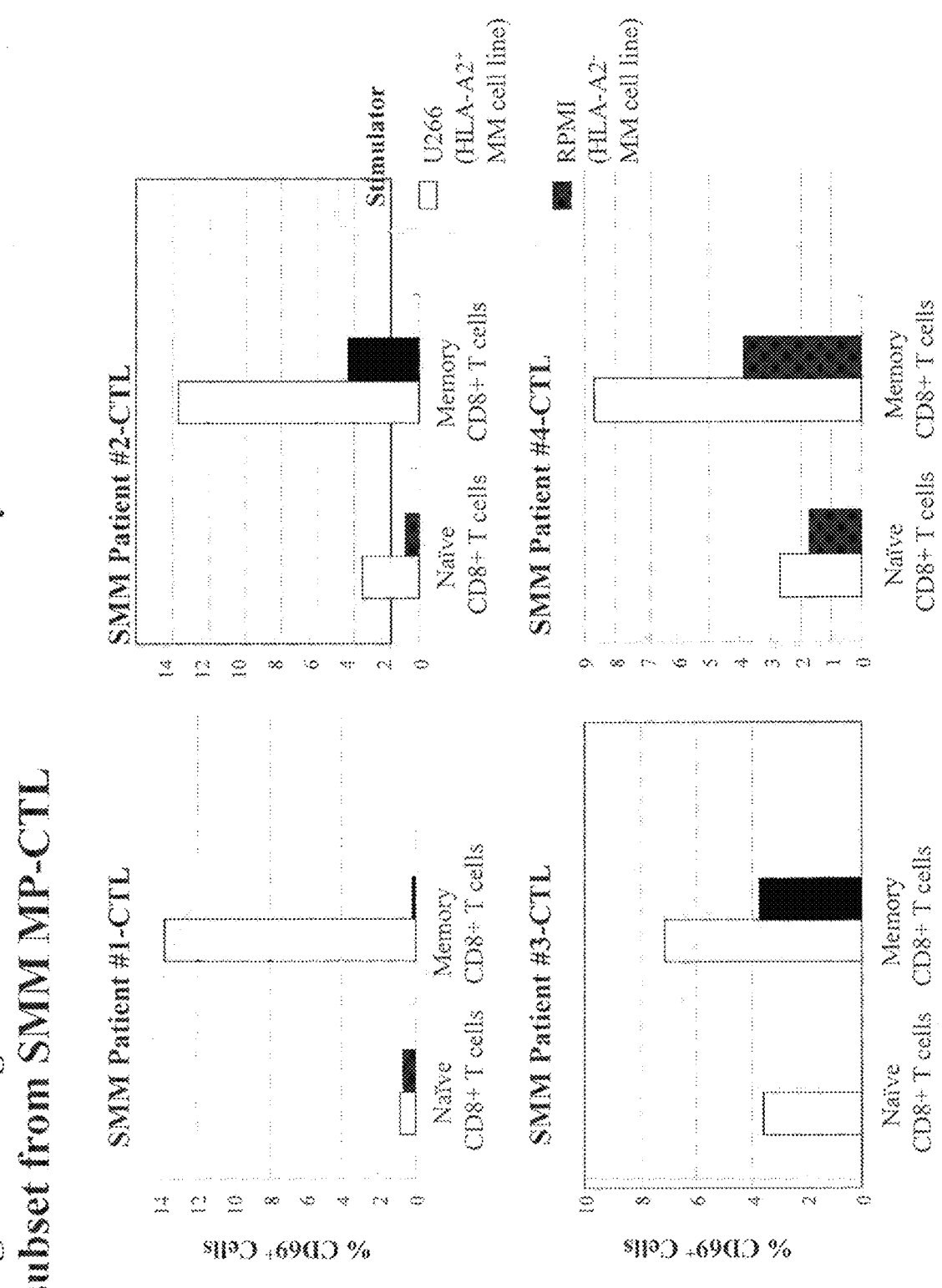
Fig. 20d Higher cell activation in memory than naïve CD8+ T cells subset from SMM MP-CTL Fig. 21 HLA-A24 Peptide Affinity
High Dose (1 mg/ml)
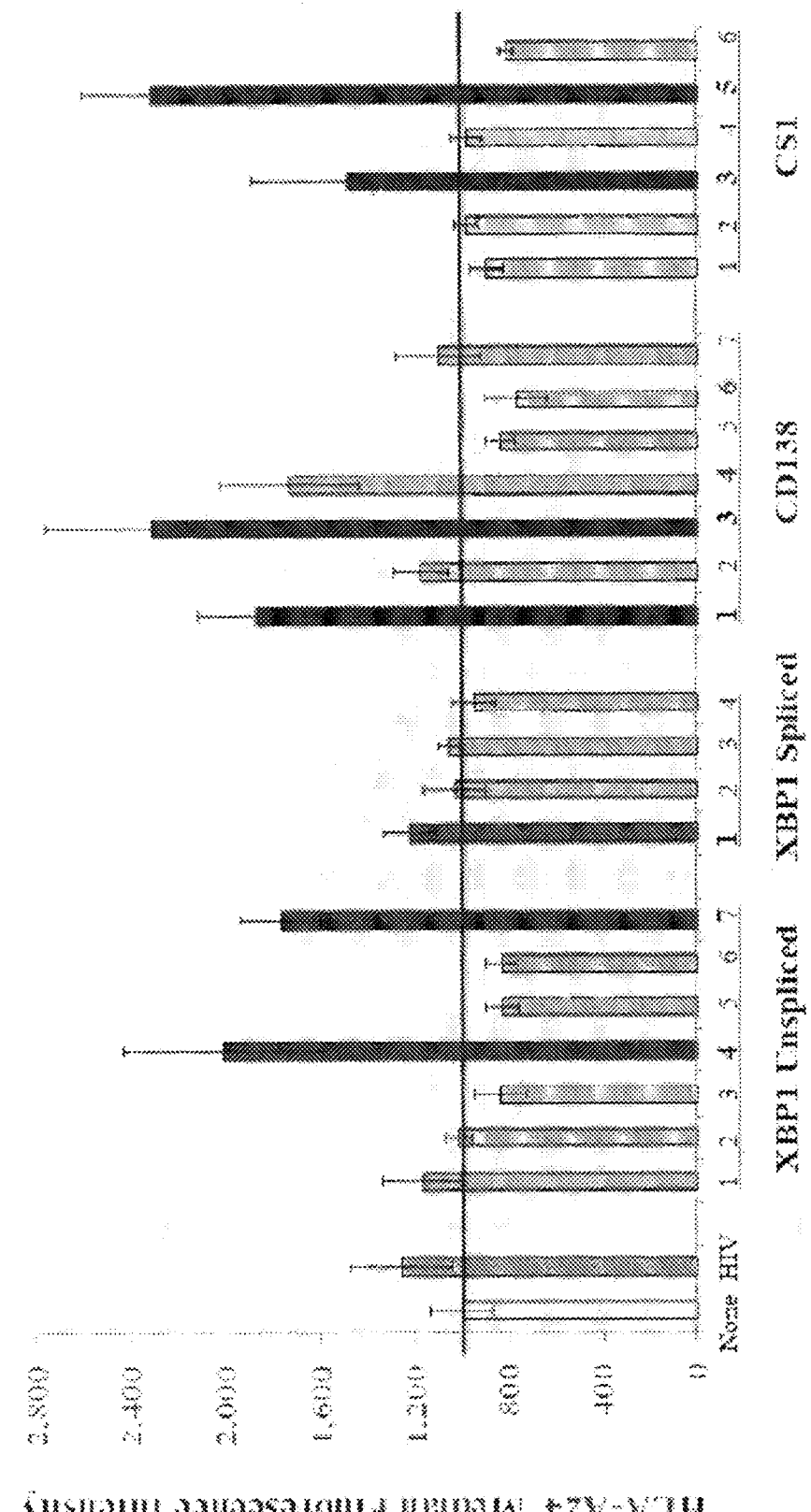

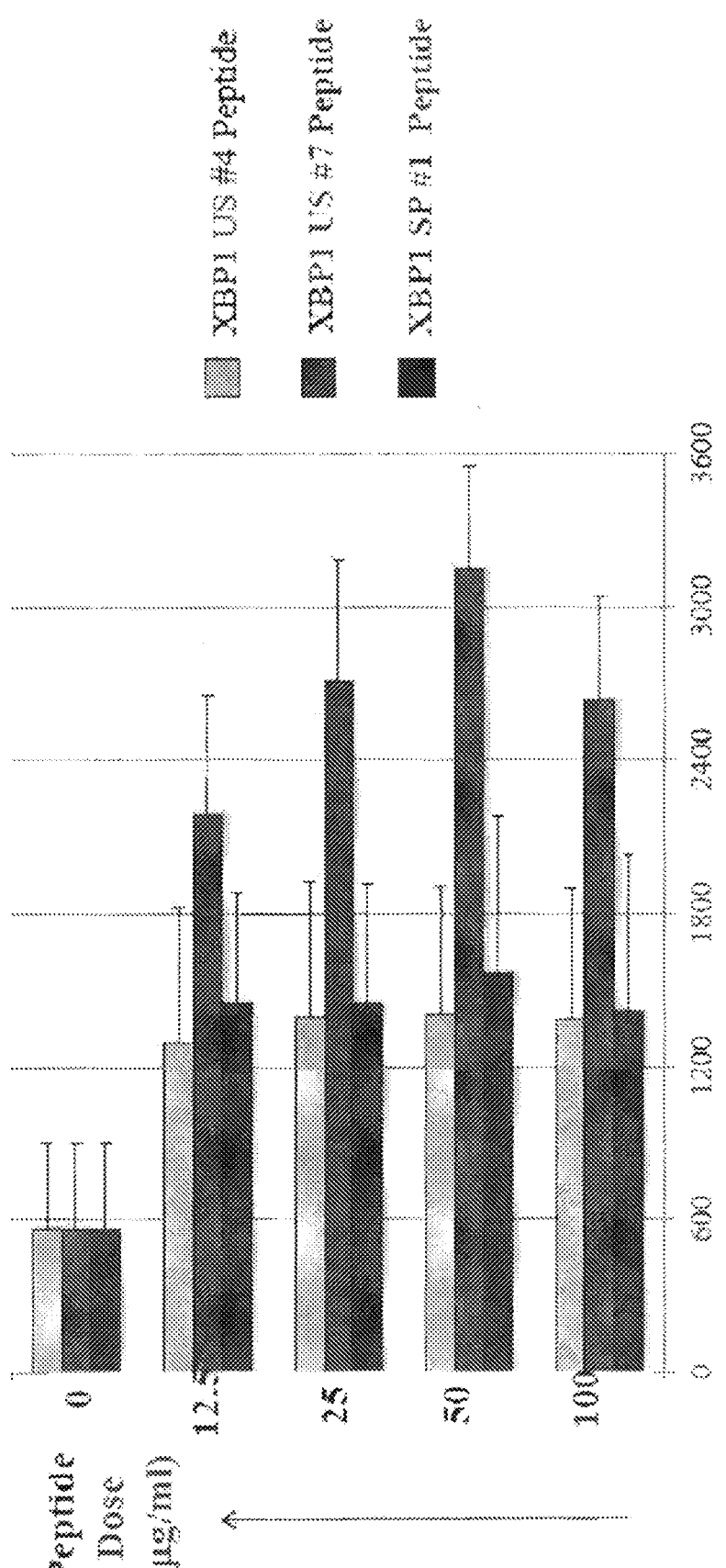
Fig. 22 XBP1 HLA-A24 Peptide Affinity Low Dose (12.5-100 µg/ml)

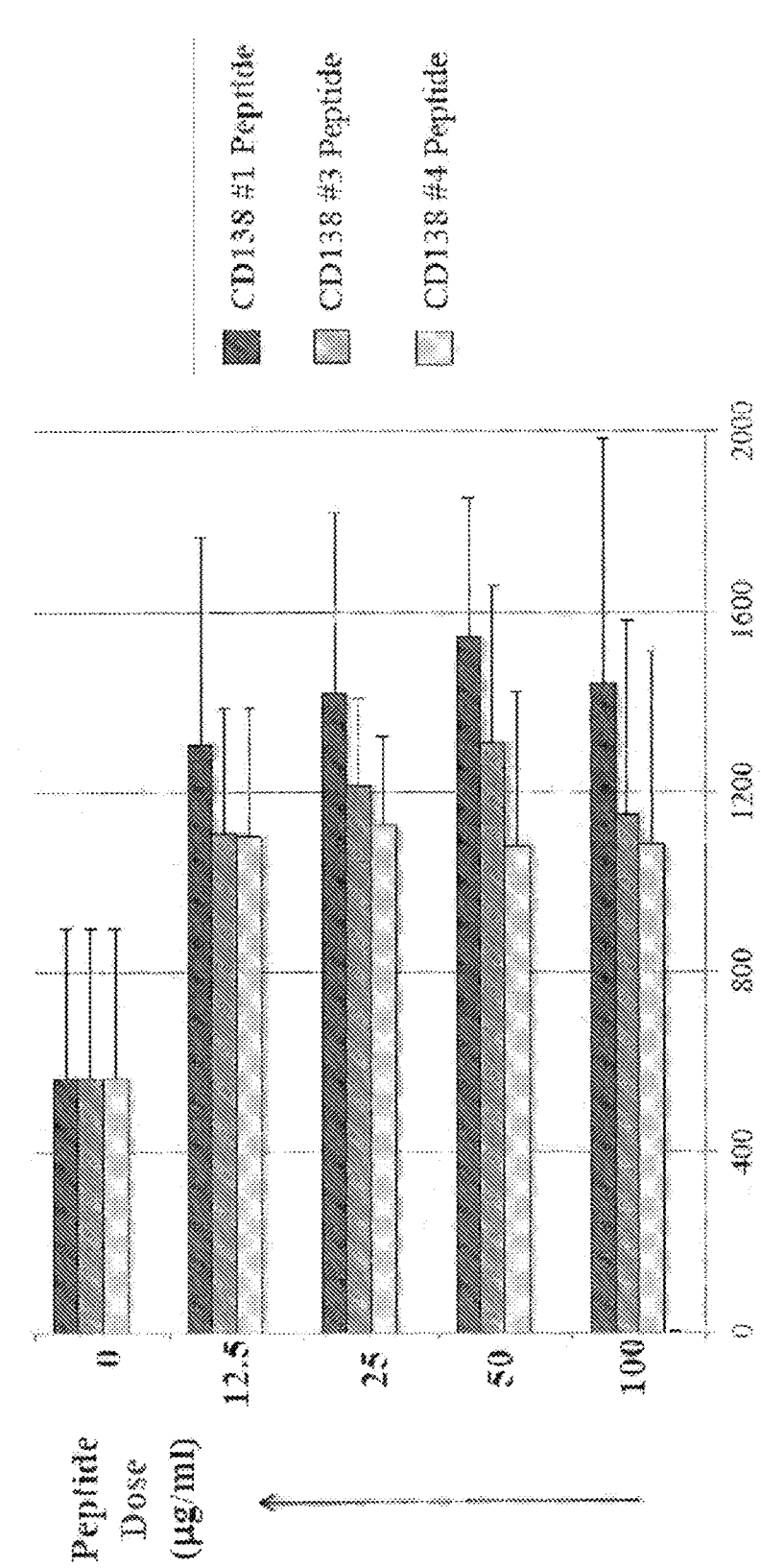
Fig. 23 CD138 HLA-A24 Peptide Affinity Low Dose (12.5-100 µg/ml)

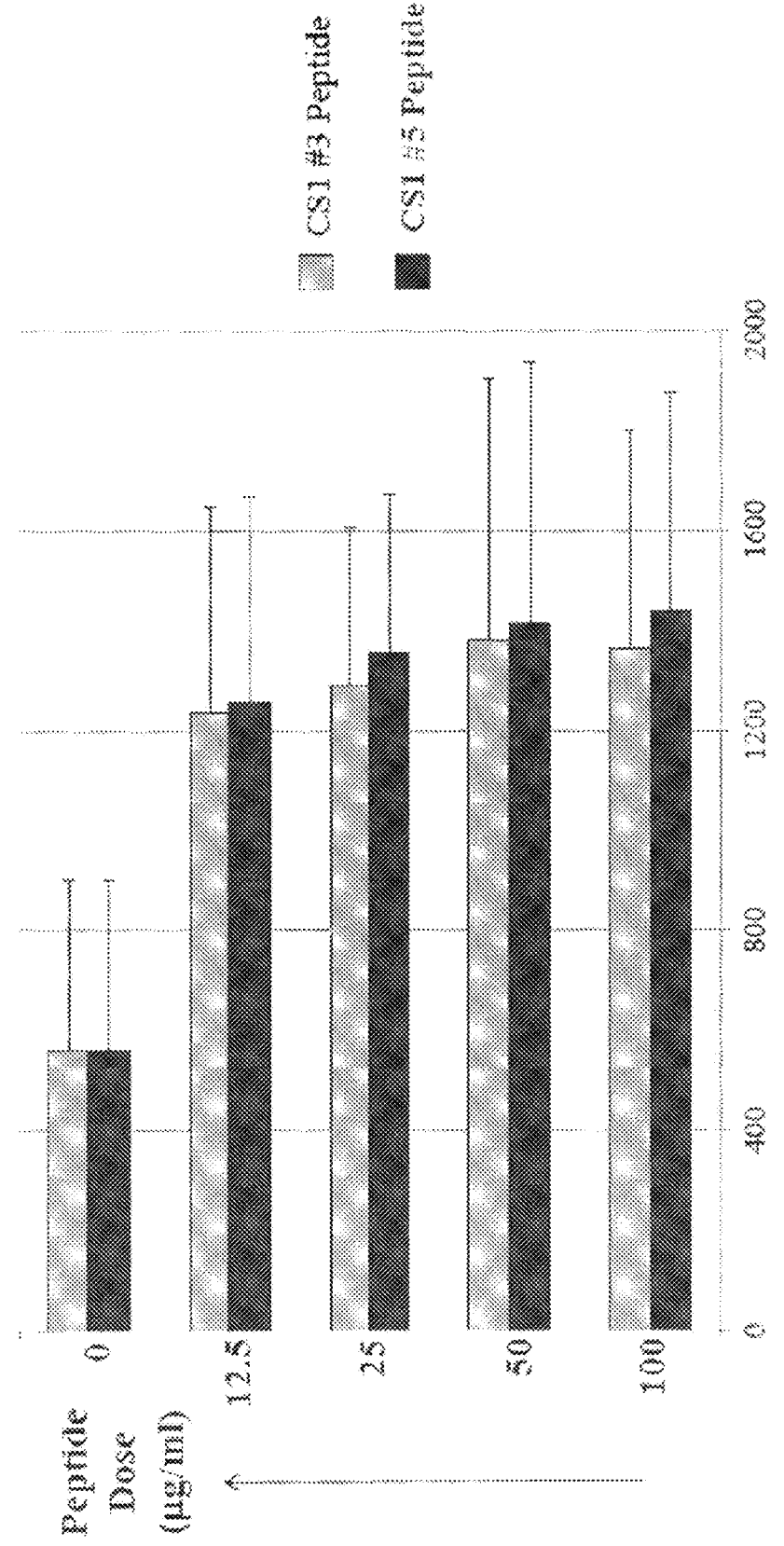
Fig. 24 CS1 HLA-A24 Peptide Affinity Low Dose (12.5-100 μg/ml)

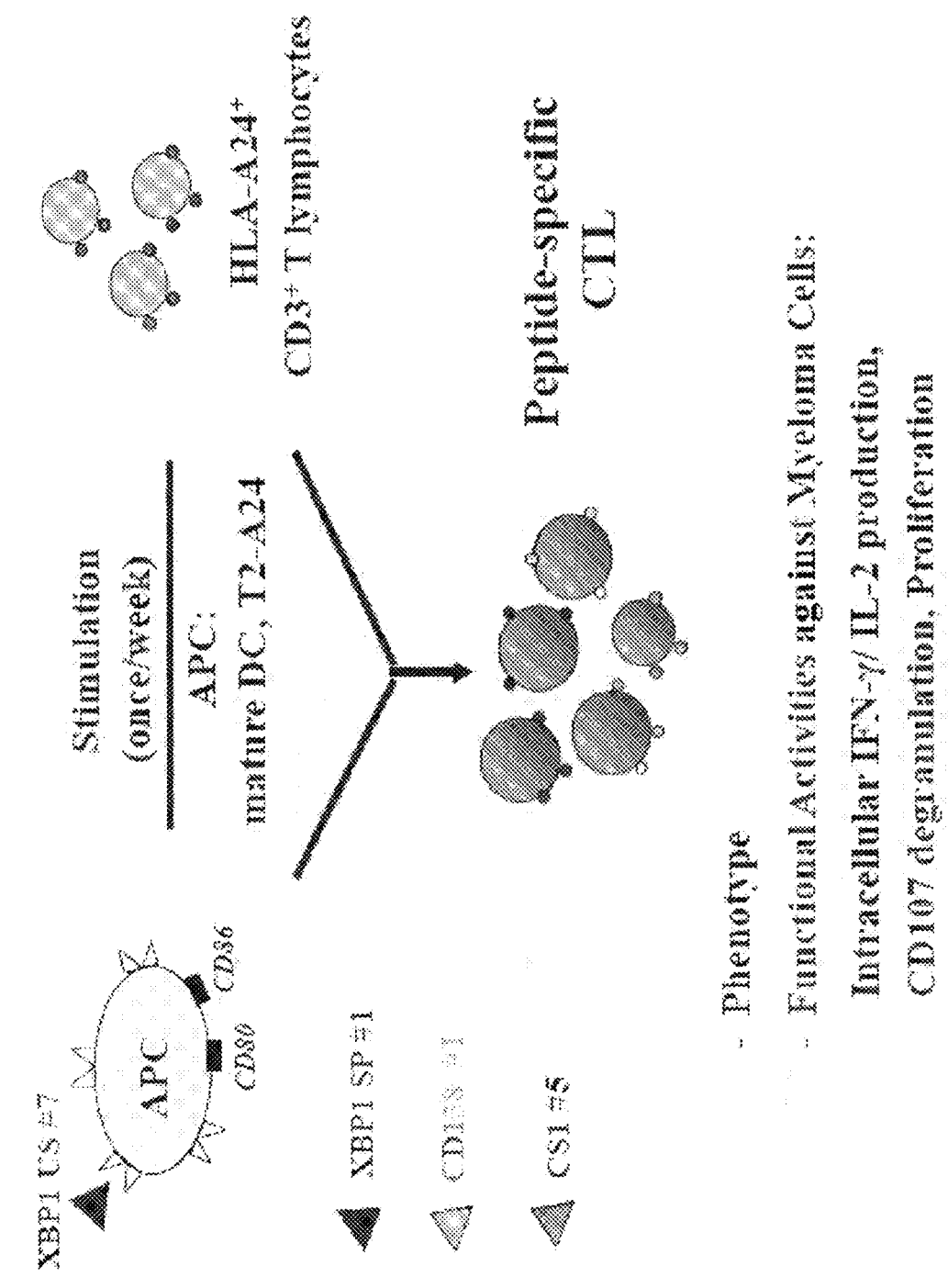
Fig. 25 Generation of A24 Peptide-specific CTL

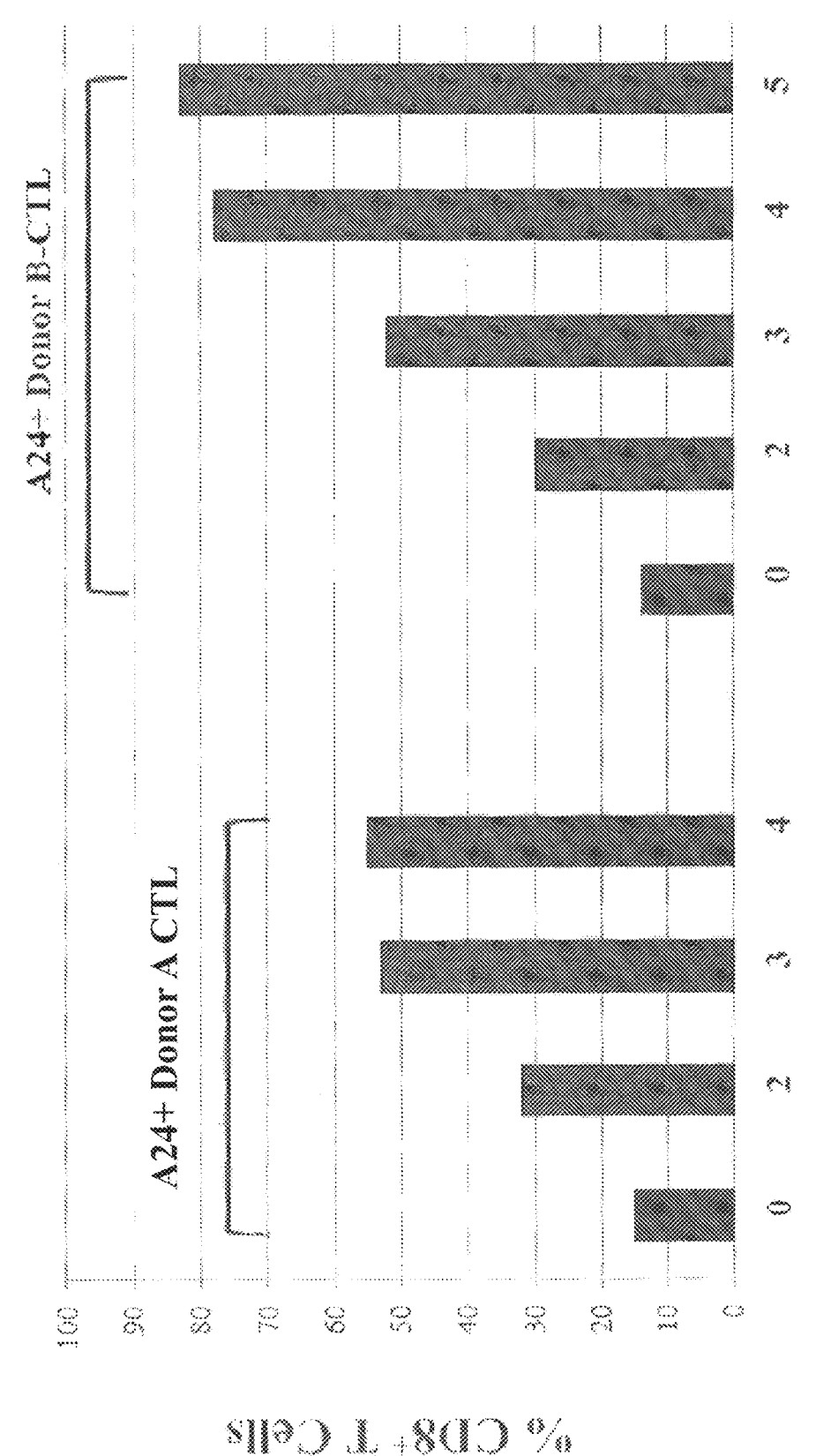
Fig. 26a Generation and Expansion of CD8+ Tc cells w. XBP1 US #7 HLA-A24 Peptide Stimulation Fig. 26b Generation and Expansion of CD8+ Tc cells w. XBP1 SP #1 HLA-A24 Peptide Stimulation

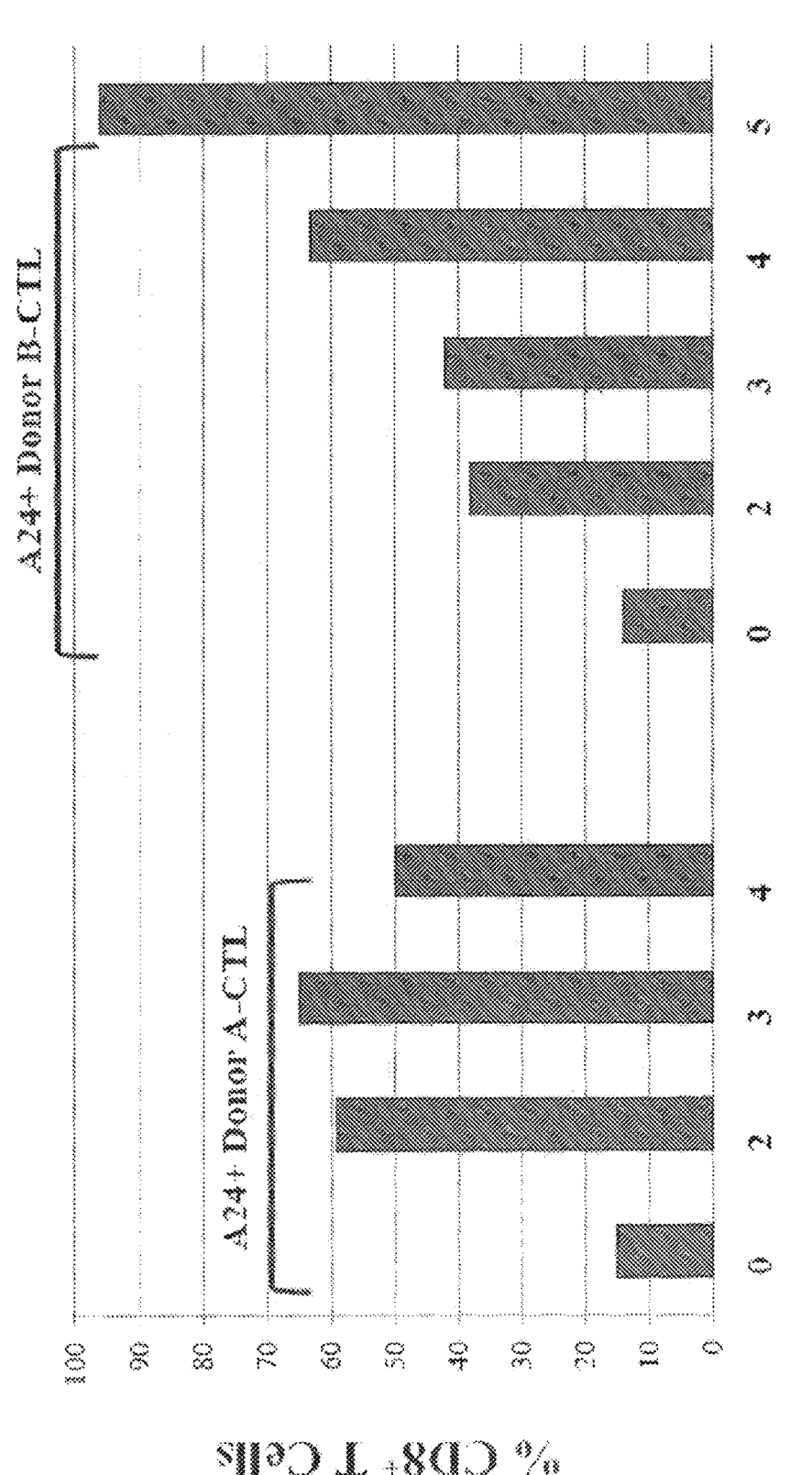
Fig. 26c Generation and Expansion of CD8+ Tc cells w. CD138 #1 HLA-A24 Peptide Stimulation

Fig. 26d Generation and Expansion of CD8+ Tc cells w. CS #1 HLA-A24 Peptide Stimulation

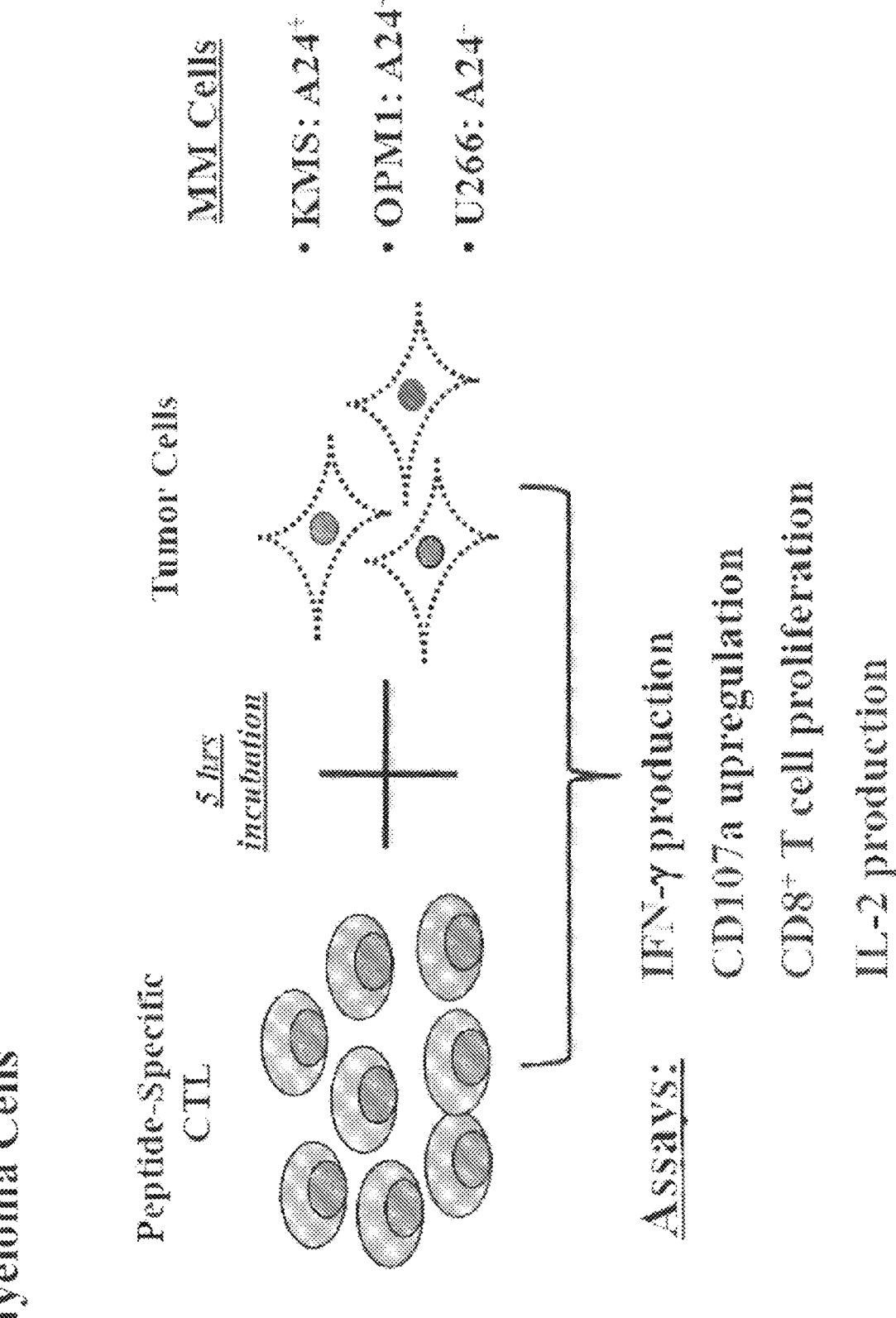
Fig. 27 Evaluation of CTL Functional Activities against Multiple Myeloma Cells

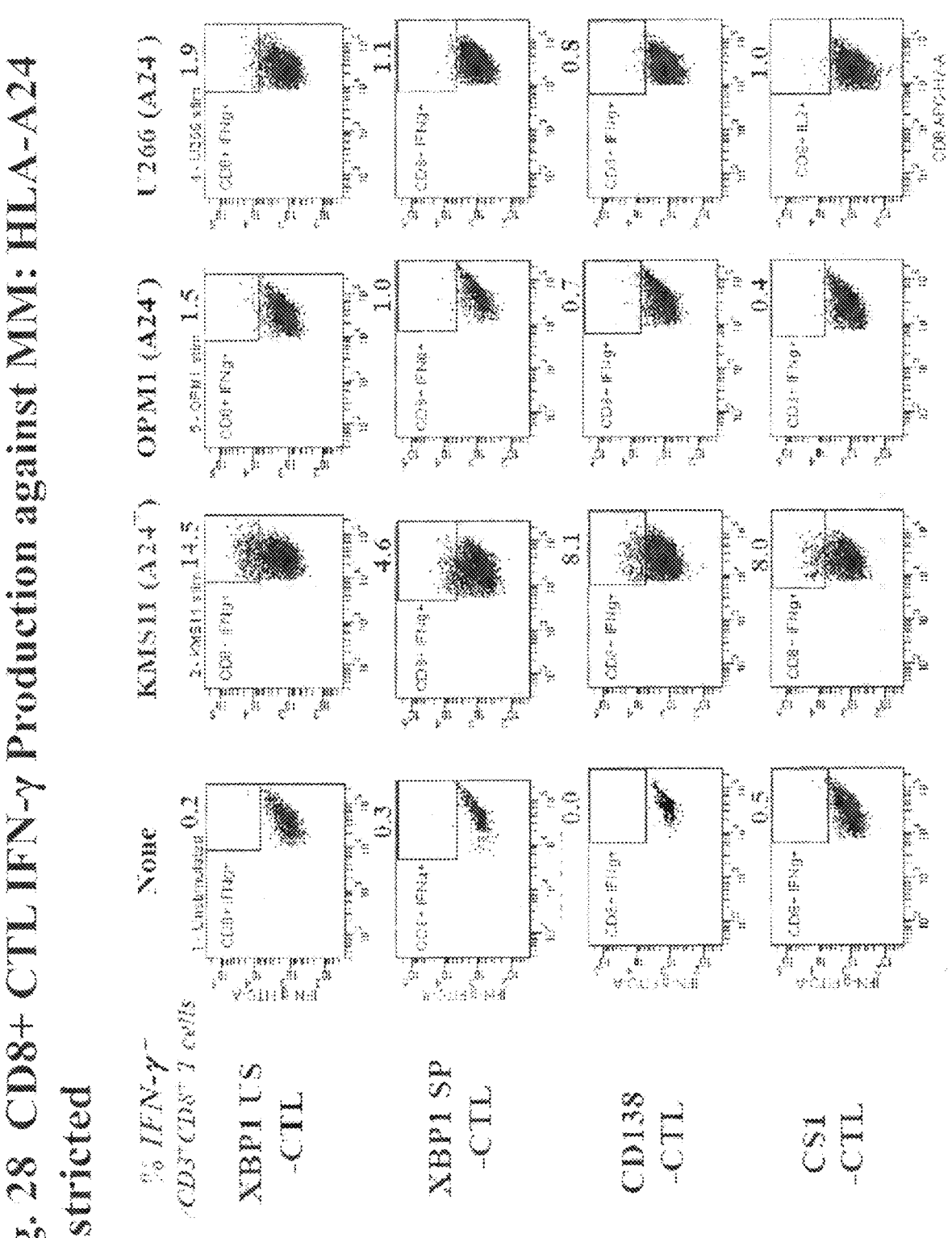
Fig. 28 CD8+ CTL IFN-γ Production against MM: HLA-A24 Restricted

Fig. 29a Myeloma Induced IFN-γ Production by CD8+ T cells: XBP1 Unspliced-CTL
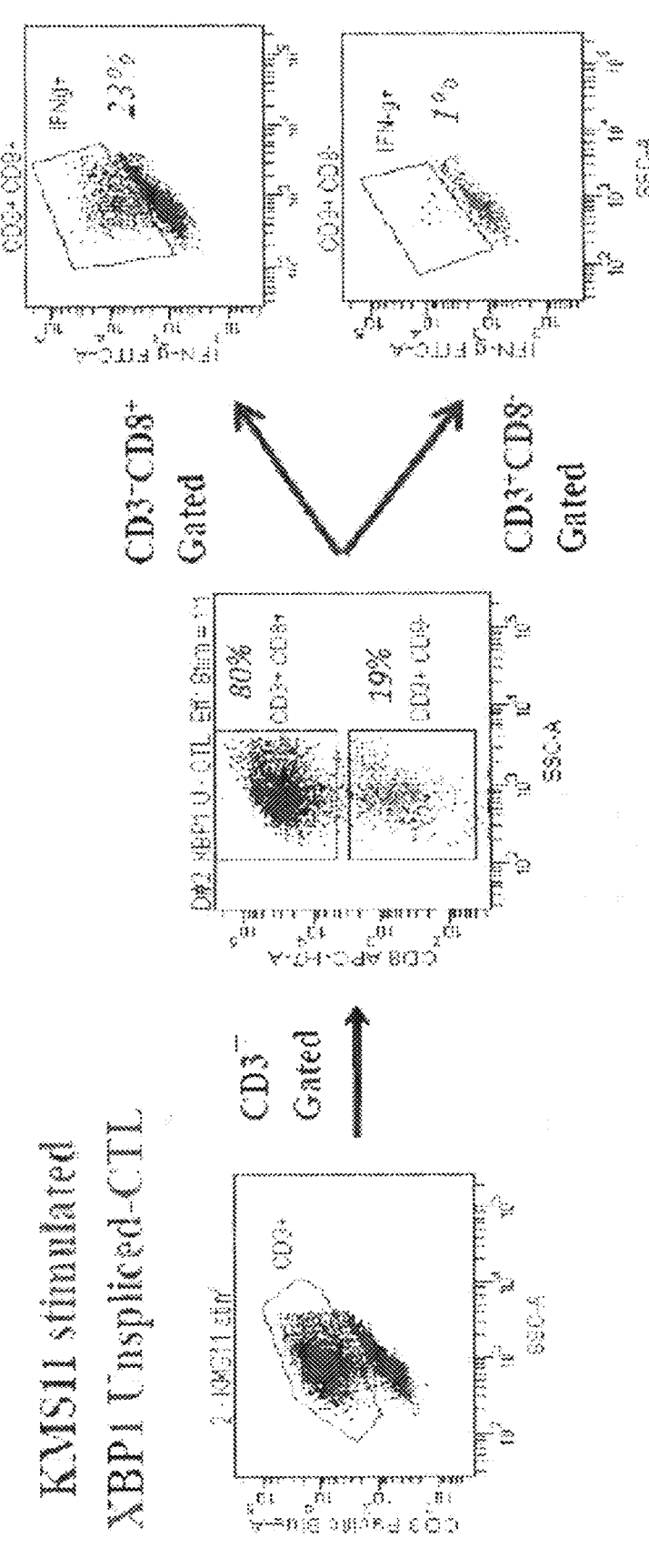

Fig. 29b Myeloma Induced IFN-γ Production by CD8+ T cells: XBP1 Spliced-CTL
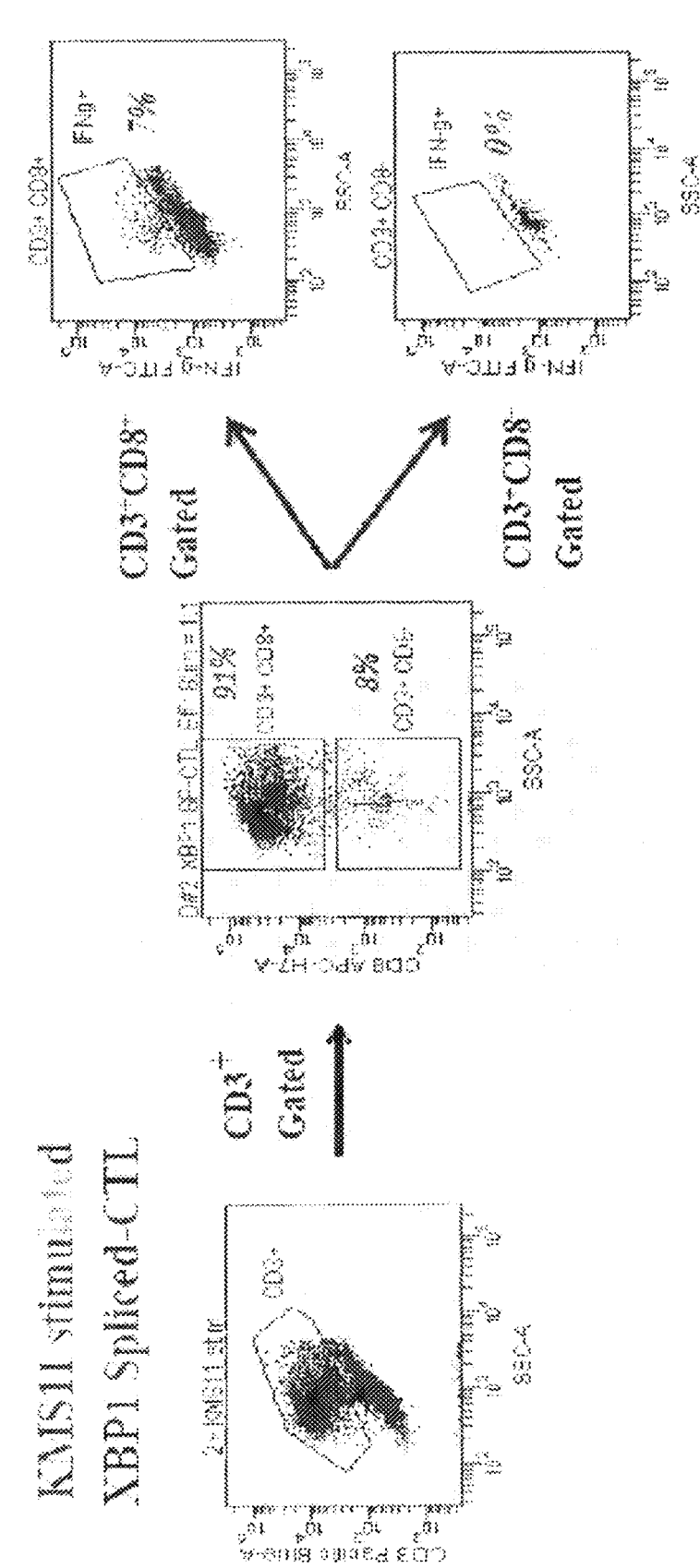

Fig. 29c Myeloma Induced IFN-γ Production by CD8+ T cells: CD138-CTL
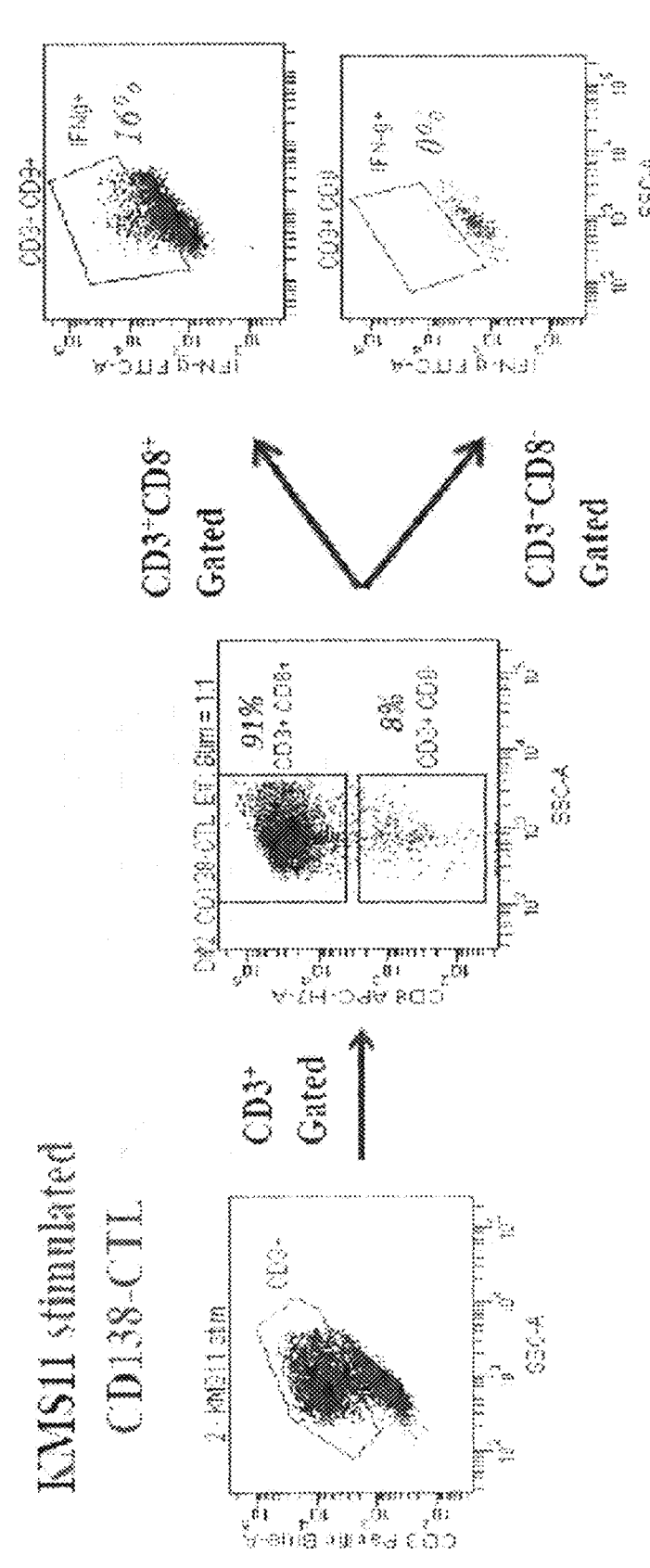

Fig. 29d Myeloma Induced IFN-γ Production by CD8+ T cells: CS1-CTL
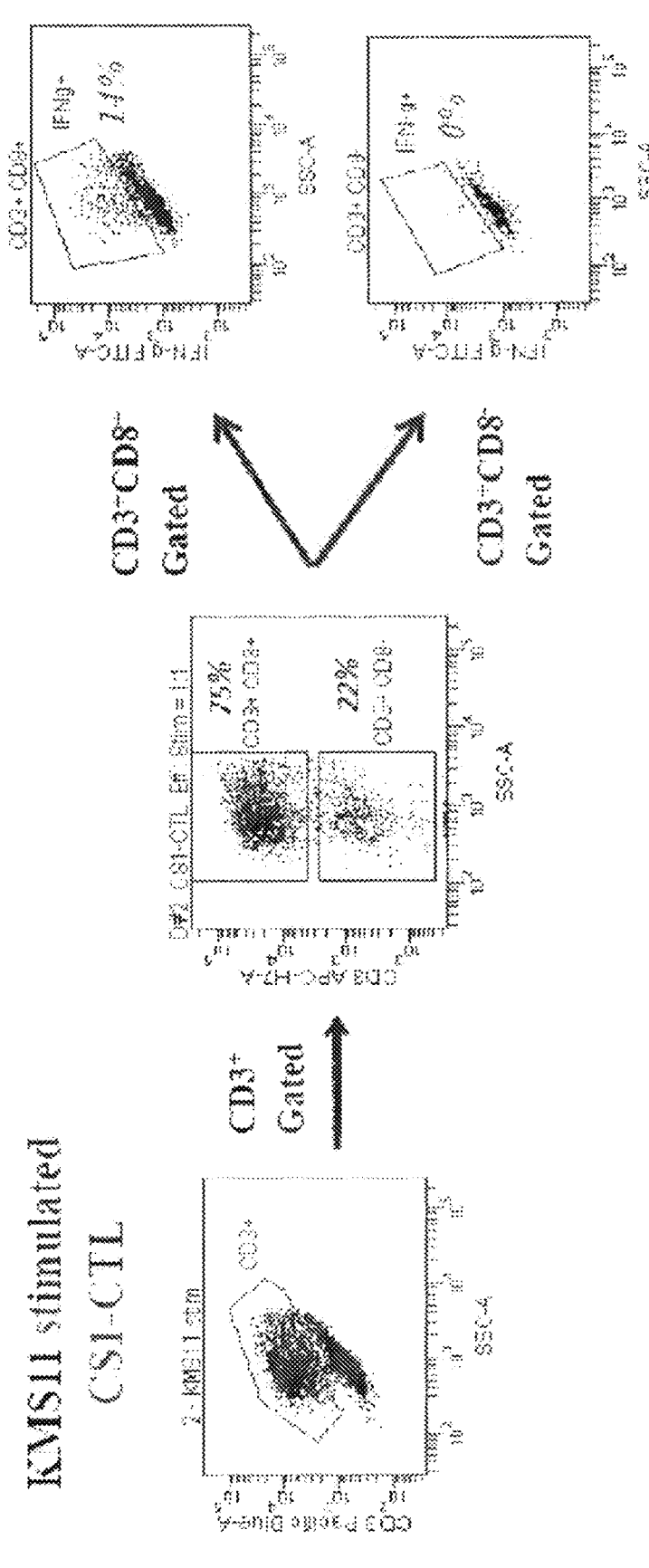

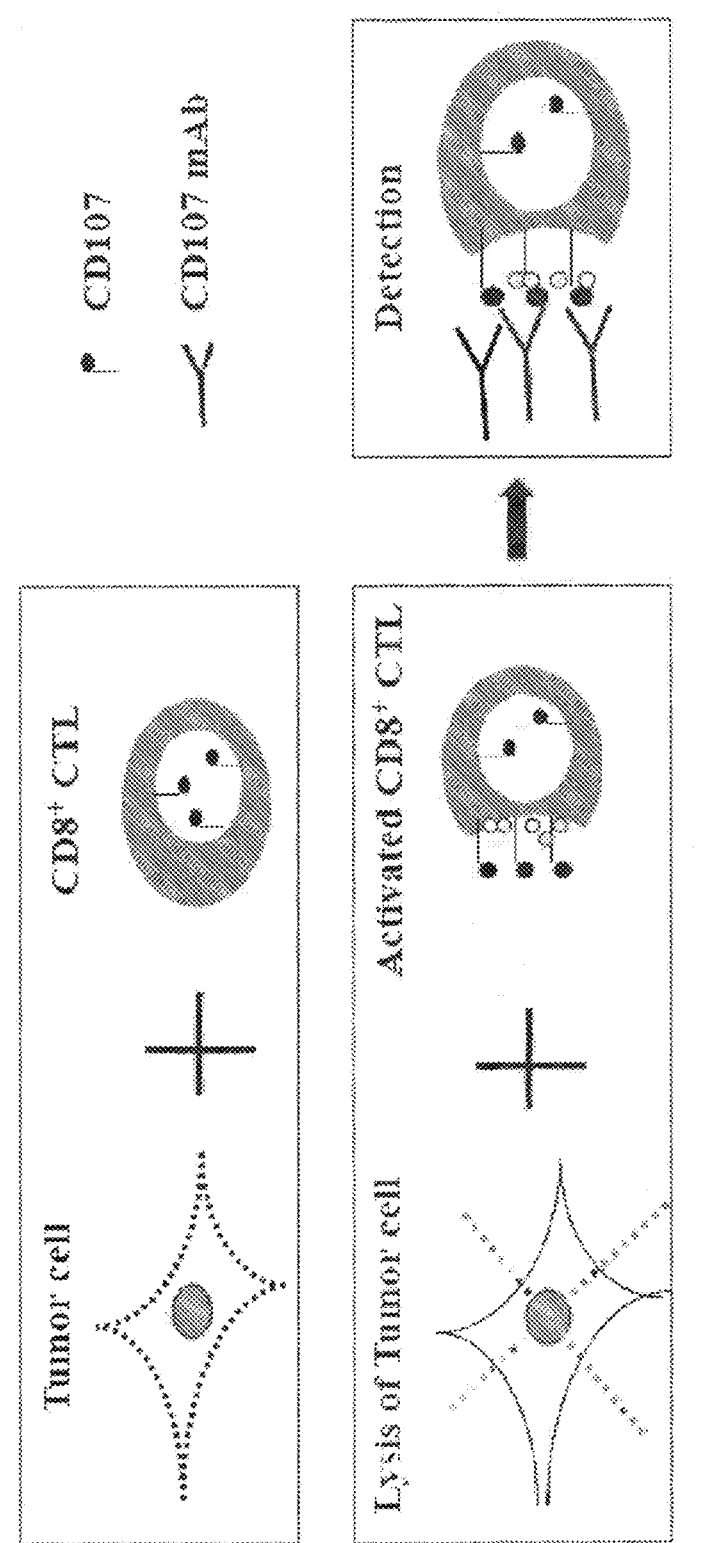
Fig. 30 CD107a Up-regulation / CD8+ CTL

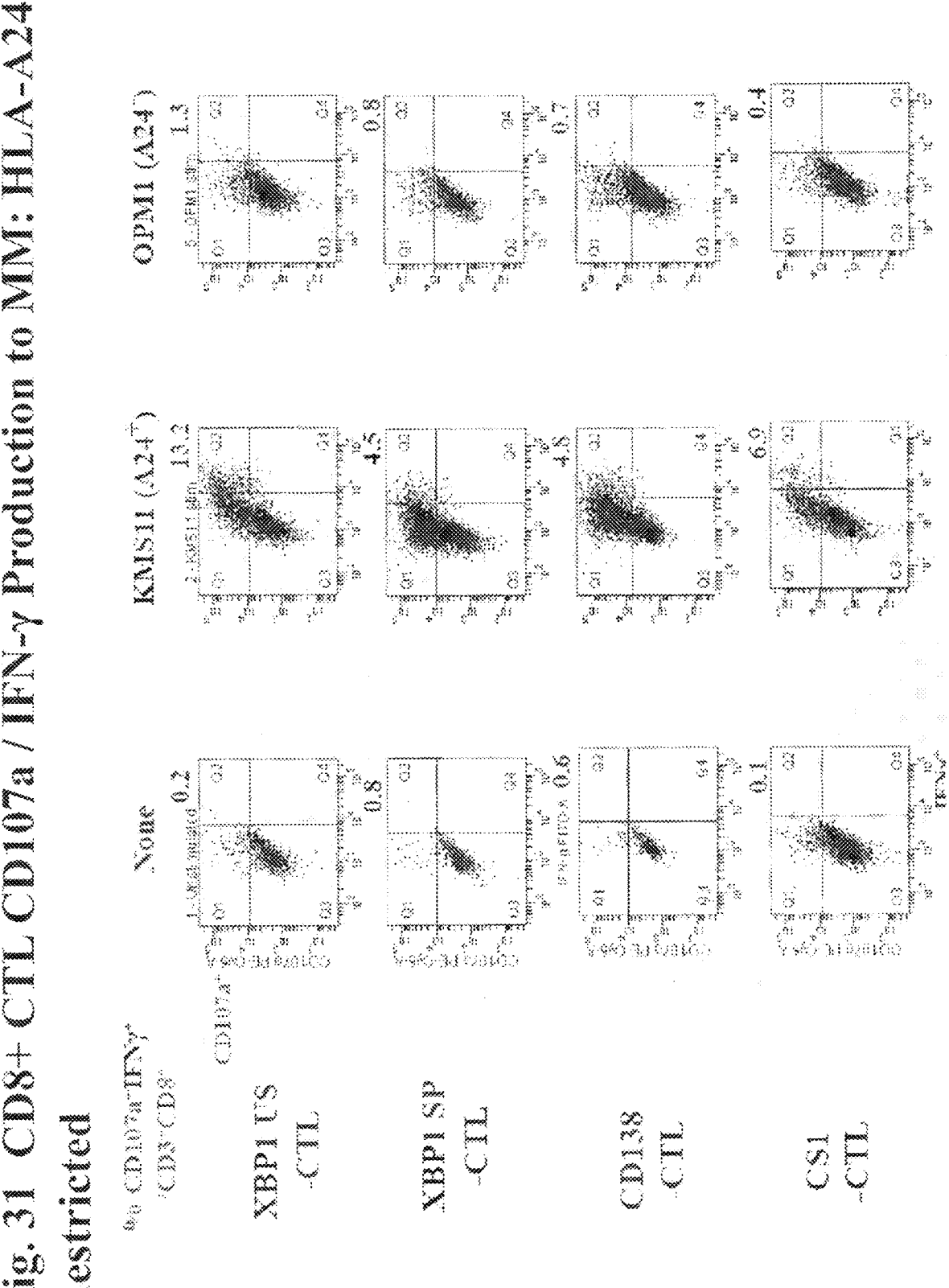
Fig. 31 CD8+ CTL CD107a / IFN-γ Production to MM: HLA-A24 Restricted

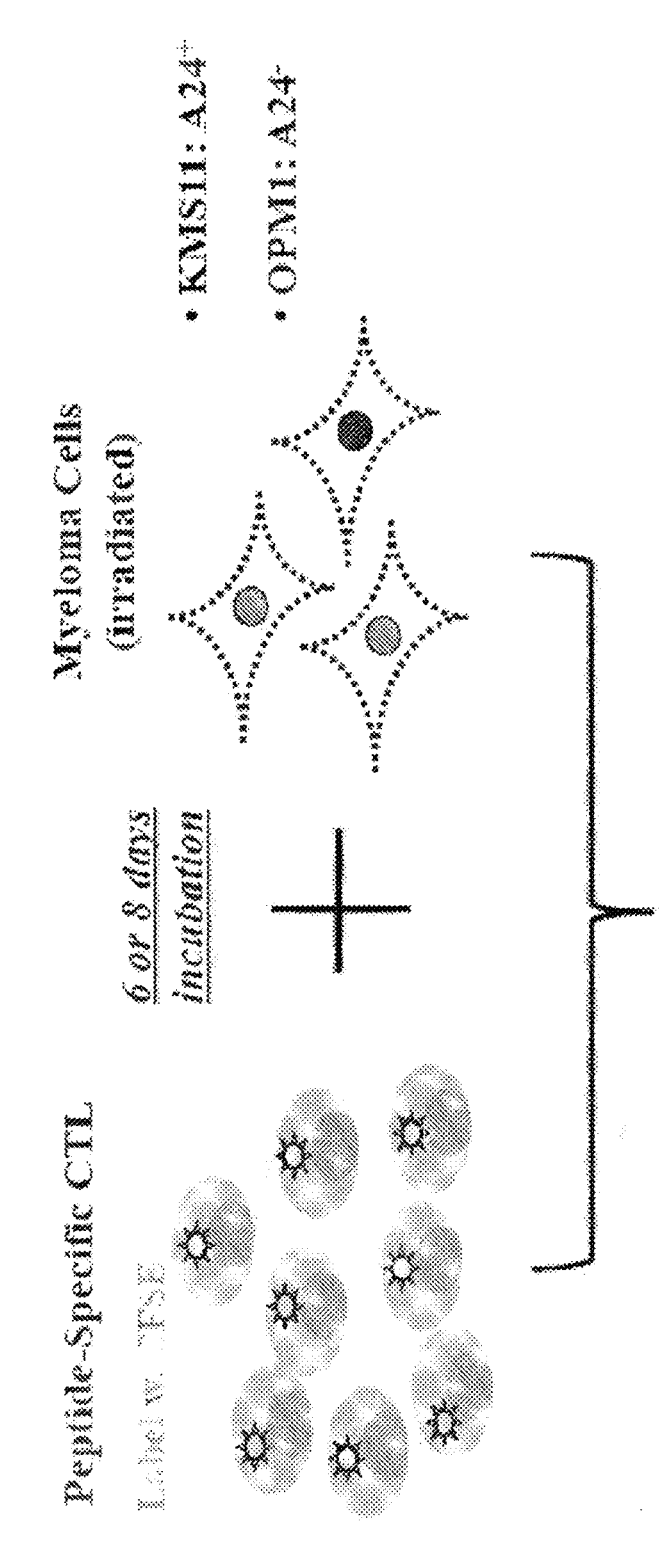
Fig. 32 Proliferation of CD8+ CTL in Response to Myeloma Cells

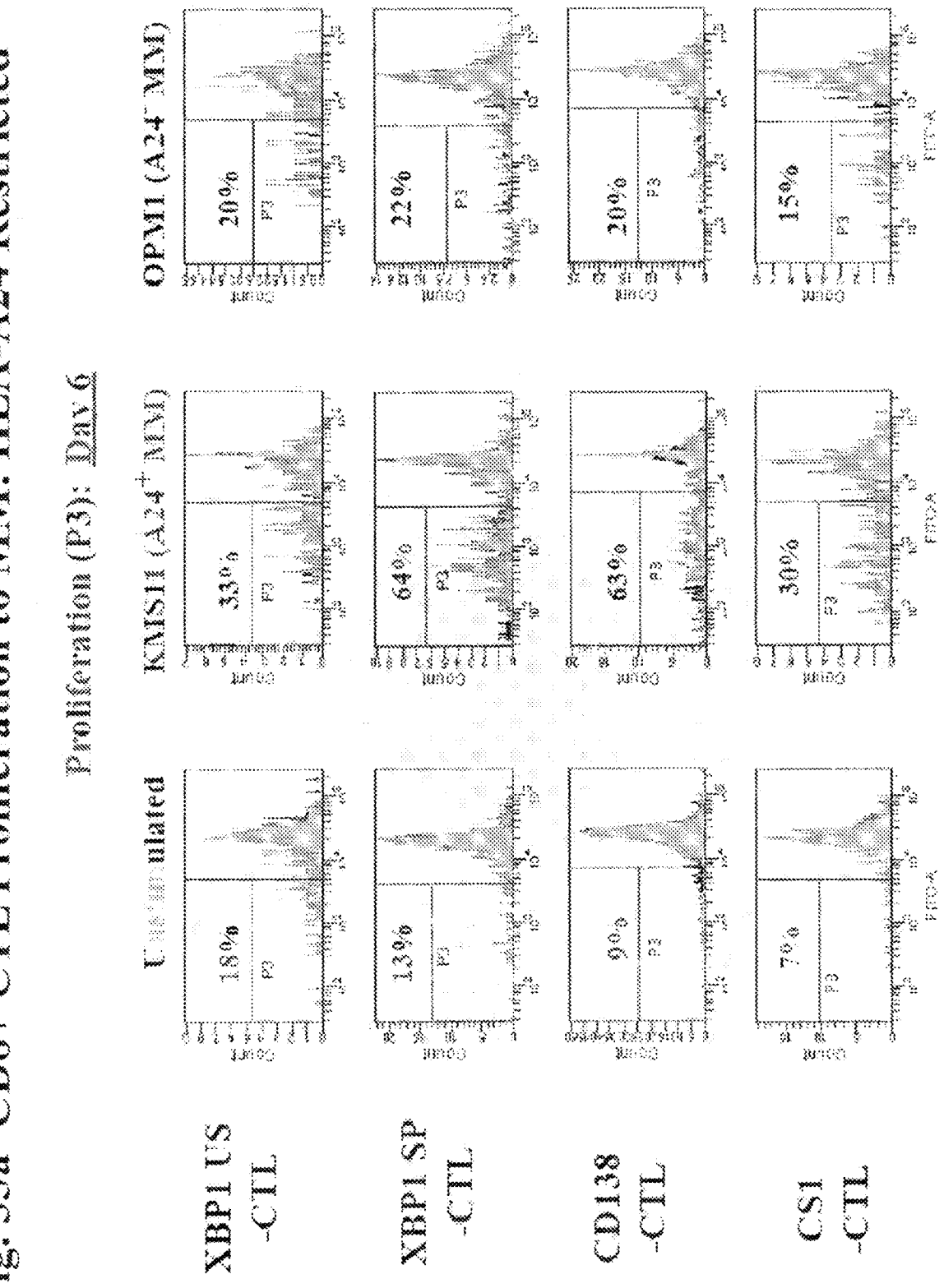
Fig. 33a CD8+ CTL Proliferation to MM: HLA-A24 Restricted

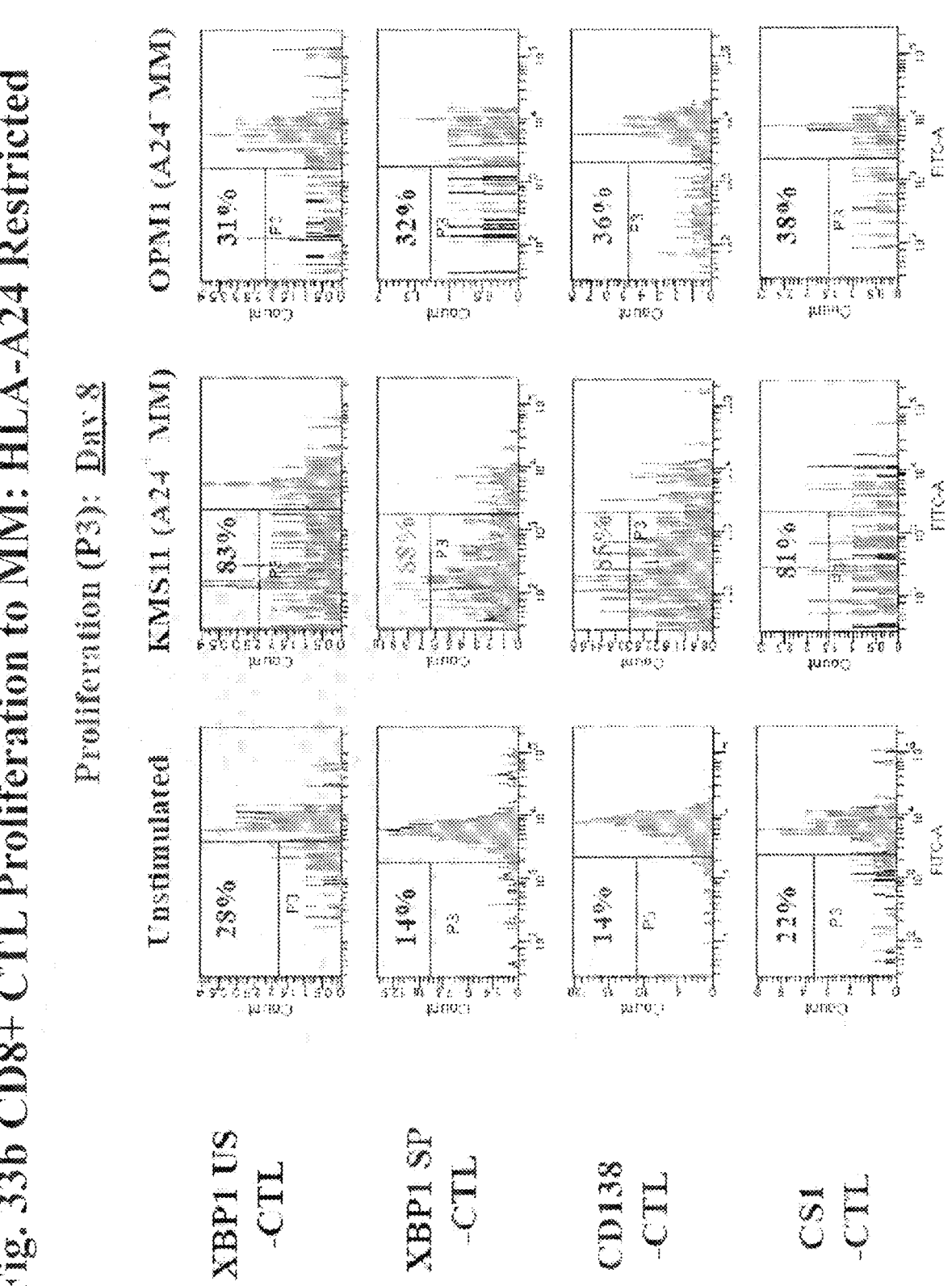
Fig. 33b CD8+ CTL Proliferation to MM: HLA-A24 Restricted

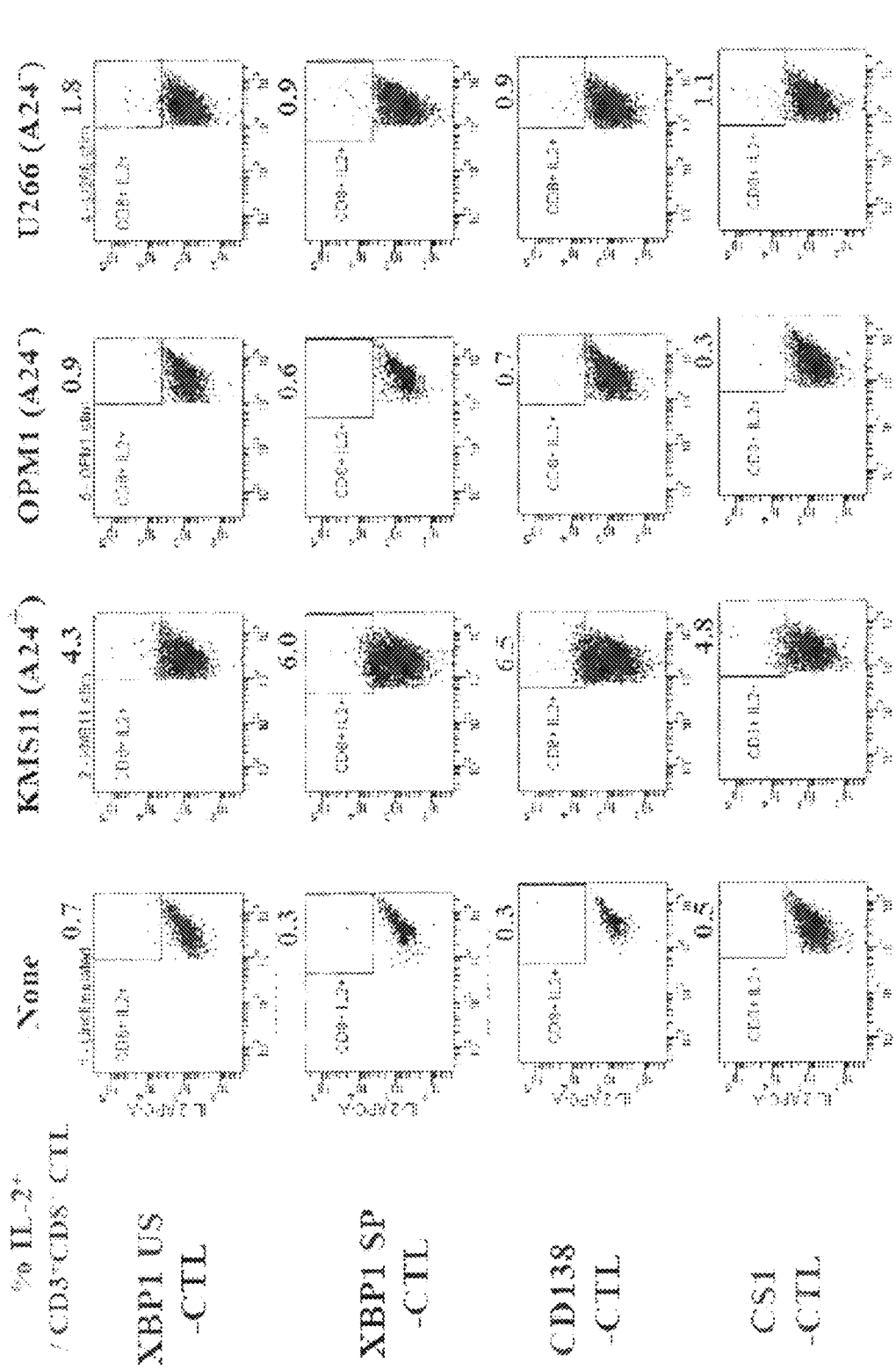
Fig. 34 CD8+ CTL IL-2 Production to MM: HLA-A24 Restricted

Fig. 35 Donor A CTL: IFN-γ production to HLA-A24+ Colon Cancer
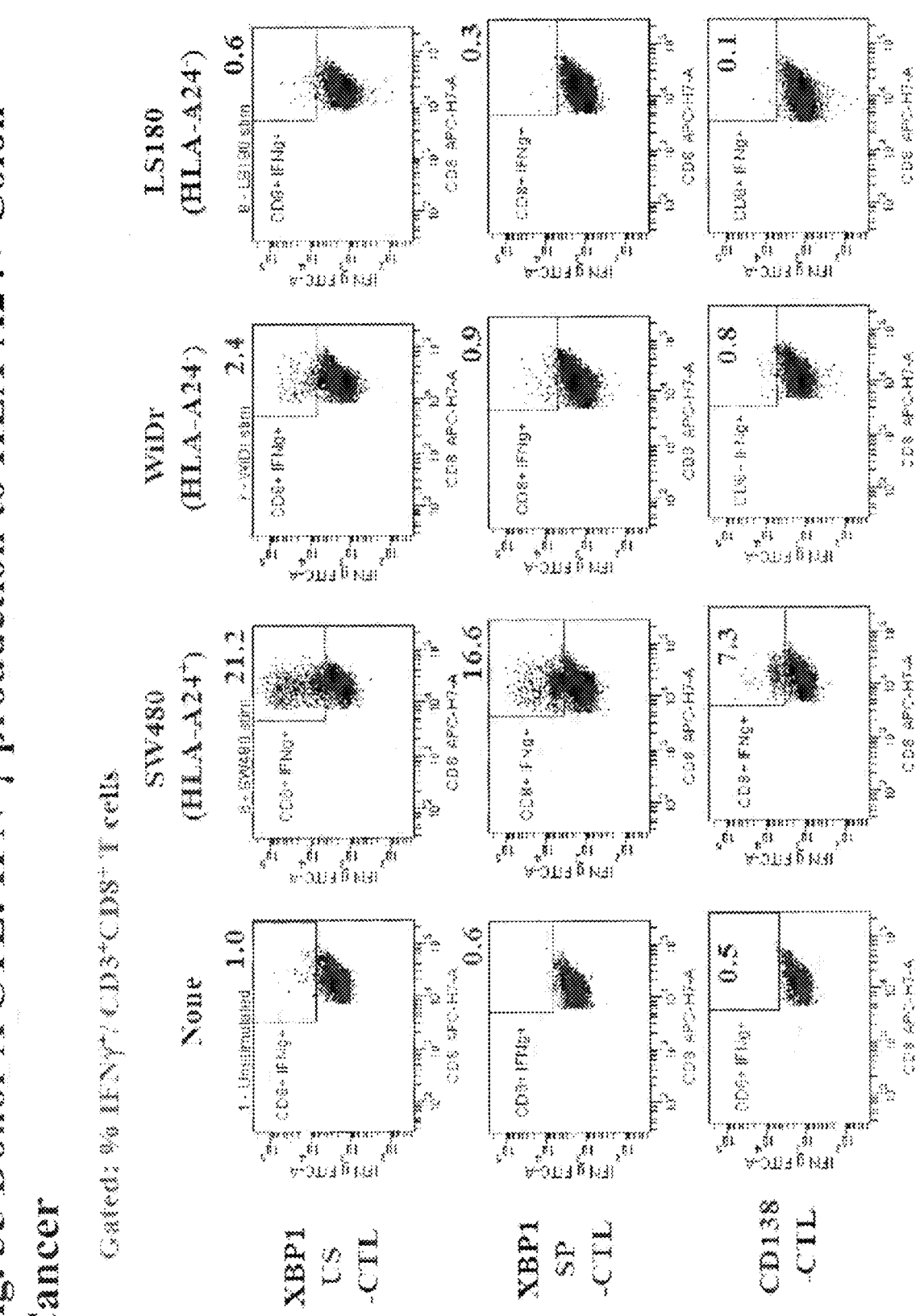

Fig. 36 Donor A CTL: CD107a++/IFN-γ production to A24+ Colon Cancer
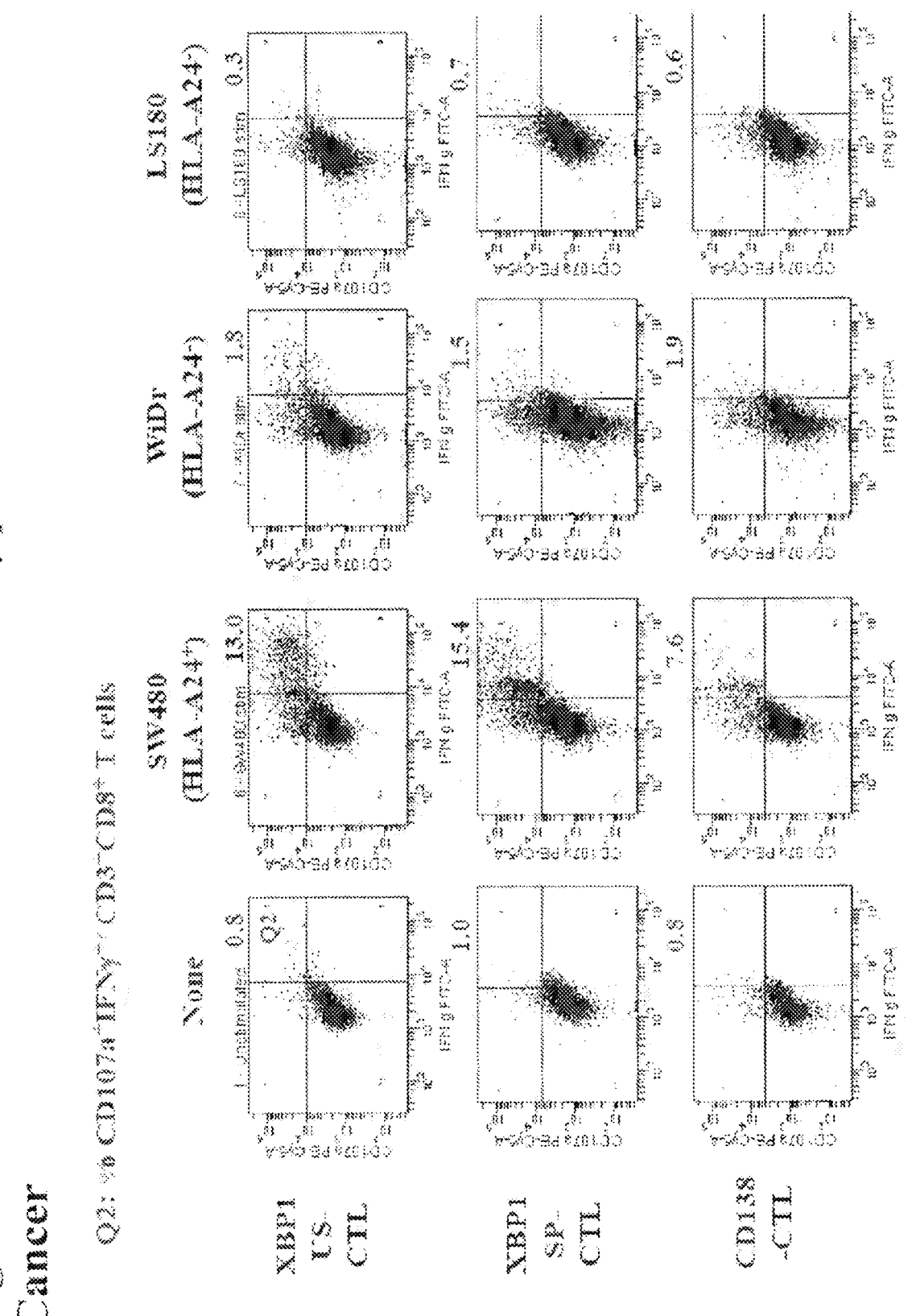

Fig. 37 Donor B CTL: IFN-γ production to HLA-A24+ Colon Cancer
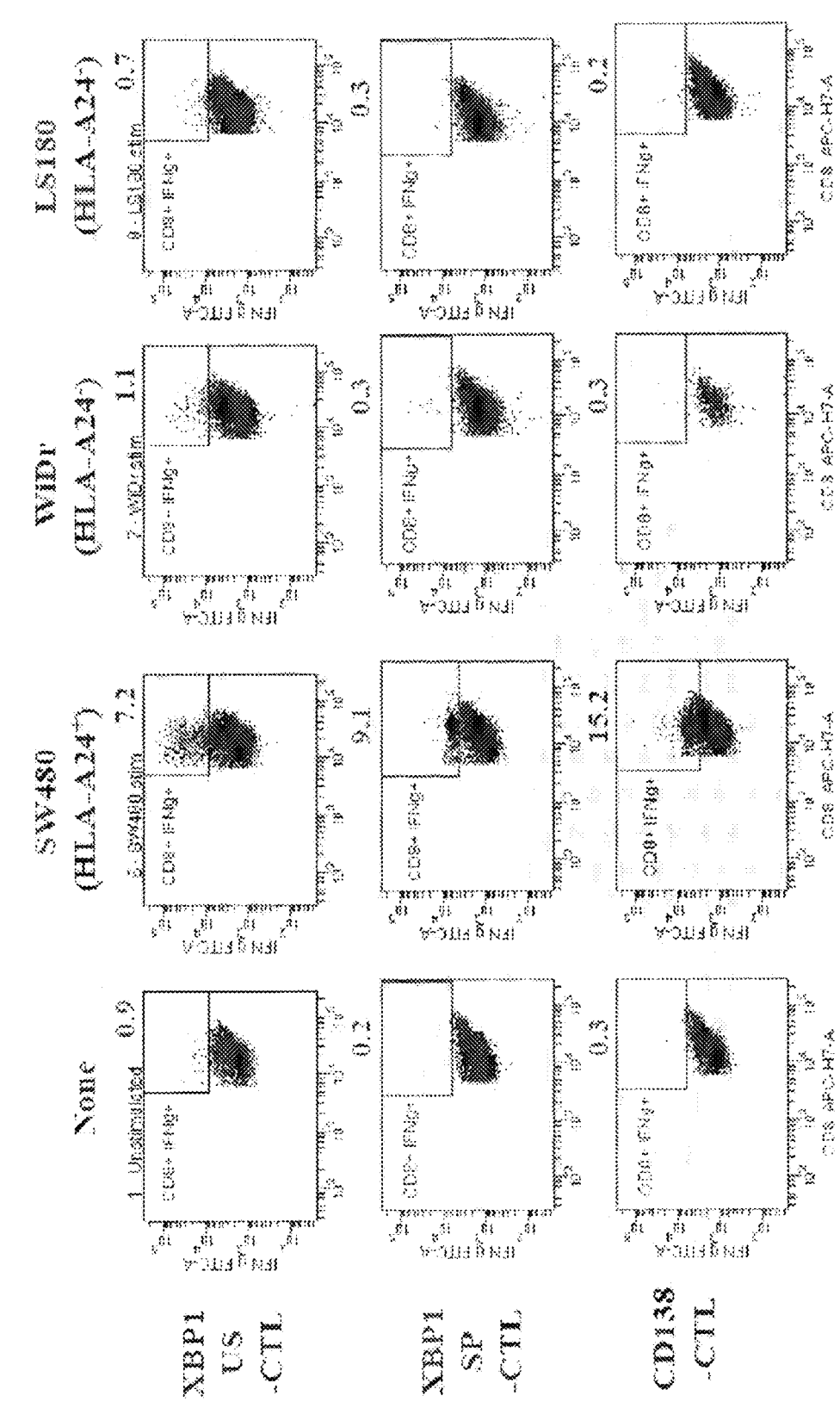

Fig. 38 Donor B CTL: CD107a+/IFN-γ production to A24+ Colon Cancer

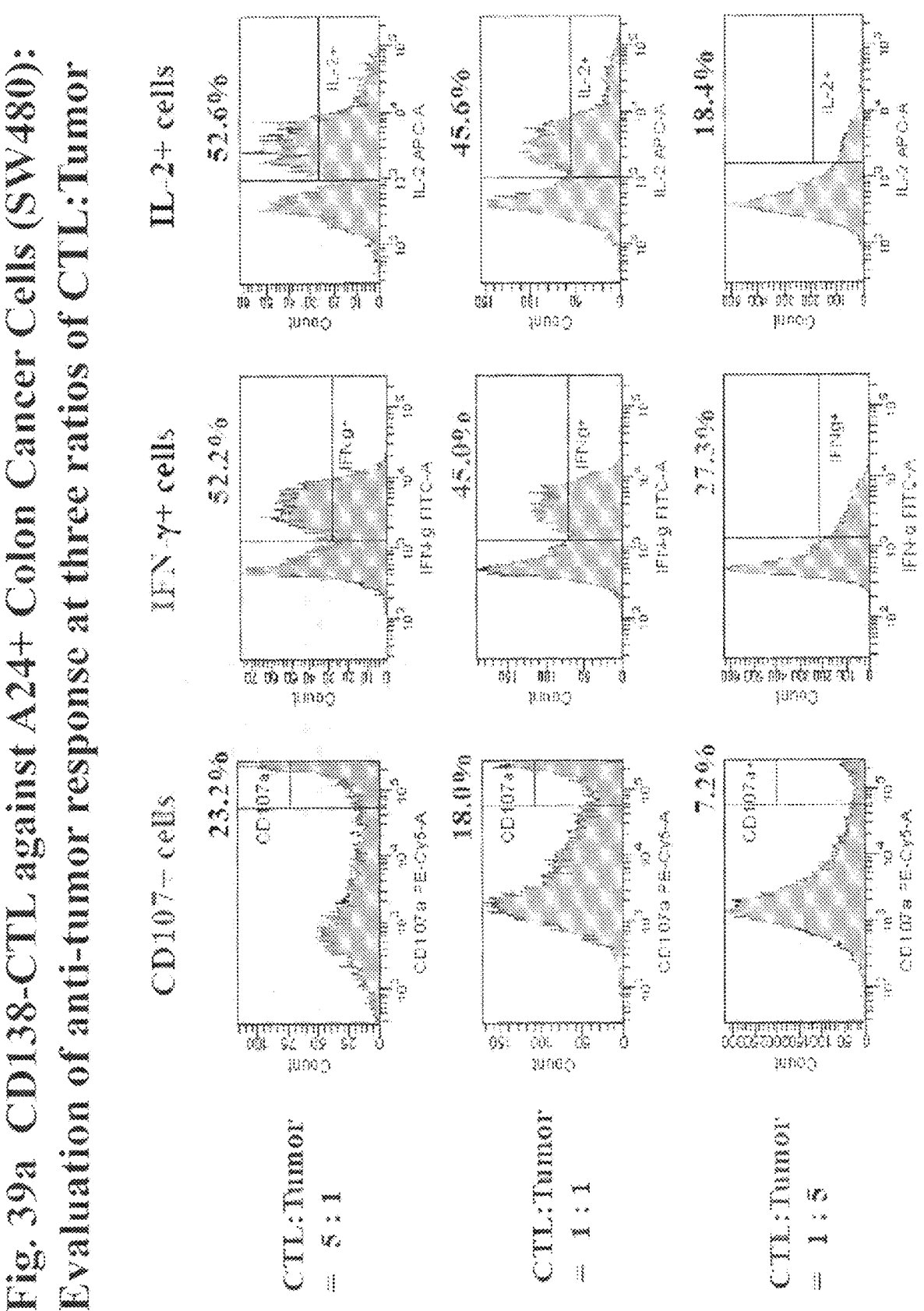
Fig. 39a CD138-CTL against A24+ Colon Cancer Cells (SW480): Evaluation of anti-tumor response at three ratios of CTL:Tumor

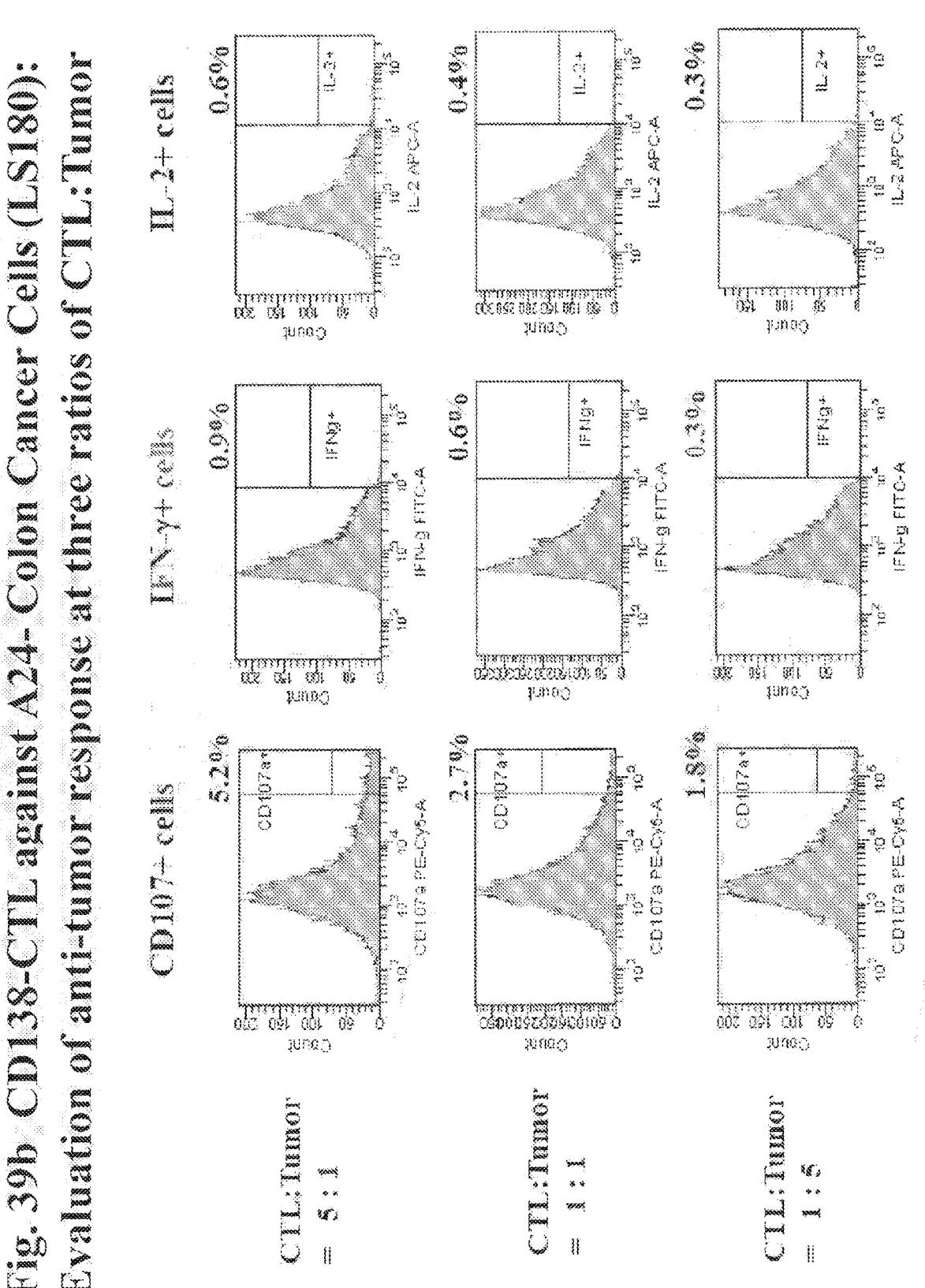
Fig. 39b CD138-CTL against A24- Colon Cancer Cells (LS180): Evaluation of anti-tumor response at three ratios of CTL:Tumor

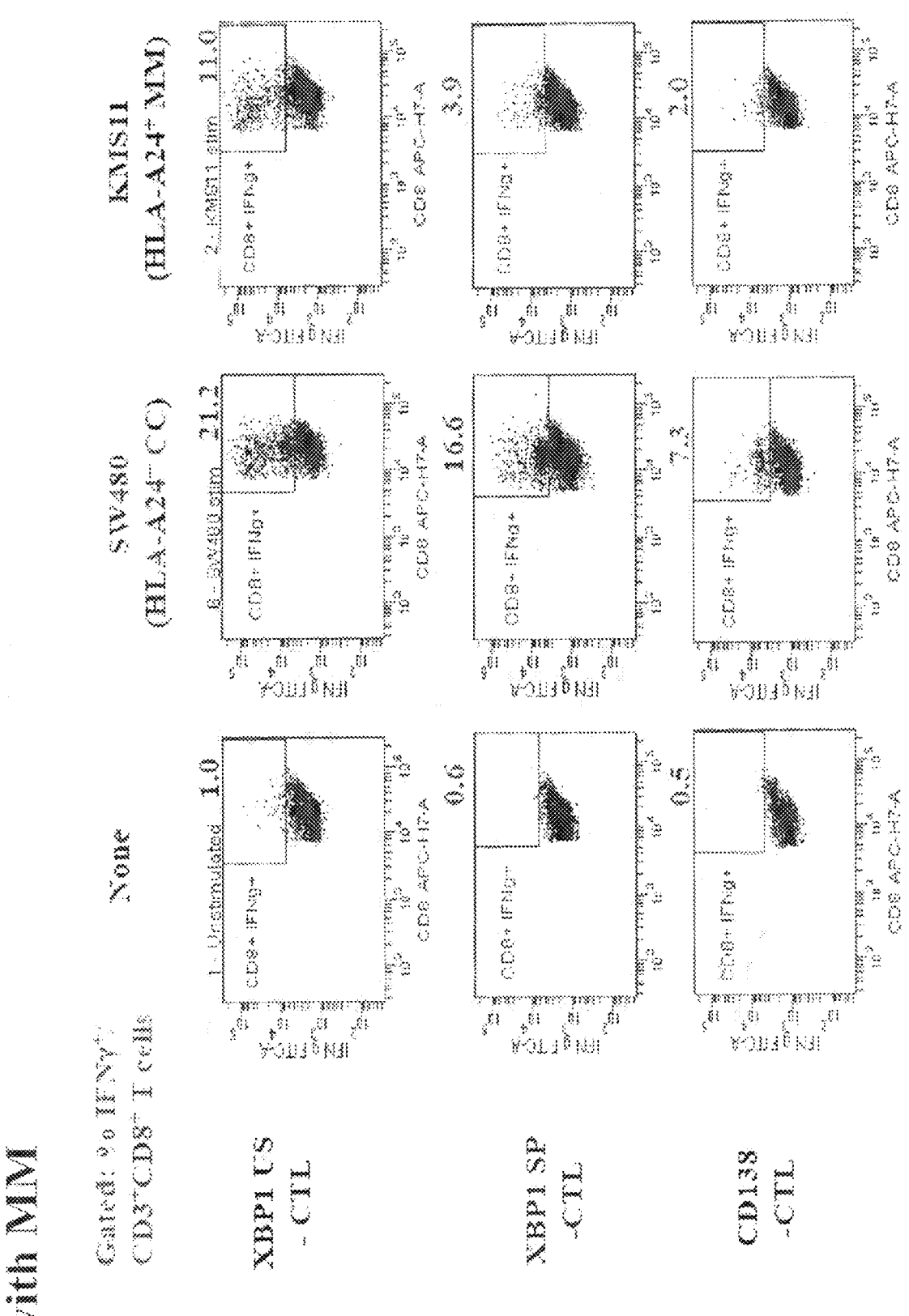
Fig. 40a HLA-A24 CTL from A24+ Donor A: Comparison CC with MM

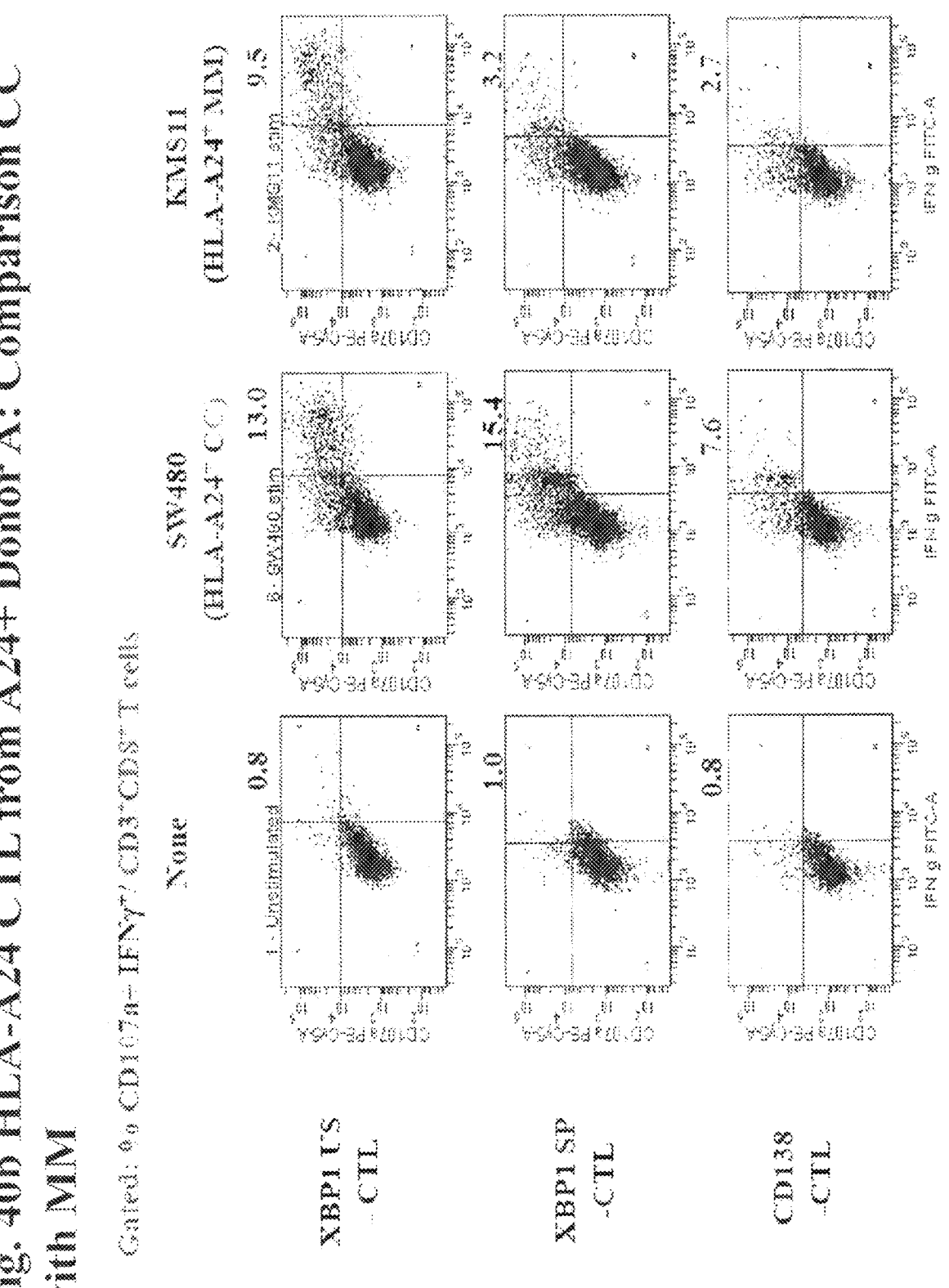
Fig. 40b HLA-A24 CTL from A24+ Donor A: Comparison CC with MM

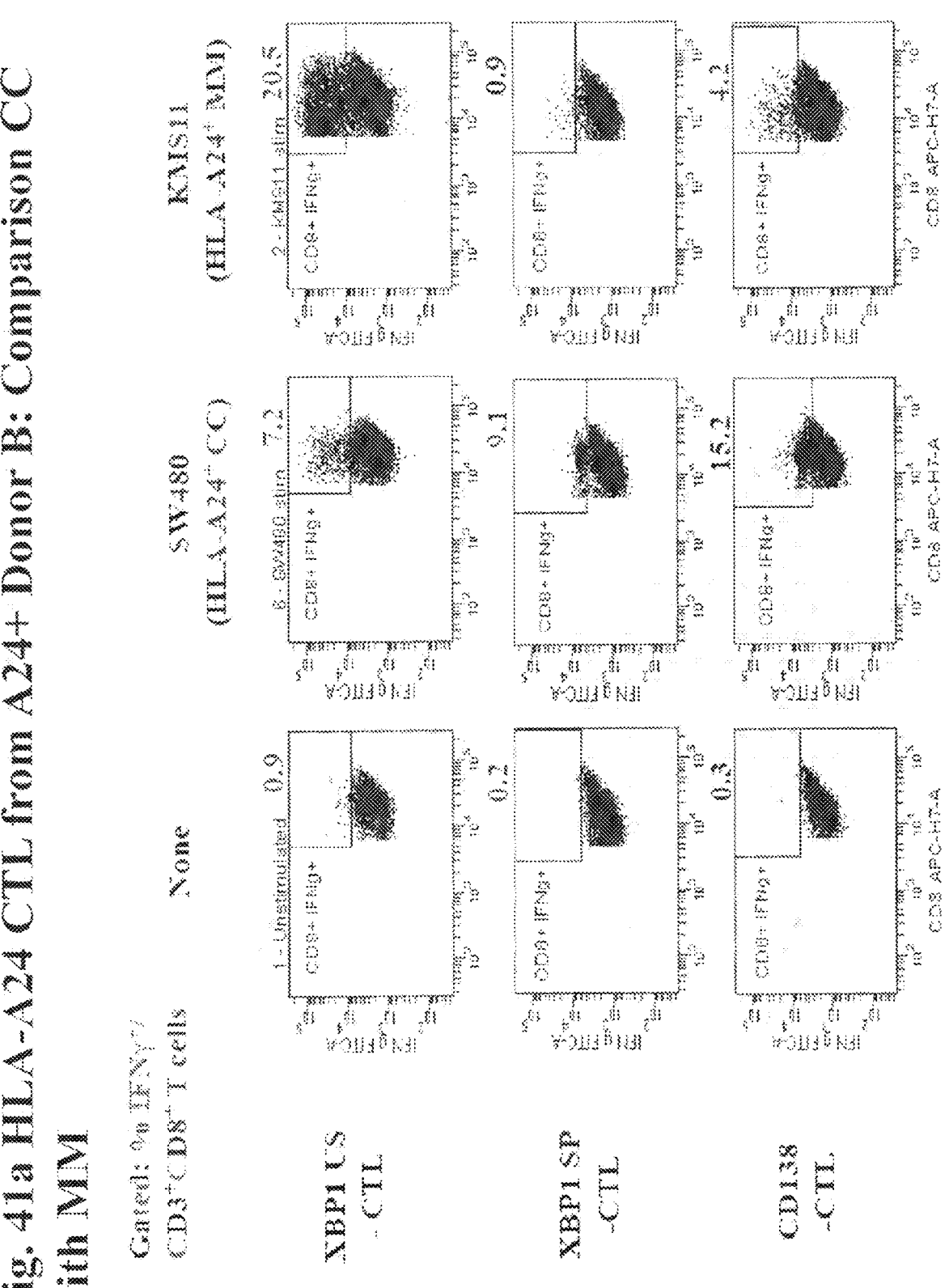
Fig. 41a HLA-A24 CTL from A24+ Donor B: Comparison CC with MM

Figure 41B:
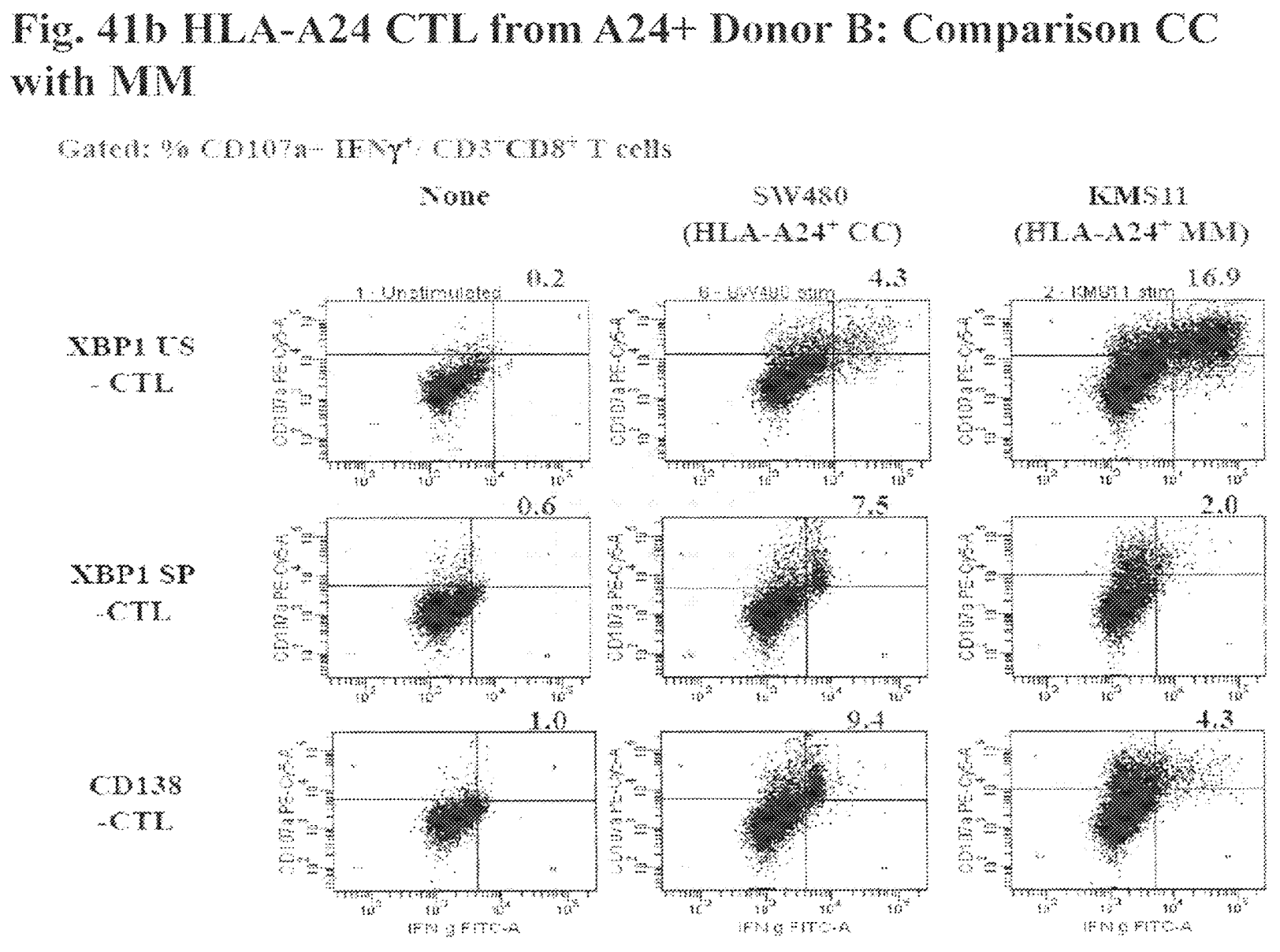

Fig. 41b HLA-A24 CTL from A24+ Donor B: Comparison CC with MM

Gated: % CD107a− IFNγ+ CD3+CD8+ T cells

Columns: None | SW480 (HLA-A24+ CC) | KMS11 (HLA-A24+ MM)

Rows: XBP1 US -CTL | XBP1 SP -CTL | CD138 -CTL

Fig. 42 HLA-A24 CTL from A24+ Donor B against Pancreatic Cancer Cells
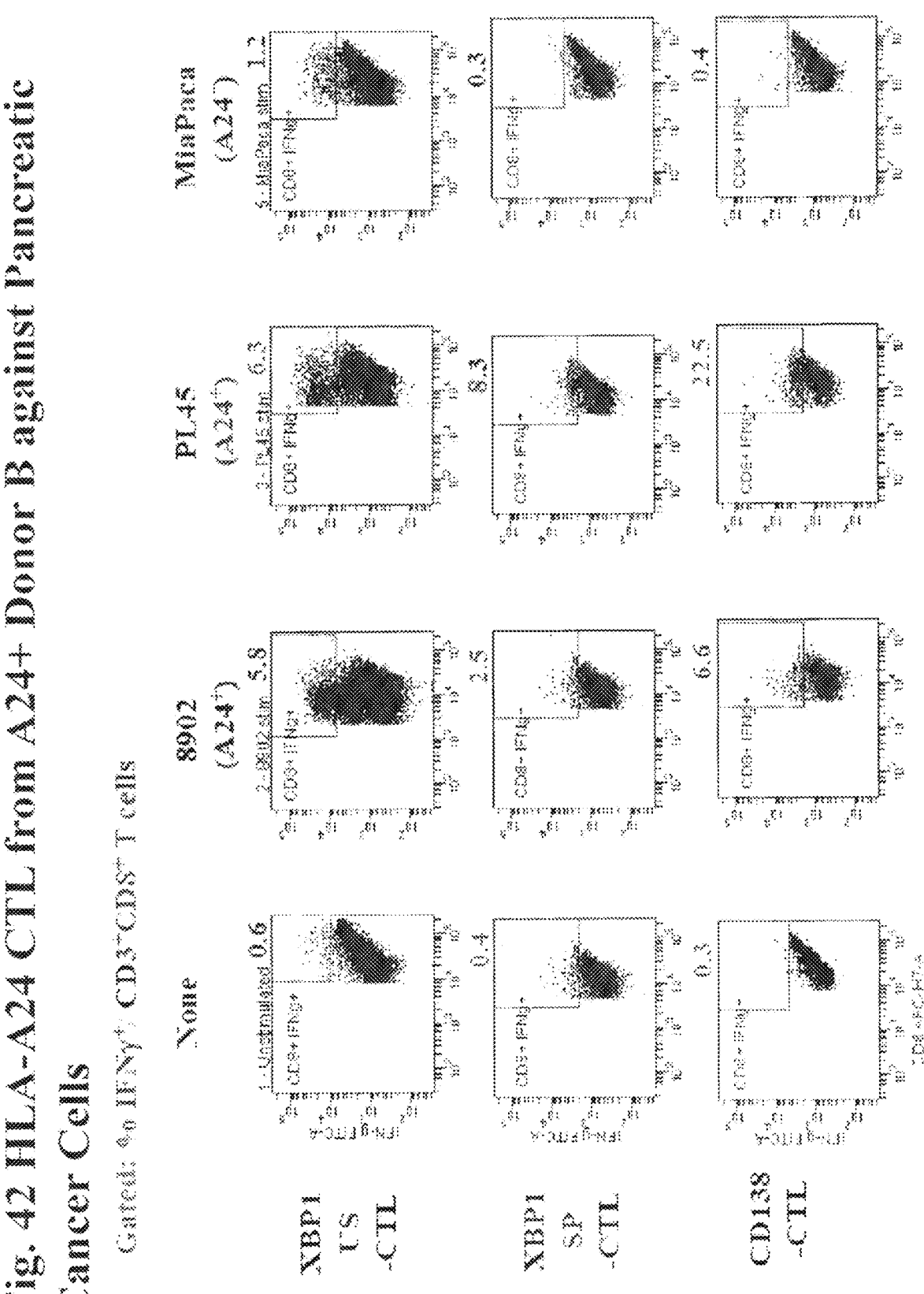

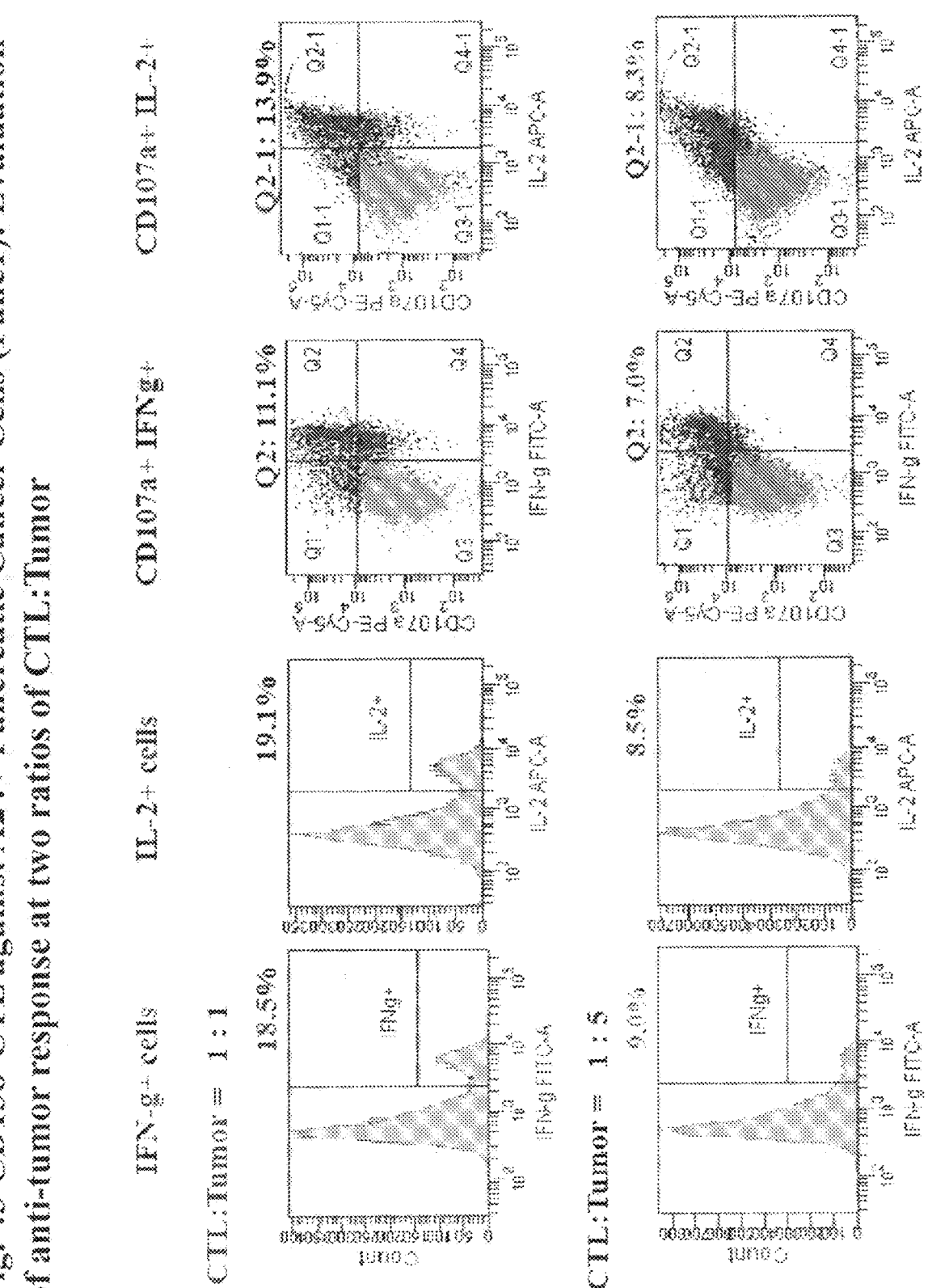
Fig. 43 CD138-CTL against A24+ Pancreatic Cancer Cells (Panc1): Evaluation of anti-tumor response at two ratios of CTL:Tumor A: No stimulated B: Post-2 stim. Day 6

C: Post-3 stim. Day 2

D: Post-3 stim. Day 4

E: Post-3 stim. Day 6

F: Post-5 stim. Day 6

% Positive Cells

Fig. 50    IFN-γ Production by XBP1-CTL: CM > EM

Fig. 51    IFN-γ Production by XBP1-CTL: CM > EM

IL-2 Production by XBP1-CTL: CM > EM
Fig. 52
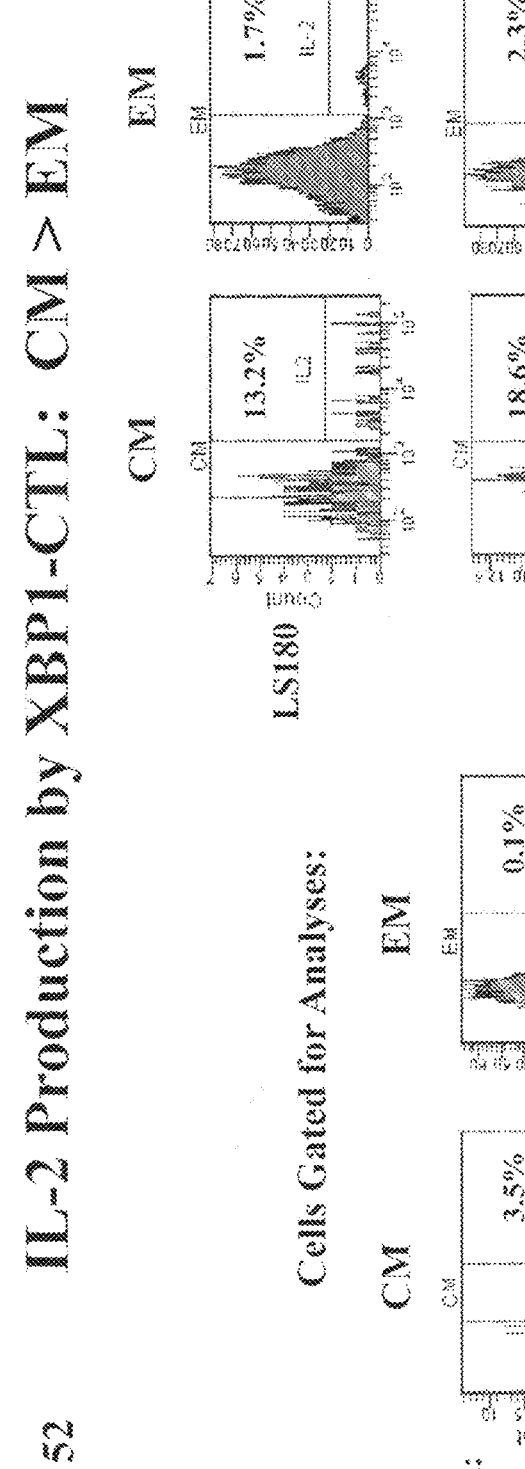
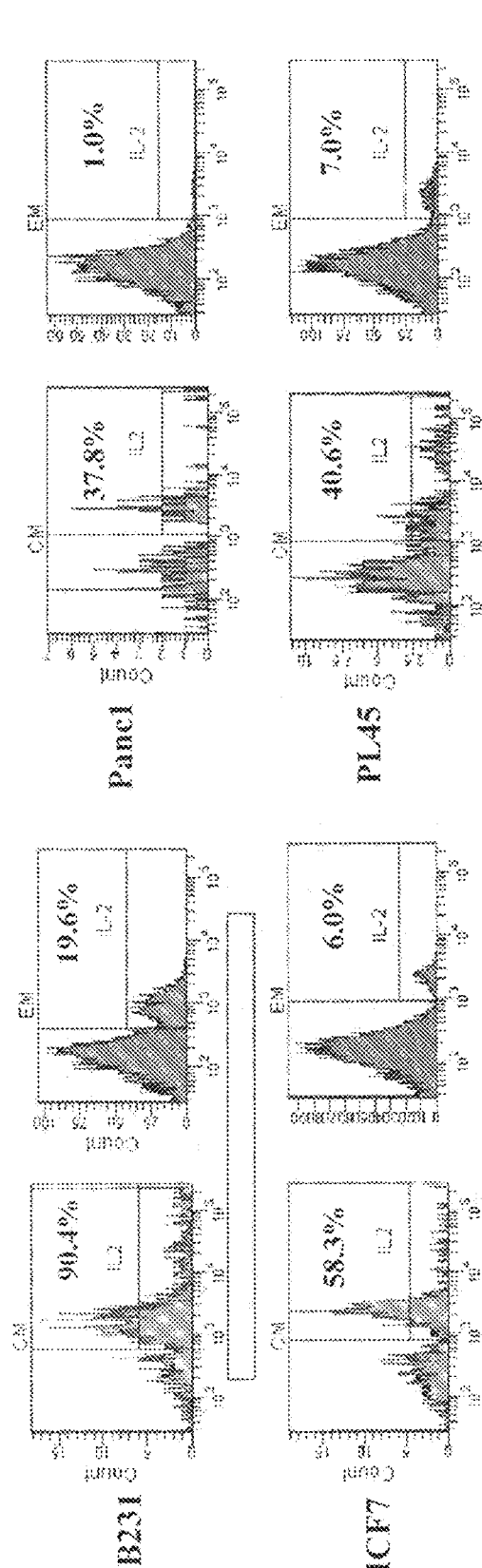
Cells Gated for Analyses:

IL-2 Production by XBP1-CTL: CM > EM

Fig. 54    Cytotoxicity of XBP1-CTL: CM > EM

Fig. 55    Cytotoxicity of XBP1-CTL: CM > EM

Highest Tbet+ cells in Effector Memory cells of XBP1-CTL

Fig. 59    T-bet/IFNg-specific XBP1-CTL activity to MB231

Fig. 60    T-bet/IFNg-specific XBP1-CTL activity to Panc1

Fig. 61    T-bet/IFNg-specific XBP1-CTL activity to SW480

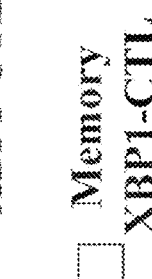
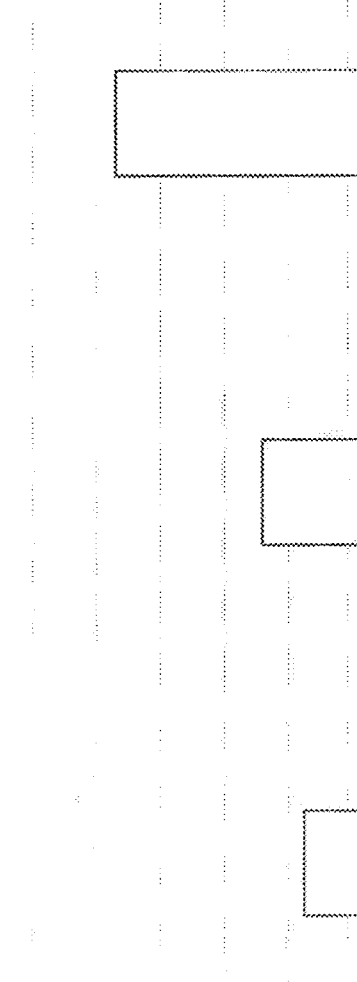
Fig. 62
XBP1-CTL Memory cells:
High Eomes expression

Highest Eomes⁺ cells in Effector Memory T cells of XBP1-CTL

Higher Eomes⁺ IFN-γ⁺ cells in Memory T cells

Highest Eomes⁺ IFN-γ⁺ cells in CM of XBP1-CTL against Panc1

XBP1-CTL Memory cells:
High Granzyme B upregulation
against breast, pancreatic and colon cancer cells

Fig. 72

Increase of Memory CD8$^+$ T cells of XBP1-CTL by Lenalidomide treatment

Constant Increase of CM
of XBP1-CTL by Lenalidomide treatment

Fig. 74

Increase of Critical Antigens on XBP1-CTL

Increase of T-bet$^+$ IFN-g$^+$ cells of XBP1-CTL to MB231 by Lenalidomide treatment Increase of Eomes+ IFN-g+ cells of XBP1-CTL to MB231 by Lenalidomide treatment

Fig. 78

Increase of Eomes+ IFN-g+ cells of XBP1-CTL to Panc1 by Lenalidomide treatment

Increase of T-bet⁺ IFN-g⁺ cells of XBP1-CTL to SW480 by Lenalidomide treatment

Increase of GrB⁺ IFN-g⁺ cells of XBP1-CTL to Panc1 by Lenalidomide treatment

Increase of GrB⁺ IFN-g⁺ cells of XBP1-CTL to SW480 by Lenalidomide treatment

SEQUENCE LISTING

```
<160> NUMBER OF SEQ ID NOS: 544

<210> SEQ ID NO 1
<211> LENGTH: 9
<212> TYPE: PRT
<213> ORGANISM: Homo sapiens

<400> SEQUENCE: 1

Leu Leu Arg Glu Lys Thr His Gly Leu
1               5

<210> SEQ ID NO 2
<211> LENGTH: 9
<212> TYPE: PRT
<213> ORGANISM: Homo sapiens

<400> SEQUENCE: 2

Asn Ile Ser Pro Trp Ile Leu Ala Val
1               5

<210> SEQ ID NO 3
```

```
<211> LENGTH: 9
<212> TYPE: PRT
<213> ORGANISM: Homo sapiens

<400> SEQUENCE: 3

Ile Leu Ala Val Leu Thr Leu Gln Ile
1               5

<210> SEQ ID NO 4
<211> LENGTH: 9
<212> TYPE: PRT
<213> ORGANISM: Homo sapiens

<400> SEQUENCE: 4

Val Leu Thr Leu Gln Ile Gln Ser Leu
1               5

<210> SEQ ID NO 5
<211> LENGTH: 9
<212> TYPE: PRT
<213> ORGANISM: Homo sapiens

<400> SEQUENCE: 5

Lys Leu Leu Leu Glu Asn Gln Leu Leu
1               5

<210> SEQ ID NO 6
<211> LENGTH: 9
<212> TYPE: PRT
<213> ORGANISM: Homo sapiens

<400> SEQUENCE: 6

Tyr Ile Ser Pro Trp Ile Leu Ala Val
1               5

<210> SEQ ID NO 7
<211> LENGTH: 9
<212> TYPE: PRT
<213> ORGANISM: Homo sapiens

<400> SEQUENCE: 7

Gly Ile Leu Asp Asn Leu Asp Pro Val
1               5

<210> SEQ ID NO 8
<211> LENGTH: 9
<212> TYPE: PRT
<213> ORGANISM: Homo sapiens

<400> SEQUENCE: 8

Ile Leu Leu Gly Ile Leu Asp Asn Leu
1               5

<210> SEQ ID NO 9
<211> LENGTH: 9
<212> TYPE: PRT
<213> ORGANISM: Homo sapiens

<400> SEQUENCE: 9

Glu Leu Phe Pro Gln Leu Ile Ser Val
1               5

<210> SEQ ID NO 10
<211> LENGTH: 9
<212> TYPE: PRT
```

<213> ORGANISM: Homo sapiens

<400> SEQUENCE: 10

Tyr Leu Phe Pro Gln Leu Ile Ser Val
1               5

<210> SEQ ID NO 11
<211> LENGTH: 9
<212> TYPE: PRT
<213> ORGANISM: Homo sapiens

<400> SEQUENCE: 11

Val Ile Ala Gly Gly Leu Val Gly Leu
1               5

<210> SEQ ID NO 12
<211> LENGTH: 9
<212> TYPE: PRT
<213> ORGANISM: Homo sapiens

<400> SEQUENCE: 12

Gly Leu Val Gly Leu Ile Phe Ala Val
1               5

<210> SEQ ID NO 13
<211> LENGTH: 9
<212> TYPE: PRT
<213> ORGANISM: Homo sapiens

<400> SEQUENCE: 13

Ala Leu Trp Leu Trp Leu Cys Ala Leu
1               5

<210> SEQ ID NO 14
<211> LENGTH: 9
<212> TYPE: PRT
<213> ORGANISM: Homo sapiens

<400> SEQUENCE: 14

Trp Leu Trp Leu Cys Ala Leu Ala Leu
1               5

<210> SEQ ID NO 15
<211> LENGTH: 10
<212> TYPE: PRT
<213> ORGANISM: Homo sapiens

<400> SEQUENCE: 15

Leu Leu Leu Ser Leu Phe Val Leu Gly Leu
1               5                   10

<210> SEQ ID NO 16
<211> LENGTH: 9
<212> TYPE: PRT
<213> ORGANISM: Homo sapiens

<400> SEQUENCE: 16

Ser Leu Phe Val Leu Gly Leu Phe Leu
1               5

<210> SEQ ID NO 17
<211> LENGTH: 9
<212> TYPE: PRT
<213> ORGANISM: Homo sapiens

-continued

<400> SEQUENCE: 17

```
Leu Leu Val Pro Leu Leu Leu Ser Leu
1               5
```

<210> SEQ ID NO 18
<211> LENGTH: 9
<212> TYPE: PRT
<213> ORGANISM: Homo sapiens

<400> SEQUENCE: 18

```
Thr Leu Ile Tyr Ile Leu Trp Gln Leu
1               5
```

<210> SEQ ID NO 19
<211> LENGTH: 261
<212> TYPE: PRT
<213> ORGANISM: Homo sapiens

<400> SEQUENCE: 19

```
Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
            115                 120                 125

Glu Asn Gln Glu Leu Arg Gln Arg Leu Gly Met Asp Ala Leu Val Ala
        130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
            180                 185                 190

Val Leu Thr Leu Gln Ile Gln Ser Leu Ile Ser Cys Trp Ala Phe Trp
            195                 200                 205

Thr Thr Trp Thr Gln Ser Cys Ser Ser Asn Ala Leu Pro Gln Ser Leu
    210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260
```

<210> SEQ ID NO 20
<211> LENGTH: 376
<212> TYPE: PRT

<213> ORGANISM: Homo sapiens

<400> SEQUENCE: 20

```
Met Val Val Val Ala Ala Ala Pro Asn Pro Ala Asp Gly Thr Pro Lys
1               5               10              15

Val Leu Leu Leu Ser Gly Gln Pro Ala Ser Ala Ala Gly Ala Pro Ala
            20              25              30

Gly Gln Ala Leu Pro Leu Met Val Pro Ala Gln Arg Gly Ala Ser Pro
        35              40              45

Glu Ala Ala Ser Gly Gly Leu Pro Gln Ala Arg Lys Arg Gln Arg Leu
    50              55              60

Thr His Leu Ser Pro Glu Glu Lys Ala Leu Arg Arg Lys Leu Lys Asn
65              70              75              80

Arg Val Ala Ala Gln Thr Ala Arg Asp Arg Lys Lys Ala Arg Met Ser
            85              90              95

Glu Leu Glu Gln Gln Val Val Asp Leu Glu Glu Glu Asn Gln Lys Leu
            100             105             110

Leu Leu Glu Asn Gln Leu Leu Arg Glu Lys Thr His Gly Leu Val Val
        115             120             125

Glu Asn Gln Glu Leu Arg Gln Arg Leu Gly Met Asp Ala Leu Val Ala
    130             135             140

Glu Glu Glu Ala Glu Ala Lys Gly Asn Glu Val Arg Pro Val Ala Gly
145             150             155             160

Ser Ala Glu Ser Ala Ala Gly Ala Gly Pro Val Val Thr Pro Pro Glu
            165             170             175

His Leu Pro Met Asp Ser Gly Gly Ile Asp Ser Ser Asp Ser Glu Ser
            180             185             190

Asp Ile Leu Leu Gly Ile Leu Asp Asn Leu Asp Pro Val Met Phe Phe
            195             200             205

Lys Cys Pro Ser Pro Glu Pro Ala Ser Leu Glu Glu Leu Pro Glu Val
    210             215             220

Tyr Pro Glu Gly Pro Ser Ser Leu Pro Ala Ser Leu Ser Leu Ser Val
225             230             235             240

Gly Thr Ser Ser Ala Lys Leu Glu Ala Ile Asn Glu Leu Ile Arg Phe
            245             250             255

Asp His Ile Tyr Thr Lys Pro Leu Val Leu Glu Ile Pro Ser Glu Thr
            260             265             270

Glu Ser Gln Ala Asn Val Val Val Lys Ile Glu Glu Ala Pro Leu Ser
    275             280             285

Pro Ser Glu Asn Asp His Pro Glu Phe Ile Val Ser Val Lys Glu Glu
    290             295             300

Pro Val Glu Asp Asp Leu Val Pro Glu Leu Gly Ile Ser Asn Leu Leu
305             310             315             320

Ser Ser Ser His Cys Pro Lys Pro Ser Ser Cys Leu Leu Asp Ala Tyr
            325             330             335

Ser Asp Cys Gly Tyr Gly Gly Ser Leu Ser Pro Phe Ser Asp Met Ser
            340             345             350

Ser Leu Leu Gly Val Asn His Ser Trp Glu Asp Thr Phe Ala Asn Glu
            355             360             365

Leu Phe Pro Gln Leu Ile Ser Val
    370             375
```

<210> SEQ ID NO 21
<211> LENGTH: 310

-continued

```
<212> TYPE: PRT
<213> ORGANISM: Homo sapiens

<400> SEQUENCE: 21

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
        210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
            245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
        290                 295                 300

Gln Glu Glu Phe Tyr Ala
305                 310

<210> SEQ ID NO 22
<211> LENGTH: 335
<212> TYPE: PRT
<213> ORGANISM: Homo sapiens

<400> SEQUENCE: 22

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30
```

```
Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
                100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
            195                 200                 205

Ile Leu Ala Arg Lys Leu Cys Glu Gly Ala Ala Asp Asp Pro Asp Ser
    210                 215                 220

Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
            245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
    275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 23
<211> LENGTH: 4
<212> TYPE: PRT
<213> ORGANISM: Unknown
<220> FEATURE:
<223> OTHER INFORMATION: Description of Unknown: "KDEL" motif
      peptide

<400> SEQUENCE: 23

Lys Asp Glu Leu
1

<210> SEQ ID NO 24
<211> LENGTH: 9
<212> TYPE: PRT
<213> ORGANISM: Homo sapiens

<400> SEQUENCE: 24
```

-continued

```
Tyr Ile Leu Asp Asn Leu Asp Pro Val
1               5

<210> SEQ ID NO 25
<211> LENGTH: 9
<212> TYPE: PRT
<213> ORGANISM: Influenza virus

<400> SEQUENCE: 25

Gly Ile Leu Gly Phe Val Phe Thr Leu
1               5

<210> SEQ ID NO 26
<211> LENGTH: 9
<212> TYPE: PRT
<213> ORGANISM: Influenza virus

<400> SEQUENCE: 26

Phe Leu Trp Gly Pro Arg Ala Leu Val
1               5

<210> SEQ ID NO 27
<211> LENGTH: 9
<212> TYPE: PRT
<213> ORGANISM: Homo sapiens

<400> SEQUENCE: 27

Arg Met Ser Glu Leu Glu Gln Gln Val
1               5

<210> SEQ ID NO 28
<211> LENGTH: 9
<212> TYPE: PRT
<213> ORGANISM: Homo sapiens

<400> SEQUENCE: 28

Asn Leu Val Pro Met Val Ala Thr Val
1               5

<210> SEQ ID NO 29
<211> LENGTH: 9
<212> TYPE: PRT
<213> ORGANISM: Homo sapiens

<400> SEQUENCE: 29

Ile Ser Pro Trp Ile Leu Ala Val Leu
1               5

<210> SEQ ID NO 30
<211> LENGTH: 9
<212> TYPE: PRT
<213> ORGANISM: Homo sapiens

<400> SEQUENCE: 30

Val Tyr Pro Glu Gly Pro Ser Ser Leu
1               5

<210> SEQ ID NO 31
<211> LENGTH: 9
<212> TYPE: PRT
<213> ORGANISM: Homo sapiens

<400> SEQUENCE: 31

Ile Phe Ala Val Cys Leu Val Gly Phe
1               5
```

<210> SEQ ID NO 32
<211> LENGTH: 9
<212> TYPE: PRT
<213> ORGANISM: Homo sapiens

<400> SEQUENCE: 32

Leu Phe Val Leu Gly Leu Phe Leu Trp
1               5

<210> SEQ ID NO 33
<211> LENGTH: 9
<212> TYPE: PRT
<213> ORGANISM: Homo sapiens

<400> SEQUENCE: 33

Pro Trp Ile Leu Ala Val Leu Thr Leu
1               5

<210> SEQ ID NO 34
<211> LENGTH: 9
<212> TYPE: PRT
<213> ORGANISM: Homo sapiens

<400> SEQUENCE: 34

Glu Asn Gln Glu Leu Arg Gln Arg Leu
1               5

<210> SEQ ID NO 35
<211> LENGTH: 9
<212> TYPE: PRT
<213> ORGANISM: Homo sapiens

<400> SEQUENCE: 35

Asp Gly Thr Pro Lys Val Leu Leu Leu
1               5

<210> SEQ ID NO 36
<211> LENGTH: 9
<212> TYPE: PRT
<213> ORGANISM: Homo sapiens

<400> SEQUENCE: 36

Asp Leu Glu Glu Glu Asn Gln Lys Leu
1               5

<210> SEQ ID NO 37
<211> LENGTH: 9
<212> TYPE: PRT
<213> ORGANISM: Homo sapiens

<400> SEQUENCE: 37

Ser Ser Asn Ala Leu Pro Gln Ser Leu
1               5

<210> SEQ ID NO 38
<211> LENGTH: 9
<212> TYPE: PRT
<213> ORGANISM: Homo sapiens

<400> SEQUENCE: 38

Gly Tyr Gly Gly Ser Leu Ser Pro Phe
1               5

<210> SEQ ID NO 39
<211> LENGTH: 9
<212> TYPE: PRT
<213> ORGANISM: Homo sapiens

<400> SEQUENCE: 39

Pro Phe Ser Asp Met Ser Ser Leu Leu
1               5

<210> SEQ ID NO 40
<211> LENGTH: 9
<212> TYPE: PRT
<213> ORGANISM: Homo sapiens

<400> SEQUENCE: 40

Val Leu Pro Glu Val Glu Pro Gly Leu
1               5

<210> SEQ ID NO 41
<211> LENGTH: 9
<212> TYPE: PRT
<213> ORGANISM: Homo sapiens

<400> SEQUENCE: 41

Leu Pro Gln Ile Val Ala Thr Asn Leu
1               5

<210> SEQ ID NO 42
<211> LENGTH: 9
<212> TYPE: PRT
<213> ORGANISM: Homo sapiens

<400> SEQUENCE: 42

Leu Ala Leu Ser Leu Gln Pro Ala Leu
1               5

<210> SEQ ID NO 43
<211> LENGTH: 9
<212> TYPE: PRT
<213> ORGANISM: Homo sapiens

<400> SEQUENCE: 43

Gly Leu Leu Asp Arg Lys Glu Val Leu
1               5

<210> SEQ ID NO 44
<211> LENGTH: 9
<212> TYPE: PRT
<213> ORGANISM: Homo sapiens

<400> SEQUENCE: 44

Val Gly Leu Ile Phe Ala Val Cys Leu
1               5

<210> SEQ ID NO 45
<211> LENGTH: 9
<212> TYPE: PRT
<213> ORGANISM: Homo sapiens

<400> SEQUENCE: 45

Ser Leu Gln Pro Ala Leu Pro Gln Ile
1               5

<210> SEQ ID NO 46
<211> LENGTH: 9

-continued

```
<212> TYPE: PRT
<213> ORGANISM: Homo sapiens

<400> SEQUENCE: 46

Gly Tyr Ser Leu Lys Leu Ser Lys Leu
1               5

<210> SEQ ID NO 47
<211> LENGTH: 9
<212> TYPE: PRT
<213> ORGANISM: Homo sapiens

<400> SEQUENCE: 47

Asp Phe Pro Asp Gly Gly Tyr Ser Leu
1               5

<210> SEQ ID NO 48
<211> LENGTH: 9
<212> TYPE: PRT
<213> ORGANISM: Homo sapiens

<400> SEQUENCE: 48

Thr Met Pro Asp Thr Pro Arg Leu Phe
1               5

<210> SEQ ID NO 49
<211> LENGTH: 9
<212> TYPE: PRT
<213> ORGANISM: Homo sapiens

<400> SEQUENCE: 49

Arg Trp Gly Glu Ser Asp Met Thr Phe
1               5

<210> SEQ ID NO 50
<211> LENGTH: 9
<212> TYPE: PRT
<213> ORGANISM: Homo sapiens

<400> SEQUENCE: 50

Lys Met Glu Asn Pro His Ser Leu Leu
1               5

<210> SEQ ID NO 51
<211> LENGTH: 15
<212> TYPE: PRT
<213> ORGANISM: Homo sapiens

<400> SEQUENCE: 51

Leu Ser Pro Leu Gln Asn Ile Ser Pro Trp Ile Leu Ala Val Leu
1               5                   10                  15

<210> SEQ ID NO 52
<211> LENGTH: 16
<212> TYPE: PRT
<213> ORGANISM: Homo sapiens

<400> SEQUENCE: 52

Leu Ser Pro Leu Gln Asn Ile Ser Pro Trp Ile Leu Ala Val Leu Thr
1               5                   10                  15

<210> SEQ ID NO 53
<211> LENGTH: 17
<212> TYPE: PRT
<213> ORGANISM: Homo sapiens
```

<400> SEQUENCE: 53

Leu Ser Pro Leu Gln Asn Ile Ser Pro Trp Ile Leu Ala Val Leu Thr
1               5                   10                  15

Leu

<210> SEQ ID NO 54
<211> LENGTH: 18
<212> TYPE: PRT
<213> ORGANISM: Homo sapiens

<400> SEQUENCE: 54

Leu Ser Pro Leu Gln Asn Ile Ser Pro Trp Ile Leu Ala Val Leu Thr
1               5                   10                  15

Leu Gln

<210> SEQ ID NO 55
<211> LENGTH: 19
<212> TYPE: PRT
<213> ORGANISM: Homo sapiens

<400> SEQUENCE: 55

Leu Ser Pro Leu Gln Asn Ile Ser Pro Trp Ile Leu Ala Val Leu Thr
1               5                   10                  15

Leu Gln Ile

<210> SEQ ID NO 56
<211> LENGTH: 20
<212> TYPE: PRT
<213> ORGANISM: Homo sapiens

<400> SEQUENCE: 56

Leu Ser Pro Leu Gln Asn Ile Ser Pro Trp Ile Leu Ala Val Leu Thr
1               5                   10                  15

Leu Gln Ile Gln
            20

<210> SEQ ID NO 57
<211> LENGTH: 21
<212> TYPE: PRT
<213> ORGANISM: Homo sapiens

<400> SEQUENCE: 57

Leu Ser Pro Leu Gln Asn Ile Ser Pro Trp Ile Leu Ala Val Leu Thr
1               5                   10                  15

Leu Gln Ile Gln Ser
            20

<210> SEQ ID NO 58
<211> LENGTH: 22
<212> TYPE: PRT
<213> ORGANISM: Homo sapiens

<400> SEQUENCE: 58

Leu Ser Pro Leu Gln Asn Ile Ser Pro Trp Ile Leu Ala Val Leu Thr
1               5                   10                  15

Leu Gln Ile Gln Ser Leu
            20

<210> SEQ ID NO 59
<211> LENGTH: 23

<212> TYPE: PRT
<213> ORGANISM: Homo sapiens

<400> SEQUENCE: 59

Leu Ser Pro Leu Gln Asn Ile Ser Pro Trp Ile Leu Ala Val Leu Thr
1               5                   10                  15

Leu Gln Ile Gln Ser Leu Ile
            20

<210> SEQ ID NO 60
<211> LENGTH: 24
<212> TYPE: PRT
<213> ORGANISM: Homo sapiens

<400> SEQUENCE: 60

Leu Ser Pro Leu Gln Asn Ile Ser Pro Trp Ile Leu Ala Val Leu Thr
1               5                   10                  15

Leu Gln Ile Gln Ser Leu Ile Ser
            20

<210> SEQ ID NO 61
<211> LENGTH: 25
<212> TYPE: PRT
<213> ORGANISM: Homo sapiens

<400> SEQUENCE: 61

Leu Ser Pro Leu Gln Asn Ile Ser Pro Trp Ile Leu Ala Val Leu Thr
1               5                   10                  15

Leu Gln Ile Gln Ser Leu Ile Ser Cys
            20                  25

<210> SEQ ID NO 62
<211> LENGTH: 26
<212> TYPE: PRT
<213> ORGANISM: Homo sapiens

<400> SEQUENCE: 62

Leu Ser Pro Leu Gln Asn Ile Ser Pro Trp Ile Leu Ala Val Leu Thr
1               5                   10                  15

Leu Gln Ile Gln Ser Leu Ile Ser Cys Trp
            20                  25

<210> SEQ ID NO 63
<211> LENGTH: 27
<212> TYPE: PRT
<213> ORGANISM: Homo sapiens

<400> SEQUENCE: 63

Leu Ser Pro Leu Gln Asn Ile Ser Pro Trp Ile Leu Ala Val Leu Thr
1               5                   10                  15

Leu Gln Ile Gln Ser Leu Ile Ser Cys Trp Ala
            20                  25

<210> SEQ ID NO 64
<211> LENGTH: 14
<212> TYPE: PRT
<213> ORGANISM: Homo sapiens

<400> SEQUENCE: 64

Ser Pro Leu Gln Asn Ile Ser Pro Trp Ile Leu Ala Val Leu
1               5                   10

-continued

```
<210> SEQ ID NO 65
<211> LENGTH: 15
<212> TYPE: PRT
<213> ORGANISM: Homo sapiens

<400> SEQUENCE: 65

Ser Pro Leu Gln Asn Ile Ser Pro Trp Ile Leu Ala Val Leu Thr
1               5                   10                  15

<210> SEQ ID NO 66
<211> LENGTH: 16
<212> TYPE: PRT
<213> ORGANISM: Homo sapiens

<400> SEQUENCE: 66

Ser Pro Leu Gln Asn Ile Ser Pro Trp Ile Leu Ala Val Leu Thr Leu
1               5                   10                  15

<210> SEQ ID NO 67
<211> LENGTH: 17
<212> TYPE: PRT
<213> ORGANISM: Homo sapiens

<400> SEQUENCE: 67

Ser Pro Leu Gln Asn Ile Ser Pro Trp Ile Leu Ala Val Leu Thr Leu
1               5                   10                  15

Gln

<210> SEQ ID NO 68
<211> LENGTH: 18
<212> TYPE: PRT
<213> ORGANISM: Homo sapiens

<400> SEQUENCE: 68

Ser Pro Leu Gln Asn Ile Ser Pro Trp Ile Leu Ala Val Leu Thr Leu
1               5                   10                  15

Gln Ile

<210> SEQ ID NO 69
<211> LENGTH: 19
<212> TYPE: PRT
<213> ORGANISM: Homo sapiens

<400> SEQUENCE: 69

Ser Pro Leu Gln Asn Ile Ser Pro Trp Ile Leu Ala Val Leu Thr Leu
1               5                   10                  15

Gln Ile Gln

<210> SEQ ID NO 70
<211> LENGTH: 20
<212> TYPE: PRT
<213> ORGANISM: Homo sapiens

<400> SEQUENCE: 70

Ser Pro Leu Gln Asn Ile Ser Pro Trp Ile Leu Ala Val Leu Thr Leu
1               5                   10                  15

Gln Ile Gln Ser
            20

<210> SEQ ID NO 71
<211> LENGTH: 21
<212> TYPE: PRT
<213> ORGANISM: Homo sapiens
```

-continued

<400> SEQUENCE: 71

Ser Pro Leu Gln Asn Ile Ser Pro Trp Ile Leu Ala Val Leu Thr Leu
1               5                   10                  15

Gln Ile Gln Ser Leu
            20

<210> SEQ ID NO 72
<211> LENGTH: 22
<212> TYPE: PRT
<213> ORGANISM: Homo sapiens

<400> SEQUENCE: 72

Ser Pro Leu Gln Asn Ile Ser Pro Trp Ile Leu Ala Val Leu Thr Leu
1               5                   10                  15

Gln Ile Gln Ser Leu Ile
            20

<210> SEQ ID NO 73
<211> LENGTH: 23
<212> TYPE: PRT
<213> ORGANISM: Homo sapiens

<400> SEQUENCE: 73

Ser Pro Leu Gln Asn Ile Ser Pro Trp Ile Leu Ala Val Leu Thr Leu
1               5                   10                  15

Gln Ile Gln Ser Leu Ile Ser
            20

<210> SEQ ID NO 74
<211> LENGTH: 24
<212> TYPE: PRT
<213> ORGANISM: Homo sapiens

<400> SEQUENCE: 74

Ser Pro Leu Gln Asn Ile Ser Pro Trp Ile Leu Ala Val Leu Thr Leu
1               5                   10                  15

Gln Ile Gln Ser Leu Ile Ser Cys
            20

<210> SEQ ID NO 75
<211> LENGTH: 25
<212> TYPE: PRT
<213> ORGANISM: Homo sapiens

<400> SEQUENCE: 75

Ser Pro Leu Gln Asn Ile Ser Pro Trp Ile Leu Ala Val Leu Thr Leu
1               5                   10                  15

Gln Ile Gln Ser Leu Ile Ser Cys Trp
            20                  25

<210> SEQ ID NO 76
<211> LENGTH: 26
<212> TYPE: PRT
<213> ORGANISM: Homo sapiens

<400> SEQUENCE: 76

Ser Pro Leu Gln Asn Ile Ser Pro Trp Ile Leu Ala Val Leu Thr Leu
1               5                   10                  15

Gln Ile Gln Ser Leu Ile Ser Cys Trp Ala
            20                  25

-continued

```
<210> SEQ ID NO 77
<211> LENGTH: 13
<212> TYPE: PRT
<213> ORGANISM: Homo sapiens

<400> SEQUENCE: 77

Pro Leu Gln Asn Ile Ser Pro Trp Ile Leu Ala Val Leu
1               5                   10

<210> SEQ ID NO 78
<211> LENGTH: 14
<212> TYPE: PRT
<213> ORGANISM: Homo sapiens

<400> SEQUENCE: 78

Pro Leu Gln Asn Ile Ser Pro Trp Ile Leu Ala Val Leu Thr
1               5                   10

<210> SEQ ID NO 79
<211> LENGTH: 15
<212> TYPE: PRT
<213> ORGANISM: Homo sapiens

<400> SEQUENCE: 79

Pro Leu Gln Asn Ile Ser Pro Trp Ile Leu Ala Val Leu Thr Leu
1               5                   10                  15

<210> SEQ ID NO 80
<211> LENGTH: 16
<212> TYPE: PRT
<213> ORGANISM: Homo sapiens

<400> SEQUENCE: 80

Pro Leu Gln Asn Ile Ser Pro Trp Ile Leu Ala Val Leu Thr Leu Gln
1               5                   10                  15

<210> SEQ ID NO 81
<211> LENGTH: 17
<212> TYPE: PRT
<213> ORGANISM: Homo sapiens

<400> SEQUENCE: 81

Pro Leu Gln Asn Ile Ser Pro Trp Ile Leu Ala Val Leu Thr Leu Gln
1               5                   10                  15

Ile

<210> SEQ ID NO 82
<211> LENGTH: 18
<212> TYPE: PRT
<213> ORGANISM: Homo sapiens

<400> SEQUENCE: 82

Pro Leu Gln Asn Ile Ser Pro Trp Ile Leu Ala Val Leu Thr Leu Gln
1               5                   10                  15

Ile Gln

<210> SEQ ID NO 83
<211> LENGTH: 19
<212> TYPE: PRT
<213> ORGANISM: Homo sapiens

<400> SEQUENCE: 83

Pro Leu Gln Asn Ile Ser Pro Trp Ile Leu Ala Val Leu Thr Leu Gln
```

-continued

```
1               5               10              15

Ile Gln Ser

<210> SEQ ID NO 84
<211> LENGTH: 20
<212> TYPE: PRT
<213> ORGANISM: Homo sapiens

<400> SEQUENCE: 84

Pro Leu Gln Asn Ile Ser Pro Trp Ile Leu Ala Val Leu Thr Leu Gln
1               5               10              15

Ile Gln Ser Leu
        20

<210> SEQ ID NO 85
<211> LENGTH: 21
<212> TYPE: PRT
<213> ORGANISM: Homo sapiens

<400> SEQUENCE: 85

Pro Leu Gln Asn Ile Ser Pro Trp Ile Leu Ala Val Leu Thr Leu Gln
1               5               10              15

Ile Gln Ser Leu Ile
        20

<210> SEQ ID NO 86
<211> LENGTH: 22
<212> TYPE: PRT
<213> ORGANISM: Homo sapiens

<400> SEQUENCE: 86

Pro Leu Gln Asn Ile Ser Pro Trp Ile Leu Ala Val Leu Thr Leu Gln
1               5               10              15

Ile Gln Ser Leu Ile Ser
        20

<210> SEQ ID NO 87
<211> LENGTH: 23
<212> TYPE: PRT
<213> ORGANISM: Homo sapiens

<400> SEQUENCE: 87

Pro Leu Gln Asn Ile Ser Pro Trp Ile Leu Ala Val Leu Thr Leu Gln
1               5               10              15

Ile Gln Ser Leu Ile Ser Cys
        20

<210> SEQ ID NO 88
<211> LENGTH: 24
<212> TYPE: PRT
<213> ORGANISM: Homo sapiens

<400> SEQUENCE: 88

Pro Leu Gln Asn Ile Ser Pro Trp Ile Leu Ala Val Leu Thr Leu Gln
1               5               10              15

Ile Gln Ser Leu Ile Ser Cys Trp
        20

<210> SEQ ID NO 89
<211> LENGTH: 25
<212> TYPE: PRT
<213> ORGANISM: Homo sapiens
```

-continued

```
<400> SEQUENCE: 89

Pro Leu Gln Asn Ile Ser Pro Trp Ile Leu Ala Val Leu Thr Leu Gln
1               5                   10                  15

Ile Gln Ser Leu Ile Ser Cys Trp Ala
            20                  25

<210> SEQ ID NO 90
<211> LENGTH: 12
<212> TYPE: PRT
<213> ORGANISM: Homo sapiens

<400> SEQUENCE: 90

Leu Gln Asn Ile Ser Pro Trp Ile Leu Ala Val Leu
1               5                   10

<210> SEQ ID NO 91
<211> LENGTH: 13
<212> TYPE: PRT
<213> ORGANISM: Homo sapiens

<400> SEQUENCE: 91

Leu Gln Asn Ile Ser Pro Trp Ile Leu Ala Val Leu Thr
1               5                   10

<210> SEQ ID NO 92
<211> LENGTH: 14
<212> TYPE: PRT
<213> ORGANISM: Homo sapiens

<400> SEQUENCE: 92

Leu Gln Asn Ile Ser Pro Trp Ile Leu Ala Val Leu Thr Leu
1               5                   10

<210> SEQ ID NO 93
<211> LENGTH: 15
<212> TYPE: PRT
<213> ORGANISM: Homo sapiens

<400> SEQUENCE: 93

Leu Gln Asn Ile Ser Pro Trp Ile Leu Ala Val Leu Thr Leu Gln
1               5                   10                  15

<210> SEQ ID NO 94
<211> LENGTH: 16
<212> TYPE: PRT
<213> ORGANISM: Homo sapiens

<400> SEQUENCE: 94

Leu Gln Asn Ile Ser Pro Trp Ile Leu Ala Val Leu Thr Leu Gln Ile
1               5                   10                  15

<210> SEQ ID NO 95
<211> LENGTH: 17
<212> TYPE: PRT
<213> ORGANISM: Homo sapiens

<400> SEQUENCE: 95

Leu Gln Asn Ile Ser Pro Trp Ile Leu Ala Val Leu Thr Leu Gln Ile
1               5                   10                  15

Gln

<210> SEQ ID NO 96
```

-continued

```
<211> LENGTH: 18
<212> TYPE: PRT
<213> ORGANISM: Homo sapiens

<400> SEQUENCE: 96

Leu Gln Asn Ile Ser Pro Trp Ile Leu Ala Val Leu Thr Leu Gln Ile
1               5                   10                  15

Gln Ser

<210> SEQ ID NO 97
<211> LENGTH: 19
<212> TYPE: PRT
<213> ORGANISM: Homo sapiens

<400> SEQUENCE: 97

Leu Gln Asn Ile Ser Pro Trp Ile Leu Ala Val Leu Thr Leu Gln Ile
1               5                   10                  15

Gln Ser Leu

<210> SEQ ID NO 98
<211> LENGTH: 20
<212> TYPE: PRT
<213> ORGANISM: Homo sapiens

<400> SEQUENCE: 98

Leu Gln Asn Ile Ser Pro Trp Ile Leu Ala Val Leu Thr Leu Gln Ile
1               5                   10                  15

Gln Ser Leu Ile
            20

<210> SEQ ID NO 99
<211> LENGTH: 21
<212> TYPE: PRT
<213> ORGANISM: Homo sapiens

<400> SEQUENCE: 99

Leu Gln Asn Ile Ser Pro Trp Ile Leu Ala Val Leu Thr Leu Gln Ile
1               5                   10                  15

Gln Ser Leu Ile Ser
            20

<210> SEQ ID NO 100
<211> LENGTH: 22
<212> TYPE: PRT
<213> ORGANISM: Homo sapiens

<400> SEQUENCE: 100

Leu Gln Asn Ile Ser Pro Trp Ile Leu Ala Val Leu Thr Leu Gln Ile
1               5                   10                  15

Gln Ser Leu Ile Ser Cys
            20

<210> SEQ ID NO 101
<211> LENGTH: 23
<212> TYPE: PRT
<213> ORGANISM: Homo sapiens

<400> SEQUENCE: 101

Leu Gln Asn Ile Ser Pro Trp Ile Leu Ala Val Leu Thr Leu Gln Ile
1               5                   10                  15

Gln Ser Leu Ile Ser Cys Trp
            20
```

```
<210> SEQ ID NO 102
<211> LENGTH: 24
<212> TYPE: PRT
<213> ORGANISM: Homo sapiens

<400> SEQUENCE: 102

Leu Gln Asn Ile Ser Pro Trp Ile Leu Ala Val Leu Thr Leu Gln Ile
1               5                   10                  15

Gln Ser Leu Ile Ser Cys Trp Ala
            20

<210> SEQ ID NO 103
<211> LENGTH: 11
<212> TYPE: PRT
<213> ORGANISM: Homo sapiens

<400> SEQUENCE: 103

Gln Asn Ile Ser Pro Trp Ile Leu Ala Val Leu
1               5                   10

<210> SEQ ID NO 104
<211> LENGTH: 12
<212> TYPE: PRT
<213> ORGANISM: Homo sapiens

<400> SEQUENCE: 104

Gln Asn Ile Ser Pro Trp Ile Leu Ala Val Leu Thr
1               5                   10

<210> SEQ ID NO 105
<211> LENGTH: 13
<212> TYPE: PRT
<213> ORGANISM: Homo sapiens

<400> SEQUENCE: 105

Gln Asn Ile Ser Pro Trp Ile Leu Ala Val Leu Thr Leu
1               5                   10

<210> SEQ ID NO 106
<211> LENGTH: 14
<212> TYPE: PRT
<213> ORGANISM: Homo sapiens

<400> SEQUENCE: 106

Gln Asn Ile Ser Pro Trp Ile Leu Ala Val Leu Thr Leu Gln
1               5                   10

<210> SEQ ID NO 107
<211> LENGTH: 15
<212> TYPE: PRT
<213> ORGANISM: Homo sapiens

<400> SEQUENCE: 107

Gln Asn Ile Ser Pro Trp Ile Leu Ala Val Leu Thr Leu Gln Ile
1               5                   10                  15

<210> SEQ ID NO 108
<211> LENGTH: 16
<212> TYPE: PRT
<213> ORGANISM: Homo sapiens

<400> SEQUENCE: 108

Gln Asn Ile Ser Pro Trp Ile Leu Ala Val Leu Thr Leu Gln Ile Gln
```

-continued

```
1               5                   10                  15

<210> SEQ ID NO 109
<211> LENGTH: 17
<212> TYPE: PRT
<213> ORGANISM: Homo sapiens

<400> SEQUENCE: 109

Gln Asn Ile Ser Pro Trp Ile Leu Ala Val Leu Thr Leu Gln Ile Gln
1               5                   10                  15

Ser

<210> SEQ ID NO 110
<211> LENGTH: 18
<212> TYPE: PRT
<213> ORGANISM: Homo sapiens

<400> SEQUENCE: 110

Gln Asn Ile Ser Pro Trp Ile Leu Ala Val Leu Thr Leu Gln Ile Gln
1               5                   10                  15

Ser Leu

<210> SEQ ID NO 111
<211> LENGTH: 19
<212> TYPE: PRT
<213> ORGANISM: Homo sapiens

<400> SEQUENCE: 111

Gln Asn Ile Ser Pro Trp Ile Leu Ala Val Leu Thr Leu Gln Ile Gln
1               5                   10                  15

Ser Leu Ile

<210> SEQ ID NO 112
<211> LENGTH: 20
<212> TYPE: PRT
<213> ORGANISM: Homo sapiens

<400> SEQUENCE: 112

Gln Asn Ile Ser Pro Trp Ile Leu Ala Val Leu Thr Leu Gln Ile Gln
1               5                   10                  15

Ser Leu Ile Ser
            20

<210> SEQ ID NO 113
<211> LENGTH: 21
<212> TYPE: PRT
<213> ORGANISM: Homo sapiens

<400> SEQUENCE: 113

Gln Asn Ile Ser Pro Trp Ile Leu Ala Val Leu Thr Leu Gln Ile Gln
1               5                   10                  15

Ser Leu Ile Ser Cys
            20

<210> SEQ ID NO 114
<211> LENGTH: 22
<212> TYPE: PRT
<213> ORGANISM: Homo sapiens

<400> SEQUENCE: 114

Gln Asn Ile Ser Pro Trp Ile Leu Ala Val Leu Thr Leu Gln Ile Gln
1               5                   10                  15
```

Ser Leu Ile Ser Cys Trp
            20

<210> SEQ ID NO 115
<211> LENGTH: 23
<212> TYPE: PRT
<213> ORGANISM: Homo sapiens

<400> SEQUENCE: 115

Gln Asn Ile Ser Pro Trp Ile Leu Ala Val Leu Thr Leu Gln Ile Gln
1               5                   10                  15

Ser Leu Ile Ser Cys Trp Ala
            20

<210> SEQ ID NO 116
<211> LENGTH: 10
<212> TYPE: PRT
<213> ORGANISM: Homo sapiens

<400> SEQUENCE: 116

Asn Ile Ser Pro Trp Ile Leu Ala Val Leu
1               5                   10

<210> SEQ ID NO 117
<211> LENGTH: 11
<212> TYPE: PRT
<213> ORGANISM: Homo sapiens

<400> SEQUENCE: 117

Asn Ile Ser Pro Trp Ile Leu Ala Val Leu Thr
1               5                   10

<210> SEQ ID NO 118
<211> LENGTH: 12
<212> TYPE: PRT
<213> ORGANISM: Homo sapiens

<400> SEQUENCE: 118

Asn Ile Ser Pro Trp Ile Leu Ala Val Leu Thr Leu
1               5                   10

<210> SEQ ID NO 119
<211> LENGTH: 13
<212> TYPE: PRT
<213> ORGANISM: Homo sapiens

<400> SEQUENCE: 119

Asn Ile Ser Pro Trp Ile Leu Ala Val Leu Thr Leu Gln
1               5                   10

<210> SEQ ID NO 120
<211> LENGTH: 14
<212> TYPE: PRT
<213> ORGANISM: Homo sapiens

<400> SEQUENCE: 120

Asn Ile Ser Pro Trp Ile Leu Ala Val Leu Thr Leu Gln Ile
1               5                   10

<210> SEQ ID NO 121
<211> LENGTH: 15
<212> TYPE: PRT
<213> ORGANISM: Homo sapiens -continued

```
<400> SEQUENCE: 121

Asn Ile Ser Pro Trp Ile Leu Ala Val Leu Thr Leu Gln Ile Gln
1               5                   10                  15

<210> SEQ ID NO 122
<211> LENGTH: 16
<212> TYPE: PRT
<213> ORGANISM: Homo sapiens

<400> SEQUENCE: 122

Asn Ile Ser Pro Trp Ile Leu Ala Val Leu Thr Leu Gln Ile Gln Ser
1               5                   10                  15

<210> SEQ ID NO 123
<211> LENGTH: 17
<212> TYPE: PRT
<213> ORGANISM: Homo sapiens

<400> SEQUENCE: 123

Asn Ile Ser Pro Trp Ile Leu Ala Val Leu Thr Leu Gln Ile Gln Ser
1               5                   10                  15

Leu

<210> SEQ ID NO 124
<211> LENGTH: 18
<212> TYPE: PRT
<213> ORGANISM: Homo sapiens

<400> SEQUENCE: 124

Asn Ile Ser Pro Trp Ile Leu Ala Val Leu Thr Leu Gln Ile Gln Ser
1               5                   10                  15

Leu Ile

<210> SEQ ID NO 125
<211> LENGTH: 19
<212> TYPE: PRT
<213> ORGANISM: Homo sapiens

<400> SEQUENCE: 125

Asn Ile Ser Pro Trp Ile Leu Ala Val Leu Thr Leu Gln Ile Gln Ser
1               5                   10                  15

Leu Ile Ser

<210> SEQ ID NO 126
<211> LENGTH: 20
<212> TYPE: PRT
<213> ORGANISM: Homo sapiens

<400> SEQUENCE: 126

Asn Ile Ser Pro Trp Ile Leu Ala Val Leu Thr Leu Gln Ile Gln Ser
1               5                   10                  15

Leu Ile Ser Cys
            20

<210> SEQ ID NO 127
<211> LENGTH: 21
<212> TYPE: PRT
<213> ORGANISM: Homo sapiens

<400> SEQUENCE: 127

Asn Ile Ser Pro Trp Ile Leu Ala Val Leu Thr Leu Gln Ile Gln Ser
1               5                   10                  15
```

```
Leu Ile Ser Cys Trp
            20

<210> SEQ ID NO 128
<211> LENGTH: 22
<212> TYPE: PRT
<213> ORGANISM: Homo sapiens

<400> SEQUENCE: 128

Asn Ile Ser Pro Trp Ile Leu Ala Val Leu Thr Leu Gln Ile Gln Ser
1               5                   10                  15

Leu Ile Ser Cys Trp Ala
            20

<210> SEQ ID NO 129
<211> LENGTH: 10
<212> TYPE: PRT
<213> ORGANISM: Homo sapiens

<400> SEQUENCE: 129

Tyr Ile Ser Pro Trp Ile Leu Ala Val Leu
1               5                   10

<210> SEQ ID NO 130
<211> LENGTH: 11
<212> TYPE: PRT
<213> ORGANISM: Homo sapiens

<400> SEQUENCE: 130

Tyr Ile Ser Pro Trp Ile Leu Ala Val Leu Thr
1               5                   10

<210> SEQ ID NO 131
<211> LENGTH: 12
<212> TYPE: PRT
<213> ORGANISM: Homo sapiens

<400> SEQUENCE: 131

Tyr Ile Ser Pro Trp Ile Leu Ala Val Leu Thr Leu
1               5                   10

<210> SEQ ID NO 132
<211> LENGTH: 13
<212> TYPE: PRT
<213> ORGANISM: Homo sapiens

<400> SEQUENCE: 132

Tyr Ile Ser Pro Trp Ile Leu Ala Val Leu Thr Leu Gln
1               5                   10

<210> SEQ ID NO 133
<211> LENGTH: 14
<212> TYPE: PRT
<213> ORGANISM: Homo sapiens

<400> SEQUENCE: 133

Tyr Ile Ser Pro Trp Ile Leu Ala Val Leu Thr Leu Gln Ile
1               5                   10

<210> SEQ ID NO 134
<211> LENGTH: 15
<212> TYPE: PRT
<213> ORGANISM: Homo sapiens
```

-continued

```
<400> SEQUENCE: 134

Tyr Ile Ser Pro Trp Ile Leu Ala Val Leu Thr Leu Gln Ile Gln
1               5                   10                  15

<210> SEQ ID NO 135
<211> LENGTH: 16
<212> TYPE: PRT
<213> ORGANISM: Homo sapiens

<400> SEQUENCE: 135

Tyr Ile Ser Pro Trp Ile Leu Ala Val Leu Thr Leu Gln Ile Gln Ser
1               5                   10                  15

<210> SEQ ID NO 136
<211> LENGTH: 17
<212> TYPE: PRT
<213> ORGANISM: Homo sapiens

<400> SEQUENCE: 136

Tyr Ile Ser Pro Trp Ile Leu Ala Val Leu Thr Leu Gln Ile Gln Ser
1               5                   10                  15

Leu

<210> SEQ ID NO 137
<211> LENGTH: 18
<212> TYPE: PRT
<213> ORGANISM: Homo sapiens

<400> SEQUENCE: 137

Tyr Ile Ser Pro Trp Ile Leu Ala Val Leu Thr Leu Gln Ile Gln Ser
1               5                   10                  15

Leu Ile

<210> SEQ ID NO 138
<211> LENGTH: 19
<212> TYPE: PRT
<213> ORGANISM: Homo sapiens

<400> SEQUENCE: 138

Tyr Ile Ser Pro Trp Ile Leu Ala Val Leu Thr Leu Gln Ile Gln Ser
1               5                   10                  15

Leu Ile Ser

<210> SEQ ID NO 139
<211> LENGTH: 20
<212> TYPE: PRT
<213> ORGANISM: Homo sapiens

<400> SEQUENCE: 139

Tyr Ile Ser Pro Trp Ile Leu Ala Val Leu Thr Leu Gln Ile Gln Ser
1               5                   10                  15

Leu Ile Ser Cys
            20

<210> SEQ ID NO 140
<211> LENGTH: 21
<212> TYPE: PRT
<213> ORGANISM: Homo sapiens

<400> SEQUENCE: 140

Tyr Ile Ser Pro Trp Ile Leu Ala Val Leu Thr Leu Gln Ile Gln Ser
1               5                   10                  15
```

-continued

Leu Ile Ser Cys Trp
        20

<210> SEQ ID NO 141
<211> LENGTH: 22
<212> TYPE: PRT
<213> ORGANISM: Homo sapiens

<400> SEQUENCE: 141

Tyr Ile Ser Pro Trp Ile Leu Ala Val Leu Thr Leu Gln Ile Gln Ser
1               5                   10                  15

Leu Ile Ser Cys Trp Ala
        20

<210> SEQ ID NO 142
<211> LENGTH: 9
<212> TYPE: PRT
<213> ORGANISM: Homo sapiens

<400> SEQUENCE: 142

Ile Ser Pro Trp Ile Leu Ala Val Leu
1               5

<210> SEQ ID NO 143
<211> LENGTH: 10
<212> TYPE: PRT
<213> ORGANISM: Homo sapiens

<400> SEQUENCE: 143

Ile Ser Pro Trp Ile Leu Ala Val Leu Thr
1               5                   10

<210> SEQ ID NO 144
<211> LENGTH: 11
<212> TYPE: PRT
<213> ORGANISM: Homo sapiens

<400> SEQUENCE: 144

Ile Ser Pro Trp Ile Leu Ala Val Leu Thr Leu
1               5                   10

<210> SEQ ID NO 145
<211> LENGTH: 12
<212> TYPE: PRT
<213> ORGANISM: Homo sapiens

<400> SEQUENCE: 145

Ile Ser Pro Trp Ile Leu Ala Val Leu Thr Leu Gln
1               5                   10

<210> SEQ ID NO 146
<211> LENGTH: 13
<212> TYPE: PRT
<213> ORGANISM: Homo sapiens

<400> SEQUENCE: 146

Ile Ser Pro Trp Ile Leu Ala Val Leu Thr Leu Gln Ile
1               5                   10

<210> SEQ ID NO 147
<211> LENGTH: 14
<212> TYPE: PRT
<213> ORGANISM: Homo sapiens

```
<400> SEQUENCE: 147

Ile Ser Pro Trp Ile Leu Ala Val Leu Thr Leu Gln Ile Gln
1               5                   10

<210> SEQ ID NO 148
<211> LENGTH: 15
<212> TYPE: PRT
<213> ORGANISM: Homo sapiens

<400> SEQUENCE: 148

Ile Ser Pro Trp Ile Leu Ala Val Leu Thr Leu Gln Ile Gln Ser
1               5                   10                  15

<210> SEQ ID NO 149
<211> LENGTH: 16
<212> TYPE: PRT
<213> ORGANISM: Homo sapiens

<400> SEQUENCE: 149

Ile Ser Pro Trp Ile Leu Ala Val Leu Thr Leu Gln Ile Gln Ser Leu
1               5                   10                  15

<210> SEQ ID NO 150
<211> LENGTH: 17
<212> TYPE: PRT
<213> ORGANISM: Homo sapiens

<400> SEQUENCE: 150

Ile Ser Pro Trp Ile Leu Ala Val Leu Thr Leu Gln Ile Gln Ser Leu
1               5                   10                  15

Ile

<210> SEQ ID NO 151
<211> LENGTH: 18
<212> TYPE: PRT
<213> ORGANISM: Homo sapiens

<400> SEQUENCE: 151

Ile Ser Pro Trp Ile Leu Ala Val Leu Thr Leu Gln Ile Gln Ser Leu
1               5                   10                  15

Ile Ser

<210> SEQ ID NO 152
<211> LENGTH: 19
<212> TYPE: PRT
<213> ORGANISM: Homo sapiens

<400> SEQUENCE: 152

Ile Ser Pro Trp Ile Leu Ala Val Leu Thr Leu Gln Ile Gln Ser Leu
1               5                   10                  15

Ile Ser Cys

<210> SEQ ID NO 153
<211> LENGTH: 20
<212> TYPE: PRT
<213> ORGANISM: Homo sapiens

<400> SEQUENCE: 153

Ile Ser Pro Trp Ile Leu Ala Val Leu Thr Leu Gln Ile Gln Ser Leu
1               5                   10                  15

Ile Ser Cys Trp
            20
```

```
<210> SEQ ID NO 154
<211> LENGTH: 21
<212> TYPE: PRT
<213> ORGANISM: Homo sapiens

<400> SEQUENCE: 154

Ile Ser Pro Trp Ile Leu Ala Val Leu Thr Leu Gln Ile Gln Ser Leu
1               5                   10                  15

Ile Ser Cys Trp Ala
            20

<210> SEQ ID NO 155
<211> LENGTH: 8
<212> TYPE: PRT
<213> ORGANISM: Homo sapiens

<400> SEQUENCE: 155

Ser Pro Trp Ile Leu Ala Val Leu
1               5

<210> SEQ ID NO 156
<211> LENGTH: 9
<212> TYPE: PRT
<213> ORGANISM: Homo sapiens

<400> SEQUENCE: 156

Ser Pro Trp Ile Leu Ala Val Leu Thr
1               5

<210> SEQ ID NO 157
<211> LENGTH: 10
<212> TYPE: PRT
<213> ORGANISM: Homo sapiens

<400> SEQUENCE: 157

Ser Pro Trp Ile Leu Ala Val Leu Thr Leu
1               5                   10

<210> SEQ ID NO 158
<211> LENGTH: 11
<212> TYPE: PRT
<213> ORGANISM: Homo sapiens

<400> SEQUENCE: 158

Ser Pro Trp Ile Leu Ala Val Leu Thr Leu Gln
1               5                   10

<210> SEQ ID NO 159
<211> LENGTH: 12
<212> TYPE: PRT
<213> ORGANISM: Homo sapiens

<400> SEQUENCE: 159

Ser Pro Trp Ile Leu Ala Val Leu Thr Leu Gln Ile
1               5                   10

<210> SEQ ID NO 160
<211> LENGTH: 13
<212> TYPE: PRT
<213> ORGANISM: Homo sapiens

<400> SEQUENCE: 160

Ser Pro Trp Ile Leu Ala Val Leu Thr Leu Gln Ile Gln
```

-continued

```
1               5                   10

<210> SEQ ID NO 161
<211> LENGTH: 14
<212> TYPE: PRT
<213> ORGANISM: Homo sapiens

<400> SEQUENCE: 161

Ser Pro Trp Ile Leu Ala Val Leu Thr Leu Gln Ile Gln Ser
1               5                   10

<210> SEQ ID NO 162
<211> LENGTH: 15
<212> TYPE: PRT
<213> ORGANISM: Homo sapiens

<400> SEQUENCE: 162

Ser Pro Trp Ile Leu Ala Val Leu Thr Leu Gln Ile Gln Ser Leu
1               5                   10                  15

<210> SEQ ID NO 163
<211> LENGTH: 16
<212> TYPE: PRT
<213> ORGANISM: Homo sapiens

<400> SEQUENCE: 163

Ser Pro Trp Ile Leu Ala Val Leu Thr Leu Gln Ile Gln Ser Leu Ile
1               5                   10                  15

<210> SEQ ID NO 164
<211> LENGTH: 17
<212> TYPE: PRT
<213> ORGANISM: Homo sapiens

<400> SEQUENCE: 164

Ser Pro Trp Ile Leu Ala Val Leu Thr Leu Gln Ile Ser Ser Leu Ile
1               5                   10                  15

Ser

<210> SEQ ID NO 165
<211> LENGTH: 18
<212> TYPE: PRT
<213> ORGANISM: Homo sapiens

<400> SEQUENCE: 165

Ser Pro Trp Ile Leu Ala Val Leu Thr Leu Gln Ile Ser Ser Leu Ile
1               5                   10                  15

Ser Cys

<210> SEQ ID NO 166
<211> LENGTH: 19
<212> TYPE: PRT
<213> ORGANISM: Homo sapiens

<400> SEQUENCE: 166

Ser Pro Trp Ile Leu Ala Val Leu Thr Leu Gln Ile Ser Ser Leu Ile
1               5                   10                  15

Ser Cys Trp

<210> SEQ ID NO 167
<211> LENGTH: 20
<212> TYPE: PRT
<213> ORGANISM: Homo sapiens
```

<400> SEQUENCE: 167

Ser Pro Trp Ile Leu Ala Val Leu Thr Leu Gln Ile Ser Ser Leu Ile
1               5                   10                  15

Ser Cys Trp Ala
            20

<210> SEQ ID NO 168
<211> LENGTH: 7
<212> TYPE: PRT
<213> ORGANISM: Homo sapiens

<400> SEQUENCE: 168

Pro Trp Ile Leu Ala Val Leu
1               5

<210> SEQ ID NO 169
<211> LENGTH: 8
<212> TYPE: PRT
<213> ORGANISM: Homo sapiens

<400> SEQUENCE: 169

Pro Trp Ile Leu Ala Val Leu Thr
1               5

<210> SEQ ID NO 170
<211> LENGTH: 9
<212> TYPE: PRT
<213> ORGANISM: Homo sapiens

<400> SEQUENCE: 170

Pro Trp Ile Leu Ala Val Leu Thr Leu
1               5

<210> SEQ ID NO 171
<211> LENGTH: 10
<212> TYPE: PRT
<213> ORGANISM: Homo sapiens

<400> SEQUENCE: 171

Pro Trp Ile Leu Ala Val Leu Thr Leu Gln
1               5                   10

<210> SEQ ID NO 172
<211> LENGTH: 11
<212> TYPE: PRT
<213> ORGANISM: Homo sapiens

<400> SEQUENCE: 172

Pro Trp Ile Leu Ala Val Leu Thr Leu Gln Ile
1               5                   10

<210> SEQ ID NO 173
<211> LENGTH: 12
<212> TYPE: PRT
<213> ORGANISM: Homo sapiens

<400> SEQUENCE: 173

Pro Trp Ile Leu Ala Val Leu Thr Leu Gln Ile Gln
1               5                   10

<210> SEQ ID NO 174
<211> LENGTH: 13
<212> TYPE: PRT

-continued

<213> ORGANISM: Homo sapiens

<400> SEQUENCE: 174

Pro Trp Ile Leu Ala Val Leu Thr Leu Gln Ile Gln Ser
1               5                   10

<210> SEQ ID NO 175
<211> LENGTH: 14
<212> TYPE: PRT
<213> ORGANISM: Homo sapiens

<400> SEQUENCE: 175

Pro Trp Ile Leu Ala Val Leu Thr Leu Gln Ile Gln Ser Leu
1               5                   10

<210> SEQ ID NO 176
<211> LENGTH: 15
<212> TYPE: PRT
<213> ORGANISM: Homo sapiens

<400> SEQUENCE: 176

Pro Trp Ile Leu Ala Val Leu Thr Leu Gln Ile Gln Ser Leu Ile
1               5                   10                  15

<210> SEQ ID NO 177
<211> LENGTH: 16
<212> TYPE: PRT
<213> ORGANISM: Homo sapiens

<400> SEQUENCE: 177

Pro Trp Ile Leu Ala Val Leu Thr Leu Gln Ile Gln Ser Leu Ile Ser
1               5                   10                  15

<210> SEQ ID NO 178
<211> LENGTH: 17
<212> TYPE: PRT
<213> ORGANISM: Homo sapiens

<400> SEQUENCE: 178

Pro Trp Ile Leu Ala Val Leu Thr Leu Gln Ile Gln Ser Leu Ile Ser
1               5                   10                  15

Cys

<210> SEQ ID NO 179
<211> LENGTH: 18
<212> TYPE: PRT
<213> ORGANISM: Homo sapiens

<400> SEQUENCE: 179

Pro Trp Ile Leu Ala Val Leu Thr Leu Gln Ile Gln Ser Leu Ile Ser
1               5                   10                  15

Cys Trp

<210> SEQ ID NO 180
<211> LENGTH: 19
<212> TYPE: PRT
<213> ORGANISM: Homo sapiens

<400> SEQUENCE: 180

Pro Trp Ile Leu Ala Val Leu Thr Leu Gln Ile Gln Ser Leu Ile Ser
1               5                   10                  15

Cys Trp Ala

```
<210> SEQ ID NO 181
<211> LENGTH: 6
<212> TYPE: PRT
<213> ORGANISM: Homo sapiens

<400> SEQUENCE: 181

Trp Ile Leu Ala Val Leu
1               5

<210> SEQ ID NO 182
<211> LENGTH: 7
<212> TYPE: PRT
<213> ORGANISM: Homo sapiens

<400> SEQUENCE: 182

Trp Ile Leu Ala Val Leu Thr
1               5

<210> SEQ ID NO 183
<211> LENGTH: 8
<212> TYPE: PRT
<213> ORGANISM: Homo sapiens

<400> SEQUENCE: 183

Trp Ile Leu Ala Val Leu Thr Leu
1               5

<210> SEQ ID NO 184
<211> LENGTH: 9
<212> TYPE: PRT
<213> ORGANISM: Homo sapiens

<400> SEQUENCE: 184

Trp Ile Leu Ala Val Leu Thr Leu Gln
1               5

<210> SEQ ID NO 185
<211> LENGTH: 10
<212> TYPE: PRT
<213> ORGANISM: Homo sapiens

<400> SEQUENCE: 185

Trp Ile Leu Ala Val Leu Thr Leu Gln Ile
1               5                   10

<210> SEQ ID NO 186
<211> LENGTH: 11
<212> TYPE: PRT
<213> ORGANISM: Homo sapiens

<400> SEQUENCE: 186

Trp Ile Leu Ala Val Leu Thr Leu Gln Ile Gln
1               5                   10

<210> SEQ ID NO 187
<211> LENGTH: 12
<212> TYPE: PRT
<213> ORGANISM: Homo sapiens

<400> SEQUENCE: 187

Trp Ile Leu Ala Val Leu Thr Leu Gln Ile Gln Ser
1               5                   10

<210> SEQ ID NO 188
```

```
<211> LENGTH: 13
<212> TYPE: PRT
<213> ORGANISM: Homo sapiens

<400> SEQUENCE: 188

Trp Ile Leu Ala Val Leu Thr Leu Gln Ile Gln Ser Leu
1               5                   10

<210> SEQ ID NO 189
<211> LENGTH: 14
<212> TYPE: PRT
<213> ORGANISM: Homo sapiens

<400> SEQUENCE: 189

Trp Ile Leu Ala Val Leu Thr Leu Gln Ile Gln Ser Leu Ile
1               5                   10

<210> SEQ ID NO 190
<211> LENGTH: 15
<212> TYPE: PRT
<213> ORGANISM: Homo sapiens

<400> SEQUENCE: 190

Trp Ile Leu Ala Val Leu Thr Leu Gln Ile Gln Ser Leu Ile Ser
1               5                   10                  15

<210> SEQ ID NO 191
<211> LENGTH: 16
<212> TYPE: PRT
<213> ORGANISM: Homo sapiens

<400> SEQUENCE: 191

Trp Ile Leu Ala Val Leu Thr Leu Gln Ile Gln Ser Leu Ile Ser Cys
1               5                   10                  15

<210> SEQ ID NO 192
<211> LENGTH: 17
<212> TYPE: PRT
<213> ORGANISM: Homo sapiens

<400> SEQUENCE: 192

Trp Ile Leu Ala Val Leu Thr Leu Gln Ile Gln Ser Leu Ile Ser Cys
1               5                   10                  15

Trp

<210> SEQ ID NO 193
<211> LENGTH: 18
<212> TYPE: PRT
<213> ORGANISM: Homo sapiens

<400> SEQUENCE: 193

Trp Ile Leu Ala Val Leu Thr Leu Gln Ile Gln Ser Leu Ile Ser Cys
1               5                   10                  15

Trp Ala

<210> SEQ ID NO 194
<211> LENGTH: 5
<212> TYPE: PRT
<213> ORGANISM: Homo sapiens

<400> SEQUENCE: 194

Ile Leu Ala Val Leu
1               5
```

<210> SEQ ID NO 195
<211> LENGTH: 6
<212> TYPE: PRT
<213> ORGANISM: Homo sapiens

<400> SEQUENCE: 195

Ile Leu Ala Val Leu Thr
1               5

<210> SEQ ID NO 196
<211> LENGTH: 7
<212> TYPE: PRT
<213> ORGANISM: Homo sapiens

<400> SEQUENCE: 196

Ile Leu Ala Val Leu Thr Leu
1               5

<210> SEQ ID NO 197
<211> LENGTH: 8
<212> TYPE: PRT
<213> ORGANISM: Homo sapiens

<400> SEQUENCE: 197

Ile Leu Ala Val Leu Thr Leu Gln
1               5

<210> SEQ ID NO 198
<211> LENGTH: 9
<212> TYPE: PRT
<213> ORGANISM: Homo sapiens

<400> SEQUENCE: 198

Ile Leu Ala Val Leu Thr Leu Gln Ile
1               5

<210> SEQ ID NO 199
<211> LENGTH: 10
<212> TYPE: PRT
<213> ORGANISM: Homo sapiens

<400> SEQUENCE: 199

Ile Leu Ala Val Leu Thr Leu Gln Ile Gln
1               5                   10

<210> SEQ ID NO 200
<211> LENGTH: 11
<212> TYPE: PRT
<213> ORGANISM: Homo sapiens

<400> SEQUENCE: 200

Ile Leu Ala Val Leu Thr Leu Gln Ile Gln Ser
1               5                   10

<210> SEQ ID NO 201
<211> LENGTH: 12
<212> TYPE: PRT
<213> ORGANISM: Homo sapiens

<400> SEQUENCE: 201

Ile Leu Ala Val Leu Thr Leu Gln Ile Gln Ser Leu
1               5                   10

<210> SEQ ID NO 202

-continued

```
<211> LENGTH: 13
<212> TYPE: PRT
<213> ORGANISM: Homo sapiens

<400> SEQUENCE: 202

Ile Leu Ala Val Leu Thr Leu Gln Ile Gln Ser Leu Ile
1               5                   10

<210> SEQ ID NO 203
<211> LENGTH: 14
<212> TYPE: PRT
<213> ORGANISM: Homo sapiens

<400> SEQUENCE: 203

Ile Leu Ala Val Leu Thr Leu Gln Ile Gln Ser Leu Ile Ser
1               5                   10

<210> SEQ ID NO 204
<211> LENGTH: 15
<212> TYPE: PRT
<213> ORGANISM: Homo sapiens

<400> SEQUENCE: 204

Ile Leu Ala Val Leu Thr Leu Gln Ile Gln Ser Leu Ile Ser Cys
1               5                   10                  15

<210> SEQ ID NO 205
<211> LENGTH: 16
<212> TYPE: PRT
<213> ORGANISM: Homo sapiens

<400> SEQUENCE: 205

Ile Leu Ala Val Leu Thr Leu Gln Ile Gln Ser Leu Ile Ser Cys Trp
1               5                   10                  15

<210> SEQ ID NO 206
<211> LENGTH: 17
<212> TYPE: PRT
<213> ORGANISM: Homo sapiens

<400> SEQUENCE: 206

Ile Leu Ala Val Leu Thr Leu Gln Ile Gln Ser Leu Ile Ser Cys Trp
1               5                   10                  15

Ala

<210> SEQ ID NO 207
<211> LENGTH: 18
<212> TYPE: PRT
<213> ORGANISM: Homo sapiens

<400> SEQUENCE: 207

Glu Val Leu Gly Gly Val Ile Ala Gly Gly Leu Val Gly Leu Ile Phe
1               5                   10                  15

Ala Val

<210> SEQ ID NO 208
<211> LENGTH: 19
<212> TYPE: PRT
<213> ORGANISM: Homo sapiens

<400> SEQUENCE: 208

Glu Val Leu Gly Gly Val Ile Ala Gly Gly Leu Val Gly Leu Ile Phe
1               5                   10                  15
```

-continued

```
Ala Val Cys

<210> SEQ ID NO 209
<211> LENGTH: 20
<212> TYPE: PRT
<213> ORGANISM: Homo sapiens

<400> SEQUENCE: 209

Glu Val Leu Gly Gly Val Ile Ala Gly Gly Leu Val Gly Leu Ile Phe
1               5                   10                  15

Ala Val Cys Leu
            20

<210> SEQ ID NO 210
<211> LENGTH: 21
<212> TYPE: PRT
<213> ORGANISM: Homo sapiens

<400> SEQUENCE: 210

Glu Val Leu Gly Gly Val Ile Ala Gly Gly Leu Val Gly Leu Ile Phe
1               5                   10                  15

Ala Val Cys Leu Val
            20

<210> SEQ ID NO 211
<211> LENGTH: 22
<212> TYPE: PRT
<213> ORGANISM: Homo sapiens

<400> SEQUENCE: 211

Glu Val Leu Gly Gly Val Ile Ala Gly Gly Leu Val Gly Leu Ile Phe
1               5                   10                  15

Ala Val Cys Leu Val Gly
            20

<210> SEQ ID NO 212
<211> LENGTH: 23
<212> TYPE: PRT
<213> ORGANISM: Homo sapiens

<400> SEQUENCE: 212

Glu Val Leu Gly Gly Val Ile Ala Gly Gly Leu Val Gly Leu Ile Phe
1               5                   10                  15

Ala Val Cys Leu Val Gly Phe
            20

<210> SEQ ID NO 213
<211> LENGTH: 24
<212> TYPE: PRT
<213> ORGANISM: Homo sapiens

<400> SEQUENCE: 213

Glu Val Leu Gly Gly Val Ile Ala Gly Gly Leu Val Gly Leu Ile Phe
1               5                   10                  15

Ala Val Cys Leu Val Gly Phe Met
            20

<210> SEQ ID NO 214
<211> LENGTH: 25
<212> TYPE: PRT
<213> ORGANISM: Homo sapiens

<400> SEQUENCE: 214
```

-continued

```
Glu Val Leu Gly Gly Val Ile Ala Gly Gly Leu Val Gly Leu Ile Phe
1               5                   10                  15

Ala Val Cys Leu Val Gly Phe Met Leu
            20                  25

<210> SEQ ID NO 215
<211> LENGTH: 26
<212> TYPE: PRT
<213> ORGANISM: Homo sapiens

<400> SEQUENCE: 215

Glu Val Leu Gly Gly Val Ile Ala Gly Gly Leu Val Gly Leu Ile Phe
1               5                   10                  15

Ala Val Cys Leu Val Gly Phe Met Leu Tyr
            20                  25

<210> SEQ ID NO 216
<211> LENGTH: 27
<212> TYPE: PRT
<213> ORGANISM: Homo sapiens

<400> SEQUENCE: 216

Glu Val Leu Gly Gly Val Ile Ala Gly Gly Leu Val Gly Leu Ile Phe
1               5                   10                  15

Ala Val Cys Leu Val Gly Phe Met Leu Tyr Arg
            20                  25

<210> SEQ ID NO 217
<211> LENGTH: 28
<212> TYPE: PRT
<213> ORGANISM: Homo sapiens

<400> SEQUENCE: 217

Glu Val Leu Gly Gly Val Ile Ala Gly Gly Leu Val Gly Leu Ile Phe
1               5                   10                  15

Ala Val Cys Leu Val Gly Phe Met Leu Tyr Arg Met
            20                  25

<210> SEQ ID NO 218
<211> LENGTH: 17
<212> TYPE: PRT
<213> ORGANISM: Homo sapiens

<400> SEQUENCE: 218

Val Leu Gly Gly Val Ile Ala Gly Gly Leu Val Gly Leu Ile Phe Ala
1               5                   10                  15

Val

<210> SEQ ID NO 219
<211> LENGTH: 18
<212> TYPE: PRT
<213> ORGANISM: Homo sapiens

<400> SEQUENCE: 219

Val Leu Gly Gly Val Ile Ala Gly Gly Leu Val Gly Leu Ile Phe Ala
1               5                   10                  15

Val Cys

<210> SEQ ID NO 220
<211> LENGTH: 19
<212> TYPE: PRT
```

-continued

```
<213> ORGANISM: Homo sapiens

<400> SEQUENCE: 220

Val Leu Gly Gly Val Ile Ala Gly Gly Leu Val Gly Leu Ile Phe Ala
1               5                   10                  15

Val Cys Leu

<210> SEQ ID NO 221
<211> LENGTH: 20
<212> TYPE: PRT
<213> ORGANISM: Homo sapiens

<400> SEQUENCE: 221

Val Leu Gly Gly Val Ile Ala Gly Gly Leu Val Gly Leu Ile Phe Ala
1               5                   10                  15

Val Cys Leu Val
            20

<210> SEQ ID NO 222
<211> LENGTH: 21
<212> TYPE: PRT
<213> ORGANISM: Homo sapiens

<400> SEQUENCE: 222

Val Leu Gly Gly Val Ile Ala Gly Gly Leu Val Gly Leu Ile Phe Ala
1               5                   10                  15

Val Cys Leu Val Gly
            20

<210> SEQ ID NO 223
<211> LENGTH: 22
<212> TYPE: PRT
<213> ORGANISM: Homo sapiens

<400> SEQUENCE: 223

Val Leu Gly Gly Val Ile Ala Gly Gly Leu Val Gly Leu Ile Phe Ala
1               5                   10                  15

Val Cys Leu Val Gly Phe
            20

<210> SEQ ID NO 224
<211> LENGTH: 23
<212> TYPE: PRT
<213> ORGANISM: Homo sapiens

<400> SEQUENCE: 224

Val Leu Gly Gly Val Ile Ala Gly Gly Leu Val Gly Leu Ile Phe Ala
1               5                   10                  15

Val Cys Leu Val Gly Phe Met
            20

<210> SEQ ID NO 225
<211> LENGTH: 24
<212> TYPE: PRT
<213> ORGANISM: Homo sapiens

<400> SEQUENCE: 225

Val Leu Gly Gly Val Ile Ala Gly Gly Leu Val Gly Leu Ile Phe Ala
1               5                   10                  15

Val Cys Leu Val Gly Phe Met Leu
            20
```

```
<210> SEQ ID NO 226
<211> LENGTH: 25
<212> TYPE: PRT
<213> ORGANISM: Homo sapiens

<400> SEQUENCE: 226

Val Leu Gly Gly Val Ile Ala Gly Gly Leu Val Gly Leu Ile Phe Ala
1               5                   10                  15

Val Cys Leu Val Gly Phe Met Leu Tyr
            20                  25

<210> SEQ ID NO 227
<211> LENGTH: 26
<212> TYPE: PRT
<213> ORGANISM: Homo sapiens

<400> SEQUENCE: 227

Val Leu Gly Gly Val Ile Ala Gly Gly Leu Val Gly Leu Ile Phe Ala
1               5                   10                  15

Val Cys Leu Val Gly Phe Met Leu Tyr Arg
            20                  25

<210> SEQ ID NO 228
<211> LENGTH: 27
<212> TYPE: PRT
<213> ORGANISM: Homo sapiens

<400> SEQUENCE: 228

Val Leu Gly Gly Val Ile Ala Gly Gly Leu Val Gly Leu Ile Phe Ala
1               5                   10                  15

Val Cys Leu Val Gly Phe Met Leu Tyr Arg Met
            20                  25

<210> SEQ ID NO 229
<211> LENGTH: 16
<212> TYPE: PRT
<213> ORGANISM: Homo sapiens

<400> SEQUENCE: 229

Leu Gly Gly Val Ile Ala Gly Gly Leu Val Gly Leu Ile Phe Ala Val
1               5                   10                  15

<210> SEQ ID NO 230
<211> LENGTH: 17
<212> TYPE: PRT
<213> ORGANISM: Homo sapiens

<400> SEQUENCE: 230

Leu Gly Gly Val Ile Ala Gly Gly Leu Val Gly Leu Ile Phe Ala Val
1               5                   10                  15

Cys

<210> SEQ ID NO 231
<211> LENGTH: 18
<212> TYPE: PRT
<213> ORGANISM: Homo sapiens

<400> SEQUENCE: 231

Leu Gly Gly Val Ile Ala Gly Gly Leu Val Gly Leu Ile Phe Ala Val
1               5                   10                  15

Cys Leu
```

-continued

<210> SEQ ID NO 232
<211> LENGTH: 19
<212> TYPE: PRT
<213> ORGANISM: Homo sapiens

<400> SEQUENCE: 232

Leu Gly Gly Val Ile Ala Gly Gly Leu Val Gly Leu Ile Phe Ala Val
1               5                   10                  15

Cys Leu Val

<210> SEQ ID NO 233
<211> LENGTH: 20
<212> TYPE: PRT
<213> ORGANISM: Homo sapiens

<400> SEQUENCE: 233

Leu Gly Gly Val Ile Ala Gly Gly Leu Val Gly Leu Ile Phe Ala Val
1               5                   10                  15

Cys Leu Val Gly
            20

<210> SEQ ID NO 234
<211> LENGTH: 21
<212> TYPE: PRT
<213> ORGANISM: Homo sapiens

<400> SEQUENCE: 234

Leu Gly Gly Val Ile Ala Gly Gly Leu Val Gly Leu Ile Phe Ala Val
1               5                   10                  15

Cys Leu Val Gly Phe
            20

<210> SEQ ID NO 235
<211> LENGTH: 22
<212> TYPE: PRT
<213> ORGANISM: Homo sapiens

<400> SEQUENCE: 235

Leu Gly Gly Val Ile Ala Gly Gly Leu Val Gly Leu Ile Phe Ala Val
1               5                   10                  15

Cys Leu Val Gly Phe Met
            20

<210> SEQ ID NO 236
<211> LENGTH: 23
<212> TYPE: PRT
<213> ORGANISM: Homo sapiens

<400> SEQUENCE: 236

Leu Gly Gly Val Ile Ala Gly Gly Leu Val Gly Leu Ile Phe Ala Val
1               5                   10                  15

Cys Leu Val Gly Phe Met Leu
            20

<210> SEQ ID NO 237
<211> LENGTH: 24
<212> TYPE: PRT
<213> ORGANISM: Homo sapiens

<400> SEQUENCE: 237

Leu Gly Gly Val Ile Ala Gly Gly Leu Val Gly Leu Ile Phe Ala Val
1               5                   10                  15

-continued

```
Cys Leu Val Gly Phe Met Leu Tyr
            20

<210> SEQ ID NO 238
<211> LENGTH: 25
<212> TYPE: PRT
<213> ORGANISM: Homo sapiens

<400> SEQUENCE: 238

Leu Gly Gly Val Ile Ala Gly Gly Leu Val Gly Leu Ile Phe Ala Val
1               5                   10                  15

Cys Leu Val Gly Phe Met Leu Tyr Arg
            20                  25

<210> SEQ ID NO 239
<211> LENGTH: 26
<212> TYPE: PRT
<213> ORGANISM: Homo sapiens

<400> SEQUENCE: 239

Leu Gly Gly Val Ile Ala Gly Gly Leu Val Gly Leu Ile Phe Ala Val
1               5                   10                  15

Cys Leu Val Gly Phe Met Leu Tyr Arg Met
            20                  25

<210> SEQ ID NO 240
<211> LENGTH: 15
<212> TYPE: PRT
<213> ORGANISM: Homo sapiens

<400> SEQUENCE: 240

Gly Gly Val Ile Ala Gly Gly Leu Val Gly Leu Ile Phe Ala Val
1               5                   10                  15

<210> SEQ ID NO 241
<211> LENGTH: 16
<212> TYPE: PRT
<213> ORGANISM: Homo sapiens

<400> SEQUENCE: 241

Gly Gly Val Ile Ala Gly Gly Leu Val Gly Leu Ile Phe Ala Val Cys
1               5                   10                  15

<210> SEQ ID NO 242
<211> LENGTH: 17
<212> TYPE: PRT
<213> ORGANISM: Homo sapiens

<400> SEQUENCE: 242

Gly Gly Val Ile Ala Gly Gly Leu Val Gly Leu Ile Phe Ala Val Cys
1               5                   10                  15

Leu

<210> SEQ ID NO 243
<211> LENGTH: 18
<212> TYPE: PRT
<213> ORGANISM: Homo sapiens

<400> SEQUENCE: 243

Gly Gly Val Ile Ala Gly Gly Leu Val Gly Leu Ile Phe Ala Val Cys
1               5                   10                  15

Leu Val
```

-continued

```
<210> SEQ ID NO 244
<211> LENGTH: 19
<212> TYPE: PRT
<213> ORGANISM: Homo sapiens

<400> SEQUENCE: 244

Gly Gly Val Ile Ala Gly Gly Leu Val Gly Leu Ile Phe Ala Val Cys
1               5                   10                  15

Leu Val Gly

<210> SEQ ID NO 245
<211> LENGTH: 20
<212> TYPE: PRT
<213> ORGANISM: Homo sapiens

<400> SEQUENCE: 245

Gly Gly Val Ile Ala Gly Gly Leu Val Gly Leu Ile Phe Ala Val Cys
1               5                   10                  15

Leu Val Gly Phe
            20

<210> SEQ ID NO 246
<211> LENGTH: 21
<212> TYPE: PRT
<213> ORGANISM: Homo sapiens

<400> SEQUENCE: 246

Gly Gly Val Ile Ala Gly Gly Leu Val Gly Leu Ile Phe Ala Val Cys
1               5                   10                  15

Leu Val Gly Phe Met
            20

<210> SEQ ID NO 247
<211> LENGTH: 22
<212> TYPE: PRT
<213> ORGANISM: Homo sapiens

<400> SEQUENCE: 247

Gly Gly Val Ile Ala Gly Gly Leu Val Gly Leu Ile Phe Ala Val Cys
1               5                   10                  15

Leu Val Gly Phe Met Leu
            20

<210> SEQ ID NO 248
<211> LENGTH: 23
<212> TYPE: PRT
<213> ORGANISM: Homo sapiens

<400> SEQUENCE: 248

Gly Gly Val Ile Ala Gly Gly Leu Val Gly Leu Ile Phe Ala Val Cys
1               5                   10                  15

Leu Val Gly Phe Met Leu Tyr
            20

<210> SEQ ID NO 249
<211> LENGTH: 24
<212> TYPE: PRT
<213> ORGANISM: Homo sapiens

<400> SEQUENCE: 249

Gly Gly Val Ile Ala Gly Gly Leu Val Gly Leu Ile Phe Ala Val Cys
```

-continued

```
1               5               10              15

Leu Val Gly Phe Met Leu Tyr Arg
            20

<210> SEQ ID NO 250
<211> LENGTH: 25
<212> TYPE: PRT
<213> ORGANISM: Homo sapiens

<400> SEQUENCE: 250

Gly Gly Val Ile Ala Gly Gly Leu Val Gly Leu Ile Phe Ala Val Cys
1               5               10              15

Leu Val Gly Phe Met Leu Tyr Arg Met
            20              25

<210> SEQ ID NO 251
<211> LENGTH: 14
<212> TYPE: PRT
<213> ORGANISM: Homo sapiens

<400> SEQUENCE: 251

Gly Val Ile Ala Gly Gly Leu Val Gly Leu Ile Phe Ala Val
1               5               10

<210> SEQ ID NO 252
<211> LENGTH: 15
<212> TYPE: PRT
<213> ORGANISM: Homo sapiens

<400> SEQUENCE: 252

Gly Val Ile Ala Gly Gly Leu Val Gly Leu Ile Phe Ala Val Cys
1               5               10              15

<210> SEQ ID NO 253
<211> LENGTH: 16
<212> TYPE: PRT
<213> ORGANISM: Homo sapiens

<400> SEQUENCE: 253

Gly Val Ile Ala Gly Gly Leu Val Gly Leu Ile Phe Ala Val Cys Leu
1               5               10              15

<210> SEQ ID NO 254
<211> LENGTH: 17
<212> TYPE: PRT
<213> ORGANISM: Homo sapiens

<400> SEQUENCE: 254

Gly Val Ile Ala Gly Gly Leu Val Gly Leu Ile Phe Ala Val Cys Leu
1               5               10              15

Val

<210> SEQ ID NO 255
<211> LENGTH: 18
<212> TYPE: PRT
<213> ORGANISM: Homo sapiens

<400> SEQUENCE: 255

Gly Val Ile Ala Gly Gly Leu Val Gly Leu Ile Phe Ala Val Cys Leu
1               5               10              15

Val Gly
```

-continued

```
<210> SEQ ID NO 256
<211> LENGTH: 19
<212> TYPE: PRT
<213> ORGANISM: Homo sapiens

<400> SEQUENCE: 256

Gly Val Ile Ala Gly Gly Leu Val Gly Leu Ile Phe Ala Val Cys Leu
1               5                   10                  15

Val Gly Phe

<210> SEQ ID NO 257
<211> LENGTH: 20
<212> TYPE: PRT
<213> ORGANISM: Homo sapiens

<400> SEQUENCE: 257

Gly Val Ile Ala Gly Gly Leu Val Gly Leu Ile Phe Ala Val Cys Leu
1               5                   10                  15

Val Gly Phe Met
            20

<210> SEQ ID NO 258
<211> LENGTH: 21
<212> TYPE: PRT
<213> ORGANISM: Homo sapiens

<400> SEQUENCE: 258

Gly Val Ile Ala Gly Gly Leu Val Gly Leu Ile Phe Ala Val Cys Leu
1               5                   10                  15

Val Gly Phe Met Leu
            20

<210> SEQ ID NO 259
<211> LENGTH: 22
<212> TYPE: PRT
<213> ORGANISM: Homo sapiens

<400> SEQUENCE: 259

Gly Val Ile Ala Gly Gly Leu Val Gly Leu Ile Phe Ala Val Cys Leu
1               5                   10                  15

Val Gly Phe Met Leu Tyr
            20

<210> SEQ ID NO 260
<211> LENGTH: 23
<212> TYPE: PRT
<213> ORGANISM: Homo sapiens

<400> SEQUENCE: 260

Gly Val Ile Ala Gly Gly Leu Val Gly Leu Ile Phe Ala Val Cys Leu
1               5                   10                  15

Val Gly Phe Met Leu Tyr Arg
            20

<210> SEQ ID NO 261
<211> LENGTH: 24
<212> TYPE: PRT
<213> ORGANISM: Homo sapiens

<400> SEQUENCE: 261

Gly Val Ile Ala Gly Gly Leu Val Gly Leu Ile Phe Ala Val Cys Leu
1               5                   10                  15
```

```
Val Gly Phe Met Leu Tyr Arg Met
          20

<210> SEQ ID NO 262
<211> LENGTH: 13
<212> TYPE: PRT
<213> ORGANISM: Homo sapiens

<400> SEQUENCE: 262

Val Ile Ala Gly Gly Leu Val Gly Leu Ile Phe Ala Val
1               5                   10

<210> SEQ ID NO 263
<211> LENGTH: 14
<212> TYPE: PRT
<213> ORGANISM: Homo sapiens

<400> SEQUENCE: 263

Val Ile Ala Gly Gly Leu Val Gly Leu Ile Phe Ala Val Cys
1               5                   10

<210> SEQ ID NO 264
<211> LENGTH: 15
<212> TYPE: PRT
<213> ORGANISM: Homo sapiens

<400> SEQUENCE: 264

Val Ile Ala Gly Gly Leu Val Gly Leu Ile Phe Ala Val Cys Leu
1               5                   10                  15

<210> SEQ ID NO 265
<211> LENGTH: 16
<212> TYPE: PRT
<213> ORGANISM: Homo sapiens

<400> SEQUENCE: 265

Val Ile Ala Gly Gly Leu Val Gly Leu Ile Phe Ala Val Cys Leu Val
1               5                   10                  15

<210> SEQ ID NO 266
<211> LENGTH: 17
<212> TYPE: PRT
<213> ORGANISM: Homo sapiens

<400> SEQUENCE: 266

Val Ile Ala Gly Gly Leu Val Gly Leu Ile Phe Ala Val Cys Leu Val
1               5                   10                  15

Gly

<210> SEQ ID NO 267
<211> LENGTH: 18
<212> TYPE: PRT
<213> ORGANISM: Homo sapiens

<400> SEQUENCE: 267

Val Ile Ala Gly Gly Leu Val Gly Leu Ile Phe Ala Val Cys Leu Val
1               5                   10                  15

Gly Phe

<210> SEQ ID NO 268
<211> LENGTH: 19
<212> TYPE: PRT
<213> ORGANISM: Homo sapiens
```

<400> SEQUENCE: 268

Val Ile Ala Gly Gly Leu Val Gly Leu Ile Phe Ala Val Cys Leu Val
1               5                   10                  15

Gly Phe Met

<210> SEQ ID NO 269
<211> LENGTH: 20
<212> TYPE: PRT
<213> ORGANISM: Homo sapiens

<400> SEQUENCE: 269

Val Ile Ala Gly Gly Leu Val Gly Leu Ile Phe Ala Val Cys Leu Val
1               5                   10                  15

Gly Phe Met Leu
            20

<210> SEQ ID NO 270
<211> LENGTH: 21
<212> TYPE: PRT
<213> ORGANISM: Homo sapiens

<400> SEQUENCE: 270

Val Ile Ala Gly Gly Leu Val Gly Leu Ile Phe Ala Val Cys Leu Val
1               5                   10                  15

Gly Phe Met Leu Tyr
            20

<210> SEQ ID NO 271
<211> LENGTH: 22
<212> TYPE: PRT
<213> ORGANISM: Homo sapiens

<400> SEQUENCE: 271

Val Ile Ala Gly Gly Leu Val Gly Leu Ile Phe Ala Val Cys Leu Val
1               5                   10                  15

Gly Phe Met Leu Tyr Arg
            20

<210> SEQ ID NO 272
<211> LENGTH: 23
<212> TYPE: PRT
<213> ORGANISM: Homo sapiens

<400> SEQUENCE: 272

Val Ile Ala Gly Gly Leu Val Gly Leu Ile Phe Ala Val Cys Leu Val
1               5                   10                  15

Gly Phe Met Leu Tyr Arg Met
            20

<210> SEQ ID NO 273
<211> LENGTH: 12
<212> TYPE: PRT
<213> ORGANISM: Homo sapiens

<400> SEQUENCE: 273

Ile Ala Gly Gly Leu Val Gly Leu Ile Phe Ala Val
1               5                   10

<210> SEQ ID NO 274
<211> LENGTH: 13
<212> TYPE: PRT
<213> ORGANISM: Homo sapiens -continued

<400> SEQUENCE: 274

Ile Ala Gly Gly Leu Val Gly Leu Ile Phe Ala Val Cys
1               5                   10

<210> SEQ ID NO 275
<211> LENGTH: 14
<212> TYPE: PRT
<213> ORGANISM: Homo sapiens

<400> SEQUENCE: 275

Ile Ala Gly Gly Leu Val Gly Leu Ile Phe Ala Val Cys Leu
1               5                   10

<210> SEQ ID NO 276
<211> LENGTH: 15
<212> TYPE: PRT
<213> ORGANISM: Homo sapiens

<400> SEQUENCE: 276

Ile Ala Gly Gly Leu Val Gly Leu Ile Phe Ala Val Cys Leu Val
1               5                   10                  15

<210> SEQ ID NO 277
<211> LENGTH: 16
<212> TYPE: PRT
<213> ORGANISM: Homo sapiens

<400> SEQUENCE: 277

Ile Ala Gly Gly Leu Val Gly Leu Ile Phe Ala Val Cys Leu Val Gly
1               5                   10                  15

<210> SEQ ID NO 278
<211> LENGTH: 17
<212> TYPE: PRT
<213> ORGANISM: Homo sapiens

<400> SEQUENCE: 278

Ile Ala Gly Gly Leu Val Gly Leu Ile Phe Ala Val Cys Leu Val Gly
1               5                   10                  15

Phe

<210> SEQ ID NO 279
<211> LENGTH: 18
<212> TYPE: PRT
<213> ORGANISM: Homo sapiens

<400> SEQUENCE: 279

Ile Ala Gly Gly Leu Val Gly Leu Ile Phe Ala Val Cys Leu Val Gly
1               5                   10                  15

Phe Met

<210> SEQ ID NO 280
<211> LENGTH: 19
<212> TYPE: PRT
<213> ORGANISM: Homo sapiens

<400> SEQUENCE: 280

Ile Ala Gly Gly Leu Val Gly Leu Ile Phe Ala Val Cys Leu Val Gly
1               5                   10                  15

Phe Met Leu

```
<210> SEQ ID NO 281
<211> LENGTH: 20
<212> TYPE: PRT
<213> ORGANISM: Homo sapiens

<400> SEQUENCE: 281

Ile Ala Gly Gly Leu Val Gly Leu Ile Phe Ala Val Cys Leu Val Gly
1               5                   10                  15

Phe Met Leu Tyr
            20

<210> SEQ ID NO 282
<211> LENGTH: 21
<212> TYPE: PRT
<213> ORGANISM: Homo sapiens

<400> SEQUENCE: 282

Ile Ala Gly Gly Leu Val Gly Leu Ile Phe Ala Val Cys Leu Val Gly
1               5                   10                  15

Phe Met Leu Tyr Arg
            20

<210> SEQ ID NO 283
<211> LENGTH: 22
<212> TYPE: PRT
<213> ORGANISM: Homo sapiens

<400> SEQUENCE: 283

Ile Ala Gly Gly Leu Val Gly Leu Ile Phe Ala Val Cys Leu Val Gly
1               5                   10                  15

Phe Met Leu Tyr Arg Met
            20

<210> SEQ ID NO 284
<211> LENGTH: 11
<212> TYPE: PRT
<213> ORGANISM: Homo sapiens

<400> SEQUENCE: 284

Ala Gly Gly Leu Val Gly Leu Ile Phe Ala Val
1               5                   10

<210> SEQ ID NO 285
<211> LENGTH: 12
<212> TYPE: PRT
<213> ORGANISM: Homo sapiens

<400> SEQUENCE: 285

Ala Gly Gly Leu Val Gly Leu Ile Phe Ala Val Cys
1               5                   10

<210> SEQ ID NO 286
<211> LENGTH: 13
<212> TYPE: PRT
<213> ORGANISM: Homo sapiens

<400> SEQUENCE: 286

Ala Gly Gly Leu Val Gly Leu Ile Phe Ala Val Cys Leu
1               5                   10

<210> SEQ ID NO 287
<211> LENGTH: 14
<212> TYPE: PRT
<213> ORGANISM: Homo sapiens
```

<400> SEQUENCE: 287

Ala Gly Gly Leu Val Gly Leu Ile Phe Ala Val Cys Leu Val
1               5                   10

<210> SEQ ID NO 288
<211> LENGTH: 15
<212> TYPE: PRT
<213> ORGANISM: Homo sapiens

<400> SEQUENCE: 288

Ala Gly Gly Leu Val Gly Leu Ile Phe Ala Val Cys Leu Val Gly
1               5                   10                  15

<210> SEQ ID NO 289
<211> LENGTH: 16
<212> TYPE: PRT
<213> ORGANISM: Homo sapiens

<400> SEQUENCE: 289

Ala Gly Gly Leu Val Gly Leu Ile Phe Ala Val Cys Leu Val Gly Phe
1               5                   10                  15

<210> SEQ ID NO 290
<211> LENGTH: 17
<212> TYPE: PRT
<213> ORGANISM: Homo sapiens

<400> SEQUENCE: 290

Ala Gly Gly Leu Val Gly Leu Ile Phe Ala Val Cys Leu Val Gly Phe
1               5                   10                  15

Met

<210> SEQ ID NO 291
<211> LENGTH: 18
<212> TYPE: PRT
<213> ORGANISM: Homo sapiens

<400> SEQUENCE: 291

Ala Gly Gly Leu Val Gly Leu Ile Phe Ala Val Cys Leu Val Gly Phe
1               5                   10                  15

Met Leu

<210> SEQ ID NO 292
<211> LENGTH: 19
<212> TYPE: PRT
<213> ORGANISM: Homo sapiens

<400> SEQUENCE: 292

Ala Gly Gly Leu Val Gly Leu Ile Phe Ala Val Cys Leu Val Gly Phe
1               5                   10                  15

Met Leu Tyr

<210> SEQ ID NO 293
<211> LENGTH: 20
<212> TYPE: PRT
<213> ORGANISM: Homo sapiens

<400> SEQUENCE: 293

Ala Gly Gly Leu Val Gly Leu Ile Phe Ala Val Cys Leu Val Gly Phe
1               5                   10                  15

Met Leu Tyr Arg

```
                    20

<210> SEQ ID NO 294
<211> LENGTH: 21
<212> TYPE: PRT
<213> ORGANISM: Homo sapiens

<400> SEQUENCE: 294

Ala Gly Gly Leu Val Gly Leu Ile Phe Ala Val Cys Leu Val Gly Phe
1               5                   10                  15

Met Leu Tyr Arg Met
            20

<210> SEQ ID NO 295
<211> LENGTH: 10
<212> TYPE: PRT
<213> ORGANISM: Homo sapiens

<400> SEQUENCE: 295

Gly Gly Leu Val Gly Leu Ile Phe Ala Val
1               5                   10

<210> SEQ ID NO 296
<211> LENGTH: 11
<212> TYPE: PRT
<213> ORGANISM: Homo sapiens

<400> SEQUENCE: 296

Gly Gly Leu Val Gly Leu Ile Phe Ala Val Cys
1               5                   10

<210> SEQ ID NO 297
<211> LENGTH: 12
<212> TYPE: PRT
<213> ORGANISM: Homo sapiens

<400> SEQUENCE: 297

Gly Gly Leu Val Gly Leu Ile Phe Ala Val Cys Leu
1               5                   10

<210> SEQ ID NO 298
<211> LENGTH: 13
<212> TYPE: PRT
<213> ORGANISM: Homo sapiens

<400> SEQUENCE: 298

Gly Gly Leu Val Gly Leu Ile Phe Ala Val Cys Leu Val
1               5                   10

<210> SEQ ID NO 299
<211> LENGTH: 14
<212> TYPE: PRT
<213> ORGANISM: Homo sapiens

<400> SEQUENCE: 299

Gly Gly Leu Val Gly Leu Ile Phe Ala Val Cys Leu Val Gly
1               5                   10

<210> SEQ ID NO 300
<211> LENGTH: 15
<212> TYPE: PRT
<213> ORGANISM: Homo sapiens

<400> SEQUENCE: 300
```

```
Gly Gly Leu Val Gly Leu Ile Phe Ala Val Cys Leu Val Gly Phe
1               5                   10                  15
```

<210> SEQ ID NO 301
<211> LENGTH: 16
<212> TYPE: PRT
<213> ORGANISM: Homo sapiens

<400> SEQUENCE: 301

```
Gly Gly Leu Val Gly Leu Ile Phe Ala Val Cys Leu Val Gly Phe Met
1               5                   10                  15
```

<210> SEQ ID NO 302
<211> LENGTH: 17
<212> TYPE: PRT
<213> ORGANISM: Homo sapiens

<400> SEQUENCE: 302

```
Gly Gly Leu Val Gly Leu Ile Phe Ala Val Cys Leu Val Gly Phe Met
1               5                   10                  15

Leu
```

<210> SEQ ID NO 303
<211> LENGTH: 18
<212> TYPE: PRT
<213> ORGANISM: Homo sapiens

<400> SEQUENCE: 303

```
Gly Gly Leu Val Gly Leu Ile Phe Ala Val Cys Leu Val Gly Phe Met
1               5                   10                  15

Leu Tyr
```

<210> SEQ ID NO 304
<211> LENGTH: 19
<212> TYPE: PRT
<213> ORGANISM: Homo sapiens

<400> SEQUENCE: 304

```
Gly Gly Leu Val Gly Leu Ile Phe Ala Val Cys Leu Val Gly Phe Met
1               5                   10                  15

Leu Tyr Arg
```

<210> SEQ ID NO 305
<211> LENGTH: 20
<212> TYPE: PRT
<213> ORGANISM: Homo sapiens

<400> SEQUENCE: 305

```
Gly Gly Leu Val Gly Leu Ile Phe Ala Val Cys Leu Val Gly Phe Met
1               5                   10                  15

Leu Tyr Arg Met
            20
```

<210> SEQ ID NO 306
<211> LENGTH: 9
<212> TYPE: PRT
<213> ORGANISM: Homo sapiens

<400> SEQUENCE: 306

```
Gly Leu Val Gly Leu Ile Phe Ala Val
1               5
```

<210> SEQ ID NO 307
<211> LENGTH: 10
<212> TYPE: PRT
<213> ORGANISM: Homo sapiens

<400> SEQUENCE: 307

Gly Leu Val Gly Leu Ile Phe Ala Val Cys
1               5                   10

<210> SEQ ID NO 308
<211> LENGTH: 11
<212> TYPE: PRT
<213> ORGANISM: Homo sapiens

<400> SEQUENCE: 308

Gly Leu Val Gly Leu Ile Phe Ala Val Cys Leu
1               5                   10

<210> SEQ ID NO 309
<211> LENGTH: 12
<212> TYPE: PRT
<213> ORGANISM: Homo sapiens

<400> SEQUENCE: 309

Gly Leu Val Gly Leu Ile Phe Ala Val Cys Leu Val
1               5                   10

<210> SEQ ID NO 310
<211> LENGTH: 13
<212> TYPE: PRT
<213> ORGANISM: Homo sapiens

<400> SEQUENCE: 310

Gly Leu Val Gly Leu Ile Phe Ala Val Cys Leu Val Gly
1               5                   10

<210> SEQ ID NO 311
<211> LENGTH: 14
<212> TYPE: PRT
<213> ORGANISM: Homo sapiens

<400> SEQUENCE: 311

Gly Leu Val Gly Leu Ile Phe Ala Val Cys Leu Val Gly Phe
1               5                   10

<210> SEQ ID NO 312
<211> LENGTH: 15
<212> TYPE: PRT
<213> ORGANISM: Homo sapiens

<400> SEQUENCE: 312

Gly Leu Val Gly Leu Ile Phe Ala Val Cys Leu Val Gly Phe Met
1               5                   10                  15

<210> SEQ ID NO 313
<211> LENGTH: 16
<212> TYPE: PRT
<213> ORGANISM: Homo sapiens

<400> SEQUENCE: 313

Gly Leu Val Gly Leu Ile Phe Ala Val Cys Leu Val Gly Phe Met Leu
1               5                   10                  15

<210> SEQ ID NO 314
<211> LENGTH: 17

<212> TYPE: PRT
<213> ORGANISM: Homo sapiens

<400> SEQUENCE: 314

Gly Leu Val Gly Leu Ile Phe Ala Val Cys Leu Val Gly Phe Met Leu
1               5                   10                  15

Tyr

<210> SEQ ID NO 315
<211> LENGTH: 18
<212> TYPE: PRT
<213> ORGANISM: Homo sapiens

<400> SEQUENCE: 315

Gly Leu Val Gly Leu Ile Phe Ala Val Cys Leu Val Gly Phe Met Leu
1               5                   10                  15

Tyr Arg

<210> SEQ ID NO 316
<211> LENGTH: 19
<212> TYPE: PRT
<213> ORGANISM: Homo sapiens

<400> SEQUENCE: 316

Gly Leu Val Gly Leu Ile Phe Ala Val Cys Leu Val Gly Phe Met Leu
1               5                   10                  15

Tyr Arg Met

<210> SEQ ID NO 317
<211> LENGTH: 8
<212> TYPE: PRT
<213> ORGANISM: Homo sapiens

<400> SEQUENCE: 317

Leu Val Gly Leu Ile Phe Ala Val
1               5

<210> SEQ ID NO 318
<211> LENGTH: 9
<212> TYPE: PRT
<213> ORGANISM: Homo sapiens

<400> SEQUENCE: 318

Leu Val Gly Leu Ile Phe Ala Val Cys
1               5

<210> SEQ ID NO 319
<211> LENGTH: 10
<212> TYPE: PRT
<213> ORGANISM: Homo sapiens

<400> SEQUENCE: 319

Leu Val Gly Leu Ile Phe Ala Val Cys Leu
1               5                   10

<210> SEQ ID NO 320
<211> LENGTH: 11
<212> TYPE: PRT
<213> ORGANISM: Homo sapiens

<400> SEQUENCE: 320

Leu Val Gly Leu Ile Phe Ala Val Cys Leu Val
1               5                   10

```
<210> SEQ ID NO 321
<211> LENGTH: 12
<212> TYPE: PRT
<213> ORGANISM: Homo sapiens

<400> SEQUENCE: 321

Leu Val Gly Leu Ile Phe Ala Val Cys Leu Val Gly
1               5                   10

<210> SEQ ID NO 322
<211> LENGTH: 13
<212> TYPE: PRT
<213> ORGANISM: Homo sapiens

<400> SEQUENCE: 322

Leu Val Gly Leu Ile Phe Ala Val Cys Leu Val Gly Phe
1               5                   10

<210> SEQ ID NO 323
<211> LENGTH: 14
<212> TYPE: PRT
<213> ORGANISM: Homo sapiens

<400> SEQUENCE: 323

Leu Val Gly Leu Ile Phe Ala Val Cys Leu Val Gly Phe Met
1               5                   10

<210> SEQ ID NO 324
<211> LENGTH: 15
<212> TYPE: PRT
<213> ORGANISM: Homo sapiens

<400> SEQUENCE: 324

Leu Val Gly Leu Ile Phe Ala Val Cys Leu Val Gly Phe Met Leu
1               5                   10                  15

<210> SEQ ID NO 325
<211> LENGTH: 16
<212> TYPE: PRT
<213> ORGANISM: Homo sapiens

<400> SEQUENCE: 325

Leu Val Gly Leu Ile Phe Ala Val Cys Leu Val Gly Phe Met Leu Tyr
1               5                   10                  15

<210> SEQ ID NO 326
<211> LENGTH: 17
<212> TYPE: PRT
<213> ORGANISM: Homo sapiens

<400> SEQUENCE: 326

Leu Val Gly Leu Ile Phe Ala Val Cys Leu Val Gly Phe Met Leu Tyr
1               5                   10                  15

Arg

<210> SEQ ID NO 327
<211> LENGTH: 18
<212> TYPE: PRT
<213> ORGANISM: Homo sapiens

<400> SEQUENCE: 327

Leu Val Gly Leu Ile Phe Ala Val Cys Leu Val Gly Phe Met Leu Tyr
1               5                   10                  15
```

-continued

Arg Met

<210> SEQ ID NO 328
<211> LENGTH: 7
<212> TYPE: PRT
<213> ORGANISM: Homo sapiens

<400> SEQUENCE: 328

Val Gly Leu Ile Phe Ala Val
1               5

<210> SEQ ID NO 329
<211> LENGTH: 8
<212> TYPE: PRT
<213> ORGANISM: Homo sapiens

<400> SEQUENCE: 329

Val Gly Leu Ile Phe Ala Val Cys
1               5

<210> SEQ ID NO 330
<211> LENGTH: 9
<212> TYPE: PRT
<213> ORGANISM: Homo sapiens

<400> SEQUENCE: 330

Val Gly Leu Ile Phe Ala Val Cys Leu
1               5

<210> SEQ ID NO 331
<211> LENGTH: 10
<212> TYPE: PRT
<213> ORGANISM: Homo sapiens

<400> SEQUENCE: 331

Val Gly Leu Ile Phe Ala Val Cys Leu Val
1               5                   10

<210> SEQ ID NO 332
<211> LENGTH: 11
<212> TYPE: PRT
<213> ORGANISM: Homo sapiens

<400> SEQUENCE: 332

Val Gly Leu Ile Phe Ala Val Cys Leu Val Gly
1               5                   10

<210> SEQ ID NO 333
<211> LENGTH: 12
<212> TYPE: PRT
<213> ORGANISM: Homo sapiens

<400> SEQUENCE: 333

Val Gly Leu Ile Phe Ala Val Cys Leu Val Gly Phe
1               5                   10

<210> SEQ ID NO 334
<211> LENGTH: 13
<212> TYPE: PRT
<213> ORGANISM: Homo sapiens

<400> SEQUENCE: 334

Val Gly Leu Ile Phe Ala Val Cys Leu Val Gly Phe Met
1               5                   10

-continued

```
<210> SEQ ID NO 335
<211> LENGTH: 14
<212> TYPE: PRT
<213> ORGANISM: Homo sapiens

<400> SEQUENCE: 335

Val Gly Leu Ile Phe Ala Val Cys Leu Val Gly Phe Met Leu
1               5                   10

<210> SEQ ID NO 336
<211> LENGTH: 15
<212> TYPE: PRT
<213> ORGANISM: Homo sapiens

<400> SEQUENCE: 336

Val Gly Leu Ile Phe Ala Val Cys Leu Val Gly Phe Met Leu Tyr
1               5                   10                  15

<210> SEQ ID NO 337
<211> LENGTH: 16
<212> TYPE: PRT
<213> ORGANISM: Homo sapiens

<400> SEQUENCE: 337

Val Gly Leu Ile Phe Ala Val Cys Leu Val Gly Phe Met Leu Tyr Arg
1               5                   10                  15

<210> SEQ ID NO 338
<211> LENGTH: 17
<212> TYPE: PRT
<213> ORGANISM: Homo sapiens

<400> SEQUENCE: 338

Val Gly Leu Ile Phe Ala Val Cys Leu Val Gly Phe Met Leu Tyr Arg
1               5                   10                  15

Met

<210> SEQ ID NO 339
<211> LENGTH: 6
<212> TYPE: PRT
<213> ORGANISM: Homo sapiens

<400> SEQUENCE: 339

Gly Leu Ile Phe Ala Val
1               5

<210> SEQ ID NO 340
<211> LENGTH: 7
<212> TYPE: PRT
<213> ORGANISM: Homo sapiens

<400> SEQUENCE: 340

Gly Leu Ile Phe Ala Val Cys
1               5

<210> SEQ ID NO 341
<211> LENGTH: 8
<212> TYPE: PRT
<213> ORGANISM: Homo sapiens

<400> SEQUENCE: 341

Gly Leu Ile Phe Ala Val Cys Leu
1               5
```

```
<210> SEQ ID NO 342
<211> LENGTH: 9
<212> TYPE: PRT
<213> ORGANISM: Homo sapiens

<400> SEQUENCE: 342

Gly Leu Ile Phe Ala Val Cys Leu Val
1               5

<210> SEQ ID NO 343
<211> LENGTH: 10
<212> TYPE: PRT
<213> ORGANISM: Homo sapiens

<400> SEQUENCE: 343

Gly Leu Ile Phe Ala Val Cys Leu Val Gly
1               5                   10

<210> SEQ ID NO 344
<211> LENGTH: 11
<212> TYPE: PRT
<213> ORGANISM: Homo sapiens

<400> SEQUENCE: 344

Gly Leu Ile Phe Ala Val Cys Leu Val Gly Phe
1               5                   10

<210> SEQ ID NO 345
<211> LENGTH: 12
<212> TYPE: PRT
<213> ORGANISM: Homo sapiens

<400> SEQUENCE: 345

Gly Leu Ile Phe Ala Val Cys Leu Val Gly Phe Met
1               5                   10

<210> SEQ ID NO 346
<211> LENGTH: 13
<212> TYPE: PRT
<213> ORGANISM: Homo sapiens

<400> SEQUENCE: 346

Gly Leu Ile Phe Ala Val Cys Leu Val Gly Phe Met Leu
1               5                   10

<210> SEQ ID NO 347
<211> LENGTH: 14
<212> TYPE: PRT
<213> ORGANISM: Homo sapiens

<400> SEQUENCE: 347

Gly Leu Ile Phe Ala Val Cys Leu Val Gly Phe Met Leu Tyr
1               5                   10

<210> SEQ ID NO 348
<211> LENGTH: 15
<212> TYPE: PRT
<213> ORGANISM: Homo sapiens

<400> SEQUENCE: 348

Gly Leu Ile Phe Ala Val Cys Leu Val Gly Phe Met Leu Tyr Arg
1               5                   10                  15
```

<210> SEQ ID NO 349
<211> LENGTH: 16
<212> TYPE: PRT
<213> ORGANISM: Homo sapiens

<400> SEQUENCE: 349

Gly Leu Ile Phe Ala Val Cys Leu Val Gly Phe Met Leu Tyr Arg Met
1               5                   10                  15

<210> SEQ ID NO 350
<211> LENGTH: 5
<212> TYPE: PRT
<213> ORGANISM: Homo sapiens

<400> SEQUENCE: 350

Leu Ile Phe Ala Val
1               5

<210> SEQ ID NO 351
<211> LENGTH: 6
<212> TYPE: PRT
<213> ORGANISM: Homo sapiens

<400> SEQUENCE: 351

Leu Ile Phe Ala Val Cys
1               5

<210> SEQ ID NO 352
<211> LENGTH: 7
<212> TYPE: PRT
<213> ORGANISM: Homo sapiens

<400> SEQUENCE: 352

Leu Ile Phe Ala Val Cys Leu
1               5

<210> SEQ ID NO 353
<211> LENGTH: 8
<212> TYPE: PRT
<213> ORGANISM: Homo sapiens

<400> SEQUENCE: 353

Leu Ile Phe Ala Val Cys Leu Val
1               5

<210> SEQ ID NO 354
<211> LENGTH: 9
<212> TYPE: PRT
<213> ORGANISM: Homo sapiens

<400> SEQUENCE: 354

Leu Ile Phe Ala Val Cys Leu Val Gly
1               5

<210> SEQ ID NO 355
<211> LENGTH: 10
<212> TYPE: PRT
<213> ORGANISM: Homo sapiens

<400> SEQUENCE: 355

Leu Ile Phe Ala Val Cys Leu Val Gly Phe
1               5                   10

<210> SEQ ID NO 356
<211> LENGTH: 11

-continued

```
<212> TYPE: PRT
<213> ORGANISM: Homo sapiens

<400> SEQUENCE: 356

Leu Ile Phe Ala Val Cys Leu Val Gly Phe Met
1               5                   10

<210> SEQ ID NO 357
<211> LENGTH: 12
<212> TYPE: PRT
<213> ORGANISM: Homo sapiens

<400> SEQUENCE: 357

Leu Ile Phe Ala Val Cys Leu Val Gly Phe Met Leu
1               5                   10

<210> SEQ ID NO 358
<211> LENGTH: 13
<212> TYPE: PRT
<213> ORGANISM: Homo sapiens

<400> SEQUENCE: 358

Leu Ile Phe Ala Val Cys Leu Val Gly Phe Met Leu Tyr
1               5                   10

<210> SEQ ID NO 359
<211> LENGTH: 14
<212> TYPE: PRT
<213> ORGANISM: Homo sapiens

<400> SEQUENCE: 359

Leu Ile Phe Ala Val Cys Leu Val Gly Phe Met Leu Tyr Arg
1               5                   10

<210> SEQ ID NO 360
<211> LENGTH: 15
<212> TYPE: PRT
<213> ORGANISM: Homo sapiens

<400> SEQUENCE: 360

Leu Ile Phe Ala Val Cys Leu Val Gly Phe Met Leu Tyr Arg Met
1               5                   10                  15

<210> SEQ ID NO 361
<211> LENGTH: 4
<212> TYPE: PRT
<213> ORGANISM: Homo sapiens

<400> SEQUENCE: 361

Ile Phe Ala Val
1

<210> SEQ ID NO 362
<211> LENGTH: 5
<212> TYPE: PRT
<213> ORGANISM: Homo sapiens

<400> SEQUENCE: 362

Ile Phe Ala Val Cys
1               5

<210> SEQ ID NO 363
<211> LENGTH: 6
<212> TYPE: PRT
<213> ORGANISM: Homo sapiens
```

<400> SEQUENCE: 363

Ile Phe Ala Val Cys Leu
1               5

<210> SEQ ID NO 364
<211> LENGTH: 7
<212> TYPE: PRT
<213> ORGANISM: Homo sapiens

<400> SEQUENCE: 364

Ile Phe Ala Val Cys Leu Val
1               5

<210> SEQ ID NO 365
<211> LENGTH: 8
<212> TYPE: PRT
<213> ORGANISM: Homo sapiens

<400> SEQUENCE: 365

Ile Phe Ala Val Cys Leu Val Gly
1               5

<210> SEQ ID NO 366
<211> LENGTH: 9
<212> TYPE: PRT
<213> ORGANISM: Homo sapiens

<400> SEQUENCE: 366

Ile Phe Ala Val Cys Leu Val Gly Phe
1               5

<210> SEQ ID NO 367
<211> LENGTH: 10
<212> TYPE: PRT
<213> ORGANISM: Homo sapiens

<400> SEQUENCE: 367

Ile Phe Ala Val Cys Leu Val Gly Phe Met
1               5                   10

<210> SEQ ID NO 368
<211> LENGTH: 11
<212> TYPE: PRT
<213> ORGANISM: Homo sapiens

<400> SEQUENCE: 368

Ile Phe Ala Val Cys Leu Val Gly Phe Met Leu
1               5                   10

<210> SEQ ID NO 369
<211> LENGTH: 12
<212> TYPE: PRT
<213> ORGANISM: Homo sapiens

<400> SEQUENCE: 369

Ile Phe Ala Val Cys Leu Val Gly Phe Met Leu Tyr
1               5                   10

<210> SEQ ID NO 370
<211> LENGTH: 13
<212> TYPE: PRT
<213> ORGANISM: Homo sapiens

<400> SEQUENCE: 370

```
Ile Phe Ala Val Cys Leu Val Gly Phe Met Leu Tyr Arg
1               5                   10

<210> SEQ ID NO 371
<211> LENGTH: 14
<212> TYPE: PRT
<213> ORGANISM: Homo sapiens

<400> SEQUENCE: 371

Ile Phe Ala Val Cys Leu Val Gly Phe Met Leu Tyr Arg Met
1               5                   10

<210> SEQ ID NO 372
<211> LENGTH: 16
<212> TYPE: PRT
<213> ORGANISM: Homo sapiens

<400> SEQUENCE: 372

Val Leu Leu Cys Leu Leu Leu Val Pro Leu Leu Leu Ser Leu Phe Val
1               5                   10                  15

<210> SEQ ID NO 373
<211> LENGTH: 17
<212> TYPE: PRT
<213> ORGANISM: Homo sapiens

<400> SEQUENCE: 373

Val Leu Leu Cys Leu Leu Leu Val Pro Leu Leu Leu Ser Leu Phe Val
1               5                   10                  15

Leu

<210> SEQ ID NO 374
<211> LENGTH: 18
<212> TYPE: PRT
<213> ORGANISM: Homo sapiens

<400> SEQUENCE: 374

Val Leu Leu Cys Leu Leu Leu Val Pro Leu Leu Leu Ser Leu Phe Val
1               5                   10                  15

Leu Gly

<210> SEQ ID NO 375
<211> LENGTH: 19
<212> TYPE: PRT
<213> ORGANISM: Homo sapiens

<400> SEQUENCE: 375

Val Leu Leu Cys Leu Leu Leu Val Pro Leu Leu Leu Ser Leu Phe Val
1               5                   10                  15

Leu Gly Leu

<210> SEQ ID NO 376
<211> LENGTH: 20
<212> TYPE: PRT
<213> ORGANISM: Homo sapiens

<400> SEQUENCE: 376

Val Leu Leu Cys Leu Leu Leu Val Pro Leu Leu Leu Ser Leu Phe Val
1               5                   10                  15

Leu Gly Leu Phe
        20
```

-continued

```
<210> SEQ ID NO 377
<211> LENGTH: 21
<212> TYPE: PRT
<213> ORGANISM: Homo sapiens

<400> SEQUENCE: 377

Val Leu Leu Cys Leu Leu Leu Val Pro Leu Leu Ser Leu Phe Val
1               5                   10                  15

Leu Gly Leu Phe Leu
            20

<210> SEQ ID NO 378
<211> LENGTH: 22
<212> TYPE: PRT
<213> ORGANISM: Homo sapiens

<400> SEQUENCE: 378

Val Leu Leu Cys Leu Leu Leu Val Pro Leu Leu Ser Leu Phe Val
1               5                   10                  15

Leu Gly Leu Phe Leu Trp
            20

<210> SEQ ID NO 379
<211> LENGTH: 23
<212> TYPE: PRT
<213> ORGANISM: Homo sapiens

<400> SEQUENCE: 379

Val Leu Leu Cys Leu Leu Leu Val Pro Leu Leu Ser Leu Phe Val
1               5                   10                  15

Leu Gly Leu Phe Leu Trp Phe
            20

<210> SEQ ID NO 380
<211> LENGTH: 24
<212> TYPE: PRT
<213> ORGANISM: Homo sapiens

<400> SEQUENCE: 380

Val Leu Leu Cys Leu Leu Leu Val Pro Leu Leu Ser Leu Phe Val
1               5                   10                  15

Leu Gly Leu Phe Leu Trp Phe Leu
            20

<210> SEQ ID NO 381
<211> LENGTH: 25
<212> TYPE: PRT
<213> ORGANISM: Homo sapiens

<400> SEQUENCE: 381

Val Leu Leu Cys Leu Leu Leu Val Pro Leu Leu Ser Leu Phe Val
1               5                   10                  15

Leu Gly Leu Phe Leu Trp Phe Leu Lys
            20                  25

<210> SEQ ID NO 382
<211> LENGTH: 26
<212> TYPE: PRT
<213> ORGANISM: Homo sapiens

<400> SEQUENCE: 382

Val Leu Leu Cys Leu Leu Leu Val Pro Leu Leu Leu Ser Leu Phe Val
```

-continued

```
1               5               10              15

Leu Gly Leu Phe Leu Trp Phe Leu Lys Arg
            20              25

<210> SEQ ID NO 383
<211> LENGTH: 27
<212> TYPE: PRT
<213> ORGANISM: Homo sapiens

<400> SEQUENCE: 383

Val Leu Leu Cys Leu Leu Leu Val Pro Leu Leu Leu Ser Leu Phe Val
1               5               10              15

Leu Gly Leu Phe Leu Trp Phe Leu Lys Arg Glu
            20              25

<210> SEQ ID NO 384
<211> LENGTH: 15
<212> TYPE: PRT
<213> ORGANISM: Homo sapiens

<400> SEQUENCE: 384

Leu Leu Cys Leu Leu Leu Val Pro Leu Leu Leu Ser Leu Phe Val
1               5               10              15

<210> SEQ ID NO 385
<211> LENGTH: 16
<212> TYPE: PRT
<213> ORGANISM: Homo sapiens

<400> SEQUENCE: 385

Leu Leu Cys Leu Leu Leu Val Pro Leu Leu Leu Ser Leu Phe Val Leu
1               5               10              15

<210> SEQ ID NO 386
<211> LENGTH: 17
<212> TYPE: PRT
<213> ORGANISM: Homo sapiens

<400> SEQUENCE: 386

Leu Leu Cys Leu Leu Leu Val Pro Leu Leu Leu Ser Leu Phe Val Leu
1               5               10              15

Gly

<210> SEQ ID NO 387
<211> LENGTH: 18
<212> TYPE: PRT
<213> ORGANISM: Homo sapiens

<400> SEQUENCE: 387

Leu Leu Cys Leu Leu Leu Val Pro Leu Leu Leu Ser Leu Phe Val Leu
1               5               10              15

Gly Leu

<210> SEQ ID NO 388
<211> LENGTH: 19
<212> TYPE: PRT
<213> ORGANISM: Homo sapiens

<400> SEQUENCE: 388

Leu Leu Cys Leu Leu Leu Val Pro Leu Leu Leu Ser Leu Phe Val Leu
1               5               10              15

Gly Leu Phe
```

<210> SEQ ID NO 389
<211> LENGTH: 20
<212> TYPE: PRT
<213> ORGANISM: Homo sapiens

<400> SEQUENCE: 389

Leu Leu Cys Leu Leu Leu Val Pro Leu Leu Leu Ser Leu Phe Val Leu
1               5                   10                  15

Gly Leu Phe Leu
            20

<210> SEQ ID NO 390
<211> LENGTH: 21
<212> TYPE: PRT
<213> ORGANISM: Homo sapiens

<400> SEQUENCE: 390

Leu Leu Cys Leu Leu Leu Val Pro Leu Leu Leu Ser Leu Phe Val Leu
1               5                   10                  15

Gly Leu Phe Leu Trp
            20

<210> SEQ ID NO 391
<211> LENGTH: 22
<212> TYPE: PRT
<213> ORGANISM: Homo sapiens

<400> SEQUENCE: 391

Leu Leu Cys Leu Leu Leu Val Pro Leu Leu Leu Ser Leu Phe Val Leu
1               5                   10                  15

Gly Leu Phe Leu Trp Phe
            20

<210> SEQ ID NO 392
<211> LENGTH: 23
<212> TYPE: PRT
<213> ORGANISM: Homo sapiens

<400> SEQUENCE: 392

Leu Leu Cys Leu Leu Leu Val Pro Leu Leu Leu Ser Leu Phe Val Leu
1               5                   10                  15

Gly Leu Phe Leu Trp Phe Leu
            20

<210> SEQ ID NO 393
<211> LENGTH: 24
<212> TYPE: PRT
<213> ORGANISM: Homo sapiens

<400> SEQUENCE: 393

Leu Leu Cys Leu Leu Leu Val Pro Leu Leu Leu Ser Leu Phe Val Leu
1               5                   10                  15

Gly Leu Phe Leu Trp Phe Leu Lys
            20

<210> SEQ ID NO 394
<211> LENGTH: 25
<212> TYPE: PRT
<213> ORGANISM: Homo sapiens

<400> SEQUENCE: 394

```
Leu Leu Cys Leu Leu Leu Val Pro Leu Leu Leu Ser Leu Phe Val Leu
1               5                   10                  15

Gly Leu Phe Leu Trp Phe Leu Lys Arg
            20                  25

<210> SEQ ID NO 395
<211> LENGTH: 26
<212> TYPE: PRT
<213> ORGANISM: Homo sapiens

<400> SEQUENCE: 395

Leu Leu Cys Leu Leu Leu Val Pro Leu Leu Leu Ser Leu Phe Val Leu
1               5                   10                  15

Gly Leu Phe Leu Trp Phe Leu Lys Arg Glu
            20                  25

<210> SEQ ID NO 396
<211> LENGTH: 14
<212> TYPE: PRT
<213> ORGANISM: Homo sapiens

<400> SEQUENCE: 396

Leu Cys Leu Leu Leu Val Pro Leu Leu Leu Ser Leu Phe Val
1               5                   10

<210> SEQ ID NO 397
<211> LENGTH: 15
<212> TYPE: PRT
<213> ORGANISM: Homo sapiens

<400> SEQUENCE: 397

Leu Cys Leu Leu Leu Val Pro Leu Leu Leu Ser Leu Phe Val Leu
1               5                   10                  15

<210> SEQ ID NO 398
<211> LENGTH: 16
<212> TYPE: PRT
<213> ORGANISM: Homo sapiens

<400> SEQUENCE: 398

Leu Cys Leu Leu Leu Val Pro Leu Leu Leu Ser Leu Phe Val Leu Gly
1               5                   10                  15

<210> SEQ ID NO 399
<211> LENGTH: 17
<212> TYPE: PRT
<213> ORGANISM: Homo sapiens

<400> SEQUENCE: 399

Leu Cys Leu Leu Leu Val Pro Leu Leu Leu Ser Leu Phe Val Leu Gly
1               5                   10                  15

Leu

<210> SEQ ID NO 400
<211> LENGTH: 18
<212> TYPE: PRT
<213> ORGANISM: Homo sapiens

<400> SEQUENCE: 400

Leu Cys Leu Leu Leu Val Pro Leu Leu Leu Ser Leu Phe Val Leu Gly
1               5                   10                  15

Leu Phe
```

```
<210> SEQ ID NO 401
<211> LENGTH: 19
<212> TYPE: PRT
<213> ORGANISM: Homo sapiens

<400> SEQUENCE: 401

Leu Cys Leu Leu Leu Val Pro Leu Leu Leu Ser Leu Phe Val Leu Gly
1               5                   10                  15

Leu Phe Leu

<210> SEQ ID NO 402
<211> LENGTH: 20
<212> TYPE: PRT
<213> ORGANISM: Homo sapiens

<400> SEQUENCE: 402

Leu Cys Leu Leu Leu Val Pro Leu Leu Leu Ser Leu Phe Val Leu Gly
1               5                   10                  15

Leu Phe Leu Trp
            20

<210> SEQ ID NO 403
<211> LENGTH: 21
<212> TYPE: PRT
<213> ORGANISM: Homo sapiens

<400> SEQUENCE: 403

Leu Cys Leu Leu Leu Val Pro Leu Leu Leu Ser Leu Phe Val Leu Gly
1               5                   10                  15

Leu Phe Leu Trp Phe
            20

<210> SEQ ID NO 404
<211> LENGTH: 22
<212> TYPE: PRT
<213> ORGANISM: Homo sapiens

<400> SEQUENCE: 404

Leu Cys Leu Leu Leu Val Pro Leu Leu Leu Ser Leu Phe Val Leu Gly
1               5                   10                  15

Leu Phe Leu Trp Phe Leu
            20

<210> SEQ ID NO 405
<211> LENGTH: 23
<212> TYPE: PRT
<213> ORGANISM: Homo sapiens

<400> SEQUENCE: 405

Leu Cys Leu Leu Leu Val Pro Leu Leu Leu Ser Leu Phe Val Leu Gly
1               5                   10                  15

Leu Phe Leu Trp Phe Leu Lys
            20

<210> SEQ ID NO 406
<211> LENGTH: 24
<212> TYPE: PRT
<213> ORGANISM: Homo sapiens

<400> SEQUENCE: 406

Leu Cys Leu Leu Leu Val Pro Leu Leu Leu Ser Leu Phe Val Leu Gly
1               5                   10                  15
```

```
Leu Phe Leu Trp Phe Leu Lys Arg
            20

<210> SEQ ID NO 407
<211> LENGTH: 25
<212> TYPE: PRT
<213> ORGANISM: Homo sapiens

<400> SEQUENCE: 407

Leu Cys Leu Leu Leu Val Pro Leu Leu Leu Ser Leu Phe Val Leu Gly
1               5                   10                  15

Leu Phe Leu Trp Phe Leu Lys Arg Glu
            20                  25

<210> SEQ ID NO 408
<211> LENGTH: 13
<212> TYPE: PRT
<213> ORGANISM: Homo sapiens

<400> SEQUENCE: 408

Cys Leu Leu Leu Val Pro Leu Leu Leu Ser Leu Phe Val
1               5                   10

<210> SEQ ID NO 409
<211> LENGTH: 14
<212> TYPE: PRT
<213> ORGANISM: Homo sapiens

<400> SEQUENCE: 409

Cys Leu Leu Leu Val Pro Leu Leu Leu Ser Leu Phe Val Leu
1               5                   10

<210> SEQ ID NO 410
<211> LENGTH: 15
<212> TYPE: PRT
<213> ORGANISM: Homo sapiens

<400> SEQUENCE: 410

Cys Leu Leu Leu Val Pro Leu Leu Leu Ser Leu Phe Val Leu Gly
1               5                   10                  15

<210> SEQ ID NO 411
<211> LENGTH: 16
<212> TYPE: PRT
<213> ORGANISM: Homo sapiens

<400> SEQUENCE: 411

Cys Leu Leu Leu Val Pro Leu Leu Leu Ser Leu Phe Val Leu Gly Leu
1               5                   10                  15

<210> SEQ ID NO 412
<211> LENGTH: 17
<212> TYPE: PRT
<213> ORGANISM: Homo sapiens

<400> SEQUENCE: 412

Cys Leu Leu Leu Val Pro Leu Leu Leu Ser Leu Phe Val Leu Gly Leu
1               5                   10                  15

Phe

<210> SEQ ID NO 413
<211> LENGTH: 18
<212> TYPE: PRT
```

<213> ORGANISM: Homo sapiens

<400> SEQUENCE: 413

Cys Leu Leu Leu Val Pro Leu Leu Leu Ser Leu Phe Val Leu Gly Leu
1               5                   10                  15

Phe Leu

<210> SEQ ID NO 414
<211> LENGTH: 19
<212> TYPE: PRT
<213> ORGANISM: Homo sapiens

<400> SEQUENCE: 414

Cys Leu Leu Leu Val Pro Leu Leu Leu Ser Leu Phe Val Leu Gly Leu
1               5                   10                  15

Phe Leu Trp

<210> SEQ ID NO 415
<211> LENGTH: 20
<212> TYPE: PRT
<213> ORGANISM: Homo sapiens

<400> SEQUENCE: 415

Cys Leu Leu Leu Val Pro Leu Leu Leu Ser Leu Phe Val Leu Gly Leu
1               5                   10                  15

Phe Leu Trp Phe
            20

<210> SEQ ID NO 416
<211> LENGTH: 21
<212> TYPE: PRT
<213> ORGANISM: Homo sapiens

<400> SEQUENCE: 416

Cys Leu Leu Leu Val Pro Leu Leu Leu Ser Leu Phe Val Leu Gly Leu
1               5                   10                  15

Phe Leu Trp Phe Leu
            20

<210> SEQ ID NO 417
<211> LENGTH: 22
<212> TYPE: PRT
<213> ORGANISM: Homo sapiens

<400> SEQUENCE: 417

Cys Leu Leu Leu Val Pro Leu Leu Leu Ser Leu Phe Val Leu Gly Leu
1               5                   10                  15

Phe Leu Trp Phe Leu Lys
            20

<210> SEQ ID NO 418
<211> LENGTH: 23
<212> TYPE: PRT
<213> ORGANISM: Homo sapiens

<400> SEQUENCE: 418

Cys Leu Leu Leu Val Pro Leu Leu Leu Ser Leu Phe Val Leu Gly Leu
1               5                   10                  15

Phe Leu Trp Phe Leu Lys Arg
            20

<210> SEQ ID NO 419
<211> LENGTH: 24
<212> TYPE: PRT
<213> ORGANISM: Homo sapiens

<400> SEQUENCE: 419

Cys Leu Leu Leu Val Pro Leu Leu Leu Ser Leu Phe Val Leu Gly Leu
1               5                   10                  15

Phe Leu Trp Phe Leu Lys Arg Glu
            20

<210> SEQ ID NO 420
<211> LENGTH: 12
<212> TYPE: PRT
<213> ORGANISM: Homo sapiens

<400> SEQUENCE: 420

Leu Leu Leu Val Pro Leu Leu Leu Ser Leu Phe Val
1               5                   10

<210> SEQ ID NO 421
<211> LENGTH: 13
<212> TYPE: PRT
<213> ORGANISM: Homo sapiens

<400> SEQUENCE: 421

Leu Leu Leu Val Pro Leu Leu Leu Ser Leu Phe Val Leu
1               5                   10

<210> SEQ ID NO 422
<211> LENGTH: 14
<212> TYPE: PRT
<213> ORGANISM: Homo sapiens

<400> SEQUENCE: 422

Leu Leu Leu Val Pro Leu Leu Leu Ser Leu Phe Val Leu Gly
1               5                   10

<210> SEQ ID NO 423
<211> LENGTH: 15
<212> TYPE: PRT
<213> ORGANISM: Homo sapiens

<400> SEQUENCE: 423

Leu Leu Leu Val Pro Leu Leu Leu Ser Leu Phe Val Leu Gly Leu
1               5                   10                  15

<210> SEQ ID NO 424
<211> LENGTH: 16
<212> TYPE: PRT
<213> ORGANISM: Homo sapiens

<400> SEQUENCE: 424

Leu Leu Leu Val Pro Leu Leu Leu Ser Leu Phe Val Leu Gly Leu Phe
1               5                   10                  15

<210> SEQ ID NO 425
<211> LENGTH: 17
<212> TYPE: PRT
<213> ORGANISM: Homo sapiens

<400> SEQUENCE: 425

Leu Leu Leu Val Pro Leu Leu Leu Ser Leu Phe Val Leu Gly Leu Phe
1               5                   10                  15

```
Leu

<210> SEQ ID NO 426
<211> LENGTH: 18
<212> TYPE: PRT
<213> ORGANISM: Homo sapiens

<400> SEQUENCE: 426

Leu Leu Leu Val Pro Leu Leu Leu Ser Leu Phe Val Leu Gly Leu Phe
1               5                   10                  15

Leu Trp

<210> SEQ ID NO 427
<211> LENGTH: 19
<212> TYPE: PRT
<213> ORGANISM: Homo sapiens

<400> SEQUENCE: 427

Leu Leu Leu Val Pro Leu Leu Leu Ser Leu Phe Val Leu Gly Leu Phe
1               5                   10                  15

Leu Trp Phe

<210> SEQ ID NO 428
<211> LENGTH: 20
<212> TYPE: PRT
<213> ORGANISM: Homo sapiens

<400> SEQUENCE: 428

Leu Leu Leu Val Pro Leu Leu Leu Ser Leu Phe Val Leu Gly Leu Phe
1               5                   10                  15

Leu Trp Phe Leu
            20

<210> SEQ ID NO 429
<211> LENGTH: 21
<212> TYPE: PRT
<213> ORGANISM: Homo sapiens

<400> SEQUENCE: 429

Leu Leu Leu Val Pro Leu Leu Leu Ser Leu Phe Val Leu Gly Leu Phe
1               5                   10                  15

Leu Trp Phe Leu Lys
            20

<210> SEQ ID NO 430
<211> LENGTH: 22
<212> TYPE: PRT
<213> ORGANISM: Homo sapiens

<400> SEQUENCE: 430

Leu Leu Leu Val Pro Leu Leu Leu Ser Leu Phe Val Leu Gly Leu Phe
1               5                   10                  15

Leu Trp Phe Leu Lys Arg
            20

<210> SEQ ID NO 431
<211> LENGTH: 23
<212> TYPE: PRT
<213> ORGANISM: Homo sapiens

<400> SEQUENCE: 431

Leu Leu Leu Val Pro Leu Leu Leu Ser Leu Phe Val Leu Gly Leu Phe
```

-continued

```
1               5                    10                   15

Leu Trp Phe Leu Lys Arg Glu
                20

<210> SEQ ID NO 432
<211> LENGTH: 11
<212> TYPE: PRT
<213> ORGANISM: Homo sapiens

<400> SEQUENCE: 432

Leu Leu Val Pro Leu Leu Leu Ser Leu Phe Val
1               5                    10

<210> SEQ ID NO 433
<211> LENGTH: 12
<212> TYPE: PRT
<213> ORGANISM: Homo sapiens

<400> SEQUENCE: 433

Leu Leu Val Pro Leu Leu Leu Ser Leu Phe Val Leu
1               5                    10

<210> SEQ ID NO 434
<211> LENGTH: 13
<212> TYPE: PRT
<213> ORGANISM: Homo sapiens

<400> SEQUENCE: 434

Leu Leu Val Pro Leu Leu Leu Ser Leu Phe Val Leu Gly
1               5                    10

<210> SEQ ID NO 435
<211> LENGTH: 14
<212> TYPE: PRT
<213> ORGANISM: Homo sapiens

<400> SEQUENCE: 435

Leu Leu Val Pro Leu Leu Leu Ser Leu Phe Val Leu Gly Leu
1               5                    10

<210> SEQ ID NO 436
<211> LENGTH: 15
<212> TYPE: PRT
<213> ORGANISM: Homo sapiens

<400> SEQUENCE: 436

Leu Leu Val Pro Leu Leu Leu Ser Leu Phe Val Leu Gly Leu Phe
1               5                    10                   15

<210> SEQ ID NO 437
<211> LENGTH: 16
<212> TYPE: PRT
<213> ORGANISM: Homo sapiens

<400> SEQUENCE: 437

Leu Leu Val Pro Leu Leu Leu Ser Leu Phe Val Leu Gly Leu Phe Leu
1               5                    10                   15

<210> SEQ ID NO 438
<211> LENGTH: 17
<212> TYPE: PRT
<213> ORGANISM: Homo sapiens

<400> SEQUENCE: 438
```

```
Leu Leu Val Pro Leu Leu Leu Ser Leu Phe Val Leu Gly Leu Phe Leu
1               5                   10                  15

Trp

<210> SEQ ID NO 439
<211> LENGTH: 18
<212> TYPE: PRT
<213> ORGANISM: Homo sapiens

<400> SEQUENCE: 439

Leu Leu Val Pro Leu Leu Leu Ser Leu Phe Val Leu Gly Leu Phe Leu
1               5                   10                  15

Trp Phe

<210> SEQ ID NO 440
<211> LENGTH: 19
<212> TYPE: PRT
<213> ORGANISM: Homo sapiens

<400> SEQUENCE: 440

Leu Leu Val Pro Leu Leu Leu Ser Leu Phe Val Leu Gly Leu Phe Leu
1               5                   10                  15

Trp Phe Leu

<210> SEQ ID NO 441
<211> LENGTH: 20
<212> TYPE: PRT
<213> ORGANISM: Homo sapiens

<400> SEQUENCE: 441

Leu Leu Val Pro Leu Leu Leu Ser Leu Phe Val Leu Gly Leu Phe Leu
1               5                   10                  15

Trp Phe Leu Lys
            20

<210> SEQ ID NO 442
<211> LENGTH: 21
<212> TYPE: PRT
<213> ORGANISM: Homo sapiens

<400> SEQUENCE: 442

Leu Leu Val Pro Leu Leu Leu Ser Leu Phe Val Leu Gly Leu Phe Leu
1               5                   10                  15

Trp Phe Leu Lys Arg
            20

<210> SEQ ID NO 443
<211> LENGTH: 22
<212> TYPE: PRT
<213> ORGANISM: Homo sapiens

<400> SEQUENCE: 443

Leu Leu Val Pro Leu Leu Leu Ser Leu Phe Val Leu Gly Leu Phe Leu
1               5                   10                  15

Trp Phe Leu Lys Arg Glu
            20

<210> SEQ ID NO 444
<211> LENGTH: 10
<212> TYPE: PRT
<213> ORGANISM: Homo sapiens
```

```
<400> SEQUENCE: 444

Leu Val Pro Leu Leu Leu Ser Leu Phe Val
1               5                   10

<210> SEQ ID NO 445
<211> LENGTH: 11
<212> TYPE: PRT
<213> ORGANISM: Homo sapiens

<400> SEQUENCE: 445

Leu Val Pro Leu Leu Leu Ser Leu Phe Val Leu
1               5                   10

<210> SEQ ID NO 446
<211> LENGTH: 12
<212> TYPE: PRT
<213> ORGANISM: Homo sapiens

<400> SEQUENCE: 446

Leu Val Pro Leu Leu Leu Ser Leu Phe Val Leu Gly
1               5                   10

<210> SEQ ID NO 447
<211> LENGTH: 13
<212> TYPE: PRT
<213> ORGANISM: Homo sapiens

<400> SEQUENCE: 447

Leu Val Pro Leu Leu Leu Ser Leu Phe Val Leu Gly Leu
1               5                   10

<210> SEQ ID NO 448
<211> LENGTH: 14
<212> TYPE: PRT
<213> ORGANISM: Homo sapiens

<400> SEQUENCE: 448

Leu Val Pro Leu Leu Leu Ser Leu Phe Val Leu Gly Leu Phe
1               5                   10

<210> SEQ ID NO 449
<211> LENGTH: 15
<212> TYPE: PRT
<213> ORGANISM: Homo sapiens

<400> SEQUENCE: 449

Leu Val Pro Leu Leu Leu Ser Leu Phe Val Leu Gly Leu Phe Leu
1               5                   10                  15

<210> SEQ ID NO 450
<211> LENGTH: 16
<212> TYPE: PRT
<213> ORGANISM: Homo sapiens

<400> SEQUENCE: 450

Leu Val Pro Leu Leu Leu Ser Leu Phe Val Leu Gly Leu Phe Leu Trp
1               5                   10                  15

<210> SEQ ID NO 451
<211> LENGTH: 17
<212> TYPE: PRT
<213> ORGANISM: Homo sapiens

<400> SEQUENCE: 451
```

-continued

```
Leu Val Pro Leu Leu Leu Ser Leu Phe Val Leu Gly Leu Phe Leu Trp
1               5                   10                  15

Phe

<210> SEQ ID NO 452
<211> LENGTH: 18
<212> TYPE: PRT
<213> ORGANISM: Homo sapiens

<400> SEQUENCE: 452

Leu Val Pro Leu Leu Leu Ser Leu Phe Val Leu Gly Leu Phe Leu Trp
1               5                   10                  15

Phe Leu

<210> SEQ ID NO 453
<211> LENGTH: 19
<212> TYPE: PRT
<213> ORGANISM: Homo sapiens

<400> SEQUENCE: 453

Leu Val Pro Leu Leu Leu Ser Leu Phe Val Leu Gly Leu Phe Leu Trp
1               5                   10                  15

Phe Leu Lys

<210> SEQ ID NO 454
<211> LENGTH: 20
<212> TYPE: PRT
<213> ORGANISM: Homo sapiens

<400> SEQUENCE: 454

Leu Val Pro Leu Leu Leu Ser Leu Phe Val Leu Gly Leu Phe Leu Trp
1               5                   10                  15

Phe Leu Lys Arg
            20

<210> SEQ ID NO 455
<211> LENGTH: 21
<212> TYPE: PRT
<213> ORGANISM: Homo sapiens

<400> SEQUENCE: 455

Leu Val Pro Leu Leu Leu Ser Leu Phe Val Leu Gly Leu Phe Leu Trp
1               5                   10                  15

Phe Leu Lys Arg Glu
            20

<210> SEQ ID NO 456
<211> LENGTH: 9
<212> TYPE: PRT
<213> ORGANISM: Homo sapiens

<400> SEQUENCE: 456

Val Pro Leu Leu Leu Ser Leu Phe Val
1               5

<210> SEQ ID NO 457
<211> LENGTH: 10
<212> TYPE: PRT
<213> ORGANISM: Homo sapiens

<400> SEQUENCE: 457

Val Pro Leu Leu Leu Ser Leu Phe Val Leu
```

```
1               5                    10

<210> SEQ ID NO 458
<211> LENGTH: 11
<212> TYPE: PRT
<213> ORGANISM: Homo sapiens

<400> SEQUENCE: 458

Val Pro Leu Leu Leu Ser Leu Phe Val Leu Gly
1               5                    10

<210> SEQ ID NO 459
<211> LENGTH: 12
<212> TYPE: PRT
<213> ORGANISM: Homo sapiens

<400> SEQUENCE: 459

Val Pro Leu Leu Leu Ser Leu Phe Val Leu Gly Leu
1               5                    10

<210> SEQ ID NO 460
<211> LENGTH: 13
<212> TYPE: PRT
<213> ORGANISM: Homo sapiens

<400> SEQUENCE: 460

Val Pro Leu Leu Leu Ser Leu Phe Val Leu Gly Leu Phe
1               5                    10

<210> SEQ ID NO 461
<211> LENGTH: 14
<212> TYPE: PRT
<213> ORGANISM: Homo sapiens

<400> SEQUENCE: 461

Val Pro Leu Leu Leu Ser Leu Phe Val Leu Gly Leu Phe Leu
1               5                    10

<210> SEQ ID NO 462
<211> LENGTH: 15
<212> TYPE: PRT
<213> ORGANISM: Homo sapiens

<400> SEQUENCE: 462

Val Pro Leu Leu Leu Ser Leu Phe Val Leu Gly Leu Phe Leu Trp
1               5                    10                   15

<210> SEQ ID NO 463
<211> LENGTH: 16
<212> TYPE: PRT
<213> ORGANISM: Homo sapiens

<400> SEQUENCE: 463

Val Pro Leu Leu Leu Ser Leu Phe Val Leu Gly Leu Phe Leu Trp Phe
1               5                    10                   15

<210> SEQ ID NO 464
<211> LENGTH: 17
<212> TYPE: PRT
<213> ORGANISM: Homo sapiens

<400> SEQUENCE: 464

Val Pro Leu Leu Leu Ser Leu Phe Val Leu Gly Leu Phe Leu Trp Phe
1               5                    10                   15
```

Leu

<210> SEQ ID NO 465
<211> LENGTH: 18
<212> TYPE: PRT
<213> ORGANISM: Homo sapiens

<400> SEQUENCE: 465

Val Pro Leu Leu Leu Ser Leu Phe Val Leu Gly Leu Phe Leu Trp Phe
1               5                   10                  15

Leu Lys

<210> SEQ ID NO 466
<211> LENGTH: 19
<212> TYPE: PRT
<213> ORGANISM: Homo sapiens

<400> SEQUENCE: 466

Val Pro Leu Leu Leu Ser Leu Phe Val Leu Gly Leu Phe Leu Trp Phe
1               5                   10                  15

Leu Lys Arg

<210> SEQ ID NO 467
<211> LENGTH: 20
<212> TYPE: PRT
<213> ORGANISM: Homo sapiens

<400> SEQUENCE: 467

Val Pro Leu Leu Leu Ser Leu Phe Val Leu Gly Leu Phe Leu Trp Phe
1               5                   10                  15

Leu Lys Arg Glu
            20

<210> SEQ ID NO 468
<211> LENGTH: 8
<212> TYPE: PRT
<213> ORGANISM: Homo sapiens

<400> SEQUENCE: 468

Pro Leu Leu Leu Ser Leu Phe Val
1               5

<210> SEQ ID NO 469
<211> LENGTH: 9
<212> TYPE: PRT
<213> ORGANISM: Homo sapiens

<400> SEQUENCE: 469

Pro Leu Leu Leu Ser Leu Phe Val Leu
1               5

<210> SEQ ID NO 470
<211> LENGTH: 10
<212> TYPE: PRT
<213> ORGANISM: Homo sapiens

<400> SEQUENCE: 470

Pro Leu Leu Leu Ser Leu Phe Val Leu Gly
1               5                   10

<210> SEQ ID NO 471
<211> LENGTH: 11
<212> TYPE: PRT

<213> ORGANISM: Homo sapiens

<400> SEQUENCE: 471

Pro Leu Leu Leu Ser Leu Phe Val Leu Gly Leu
1               5                   10

<210> SEQ ID NO 472
<211> LENGTH: 12
<212> TYPE: PRT
<213> ORGANISM: Homo sapiens

<400> SEQUENCE: 472

Pro Leu Leu Leu Ser Leu Phe Val Leu Gly Leu Phe
1               5                   10

<210> SEQ ID NO 473
<211> LENGTH: 13
<212> TYPE: PRT
<213> ORGANISM: Homo sapiens

<400> SEQUENCE: 473

Pro Leu Leu Leu Ser Leu Phe Val Leu Gly Leu Phe Leu
1               5                   10

<210> SEQ ID NO 474
<211> LENGTH: 14
<212> TYPE: PRT
<213> ORGANISM: Homo sapiens

<400> SEQUENCE: 474

Pro Leu Leu Leu Ser Leu Phe Val Leu Gly Leu Phe Leu Trp
1               5                   10

<210> SEQ ID NO 475
<211> LENGTH: 15
<212> TYPE: PRT
<213> ORGANISM: Homo sapiens

<400> SEQUENCE: 475

Pro Leu Leu Leu Ser Leu Phe Val Leu Gly Leu Phe Leu Trp Phe
1               5                   10                  15

<210> SEQ ID NO 476
<211> LENGTH: 16
<212> TYPE: PRT
<213> ORGANISM: Homo sapiens

<400> SEQUENCE: 476

Pro Leu Leu Leu Ser Leu Phe Val Leu Gly Leu Phe Leu Trp Phe Leu
1               5                   10                  15

<210> SEQ ID NO 477
<211> LENGTH: 17
<212> TYPE: PRT
<213> ORGANISM: Homo sapiens

<400> SEQUENCE: 477

Pro Leu Leu Leu Ser Leu Phe Val Leu Gly Leu Phe Leu Trp Phe Leu
1               5                   10                  15

Lys

<210> SEQ ID NO 478
<211> LENGTH: 18
<212> TYPE: PRT

<213> ORGANISM: Homo sapiens

<400> SEQUENCE: 478

Pro Leu Leu Leu Ser Leu Phe Val Leu Gly Leu Phe Leu Trp Phe Leu
1               5               10              15

Lys Arg

<210> SEQ ID NO 479
<211> LENGTH: 19
<212> TYPE: PRT
<213> ORGANISM: Homo sapiens

<400> SEQUENCE: 479

Pro Leu Leu Leu Ser Leu Phe Val Leu Gly Leu Phe Leu Trp Phe Leu
1               5               10              15

Lys Arg Glu

<210> SEQ ID NO 480
<211> LENGTH: 7
<212> TYPE: PRT
<213> ORGANISM: Homo sapiens

<400> SEQUENCE: 480

Leu Leu Leu Ser Leu Phe Val
1               5

<210> SEQ ID NO 481
<211> LENGTH: 8
<212> TYPE: PRT
<213> ORGANISM: Homo sapiens

<400> SEQUENCE: 481

Leu Leu Leu Ser Leu Phe Val Leu
1               5

<210> SEQ ID NO 482
<211> LENGTH: 9
<212> TYPE: PRT
<213> ORGANISM: Homo sapiens

<400> SEQUENCE: 482

Leu Leu Leu Ser Leu Phe Val Leu Gly
1               5

<210> SEQ ID NO 483
<211> LENGTH: 10
<212> TYPE: PRT
<213> ORGANISM: Homo sapiens

<400> SEQUENCE: 483

Leu Leu Leu Ser Leu Phe Val Leu Gly Leu
1               5               10

<210> SEQ ID NO 484
<211> LENGTH: 11
<212> TYPE: PRT
<213> ORGANISM: Homo sapiens

<400> SEQUENCE: 484

Leu Leu Leu Ser Leu Phe Val Leu Gly Leu Phe
1               5               10

<210> SEQ ID NO 485

<211> LENGTH: 12
<212> TYPE: PRT
<213> ORGANISM: Homo sapiens

<400> SEQUENCE: 485

Leu Leu Leu Ser Leu Phe Val Leu Gly Leu Phe Leu
1               5                   10

<210> SEQ ID NO 486
<211> LENGTH: 13
<212> TYPE: PRT
<213> ORGANISM: Homo sapiens

<400> SEQUENCE: 486

Leu Leu Leu Ser Leu Phe Val Leu Gly Leu Phe Leu Trp
1               5                   10

<210> SEQ ID NO 487
<211> LENGTH: 14
<212> TYPE: PRT
<213> ORGANISM: Homo sapiens

<400> SEQUENCE: 487

Leu Leu Leu Ser Leu Phe Val Leu Gly Leu Phe Leu Trp Phe
1               5                   10

<210> SEQ ID NO 488
<211> LENGTH: 15
<212> TYPE: PRT
<213> ORGANISM: Homo sapiens

<400> SEQUENCE: 488

Leu Leu Leu Ser Leu Phe Val Leu Gly Leu Phe Leu Trp Phe Leu
1               5                   10                  15

<210> SEQ ID NO 489
<211> LENGTH: 16
<212> TYPE: PRT
<213> ORGANISM: Homo sapiens

<400> SEQUENCE: 489

Leu Leu Leu Ser Leu Phe Val Leu Gly Leu Phe Leu Trp Phe Leu Lys
1               5                   10                  15

<210> SEQ ID NO 490
<211> LENGTH: 17
<212> TYPE: PRT
<213> ORGANISM: Homo sapiens

<400> SEQUENCE: 490

Leu Leu Leu Ser Leu Phe Val Leu Gly Leu Phe Leu Trp Phe Leu Lys
1               5                   10                  15

Arg

<210> SEQ ID NO 491
<211> LENGTH: 18
<212> TYPE: PRT
<213> ORGANISM: Homo sapiens

<400> SEQUENCE: 491

Leu Leu Leu Ser Leu Phe Val Leu Gly Leu Phe Leu Trp Phe Leu Lys
1               5                   10                  15

Arg Glu

<210> SEQ ID NO 492
<211> LENGTH: 6
<212> TYPE: PRT
<213> ORGANISM: Homo sapiens

<400> SEQUENCE: 492

Leu Leu Ser Leu Phe Val
1               5

<210> SEQ ID NO 493
<211> LENGTH: 7
<212> TYPE: PRT
<213> ORGANISM: Homo sapiens

<400> SEQUENCE: 493

Leu Leu Ser Leu Phe Val Leu
1               5

<210> SEQ ID NO 494
<211> LENGTH: 8
<212> TYPE: PRT
<213> ORGANISM: Homo sapiens

<400> SEQUENCE: 494

Leu Leu Ser Leu Phe Val Leu Gly
1               5

<210> SEQ ID NO 495
<211> LENGTH: 9
<212> TYPE: PRT
<213> ORGANISM: Homo sapiens

<400> SEQUENCE: 495

Leu Leu Ser Leu Phe Val Leu Gly Leu
1               5

<210> SEQ ID NO 496
<211> LENGTH: 10
<212> TYPE: PRT
<213> ORGANISM: Homo sapiens

<400> SEQUENCE: 496

Leu Leu Ser Leu Phe Val Leu Gly Leu Phe
1               5                   10

<210> SEQ ID NO 497
<211> LENGTH: 11
<212> TYPE: PRT
<213> ORGANISM: Homo sapiens

<400> SEQUENCE: 497

Leu Leu Ser Leu Phe Val Leu Gly Leu Phe Leu
1               5                   10

<210> SEQ ID NO 498
<211> LENGTH: 12
<212> TYPE: PRT
<213> ORGANISM: Homo sapiens

<400> SEQUENCE: 498

Leu Leu Ser Leu Phe Val Leu Gly Leu Phe Leu Trp
1               5                   10

<210> SEQ ID NO 499

<211> LENGTH: 13
<212> TYPE: PRT
<213> ORGANISM: Homo sapiens

<400> SEQUENCE: 499

Leu Leu Ser Leu Phe Val Leu Gly Leu Phe Leu Trp Phe
1               5                   10

<210> SEQ ID NO 500
<211> LENGTH: 14
<212> TYPE: PRT
<213> ORGANISM: Homo sapiens

<400> SEQUENCE: 500

Leu Leu Ser Leu Phe Val Leu Gly Leu Phe Leu Trp Phe Leu
1               5                   10

<210> SEQ ID NO 501
<211> LENGTH: 15
<212> TYPE: PRT
<213> ORGANISM: Homo sapiens

<400> SEQUENCE: 501

Leu Leu Ser Leu Phe Val Leu Gly Leu Phe Leu Trp Phe Leu Lys
1               5                   10                  15

<210> SEQ ID NO 502
<211> LENGTH: 16
<212> TYPE: PRT
<213> ORGANISM: Homo sapiens

<400> SEQUENCE: 502

Leu Leu Ser Leu Phe Val Leu Gly Leu Phe Leu Trp Phe Leu Lys Arg
1               5                   10                  15

<210> SEQ ID NO 503
<211> LENGTH: 17
<212> TYPE: PRT
<213> ORGANISM: Homo sapiens

<400> SEQUENCE: 503

Leu Leu Ser Leu Phe Val Leu Gly Leu Phe Leu Trp Phe Leu Lys Arg
1               5                   10                  15

Glu

<210> SEQ ID NO 504
<211> LENGTH: 5
<212> TYPE: PRT
<213> ORGANISM: Homo sapiens

<400> SEQUENCE: 504

Leu Ser Leu Phe Val
1               5

<210> SEQ ID NO 505
<211> LENGTH: 6
<212> TYPE: PRT
<213> ORGANISM: Homo sapiens

<400> SEQUENCE: 505

Leu Ser Leu Phe Val Leu
1               5

<210> SEQ ID NO 506

```
<211> LENGTH: 7
<212> TYPE: PRT
<213> ORGANISM: Homo sapiens

<400> SEQUENCE: 506

Leu Ser Leu Phe Val Leu Gly
1               5

<210> SEQ ID NO 507
<211> LENGTH: 8
<212> TYPE: PRT
<213> ORGANISM: Homo sapiens

<400> SEQUENCE: 507

Leu Ser Leu Phe Val Leu Gly Leu
1               5

<210> SEQ ID NO 508
<211> LENGTH: 9
<212> TYPE: PRT
<213> ORGANISM: Homo sapiens

<400> SEQUENCE: 508

Leu Ser Leu Phe Val Leu Gly Leu Phe
1               5

<210> SEQ ID NO 509
<211> LENGTH: 10
<212> TYPE: PRT
<213> ORGANISM: Homo sapiens

<400> SEQUENCE: 509

Leu Ser Leu Phe Val Leu Gly Leu Phe Leu
1               5                   10

<210> SEQ ID NO 510
<211> LENGTH: 11
<212> TYPE: PRT
<213> ORGANISM: Homo sapiens

<400> SEQUENCE: 510

Leu Ser Leu Phe Val Leu Gly Leu Phe Leu Trp
1               5                   10

<210> SEQ ID NO 511
<211> LENGTH: 12
<212> TYPE: PRT
<213> ORGANISM: Homo sapiens

<400> SEQUENCE: 511

Leu Ser Leu Phe Val Leu Gly Leu Phe Leu Trp Phe
1               5                   10

<210> SEQ ID NO 512
<211> LENGTH: 13
<212> TYPE: PRT
<213> ORGANISM: Homo sapiens

<400> SEQUENCE: 512

Leu Ser Leu Phe Val Leu Gly Leu Phe Leu Trp Phe Leu
1               5                   10

<210> SEQ ID NO 513
<211> LENGTH: 14
<212> TYPE: PRT
```

<213> ORGANISM: Homo sapiens

<400> SEQUENCE: 513

Leu Ser Leu Phe Val Leu Gly Leu Phe Leu Trp Phe Leu Lys
1               5                   10

<210> SEQ ID NO 514
<211> LENGTH: 15
<212> TYPE: PRT
<213> ORGANISM: Homo sapiens

<400> SEQUENCE: 514

Leu Ser Leu Phe Val Leu Gly Leu Phe Leu Trp Phe Leu Lys Arg
1               5                   10                  15

<210> SEQ ID NO 515
<211> LENGTH: 16
<212> TYPE: PRT
<213> ORGANISM: Homo sapiens

<400> SEQUENCE: 515

Leu Ser Leu Phe Val Leu Gly Leu Phe Leu Trp Phe Leu Lys Arg Glu
1               5                   10                  15

<210> SEQ ID NO 516
<211> LENGTH: 5
<212> TYPE: PRT
<213> ORGANISM: Homo sapiens

<400> SEQUENCE: 516

Ser Leu Phe Val Leu
1               5

<210> SEQ ID NO 517
<211> LENGTH: 6
<212> TYPE: PRT
<213> ORGANISM: Homo sapiens

<400> SEQUENCE: 517

Ser Leu Phe Val Leu Gly
1               5

<210> SEQ ID NO 518
<211> LENGTH: 7
<212> TYPE: PRT
<213> ORGANISM: Homo sapiens

<400> SEQUENCE: 518

Ser Leu Phe Val Leu Gly Leu
1               5

<210> SEQ ID NO 519
<211> LENGTH: 8
<212> TYPE: PRT
<213> ORGANISM: Homo sapiens

<400> SEQUENCE: 519

Ser Leu Phe Val Leu Gly Leu Phe
1               5

<210> SEQ ID NO 520
<211> LENGTH: 9
<212> TYPE: PRT
<213> ORGANISM: Homo sapiens

<400> SEQUENCE: 520

Ser Leu Phe Val Leu Gly Leu Phe Leu
1               5

<210> SEQ ID NO 521
<211> LENGTH: 10
<212> TYPE: PRT
<213> ORGANISM: Homo sapiens

<400> SEQUENCE: 521

Ser Leu Phe Val Leu Gly Leu Phe Leu Trp
1               5                   10

<210> SEQ ID NO 522
<211> LENGTH: 11
<212> TYPE: PRT
<213> ORGANISM: Homo sapiens

<400> SEQUENCE: 522

Ser Leu Phe Val Leu Gly Leu Phe Leu Trp Phe
1               5                   10

<210> SEQ ID NO 523
<211> LENGTH: 12
<212> TYPE: PRT
<213> ORGANISM: Homo sapiens

<400> SEQUENCE: 523

Ser Leu Phe Val Leu Gly Leu Phe Leu Trp Phe Leu
1               5                   10

<210> SEQ ID NO 524
<211> LENGTH: 13
<212> TYPE: PRT
<213> ORGANISM: Homo sapiens

<400> SEQUENCE: 524

Ser Leu Phe Val Leu Gly Leu Phe Leu Trp Phe Leu Lys
1               5                   10

<210> SEQ ID NO 525
<211> LENGTH: 14
<212> TYPE: PRT
<213> ORGANISM: Homo sapiens

<400> SEQUENCE: 525

Ser Leu Phe Val Leu Gly Leu Phe Leu Trp Phe Leu Lys Arg
1               5                   10

<210> SEQ ID NO 526
<211> LENGTH: 15
<212> TYPE: PRT
<213> ORGANISM: Homo sapiens

<400> SEQUENCE: 526

Ser Leu Phe Val Leu Gly Leu Phe Leu Trp Phe Leu Lys Arg Glu
1               5                   10                  15

<210> SEQ ID NO 527
<211> LENGTH: 5
<212> TYPE: PRT
<213> ORGANISM: Homo sapiens

<400> SEQUENCE: 527

Leu Phe Val Leu Gly
1               5

<210> SEQ ID NO 528
<211> LENGTH: 6
<212> TYPE: PRT
<213> ORGANISM: Homo sapiens

<400> SEQUENCE: 528

Leu Phe Val Leu Gly Leu
1               5

<210> SEQ ID NO 529
<211> LENGTH: 7
<212> TYPE: PRT
<213> ORGANISM: Homo sapiens

<400> SEQUENCE: 529

Leu Phe Val Leu Gly Leu Phe
1               5

<210> SEQ ID NO 530
<211> LENGTH: 8
<212> TYPE: PRT
<213> ORGANISM: Homo sapiens

<400> SEQUENCE: 530

Leu Phe Val Leu Gly Leu Phe Leu
1               5

<210> SEQ ID NO 531
<211> LENGTH: 9
<212> TYPE: PRT
<213> ORGANISM: Homo sapiens

<400> SEQUENCE: 531

Leu Phe Val Leu Gly Leu Phe Leu Trp
1               5

<210> SEQ ID NO 532
<211> LENGTH: 10
<212> TYPE: PRT
<213> ORGANISM: Homo sapiens

<400> SEQUENCE: 532

Leu Phe Val Leu Gly Leu Phe Leu Trp Phe
1               5                    10

<210> SEQ ID NO 533
<211> LENGTH: 11
<212> TYPE: PRT
<213> ORGANISM: Homo sapiens

<400> SEQUENCE: 533

Leu Phe Val Leu Gly Leu Phe Leu Trp Phe Leu
1               5                    10

<210> SEQ ID NO 534
<211> LENGTH: 12
<212> TYPE: PRT
<213> ORGANISM: Homo sapiens

<400> SEQUENCE: 534

Leu Phe Val Leu Gly Leu Phe Leu Trp Phe Leu Lys
1               5                    10

```
<210> SEQ ID NO 535
<211> LENGTH: 13
<212> TYPE: PRT
<213> ORGANISM: Homo sapiens

<400> SEQUENCE: 535

Leu Phe Val Leu Gly Leu Phe Leu Trp Phe Leu Lys Arg
1               5                   10

<210> SEQ ID NO 536
<211> LENGTH: 14
<212> TYPE: PRT
<213> ORGANISM: Homo sapiens

<400> SEQUENCE: 536

Leu Phe Val Leu Gly Leu Phe Leu Trp Phe Leu Lys Arg Glu
1               5                   10

<210> SEQ ID NO 537
<211> LENGTH: 9
<212> TYPE: PRT
<213> ORGANISM: Human immunodeficiency virus

<400> SEQUENCE: 537

Arg Tyr Leu Lys Asp Gln Gln Leu Leu
1               5

<210> SEQ ID NO 538
<211> LENGTH: 9
<212> TYPE: PRT
<213> ORGANISM: Homo sapiens

<400> SEQUENCE: 538

Arg Met Phe Pro Asn Ala Pro Tyr Leu
1               5

<210> SEQ ID NO 539
<211> LENGTH: 9
<212> TYPE: PRT
<213> ORGANISM: Homo sapiens

<400> SEQUENCE: 539

Tyr Met Phe Pro Asn Ala Pro Tyr Leu
1               5

<210> SEQ ID NO 540
<211> LENGTH: 19
<212> TYPE: PRT
<213> ORGANISM: Homo sapiens

<400> SEQUENCE: 540

Arg Ser Asp Glu Leu Val Arg His His Asn Met His Gln Arg Asn Met
1               5                   10                  15

Thr Lys Leu

<210> SEQ ID NO 541
<211> LENGTH: 22
<212> TYPE: PRT
<213> ORGANISM: Homo sapiens

<400> SEQUENCE: 541

Pro Gly Cys Asn Lys Arg Tyr Phe Lys Leu Ser His Leu Gln Met His
1               5                   10                  15
```

```
Ser Arg Lys His Thr Gly
            20

<210> SEQ ID NO 542
<211> LENGTH: 19
<212> TYPE: PRT
<213> ORGANISM: Homo sapiens

<400> SEQUENCE: 542

Ser Gly Gln Ala Arg Met Phe Pro Asn Ala Pro Tyr Leu Pro Ser Cys
1               5                   10                  15

Leu Glu Ser

<210> SEQ ID NO 543
<211> LENGTH: 19
<212> TYPE: PRT
<213> ORGANISM: Homo sapiens

<400> SEQUENCE: 543

Ser Gly Gln Ala Tyr Met Phe Pro Asn Ala Pro Tyr Leu Pro Ser Cys
1               5                   10                  15

Leu Glu Ser

<210> SEQ ID NO 544
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 544

His His His His His His
1               5
```

XBP1, CD138, AND CS1 PEPTIDES, PHARMACEUTICAL COMPOSITIONS THAT INCLUDE THE PEPTIDES, AND METHODS OF USING SUCH PEPTIDES AND COMPOSITIONS

CROSS REFERENCE TO RELATED APPLICATIONS

This application is a continuation of U.S. application Ser. No. 15/689,159, filed Aug. 29, 2017, which is a continuation of U.S. application Ser. No. 14/440,442, filed Nov. 5, 2013, which is a U.S. National Phase Application under 35 U.S.C. § 371 of International Application No. PCT/US2013/068582, filed Nov. 5, 2013, which claims priority to U.S. Ser. No. 61/722,446 filed Nov. 5, 2012, and U.S. Ser. No. 61/790,780 filed Mar. 15, 2013 the entire contents of which are incorporated herein by reference.

STATEMENT REGARDING FEDERALLY SPONSORED RESEARCH OR DEVELOPMENT

This invention was made with government support under grant numbers P01CA078378, P01CA155258, and P50CA100707 awarded by The National Institute of Health. The government has certain rights in the invention.

SEQUENCE LISTING

The instant application contains a Sequence Listing which has been submitted electronically in ASCII format. Said ASCII copy, created on Dec. 9, 2013, is named 02017-7001WO_SL.txt and is 117,979 bytes in size.

BACKGROUND

Several types of vaccines have been developed for the prevention of infectious diseases including attenuated microorganisms, recombinant proteins and DNA vaccines. Recently, research has been carried out on the development of vaccine immunotherapy to treat cancer patients.

SUMMARY

The present disclosure relates to immunogenic peptides that bind to MHC class 1 molecules such as HLA-A molecules. It was found that peptides from X-Box Protein 1 (XBP1)-, CD138-, and CD2 Subset 1 (CS1) are immunogenic and are useful, e.g., to induce an immune response against various cancer cells. In some embodiments the peptides possess elevated affinity for HLA-A molecules, elevated stability within the peptide binding cleft of HLA-A, and the ability, when expressed on the surface of cell (e.g., a cancer cell) in the context of an MHC molecule, to induce the activation and proliferation of T cells (e.g., effector memory T cells and/or central memory T cells).

In addition, it was found that combinations of these peptides can induce a broad spectrum of immune responses against the target antigens and this broad spectrum response can overcome major therapeutic hurdles including, inter alia, the heterogeneity of tumor associated antigen expression, frequent mutations of specific antigens and the variability of the human T-cell repertoire among individuals. Thus, administration of various combinations of these peptides, e.g., combined in a pharmaceutical composition, may provide an enhanced immune response against various cancers.

It will be evident from the following description that the peptides (and pharmaceutical compositions thereof) can be used in a variety of applications such as methods for inducing an immune response, methods for activating a T cell (e.g., including effectory memory T cells and/or central memory T cells), methods for producing an antibody, and methods for treating, e.g., a cancer (e.g., breast cancer, colon cancer, pancreatic cancer, prostate cancer, leukemia, e.g., AML or CML), multiple myeloma, Waldenstrom's Macroglobulinemia and precancerous conditions, e.g., smoldering multiple myeloma.

In one aspect, the disclosure features peptides, e.g., XBP1 peptides, CD138 peptides and CS-1 peptides, that have affinity for multiple MHC molecules, e.g., HLA-A molecules such as HLA-A2 and HLA-A24, elevated stability within the peptide binding cleft of multiple MHC molecules, e.g., HLA-A2 and HLA-A24, and the ability, when expressed on the surface of cell (e.g., a cancer cell) in the context of an MHC molecule, e.g., HLA-A2 or HLA-A24, to induce the activation and proliferation of T cells including, e.g., effector memory T cells and/or central memory T cells).

It will be evident from the following description that the peptides (and pharmaceutical compositions thereof) can be used in a variety of applications such as methods for inducing an immune response, methods for activating a T cell (e.g., effector memory T cells and/or central memory T cells), methods for producing an antibody, and methods for treating, e.g., a cancer (e.g., lung cancer, liver cancer, bile duct cancer, stomach cancer, cervical cancer, nasopharyngeal cancer, breast cancer, colon cancer, pancreatic cancer, prostate cancer, leukemia, e.g., AML or CML), multiple myeloma and precancerous conditions, e.g., smoldering multiple myeloma.

In one aspect, the disclosure features an isolated peptide comprising an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS: 51-536. The peptide can bind to a major histocompatibility complex (MHC) molecule such as an MHC class I or class II molecule. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 51-536 or an amino acid sequence that is at least 70%, 75%, 80%, 85%, 90%, 95%, 96%, 97%, 98% or 99% identical to any of SEQ ID NOs: 51-536. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 51-536. In one embodiment, the peptide is 9, 10, 11, 12, 13, 14, 15, 16, 17, 18, 19, 20, up to 25, 30 or 35 amino acids in length and the peptide comprises an amino acid sequence with three, two, or one substitution(s) of any one of SEQ ID NOs: 51-536. The substitutions can be conservative or non-conservative. In one embodiment, the peptide is used to treat a subject having or at risk of having cancer, e.g., a cancer described herein, e.g., lung cancer, liver cancer, bile duct cancer, stomach cancer, cervical cancer, nasopharyngeal cancer, breast cancer, colon cancer, pancreatic cancer, prostate cancer, leukemia, e.g., AML or CML, or multiple myeloma.

In one embodiment, the peptide is used to treat a subject having a precancerous condition, e.g., smoldering multiple myeloma.

In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer). In one embodiment, the cancer is breast cancer (e.g., invasive lobular, invasive ductal, mixed lobular and ductal, intraductal cribriform, invasive ductal and lobular or invasive carcinoma). In one embodiment, the cancer is a colon adenocarcinoma (e.g., mucinous adenocarcinoma).

In one embodiment, the peptide consists of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS: 51-536. In one embodiment, the peptide consists of an amino acid sequence with three, two or one substitution of any one of SEQ ID NOS:51-536. In one embodiment, the peptide consists of an amino acid sequence of any one of SEQ ID NOS: 51-536.

In one embodiment, the peptide is a non-spliced XBP1 peptide of Group C (see, e.g., Table 3), e.g., a non-spliced XBP-1 peptide comprising an amino acid sequence of any one of SEQ ID NOS: 51-206 or a non-spliced XBP1 peptide comprising an amino acid sequence having 70%, 75%, 80%, 85%, 90%, 95%, 96%, 97%, 98%, or 99% identity with any one of SEQ ID NOS: 51-206. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 51-206 or an amino acid sequence having 70%, 75%, 80%, 85%, 90%, 95%, 96%, 97%, 98%, or 99% identity with any one of SEQ ID NOS: 51-206. In one embodiment, the non-spliced XBP1 peptide of Group C is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 51-206. The substitutions can be conservative or non-conservative. In one embodiment, the non-spliced XBP1 peptide of Group C consists of an amino acid sequence of any one of SEQ ID NOS: 51-206.

In one embodiment, the peptide is a CD138 peptide of Group C, e.g., a CD138 peptide comprising an amino acid sequence of any one of SEQ ID NOS: 207-371 or a CD138 peptide comprising an amino acid sequence having 70%, 75%, 80%, 85%, 90%, 95%, 96%, 97%, 98%, or 99% identity with an amino acid sequence of any one of SEQ ID NOS: 207-371. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 207-371 or an amino acid sequence having 70%, 75%, 80%, 85%, 90%, 95%, 96%, 97%, 98%, or 99% identity with any one of SEQ ID NOS: 207-371. In one embodiment, the CD138 peptide of Group C is 9, 10, 11, 12, 13, 14, 15, 16, 17, 18, 19, 20, up to 25, 30 or 35 amino acids in length and the peptide comprises an amino acid sequence with three, two, one substitutions of an amino acid sequence of any one of SEQ ID NOS: 207-371. The substitutions can be conservative or non-conservative. In one embodiment, the CD138 peptide of Group C consists of an amino acid sequence of any one of SEQ ID NOS: 207-371.

In one embodiment, the peptide is a CS-1 peptide of Group C, e.g., a CS-1 peptide comprising an amino acid sequence of any one of SEQ ID NOS: 372-536 or a CS-1 peptide comprising an amino acid sequence having 70%, 75%, 80%, 85%, 90%, 95%, 96%, 97%, 98%, or 99% identity with an amino acid sequence of any one of SEQ ID NOS: 372-536. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 372-536 or an amino acid sequence having 70%, 75%, 80%, 85%, 90%, 95%, 96%, 97%, 98%, or 99% identity with any one of SEQ ID NOS: 372-536. In one embodiment, the CS-1 peptide of Group C is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 372-536. The substitutions can be conservative or non-conservative. In one embodiment, the CS-1 peptide of Group C consists of an amino acid sequence of any one of SEQ ID NOS: 372-536.

In one embodiment, the peptide of Group C, e.g., the XBP peptide, the CD138 peptide and/or the CS-1 peptide, is used to treat a subject having or at risk of having cancer, e.g., a cancer described herein, e.g., lung cancer, liver cancer, bile duct cancer, stomach cancer, cervical cancer, nasopharyngeal cancer, breast cancer, colon cancer, pancreatic cancer, prostate cancer, leukemia, e.g., AML or CML. In one embodiment, the peptide of Group C is used to treat a subject having a precancerous condition, e.g., smoldering multiple myeloma. In an embodiment, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer).

In some embodiments, any of the isolated peptides described herein can bind to a major histocompatibility complex (MHC) molecule (e.g., an MHC class I or class II molecule). The MHC molecule can be, e.g., a human MHC molecule. The MHC molecule can be, e.g., an HLA-A molecule, an HLA-B molecule and/or an HLA-C molecule. Preferably, the MHC molecule is one or more HLA-A molecule (e.g., HLA-A1, HLA-A2, HLA-A3 and HLA-A24).

In one aspect, the disclosure features immunogenic X-Box Protein 1 (XBP1)-, CD138-, and CD2 Subset 1 (CS1)-derived peptides, e.g., which possess elevated affinity for HLA-A2 molecules, elevated stability within the peptide binding cleft of HLA-A2, and the ability, when expressed on the surface of cell (e.g., a cancer cell) in the context of an MHC molecule, to induce the activation and proliferation of T cells (e.g., effector memory T cells and/or central memory T cells). For example, all or a subset of these peptides are expressed on the surface of various cancer cells, including multiple myeloma cells, and specifically smoldering multiple myeloma cells, colon cancer cells, breast cancer cells, pancreatic cancer cells, prostate cancer cells and leukemia, e.g., acute myeloid leukemia (AML) cells, in the context of an MHC molecule, and the presence of these peptides induces activation and proliferation of T cells against these and other cancers.

In addition, it was found that combinations of these peptides can induce a broad spectrum of immune responses against the target antigens and this broad spectrum response can overcome major therapeutic hurdles including, inter alia, the heterogeneity of tumor associated antigen expression, frequent mutations of specific antigens and the variability of the human T-cell repertoire among individuals. Thus, administration of combinations of these peptides, e.g., combined in a pharmaceutical composition, may provide an enhanced immune response against various cancers.

It will be evident from the following description that the peptides (and pharmaceutical compositions thereof) can be used in a variety of applications such as methods for inducing an immune response, methods for activating a T cell (e.g., effector memory T cells and/or central memory T cells), methods for producing an antibody, and methods for treating, e.g., a cancer (e.g., breast cancer, colon cancer, pancreatic cancer, prostate cancer, leukemia, e.g., AML or CML), multiple myeloma and precancerous conditions, e.g., smoldering multiple myeloma.

In one aspect, the disclosure features an isolated peptide comprising an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-18. The peptide can bind to a major histocompatibility complex (MHC) molecule such as an MHC class I or class II molecule. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:1-18, or an amino acid sequence that is at least 70%, 75%, 80%, 85%, 90%, 95%, 96%, 97%, 98% or 99% identical to an amino acid sequence of SEQ ID NOS:1-18. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:1-18. In one embodiment, the peptide is 9, 10, 11, 12, 13, 14, 15, 16, 17, 18, 19, 20, up to 25, 30 or 35 amino acids in length and the peptide comprises an amino acid sequence with three, two, or one substitution(s) of an amino acid sequence of any one of SEQ ID NOS:1-18. The substitutions can be conservative or non-conservative. In one embodiment, the peptide is used to treat a subject having or at risk of having cancer, e.g., a cancer described herein, e.g., breast cancer (e.g., invasive lobular, invasive ductal, mixed lobular and ductal, intraductal cribriform, invasive lobular and ductal, invasive carcinoma), colon cancer (e.g., adenocarcinoma, e.g., mucinous adenocarcinoma), pancreatic cancer, prostate cancer, leukemia, e.g., AML or CML, or multiple myeloma.

In one embodiment, the peptide is used to treat a subject having a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck.

In one embodiment, the peptide consists of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-18. In one embodiment, the peptide consists of any of amino acid sequences of SEQ ID NOS;1-18 with three, two or one substitution. In one embodiment, the peptide consists of an amino acid sequence of any one of SEQ ID NOS:1-18.

In one embodiment, the peptide is a non-spliced XBP1 peptide of Group A (see, e.g., Table 1), e.g., a non-spliced XBP-1 peptide comprising an amino acid sequence of any one of SEQ ID NOS: 1-6, a non-spliced XBP1 peptide comprising an amino acid sequence having 70%, 75%, 80%, 85%, 90%, 95%, 96%, 97%, 98%, or 99% identity with an amino acid sequence of any one of SEQ ID NOS:1-6. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:1-6 or an amino acid sequence having 70%, 75%, 80%, 85%, 90%, 95%, 96%, 97%, 98%, or 99% identity with an amino acid sequence of any one of SEQ ID NOS:1-6. In one embodiment, the non-spliced XBP1 peptide of Group A is 9, 10, 11, 12, 13, 14, 15, 16, 17, 18, 19, 20, up to 25, 30 or 35 amino acids in length and the peptide comprises an amino acid sequence with three, two, one substitutions of an amino acid sequence of any one of SEQ ID NOS:1-6. The substitutions can be conservative or non-conservative. In one embodiment, the non-spliced XBP1 peptide of Group A consists of an amino acid sequence of any one of SEQ ID NOS:1-6.

In one embodiment, the peptide is a spliced XBP1 peptide of Group A, e.g., a spliced XBP-1 peptide comprising an amino acid sequence of any one of SEQ ID NOS: 7-10, a spliced XBP1 peptide comprising an amino acid sequence having 70%, 75%, 80%, 85%, 90%, 95%, 96%, 97%, 98%, or 99% identity with an amino acid sequence of any one of SEQ ID NOS:7-10. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:7-10 or an amino acid sequence having 70%, 75%, 80%, 85%, 90%, 95%, 96%, 97%, 98%, or 99% identity with an amino acid sequence of any one of SEQ ID NOS:7-10. In one embodiment, the spliced XBP1 peptide of Group A is 9, 10, 11, 12, 13, 14, 15, 16, 17, 18, 19, 20, up to 25, 30 or 35 amino acids in length and the peptide comprises an amino acid sequence with three, two, one substitutions of an amino acid sequence of any one of SEQ ID NOS:7-10. The substitutions can be conservative or non-conservative. In one embodiment, the spliced XBP1 peptide of Group A consists of an amino acid sequence of any one of SEQ ID NOS:7-10.

In one embodiment, the peptide is a CD138 peptide of Group A, e.g., a CD138 peptide comprising an amino acid sequence of any one of SEQ ID NOS: 11-14, a CD138 peptide comprising an amino acid sequence having 70%, 75%, 80%, 85%, 90%, 95%, 96%, 97%, 98%, or 99% identity with an amino acid sequence of any one of SEQ ID NOS:11-14. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:11-14 or an amino acid sequence having 70%, 75%, 80%, 85%, 90%, 95%, 96%, 97%, 98%, or 99% identity with an amino acid sequence of any one of SEQ ID NOS:11-14. In one embodiment, the CD138 peptide of Group A is 9, 10, 11, 12, 13, 14, 15, 16, 17, 18, 19, 20, up to 25, 30 or 35 amino acids in length and the peptide comprises an amino acid sequence with three, two, one substitutions of an amino acid sequence of any one of SEQ ID NOS:11-14. The substitutions can be conservative or non-conservative. In one embodiment, the CD138 peptide of Group A consists of an amino acid sequence of any one of SEQ ID NOS:11-14.

In one embodiment, the peptide is a CS-1 peptide of Group A, e.g., a CS-1 peptide comprising an amino acid sequence of any one of SEQ ID NOS: 15-18, a CS-1 peptide comprising an amino acid sequence having 70%, 75%, 80%, 85%, 90%, 95%, 96%, 97%, 98%, or 99% identity with an amino acid sequence of any one of SEQ ID NOS:15-18. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:15-18 or an amino acid sequence having 70%, 75%, 80%, 85%, 90%, 95%, 96%, 97%, 98%, or 99% identity with an amino acid sequence of any one of SEQ ID NOS:15-18. In one embodiment, the CS-1 peptide of Group A is 9, 10, 11, 12, 13, 14, 15, 16, 17, 18, 19, 20, up to 25, 30 or 35 amino acids in length and the peptide comprises an amino acid sequence with three, two, one substitutions of an amino acid sequence of any one of SEQ ID NOS:15-18. The substitutions can be conservative or non-conservative. In one embodiment, the CS-1 peptide of Group A consists of an amino acid sequence of any one of SEQ ID NOS:15-18.

In one embodiment, the peptide of Group A, e.g., the non-spliced XBP1 peptide, the spliced XBP1 peptide, the CD138 peptide and/or the CS-1 peptide, is used to treat a subject having or at risk of having cancer, e.g., a cancer described herein, e.g., breast cancer, colon cancer, pancreatic cancer, prostate cancer, leukemia, e.g., AML or CML. In one embodiment, the peptide of Group A, e.g., the non-spliced XBP1 peptide, the spliced XBP1 peptide, the CD138 peptide and/or the CS-1 peptide, is used to treat a subject having a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck.

In some embodiments, any of the isolated peptides described herein can bind to a major histocompatibility complex (MHC) molecule (e.g., an MHC class I or class II molecule). The MHC molecule can be, e.g., an HLA-A2 molecule. The MHC molecule can be, e.g., a human MHC molecule.

In another aspect, the disclosure features immunogenic X-Box Protein 1 (XBP1)-, CD138-, and CD2 Subset 1 (CS1)-derived peptides, e.g., which possess elevated affinity for HLA-A24 molecules, elevated stability within the peptide binding cleft of HLA-A24, and the ability, when expressed on the surface of cell (e.g., a cancer cell) in the context of an MHC molecule, to induce the activation and proliferation of T cells (e.g., effector memory T cells and/or central memory T cells). For example, all or a subset of these peptides are expressed on the surface of various cancer cells, including multiple myeloma cells, colon cancer cells, breast cancer cells, pancreatic cancer cells, prostate cancer cells and leukemia, e.g., acute myeloid leukemia (AML) cells, in the context of an MHC molecule, and the presence of these peptides induces activation and proliferation of T cells against these and other cancers.

It will be evident from the following description that the peptides (and pharmaceutical compositions thereof) can be used in a variety of applications such as methods for inducing an immune response, methods for activating a T cell (e.g., effector memory T cells and/or central memory T cells), methods for producing an antibody, and methods for treating, e.g., a cancer (e.g., lung cancer, liver cancer, bile duct cancer, stomach cancer, cervical cancer, nasopharyngeal cancer, breast cancer, colon cancer, pancreatic cancer, prostate cancer, leukemia, e.g., AML or CML), multiple myeloma and precancerous conditions, e.g., smoldering multiple myeloma.

In one aspect, the disclosure features an isolated peptide comprising an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS: 29-50. The peptide can bind to a major histocompatibility complex (MHC) molecule such as an MHC class I or class II molecule. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 29-50, or an amino acid sequence that is at least 70%, 75%, 80%, 85%, 90%, 95%, 96%, 97%, 98% or 99% identical to an amino acid sequence of SEQ ID NOS: 29-50. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 29-50. In one embodiment, the peptide is 9, 10, 11, 12, 13, 14, 15, 16, 17, 18, 19, 20, up to 25, 30 or 35 amino acids in length and the peptide comprises an amino acid sequence with three, two, or one substitution(s) of an amino acid sequence of any one of SEQ ID NOS: 29-50. The substitutions can be conservative or non-conservative. In one embodiment, the peptide is used to treat a subject having or at risk of having cancer, e.g., a cancer described herein, e.g., lung cancer, liver cancer, bile duct cancer, stomach cancer, cervical cancer, nasopharyngeal cancer, breast cancer (e.g., invasive lobular, invasive ductal, mixed lobular and ductal, intraductal cribriform, invasive lobular and ductal, invasive carcinoma), colon cancer (e.g., colon adenocarcinoma, e.g., mucinous adenocarcinoma), pancreatic cancer, prostate cancer, leukemia, e.g., AML or CML, or multiple myeloma.

In one embodiment, the peptide is used to treat a subject having a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer).

In one embodiment, the peptide consists of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS: 29-50. In one embodiment, the peptide consists of an amino acid sequence of any one of SEQ ID NOS:29-50 with three, two or one substitution. In one embodiment, the peptide consists of an amino acid sequence of any one of SEQ ID NOS: 29-50.

In one embodiment, the peptide is a non-spliced XBP1 peptide from Group B (see Table 2), e.g., a non-spliced XBP-1 peptide comprising an amino acid sequence of any one of SEQ ID NOS: 29 and 33-37 or a non-spliced XBP1 peptide comprising an amino acid sequence having 70%, 75%, 80%, 85%, 90%, 95%, 96%, 97%, 98%, or 99% identity with any one of SEQ ID NOS: 29 and 33-37. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 29 and 33-37 or an amino acid sequence having 70%, 75%, 80%, 85%, 90%, 95%, 96%, 97%, 98%, or 99% identity with any one of SEQ ID NOS: 29 and 33-37. In one embodiment, the non-spliced XBP1 peptide from Group B is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 29 and 33-37. The substitutions can be conservative or non-conservative. In one embodiment, the non-spliced XBP1 peptide is from amino acid sequence SEQ ID NO:19 and comprises the amino acid sequence of SEQ ID NO:29 and 1, 2, 3, 4, 5, 6, 7, 8, 9 or more (e.g., 1, 2, 3) amino acids C-terminal to SEQ ID NO:29 in SEQ ID NO:19. In one embodiment, the non-spliced XBP1 peptide is from amino acid sequence SEQ ID NO:19 and comprises the amino acid sequence of SEQ ID NO:33 and 1, 2, 3, 4, 5, or more (e.g., 1, or 2) amino acids N-terminal to SEQ ID NO:33 in SEQ ID NO:19 and/or 1, 2, 3 or moiré (e.g., 1) amino acids C-terminal to SEQ ID NO:33 in SEQ ID NO:19. In one embodiment, the non-spliced XBP1 peptide is from amino acid sequence SEQ ID NO:19 and comprises the amino acid sequence of SEQ ID NO:36 and 1, 2, 3, 4, 5, 6, 7, 8, 9 or more (e.g., 1, 2, 3, or 4) amino acids N-terminal to SEQ ID NO:36 in SEQ ID NO:19 and/or 1, 2, 3, 5, 6 or more (e.g., 1, 2, 3, 4, 5 or 6) amino acids C-terminal to SEQ ID NO:36 in SEQ ID NO:19. In one embodiment, the non-spliced XBP1 peptide is from amino acid sequence SEQ ID NO:19 and comprises the amino acid sequence of any one of SEQ ID NOS: 34, 35 or 37 and 1, 2, 3, 4, 5, 6, 7, 8, 9 or more (e.g., 1, 2, 3) amino acids N-terminal and/or C-terminal to any one of SEQ ID NOS: 34, 35 or 37 in SEQ ID NO:19. In one embodiment, the non-spliced XBP1 peptide from Group B consists of an amino acid sequence of any one of SEQ ID NOS: 29 and 33-37.

In one embodiment, the peptide is a spliced XBP1 peptide from Group B, e.g., a spliced XBP-1 peptide comprising an amino acid sequence of any one of SEQ ID NOS: 30, 38 and 39 or a spliced XBP1 peptide comprising an amino acid sequence having 70%, 75%, 80%, 85%, 90%, 95%, 96%, 97%, 98%, or 99% identity with any one of SEQ ID NOS: 30, 38 and 39. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 30, 38 and 39 or an amino acid sequence having 70%, 75%, 80%, 85%, 90%, 95%, 96%, 97%, 98%, or 99% identity with any one of SEQ ID NOS: 30, 38 and 39. In one embodiment, the spliced XBP1 peptide from Group B is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 30, 38 and 39. The substitutions can be conservative or non-conservative. In one embodiment, the spliced XBP1 peptide is from amino acid sequence SEQ ID NO:20 and comprises the amino acid sequence of any one of SEQ ID NOS: 30, 38 and 39 and 1, 2, 3, 4, 5, 6, 7, 8, 9 or more (e.g., 1, 2, 3) amino acids N-terminal and/or C-terminal to any one of SEQ ID NOS: 30, 38, and 39 in SEQ ID NO:20 In one embodiment, the spliced XBP1 peptide from Group B consists of an amino acid sequence of any one of SEQ ID NOS: 30, 38 and 39.

In one embodiment, the peptide is a CD138 peptide from Group B, e.g., a CD138 peptide comprising an amino acid sequence of any one of SEQ ID NOS: 31 or a CD138 peptide comprising an amino acid sequence having 70%, 75%, 80%, 85%, 90%, 95%, 96%, 97%, 98%, or 99% identity with any one of SEQ ID NOS: 31 and 40-45. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 31 and 40-45 or an amino acid sequence having 70%, 75%, 80%, 85%, 90%, 95%, 96%, 97%, 98%, or 99% identity with any one of SEQ ID NOS: 31 and 40-45. In one embodiment, the CD138 peptide from Group B is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 31 and 40-45.

The substitutions can be conservative or non-conservative. In one embodiment, the CD138 peptide is from amino acid sequence SEQ ID NO:21 and comprises the amino acid sequence of SEQ ID NO:31 and 1, 2, 3, 4, 5, 6, 7, 8 or more (e.g., 1, 2, 3, 4) amino acids N-terminal to SEQ ID NO:31 in SEQ ID NO:21. In one embodiment, the CD138 peptide is from amino acid sequence SEQ ID NO:21 and comprises the amino acid sequence of SEQ ID NO:42 or 44 and 1, 2, 3, 4, 5, or more (e.g., 1, 2, 3, 4) amino acids N-terminal to SEQ ID NO:42 or 44 in SEQ ID NO:21 and/or 1, 2, 3, 4, 5, 6, 7, 8, 9 or more (e.g., 1, 2, 3, 4, 5, 6) amino acids C-terminal to SEQ ID NO:42 or 44 in SEQ ID NO:21. In one embodiment, the CD138 peptide is from amino acid sequence SEQ ID NO:21 and comprises the amino acid sequence of SEQ ID NO:45 and 1, 2, 3, 4, 5, 6, 7, 8, or more (e.g., 1, 2, 3, or 4) amino acids N-terminal to SEQ ID NO:45 in SEQ ID NO:21 and/or 1, 2, 3, 5, 6, 7, 8, 9 or more (e.g., 1, 2, 3, 4, 5 or 6) amino acids C-terminal to SEQ ID NO:45 in SEQ ID NO:21. In one embodiment, the CD138 peptide is from amino acid sequence SEQ ID NO:21 and comprises the amino acid sequence of any one of SEQ ID NOS: 40, 41 or 43 and 1, 2, 3, 4, 5, 6, 7, 8, 9 or more (e.g., 1, 2, 3) amino acids N-terminal and/or C-terminal to any one of SEQ ID NOS: 40, 41 or 43 in SEQ ID NO:21. In one embodiment, the CD138 peptide from Group B consists of an amino acid sequence of any one of SEQ ID NOS: 31 and 40-45.

In one embodiment, the peptide is a CS-1 peptide from Group B, e.g., a CS-1 peptide comprising an amino acid sequence of any one of SEQ ID NOS: 32 and 46-50 or a CS-1 peptide comprising an amino acid sequence having 70%, 75%, 80%, 85%, 90%, 95%, 96%, 97%, 98%, or 99% identity with any one of SEQ ID NOS: 32 and 46-50. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS: 32 and 46-50 or an amino acid sequence having 70%, 75%, 80%, 85%, 90%, 95%, 96%, 97%, 98%, or 99% identity with any one of SEQ ID NOS: 32 and 46-50. In one embodiment, the CS-1 peptide from Group B is 9, 10, 11, 12, 13, 14, 15, 16, 17, 18, 19, 20, up to 25, 30 or 35 amino acids in length and the peptide comprises an amino acid sequence with three, two, one substitutions of any one of SEQ ID NOS: 32 and 46-50. The substitutions can be conservative or non-conservative. In one embodiment, the CS-1 peptide is from amino acid sequence SEQ ID NO:22 and comprises the amino acid sequence of SEQ ID NOS: 32 and 1, 2, 3, 4, 5, 6, 7, 8, 9 or more (e.g., 1, 2, 3) amino acids C-terminal to SEQ ID NOS:32 in SEQ ID NO:22. In one embodiment, the CS-1 peptide is from amino acid sequence SEQ ID NO:22 and comprises the amino acid sequence of any one of SEQ ID NOS: 46-50 and 1, 2, 3, 4, 5, 6, 7, 8, 9 or more (e.g., 1, 2, 3) amino acids N-terminal and/or C-terminal to any one of SEQ ID NOS: 46-50 in SEQ ID NO:22. In one embodiment, the CS-1 peptide from Group B consists of an amino acid sequence of any one of SEQ ID NOS: 32 and 46-50.

In one embodiment, the peptide of Group B, e.g., a non-spliced XBP1 peptide, a spliced XBP1 peptide, a CD138 peptide and/or a CS-1 peptide, is used to treat a subject having or at risk of having cancer, e.g., a cancer described herein, e.g., lung cancer, liver cancer, bile duct cancer, stomach cancer, cervical cancer, nasopharyngeal cancer, breast cancer, colon cancer, pancreatic cancer, prostate cancer, leukemia, e.g., AML or CML. In one embodiment, the peptide of Group B, e.g., a non-spliced XBP1 peptide, a spliced XBP1 peptide, a CD138 peptide and/or a CS-1 peptide, is used to treat a subject having a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer).

In some embodiments, any of the isolated peptides described herein can, in association with a major histocompatibility complex (MHC) molecule, be recognized by an antigen specific T cell receptor on a T cell.

In another aspect, the disclosure features a fusion protein that comprises a first amino acid sequence consisting of a peptide described herein, e.g., a non-spliced XBP1 peptide from Group A, Group B or Group C, a spliced XBP1 peptide from Group A or Group B, a CD138 peptide from Group A, Group B or Group C and/or a CS-1 peptide from Group A, Group B or Group C, e.g., described herein; and a second amino acid sequence that is heterologous to the first amino acid sequence.

In some embodiments, the second amino acid sequence can comprise, or be, a targeting polypeptide, an immune stimulatory molecule, an immunoglobulin or antigen-binding fragment thereof, an Fc receptor-binding region of an immunoglobulin molecule, or a carrier polypeptide. The targeting polypeptide can be, e.g., one that targets the isolated peptide to an antigen presenting cell (e.g., a dendritic cell, a macrophage, a monocyte, or a B cell). The immune stimulatory molecule can be, e.g., a cytokine or a T helper epitope. The immunoglobulin can be, e.g., a single chain Fv immunoglobulin fragment or an entire immunoglobulin molecule. The carrier polypeptide can comprise, or be, a KLH (keyhole limpet hemocyanin) polypeptide, or an albumin polypeptide.

In some embodiments, any of the isolated peptides described herein can contain a linker sequence. The linker sequence can directly or indirectly connect a first amino acid sequence to a second amino acid sequence. The linker sequence can comprise, or consist of, one or more amino acids, e.g., at least one, two, three, four, five, six, seven, eight, nine or ten amino acids. In one embodiment, the linker can comprise, or consist of, at least one (e.g., one, two, three, four, five, six, seven, eight, nine, or 10 or more) protease cleavage site.

In some embodiments, the second amino acid sequence can be amino terminal or carboxy terminal to the first amino acid sequence.

In some embodiments, any of the isolated peptides or fusion proteins described herein can be detectably labeled. The detectable label can be selected from the group consisting of luminescent labels, fluorescent labels, radioactive labels, and enzymatic labels.

In yet another aspect, the disclosure features: (i) an isolated nucleic acid encoding any of the isolated peptides described herein; (ii) a vector comprising the isolated nucleic acid of (i); or (iii) a cultured cell comprising the vector of (ii). The vector can be operably linked to an expression control sequence. The cultured cell can be a prokaryotic cell or eukaryotic cell. The cultured cell can be, e.g., a fungal cell, a plant cell, or an animal cell (e.g., a nematode cell, an insect cell, a bird cell, a fish cell, or a mammalian cell (e.g., a human cell)). The cultured cell can be an immune cell such as any of the immune cells described herein.

In another aspect, the disclosure features a method of producing a peptide. The method involves the step of culturing any of the cultured cells described herein under conditions that permit the expression of the peptide. The method can also include the step of isolating the peptide from the cell or from the medium in which the cell was cultured.

In another aspect, the disclosure features a pharmaceutical composition comprising one or more of any of the isolated peptides (or fusion proteins) described herein and a pharmaceutically acceptable carrier. In one embodiment, the composition comprises at least two peptides, e.g., 2, 3, 4, 5, 6, 7, 8, 9, 10, 11, 12, 13, 14 or more of the peptides described herein. For example, in one embodiment, the composition comprises at least two, three or four of the peptides described herein.

In one embodiment, the composition comprises at least two peptides. For example, the composition comprises a non-spliced XBP1 peptide, e.g., a non-spliced XBP1 peptide from Group A, and a spliced XBP1 peptide, e.g., a spliced XBP1 peptide from Group A; the composition comprises a non-spliced XBP1 peptide, e.g., a non-spliced XBP1 peptide from Group A, and a CD138 peptide, e.g., a CD138 peptide from Group A; the composition comprises a non-spliced XBP1 peptide, e.g., a non-spliced XBP1 peptide from Group A, and a CS-1 peptide, e.g., a CS-1 peptide from Group A; the composition comprises a spliced XBP1 peptide, e.g., a spliced XBP1 peptide from Group A, and a CD138 peptide, e.g., a CD138 peptide from Group A; the composition comprises a spliced XBP1 peptide, e.g., a spliced XBP1 peptide from Group A, and a CS-1 peptide from Group A; the composition comprises a CD138 peptide, e.g., a CD138 peptide from Group A, and a CS-1 peptide, e.g., a CS-1 peptide from Group A.

In one embodiment, the composition comprises at least three peptides. For example, the composition comprises a non-spliced XBP1 peptide, e.g., a non-spliced XBP1 peptide described from Group A, a spliced XBP1 peptide, e.g., a spliced XBP1 peptide from Group A, and a CD138 peptide, e.g., a CD138 peptide from Group A; the composition comprises a non-spliced XBP1 peptide, e.g., a non-spliced XBP1 peptide from Group A, a spliced XBP1 peptide, e.g., a spliced XBP1 peptide from Group A and a CS-1 peptide, e.g., a CS-1 peptide from Group A; the composition comprises a non-spliced XBP1 peptide, e.g., a non-spliced XBP1 peptide from Group A, a CD138 peptide, e.g., a CD138 peptide from Group A and a CS-1 peptide, e.g., a CS-1 peptide from Group A; the composition comprises a spliced XBP1 peptide, e.g., a spliced XBP1 peptide from Group A, a CD138 peptide, e.g., a CD138 peptide from Group A and a CS-1 peptide, e.g., a CS-1 peptide from Group A. In one embodiment, the composition comprises at least three peptides, e.g., a non-spliced XBP1 peptide (e.g., a non-spliced XBP1 peptide from Group A), a spliced XBP1 peptide (e.g., a spliced XBP-1 peptide from Group A), and a CD138 peptide (e.g., a CD138 peptide from Group A).

In one embodiment, the composition comprises four peptides, e.g., the composition comprises a non-spliced XBP1 peptide, e.g., a non-spliced XBP1 peptide from Group A, a spliced XBP1 peptide, e.g., a spliced XBP1 peptide from Group A, a CD138 peptide, e.g., a CD138 peptide from Group A, and a CS-1 peptide, e.g., a CS-1 peptide from Group A.

In one embodiment, the composition comprises a non-spliced XBP1 peptide from Group A that is 9, 10, 11, 12, 13, 14, 15, 16, 17, 18, 19, 20, up to 25, 30 or 35 amino acids in length and comprises an amino acid sequence of any of SEQ ID NOS:1-6, e.g., SEQ ID NO:6. In one embodiment, the composition comprises a spliced XBP1 peptide from Group A that is 9, 10, 11, 12, 13, 14, 15, 16, 17, 18, 19, 20, up to 25, 30 or 35 amino acids in length and comprises an amino acid sequence of any of SEQ ID NOS:7-10, e.g., SEQ ID NO:10. In one embodiment, the composition comprises a CD138 peptide from Group A that is 9, 10, 11, 12, 13, 14, 15, 16, 17, 18, 19, 20, up to 25, 30 or 35 amino acids in length and comprises an amino acid sequence of any of SEQ ID NOS:11-14, e.g., SEQ ID NO:12. In one embodiment, the composition comprises a CS-1 peptide from Group A that is 9, 10, 11, 12, 13, 14, 15, 16, 17, 18, 19, 20, up to 25, 30 or 35 amino acids in length and comprises an amino acid sequence of any of SEQ ID NOS:15-18, e.g., SEQ ID NO:16.

In one embodiment, the composition comprises four peptides and the four peptides are a peptide from Group A that comprises (e.g., consists of) the amino acid sequence of SEQ ID NO:6, a peptide from Group A that comprises (e.g., consists of) the amino acid sequence of SEQ ID NO:10, a peptide from Group A that comprises (e.g., consists of) the amino acid sequence of SEQ ID NO:12, and a peptide from Group A that comprises (e.g., consists of) the amino acid sequence of SEQ ID NO:16.

In one embodiment, the composition comprises at least two peptides. For example, the composition comprises a non-spliced XBP1 peptide, e.g., a non-spliced XBP1 peptide from Group B, and a spliced XBP1 peptide, e.g., a spliced XBP1 peptide from Group B; the composition comprises a non-spliced XBP1 peptide, e.g., a non-spliced XBP1 peptide from Group B, and a CD138 peptide, e.g., a CD138 peptide from Group B; the composition comprises a non-spliced XBP1 peptide, e.g., a non-spliced XBP1 peptide from Group B, and a CS-1 peptide, e.g., a CS-1 peptide from Group B; the composition comprises a spliced XBP1 peptide, e.g., a spliced XBP1 peptide from Group B, and a CD138 peptide, e.g., a CD138 peptide from Group B; the composition comprises a spliced XBP1 peptide, e.g., a spliced XBP1 peptide from Group B, and a CS-1 peptide, e.g., a CS-1 peptide from Group B; the composition comprises a CD138 peptide, e.g., a CD138 peptide from Group B, and a CS-1 peptide, e.g., a CS-1 peptide from Group B.

In one embodiment, the composition comprises at least three peptides. For example, the composition comprises a non-spliced XBP1 peptide, e.g., a non-spliced XBP1 peptide described from Group B, a spliced XBP1 peptide, e.g., a spliced XBP1 peptide from Group B, and a CD138 peptide, e.g., a CD138 peptide from Group B; the composition comprises a non-spliced XBP1 peptide, e.g., a non-spliced XBP1 peptide from Group B, a spliced XBP1 peptide, e.g., a spliced XBP1 peptide from Group B and a CS-1 peptide, e.g., a CS-1 peptide from Group B; the composition comprises a non-spliced XBP1 peptide, e.g., a non-spliced XBP1 peptide from Group B, a CD138 peptide, e.g., a CD138 peptide from Group B and a CS-1 peptide, e.g., a CS-1 peptide from Group B; the composition comprises a spliced XBP1 peptide, e.g., a spliced XBP1 peptide from Group B, a CD138 peptide, e.g., a CD138 peptide from Group B and a CS-1 peptide, e.g., a CS-1 peptide from Group B. In one embodiment, the composition comprises at least three peptides, e.g., a non-spliced XBP1 peptide (e.g., a non-spliced XBP1 peptide from Group B), a spliced XBP1 peptide (e.g., a spliced XBP-1 peptide from Group B), and a CD138 peptide (e.g., a CD138 peptide from Group B).

In one embodiment, the composition comprises four peptides, e.g., the composition comprises a non-spliced XBP1 peptide, e.g., a non-spliced XBP1 peptide from Group B, a spliced XBP1 peptide, e.g., a spliced XBP1 peptide from Group B, a CD138 peptide, e.g., a CD138 peptide from Group B, and a CS-1 peptide, e.g., a CS-1 peptide from Group B.

In one embodiment, the composition comprises a non-spliced XBP1 peptide from Group B that is 9, 10, 11, 12, 13, 14, 15, 16, 17, 18, 19, 20, up to 25, 30 or 35 amino acids in length and comprises an amino acid sequence of any one of SEQ ID NOS: 29 and 33-37. In one embodiment, the composition comprises a spliced XBP1 peptide from Group B that is 9, 10, 11, 12, 13, 14, 15, 16, 17, 18, 19, 20, up to 25, 30 or 35 amino acids in length and comprises an amino acid sequence of any one of SEQ ID NOS: 30, 38 and 39. In one embodiment, the composition comprises a CD138 peptide from Group B that is 9, 10, 11, 12, 13, 14, 15, 16, 17, 18, 19, 20, up to 25, 30 or 35 amino acids in length and comprises an amino acid sequence of any one of SEQ ID NOS: 31 and 40-45. In one embodiment, the composition comprises a CS-1 peptide from Group B that is 9, 10, 11, 12, 13, 14, 15, 16, 17, 18, 19, 20, up to 25, 30 or 35 amino acids in length and comprises an amino acid sequence of any one of SEQ ID NOS: 32 and 46-50.

In one embodiment, the composition comprises four peptides and the four peptides are a peptide from Group B that comprises (e.g., consists of) the amino acid sequence of any one of SEQ ID NOS: 29 and 33-37, a peptide from Group B that comprises (e.g., consists of) the amino acid sequence of any one of SEQ ID NOS: 30, 38 and 39, a peptide from Group B that comprises (e.g., consists of) the amino acid sequence of any one of SEQ ID NOS: 31 and 40-45, and a peptide from Group B that comprises (e.g., consists of) the amino acid sequence of any one of SEQ ID NOS: 32 and 46-50.

In one embodiment, the composition comprises peptides from Group A and Group B. For example, the composition comprises 1, 2, 3, 4 or more peptides from Group A and 1, 2, 3, 4, or more peptides from Group B.

The composition can also include, e.g., one or more additional agents, e.g., one or more therapeutic agents, diagnostic agents, or prophylactic agents, or immune stimulating or modulating agents. Immune stimulating agents include, but are not limited to, e.g., a T helper epitope, an altered peptide ligand, an adjuvant, or any other immune stimulating agent described herein. The T helper epitope can be, e.g., a PADRE sequence or a universal Tetanus Toxoid T helper (TT Th) epitope. The adjuvant can be selected from the group consisting of Freund's complete adjuvant, Freund's incomplete adjuvant, alum, a ligand for a Toll receptor, saponin (e.g., QS21), RIBI, cholera toxin (CT), *E. coli* heat labile toxin (LT), mutant CT (MCT), mutant *E. coli* heat labile toxin (MLT), an adjuvant comprising carboxymethylcellulose, polyinosinic-polycytidylic acid, and poly-L-lysine double-stranded RNA (e.g., poly IC-LC, e.g., hiltonol), an adjuvant comprising a water-and-oil emulsion (e.g., montanide), and an adjuvant comprising a protein (e.g., cytokines, complements, GCSF, GM-CSF). In one embodiment, the immune stimulating agent is an adjuvant comprising carboxymethylcellulose, polyinosinic-polycytidylic acid, and poly-L-lysine double-stranded RNA, e.g., poly IC-LC, e.g., hiltonol. In one embodiment the adjuvant is a water-and-oil emulsion, e.g., montanide. In one embodiment, the adjuvant is a protein, e.g., a cytokine, a complement, GCSF, GM-CSF. In one embodiment, the immune modulating agent can be a protein, e.g., an antibody which modulates the immune system. For example, an antibody which modulates the immune system can be an anti-CTLA4 antibody, e.g., ipilimumab or tremelimumab, or an anti-PD-1 antibody, or anti-PDL-1 antibody. In one embodiment, the immune modulating agent can be a small molecule adjuvant, e.g., thalidomide or a thalidomide derivative, e.g., lenalidomide.

The composition may also include an immunogenic peptide other than one disclosed above, e.g., an immunogenic peptide from WT1 or a derivative thereof. Exemplary WT1 peptides are described in U.S. Pat. No. 7,598,221, the contents of which is incorporated herein by reference. In one embodiment, the composition comprises one or more immunogenic peptide from WT1 or a derivative thereof, e.g., selected from one or more of: a WT1 class 1 epitope; a peptide comprising (or consisting of) RMFPNAPYL (SEQ ID NO: 538) (WT1 126-134); a peptide comprising (or consisting of) YMFPNAPYL (SEQ ID NO: 539); a peptide comprising (or consisting of) RSDELVRHHNMHQRNMTKL (SEQ ID NO: 540) (WT1 427-445); a peptide comprising (or consisting of) PGCNK-RYFKLSHLQMHSRKHTG (SEQ ID NO: 541) (WT1 331-352); a peptide comprising (or consisting of) SGQARMFPNAPYLPSCLES (SEQ ID NO: 542) (WT1 122-140); and a peptide comprising (or consisting of) SGQAYMFPNAPYLPSCLES (SEQ ID NO: 543). Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

In one embodiment, the composition described herein is used to treat a subject having or at risk of having cancer, e.g., a cancer described herein, e.g., breast cancer (e.g., invasive lobular, invasive ductal, mixed lobular and ductal, intraductal cribriform, invasive lobular and ductal, invasive carcinoma), colon cancer (e.g., colon adenocarcinoma, e.g., mucinous adenocarcinoma), pancreatic cancer, prostate cancer, leukemia, e.g., AML or CML, or multiple myeloma. In one embodiment, the composition described herein is used to treat a subject having a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroe-sophageal, upper gastric or lower gastric cancer), gastroin-testinal cancer (e.g., anal cancer or bile duct cancer), gall bladder, thyroid, leukemia (e.g., acute myeloid leukemia), neural and glial cell cancers (e.g., glioblastoma multiforme), and head and neck.

In yet another aspect, the disclosure features a kit com-prising: (i) one or more of any of the isolated peptides from Group A, from Group B and/or Group C; and instructions for administering the peptide to a subject, e.g., a subject having cancer, e.g., a cancer described herein, e.g., breast cancer, colon cancer, pancreatic cancer, prostate cancer, leukemia, e.g., AML or CML, or multiple myeloma or a subject having a precancerous condition, e.g., smoldering multiple myeloma; (ii) a composition described herein and instruc-tions for administering the peptide to a subject, e.g., a subject having cancer, e.g., a cancer described herein, e.g., breast cancer, colon cancer, pancreatic cancer, prostate can-cer, leukemia, e.g., AML or CML, or multiple myeloma or a subject having a precancerous condition, e.g., smoldering multiple myeloma; and/or (iii) one or more of the isolated nucleic acids encoding the isolated peptides, one or more vectors containing the isolated nucleic acids, or one or more cultured cells containing the vectors, and instructions for producing the isolated peptides. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carci-noma, clear cell carcinoma, chromphobic carcinoma)), liver, lung (including small cell lung cancer and non-small cell lung cancer (including adenocarcinoma, squamous cell car-cinoma, bronchoalveolar carcinoma and large cell carci-noma)), genitourinary tract, e.g., ovary (including fallopian, endometrial and peritoneal cancers), cervix, prostate and testes, lymphatic system, rectum, larynx, pancreas (includ-ing exocrine pancreatic carcinoma), stomach (e.g., gastroe-sophageal, upper gastric or lower gastric cancer), gastroin-testinal cancer (e.g., anal cancer or bile duct cancer), gall bladder, thyroid, leukemia (e.g., acute myeloid leukemia), neural and glial cell cancers (e.g., glioblastoma multiforme), and head and neck.

In some embodiments, the kits can also include, e.g., one or more pharmaceutically acceptable carriers, one or more immune stimulating or modulating agents, or one or more therapeutic agents, diagnostic agents, or prophylactic agents. In one embodiment, the immune stimulating agent is an immune stimulating agent described herein. The one or more immune stimulating agents can be selected from the group consisting of a T helper epitope, an altered peptide ligand, and an adjuvant. In one embodiment, the immune stimulat-ing agent is an adjuvant comprising carboxymethylcellulose, polyinosinic-polycytidylic acid, and poly-L-lysine double-stranded RNA (e.g., poly IC-LC t, e.g., hiltonol); an adjuvant comprising a water-and-oil emulsion (e.g., montanide); an adjuvant comprising a protein (e.g., a cytokine, a comple-ment, GCSF, GM-CSF). In one embodiment, the immune modulating agent is an immune modulating agent described herein, e.g., a protein, e.g., an antibody which modulates the immune system (e.g., an anti-CTLA4 antibody, e.g., ipili-mumab or tremelimumab, an anti-PD-1 antibody, an anti-PDL-1 antibody), a small molecule adjuvant (e.g., thalido-mide or a thalidomide derivative, e.g., lenalidomide). In one embodiment, the kit further comprises instructions for administering an immune stimulating agent and/or immune modulating agent in combination with a peptide or peptides described herein or a composition described herein.

In one embodiment, the kit further comprises an addi-tional immunogenic peptide, e.g., an immunogenic peptide from WO or a derivative thereof, e.g., an immunogenic WT1 peptide described herein. Other immunogenic peptides include, but are not limited to, an immunogenic peptide from MUC1, an immunogenic peptide from gp100, an immuno-genic peptide from TRP-2, an immunogenic peptide from MAG1, an immunogenic peptide from NY-ESO1, an immu-nogenic peptide from HER-2; and an immunogenic peptide from AIM2. In one embodiment, the kit further comprises instructions for administering an additional immunogenic peptide, e g., a WT1 peptide, in combination with a peptide or peptides described herein or a composition described herein.

In another aspect, the disclosure features an article of manufacture comprising: a container; and a composition contained within the container, wherein the composition is a composition described herein. The container can have a label indicating that the composition is for use in inducing an immune response in a mammal, e.g., a human. The label can further indicate that the composition is to be adminis-tered to a mammal having, suspected of having, or at risk of developing, cancer, e.g., a cancer described herein, e.g., breast cancer, colon cancer, pancreatic cancer, prostate can-cer, leukemia, e.g., AML or CML, or multiple myeloma or a subject having a precancerous condition, e.g., smoldering multiple myeloma. The article of manufacture can also include instructions for administering the composition to the mammal, e.g., human. The composition can be, e.g., in solution, dried, or lyophilized.

In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast can-cer, HER-2 negative breast cancer, triple negative breast cancer, inflammatory breast cancer), colon (including col-orectal cancer), kidney (e.g., renal cell carcinoma (e.g., papillary renal cell carcinoma, clear cell carcinoma, chrom-phobic carcinoma)), liver, lung (including small cell lung cancer and non-small cell lung cancer (including adenocar-cinoma, squamous cell carcinoma, bronchoalveolar carci-noma and large cell carcinoma)), genitourinary tract, e.g., ovary (including fallopian, endometrial and peritoneal can-cers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glio-blastoma multiforme), and head and neck.

In yet another aspect, the disclosure features a method for inducing an immune response in a subject, which method includes the step of delivering, e.g., administering, to a subject one or more of any of the isolated peptides described herein and/or a composition described herein. In one embodiment, the subject is administered at least two, e.g., 2, 3 or 4, of the peptides from Group A. For example, the subject can be administered two or more of a non-spliced XBP1 peptide from Group A, a spliced XBP1 peptide from Group A, a CD138 peptide from Group A, a CS-1 peptide from Group A, and combinations thereof. In one embodi-ment, the subject is administered a non-spliced XBP1 peptide from Group A (e.g., a non-spliced XBP1 peptide comprising SEQ ID NO:6), a spliced XBP1 peptide from Group A (e.g., a spliced XBP1 peptide comprising SEQ ID NO:10), a CD138 peptide from Group A (e.g., a CD138 peptide comprising SEQ ID NO:12) and a CS-1 peptide from Group A (e.g., a CS-1 peptide comprising SEQ ID NO:16). In one embodiment, the subject is administered at least two, e.g., 2, 3 or 4, of the peptides from Group B. For example, the subject can be administered a non-spliced XBP1 peptide from Group B, a spliced XBP1 peptide from Group B, a CD138 peptide from Group B, a CS-1 peptide from Group B, and combinations thereof. In one embodiment, the subject is administered a non-spliced XBP1 peptide from Group B (e.g., a non-spliced XBP1 peptide comprising SEQ ID NO:29), a spliced XBP1 peptide from Group B (e.g., a spliced XBP1 peptide comprising SEQ ID NO:30), a CD138 peptide from Group B (e.g., a CD138 peptide comprising SEQ ID NO:31) and a CS-1 peptide from Group B (e.g., a CS-1 peptide comprising SEQ ID NO:32). In one embodiment, the subject is administered at least two (e.g., 2, 3, 4, 5, 6, 7, 8, 9, 10, 11, 12, 13, 14, 15, 16, 17, 18, 19, 20 or more) of the peptides from Group C. In another embodiment, the subject is administered two or more peptides from a Group A and Group C or Group B and Group C.

The method can also include the step of, after delivering the one or more peptides or composition to the subject, determining if an immune response occurred in the subject. The one or more peptides can be delivered to the subject as a pharmaceutical composition, e.g., a pharmaceutical composition described herein. The subject can be, e.g., a mammal (e.g., a human) or any other subject described herein. The subject can have, be suspected of having, at risk of developing, or in remission from cancer, e.g., a cancer described herein, e.g., breast cancer, colon cancer, pancreatic cancer, prostate cancer, leukemia, e.g., AML or CML, or multiple myeloma. In one embodiment, the subject has a precancerous condition, e.g., smoldering multiple myeloma. In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck.

In some embodiments, the method can include determining whether the cancer cell (or cells) expresses one or more of XBP1, CD138, or CS-1.

In some embodiments, the method can further include administering to the subject one or more additional treatment, e.g., a chemotherapeutic agent, ionizing radiation, surgery or one or more additional immunotherapy agents. The one or more forms of ionizing radiation can be, e.g., gamma-irradiation, X-irradiation, or beta-irradiation. The one or more chemotherapeutic agents can be a chemotherapeutic agent described herein, e.g., a chemotherapeutic agent selected from the group consisting of a platinum based agent, a taxane, a topisomerase inhibitor, an antimetabolite, an alkylating agent, a protease inhibitor, and a vinca alkaloid. Exemplary chemotherapeutic agents, include, but are not limited to: cisplatin, carboplatin procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, taxol, transplatinum, 5-flurouracil, vincristin, vinblastin, methotrexate, and an analog of any of the aforementioned. The method can also include administering to the subject one or more immune stimulating agents, e.g., one or more immune stimulating agents described herein.

In one embodiment, the method further comprises administering an additional immunogenic peptide, e.g., an immunogenic peptide from WT1 or a derivative thereof, e.g., an immunogenic WT1 peptide described herein, in combination with the one or more peptides described herein. Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

In some embodiments, the delivering comprises administering to the subject the one or more peptides from Group A, Group B and/or Group C or a composition described herein. In some embodiments, the delivering comprises administering to the subject one or more nucleic acids, each of which comprises a nucleotide sequence encoding the one or more peptides, the nucleotide sequence being operably-linked to an expression control sequence. The nucleic acid can be in a recombinant cell transfected with the nucleic acid and expressing the one or more peptides. The recombinant cell can be a transfected cell, or the progeny of a transfected cell, made by transfecting a cell obtained from the subject. The recombinant cell can be an antigen presenting cell such as, but not limited to, a dendritic cell, a macrophage, a monocyte, or a B cell.

In some embodiments of any of the above-described methods, the delivering includes: contacting the one or more peptides to a cell; and after contacting the one or more peptides to the cell, delivering the cell to the subject. The cell can be, e.g., an antigen presenting cell such as any of those described herein. The cell can be, e.g., a cell, or the progeny of a cell, obtained from the subject. In some embodiments, the cell can be a cell, or the progeny of a cell, obtained from another subject of the same species as the subject. The other subject can express at least one MHC molecule in common with the subject. The at least one MHC molecule can be, e.g., an MHC class I molecule such as an HLA-A2 molecule and/or an HLA-A24 molecule.

In another aspect, the disclosure features a method for treating a subject having cancer, e.g., a cancer described herein, e.g., breast cancer, colon cancer, pancreatic cancer, prostate cancer, leukemia, e.g., AML or CML, or multiple myeloma or a subject having a precancerous condition, e.g., smoldering multiple myeloma. In one embodiment, the method includes the step of administering to a subject one or more (e.g., one, two, three, four, five, six, seven, eight, nine, 10, 11, 12, 13, 14, 15, 16, 17, or 18) of any of the peptides from Group A or a composition described herein, wherein the subject has, or is at risk of developing, a cancer, e.g., a cancer described herein, e.g., breast cancer (e.g., invasive lobular, invasive ductal, mixed lobular and ductal, intraductal cribriform, invasive lobular and ductal, invasive carcinoma), colon cancer (e.g., colon adenocarcinoma, e.g., mucinous adenocarcinoma), pancreatic cancer, prostate cancer, leukemia, e.g., AML or CML, or multiple myeloma or the subject has a precancerous condition, e.g., smoldering multiple myeloma. In one embodiment, the method includes the step of administering to a subject one or more (e.g., one, two, three, or four) of any of the peptides from Group B or a composition described herein, wherein the subject has, or is at risk of developing, a cancer, a cancer described herein, e.g., lung cancer, liver cancer, bile duct cancer, stomach cancer, cervical cancer, nasopharyngeal cancer, breast cancer (e.g., invasive lobular, invasive ductal, mixed lobular and ductal, intraductal cribriform, invasive lobular and ductal, invasive carcinoma), colon cancer (e.g., colon adenocarcinoma, e.g., mucinous adenocarcinoma), pancreatic cancer, prostate cancer, leukemia, e.g., AML or CML, or multiple myeloma. In one embodiment, the method includes the step of administering to a subject one or more (e.g., one, two, three, four, five, six, seven, eight, nine, 10, 11, 12, 13, 14, 15, 16, 17, 18, 19 20 or more) of any of the peptides from Group C or a composition described herein, wherein the subject has, or is at risk of developing, a cancer, e.g., a cancer described herein, e.g., breast cancer (e.g., invasive lobular, invasive ductal, mixed lobular and ductal, intraductal cribriform, invasive lobular and ductal, invasive carcinoma), colon cancer (e.g., colon adenocarcinoma, e.g., mucinous adenocarcinoma), pancreatic cancer, prostate cancer, leukemia, e.g., AML or CML, or multiple myeloma or the subject has a precancerous condition, e.g., smoldering multiple myeloma.

In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck.

In one embodiment, the subject is administered at least two, e.g., 2, 3 or 4, of the peptides from Group A. For example, the subject can be administered two or more of a non-spliced XBP1 peptide from Group A, a spliced XBP1 peptide from Group A, a CD138 peptide from Group A, a CS-1 peptide from Group A, and combinations thereof. In one embodiment, the subject is administered a non-spliced XBP1 peptide from Group A (e.g., a non-spliced XBP1 peptide comprising SEQ ID NO:6), a spliced XBP1 peptide from Group A (e.g., a spliced XBP1 peptide comprising SEQ ID NO:10), a CD138 peptide from Group A (e.g., a CD138 peptide comprising SEQ ID NO:12) and a CS-1 peptide (e.g., a CS-1 peptide comprising SEQ ID NO:16). The one or more peptides can be delivered to the subject as a pharmaceutical composition, e.g., a pharmaceutical composition from Group A.

In one embodiment, the subject is administered at least two, e.g., 2, 3 or 4, of the peptides from Group B. For example, the subject can be administered a non-spliced XBP1 peptide from Group B, a spliced XBP1 peptide from Group B, a CD138 peptide from Group B, a CS-1 peptide from Group B, and combinations thereof. In one embodiment, the subject is administered a non-spliced XBP1 peptide from Group B (e.g., a non-spliced XBP1 peptide comprising SEQ ID NO:29), a spliced XBP1 peptide from Group B (e.g., a spliced XBP1 peptide comprising SEQ ID NO:30), a CD138 peptide from Group B (e.g., a CD138 peptide comprising SEQ ID NO:31) and a CS-1 peptide from Group B (e.g., a CS-1 peptide comprising SEQ ID NO:32).

In one embodiment, the subject is administered at least two (e.g., 2, 3, 4, 5, 6, 7, 8, 9, 10, 11, 12, 13, 14, 15, 16, 17, 18, 19, 20 or more) of the peptides from Group C. In another embodiment, the subject is administered two or more peptides from a Group A and Group C or Group B and Group C.

In one embodiment, the method further comprises administering an additional agent to the subject, e.g., administering a chemotherapeutic agent and/or an immune stimulating agent and/or an immune modulating agent. In one embodiment, the additional agent is an immune stimulating agent, e.g., an immune stimulating agent described herein. In one embodiment, the immune stimulating agent is an adjuvant comprising carboxymethylcellulose, polyinosinic-polycytidylic acid, and poly-L-lysine double-stranded RNA (e.g., poly IC-LC, e.g., hiltonol); an adjuvant comprising a water-and-oil emulsion (e.g., montanide); an adjuvant comprising a protein (e.g., a cytokine, a complement, GCSF, GM-CSF). In one embodiment, the additional agent is an immune modulating agent, e.g., an immune modulating agent described herein. In one embodiment, the immune modulating agent is a protein, e.g., an antibody which activates the immune system (e.g., an anti-CTLA4 antibody, e.g., ipilimumab or tremelimumab, an anti-PD-1 antibody, an anti-PDL-1 antibody); a small molecule adjuvant (e.g., thalidomide or a thalidomide derivative, e.g., lenalidomide. In one embodiment, the method comprises administering an additional immunogenic peptide, e.g., an immunogenic peptide from WT1 or a derivative thereof, e.g., a WT1 peptide described herein, in combination with the one or more of the peptides. Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

In one embodiment, the method further comprises administered one or more additional dose of a peptide from Group A. Group B and/or Group C or composition described herein. In one embodiment, the subject is administered one or more additional dose about 14 days after the previous dose, e.g., the subject is administered 2, 3, 4, 5, 6, 7, 8, 9 or 10 doses of a peptide from Group A, Group B and/or Group C or composition described herein, every other week.

In another aspect, the disclosure features a method for selecting a treatment for a mammal in need thereof. The method includes the steps of: determining if one or more cancer cells of a cancer in a mammal express XBP1, e.g., a cancer described herein, e.g., a breast cancer cell, a colon cancer cell, a pancreatic cancer cell, prostate cancer, a blood cell, e.g., a plasma cell; and if one or more of the cancer cells express XBP1, selecting as a therapeutic agent for the mammal one or more of the peptides from Group A, Group B and/or Group C, fusion proteins comprising such peptides, or compositions described herein. The method can also include the step of, after determining that one or more of the cells of the cancer express XBP1, delivering to the subject one or more of the peptides from Group A, Group B and/or Group C, fusion proteins comprising such peptides, or compositions described herein.

In yet another aspect, the disclosure features a method for selecting a treatment for a mammal with cancer. The method includes the steps of: determining if one or more cancer cells of a cancer in a mammal express CD138, e.g., a cancer described herein, e.g., a breast cancer cell, a colon cancer cell, a pancreatic cancer cell, a prostate cancer cell, a blood cell, e.g., a plasma cell; and if one or more of the cancer cells express CD138, selecting as a therapeutic agent for the mammal one or more of the peptides from Group A, Group B and/or Group C, fusion proteins comprising such peptides, or compositions described herein. The method can also include the step of, after determining that one or more of the cells of the cancer express CD138, delivering to the subject the one or more of the peptides from Group A, group B and/or Group C, fusion proteins comprising such peptides, or compositions described herein.

In another aspect, the disclosure features a method for selecting a treatment for a mammal in need thereof. The method includes determining if one or more cancer cells of a cancer in a mammal express CS-1, e.g., a cancer described herein, e.g., a breast cancer cell, a colon cancer cell, a pancreatic cancer cell, a prostate cancer cell, a blood cell, e.g., a plasma cell; and if one or more of the cancer cells express CS-1, selecting as a therapeutic agent for the mammal one or more of the peptides from Group A, Group B and/or Group C, fusion proteins comprising such peptides, or compositions described herein. The method can also include the step of, after determining that one or more of the cells of the cancer express CS1, delivering to the subject the selected one or more of the peptides from Group A, group B and/or Group C, fusion proteins comprising such peptides, or compositions described herein.

In yet another aspect, the disclosure features a method for selecting a therapeutic agent for a mammal having a cancer, e.g., a cancer described herein, e.g., breast cancer, colon cancer, pancreatic cancer, prostate cancer, or a precancerous disorder, e.g., smoldering multiple myeloma. The method includes the step of, if one or more cancer cells of the mammal expresses XBP1, CD138 and/or CS-1, selecting as a therapeutic agent for the mammal one or more of the peptides from Group A, Group B and/or Group C, fusion proteins comprising such peptides, or compositions described herein. The method can also include the step of, after determining that one or more of the cells of the cancer express XBP1, CD138 and/or CS-1, delivering to the subject the selected one or more of the peptides from Group A, Group B and/or group C, fusion proteins comprising such peptides, or compositions described herein.

In some embodiments of any of the above methods, the subject or mammal can be one who has received a therapy for a cancer, e.g., a cancer described herein, e.g., breast, colon, pancreatic, prostate cancer, and was non-responsive to the therapy, e.g., the peptides from Group A, Group B and/or Group C, fusion proteins comprising such peptides, or compositions described herein may be a second-line, third line or fourth-line treatment.

In yet another aspect, the disclosure features a composition described herein and (ii) a major histocompatibility complex (MHC) molecule multimer, wherein the multimer comprises two or more (e.g., two, three, four, five, six, seven, eight, nine, or 10 or more) peptide-binding regions of an MHC molecule. In some embodiments, each peptide-binding region has a peptide from Group A, Group B, and/or Group C bound to it. In some embodiments, each peptide-binding region has a peptide from Group A, Group B and/or Group C non-covalently or covalently bound to it. The MHC molecule multimer can comprise two or more (e.g., two, three, four, five, six, seven, eight, nine, or 10 or more) entire MHC molecules. The MHC molecule multimer can comprise a human MHC molecule. The MHC molecule multimer can comprise an MHC class I molecule such as an HLA-A molecule, e.g., an HLA-A2 molecule or HLA-A24 molecule.

In some embodiments, the two or more peptide-binding regions can be from the same MHC molecule. In some embodiments, the two or more peptide-binding regions are from different MHC molecules. In some embodiments, the two or more peptide-binding regions can be a mixture of at least two (e.g., two, three, four, five, six, seven, eight, nine, or 10 or more) regions from the same MHC molecule and at least one (e.g., one, two, three, four, five, six, seven, eight, nine, or 10 or more) regions from a different MHC molecule.

In some embodiments, the MHC molecule multimer is capable of binding to at least one of the one of more peptides of the composition.

In some embodiments, the composition can be detectably labeled. For example, one or more of the peptides and/or one or more of the peptide-binding regions can be detectably labeled. In some embodiments, at least one of the one or more MHC molecule multimers or at least one of the one or more peptides are detectably labeled.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., methods for inducing an immune response in a subject, will be apparent from the following description, from the drawings and from the claims.

BRIEF DESCRIPTION OF THE DRAWINGS

FIG. 1a is a bar graph showing the HLA-A2 binding capacity of a multipeptide cocktail. The Y-axis represents the mean fluorescence intensity, and the X-axis represents the peptide concentration of the cocktail. Influenza virus matrix protein$_{58\_66}$ (IVMP$_{58\_66}$; GILGFVFTL) (SEQ ID NO: 25) was used as an HLA-A2-specific positive control peptide.

FIG. 1b is a bar graph showing the HLA-A2 stability of a multipeptide cocktail using T2 cells. The Y-axis represents the mean fluorescence intensity, and the X-axis represents the time after Brefeldin A (BFA) treatment. Influenza virus matrix protein$_{58\_66}$ (IVMP$_{58\_66}$; GILGFVFTL) (SEQ ID NO: 25) was used as an HLA-A2-specific positive control peptide.

FIG. 2 is a series of bar graphs showing the distinct phenotype of multipeptide-specific CTL (MP-CTL). The Y-axes indicate the percentage of cells in a given population.

FIG. 3 is a series of bar graphs showing IFN-γ production by MP-CTL in response to HLA-A2⁺ MM cell lines. The Y-axes indicates the percentage of IFN-γ+ cells in a given population.

FIG. 4 shows the induction of MP-CTL proliferation by stimulation with HLA-A2+ MM cells, including primary myeloma cells and multiple myeloma cell lines. The upper panels are representative dot plots from flow cytometry analyses. The Y-axes indicate CD8 expression, and the X-axes indicate a decrease in CFSE staining which is a direct measure of cell proliferation. The lower panels are bar graphs showing the MP-CTL proliferative responses to primary multiple myeloma cells (lower left panel) and multiple myeloma cell lines (lower right panel). The Y-axes in the bar graphs indicate the percentage of proliferating MP-CTL, and the X-axes indicate the source of the stimulatory MM cells tested.

FIG. 5 is a series of graphs showing the cytotoxic activity of MP-CTL against HLA-A2+ MM cells, including primary MM cells and cell lines. The Y-axes indicate the percent cytotoxicity, and the X-axes indicate the ratio of effector cells (MP-CTL) to target cells.

FIG. 6a is a series of dot plots showing the peptide-specific response of multipeptide-specific CTL generated from a single donor (Donor A). The Y-axes indicate CD107α expression levels, and the X-axes indicate IFN-γ expression levels.

FIG. 6b is a series of bar graphs showing peptide-specific response of multipeptide-specific CTL generated from three donors (Donor B, Donor C and Donor D). The Y-axes indicate the percentage of CD107α+ cells (upper panels) or IFN-γ+ cells (lower panels), and the X-axes indicate the peptide presented by K562-A2 cells.

FIG. 7 is a table showing the relative expression of unspliced XBP1 and spliced XBP1 in various cancer cell lines. Relative expression levels are indicated with plus or minus signs and also with numbers indicating number of plus signs.

FIG. 8a is a series of histograms showing the proliferation response at day 6 of XBP1-CTL to HLA-A2+ breast cancer cell lines. The X-axes indicate a decrease in CFSE staining, a direct measure of cell proliferation.

FIG. 8b is a series of histograms showing the proliferation response at day 7 of XBP1-CTL to HLA-A2+ breast cancer cells. The X-axes indicate a decrease in CFSE staining, a direct measure of cell proliferation FIG. 9 is a series of dot plots showing IFN-γ production and cell activation (CD69 expression) of XBP1-CTL to HLA-A2+ breast cancer cell lines. The Y-axes indicate CD69 expression and the X-axes indicate IFN-γ expression.

FIG. 10 is a series of dot plots showing the degranulation (CD107α) of XBP1-CTL to HLA-A2+ breast cancer cell lines. The Y-axes indicate CD107α expression, and the X-axes indicate CD8 expression.

FIG. 11 is a series of histograms showing the proliferation response of XBP1-CTL to HLA-A2+ pancreatic and colon cancer cell lines. The X-axes indicate a decrease in CFSE staining, a direct measure of cell proliferation.

FIG. 12 is a series of dot plots showing the IFN-γ production and degranulation responses of XBP1-CTL to HLA-A2+ pancreatic and colon cancer cell lines. The Y-axes indicate CD107a expression, and the X-axes indicate IFN-γ expression.

FIG. 13 is a table showing the relative CD138 expression in various cancer cell lines. Relative expression is indicated with plus or minus signs and also with numbers indicating number of plus signs.

FIG. 14 is a table showing the relative CS1 expression in various cancer cell lines. Relative expression is indicated with plus or minus signs and also with numbers indicating number of plus signs.

FIGS. 15a and b are a series of bar graphs showing the increase in CD8+ CTL induced by a cocktail of immunogenic XBP1-unspliced, XBP1-spliced, CD138, and CS-1 HLA-A2-specific peptides from T cells of different smoldering multiple myeloma patients. The Y-axes in the panels on the left indicate the percentage of CD3+ CD8+ CTL, the Y-axes in the panels on the right indicate the percentage of CD4+ Th cells, and the X-axes indicate the number of peptide stimulations prior to phenotypic analysis.

FIG. 16a is a series of histograms showing the proliferation response of MP-CTL generated from a smoldering multiple myeloma patient to myeloma cells in a HLA-A2-restricted manner. The X-axes indicate a decrease in CFSE staining, a direct measure of cell proliferation. The response 5 days after stimulation is shown in the upper panels, response after 6 days is shown in the middle panels, and the response after 7 days is shown in the lower panels.

FIG. 16b is a series of histograms showing the proliferation response of MP-CTL generated from a second smoldering multiple myeloma patient in response to myeloma cells in a HLA-A2-restricted manner. The Y-axes indicate numbers of cells, and the X-axes indicate CFSE staining. The response 5 days after stimulation is shown in the upper panels, response after 6 days is shown in the middle panels, and the response after 7 days is shown in the lower panels.

FIG. 17a is a series of dot plots showing the IFN-γ production of MP-CTL generated from a smoldering multiple myeloma patient in response to myeloma cell lines in a HLA-A2-restricted manner. The Y-axes indicate IFN-γ expression, and the X-axes indicate CD8 expression.

FIG. 17b is a series of bar graphs showing the IFN-γ production of MP-CTL generated from four smoldering multiple myeloma patients in response to myeloma cell lines in a HLA-A2-restricted manner. The Y-axes indicate the percentage of IFN-γ+ cells, and the X-axes indicate the type of cells used to stimulate the MP-CTL.

FIG. 18a is a series of dot plots showing the degranulation of MP-CTL generated from a smoldering multiple myeloma patient in response to myeloma cell lines in a HLA-A2-restricted manner. The Y-axes indicate CD107α expression, and the X-axes indicate CD8 expression.

FIG. 18b is a series of bar graphs showing the degranulation of MP-CTL generated from four smoldering multiple myeloma patients in response to myeloma cell lines in a HLA-A2-restricted manner. The Y-axes indicate the percentage of CD107α+ cells, and the X-axes indicate the type of cells used to stimulate the MP-CTL.

FIG. 19a is a series of dot plots showing polyfunctional IFN-γ production and degranulation (CD107α) among CD3+ CD8+ CD137+ MP-CTL generated from a smoldering multiple myeloma patient in response to K562-A2 cells presenting an individual peptide. The Y-axes indicates CD107α expression and the Y-axes indicates+ cells and the X-axes indicate IFN-γ expression.

FIG. 19b is a series of bar graphs showing polyfunctional IFN-γ production and degranulation (CD107α) among CD3+ CD8+ CD137+ MP-CTL generated from three smoldering multiple myeloma patients in response to K562-A2 cells presenting an individual peptide. The Y-axes indicate the percentage of CD3+ CD8+ CD137+ cells that express both IFN-γ and CD107a, and the X-axes indicate the peptide presented by the K562 A2+ cells.

FIG. 19c is a summary bar graph showing both IFN-γ production and degranulation (CD107α) among CD3+ CD8+ CD137+ MP-CTL generated from three smoldering multiple myeloma patients in response to K562-A2 cells presenting an individual peptide. The Y-axes indicate the percentage of CD3+ CD8+ CD137+ cells that express both IFN-γ and CD107α and the X-axes indicate the peptide presented by the K562-A2 cells.

FIG. 19d is a summary bar graph from two separate experiments showing both IFN-γ production and degranulation (CD107α) among CD3+ CD8+ CD137+ MP-CTL generated from three smoldering multiple myeloma patients in response to K562-A2 cells presenting an individual peptide. The Y-axes indicate the percentage of CD3+ CD8+ CD137+ cells that express both IFN-γ and CD107α and the X-axes indicate the peptide presented by the K562-A2 cells.

FIG. 20a is a series of dot plots (upper panels) and bar graphs (lower panels) showing an increase of memory CD8+ T cells in MP-CTL generated from four smoldering multiple myeloma patients. The Y-axes in the dot plots show CCR7 expression, and the X-axes indicate CD45RP expression. The Y-axes in the bar graphs indicate the percentage of cells positive for the T cell subsets defined on the, X-axes.

FIG. 20b is a series of bar graphs showing the increase in effector memory (EM) cells among MP-CTL generated from two smoldering multiple myeloma patients. Increasing the number of peptide stimulations from 4 to 7 resulted in an increase in the percentage of EM type cells. The Y-axes in the bar graphs indicate the percentage of cells positive for the T cell subsets defined on the X-axes.

FIG. 20c is a series of histograms showing the increase in IFN-γ+ CD107α+ among effector memory cells (EM) and terminal effector cells (TE) from three smoldering multiple myeloma patients. The Y-axes indicate the percentage of double positive IFN-γ+ CD107α+ cells, and the X-axes indicate the type of cells used to stimulate the MP-CTL.

FIG. 20d is a series of bar graphs showing CD69 activation for the naïve and memory CD8+ T cell subsets in MP-CTL generated from four smoldering multiple myeloma patients in response to MM cell lines (HLA-A2+U266 cells or HLA-A2− RPMI cells). The Y-axes show the percentage of CD69+ cell, and the X-axes indicate the CTL subpopulations.

FIG. 21 is a graph showing the affinity of peptides from unspliced XBP1, spliced XBP1, CD138, and CS1 for HLA-A24. T2 cells were exposed to indicated peptides at a concentration of 1 mg/ml. HIV envelope protein$_{583\_591}$ (RYLKDQQLL; SEQ ID NO: 537) was used as an HLA-A24-specific positive control peptide.

FIG. 22 is a graph showing the affinity of unspliced XBP1 peptide 4 (SEQ ID NO: 35), unspliced XBP1 peptide 7 (SEQ ID NO: 29), and spliced peptide 1 (SEQ ID NO: 30) for HLA-A24. T2 cells were exposed to peptides at concentrations indicated.

FIG. 23 is a graph showing the affinity of CD138 peptides 1 (SEQ ID NO: 31), 3 (SEQ ID NO: 41), and 4 (SEQ ID NO: 42) for HLA-A24. T2 cells were exposed to peptides at concentrations indicated.

FIG. 24 is a graph showing the affinity of CS1 peptides 3 (SEQ ID NO: 48) and 5 (SEQ ID NO: 32) for HLA-A24. T2 cells were exposed to peptides at concentrations indicated.

FIG. 25 is a schematic representation of the method used to generate peptide-specific CTL. APCs presenting indicated peptides were used to stimulate CD3+T lymphocytes from donors to generate peptide-specific CTL.

FIG. 26a is a bar graph showing the increase in CD8+ T cells induced by unspliced XBP1 peptide 7 presented on T lymphocytes from two donors (Donor A and Donor B). The Y-axes indicate the percentage of CD8+T lymphocytes, and the X-axes indicate the number of peptide stimulations prior to phenotypic analysis.

FIG. 26b is a bar graph showing the increase in CD8+ T cells induced by spliced XBP1 peptide 1 presented on T lymphocytes from two donors (Donor A and Donor B). The Y-axes indicate the percentage of CD8+T lymphocytes, and the X-axes indicate the number of peptide stimulations prior to phenotypic analysis.

FIG. 26c is a bar graph showing the increase in CD8+ T cells induced by CD138 peptide 1 presented on T lymphocytes from two donors (Donor A and Donor B). The Y-axes indicate the percentage of CD8+T lymphocytes, and the X-axes indicate the number of peptide stimulations prior to phenotypic analysis.

FIG. 26d is a bar graph showing the increase in CD8+ T cells induced by CS1 peptide 1 presented on T lymphocytes from two donors (Donor A and Donor B). The Y-axes indicate the percentage of CD8+T lymphocytes, and the X-axes indicate the number of peptide stimulations prior to phenotypic analysis.

FIG. 27 is a schematic representation of the method used to evaluate the response of peptide-specific CTL to various multiple myeloma tumor cells. Peptide-specific CTL were incubated for 5 hours with KMS, OPM1, or U266 multiple myeloma cells and assayed for IFN-γ production, CD107α upregulation, CD8 T cell proliferation, or IL-2 production.

FIG. 28 is a series of dot plots showing IFN-γ production and CD8 expression of peptide-specific CTL in response to multiple myeloma cells. The Y-axes indicate the level of IFN-γ expression, and the X-axes indicate CD8 expression. The peptide specificity of the CTL population analyzed is shown on the left. CD8+, IFN-γ+ populations are represented in boxed regions.

FIG. 29a is a series of dot plots showing IFN-γ expression in populations and subpopulations of CTL. CTL specific for unspliced XBP1 peptide 7 (SEQ ID NO: 29) were stimulated with KMS11 cells. Populations represented in boxed regions are indicated on graphs.

FIG. 29b is a series of dot plots showing IFN-γ expression in populations and subpopulations of CTL. CTL specific for spliced XBP1 peptide 1 (SEQ ID NO: 30) were stimulated with KMS11 cells. Populations represented in boxed regions are indicated on graphs.

FIG. 29c is a series of dot plots showing IFN-γ expression in populations and subpopulations of CTL. CTL specific for CD138 peptide 1 (SEQ ID NO: 31) were stimulated with KMS11 cells. Populations represented in boxed regions are indicated on graphs.

FIG. 29d is a series of dot plots showing IFN-γ expression in populations and subpopulations of CTL. CTL specific for CS1 peptide 5 (SEQ ID NO: 32) were stimulated with KMS11 cells. Populations represented in boxed regions are indicated on graphs.

FIG. 30 is a schematic representation of the CD107α detection assay used to measure degranulation. Release of lytic granules due to degranulation of tumor cells causes upregulation of CD107α in CTL, which can be detected by anti-CD107α antibodies.

FIG. 31 is a series of dot plots showing IFN-γ expression and degranulation in peptide-specific CTL. CTL were either unstimulated or stimulated with KMS11 or OPM1 cells, as indicated at top. Peptide specificities of CTL are shown on the left. Y-axes represent CD107α expression, and X-axes represent IFN-γ expression.

FIG. 32 is a schematic representation of the assay used to measure proliferation of peptide-specific CTL in response to multiple myeloma cells. Peptide-specific CTL and irradiated multiple myeloma cells were incubated together for 6 or 8 days, and proliferation of CTL was measured by incorporation of CFSE.

FIG. 33a is a series of histograms showing the proliferation response at day 6 of peptide-specific CTL to myeloma cells. Peptide specificities of CTL are shown on the left. The X-axes indicate a decrease in CFSE staining, a direct measure of cell proliferation.

FIG. 33b is a series of histograms showing the proliferation response at day 8 of peptide-specific CTL to myeloma cells. Peptide specificities of CTL are shown on the left. The X-axes indicate a decrease in CFSE staining, a direct measure of cell proliferation.

FIG. 34 is a series of dot plots showing IL-2 production of peptide-specific CTL in response to myeloma cells. Peptide specificities of CTL are shown on the left. Y-axes indicate IL-2 expression, and X-axes indicate CD8 expression. Boxed regions represent IL-2+ CD8+ populations.

FIG. 35 is a series of dot plots showing IFN-γ expression of peptide-specific CTL from Donor A in response to various colon cancer cell lines. CTL were either unstimulated or stimulated with SW80, WiDr, or LS180 cells, as indicated at top. Peptide specificities of CTL are shown on the left. Y-axes indicate IFN-γ expression, and X-axes indicate CD8 expression. Boxed regions represent IFN-γ+ CD8+ populations.

FIG. 36 is a series of dot plots showing IFN-γ expression and degranulation in peptide-specific CTL from Donor A in response to various colon cancer cell lines. CTL were either unstimulated or stimulated with SW80, WiDr, or LS180 cells, as indicated at top. Peptide specificities of CTL are shown on the left. Y-axes represent CD107α expression, and X-axes represent IFN-γ expression.

FIG. 37 is a series of dot plots showing IFN-γ expression of peptide-specific CTL from Donor B in response to various colon cancer cell lines. CTL were either unstimulated or stimulated with SW80, WiDr, or LS180 cells, as indicated at top. Peptide specificities of CTL are shown on the left. Y-axes indicate IFN-γ expression, and X-axes indicate CD8 expression. Boxed regions represent IFN-γ+ CD8+ populations.

FIG. 38 is a series of dot plots showing IFN-γ expression and degranulation in peptide-specific CTL from Donor B. CTL were either unstimulated or stimulated with SW80, WiDr, or LS180 cells, as indicated at top. Peptide specificities of CTL are shown on the left. Y-axes represent CD107α expression, and X-axes represent IFN-γ expression.

FIG. 39a is a series of histograms showing the degranulation response of CD138 peptide-specific CTL to SW480 tumor cells. CTL and SW480 tumor cells were co-incubated at various cell:cell ratios, as indicated on the left, and analyzed for expression of CD107α, IFN-γ, and IL-2, as indicated at top.

FIG. 39b is a series of histograms showing various response of CD138 peptide-specific CTL to LS180 tumor cells. CTL and LS180 tumor cells were co-incubated at various cell:cell ratios, as indicated on the left, and analyzed for expression of CD107α, IFN-γ, and IL-2, as indicated at top.

FIG. 40a is a series of dot plots showing IFN-γ expression of peptide-specific CTL from Donor A in response to different cancer cell types. CTL were incubated alone or co-incubated with either SW480 colon cancer cells or KMS11 multiple myeloma cells and analyzed for IFN-γ expression. Peptide specificities of CTL are shown on the left. Y-axes indicate IFN-γ expression, and X-axes indicate CD8 expression. Boxed regions represent IFN-γ+ CD8+ populations.

FIG. 40b is a series of dot plots showing degranulation and IFN-γ expression of peptide-specific CTL from Donor A in response to different cancer cell types. CTL were incubated alone or co-incubated with either SW480 colon cancer cells or KMS11 multiple myeloma cells and analyzed for IFN-γ expression. Peptide specificities of CTL are shown on the left. Y-axes indicate CD107α expression, and X-axes indicate IFN-γ expression.

FIG. 41a is a series of dot plots showing IFN-γ expression of peptide-specific CTL from Donor B in response to different cancer cell types. CTL were incubated alone or co-incubated with either SW480 colon cancer cells or KMS11 multiple myeloma cells and analyzed for IFN-γ expression. Peptide specificities of CTL are shown on the left. Y-axes indicate IFN-γ expression, and X-axes indicate CD8 expression. Boxed regions represent IFN-γ+ CD8+ populations.

FIG. 41b is a series of dot plots showing degranulation and IFN-γ expression of peptide-specific CTL from Donor B in response to different cancer cell types. CTL were incubated alone or co-incubated with either SW480 colon cancer cells or KMS11 multiple myeloma cells and analyzed for IFN-γ expression. Peptide specificities of CTL are shown on the left. Y-axes indicate CD107α expression, and X-axes indicate IFN-γ expression.

FIG. 42 is a series of dot plots showing IFN-γ expression of peptide-specific CTL from Donor B in response to various pancreatic cancer cell lines. CTL were incubated alone or co-incubated with 8902, PL45, or MiaPaca cells and analyzed for IFN-γ expression. Peptide specificities of CTL are shown on the left. Y-axes indicate IFN-γ expression, and X-axes indicate CD8 expression. Boxed regions represent IFN-γ+ CD8+ populations.

FIG. 43 is a series of histograms and dot plots showing various response of CD138 peptide-specific CTL to Panc1 pancreatic tumor cells.

CTL and Panc1 cells were co-incubated at various cell:cell ratios of 1:1 or 1:5, as indicated on the left, and analyzed for expression of CD107α, IFN-γ, and IL-2, as indicated at top. Y-axes of dot plots indicate CD107α expression, and X-axes of histograms and dot plots indicate IFN-γ or IL-2 expression, as indicated below each graph.

Figure 44:
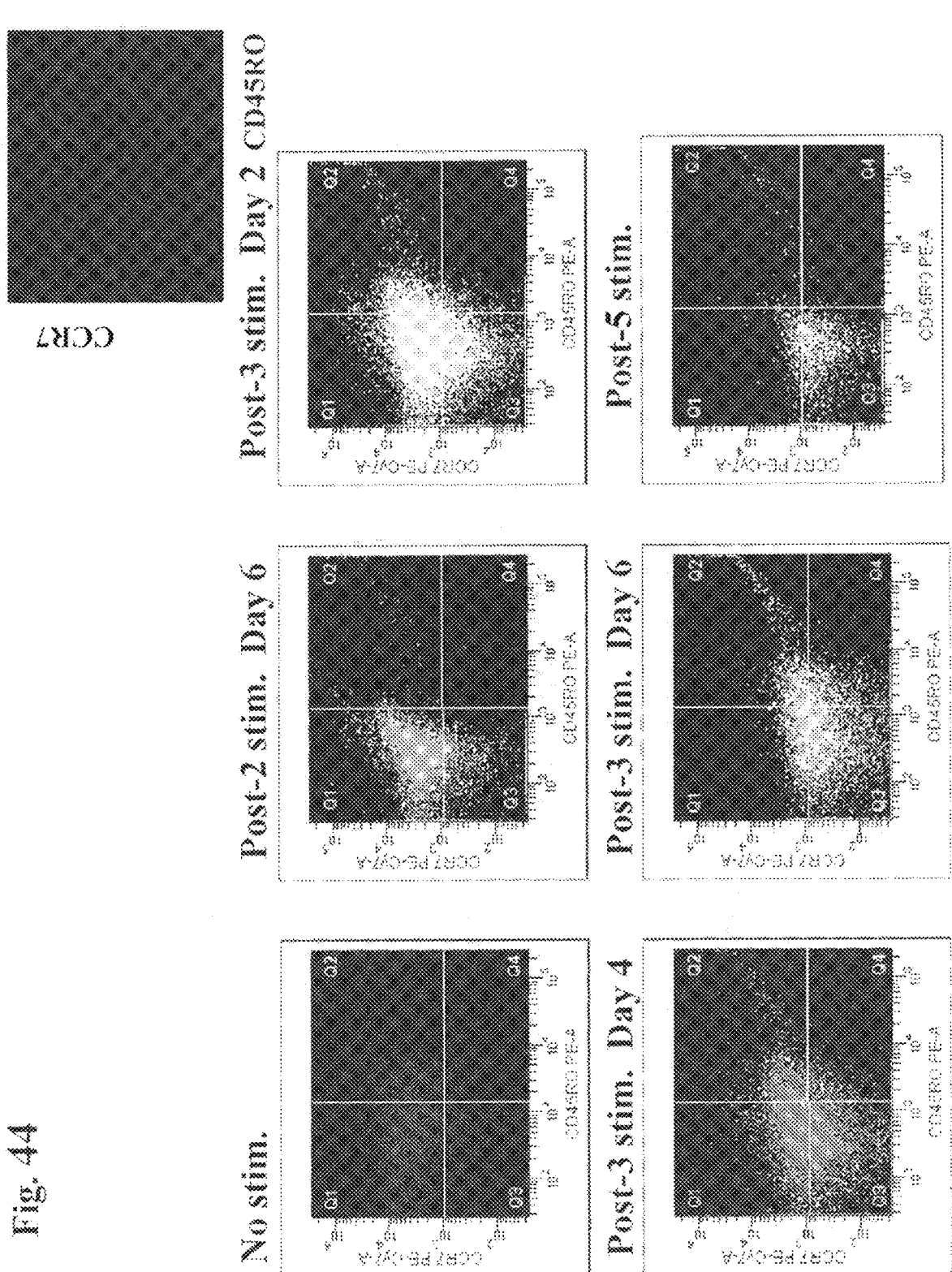

FIG. 44 is a series of dot plots showing the phenotypic changes of T cells (naïve T cells, central memory (CM), effector cells and effector memory (EM) CD8+ T cells) in CTL induced with a cocktail of heteroclitic unspliced XBP1 and heteroclitic spliced XBP1 peptides. The Y-axes in the dot plots show CCR7 expression, and the X-axes indicate CD45RP expression.

Figure 45:
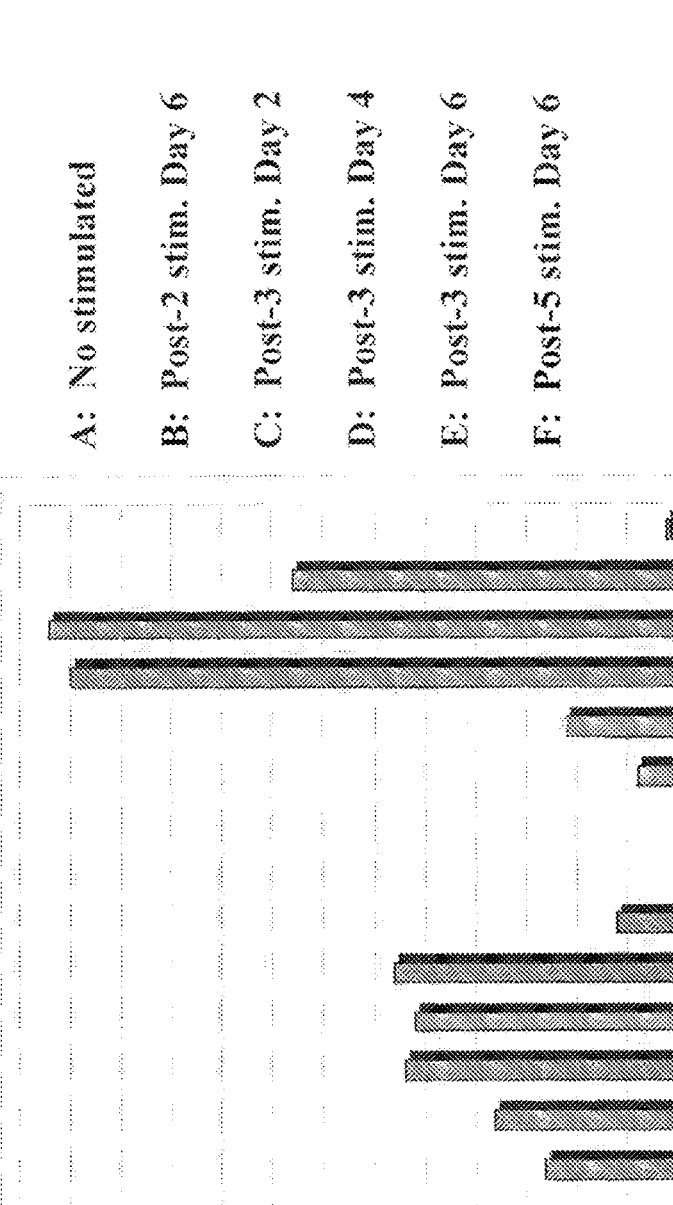

FIG. 45 is a series of bar graphs depicting the generation of central memory CD3+ CD8+ T cells in three donors in response to a cocktail of heteroclitic unspliced XBP1 and heteroclitic spliced XBP1 peptides.

Figure 46:
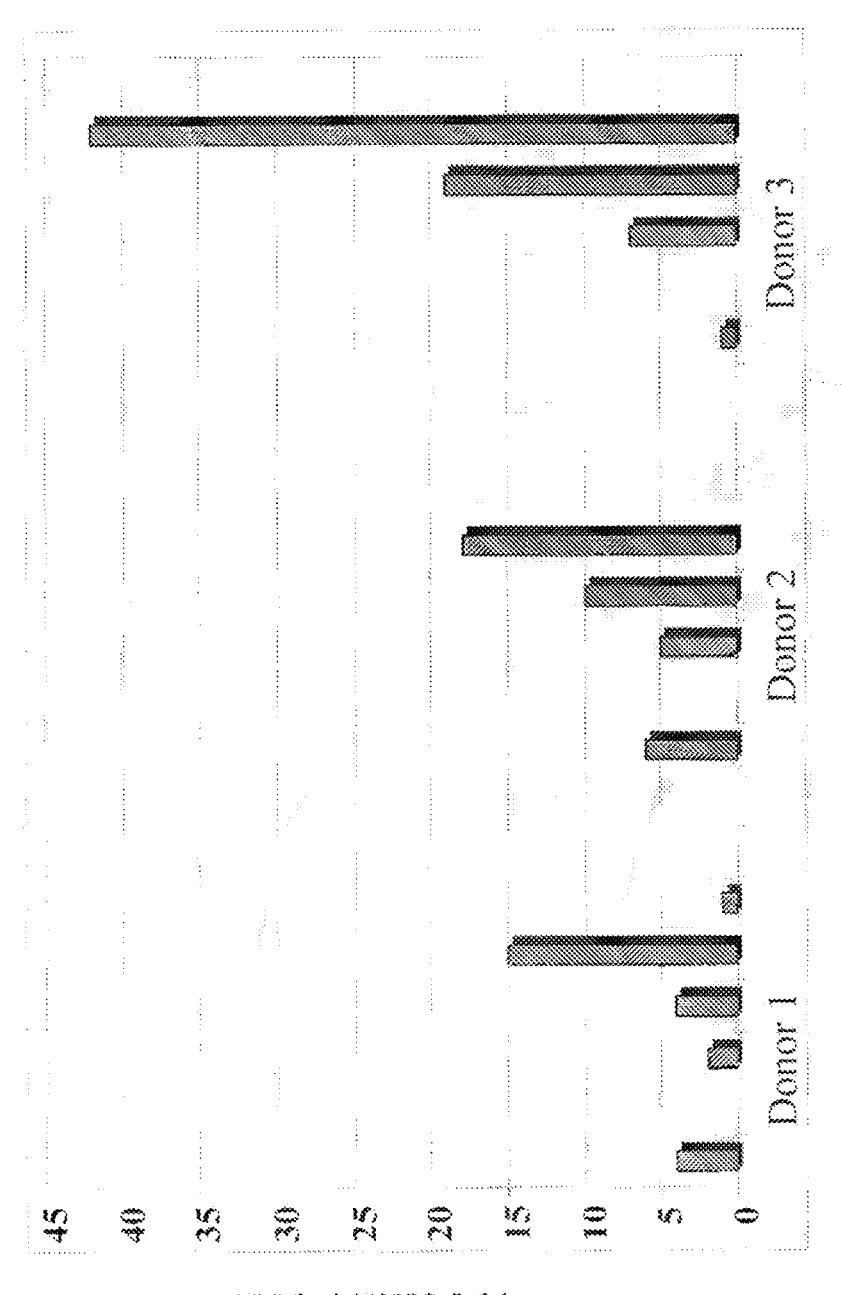

FIG. 46 is a series of bar graphs depicting the generation of effector memory CD3+ CD8+ T cells in three donors in response to a cocktail of heteroclitic unspliced XBP1 and heteroclitic spliced XBP1 peptides.

Figure 47:
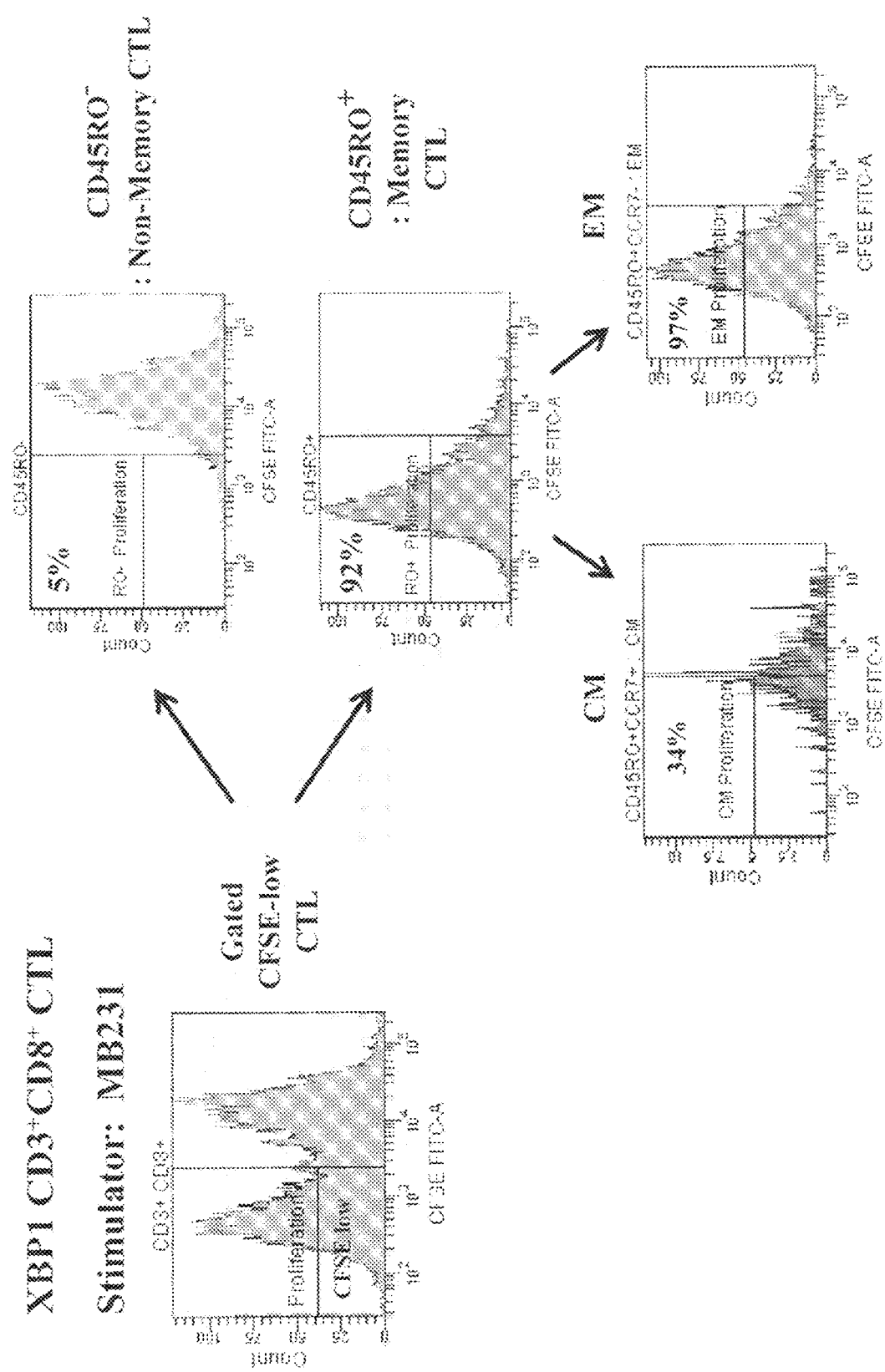

FIG. 47 is a series of histograms showing the proliferation response of the XBP1 peptide cocktail-specific CTL to MB231 breast cancer cells. The response is broken into proliferation in CD45RO– non-memory cells and CD45RO+ memory cells, and within the memory cells which proportion are CD45RO+, CCR7+ central memory T cells and which are CD45RO+, CCR7-effector memory T cells.

Figure 48:
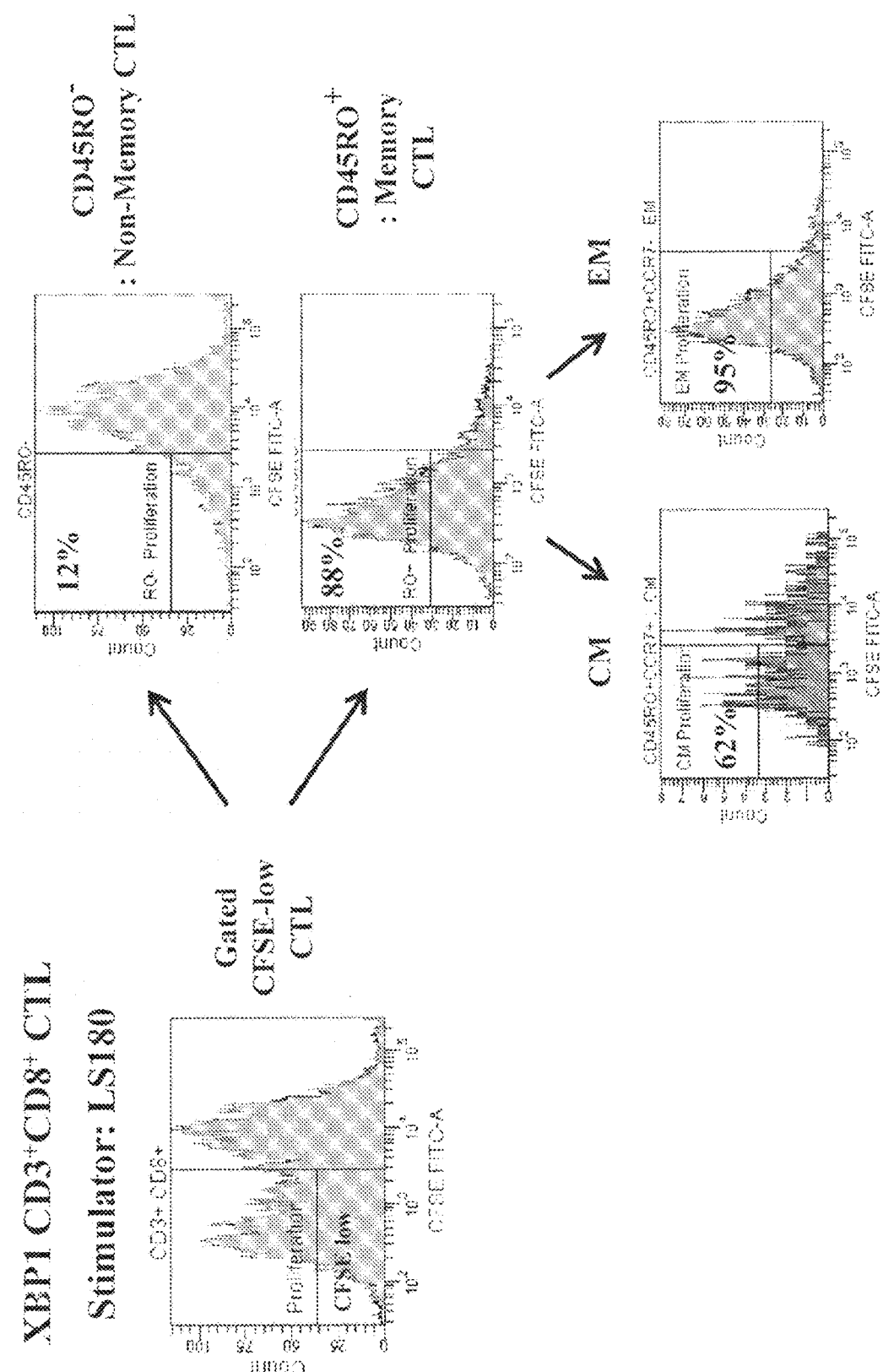

FIG. 48 is a series of histograms showing the proliferation response of the XBP1 peptide cocktail-specific CTL to LS180 colon cancer cells. The response is broken into proliferation in CD45RO– non-memory cells and CD45RO+ memory cells, and within the memory cells which proportion are CD45RO+, CCR7+ central memory T cells and which are CD45RO+, CCR7-effector memory T cells.

Figure 49:
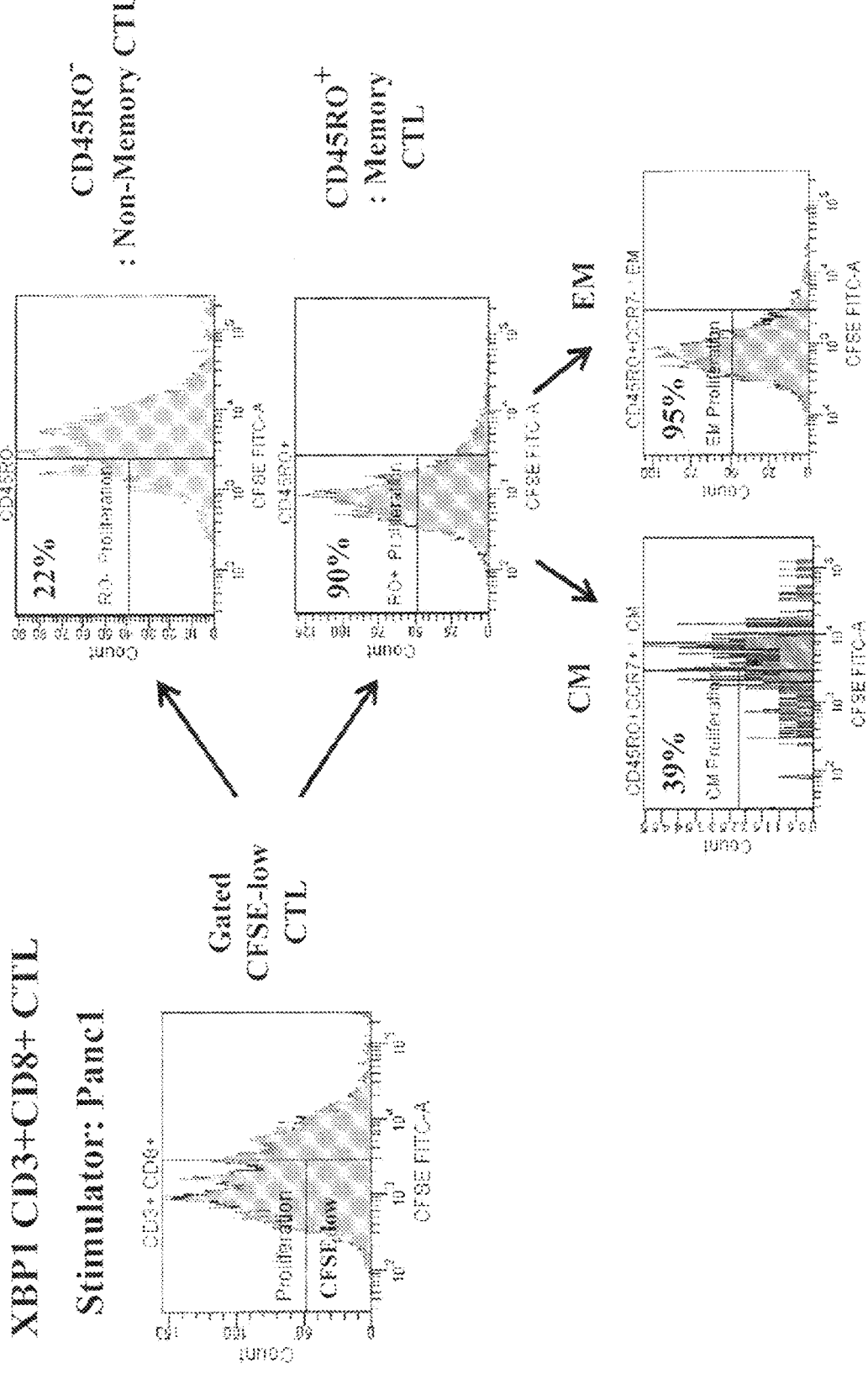

FIG. 49 is a series of histograms showing the proliferation response of the XBP1 peptide cocktail-specific CTL to Panc1 pancreatic cancer cells. The response is broken into proliferation in CD45RO– non-memory cells and CD45RO+ memory cells, and within the memory cells which proportion are CD45RO+, CCR7+ central memory T cells and which are CD45RO+, CCR7– effector memory T cells.

Figure 50:
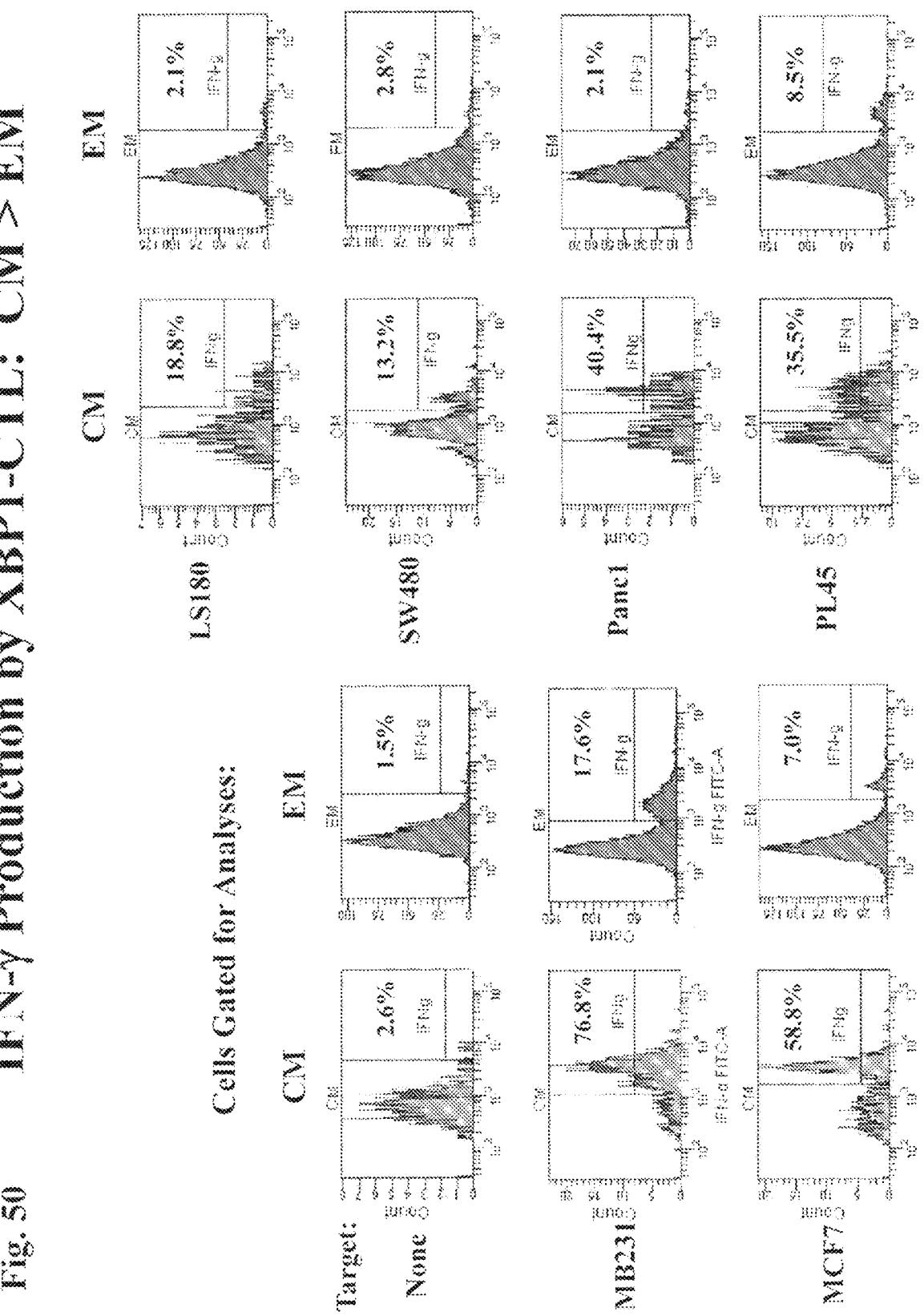

FIG. 50 is a series of histograms showing various response of the XBP1 peptide cocktail-specific CTL to various tumor cells (MB231, MCF7, LS180, SW480, Panc1 and PL45). Central memory T-cells and effector memory T cells were analyzed for expression of IFN-γ.

Figure 51:
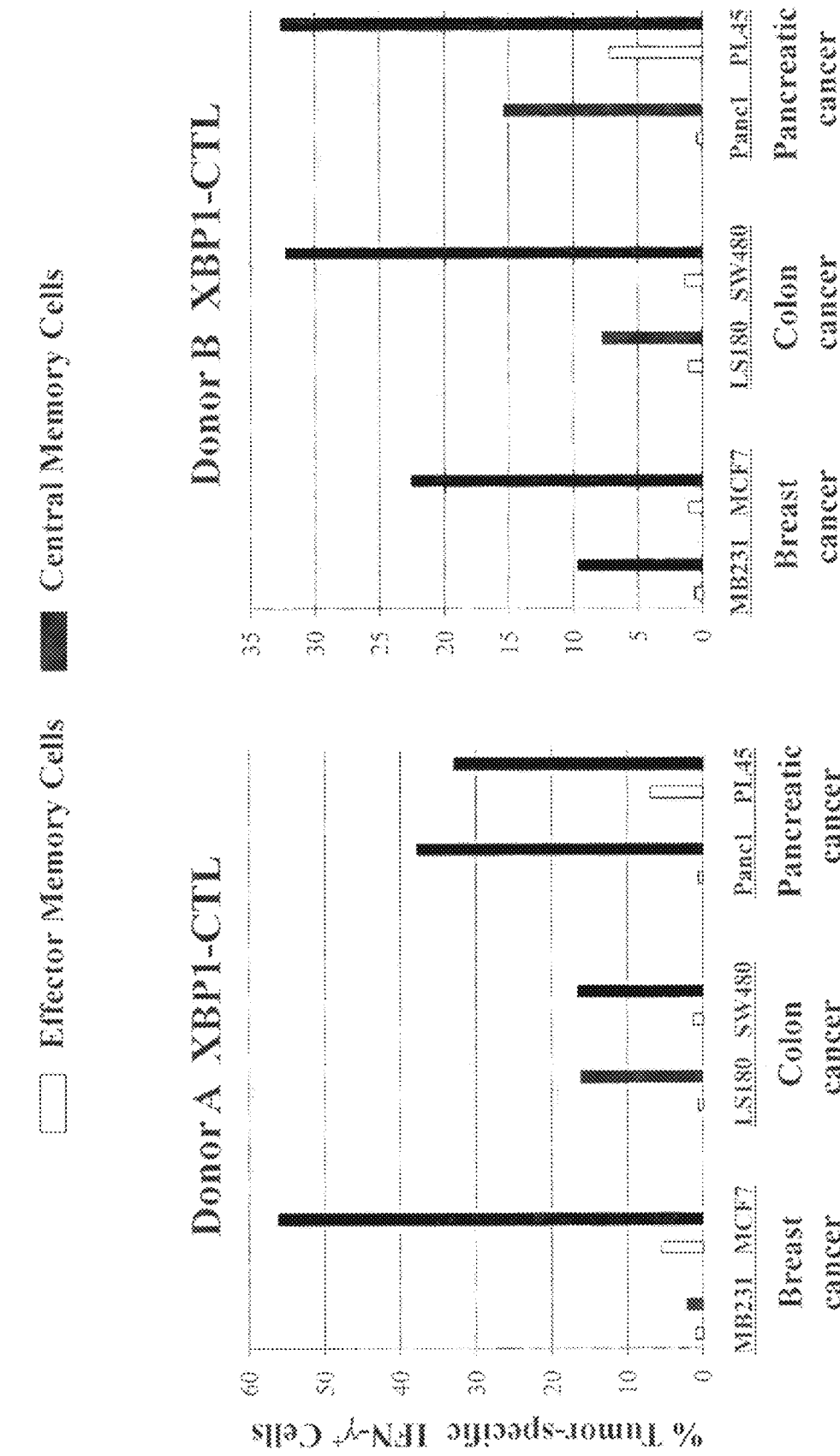

FIG. 51 are bar graphs showing expression of IFN-γ by effector memory T cells and central memory T cells of XBP1 cocktail specific-CTL to various tumor cells (MB231, MC7, LS180, SW480, Panc1 and PL45).

FIG. 52 is a series of histograms showing various response of the XBP1 peptide cocktail-specific CTL to various tumor cells (MB231, MCF7, LS180, SW480, Panc1 and PL45). Central memory T-cells and effector memory T cells were analyzed for expression of IL-2.

Figure 53:
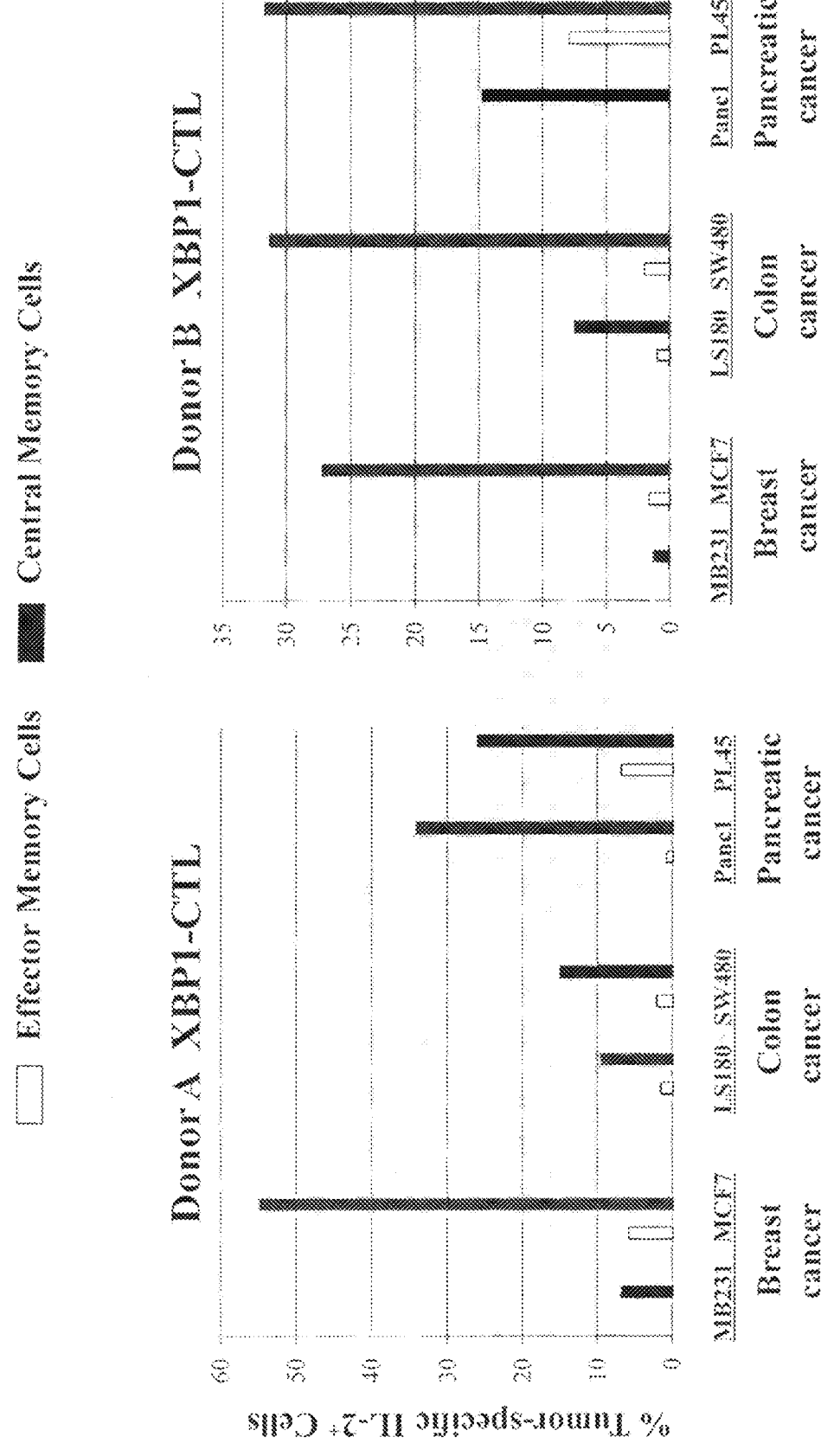

FIG. 53 depicts bar grafts showing expression of IL-2 by effector memory T cells and central memory T cells of XBP1 cocktail specific-CTL to various tumor cells (MB231, MC7, LS180, SW480, Panc1 and PL45).

Figure 54:
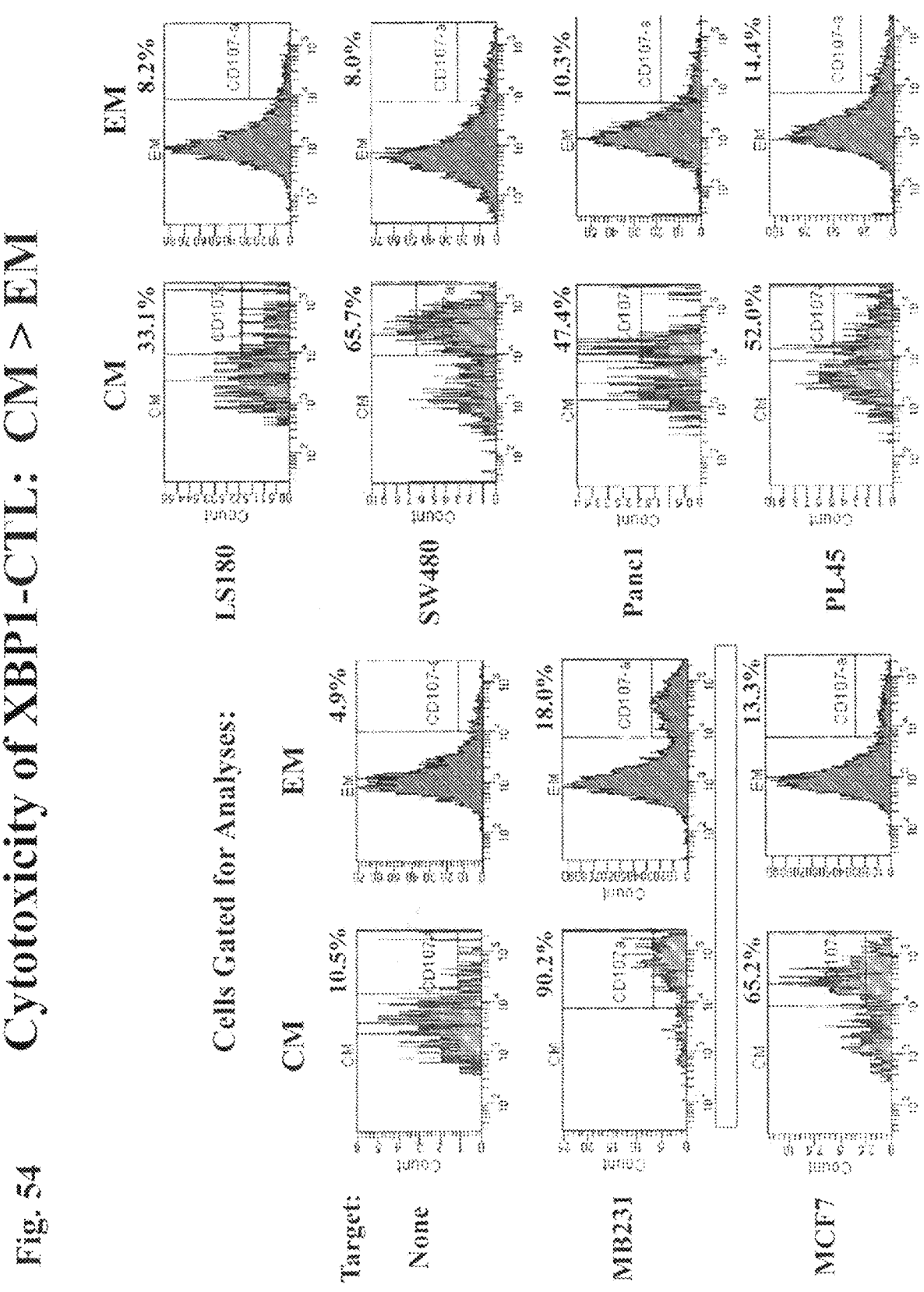

FIG. 54 is a series of histograms showing various response of the XBP1 peptide cocktail-specific CTL to various tumor cells (MB231, MCF7, LS180, SW480, Panc1 and PL45). Central memory T-cells and effector memory T cells were analyzed for cytotoxicity.

Figure 55:
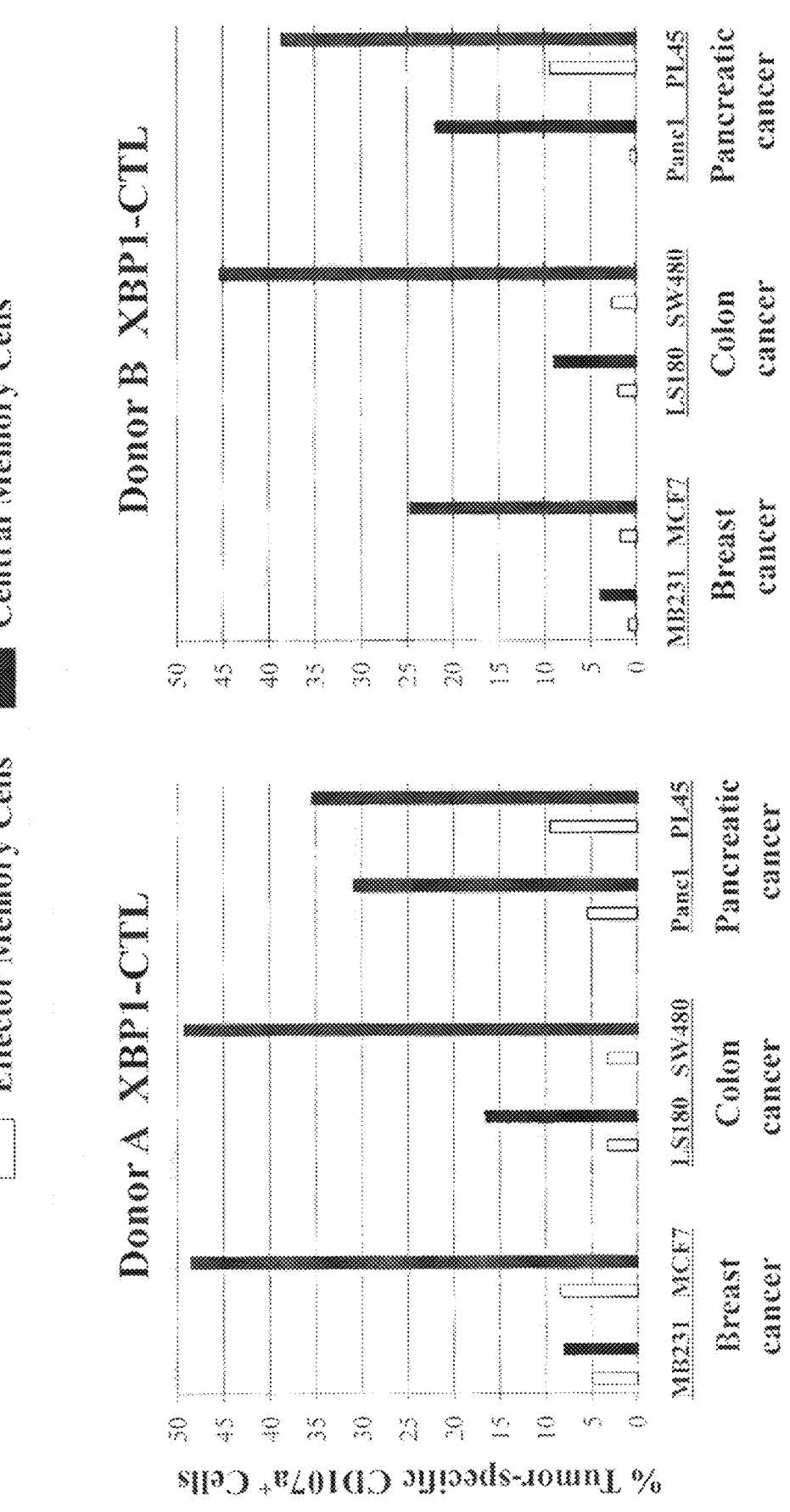

FIG. 55 depicts bar graphs showing cytotoxicity of effector memory T cells and central memory T cells of XBP1 cocktail specific-CTL to various tumor cells (MB231, MC7, LS180, SW480, Panc1 and PL45).

Figure 56:
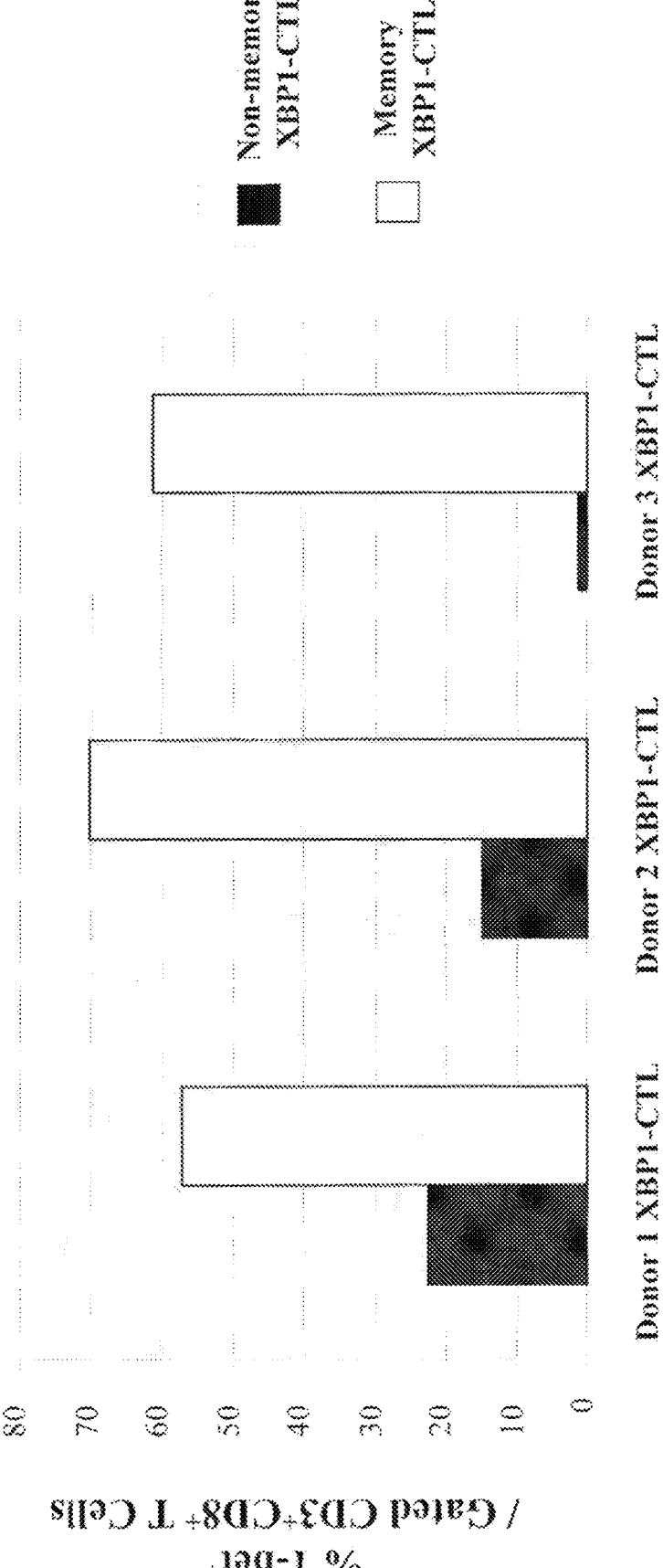

FIG. 56 depicts bar graphs showing expression of Tbet by non-memory and memory T cells of XBP1 cocktail specific-CTL.

Figure 57:
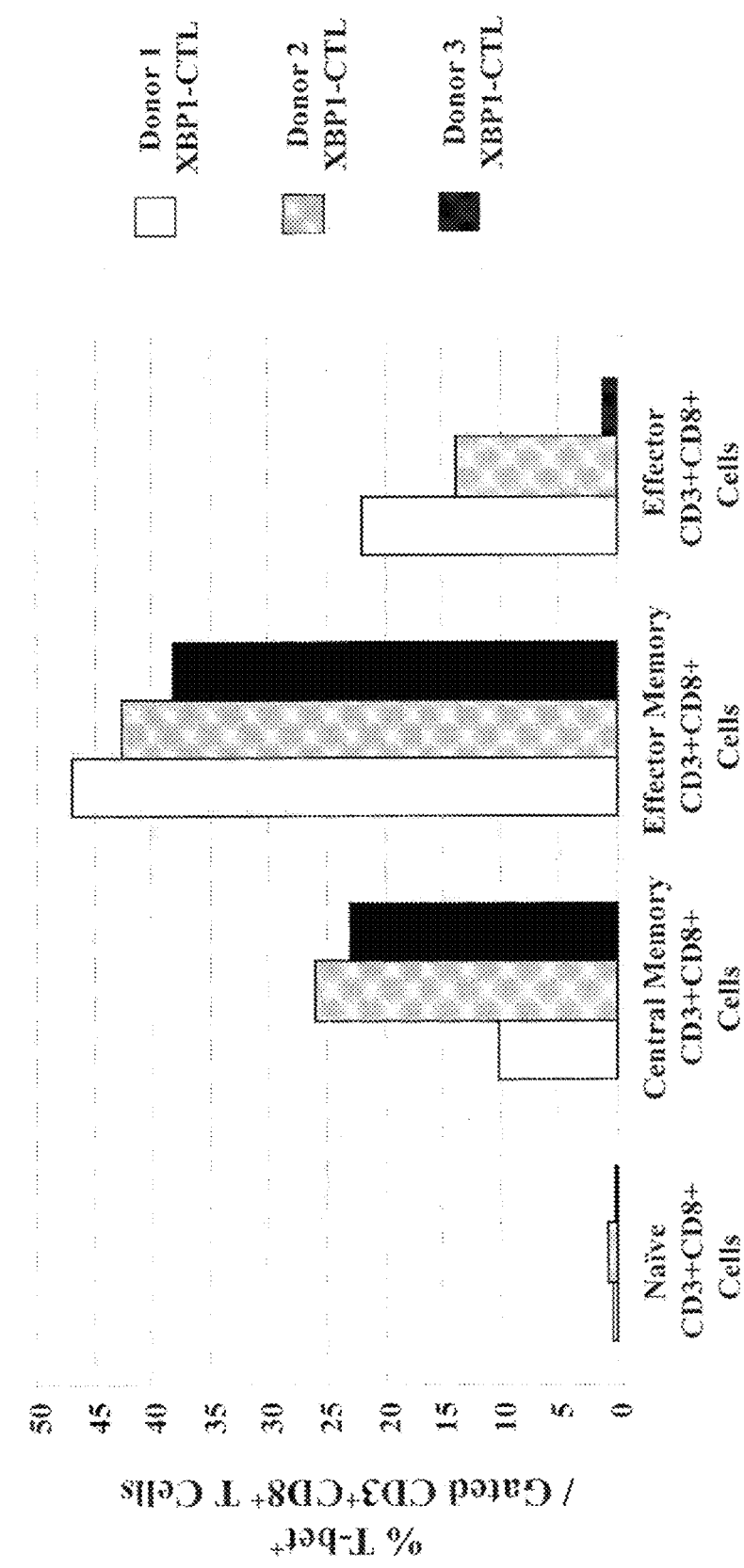

FIG. 57 depicts bar graphs showing expression of Tbet by naïve T-cells, central memory cells, effector memory cells, and effector T cells of XBP1 cocktail specific-CTL.

Figure 58:
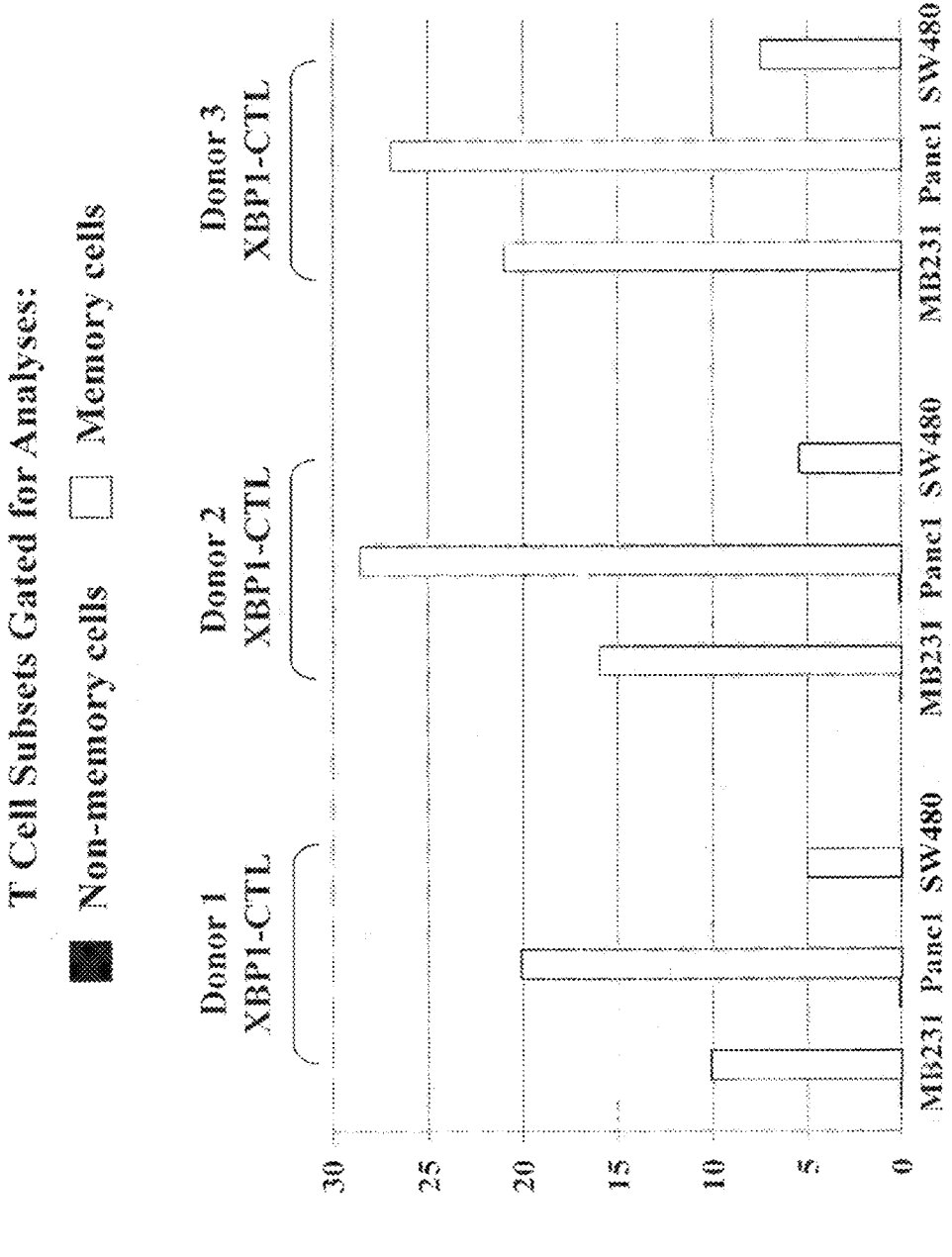

FIG. 58 depicts a bar graphs showing expression of Tbet and IFN-γ by non-memory T cells and memory T cells of XBP1 cocktail specific-CTL to various tumor cells (MB231, SW480 and Panc1).

Figure 59:
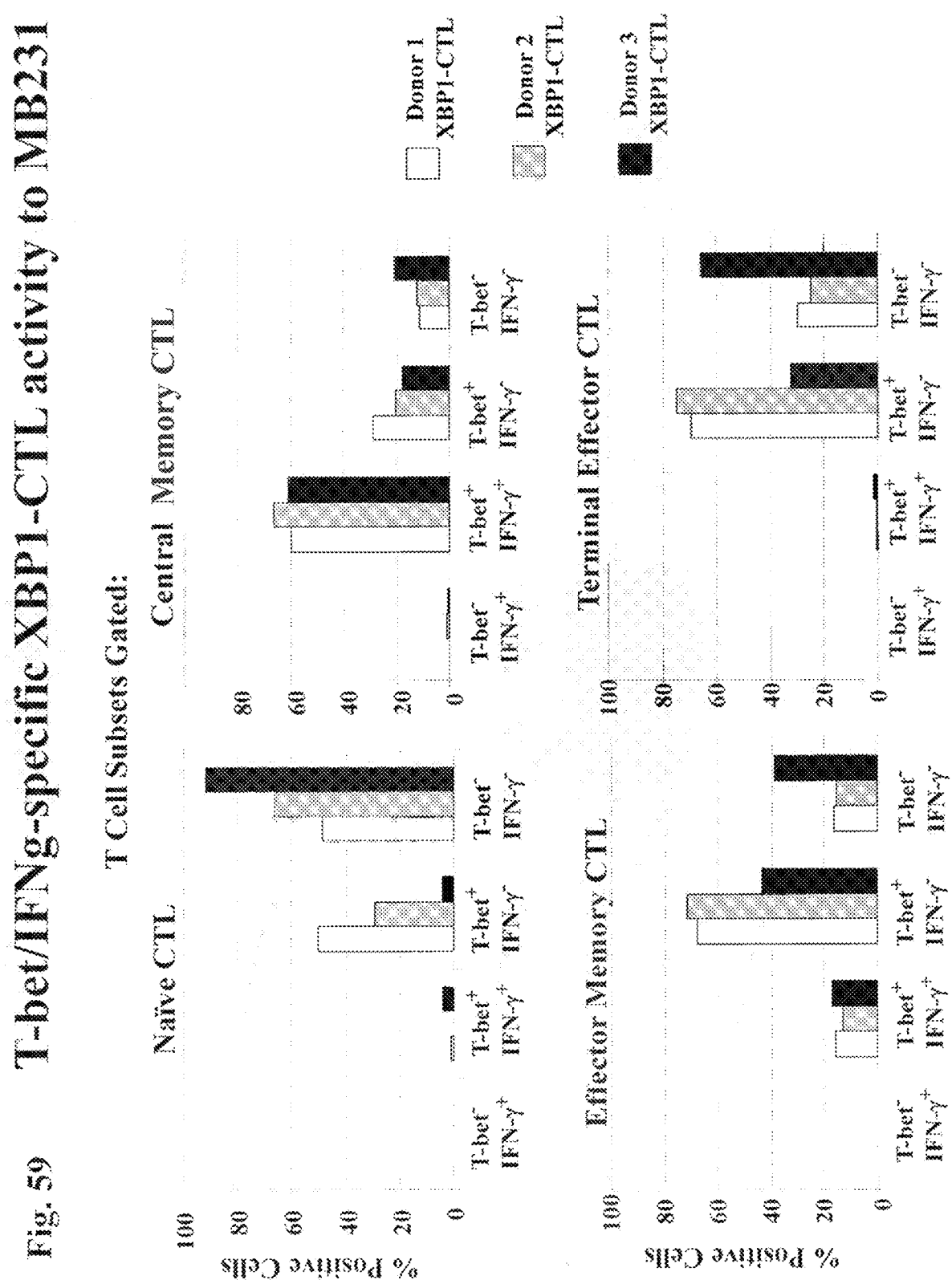

FIG. 59 depicts bar graphs showing expression of Tbet and IFN-γ by naïve T-cells, central memory cells, effector memory cells, and effector T cells of XBP1 cocktail specific-CTL to MB231 breast cancer cells.

Figure 60:
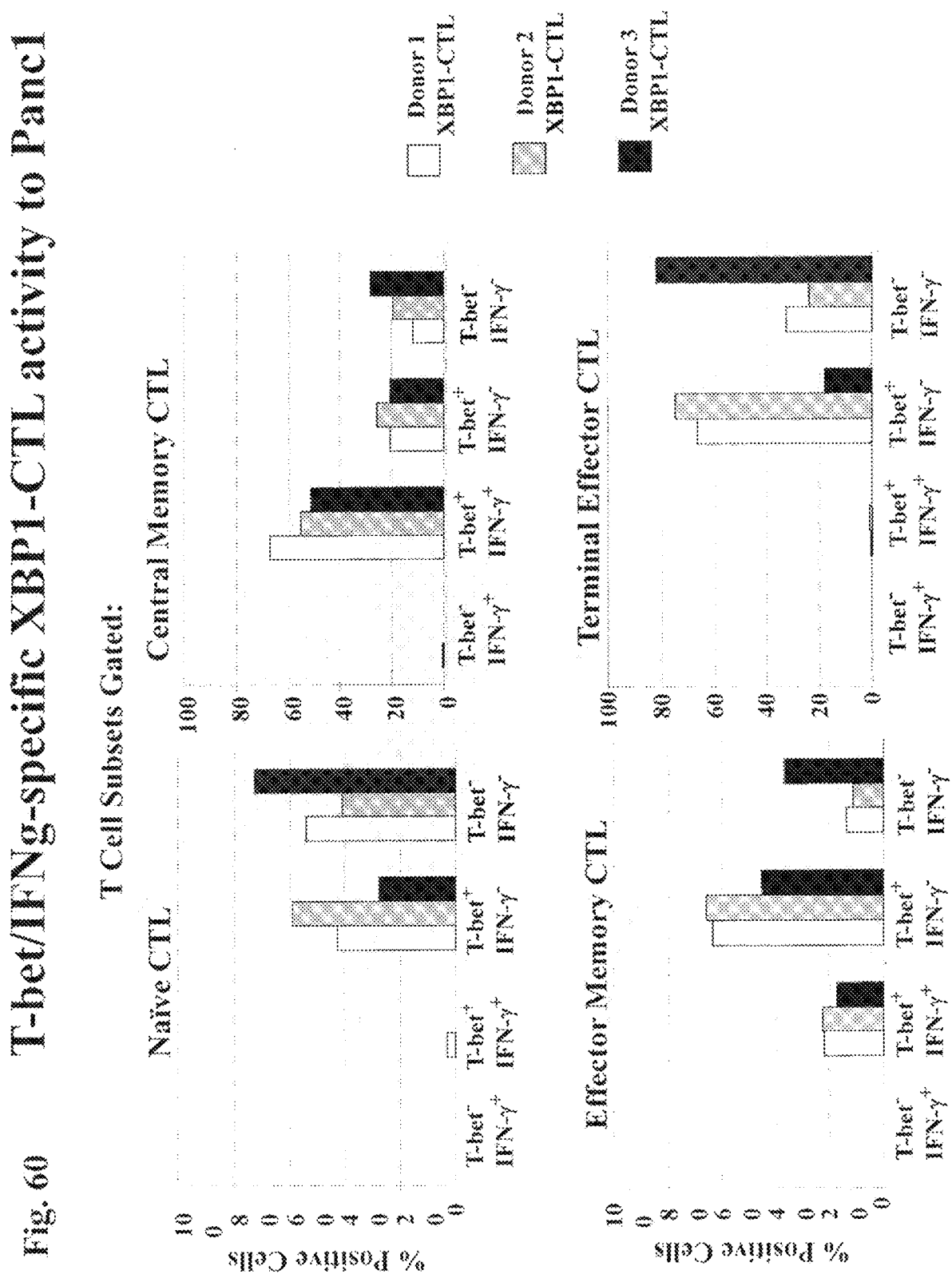

FIG. 60 depicts bar graphs showing expression of Tbet and IFN-γ by naïve T-cells, central memory cells, effector memory cells, and effector T cells of XBP1 cocktail specific-CTL to Panc1 pancreatic cancer cells.

32

Figure 61:
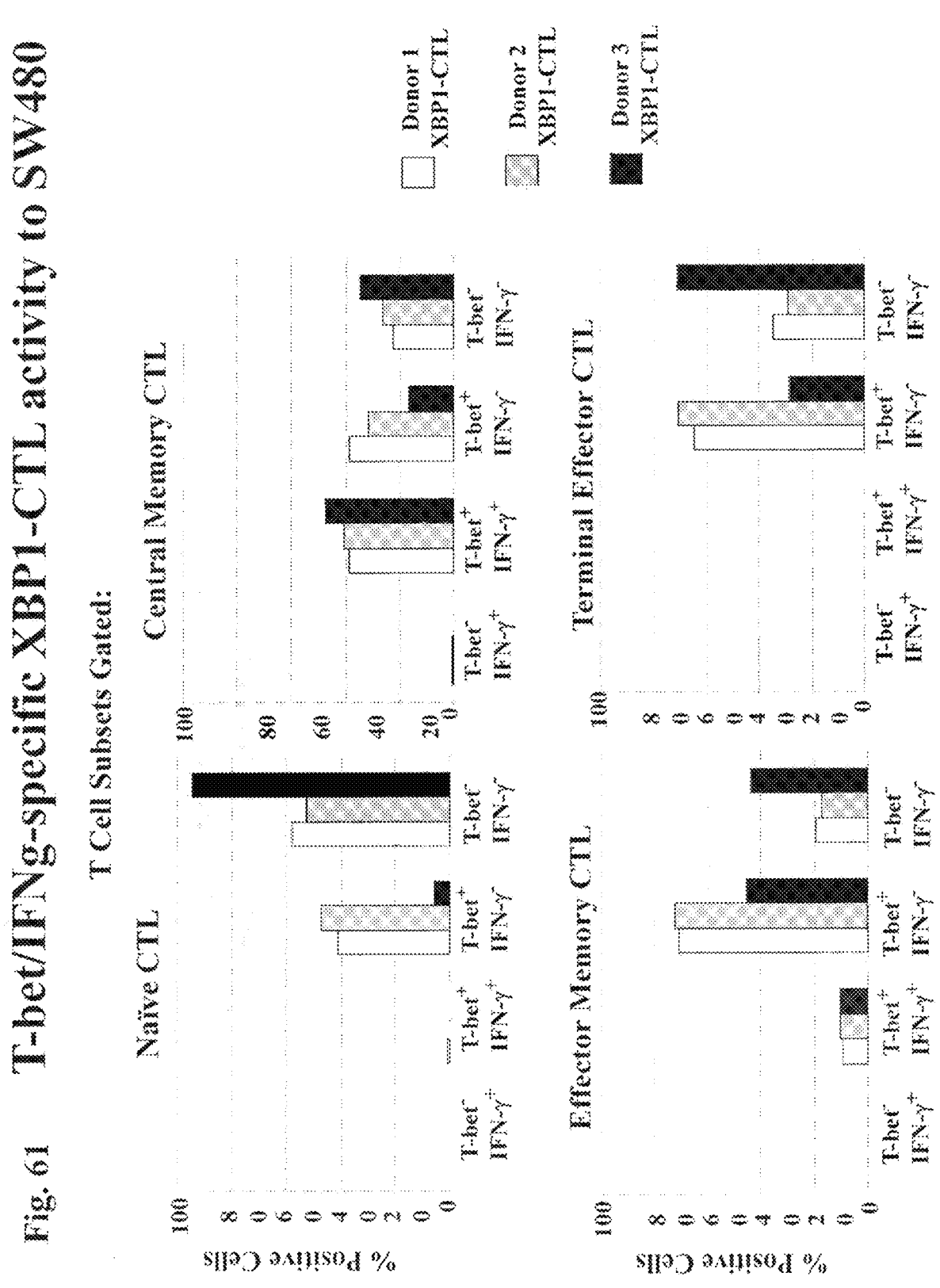

FIG. 61 depicts bar graphs showing expression of Tbet and IFN-γ by naïve T-cells, central memory cells, effector memory cells, and effector T cells of XBP1 cocktail specific-CTL to SW480 colon cancer cells.

FIG. 62 depicts bar graphs showing expression of Eomes by non-memory and memory T cells of XBP1 cocktail specific-CTL.

Figure 63:
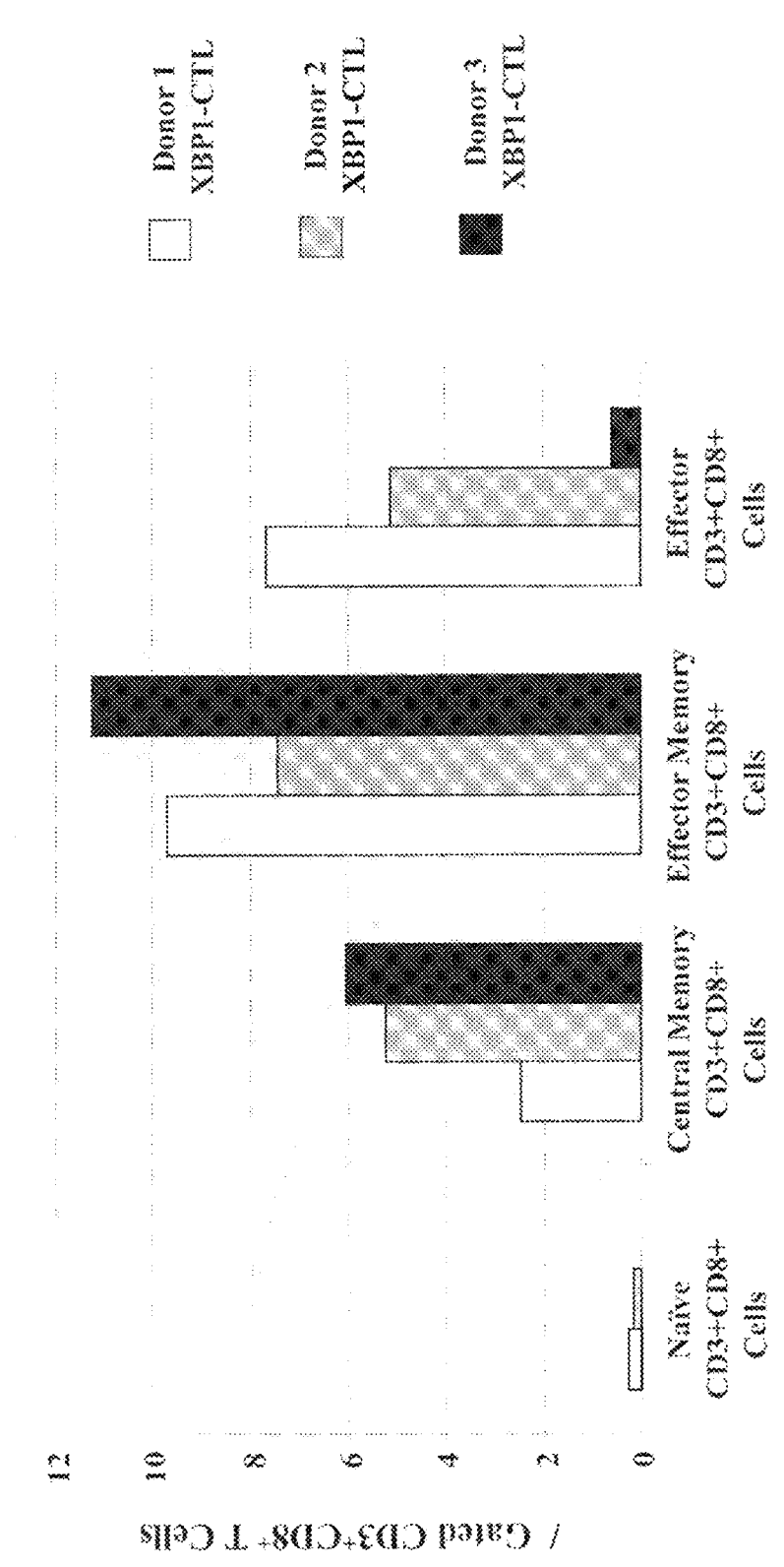

FIG. 63 depicts bar graphs showing expression of Eomes by naïve T-cells, central memory cells, effector memory cells, and effector T cells of XBP1 cocktail specific-CTL.

Figure 64:
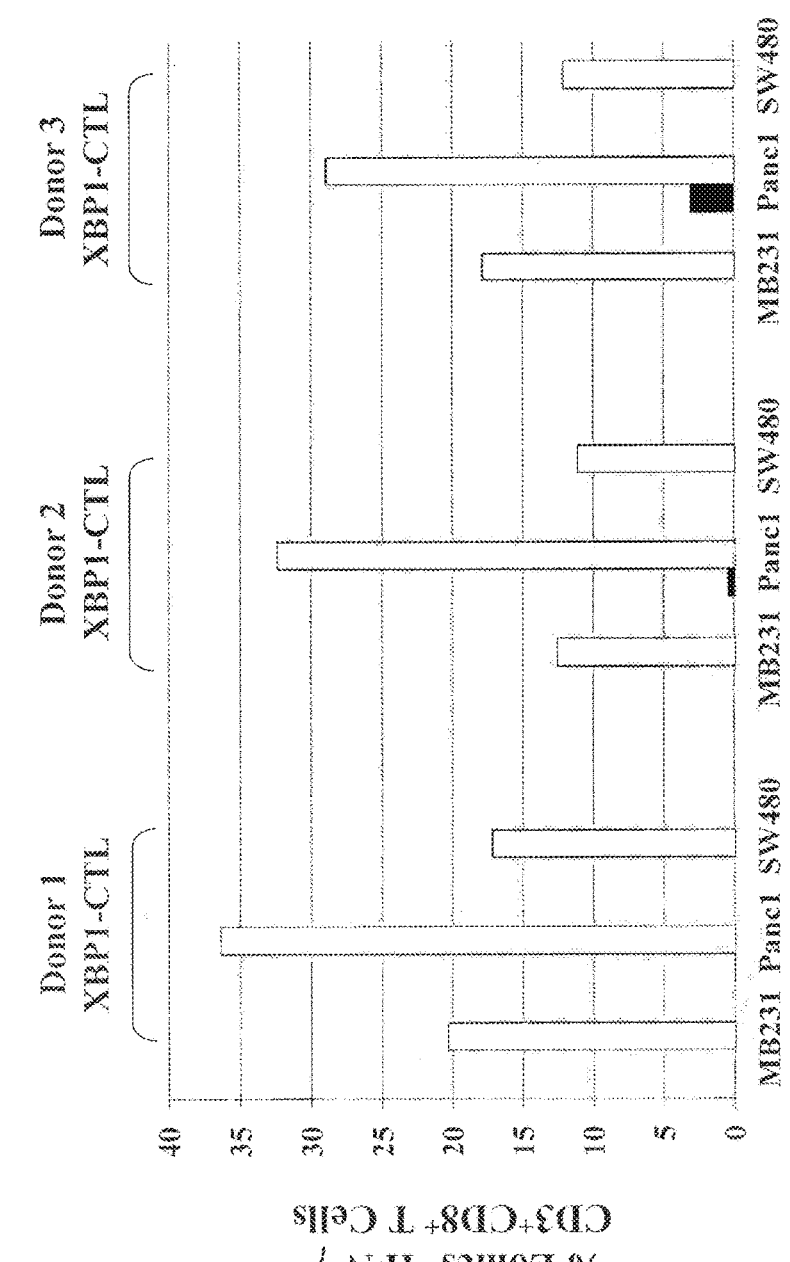

FIG. 64 depicts a bar graph showing expression of Eomes and IFN-γ by non-memory T cells and memory T cells of XBP1 cocktail specific-CTL to various tumor cells (MB231, SW480 and Panc1).

Figure 65:
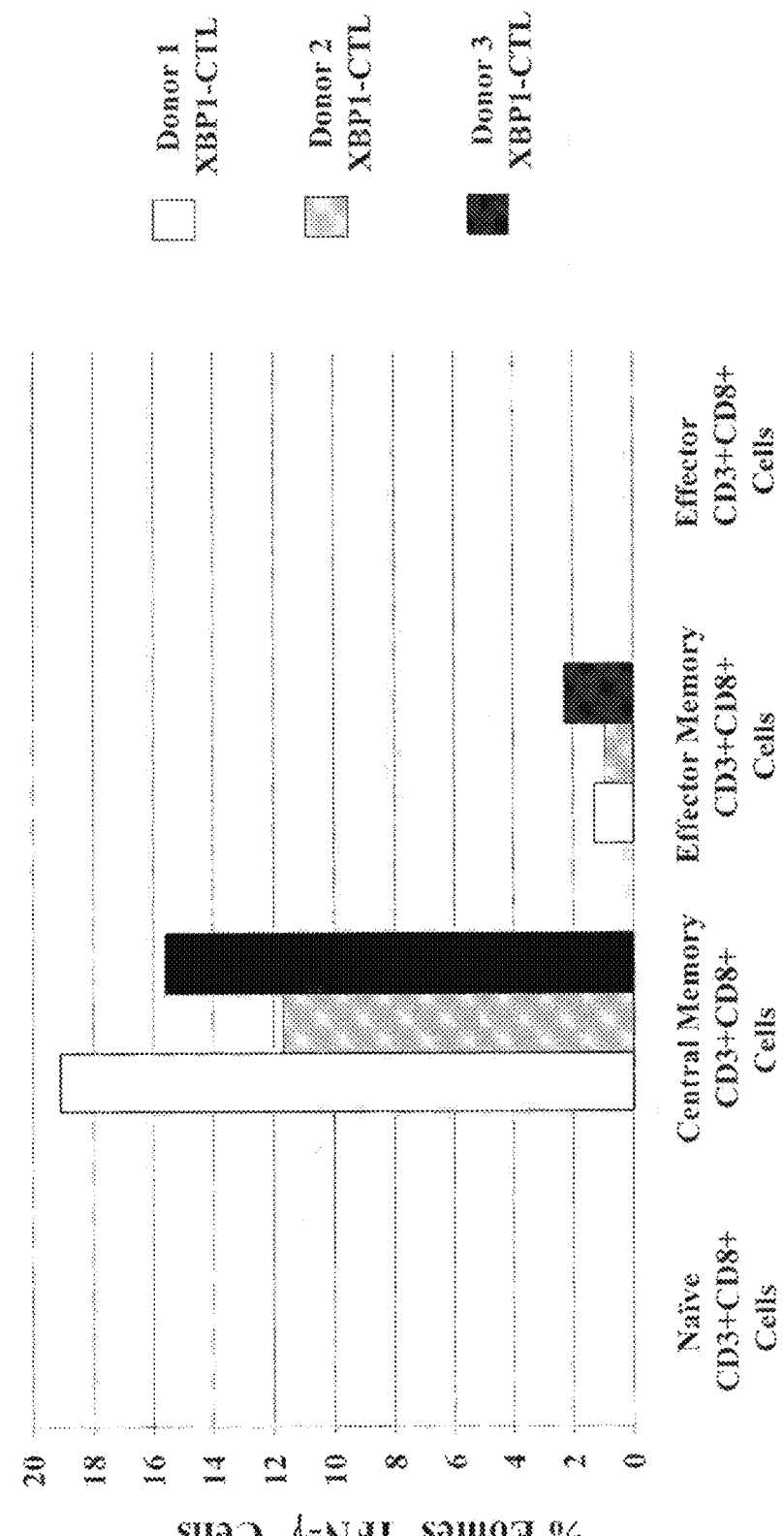

FIG. 65 depicts bar graphs showing expression of Eomes and IFN-γ by naïve T-cells, central memory cells, effector memory cells, and effector T cells of XBP1 cocktail specific-CTL to MB231 breast cancer cells.

Figure 66:
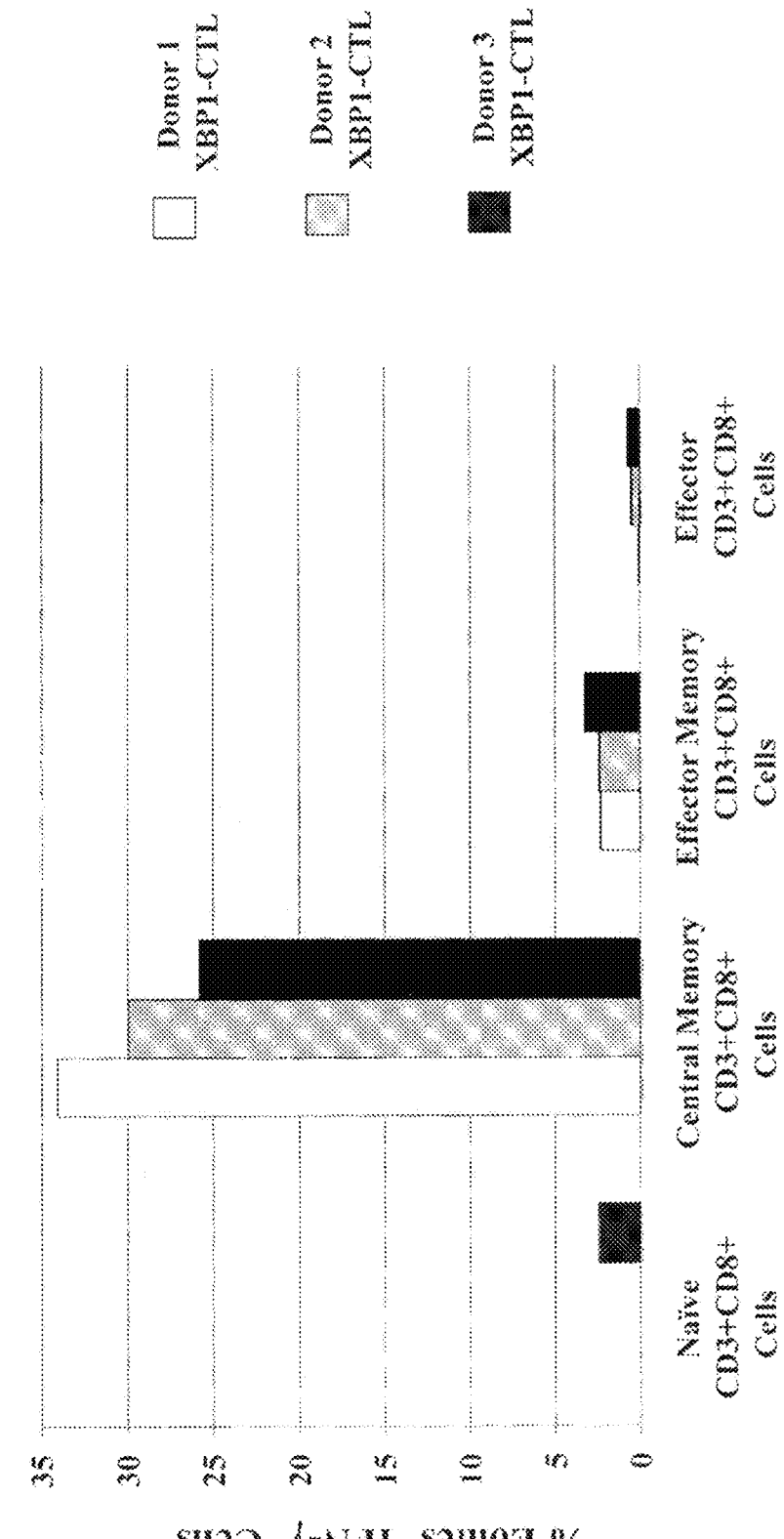

FIG. 66 depicts bar graphs showing expression of Eomes and IFN-γ by naïve T-cells, central memory cells, effector memory cells, and effector T cells of XBP1 cocktail specific-CTL to Panc1 pancreatic cancer cells.

Figure 67:
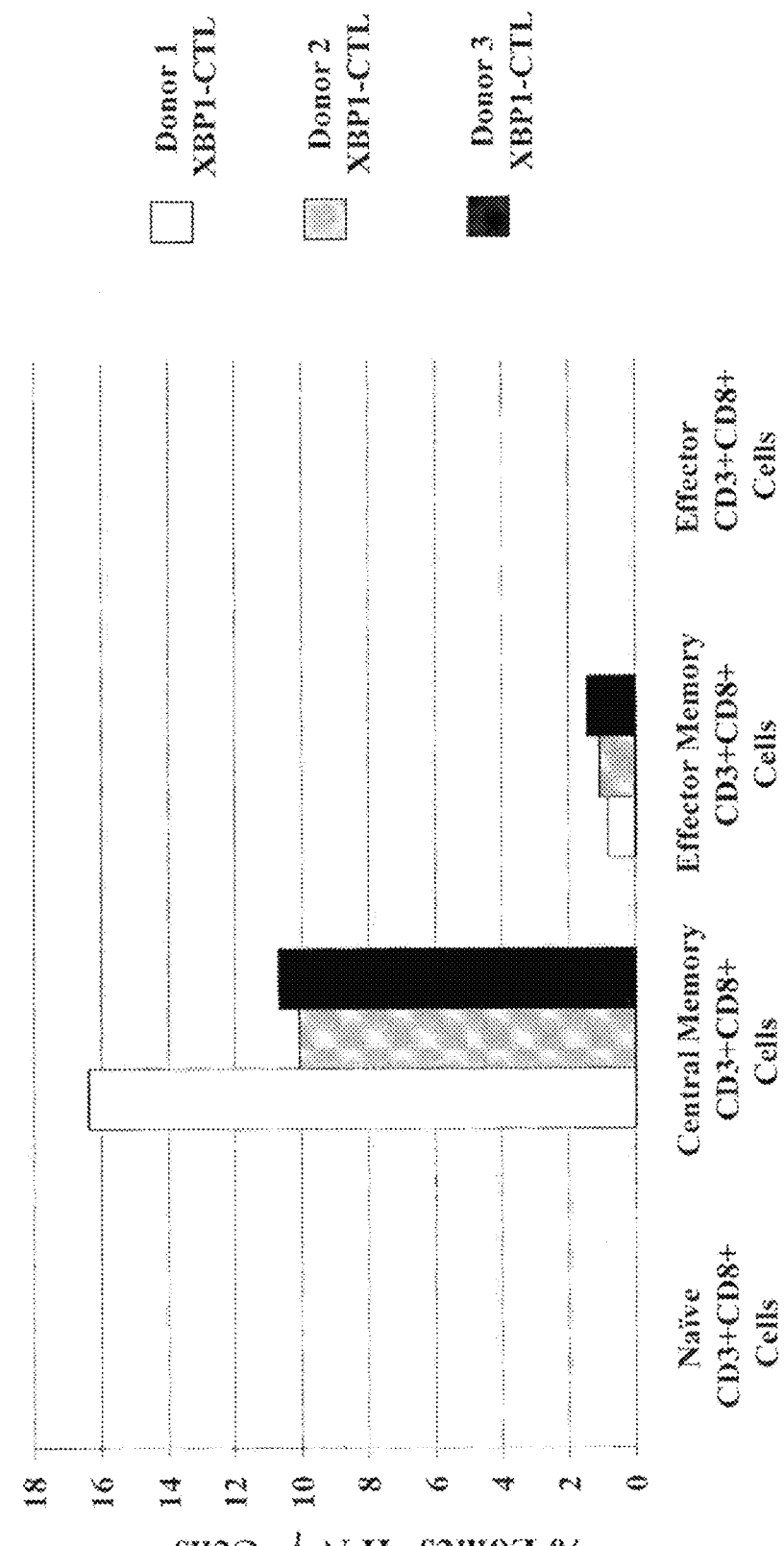

FIG. 67 depicts bar graphs showing expression of Eomes and IFN-γ by naïve T-cells, central memory cells, effector memory cells, and effector T cells of XBP1 cocktail specific-CTL to SW480 colon cancer cells.

Figure 68:
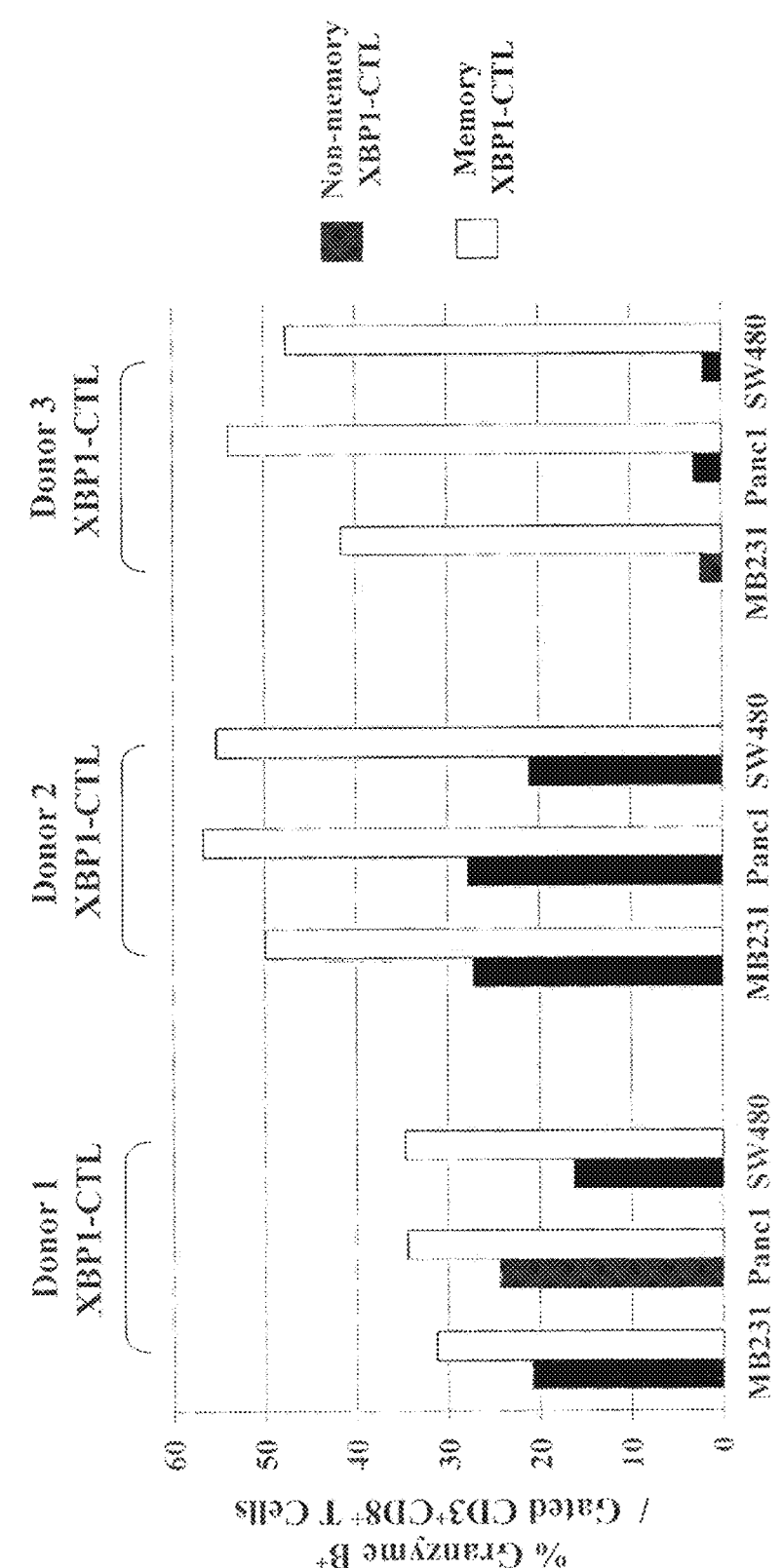

FIG. 68 depicts a bar graph showing expression of granzyme B by non-memory T cells and memory T cells of XBP1 cocktail specific-CTL to various tumor cells (MB231, SW480 and Panc1).

Figure 69:
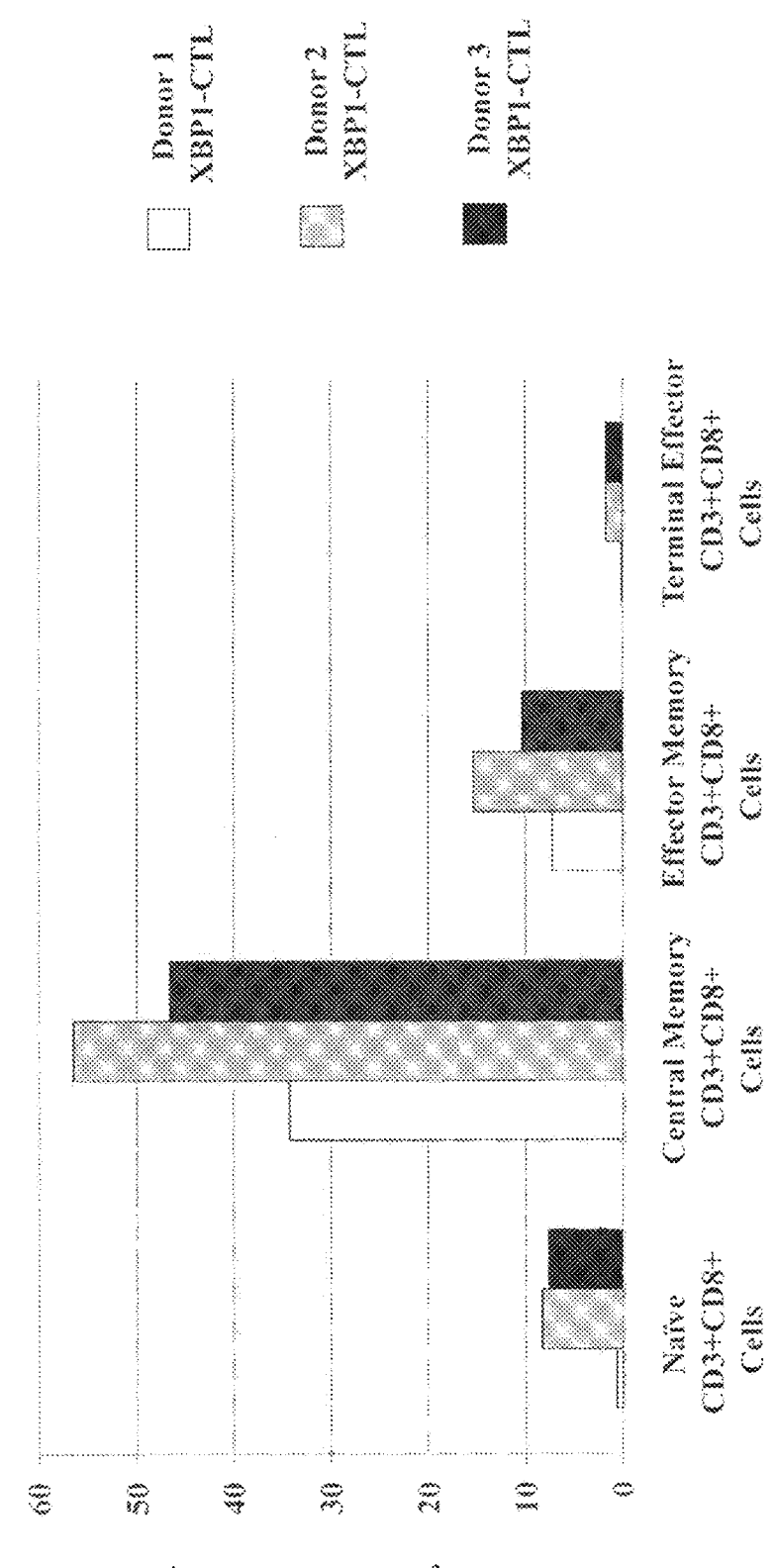

FIG. 69 depicts bar graphs showing expression of granzyme B and IFN-γ by naïve T-cells, central memory cells, effector memory cells, and effector T cells of XBP1 cocktail specific-CTL to MB231 breast cancer cells.

Figure 70:
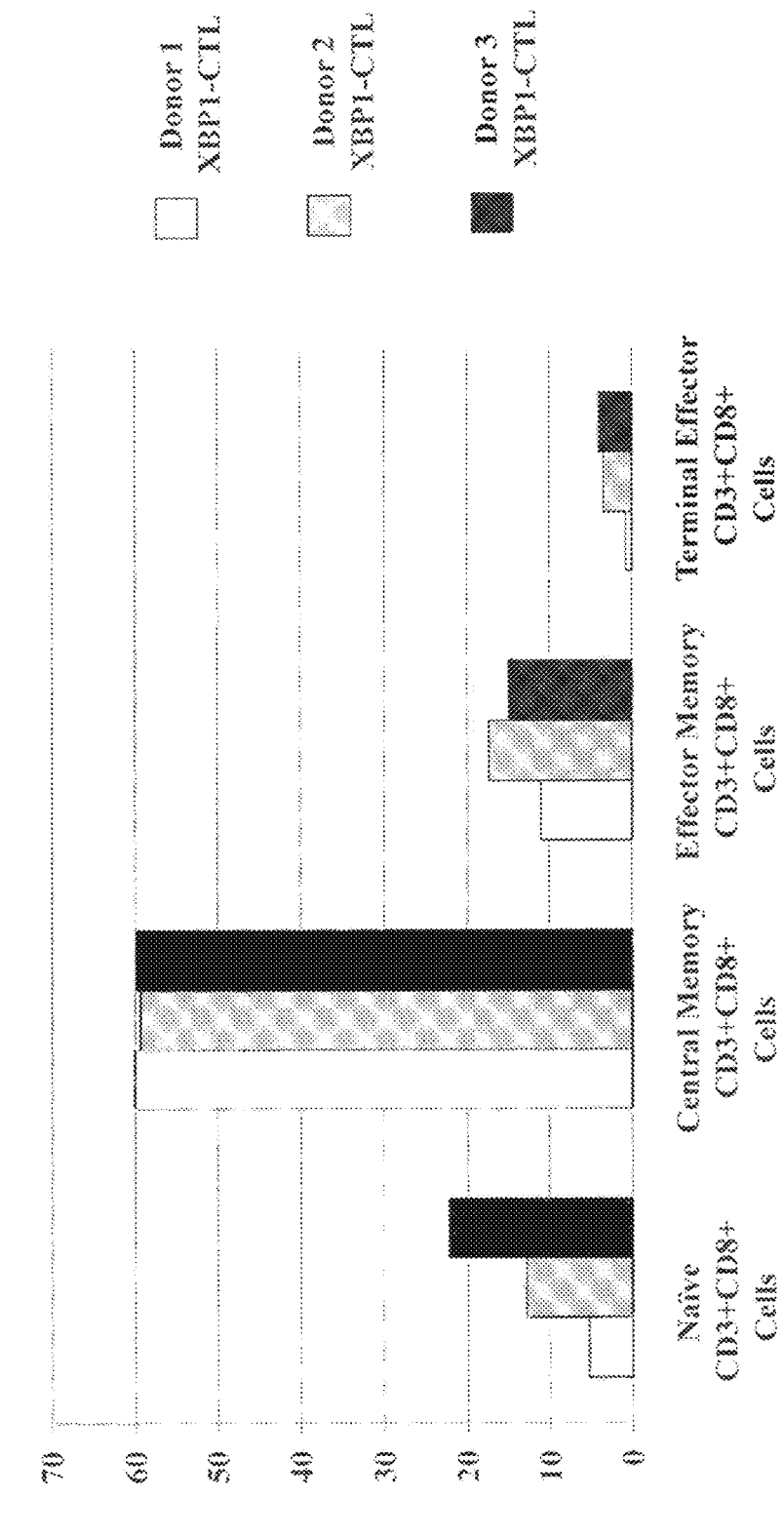

FIG. 70 depicts bar graphs showing expression of granzyme B and IFN-γ by naïve T-cells, central memory cells, effector memory cells, and effector T cells of XBP1 cocktail specific-CTL to Panc1 pancreatic cancer cells.

Figure 71:
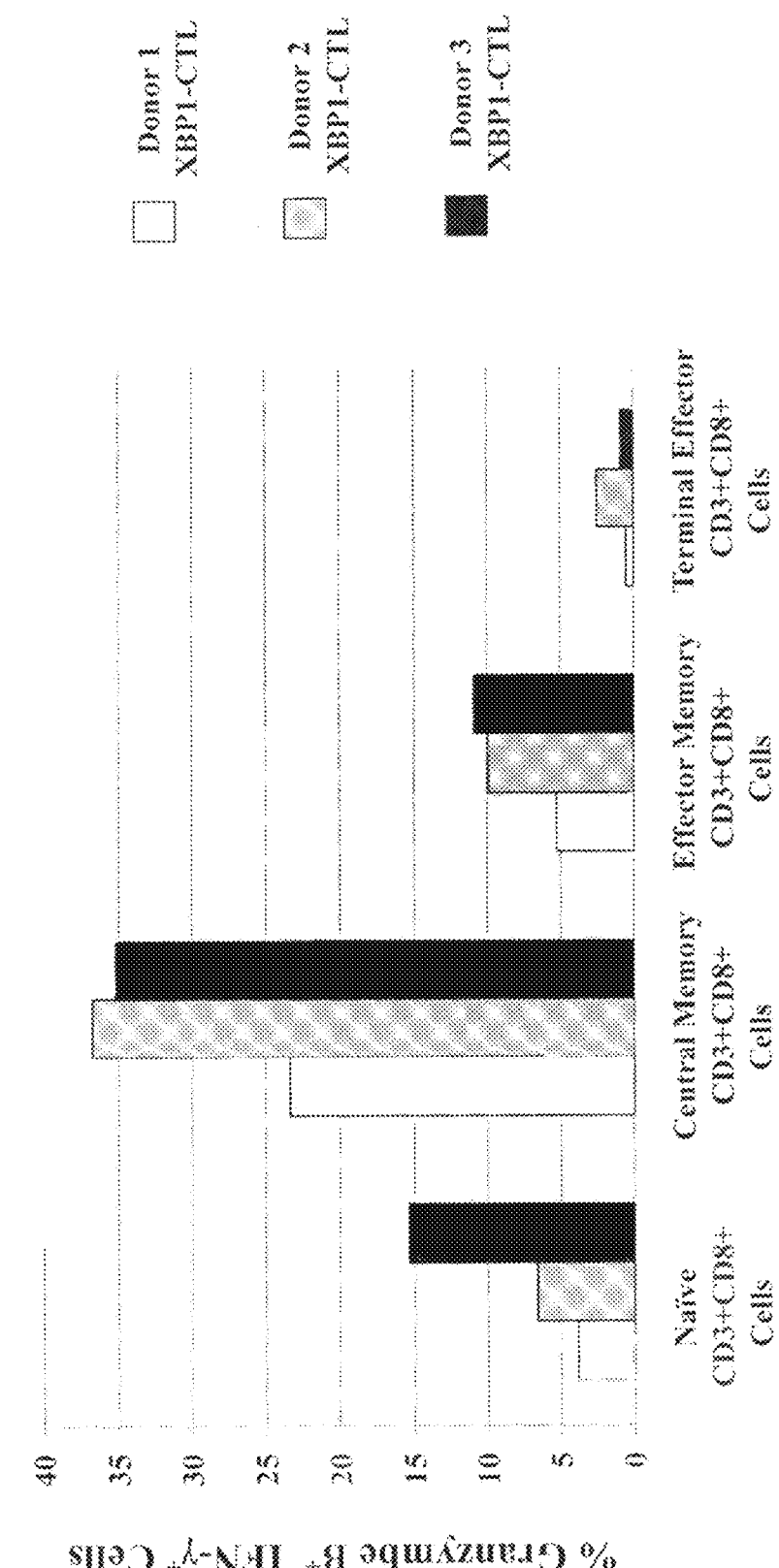

FIG. 71 depicts bar graphs showing expression of granzyme B and IFN-γ by naïve T-cells, central memory cells, effector memory cells, and effector T cells of XBP1 cocktail specific-CTL to SW480 colon cancer cells.

Figure 72:
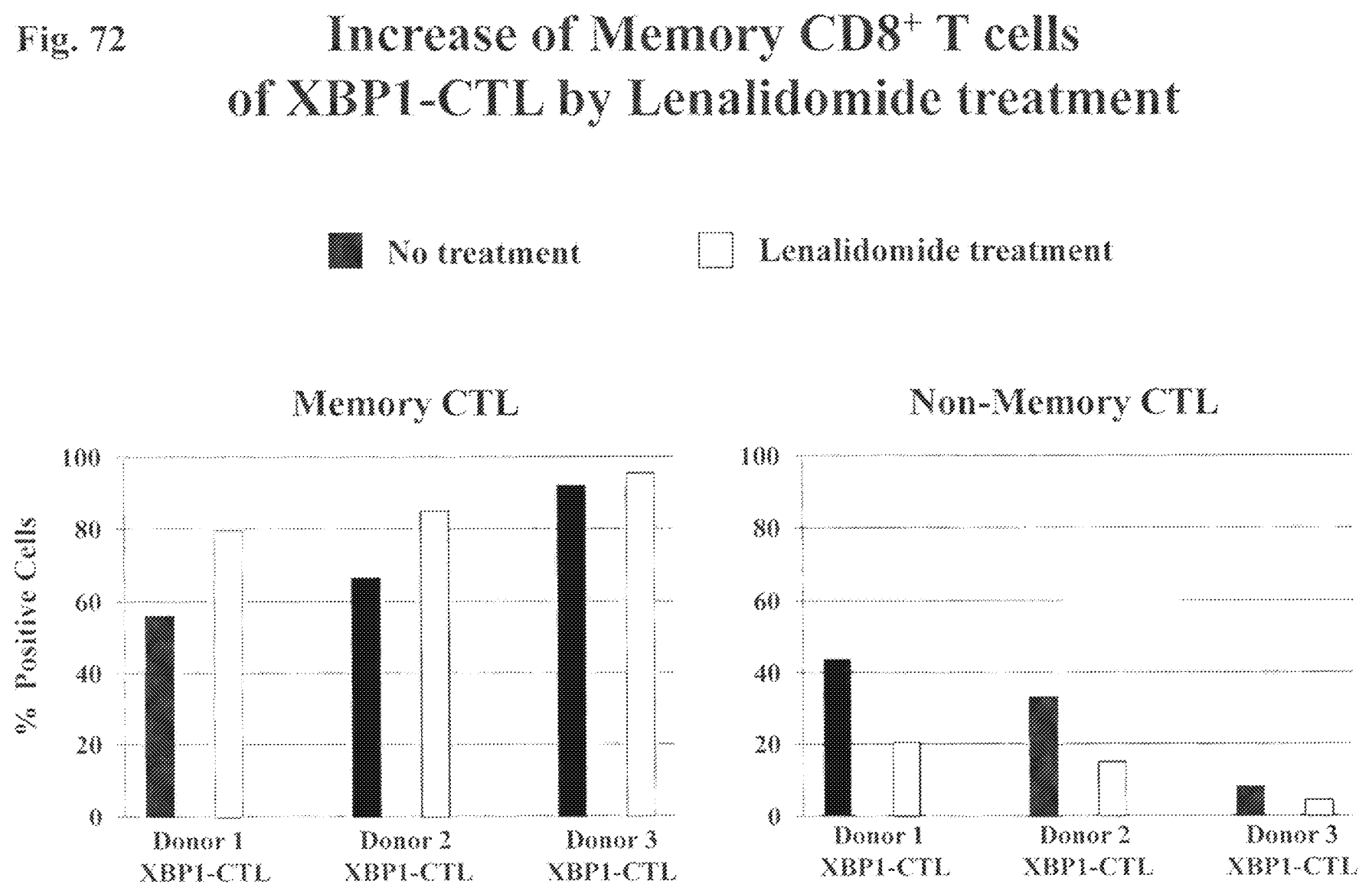

FIG. 72 depicts a bar graph showing the number of non-memory T cells and memory T cells of XBP1 cocktail specific-CTL in the presence and absence of adjuvant, lenalidomide.

Figure 73:
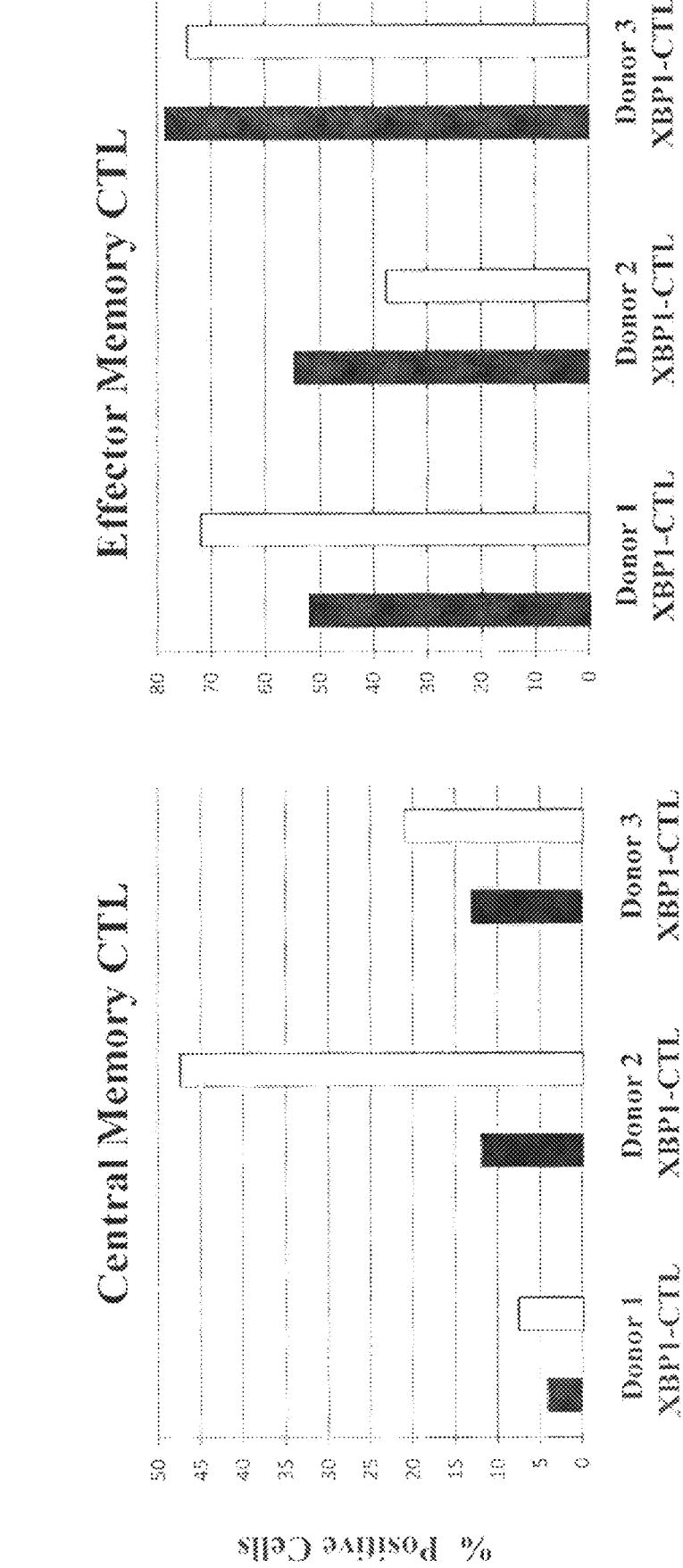

FIG. 73 depicts a bar graph showing the number of central memory T cells and effector memory T cells of XBP1 cocktail specific-CTL in the presence and absence of adjuvant, lenalidomide.

Figure 74:
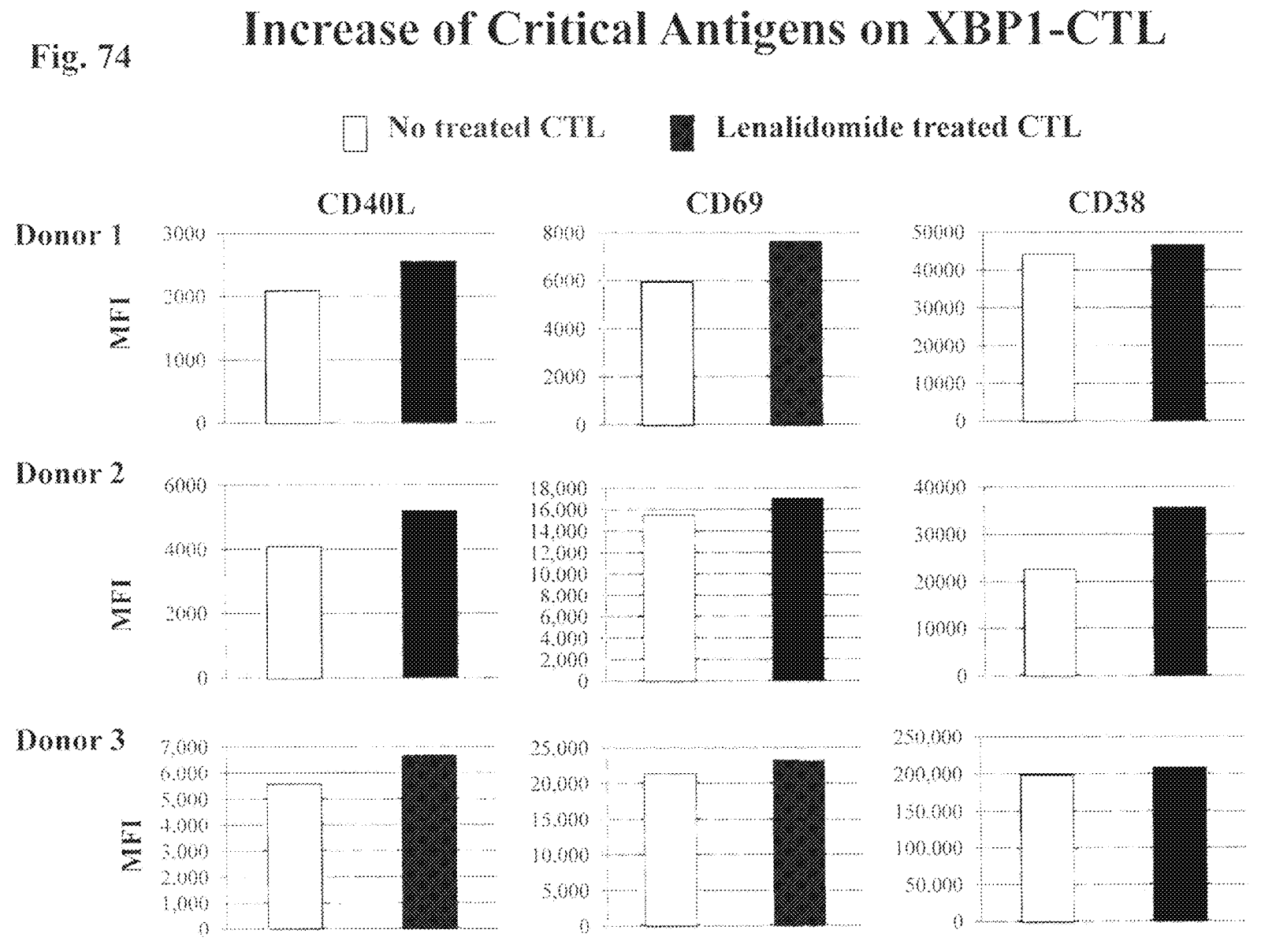

FIG. 74 depicts bar graphs showing the expression of CD40L, CD69 and CD38 in XBP1 cocktail specific-CTL in the presence and absence of adjuvant, lenalidomide.

Figure 75:
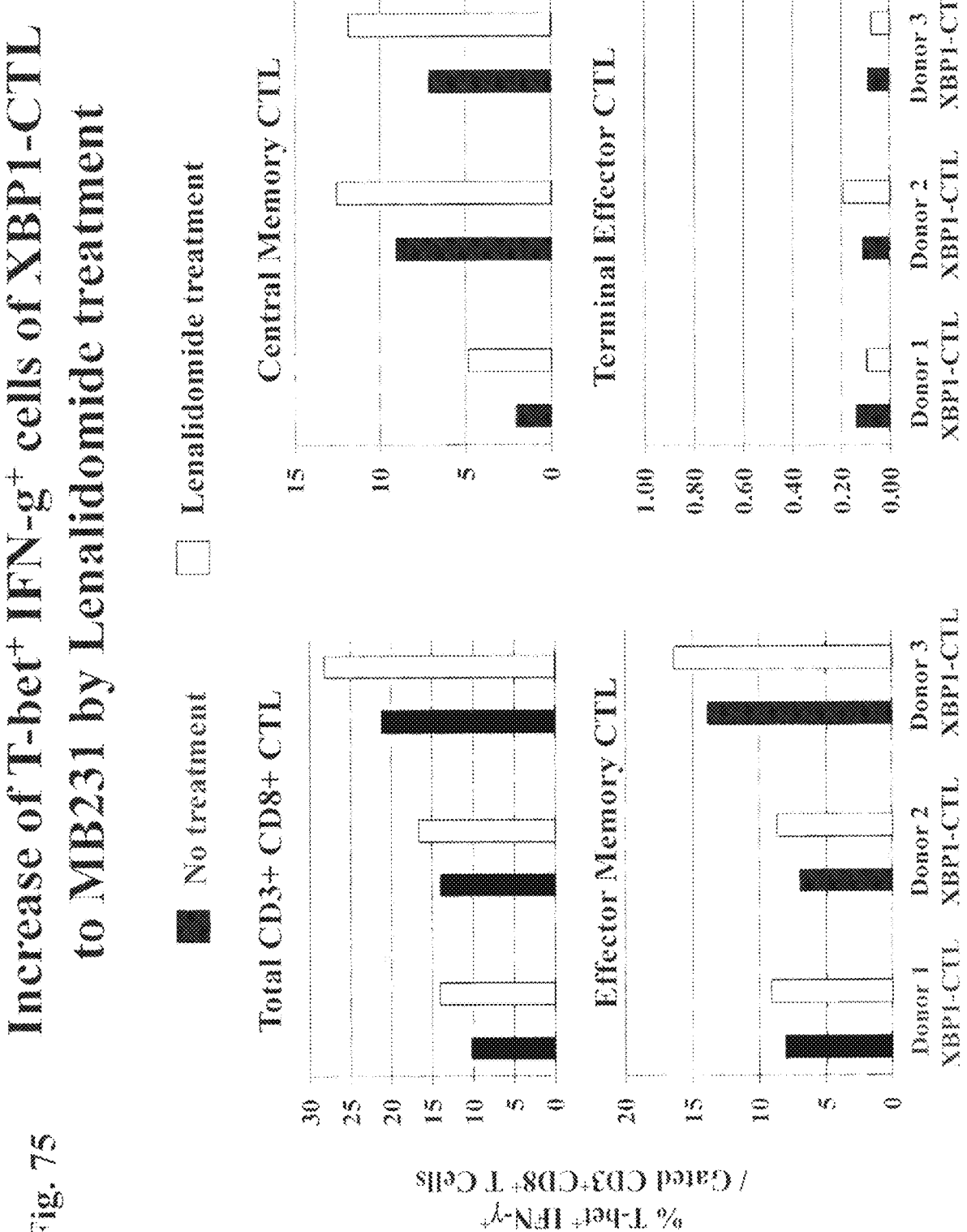

FIG. 75 depicts bar graphs showing expression of Tbet and IFN-γ by naïve T-cells, central memory cells, effector memory cells, and effector T cells of XBP1 cocktail specific-CTL to MB231 breast cancer cells in the presence or absence of adjuvant, lenalidomide.

Figure 76:
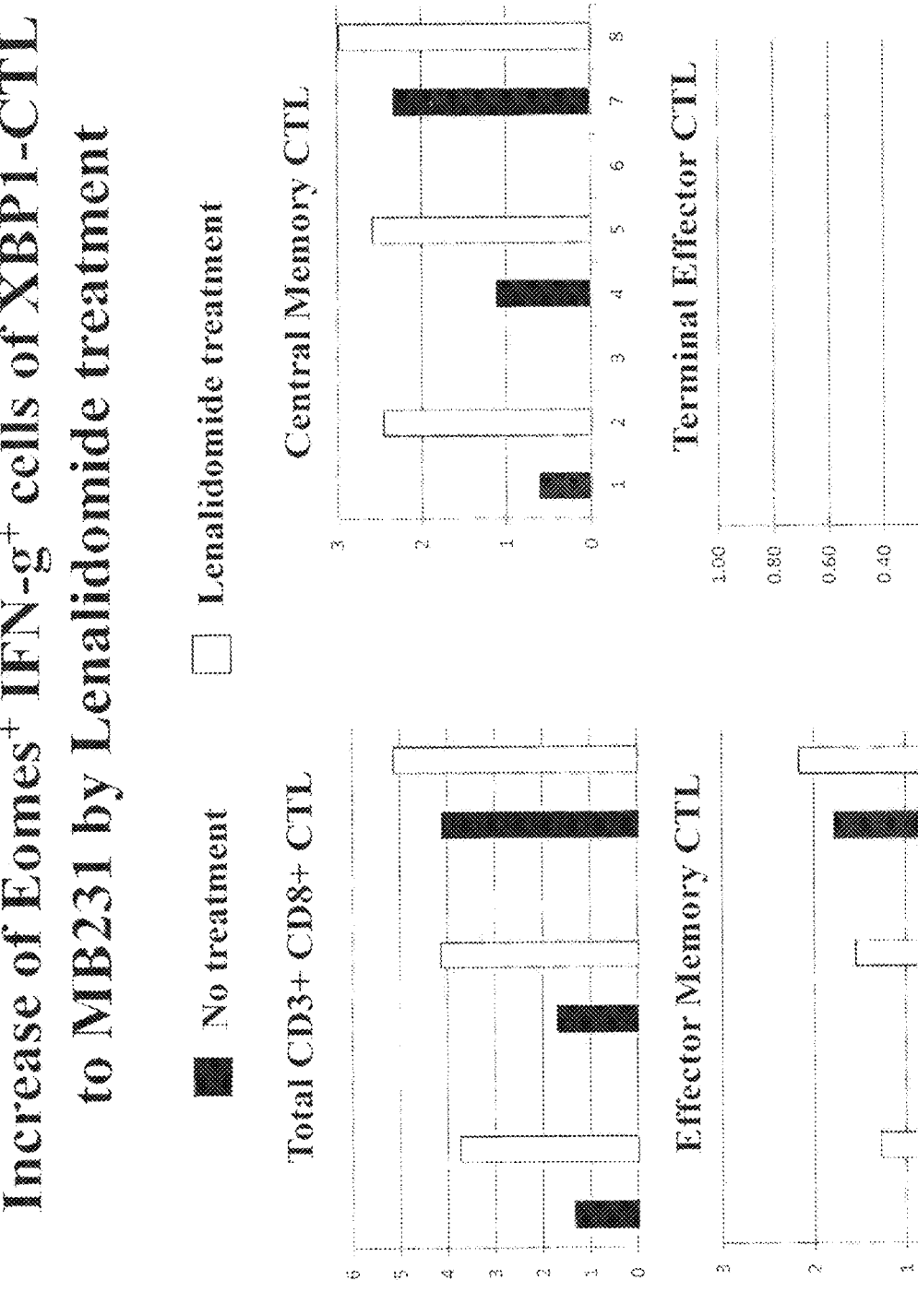

FIG. 76 depicts bar graphs showing expression of Eomes and IFN-γ by naïve T-cells, central memory cells, effector memory cells, and effector T cells of XBP1 cocktail specific-CTL to MB231 breast cancer cells in the presence or absence of adjuvant, lenalidomide.

Figure 77:
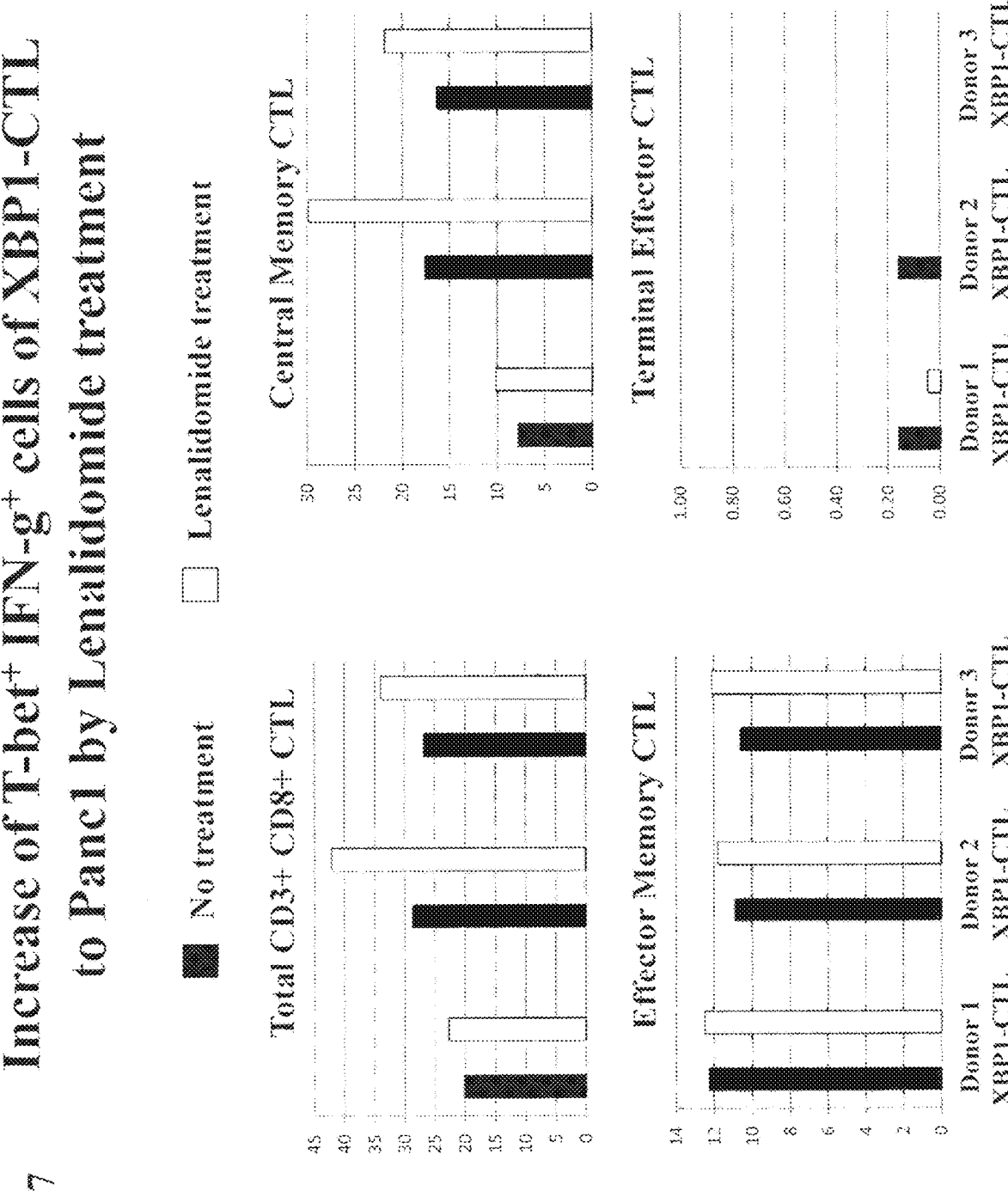

FIG. 77 depicts bar graphs showing expression of Tbet and IFN-γ by naïve T-cells, central memory cells, effector memory cells, and effector T cells of XBP1 cocktail specific- CTL to Panc1 pancreatic cancer cells in the presence or absence of adjuvant, lenalidomide.

Figure 78:
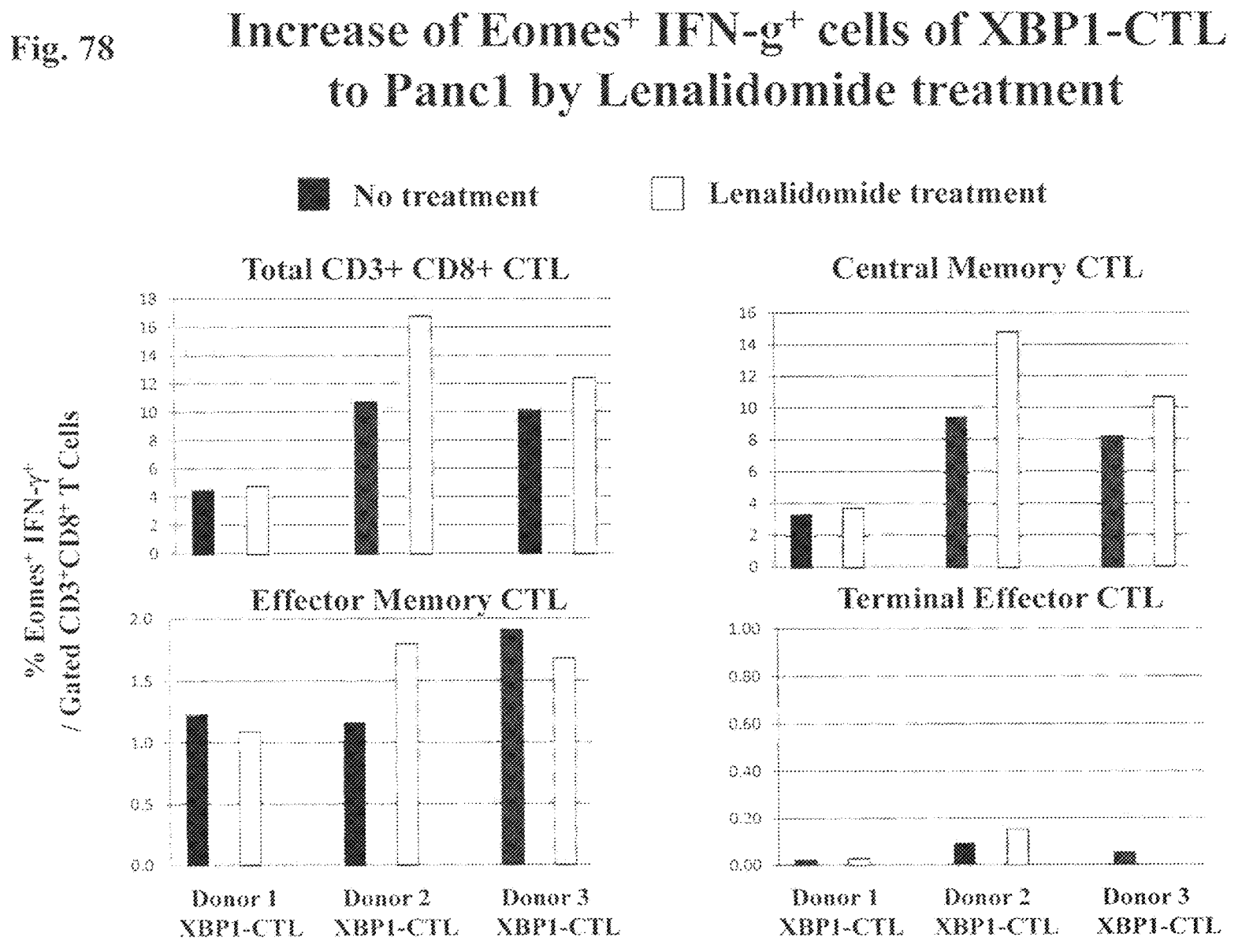

FIG. 78 depicts bar graphs showing expression of Eomes and IFN-γ by naïve T-cells, central memory cells, effector memory cells, and effector T cells of XBP1 cocktail specific-CTL to Panc1 pancreatic cancer cells in the presence or absence of adjuvant, lenalidomide.

Figure 79:
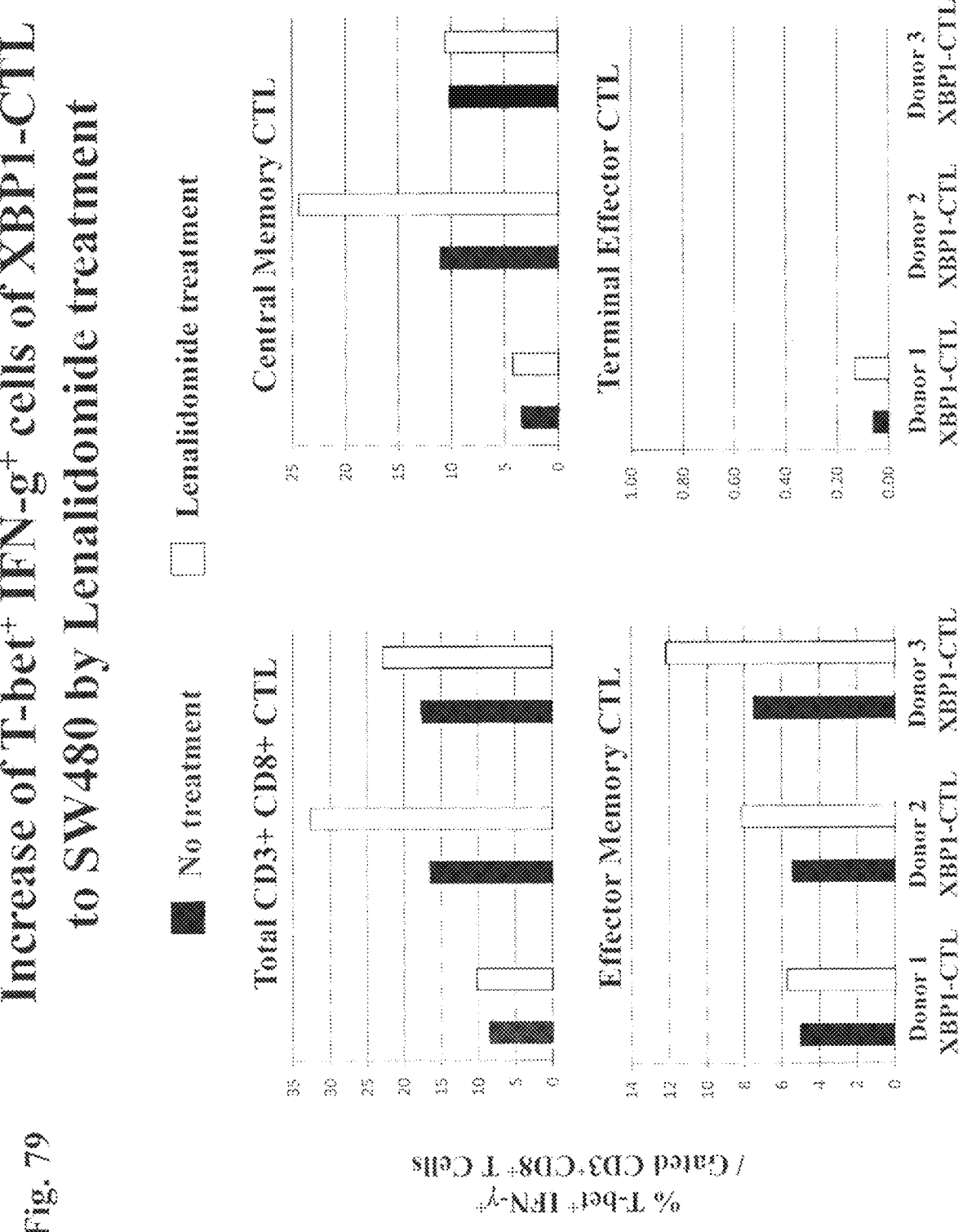

FIG. 79 depicts bar graphs showing expression of Tbet and IFN-γ by naïve T-cells, central memory cells, effector memory cells, and effector T cells of XBP1 cocktail specific-CTL to SW480 colon cancer cells in the presence or absence of adjuvant, lenalidomide.

Figure 80:
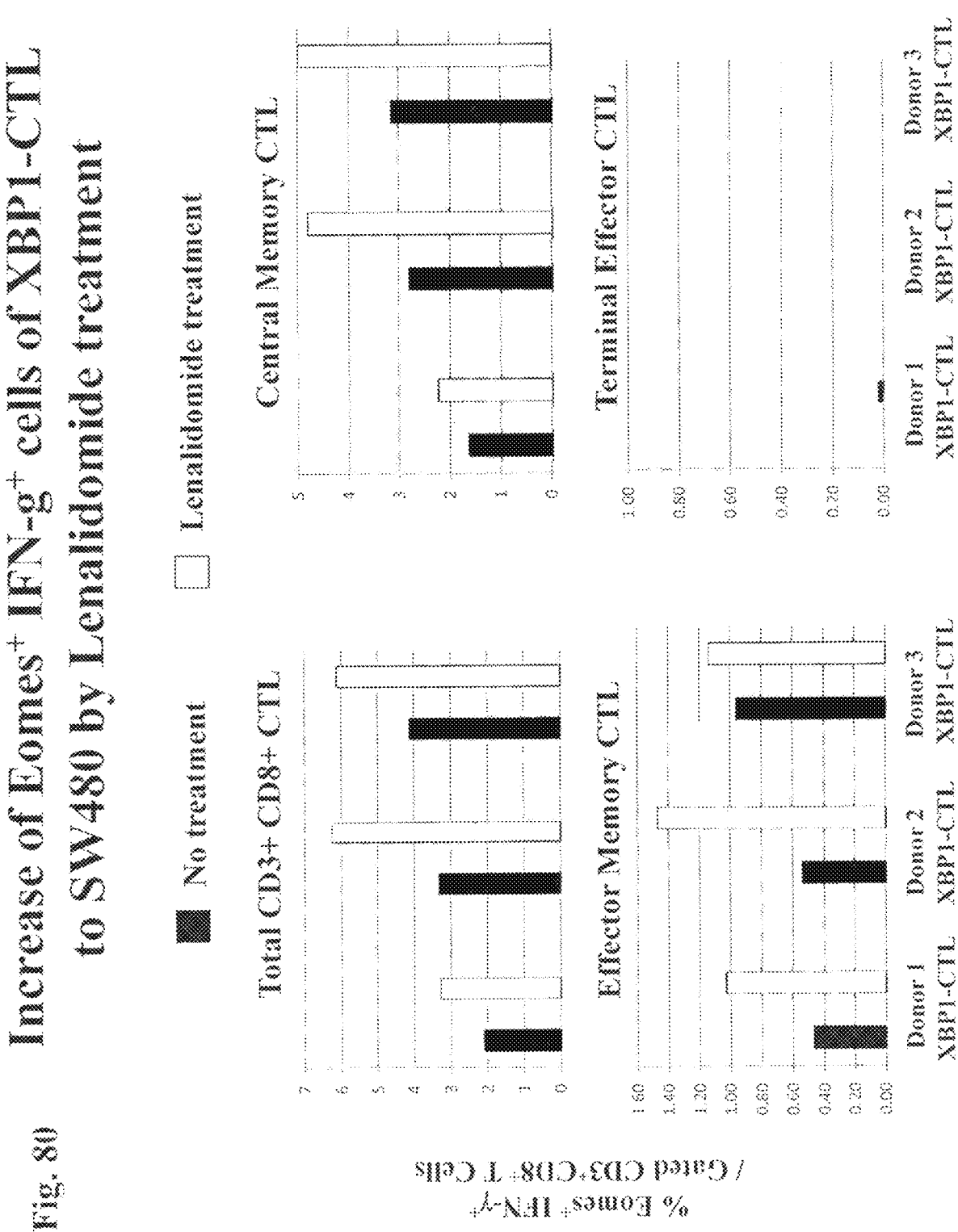

FIG. 80 depicts bar graphs showing expression of Eomes and IFN-γ by naïve T-cells, central memory cells, effector memory cells, and effector T cells of XBP1 cocktail specific-CTL to SW480 colon cancer cells in the presence or absence of adjuvant, lenalidomide.

Figure 81:
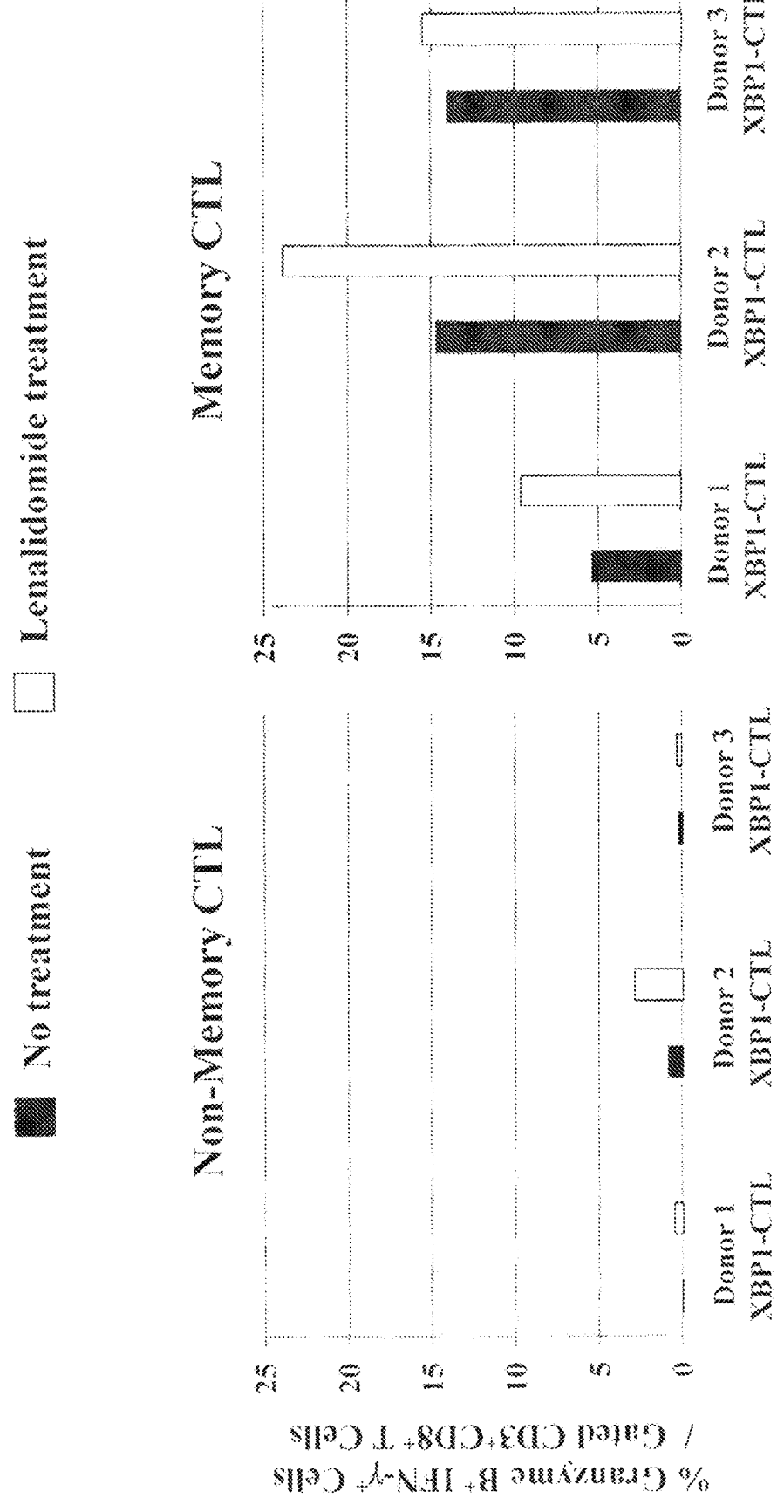

FIG. 81 depicts bar graphs showing expression of granzyme and IFN-γ by non-memory and memory T cells of XBP1 cocktail specific-CTL to MB231 breast cancer cells in the presence or absence of adjuvant, lenalidomide.

Figure 82:
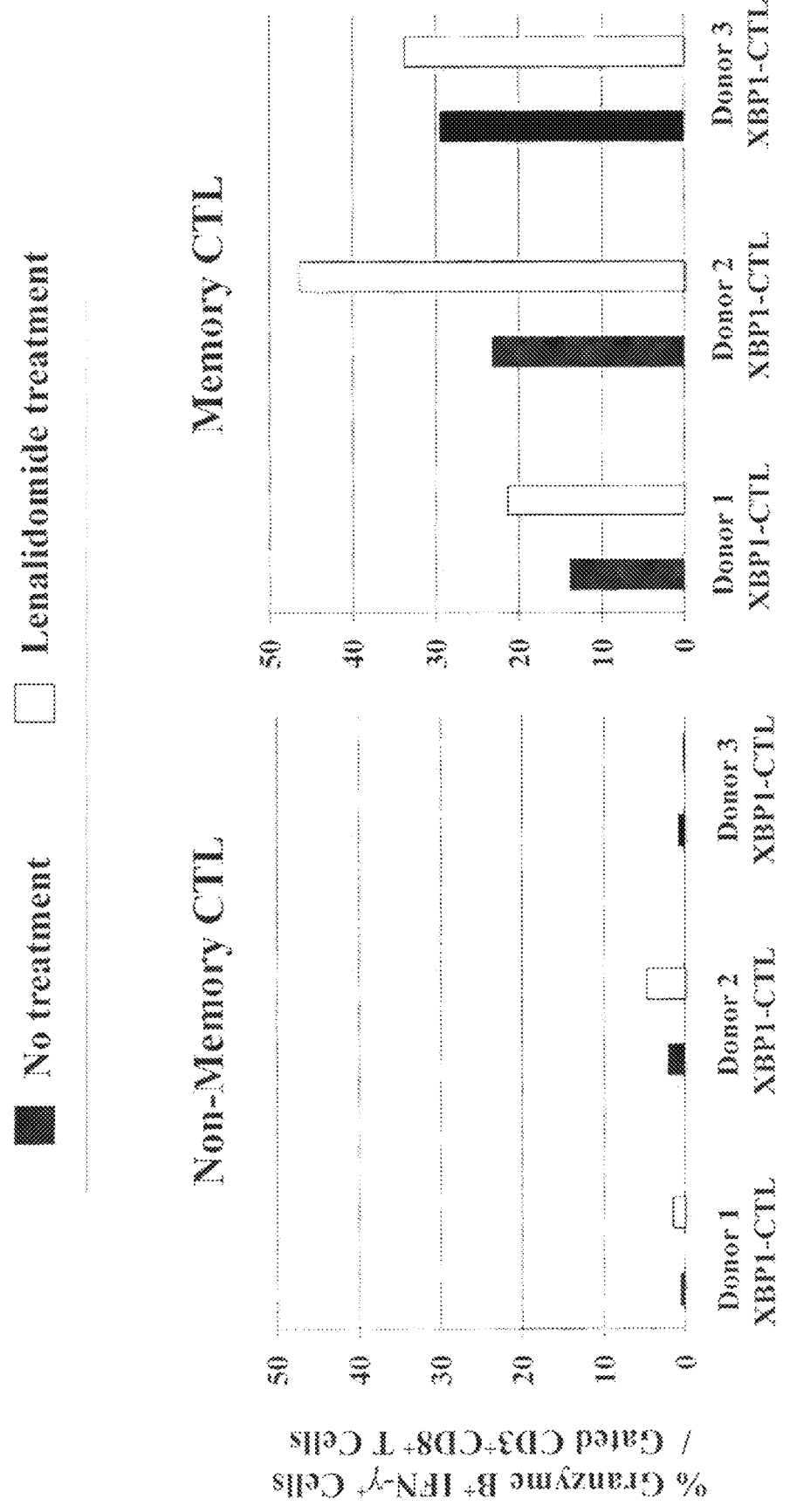

FIG. 82 depicts bar graphs showing expression of granzyme and IFN-γ by non-memory and memory T cells of XBP1 cocktail specific-CTL to Panc1 pancreatic cancer cells in the presence or absence of adjuvant, lenalidomide.

Figure 83:
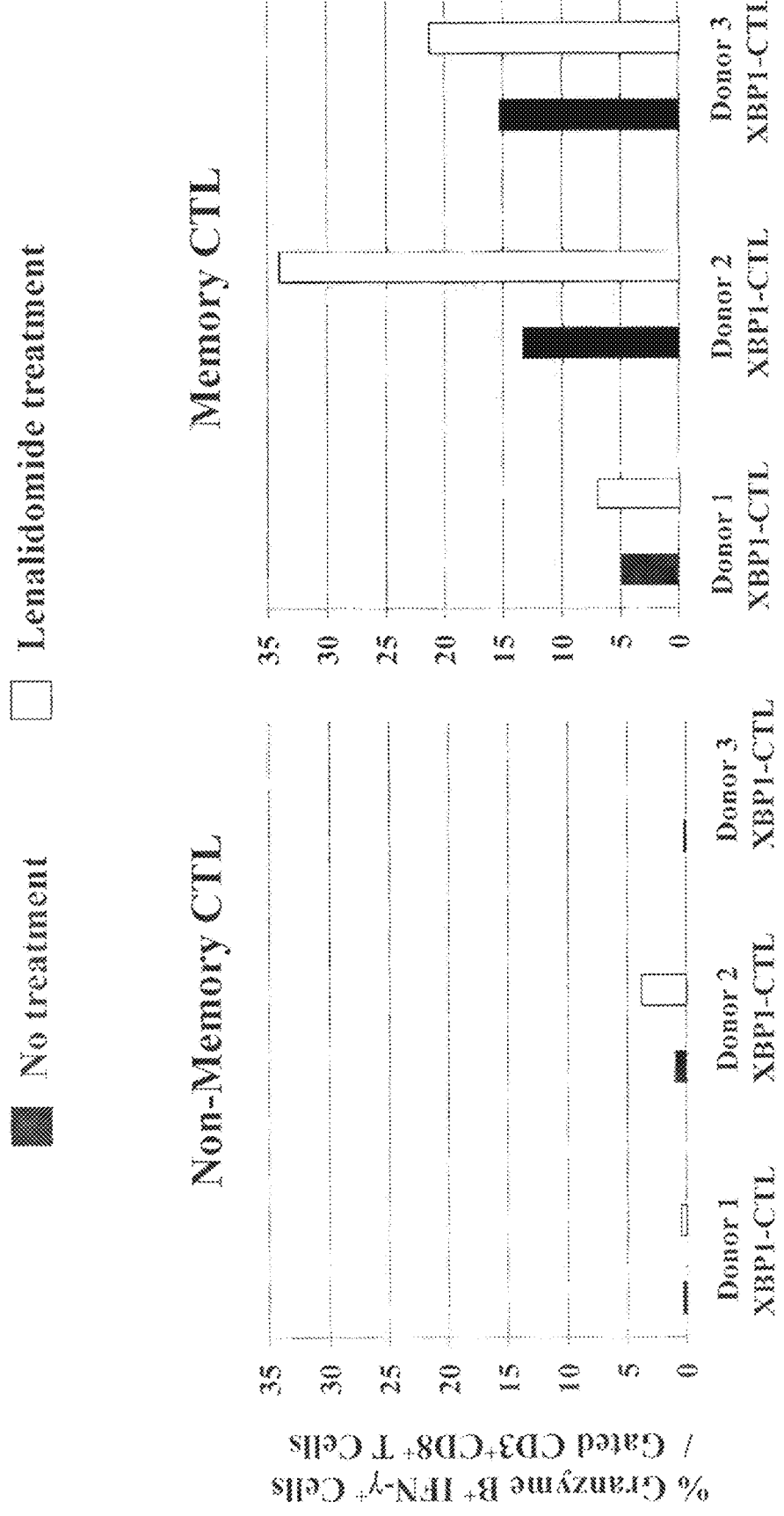

FIG. 83 depicts bar graphs showing expression of granzyme and IFN-γ by non-memory and memory T cells of XBP1 cocktail specific-CTL to SW480 colon cancer cells in the presence or absence of adjuvant, lenalidomide.

DETAILED DESCRIPTION

The disclosure features immunogenic XBP1-, CD138-, and CS-1-derived peptides (and pharmaceutical compositions thereof), which can be used to, e.g., induce an immune response (e.g., stimulate a CTL response), or stimulate the production of an antibody, in a subject. The peptides can be used in a variety of applications such as methods for inducing an immune response, methods for producing an antibody, and methods for treating a cancer (e.g., lung cancer, liver cancer, bile duct cancer, stomach cancer, cervical cancer, nasopharyngeal cancer, breast cancer, colon cancer, pancreatic cancer, prostate cancer, leukemia (e.g., AML or CML) and a plasma cell disorder such as multiple myeloma or Waldenstrom's macroglobulinemia) or a precancerous disorder (e.g., smoldering multiple myeloma)). The peptides can also be included in MHC molecule multimer compositions and used in, e.g., methods for detecting a T cell in a population of cells.

A detailed description of the peptides as well as exemplary methods for making and using the peptides are set forth below.

Peptides

Group A peptides. The disclosure features isolated peptides ("Group A peptides") comprising an amino acid sequence that has sufficient identity with or is identical to any one of SEQ ID NOS:1-18 as depicted in Table 1.

TABLE 1

Examples of Group A peptides

| Protein of Origin | Amino Acid Position | Amino Acid Sequence | SEQ ID NO: |
|---|---|---|---|
| non-spliced XBP1 | 118-126 | LLREKTHGL | 1 |
| non-spliced XBP1 | 185-193 | NISPWILAV | 2 |

TABLE 1-continued

Examples of Group A peptides

| Protein of Origin | Amino Acid Position | Amino Acid Sequence | SEQ ID NO: |
|---|---|---|---|
| non-spliced XBP1 | 190-198 | ILAVLTLQI | 3 |
| non-spliced XBP1 | 193-201 | VLTLQIQSL | 4 |
| non-spliced XBP1 | 111-119 | KLLLENQLL | 5 |
| non-spliced XBP1 | 185-193 | YISPWILAV | 6 |
| spliced XBP1 | 197-205 | GILDNLDPV | 7 |
| spliced XBP1 | 194-202 | ILLGILDNL | 8 |
| spliced XBP1 | 368-376 | ELFPQLISV | 9 |
| spliced XBP1 | 368-376 | YLFPQLISV | 10 |
| CD138 | 256-264 | VIAGGLVGL | 11 |
| CD138 | 260-268 | GLVGLIFAV | 12 |
| CD138 | 5-13 | ALWLWLCAL | 13 |
| CD138 | 7-15 | WLWLCALAL | 14 |
| CS1 | 236-245 | LLLSLFVLGL | 15 |
| CS1 | 239-247 | SLFVLGLFL | 16 |
| CS1 | 232-240 | LLVPLLLSL | 17 |
| CS1 | 9-17 | TLIYILWQL | 18 |

Bolded residues indicate amino acid changes from the corresponding wild-type amino acid sequence.

Preferably, the isolated peptide from Group A is at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprises an amino acid sequence that is at least 70%, 75%, 80%, 85%, 90%, 95%, 96%, 97%, 98%, 99% identity or is identical to an amino acid sequence of SEQ ID NOS:1-18. Other preferred peptides can be at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprise an amino acid sequence of SEQ ID NOS:1-18, or an amino acid sequence with one, two, three or four substitutions of the amino acid sequence of SEQ ID NOs:1-18 The substitution can be a conservative or nonconservative substitution.

"Non-spliced XBP1" peptides from Group A include those peptides depicted in Table 1 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the non-spliced form of human XBP1 protein having 261 amino acids and the following sequence: MVVVAAAPNPADGTPKVLLLSGQPASAAGAPAGQ-ALPLMVPAQRGASPEAASGGLPQ ARKRQRLTHL-SPEEKALRRKLKNRVAAQTARDRKKARMSELEQ-QVVDLEEENQKLLLE NQLLREKTHGLVVENQELR-QRLGMDALVAEEEAEAKGNEVRPVAGSAESAALRL-RAPL QQVQAQLSPLQNISPWILAVLTLQIQSLIS-CWAFWTTWTQSCSSNALPQSLPAWRSSQRS TQKDPVPYQPPFLCQWGRHQPSWKPLMN (SEQ ID NO:19; Genbank Accession No. NP_005071), and peptides having no more than one, two, three, four, five substitutions (e.g., conservative substitutions) of the amino acids derived from the amino acid sequence of SEQ ID NO:19. The amino acid positions referred to in Table 1 are based on SEQ ID NO: 19.

"Spliced XBP1" peptides from Group A include those peptides depicted in Table 1 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 31, 32, 33, 34 or 35) consecutive amino acids from the spliced form of human XBP1 (XBP1 spliced) protein having 376 amino acids and the following sequence: MVVVAAAPNPADGTPKVLLLSGQPASAAGAPAGQ-ALPLMVPAQRGASPEAASGGLPQ ARKRQRLTHL-SPEEKALRRKLKNRVAAQTARDRKKARMSELEQ-QVVDLEEENQKLLLE NQLLREKTHGLVVENQELRQ-RLGMDALVAEEEAEAKGNEVRPVAGSAESAAGA-GPVV TPPEHLPMDSGGIDSSDSESDILLGILDNLD-PVMFFKCPSPEPASLEELPEVYPEGPSSLPA SLSLSV-GTSSAKLEAINELIRFDHIYTKPLVLEIPSETESQAN-VVVKIEEAPLSPSENDHPEF IVSVKEEPVEDDLVPEL-GISNLLSSSHCPKPSSCLLDAYSDCGYGGSLSPFS-DMSSLLGVN HSWEDTFANELFPQLISV (SEQ ID NO: 20; Genbank Accession No. NP_001073007), and peptides having no more than one, two, three, four, five substitutions (e.g., conservative substitutions) of the amino acids derived from the amino acid sequence of SEQ ID NO:20. The amino acid positions referred to in Table 1 are based on SEQ ID NO: 20.

"CD138" peptides from Group A include those peptides depicted in Table 1 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CD138 protein having 310 amino acids and the following sequence: MRRAALWLWLCALALSLQP-ALPQIVATNLPPEDQDGSGDDSDNFSGSGAG-ALQDITLS QQTPSTWKDTQLLTAIPTSPEPTGLEA-TAASTSTLPAGEGPKEGEAVVLPEVEPGLTARE QEAT-PRPRETTQLPTTHQASTTTATTAQEPATSHPHRD-MQPGHHETSTPAGPSQADLHTP HTEDGGPSATER-AAEDGASSQLPAAEGSGEQDFTFETSGENTAVVAVE-PDRRNQSPVDQ GATGASQGLLDRKEVLGGVIAG-GLVGLIFAVCLVGFMLYRMKKKDEGSYSLEEPKQAN GGAYQKPTKQEEFYA (SEQ ID NO:21; Genbank Accession No. NP_002988) and peptides having no more than one, two, three, four, five substitutions (e.g., conservative substitutions) of the amino acids derived from the amino acid sequence of SEQ ID NO:21. The amino acid positions referred to in Table 1 are based on SEQ ID NO: 21.

"CS-1" peptides from Group A include those peptides depicted in Table 1 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CS-1 protein having 335 amino acids and the following sequence: MAGSPTCLTLIYILWQLTGSAA-SGPVKELVGSVGGAVTFPLKSKVKQVDSIVWTFN-TTP LVTIQPEGGTIIVTQNRNRERVDFPDGGYSLKL-SKLKKNDSGIYYVGIYSSSLQQPSTQEY VLHVYEHL-SKPKVTMGLQSNKNGTCVTNLTCCMEHGEED-VIYTWKALGQAANESHNG SILPISWRWGESDMTF-ICVARNPVSRNFSSPILARKLCEGAADDPDSSMV-LLCLLLVPLLL SLFVLGLFLWFLKRERQEEYIEEKK-RVDICRETPNICPHSGENTEYDTIPHTNRTILKEDPA NTVYSTVEIPKKMENPHSLLTMPDTPRLFAYENVI (SEQ ID NO:22; Genbank Accession No. NP_067004) and peptides having no more than one, two, three, four, five substitutions (e.g., conservative substitutions) of the amino acids derived from the amino acid sequence of SEQ ID NO:22. The amino acid positions referred to in Table 1 are based on SEQ ID NO: 22.

Group B peptides. The disclosure also features isolated peptides ("Group B peptides") comprising an amino acid sequence that has sufficient identity with or is identical to any one of SEQ ID NOS:29-50 as depicted in Table 2.

TABLE 2

| Examples of Group B peptides | | | |
|---|---|---|---|
| Protein of Origin | Amino Acid Position | Amino Acid Sequence | SEQ ID NO: |
| non-spliced XBP1 | 188-196 | PWILAVLTL | 33 |
| non-spliced XBP1 | 111-119 | KLLLENQLL | 5 |
| non-spliced XBP1 | 129-137 | ENQELRQRL | 34 |
| non-spliced XBP1 | 12-20 | DGTPKVLLL | 35 |
| non-spliced XBP1 | 104-112 | DLEEENQKL | 36 |
| non-spliced XBP1 | 216-224 | SSNALPQSL | 37 |
| non-spliced XBP1 | 186-194 | ISPWILAVL | 29 |
| spliced XBP1 | 224-232 | VYPEGPSSL | 30 |
| spliced XBP1 | 340-348 | GYGGSLSPF | 38 |
| spliced XBP1 | 347-355 | PFSDMSSLL | 39 |
| spliced XBP1 | 111-119 | KLLLENQLL | 5 |
| CD138 | 265-273 | IFAVCLVGF | 31 |
| CD138 | 106-114 | VLPEVEPGL | 40 |
| CD138 | 21-29 | LPQIVATNL | 41 |
| CD138 | 13-21 | LALSLQPAL | 42 |
| CD138 | 245-253 | GLLDRKEVL | 43 |
| CD138 | 262-270 | VGLIFAVCL | 44 |
| CD138 | 16-24 | SLQPALPQI | 45 |
| CS1 | 87-95 | GYSLKLSKL | 46 |
| CS1 | 82-90 | DFPDGGYSL | 47 |
| CS1 | 321-329 | TMPDTPRLF | 48 |
| CS1 | 185-193 | RWGESDMTF | 49 |
| CS1 | 240-248 | LFVLGLFLW | 32 |
| CS1 | 312-320 | KMENPHSLL | 50 |

Preferably, the isolated peptide from Group B is at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprises an amino acid sequence that is at least 70%, 75%, 80%, 85%, 90%, 95%, 96%, 97%, 98%, 99% identity or is identical to an amino acid sequence of SEQ ID NOS:29-50. Other preferred peptides can be at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprise an amino acid sequence of SEQ ID NOS:29-50, or an amino acid sequence with one, two, three or four substitutions of the amino acid sequence of SEQ ID NOs: 29-50. The substitution can be a conservative or nonconservative substitution.

"Non-spliced XBP1" peptides from Group B include those peptides depicted in Table 2 and refer to a peptide having an amino acid sequence of at least 5 (e.g., 5, 6, 7, 8, 9, 10, 11, or 12) consecutive amino acids from the non-spliced form of human XBP1 protein having 261 amino acids and the amino acid sequence of SEQ ID NO:19, and peptides having no more than one, two, three, four, five substitutions (e.g., conservative substitutions) of the amino acids derived from the amino acid sequence of SEQ ID NO:19. Non-spliced XBP1 peptides from Group B include peptides having an amino acid sequence from SEQ ID NO: 19 that comprises part or all of any one of SEQ ID NOS: 29 and 33-37, e.g., a sequence that comprises 1, 2, 3, 4, 5, 6, 7, 8, 9, 10, 11, 12, 13, 14, 15, 16, 17, 18, 19, or 20 amino acids N-terminal and/or C-terminal to any one of SEQ ID NOS: 29 and 33-37. The amino acid positions referred to in Table 2 are based SEQ ID NO: 19.

"Spliced XBP1" peptides from Group B include those peptides depicted in Table 2 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 31, 32, 33, 34 or 35) consecutive amino acids from the spliced form of human XBP1 (XBP1 spliced) protein having 376 amino acids and amino acid sequence of SEQ ID NO: 20, and peptides having no more than one, two, three, four, five substitutions (e.g., conservative substitutions) of the amino acids derived from the amino acid sequence of SEQ ID NO:20. Spliced XBP1 peptides from Group B include peptides having an amino acid sequence from SEQ ID NO: 20 that comprises part or all of any one of SEQ ID NOS: 30, 38 and 39, e.g., a sequence that comprises 1, 2, 3, 4, 5, 6, 7, 8, 9, 10, 11, 12, 13, 14, 15, 16, 17, 18, 19, or 20 amino acids N-terminal and/or C-terminal to any one of SEQ ID NOS: 30, 38, and 39. The amino acid positions referred to in Table 2 are based on SEQ ID NO: 20.

"CD138" peptides from Group B include those peptides depicted in Table 2 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CD138 protein having 310 amino acids and the amino acid sequence of SEQ ID NO:21, and peptides having no more than one, two, three, four, five substitutions (e.g., conservative substitutions) of the amino acids derived from the amino acid sequence of SEQ ID NO:21. CD138 peptides from Group B include peptides having an amino acid sequence from SEQ ID NO: 21 that comprises part or all of any one of SEQ ID NOS: 31 and 40-45, e.g., a sequence that comprises 1, 2, 3, 4, 5, 6, 7, 8, 9, 10, 11, 12, 13, 14, 15, 16, 17, 18, 19, or 20 amino acids N-terminal and/or C-terminal to any one of SEQ ID NOS: 31 and 46-50. The amino acid positions referred to in Table 2 are based on SEQ ID NO: 21.

"CS-1" peptides from Group B include those peptides depicted in Table 2 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CS-1 protein having 335 amino acids and the amino acid sequence of SEQ ID NO:22, and peptides having no more than one, two, three, four, five substitutions (e.g., conservative substitutions) of the amino acids derived from the amino acid sequence of SEQ ID NO:22. CS1 peptides from Group B include peptides having an amino acid sequence from SEQ ID NO: 22 that comprises part or all of any one of SEQ ID NOS: 32 and 46-50, e.g., a sequence that comprises 1, 2, 3, 4, 5, 6, 7, 8, 9, 10, 11, 12, 13, 14, 15, 16, 17, 18, 19, or 20 amino acids N-terminal and/or C-terminal to any one of SEQ ID NOS: 32 and 46-50. The amino acid positions referred to in Table 2 are based on SEQ ID NO: 22.

Group C peptides. The disclosure features isolated peptides ("Group C peptides") comprising an amino acid sequence that has sufficient identity with or is identical to any one of SEQ ID NOS: 51-536 as depicted in Table 3.

TABLE 3

| Examples of Group C peptides | | | |
|---|---|---|---|
| Protein of Origin | Amino Acid Position | Amino Acid Sequence | SEQ ID NO |
| non-spliced XBP1 | 180-194 | LSPLQNISPWILAVL | 51 |
| non-spliced XBP1 | 180-195 | LSPLQNISPWILAVLT | 52 |
| non-spliced XBP1 | 180-196 | LSPLQNISPWILAVLTL | 53 |
| non-spliced XBP1 | 180-197 | LSPLQNISPWILAVLTLQ | 54 |
| non-spliced XBP1 | 180-198 | LSPLQNISPWILAVLTLQI | 55 |
| non-spliced XBP1 | 180-199 | LSPLQNISPWILAVLTLQIQ | 56 |
| non-spliced XBP1 | 180-200 | LSPLQNISPWILAVLTLQIQS | 57 |
| non-spliced XBP1 | 180-201 | LSPLQNISPWILAVLTLQIQSL | 58 |
| non-spliced XBP1 | 180-202 | LSPLQNISPWILAVLTLQIQSLI | 59 |
| non-spliced XBP1 | 180-203 | LSPLQNISPWILAVLTLQIQSLIS | 60 |
| non-spliced XBP1 | 180-204 | LSPLQNISPWILAVLTLQIQSLISC | 61 |
| non-spliced XBP1 | 180-205 | LSPLQNISPWILAVLTLQIQSLISCW | 62 |
| non-spliced XBP1 | 180-206 | LSPLQNISPWILAVLTLQIQSLISCWA | 63 |
| non-spliced XBP1 | 181-194 | SPLQNISPWILAVL | 64 |

TABLE 3-continued

| Examples of Group C peptides | | | |
| Protein of Origin | Amino Acid Position | Amino Acid Sequence | SEQ ID NO |
| --- | --- | --- | --- |
| non-spliced XBP1 | 181-195 | SPLQNISPWILAVLT | 65 |
| non-spliced XBP1 | 181-196 | SPLQNISPWILAVLTL | 66 |
| non-spliced XBP1 | 181-197 | SPLQNISPWILAVLTLQ | 67 |
| non-spliced XBP1 | 181-198 | SPLQNISPWILAVLTLQI | 68 |
| non-spliced XBP1 | 181-199 | SPLQNISPWILAVLTLQIQ | 69 |
| non-spliced XBP1 | 181-200 | SPLQNISPWILAVLTLQIQS | 70 |
| non-spliced XBP1 | 181-201 | SPLQNISPWILAVLTLQIQSL | 71 |
| non-spliced XBP1 | 181-202 | SPLQNISPWILAVLTLQIQSLI | 72 |
| non-spliced XBP1 | 181-203 | SPLQNISPWILAVLTLQIQSLIS | 73 |
| non-spliced XBP1 | 181-204 | SPLQNISPWILAVLTLQIQSLISC | 74 |
| non-spliced XBP1 | 181-205 | SPLQNISPWILAVLTLQIQSLISCW | 75 |
| non-spliced XBP1 | 181-206 | SPLQNISPWILAVLTLQIQSLISCWA | 76 |
| non-spliced XBP1 | 182-194 | PLQNISPWILAVL | 77 |
| non-spliced XBP1 | 182-195 | PLQNISPWILAVLT | 78 |
| non-spliced XBP1 | 182-196 | PLQNISPWILAVLTL | 79 |
| non-spliced XBP1 | 182-197 | PLQNISPWILAVLTLQ | 80 |
| non-spliced XBP1 | 182-198 | PLQNISPWILAVLTLQI | 81 |
| non-spliced XBP1 | 182-199 | PLQNISPWILAVLTLQIQ | 82 |
| non-spliced XBP1 | 182-200 | PLQNISPWILAVLTLQIQS | 83 |
| non-spliced XBP1 | 182-201 | PLQNISPWILAVLTLQIQSL | 84 |
| non-spliced XBP1 | 182-202 | PLQNISPWILAVLTLQIQSLI | 85 |
| non-spliced XBP1 | 182-203 | PLQNISPWILAVLTLQIQSLIS | 86 |
| non-spliced XBP1 | 182-204 | PLQNISPWILAVLTLQIQSLISC | 87 |
| non-spliced XBP1 | 182-205 | PLQNISPWILAVLTLQIQSLISCW | 88 |
| non-spliced XBP1 | 182-206 | PLQNISPWILAVLTLQIQSLISCWA | 89 |
| non-spliced XBP1 | 183-194 | LQNISPWILAVL | 90 |
| non-spliced XBP1 | 183-195 | LQNISPWILAVLT | 91 |
| non-spliced XBP1 | 183-196 | LQNISPWILAVLTL | 92 |
| non-spliced XBP1 | 183-197 | LQNISPWILAVLTLQ | 93 |
| non-spliced XBP1 | 183-198 | LQNISPWILAVLTLQI | 94 |
| non-spliced XBP1 | 183-199 | LQNISPWILAVLTLQIQ | 95 |
| non-spliced XBP1 | 183-200 | LQNISPWILAVLTLQIQS | 96 |
| non-spliced XBP1 | 183-201 | LQNISPWILAVLTLQIQSL | 97 |
| non-spliced XBP1 | 183-202 | LQNISPWILAVLTLQIQSLI | 98 |
| non-spliced XBP1 | 183-203 | LQNISPWILAVLTLQIQSLIS | 99 |
| non-spliced XBP1 | 183-204 | LQNISPWILAVLTLQIQSLISC | 100 |
| non-spliced XBP1 | 183-205 | LQNISPWILAVLTLQIQSLISCW | 101 |
| non-spliced XBP1 | 183-206 | LQNISPWILAVLTLQIQSLISCWA | 102 |

TABLE 3-continued

Examples of Group C peptides

| Protein of Origin | Amino Acid Position | Amino Acid Sequence | SEQ ID NO |
|---|---|---|---|
| non-spliced XBP1 | 184-194 | QNISPWILAVL | 103 |
| non-spliced XBP1 | 184-195 | QNISPWILAVLT | 104 |
| non-spliced XBP1 | 184-196 | QNISPWILAVLTL | 105 |
| non-spliced XBP1 | 184-197 | QNISPWILAVLTLQ | 106 |
| non-spliced XBP1 | 184-198 | QNISPWILAVLTLQI | 107 |
| non-spliced XBP1 | 184-199 | QNISPWILAVLTLQIQ | 108 |
| non-spliced XBP1 | 184-200 | QNISPWILAVLTLQIQS | 109 |
| non-spliced XBP1 | 184-201 | QNISPWILAVLTLQIQSL | 110 |
| non-spliced XBP1 | 184-202 | QNISPWILAVLTLQIQSLI | 111 |
| non-spliced XBP1 | 184-203 | QNISPWILAVLTLQIQSLIS | 112 |
| non-spliced XBP1 | 184-204 | QNISPWILAVLTLQIQSLISC | 113 |
| non-spliced XBP1 | 184-205 | QNISPWILAVLTLQIQSLISCW | 114 |
| non-spliced XBP1 | 184-206 | QNISPWILAVLTLQIQSLISCWA | 115 |
| non-spliced XBP1 | 185-194 | NISPWILAVL | 116 |
| non-spliced XBP1 | 185-195 | NISPWILAVLT | 117 |
| non-spliced XBP1 | 185-196 | NISPWILAVLTL | 118 |
| non-spliced XBP1 | 185-197 | NISPWILAVLTLQ | 119 |
| non-spliced XBP1 | 185-198 | NISPWILAVLTLQI | 120 |
| non-spliced XBP1 | 185-199 | NISPWILAVLTLQIQ | 121 |
| non-spliced XBP1 | 185-200 | NISPWILAVLTLQIQS | 122 |
| non-spliced XBP1 | 185-201 | NISPWILAVLTLQIQSL | 123 |
| non-spliced XBP1 | 185-202 | NISPWILAVLTLQIQSLI | 124 |
| non-spliced XBP1 | 185-203 | NISPWILAVLTLQIQSLIS | 125 |
| non-spliced XBP1 | 185-204 | NISPWILAVLTLQIQSLISC | 126 |
| non-spliced XBP1 | 185-205 | NISPWILAVLTLQIQSLISCW | 127 |
| non-spliced XBP1 | 185-206 | NISPWILAVLTLQIQSLISCWA | 128 |
| non-spliced XBP1 | 185-194 | YISPWILAVL | 129 |
| non-spliced XBP1 | 185-195 | YISPWILAVLT | 130 |
| non-spliced XBP1 | 185-196 | YISPWILAVLTL | 131 |
| non-spliced XBP1 | 185-197 | YISPWILAVLTLQ | 132 |
| non-spliced XBP1 | 185-198 | YISPWILAVLTLQI | 133 |
| non-spliced XBP1 | 185-199 | YISPWILAVLTLQIQ | 134 |
| non-spliced XBP1 | 185-200 | YISPWILAVLTLQIQS | 135 |
| non-spliced XBP1 | 185-201 | YISPWILAVLTLQIQSL | 136 |
| non-spliced XBP1 | 185-202 | YISPWILAVLTLQIQSLI | 137 |
| non-spliced XBP1 | 185-203 | YISPWILAVLTLQIQSLIS | 138 |
| non-spliced XBP1 | 185-204 | YISPWILAVLTLQIQSLISC | 139 |
| non-spliced XBP1 | 185-205 | YISPWILAVLTLQIQSLISCW | 140 |

TABLE 3-continued

| Examples of Group C peptides | | | |
|---|---|---|---|
| Protein of Origin | Amino Acid Position | Amino Acid Sequence | SEQ ID NO |
| non-spliced XBP1 | 185-206 | YISPWILAVLTLQIQSLISCWA | 141 |
| non-spliced XBP1 | 186-194 | ISPWILAVL | 142 |
| non-spliced XBP1 | 186-195 | ISPWILAVLT | 143 |
| non-spliced XBP1 | 186-196 | ISPWILAVLTL | 144 |
| non-spliced XBP1 | 186-197 | ISPWILAVLTLQ | 145 |
| non-spliced XBP1 | 186-198 | ISPWILAVLTLQI | 146 |
| non-spliced XBP1 | 186-199 | ISPWILAVLTLQIQ | 147 |
| non-spliced XBP1 | 186-200 | ISPWILAVLTLQIQS | 148 |
| non-spliced XBP1 | 186-201 | ISPWILAVLTLQIQSL | 149 |
| non-spliced XBP1 | 186-202 | ISPWILAVLTLQIQSLI | 150 |
| non-spliced XBP1 | 186-203 | ISPWILAVLTLQIQSLIS | 151 |
| non-spliced XBP1 | 186-204 | ISPWILAVLTLQIQSLISC | 152 |
| non-spliced XBP1 | 186-205 | ISPWILAVLTLQIQSLISCW | 153 |
| non-spliced XBP1 | 186-206 | ISPWILAVLTLQIQSLISCWA | 154 |
| non-spliced XBP1 | 187-194 | SPWILAVL | 155 |
| non-spliced XBP1 | 187-195 | SPWILAVLT | 156 |
| non-spliced XBP1 | 187-196 | SPWILAVLTL | 157 |
| non-spliced XBP1 | 187-197 | SPWILAVLTLQ | 158 |
| non-spliced XBP1 | 187-198 | SPWILAVLTLQI | 159 |
| non-spliced XBP1 | 187-199 | SPWILAVLTLQIQ | 160 |
| non-spliced XBP1 | 187-200 | SPWILAVLTLQIQS | 161 |
| non-spliced XBP1 | 187-201 | SPWILAVLTLQIQSL | 162 |
| non-spliced XBP1 | 187-202 | SPWILAVLTLQIQSLI | 163 |
| non-spliced XBP1 | 187-203 | SPWILAVLTLQISSLIS | 164 |
| non-spliced XBP1 | 187-204 | SPWILAVLTLQISSLISC | 165 |
| non-spliced XBP1 | 187-205 | SPWILAVLTLQISSLISCW | 166 |
| non-spliced XBP1 | 187-206 | SPWILAVLTLQISSLISCWA | 167 |
| non-spliced XBP1 | 188-194 | PWILAVL | 168 |
| non-spliced XBP1 | 188-195 | PWILAVLT | 169 |
| non-spliced XBP1 | 188-196 | PWILAVLTL | 170 |
| non-spliced XBP1 | 188-197 | PWILAVLTLQ | 171 |
| non-spliced XBP1 | 188-198 | PWILAVLTLQI | 172 |
| non-spliced XBP1 | 188-199 | PWILAVLTLQIQ | 173 |
| non-spliced XBP1 | 188-200 | PWILAVLTLQIQS | 174 |
| non-spliced XBP1 | 188-201 | PWILAVLTLQIQSL | 175 |
| non-spliced XBP1 | 188-202 | PWILAVLTLQIQSLI | 176 |
| non-spliced XBP1 | 188-203 | PWILAVLTLQIQSLIS | 177 |
| non-spliced XBP1 | 188-204 | PWILAVLTLQIQSLISC | 178 |

TABLE 3-continued

| Examples of Group C peptides | | | |
|---|---|---|---|
| Protein of Origin | Amino Acid Position | Amino Acid Sequence | SEQ ID NO |
| non-spliced XBP1 | 188-205 | PWILAVLTLQIQSLISCW | 179 |
| non-spliced XBP1 | 188-206 | PWILAVLTLQIQSLISCWA | 180 |
| non-spliced XBP1 | 189-194 | WILAVL | 181 |
| non-spliced XBP1 | 189-195 | WILAVLT | 182 |
| non-spliced XBP1 | 189-196 | WILAVLTL | 183 |
| non-spliced XBP1 | 189-197 | WILAVLTLQ | 184 |
| non-spliced XBP1 | 189-198 | WILAVLTLQI | 185 |
| non-spliced XBP1 | 189-199 | WILAVLTLQIQ | 186 |
| non-spliced XBP1 | 189-200 | WILAVLTLQIQS | 187 |
| non-spliced XBP1 | 189-201 | WILAVLTLQIQSL | 188 |
| non-spliced XBP1 | 189-202 | WILAVLTLQIQSLI | 189 |
| non-spliced XBP1 | 189-203 | WILAVLTLQIQSLIS | 190 |
| non-spliced XBP1 | 189-204 | WILAVLTLQIQSLISC | 191 |
| non-spliced XBP1 | 189-205 | WILAVLTLQIQSLISCW | 192 |
| non-spliced XBP1 | 189-206 | WILAVLTLQIQSLISCWA | 193 |
| non-spliced XBP1 | 190-194 | ILAVL | 194 |
| non-spliced XBP1 | 190-195 | ILAVLT | 195 |
| non-spliced XBP1 | 190-196 | ILAVLTL | 196 |
| non-spliced XBP1 | 190-197 | ILAVLTLQ | 197 |
| non-spliced XBP1 | 190-198 | ILAVLTLQI | 198 |
| non-spliced XBP1 | 190-199 | ILAVLTLQIQ | 199 |
| non-spliced XBP1 | 190-200 | ILAVLTLQIQS | 200 |
| non-spliced XBP1 | 190-201 | ILAVLTLQIQSL | 201 |
| non-spliced XBP1 | 190-202 | ILAVLTLQIQSLI | 202 |
| non-spliced XBP1 | 190-203 | ILAVLTLQIQSLIS | 203 |
| non-spliced XBP1 | 190-204 | ILAVLTLQIQSLISC | 204 |
| non-spliced XBP1 | 190-205 | ILAVLTLQIQSLISCW | 205 |
| non-spliced XBP1 | 190-206 | ILAVLTLQIQSLISCWA | 206 |
| CD138 | 251-268 | EVLGGVIAGGLVGLIFAV | 207 |
| CD138 | 251-269 | EVLGGVIAGGLVGLIFAVC | 208 |
| CD138 | 251-270 | EVLGGVIAGGLVGLIFAVCL | 209 |
| CD138 | 251-271 | EVLGGVIAGGLVGLIFAVCLV | 210 |
| CD138 | 251-272 | EVLGGVIAGGLVGLIFAVCLVG | 211 |
| CD138 | 251-273 | EVLGGVIAGGLVGLIFAVCLVGF | 212 |
| CD138 | 251-274 | EVLGGVIAGGLVGLIFAVCLVGFM | 213 |
| CD138 | 251-275 | EVLGGVIAGGLVGLIFAVCLVGFML | 214 |
| CD138 | 251-276 | EVLGGVIAGGLVGLIFAVCLVGFMLY | 215 |
| CD138 | 251-277 | EVLGGVIAGGLVGLIFAVCLVGFMLYR | 216 |

TABLE 3-continued

| Examples of Group C peptides | | | |
| --- | --- | --- | --- |
| Protein of Origin | Amino Acid Position | Amino Acid Sequence | SEQ ID NO |
| CD138 | 251-278 | EVLGGVIAGGLVGLIFAVCLVGFMLYRM | 217 |
| CD138 | 252-268 | VLGGVIAGGLVGLIFAV | 218 |
| CD138 | 252-269 | VLGGVIAGGLVGLIFAVC | 219 |
| CD138 | 252-270 | VLGGVIAGGLVGLIFAVCL | 220 |
| CD138 | 252-271 | VLGGVIAGGLVGLIFAVCLV | 221 |
| CD138 | 252-272 | VLGGVIAGGLVGLIFAVCLVG | 222 |
| CD138 | 252-273 | VLGGVIAGGLVGLIFAVCLVGF | 223 |
| CD138 | 252-274 | VLGGVIAGGLVGLIFAVCLVGFM | 224 |
| CD138 | 252-275 | VLGGVIAGGLVGLIFAVCLVGFML | 225 |
| CD138 | 252-276 | VLGGVIAGGLVGLIFAVCLVGFMLY | 226 |
| CD138 | 252-277 | VLGGVIAGGLVGLIFAVCLVGFMLYR | 227 |
| CD138 | 252-278 | VLGGVIAGGLVGLIFAVCLVGFMLYRM | 228 |
| CD138 | 253-268 | LGGVIAGGLVGLIFAV | 229 |
| CD138 | 253-269 | LGGVIAGGLVGLIFAVC | 230 |
| CD138 | 253-270 | LGGVIAGGLVGLIFAVCL | 231 |
| CD138 | 253-271 | LGGVIAGGLVGLIFAVCLV | 232 |
| CD138 | 253-272 | LGGVIAGGLVGLIFAVCLVG | 233 |
| CD138 | 253-273 | LGGVIAGGLVGLIFAVCLVGF | 234 |
| CD138 | 253-274 | LGGVIAGGLVGLIFAVCLVGFM | 235 |
| CD138 | 253-275 | LGGVIAGGLVGLIFAVCLVGFML | 236 |
| CD138 | 253-276 | LGGVIAGGLVGLIFAVCLVGFMLY | 237 |
| CD138 | 253-277 | LGGVIAGGLVGLIFAVCLVGFMLYR | 238 |
| CD138 | 253-278 | LGGVIAGGLVGLIFAVCLVGFMLYRM | 239 |
| CD138 | 254-268 | GGVIAGGLVGLIFAV | 240 |
| CD138 | 254-269 | GGVIAGGLVGLIFAVC | 241 |
| CD138 | 254-270 | GGVIAGGLVGLIFAVCL | 242 |
| CD138 | 254-271 | GGVIAGGLVGLIFAVCLV | 243 |
| CD138 | 254-272 | GGVIAGGLVGLIFAVCLVG | 244 |
| CD138 | 254-273 | GGVIAGGLVGLIFAVCLVGF | 245 |
| CD138 | 254-274 | GGVIAGGLVGLIFAVCLVGFM | 246 |
| CD138 | 254-275 | GGVIAGGLVGLIFAVCLVGFML | 247 |
| CD138 | 254-276 | GGVIAGGLVGLIFAVCLVGFMLY | 248 |
| CD138 | 254-277 | GGVIAGGLVGLIFAVCLVGFMLYR | 249 |
| CD138 | 254-278 | GGVIAGGLVGLIFAVCLVGFMLYRM | 250 |
| CD138 | 255-268 | GVIAGGLVGLIFAV | 251 |
| CD138 | 255-269 | GVIAGGLVGLIFAVC | 252 |
| CD138 | 255-270 | GVIAGGLVGLIFAVCL | 253 |
| CD138 | 255-271 | GVIAGGLVGLIFAVCLV | 254 |

TABLE 3-continued

| Examples of Group C peptides | | | |
| --- | --- | --- | --- |
| Protein of Origin | Amino Acid Position | Amino Acid Sequence | SEQ ID NO |
| CD138 | 255-272 | GVIAGGLVGLIFAVCLVG | 255 |
| CD138 | 255-273 | GVIAGGLVGLIFAVCLVGF | 256 |
| CD138 | 255-274 | GVIAGGLVGLIFAVCLVGFM | 257 |
| CD138 | 255-275 | GVIAGGLVGLIFAVCLVGFML | 258 |
| CD138 | 255-276 | GVIAGGLVGLIFAVCLVGFMLY | 259 |
| CD138 | 255-277 | GVIAGGLVGLIFAVCLVGFMLYR | 260 |
| CD138 | 255-278 | GVIAGGLVGLIFAVCLVGFMLYRM | 261 |
| CD138 | 256-268 | VIAGGLVGLIFAV | 262 |
| CD138 | 256-269 | VIAGGLVGLIFAVC | 263 |
| CD138 | 256-270 | VIAGGLVGLIFAVCL | 264 |
| CD138 | 256-271 | VIAGGLVGLIFAVCLV | 265 |
| CD138 | 256-272 | VIAGGLVGLIFAVCLVG | 266 |
| CD138 | 256-273 | VIAGGLVGLIFAVCLVGF | 267 |
| CD138 | 256-274 | VIAGGLVGLIFAVCLVGFM | 268 |
| CD138 | 256-275 | VIAGGLVGLIFAVCLVGFML | 269 |
| CD138 | 256-276 | VIAGGLVGLIFAVCLVGFMLY | 270 |
| CD138 | 256-277 | VIAGGLVGLIFAVCLVGFMLYR | 271 |
| CD138 | 256-278 | VIAGGLVGLIFAVCLVGFMLYRM | 272 |
| CD138 | 257-268 | IAGGLVGLIFAV | 273 |
| CD138 | 257-269 | IAGGLVGLIFAVC | 274 |
| CD138 | 257-270 | IAGGLVGLIFAVCL | 275 |
| CD138 | 257-271 | IAGGLVGLIFAVCLV | 276 |
| CD138 | 257-272 | IAGGLVGLIFAVCLVG | 277 |
| CD138 | 257-273 | IAGGLVGLIFAVCLVGF | 278 |
| CD138 | 257-274 | IAGGLVGLIFAVCLVGFM | 279 |
| CD138 | 257-275 | IAGGLVGLIFAVCLVGFML | 280 |
| CD138 | 257-276 | IAGGLVGLIFAVCLVGFMLY | 281 |
| CD138 | 257-277 | IAGGLVGLIFAVCLVGFMLYR | 282 |
| CD138 | 257-278 | IAGGLVGLIFAVCLVGFMLYRM | 283 |
| CD138 | 258-268 | AGGLVGLIFAV | 284 |
| CD138 | 258-269 | AGGLVGLIFAVC | 285 |
| CD138 | 258-270 | AGGLVGLIFAVCL | 286 |
| CD138 | 258-271 | AGGLVGLIFAVCLV | 287 |
| CD138 | 258-272 | AGGLVGLIFAVCLVG | 288 |
| CD138 | 258-273 | AGGLVGLIFAVCLVGF | 289 |
| CD138 | 258-274 | AGGLVGLIFAVCLVGFM | 290 |
| CD138 | 258-275 | AGGLVGLIFAVCLVGFML | 291 |
| CD138 | 258-276 | AGGLVGLIFAVCLVGFMLY | 292 |

TABLE 3-continued

| Examples of Group C peptides | | | |
|---|---|---|---|
| Protein of Origin | Amino Acid Position | Amino Acid Sequence | SEQ ID NO |
| CD138 | 258-277 | AGGLVGLIFAVCLVGFMLYR | 293 |
| CD138 | 258-278 | AGGLVGLIFAVCLVGFMLYRM | 294 |
| CD138 | 259-268 | GGLVGLIFAV | 295 |
| CD138 | 259-269 | GGLVGLIFAVC | 296 |
| CD138 | 259-270 | GGLVGLIFAVCL | 297 |
| CD138 | 259-271 | GGLVGLIFAVCLV | 298 |
| CD138 | 259-272 | GGLVGLIFAVCLVG | 299 |
| CD138 | 259-273 | GGLVGLIFAVCLVGF | 300 |
| CD138 | 259-274 | GGLVGLIFAVCLVGFM | 301 |
| CD138 | 259-275 | GGLVGLIFAVCLVGFML | 302 |
| CD138 | 259-276 | GGLVGLIFAVCLVGFMLY | 303 |
| CD138 | 259-277 | GGLVGLIFAVCLVGFMLYR | 304 |
| CD138 | 259-278 | GGLVGLIFAVCLVGFMLYRM | 305 |
| CD138 | 260-268 | GLVGLIFAV | 306 |
| CD138 | 260-269 | GLVGLIFAVC | 307 |
| CD138 | 260-270 | GLVGLIFAVCL | 308 |
| CD138 | 260-271 | GLVGLIFAVCLV | 309 |
| CD138 | 260-272 | GLVGLIFAVCLVG | 310 |
| CD138 | 260-273 | GLVGLIFAVCLVGF | 311 |
| CD138 | 260-274 | GLVGLIFAVCLVGFM | 312 |
| CD138 | 260-275 | GLVGLIFAVCLVGFML | 313 |
| CD138 | 260-276 | GLVGLIFAVCLVGFMLY | 314 |
| CD138 | 260-277 | GLVGLIFAVCLVGFMLYR | 315 |
| CD138 | 260-278 | GLVGLIFAVCLVGFMLYRM | 316 |
| CD138 | 261-268 | LVGLIFAV | 317 |
| CD138 | 261-269 | LVGLIFAVC | 318 |
| CD138 | 261-270 | LVGLIFAVCL | 319 |
| CD138 | 261-271 | LVGLIFAVCLV | 320 |
| CD138 | 260-272 | LVGLIFAVCLVG | 321 |
| CD138 | 261-273 | LVGLIFAVCLVGF | 322 |
| CD138 | 261-274 | LVGLIFAVCLVGFM | 323 |
| CD138 | 261-275 | LVGLIFAVCLVGFML | 324 |
| CD138 | 261-276 | LVGLIFAVCLVGFMLY | 325 |
| CD138 | 261-277 | LVGLIFAVCLVGFMLYR | 326 |
| CD138 | 261-278 | LVGLIFAVCLVGFMLYRM | 327 |
| CD138 | 262-268 | VGLIFAV | 328 |
| CD138 | 262-269 | VGLIFAVC | 329 |
| CD138 | 262-270 | VGLIFAVCL | 330 |

TABLE 3-continued

| Examples of Group C peptides | | | |
|---|---|---|---|
| Protein of Origin | Amino Acid Position | Amino Acid Sequence | SEQ ID NO |
| CD138 | 262-271 | VGLIFAVCLV | 331 |
| CD138 | 262-272 | VGLIFAVCLVG | 332 |
| CD138 | 262-273 | VGLIFAVCLVGF | 333 |
| CD138 | 262-274 | VGLIFAVCLVGFM | 334 |
| CD138 | 262-275 | VGLIFAVCLVGFML | 335 |
| CD138 | 262-276 | VGLIFAVCLVGFMLY | 336 |
| CD138 | 262-277 | VGLIFAVCLVGFMLYR | 337 |
| CD138 | 262-278 | VGLIFAVCLVGFMLYRM | 338 |
| CD138 | 263-268 | GLIFAV | 339 |
| CD138 | 263-269 | GLIFAVC | 340 |
| CD138 | 263-270 | GLIFAVCL | 341 |
| CD138 | 263-271 | GLIFAVCLV | 342 |
| CD138 | 263-272 | GLIFAVCLVG | 343 |
| CD138 | 263-273 | GLIFAVCLVGF | 344 |
| CD138 | 263-274 | GLIFAVCLVGFM | 345 |
| CD138 | 263-275 | GLIFAVCLVGFML | 346 |
| CD138 | 263-276 | GLIFAVCLVGFMLY | 347 |
| CD138 | 263-277 | GLIFAVCLVGFMLYR | 348 |
| CD138 | 263-278 | GLIFAVCLVGFMLYRM | 349 |
| CD138 | 264-268 | LIFAV | 350 |
| CD138 | 264-269 | LIFAVC | 351 |
| CD138 | 264-270 | LIFAVCL | 352 |
| CD138 | 264-271 | LIFAVCLV | 353 |
| CD138 | 264-272 | LIFAVCLVG | 354 |
| CD138 | 264-273 | LIFAVCLVGF | 355 |
| CD138 | 264-274 | LIFAVCLVGFM | 356 |
| CD138 | 264-275 | LIFAVCLVGFML | 357 |
| CD138 | 264-276 | LIFAVCLVGFMLY | 358 |
| CD138 | 264-277 | LIFAVCLVGFMLYR | 359 |
| CD138 | 264-278 | LIFAVCLVGFMLYRM | 360 |
| CD138 | 265-268 | IFAV | 361 |
| CD138 | 265-269 | IFAVC | 362 |
| CD138 | 265-270 | IFAVCL | 363 |
| CD138 | 265-271 | IFAVCLV | 364 |
| CD138 | 265-272 | IFAVCLVG | 365 |
| CD138 | 265-273 | IFAVCLVGF | 366 |
| CD138 | 265-274 | IFAVCLVGFM | 367 |
| CD138 | 265-275 | IFAVCLVGFML | 368 |

TABLE 3-continued

| Examples of Group C peptides | | | |
|---|---|---|---|
| Protein of Origin | Amino Acid Position | Amino Acid Sequence | SEQ ID NO |
| CD138 | 265-276 | IFAVCLVGFMLY | 369 |
| CD138 | 265-277 | IFAVCLVGFMLYR | 370 |
| CD138 | 265-278 | IFAVCLVGFMLYRM | 371 |
| CS1 | 227-242 | VLLCLLLVPLLLSLFV | 372 |
| CS1 | 227-243 | VLLCLLLVPLLLSLFVL | 373 |
| CS1 | 227-244 | VLLCLLLVPLLLSLFVLG | 374 |
| CS1 | 227-245 | VLLCLLLVPLLLSLFVLGL | 375 |
| CS1 | 227-246 | VLLCLLLVPLLLSLFVLGLF | 376 |
| CS1 | 227-247 | VLLCLLLVPLLLSLFVLGLFL | 377 |
| CS1 | 227-248 | VLLCLLLVPLLLSLFVLGLFLW | 378 |
| CS1 | 227-249 | VLLCLLLVPLLLSLFVLGLFLWF | 379 |
| CS1 | 227-250 | VLLCLLLVPLLLSLFVLGLFLWFL | 380 |
| CS1 | 227-251 | VLLCLLLVPLLLSLFVLGLFLWFLK | 381 |
| CS1 | 227-252 | VLLCLLLVPLLLSLFVLGLFLWFLKR | 382 |
| CS1 | 227-253 | VLLCLLLVPLLLSLFVLGLFLWFLKRE | 383 |
| CS1 | 228-242 | LLCLLLVPLLLSLFV | 384 |
| CS1 | 228-243 | LLCLLLVPLLLSLFVL | 385 |
| CS1 | 228-244 | LLCLLLVPLLLSLFVLG | 386 |
| CS1 | 228-245 | LLCLLLVPLLLSLFVLGL | 387 |
| CS1 | 228-246 | LLCLLLVPLLLSLFVLGLF | 388 |
| CS1 | 228-247 | LLCLLLVPLLLSLFVLGLFL | 389 |
| CS1 | 228-248 | LLCLLLVPLLLSLFVLGLFLW | 390 |
| CS1 | 228-249 | LLCLLLVPLLLSLFVLGLFLWF | 391 |
| CS1 | 228-250 | LLCLLLVPLLLSLFVLGLFLWFL | 392 |
| CS1 | 228-251 | LLCLLLVPLLLSLFVLGLFLWFLK | 393 |
| CS1 | 228-252 | LLCLLLVPLLLSLFVLGLFLWFLKR | 394 |
| CS1 | 228-253 | LLCLLLVPLLLSLFVLGLFLWFLKRE | 395 |
| CS1 | 229-242 | LCLLLVPLLLSLFV | 396 |
| CS1 | 229-243 | LCLLLVPLLLSLFVL | 397 |
| CS1 | 229-244 | LCLLLVPLLLSLFVLG | 398 |
| CS1 | 229-245 | LCLLLVPLLLSLFVLGL | 399 |
| CS1 | 229-246 | LCLLLVPLLLSLFVLGLF | 400 |
| CS1 | 229-247 | LCLLLVPLLLSLFVLGLFL | 401 |
| CS1 | 229-248 | LCLLLVPLLLSLFVLGLFLW | 402 |
| CS1 | 229-249 | LCLLLVPLLLSLFVLGLFLWF | 403 |
| CS1 | 229-250 | LCLLLVPLLLSLFVLGLFLWFL | 404 |
| CS1 | 229-251 | LCLLLVPLLLSLFVLGLFLWFLK | 405 |
| CS1 | 229-252 | LCLLLVPLLLSLFVLGLFLWFLKR | 406 |

TABLE 3-continued

| Examples of Group C peptides | | | |
|---|---|---|---|
| Protein of Origin | Amino Acid Position | Amino Acid Sequence | SEQ ID NO |
| CS1 | 229-253 | LCLLLVPLLLSLFVLGLFLWFLKRE | 407 |
| CS1 | 230-242 | CLLLVPLLLSLFV | 408 |
| CS1 | 230-243 | CLLLVPLLLSLFVL | 409 |
| CS1 | 230-244 | CLLLVPLLLSLFVLG | 410 |
| CS1 | 230-245 | CLLLVPLLLSLFVLGL | 411 |
| CS1 | 230-246 | CLLLVPLLLSLFVLGLF | 412 |
| CS1 | 230-247 | CLLLVPLLLSLFVLGLFL | 413 |
| CS1 | 230-248 | CLLLVPLLLSLFVLGLFLW | 414 |
| CS1 | 230-249 | CLLLVPLLLSLFVLGLFLWF | 415 |
| CS1 | 230-250 | CLLLVPLLLSLFVLGLFLWFL | 416 |
| CS1 | 230-251 | CLLLVPLLLSLFVLGLFLWFLK | 417 |
| CS1 | 230-252 | CLLLVPLLLSLFVLGLFLWFLKR | 418 |
| CS1 | 230-253 | CLLLVPLLLSLFVLGLFLWFLKRE | 419 |
| CS1 | 231-242 | LLLVPLLLSLFV | 420 |
| CS1 | 231-243 | LLLVPLLLSLFVL | 421 |
| CS1 | 231-244 | LLLVPLLLSLFVLG | 422 |
| CS1 | 231-245 | LLLVPLLLSLFVLGL | 423 |
| CS1 | 231-246 | LLLVPLLLSLFVLGLF | 424 |
| CS1 | 231-247 | LLLVPLLLSLFVLGLFL | 425 |
| CS1 | 231-248 | LLLVPLLLSLFVLGLFLW | 426 |
| CS1 | 231-249 | LLLVPLLLSLFVLGLFLWF | 427 |
| CS1 | 231-250 | LLLVPLLLSLFVLGLFLWFL | 428 |
| CS1 | 231-251 | LLLVPLLLSLFVLGLFLWFLK | 429 |
| CS1 | 231-252 | LLLVPLLLSLFVLGLFLWFLKR | 430 |
| CS1 | 231-253 | LLLVPLLLSLFVLGLFLWFLKRE | 431 |
| CS1 | 232-242 | LLVPLLLSLFV | 432 |
| CS1 | 232-243 | LLVPLLLSLFVL | 433 |
| CS1 | 232-244 | LLVPLLLSLFVLG | 434 |
| CS1 | 232-245 | LLVPLLLSLFVLGL | 435 |
| CS1 | 232-246 | LLVPLLLSLFVLGLF | 436 |
| CS1 | 232-247 | LLVPLLLSLFVLGLFL | 437 |
| CS1 | 232-248 | LLVPLLLSLFVLGLFLW | 438 |
| CS1 | 232-249 | LLVPLLLSLFVLGLFLWF | 439 |
| CS1 | 232-250 | LLVPLLLSLFVLGLFLWFL | 440 |
| CS1 | 232-251 | LLVPLLLSLFVLGLFLWFLK | 441 |
| CS1 | 232-252 | LLVPLLLSLFVLGLFLWFLKR | 442 |
| CS1 | 232-253 | LLVPLLLSLFVLGLFLWFLKRE | 443 |
| CS1 | 233-242 | LVPLLLSLFV | 444 |

TABLE 3-continued

| | Examples of Group C peptides | | |
|---|---|---|---|
| Protein of Origin | Amino Acid Position | Amino Acid Sequence | SEQ ID NO |
| CS1 | 233-243 | LVPLLLSLFVL | 445 |
| CS1 | 233-244 | LVPLLLSLFVLG | 446 |
| CS1 | 233-245 | LVPLLLSLFVLGL | 447 |
| CS1 | 233-246 | LVPLLLSLFVLGLF | 448 |
| CS1 | 233-247 | LVPLLLSLFVLGLFL | 449 |
| CS1 | 233-248 | LVPLLLSLFVLGLFLW | 450 |
| CS1 | 233-249 | LVPLLLSLFVLGLFLWF | 451 |
| CS1 | 233-250 | LVPLLLSLFVLGLFLWFL | 452 |
| CS1 | 233-251 | LVPLLLSLFVLGLFLWFLK | 453 |
| CS1 | 233-252 | LVPLLLSLFVLGLFLWFLKR | 454 |
| CS1 | 233-253 | LVPLLLSLFVLGLFLWFLKRE | 455 |
| CS1 | 234-242 | VPLLLSLFV | 456 |
| CS1 | 234-243 | VPLLLSLFVL | 457 |
| CS1 | 234-244 | VPLLLSLFVLG | 458 |
| CS1 | 234-245 | VPLLLSLFVLGL | 459 |
| CS1 | 234-246 | VPLLLSLFVLGLF | 460 |
| CS1 | 234-247 | VPLLLSLFVLGLFL | 461 |
| CS1 | 234-248 | VPLLLSLFVLGLFLW | 462 |
| CS1 | 234-249 | VPLLLSLFVLGLFLWF | 463 |
| CS1 | 234-250 | VPLLLSLFVLGLFLWFL | 464 |
| CS1 | 234-251 | VPLLLSLFVLGLFLWFLK | 465 |
| CS1 | 234-252 | VPLLLSLFVLGLFLWFLKR | 466 |
| CS1 | 234-253 | VPLLLSLFVLGLFLWFLKRE | 467 |
| CS1 | 235-242 | PLLLSLFV | 468 |
| CS1 | 235-243 | PLLLSLFVL | 469 |
| CS1 | 235-244 | PLLLSLFVLG | 470 |
| CS1 | 235-245 | PLLLSLFVLGL | 471 |
| CS1 | 235-246 | PLLLSLFVLGLF | 472 |
| CS1 | 235-247 | PLLLSLFVLGLFL | 473 |
| CS1 | 235-248 | PLLLSLFVLGLFLW | 474 |
| CS1 | 235-249 | PLLLSLFVLGLFLWF | 475 |
| CS1 | 235-250 | PLLLSLFVLGLFLWFL | 476 |
| CS1 | 235-251 | PLLLSLFVLGLFLWFLK | 477 |
| CS1 | 235-252 | PLLLSLFVLGLFLWFLKR | 478 |
| CS1 | 235-253 | PLLLSLFVLGLFLWFLKRE | 479 |
| CS1 | 236-242 | LLLSLFV | 480 |
| CS1 | 236-243 | LLLSLFVL | 481 |
| CS1 | 236-244 | LLLSLFVLG | 482 |

TABLE 3-continued

| Examples of Group C peptides | | | |
| --- | --- | --- | --- |
| Protein of Origin | Amino Acid Position | Amino Acid Sequence | SEQ ID NO |
| CS1 | 236-245 | LLLSLFVLGL | 483 |
| CS1 | 236-246 | LLLSLFVLGLF | 484 |
| CS1 | 236-247 | LLLSLFVLGLFL | 485 |
| CS1 | 236-248 | LLLSLFVLGLFLW | 486 |
| CS1 | 236-249 | LLLSLFVLGLFLWF | 487 |
| CS1 | 236-250 | LLLSLFVLGLFLWFL | 488 |
| CS1 | 236-251 | LLLSLFVLGLFLWFLK | 489 |
| CS1 | 236-252 | LLLSLFVLGLFLWFLKR | 490 |
| CS1 | 236-253 | LLLSLFVLGLFLWFLKRE | 491 |
| CS1 | 237-242 | LLSLFV | 492 |
| CS1 | 237-243 | LLSLFVL | 493 |
| CS1 | 237-244 | LLSLFVLG | 494 |
| CS1 | 237-245 | LLSLFVLGL | 495 |
| CS1 | 237-246 | LLSLFVLGLF | 496 |
| CS1 | 237-247 | LLSLFVLGLFL | 497 |
| CS1 | 237-248 | LLSLFVLGLFLW | 498 |
| CS1 | 237-249 | LLSLFVLGLFLWF | 499 |
| CS1 | 237-250 | LLSLFVLGLFLWFL | 500 |
| CS1 | 237-251 | LLSLFVLGLFLWFLK | 501 |
| CS1 | 237-252 | LLSLFVLGLFLWFLKR | 502 |
| CS1 | 237-253 | LLSLFVLGLFLWFLKRE | 503 |
| CS1 | 238-242 | LSLFV | 504 |
| CS1 | 238-243 | LSLFVL | 505 |
| CS1 | 238-244 | LSLFVLG | 506 |
| CS1 | 238-245 | LSLFVLGL | 507 |
| CS1 | 238-246 | LSLFVLGLF | 508 |
| CS1 | 238-247 | LSLFVLGLFL | 509 |
| CS1 | 238-248 | LSLFVLGLFLW | 510 |
| CS1 | 238-249 | LSLFVLGLFLWF | 511 |
| CS1 | 238-250 | LSLFVLGLFLWFL | 512 |
| CS1 | 238-251 | LSLFVLGLFLWFLK | 513 |
| CS1 | 238-252 | LSLFVLGLFLWFLKR | 514 |
| CS1 | 238-253 | LSLFVLGLFLWFLKRE | 515 |
| CS1 | 239-243 | SLFVL | 516 |
| CS1 | 239-244 | SLFVLG | 517 |
| CS1 | 239-245 | SLFVLGL | 518 |
| CS1 | 239-246 | SLFVLGLF | 519 |
| CS1 | 239-247 | SLFVLGLFL | 520 |

TABLE 3-continued

Examples of Group C peptides

| Protein of Origin | Amino Acid Position | Amino Acid Sequence | SEQ ID NO |
|---|---|---|---|
| CS1 | 239-248 | SLFVLGLFLW | 521 |
| CS1 | 239-249 | SLFVLGLFLWF | 522 |
| CS1 | 239-250 | SLFVLGLFLWFL | 523 |
| CS1 | 239-251 | SLFVLGLFLWFLK | 524 |
| CS1 | 239-252 | SLFVLGLFLWFLKR | 525 |
| CS1 | 239-253 | SLFVLGLFLWFLKRE | 526 |
| CS1 | 240-244 | LFVLG | 527 |
| CS1 | 240-245 | LFVLGL | 528 |
| CS1 | 240-246 | LFVLGLF | 529 |
| CS1 | 240-247 | LFVLGLFL | 530 |
| CS1 | 240-248 | LFVLGLFLW | 531 |
| CS1 | 240-249 | LFVLGLFLWF | 532 |
| CS1 | 240-250 | LFVLGLFLWFL | 533 |
| CS1 | 240-251 | LFVLGLFLWFLK | 534 |
| CS1 | 240-252 | LFVLGLFLWFLKR | 535 |
| CS1 | 240-253 | LFVLGLFLWFLKRE | 536 |

Preferably, the isolated peptide from Group C is at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprises an amino acid sequence that is at least 70%, 75%, 80%, 85%, 90%, 95%, 96%, 97%, 98%, 99% identity or is identical to an amino acid sequence of SEQ ID NOS: 51-536. Other preferred peptides can be at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprise an amino acid sequence of SEQ ID NOs: 51-536, or an amino acid sequence with one, two, three or four substitutions of the amino acid sequence of SEQ ID NOs: 51-536. The substitution can be a conservative or nonconservative substitution.

"Non-spliced XBP1" peptides from Group C include those peptides depicted in Table 3 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the non-spliced form of human XBP1 protein having 261 amino acids and the amino acid sequence of SEQ ID NO:19, and peptides having no more than one, two, three, four, five substitutions (e.g., conservative substitutions) of the amino acids derived from the amino acid sequence of SEQ ID NO:19. Non-spliced XBP1 peptides from Group C include peptides having an amino acid sequence from SEQ ID NO: 19 that comprises part or all of SEQ ID NOS: 51-206. The amino acid positions referred to in Table 3 are based on SEQ ID NO: 19.

"CD138" peptides from Group C include those peptides depicted in Table 3 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CD138 protein having 310 amino acids and the amino acid sequence of SEQ ID NO:21, and peptides having no more than one, two, three, four, five substitutions (e.g., conservative substitutions) of the amino acids derived from the amino acid sequence of SEQ ID NO:21. CD138 peptides from Group C include peptides having an amino acid sequence from SEQ ID NO: 21 that comprises part or all of SEQ ID NOS: 207-371.

The amino acid positions referred to in Table 3 are based on SEQ ID NO: 21.

"CS-1" peptides from Group C include those peptides depicted in Table 3 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CS-1 protein having 335 amino acids and the amino acid sequence of SEQ ID NO:22, and peptides having no more than one, two, three, four, five substitutions (e.g., conservative substitutions) of the amino acids derived from the amino acid sequence of SEQ ID NO:22. CS-1 peptides from Group C include peptides having an amino acid sequence from SEQ ID NO: 22 that comprises part or all of SEQ ID NOS: 372-536. The amino acid positions referred to in Table 3 are based on SEQ ID NO: 22.

Peptides Generally.

The peptides described herein are often referred to using the residue number of the N and C terminal amino acids of the peptides (e.g., $XBP1_{118-126}$) as the relevant sequences occur in the wild-type, full length, mature human proteins having SEQ ID NOS: 19-22. These peptides will frequently have identical sequences to the corresponding segments of the wild-type, full-length, mature proteins having SEQ ID NOS: 19-22. It is understood, however, that the terms "nonspliced XBP1 peptides" (e.g., nonspliced XBP1 peptides having amino acid positions: 118-136, 185-193, 186-194, 190-198, 193-200, or 111-119), "spliced XBP1 peptides" (e.g., spliced XBP1 peptides having amino acid positions: 197-205, 194-202, 224-232, 368-376), "CD138 peptides" (e.g., CD138 peptides having amino acid positions: 256-264, 265-273, 260-268, 5-13, or 7-15), and CS1 peptides (e.g., CS-1 peptides have amino acid positions 236-245, 240-248, 239-247, 232-240, or 9-17) can be peptide fragments of the XBP1 nonspliced peptide, the XBP1 spliced peptide, the CD138, or CS-1 polypeptide (respectively) of a species other than human. As will be appreciated by those skilled in the art, the numbers of the N and C terminal amino acids of peptide fragments of such non-human polypeptides are not necessarily the same as those in the corresponding peptide fragments of human polypeptides. Moreover, the lengths and/or amino acids of peptide fragments of non-human polypeptides will not necessarily be the same as those in the corresponding peptide fragments of human polypeptides. Those of skill in the art will know how to establish the N and C terminal amino acids, the lengths, and amino acid sequences of peptides derived from non-human nonspliced XBP1, spliced XBP1, CD138, and CS-1 polypeptides. One useful method for doing this is sequence alignment and, in particular, maximum homology sequence alignment.

Percent identity between two peptide sequences (e.g., a peptide of SEQ ID NOS: 1-18 and 29-536) and another amino acid sequence that may be at least 66% identical to the peptide) can be determined using a variety of algorithms and computer programs including, but not limited to, Clustal W (The European Bioinformatics Institute (EMBL-EBI), BLAST-Protein (National Center for Biotechnology Information (NCBI), United States National Institutes of Health), and PSAlign (University of Texas A&M; Sze et al. (2006) Journal of Computational Biology 13:309-319).

Also disclosed herein are variants of the human and non-human peptides described above. Variants of the human and non-human peptides described herein can include forms of the peptides having: (i) not more than 4 (e.g., 3, 2, or 1) amino acid substitutions (e.g., conservative or non-conservative substitutions); (ii) terminal or internal deletions; or (iii) terminal or internal additions, all of which are elaborated on below.

The disclosure also features peptides comprising, consisting of, or consisting essentially of, an amino acid sequence of any of SEQ ID NOs: 1-18 and 29-536 (as depicted in Tables 1-3), but with not more than four (e.g., not more than three, not more than two, or not more than 1) substitutions. The substitutions can be, e.g., conservative or non-conservative (as described above).

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

In some embodiments, one or more (e.g., one, two, three, four, or all five) of positions three, four, five, six, seven, and eight of any of the peptides are not substituted. In some embodiments, one or more of positions three, four, five, six, seven, and eight of any of the peptides are identical to the amino acids of the peptides in Tables 1-3.

Also featured are fusion proteins comprising: a first amino acid sequence of a peptide described herein (e.g., a non-spliced XBP1 peptide described herein, a spliced XBP1 peptide described herein, a CD138 peptide described herein and/or a CS-1 peptide described herein); and a second amino acid sequence that is heterologous to the first amino acid sequence.

The second, heterologous amino acid sequence(s) of the peptide generally do not (and are selected such that do not) adversely affect the generation in the cell of an immunogenic peptide of any of SEQ ID NOs: 1-18 and 29-536. The cellular machinery is expected to remove any additional sequences in the peptide to yield an immunogenic peptide of any of SEQ ID NOs: 1-18 and 29-536, which peptide is presented by a class I or class II MHC molecule to stimulate an immune response against XBP1-, CD138-, or CS1-expressing cancer cells.

An amino acid sequence that is "heterologous" to a first amino acid sequence, or the term "heterologous amino acid sequence," is any amino acid sequence other than the amino acid sequence(s) flanking the first amino acid sequence as it occurs in nature. For example, two or more (e.g., two, three, four, five, six, seven, eight, nine, 10, 11, 12, 13, 14, 15, 16, 17, 18, 19, or 20 or more) and/or less than 20 (e.g., 19, 18, 17, 16, 15, 14, 13, 12, 11, 10, nine, eight, seven, six, five, four, three, two, or one) carboxy- and/or amino-terminal amino acid(s) immediately flanking LLREKTHGL (SEQ ID NO:1) in a human XBP1 are not considered to be heterologous to SEQ ID NO:1. It is understood that a fusion protein containing a first amino acid sequence that is less than 100% identical to, or contains from one to four conservative substitutions in, an amino acid sequence of any of SEQ ID NOs: 1-18 and 29-536, may not occur in nature at all.

In some embodiments, the second amino acid sequence can be a single amino acid. It is understood that an amino acid that is "heterologous" to a first amino acid sequence, or the term "heterologous amino acid," is any amino acid other than the amino acid(s) flanking the first amino acid sequence as it occurs in nature. For example, the two amino acid(s) immediately flanking LLREKTHGL (SEQ ID NO:1) in a human XBP1 are not considered to be heterologous to SEQ ID NO:1.

A heterologous sequence can be, for example, a sequence used for purification of the recombinant protein (e.g., FLAG, polyhistidine (e.g., hexahistidine) (SEQ ID NO: 544), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the fusion protein can contain a signal sequence from another protein such as a KDEL (SEQ ID NO:23) sequence or any other described herein. In some embodiments, the fusion protein can contain all or part of an immunoglobulin molecule (e.g., all or part of an immunoglobulin heavy chain constant region; see below). In some embodiments, the fusion protein can contain a therapeutic or immune-stimulating polypeptide (e.g., a T helper epitope (e.g., a PADRE epitope or a Tetanus Toxoid universal T helper cell epitope)

or all or part of a cytokine or chemokine) and/or a carrier (e.g., KLH) useful, e.g., in eliciting an immune response (e.g., for antibody generation). In some embodiments, the fusion protein can contain one or more linkers, e.g., a linker comprising a peptide sequence (see below). The fusion protein can also contain a targeting polypeptide. Heterologous sequences can be of varying length and in some cases can be longer sequences than the first amino acid sequences to which the heterologous amino acid sequences are attached. It is understood that a fusion protein containing a first amino acid sequence and a second amino acid sequence that is heterologous to the first does not correspond in sequence to a naturally occurring protein.

Targeting polypeptides, as used herein, are polypeptides that target the moiety (or moieties) they are attached to (e.g., the first amino acid sequence) to specific tissues (e.g., to a lymph node) or cells (e.g., to an antigen presenting cell or other immune cell), or where in vitro, specific isolated molecules or molecular complexes. Targeting polypeptides can be, e.g., an antibody (immunoglobulin) or antigen binding fragment thereof or a ligand for a cell surface receptor. An antibody (or antigen-binding fragment thereof) can be, e.g., a monoclonal antibody, a polyclonal antibody, a humanized antibody, a fully human antibody, a single chain antibody, a chimeric antibody, or an Fab fragment, an $F(ab')_2$ fragment, an Fab' fragment, an Fv fragment, or an scFv fragment of an antibody. Antibody fragments that include, or are, Fc regions (with or without antigen-binding regions) can also be used to target the reagents to Fc receptor-expressing cells (e.g., antigen presenting cells such as interdigitating dendritic cells, macrophages, monocytes, or B cells). A ligand for a cell surface receptor can be, e.g., a chemokine, a cytokine (e.g., interleukins 1, 2, 3, 4, 5, 6, 7, 8, 9, 10, 11, 12, 13, 14, 15, or 16), or a death receptor ligand (e.g., FasL or TNFα).

In some embodiments, the heterologous sequence can be, e.g., a "transportation sequence" that aids in the delivery of the peptide to the cell or to a specific compartment of a cell (e.g., the endoplasmic reticulum or Golgi apparatus). Transportation sequences can include, e.g., membrane translocating sequence, a transportan sequence, an antennapedia sequence, a cyclic integrin-binding peptide, and a Tat-mediated peptide, or modified versions thereof.

A linker, e.g., a linker peptide, can, directly or indirectly, connect the first amino acid sequence to one or more heterologous amino acid sequences. For example, a linker can connect the first amino acid sequence to a second amino acid sequence. A linker peptide can be, or contain, e.g., stretches of amino acids where at least four to six amino acids are glycine. (See, e.g., Mancebo et al. (1990) Mol. Cell. Biol. 10:2492-2502). A linker peptide can also be, or contain, six or more (e.g., seven, eight, nine, 10, 11, or 12 or more) histidine residues. The linker peptide can be, or contain, at least one (e.g., one, two, three, four, five, six, seven, or eight or more) protease cleavage site(s). The protease sites can be, e.g., a trypsin, a chymotrypin, or a factor Xa cleavage site. Such protease sites can be useful, e.g., to separate a first amino acid sequence from a heterologous sequence. For example, after expression and purification of a fusion protein containing a first amino acid sequence joined to a polyhistidine sequence (in this case used for purification) by a trypsin protease cleavage site, the polyhistidine sequence can be removed from first amino acid sequence by contacting the fusion protein with trypsin.

The first amino acid sequence and the second amino acid sequence can be associated with each other in a variety of ways. As used herein, "associated with" in the context of an interaction between two or more atoms or molecular units, includes any covalent or non-covalent bonding, or physical admixture, of two or more atoms or molecular units (e.g., a first amino acid sequence and a second amino acid sequence). The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). It is understood that the term "associated with" (e.g., in the context of a first amino acid sequence and a second amino acid sequence) is thus coextensive with the term "comprising."

In some embodiments, the first amino acid sequence and second amino acid sequence can be encoded by (and expressed as fusion protein from) a single nucleic acid sequence. In some instances, the first amino acid sequence and second amino acid sequence can be encoded by two or more (e.g., three, four, five, or six or more) different nucleic acid sequences. For example, the first amino acid sequence can be encoded by a first nucleic acid sequence and the second amino acid sequence can be encoded by a second nucleic acid sequence (see below under "Nucleic Acids and Methods for Producing the Peptides").

When expressed or produced separately, a first amino acid sequence and a second amino acid sequence can be cross-linked together using any of a number of known chemical cross linkers. Examples of such chemical cross-linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable chemical cross-linker, 4-succinimidyloxycarbonyl-α-methyl-α(2-pyridyldithio)toluene (SMPT), forms such a linkage between the two amino acid sequences utilizing a terminal lysine on one of the amino acid sequences and a terminal cysteine on the other. Heterobifunctional reagents which cross-link by a different coupling moiety on each amino acid sequence. In this way, the resulting "dimers" will be heterodimers (peptides containing the first and second amino acid sequences) rather than either homodimers (e.g., two first amino acid sequences or two second amino acid sequences) or a mixture of homodimers and heterodimers. Thus, the coupling moiety on a first amino acid sequence could be a cysteine residue and on the other a lysine residue. Other useful cross-linkers include, without limitation, chemicals that link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-Maleimidobenzoyl-N-hydroxysuccinimide ester), an amino group and a carboxyl group (e.g., 4-[p-Azidosalicylamido]butylamine), and an amino group and a guanadium group that is present in the side chain of arginine (e.g., p-Azidophenyl glyoxal monohydrate).

The coupling moieties will preferably be at the termini (C or N) of each amino acid sequence. They can be, as indicated above, a cysteine residue on each amino acid sequence, or a cysteine on one and a lysine on the other. Where they are two cysteine residues, cross-linking can be effected by, for example, exposing amino acid sequences to oxidizing conditions.

A fusion protein can contain a first amino acid sequence and a second amino acid sequence or the fusion protein can contain more than one (e.g., two, three, four, five, six, seven, or eight or more) additional heterologous amino acid sequences. The additional heterologous amino acid sequences can flank, or be joined to, the amino terminus and/or the carboxy-terminus of the first amino acid sequence.

Where more than two amino acid sequences are to be joined, at least one of the amino acid sequences can have more than one cross-linking moiety. For example, a first amino acid sequence can have a cross-linking moiety at the amino-terminus and carboxy-terminus. Such multimers can be constructed "sequentially." Thus, each amino acid sequence is joined to the next such that the terminal amino acid sequences in the chain only have one residue involved in an inter-domain (or inter-agent) bond while the "internal" amino acid sequence(s) each have two moieties involved in inter-domain bonds. Alternatively, one amino acid sequence (such as the first amino acid sequence) could be linked to multiple (e.g., 2, 3, 4, or 5) other amino acid sequences.

Also featured are peptide compositions comprising: a first component and a second component, wherein the first component is a peptide described herein. The second component can be, e.g., a heterologous amino acid sequence (as described above), any other antigenic peptide (e.g., a peptide other than those described herein, a detectable label (see below), a therapeutic agent, a diagnostic agent, or a prophylactic agent (see below). For example, a peptide composition can contain an amino acid sequence consisting of, or consisting essentially of, any of SEQ ID NOs: 1-18 and 29-536 and a detectable label such as a radionuclide.

It is understood that in some embodiments, a peptide described herein can have at the amino-terminal end and/or carboxy-terminal end up to 200 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200) amino acids that are heterologous.

The peptides described herein can bind to a major histocompatibility complex (MHC) molecule (e.g., an MHC class I molecule or an MHC class II molecule). The "Major Histocompatibility Complex" or "MHC" is a cluster of genes that plays a role in control of the cellular interactions responsible for physiologic immune responses. In humans, the MHC is known as the HLA complex (see, e.g., Paul et al., FUNDAMENTAL IMMUNOLOGY, 3rd Edition, Raven Press, New York, (1993) and Stites, et al., IMMUNOLOGY, 8th Edition, Lange Publishing, Los Altos, Calif. (1994)).

An "HLA supertype or family," as used herein, refers to sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms. Types of HLA class I molecules include, e.g., HLA-A1, HLA-A2, HLA-A3, HLA-A24, HLA-B7, HLA-B27, HLA-B44, HLA-B58, or HLA-B62. Such HLA molecules are described in detail in U.S. Pat. No. 7,026,443, the entire disclosure of which is incorporated by reference in its entirety.

A peptide can bind to an MHC molecule with high affinity or intermediate affinity. As used herein, "high affinity" binding of a peptide to an HLA class I molecule is defined as a binding with a dissociation constant ($K_D$) of less than 50 (e.g., 45, 40, 35, 30, 25, 20, 15, 10, 5, 1, 0.5, 0.1, or less than 0.05) nM. "Intermediate affinity" is a binding of a peptide to an HLA class I molecule with a $K_D$ of between about 50 nM and about 500 nM (e.g., 55, 60, 65, 70, 75, 80, 85, 90, 95, 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nM). "High affinity" binding of a peptide to HLA class II molecules is defined as binding with a $K_D$ of less than 100 (e.g., 95, 90, 85, 80, 75, 70, 65, 60, 55, 50, 45, 40, 35, 30, 25, 20, 15, 10, 5, 1, 0.5, 0.1, or less than 0.05) nM. "Intermediate affinity" of a peptide for an HLA class II molecule is binding with a $K_D$ of between about 100 and about 1000 nM (e.g., 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nM). Methods for determining the binding affinity of a peptide and an MHC molecule are known in the art and set forth in the accompanying Examples. Suitable methods are also described in, e.g., U.S. Pat. No. 7,026,443.

The peptides described herein can also be, in association with an MHC molecule, recognized by an antigen specific T cell receptor on a T cell. A variety of suitable methods can be used to determine whether a peptide, in association with an MHC molecule, is recognized by a T cell receptor on a T cell. For example, peripheral blood lymphocytes (PBL) from normal subjects can be cultured with a test peptide in the presence of antigen presenting cells in vitro over a period of several weeks. T cells specific for the peptide become activated during this time and can be detected using, e.g., proliferation assays (carboxyfluoroscein succinimidyl ester (CFSE) assays or ³H-thymidine assays), limiting dilution assays, cytotoxicity assays (e.g., calcein-release assays), or cytokine- (e.g., IFNγ), lymphokine-, or ⁵¹Cr-release assays (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998, the disclosures of each of which are incorporated by reference in their entirety). A suitable in vivo method involves immunizing HLA transgenic mice, wherein peptides in adjuvant are administered subcutaneously to HLA transgenic mice and several weeks following immunization, splenocytes are removed and cultured in vitro in the presence of test peptide for approximately one week and peptide-specific T cells are detected using, e.g., a ⁵¹Cr-release assay (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997, the disclosures of each of which are incorporated by reference in their entirety). Suitable methods are also set forth in the accompanying Examples. For example, the activation of a T cell by a peptide (in the context of an MHC molecule) can be determined by IFN-γ cytokine production, CD107α degranulation or calcein release cytotoxicity assays (see, e.g., Examples 13 and 14).

Additionally, direct quantification of antigen-specific T cells can be performed by staining T cells with detectably-labeled MHC complexes such as any of the MHC molecule multimer compositions described herein (see below) or HLA-I tetramers (e.g., as described in Altman, J. D. et al., Proc. Natl. Acad. Sci. USA 90:10330, 1993 and Altman, J. D. et al., Science 274:94, 1996, the disclosures of each of which are incorporated by reference in their entirety).

In some embodiments, the peptides can be modified (e.g., amino acids of the peptides can be substituted) in order to modulate (e.g., increase or decrease) one of more properties of the peptides. For example, one or more (e.g., two, three, or four) amino acids of one of the peptides depicted in Table 1 can be substituted in order to increase the affinity of the peptide for an MHC molecule. In some embodiments, an amino acid of one of the peptides described herein (e.g., a T cell Receptor contacting amino acid residue of the peptide) can be modified in order to enhance a binding interaction between a T cell receptor and the peptide (in the context of an MHC molecule). Such modified peptides are often referred to as "altered peptide ligands." (See, e.g., Kalergis et al. (2000) J Immunol. 165(1):280; Conlon et al. (2002) Science 1801; and International Publication No. WO02070003, the disclosure of each of which is incorporated by reference in their entirety).

Suitable methods for modifying the peptides as well as determining the effect of the modification are set forth in the accompanying Examples and are described in, e.g., Collins et al. (Immunlogical Reviews (1998) 163:151-160, the disclosure of which is incorporated by reference in its entirety).

Nucleic Acids and Methods for Producing the Peptides

The disclosure also features nucleic acid sequences (as well as nucleic acid vectors containing nucleic acid sequences) encoding, and methods for producing, one or more (e.g., one, two, three, four, five, six, seven, eight, nine, 10, 11, 12, 13, or 14) of any of the peptides described herein (or a fusion protein described herein). Such methods can include the steps of: optionally, providing a cell (or group of cells) comprising a nucleic acid vector containing a nucleic acid sequence encoding one of more of any of the peptides described herein (or a fusion protein described herein), the nucleic acid sequence being operably linked to an expression control sequence, and culturing the cell under conditions that permit the expression of the peptides (or fusion protein). The methods can also include the step of isolating the one or more peptides (or protein) from the cell, or from the medium in which the cell was cultured.

Suitable methods for constructing nucleic acid sequences and vectors (e.g., expression vectors) for recombinant expression of one or more of the peptides (or fusion proteins) described herein are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, New York, USA, November 1989, the disclosure of which is incorporated by reference in its entirety. The nucleic acids and vectors can be used, e.g., to express the peptides (or fusion proteins) in a wide variety of host cells including, e.g., a bacterial, a yeast, or a mammalian cell. The nucleic acids and vectors can also be used in, e.g., in vivo and ex vivo methods as described below.

The peptide-coding sequences (or fusion protein-coding sequences) can be operably-linked to promoter and/or enhancer elements that direct the expression of the peptides (or fusion proteins) encoded by the nucleic acids. Enhancers provide expression specificity in terms of time, location, and level. Unlike a promoter, an enhancer can function when located at variable distances from the transcription initiation site, provided a promoter is present. An enhancer can also be located downstream of the transcription initiation site or in an exon of the relevant gene. To bring a coding sequence under the control of a promoter, it is necessary to position the translation initiation site of the translational reading frame of the peptide between one and about fifty nucleotides downstream (3') of the promoter. Promoters of interest include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter.

The peptide-coding sequences, fusion protein-coding sequences, or vectors containing the such sequences, can contain a leader sequence that encodes a signal peptide. The leader sequence can be at the 5' end of the sequence encoding one or more of the peptides or fusion proteins described herein. The signal peptide can be immediately N-terminal of a given peptide (or fusion protein) or can be separated from it by one or more (e.g., 2, 3, 4, 6, 8, 10, 15 or 20) amino acids, provided that the leader sequence is in frame with the nucleic acid sequence encoding the peptide or fusion protein. The signal peptide, which is generally cleaved from the peptide (or fusion protein) prior to secretion (unless of course the signal peptide directs the insertion of a trasmembrane protein), directs the peptide (or fusion protein) to which it is attached into the lumen of the host cell endoplasmic reticulum (ER) during translation and the peptide (or fusion protein) is then secreted, via secretory vesicles, into the environment of the host cell. Useful signal peptides include, e.g., native leader sequences of cytokines or growth factors, KDEL (SEQ ID NO:23), or any signal sequences described in, e.g., U.S. Pat. No. 5,827,516, the disclosure of which is incorporated herein by reference in its entirety.

In some embodiments, the 5' end of a peptide-coding sequence (or fusion protein-coding sequence) can include a non-native ATG "start sequence." That is, e.g., an ATG sequence can be added to a nucleic acid encoding a peptide (or fusion protein) to ensure that the peptide (or fusion protein) is properly transcribed and translated. Although a leader sequence generally includes an ATG start sequence, in embodiments where it does not, the ATG sequence can be added at the 5' end of a nucleic acid encoding the leader sequence.

Suitable methods for constructing peptide-coding sequences and expression vectors are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, New York, USA, November 1989; the disclosure of which is incorporated herein by reference in its entirety.

A recombinant vector can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) Proc. Nat. Acad. Sci. USA 75:1929; Ito et al. (1983) J. Bacteriol. 153:163; U.S. Pat. No. 4,879,231; and Sreekrishna et al. (1987) Gene 59:115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPO-FECTAMINE®, or by contacting naked nucleic acid vectors with the cells in solution (see, e.g., Sambrook et al., supra).

Expression systems that can be used for small or large scale production of the peptides (or fusion proteins) described herein include, but are not limited to, microorganisms such as bacteria (for example, *E. coli* and *B. subtilis*) transformed with recombinant bacteriophage DNA, plasmid DNA, or cosmid DNA expression vectors; fungus (e.g., yeast (for example, *Saccharomyces* and *Pichia*)) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid); or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others).

As described above, following the expression of any of the peptides (or fusion proteins) described herein, the peptides (or fusion proteins) can be isolated from the cultured cells, or from the media in which the cells were cultured, using standard techniques (see Sambrook et al., supra). Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller peptides (e.g., peptides having less than 200 (e.g., less than 175, less than 150, less than 125, less than 100, less than 90, less than 80, less than 70, or less than 60) amino acids) can be chemically synthesized by standard chemical means such as FMOC solid-phase synthesis (see Example 1).

The peptides (and fusion proteins) described herein can, but need not, be isolated. The term "isolated," as applied to any of the peptides (or fusion proteins) described herein, refers to a peptide, a fragment thereof, (or for compositions, a macromolecular complex), that has been separated or purified from components (e.g., proteins or other naturally-occurring biological or organic molecules) which naturally accompany it. It is understood that recombinant molecules (e.g., recombinant peptides) will always be "isolated." Typically, a peptide (or fragment or macromolecular complex) is isolated when it constitutes at least 60%, by weight, of the total molecules of the same type in a preparation, e.g., 60% of the total molecules of the same type in a sample. For example, a peptide described herein is considered isolated when it constitutes at least 60%, by weight, of the total protein in a preparation or sample. In some embodiments, a molecule in the preparation consists of at least 75%, at least 90%, or at least 99%, by weight, of the total molecules of the same type in a preparation.

Similarly, the peptide-coding sequences, fusion protein-coding sequence or vectors containing such sequences described herein can also be isolated. The term "isolated," as applied to any of the peptide-coding sequences, fusion protein coding sequences or vectors described herein, refers to a peptide-coding sequence, a fusion protein coding sequence or vector, a fragment thereof that has been separated or purified from components (e.g., nucleic acids, proteins, or other naturally-occurring biological or organic molecules) which naturally accompany it. It is understood that recombinant molecules (e.g., recombinant vectors or peptide-coding or fusion protein-coding sequences) will always be "isolated." Typically, a peptide-coding sequence, fusion protein-coding sequence or vector (or fragment thereof) is isolated when it constitutes at least 60%, by weight, of the total molecules of the same type in a preparation, e.g., 60% of the total molecules of the same type in a sample. For example, a peptide-coding sequence or vector described herein is considered isolated when it constitutes at least 60%, by weight, of the total nucleic acid in a preparation or sample. In some embodiments, a molecule in the preparation consists of at least 75%, at least 90%, or at least 99%, by weight, of the total molecules of the same type in a preparation.

In some embodiments, the isolated peptides, fusion proteins, peptide-coding sequences, fusion protein-coding sequences or vectors can be frozen, lyophilized, or immobilized and stored under appropriate conditions, which allow the molecules to retain activity (e.g., the ability of a peptide to bind to an MHC molecule such as an MHC class I molecule or the ability of a vector to support expression of a peptide in a cell).

Additional Processing of the Peptides

Following the expression or synthesis of any of the peptides (or fusion proteins) described herein, the peptides (or fusion proteins) can be further processed. The further processing can include chemical or enzymatic modifications to peptides (or fusion protein) or, in cases where the peptides (or fusion proteins) are modified, the processing can include enzymatic or chemical alterations of existing modifications, or both. The additional processing of the peptides can include the addition (covalent or non-covalent joining) of a heterologous amino acid sequence such as, but not limited to, any of the heterologous amino acid sequences described above. Enzymatic treatment can involve contacting a peptide with, e.g., one or more proteases, phosphatases, or kinases under conditions that allow the peptide to be modified. Enzymatic treatment can involve contacting a peptide with one or more enzymes (e.g., an oligosaccharyltransferase or a mannosidase) capable of glycosylating, or modifying the glycosylation of, the peptide.

The processing can include the addition of, e.g., a detectable label to a peptide. For example, a peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radionuclide (e.g., $^{3}$H, $^{32}$P, $^{33}$P, $^{125}$I, or $^{35}$S).

The processing can also involve the coupling of the peptide (or fusion protein) to a polymer (e.g., a polyalkylene glycol moiety such as a polyethylene glycol moiety). In some embodiments, the polymer is coupled to the peptide at a site on the peptide that is an N terminus. In some embodiments, a peptide can contain one or more internal amino acid insertions that provide an internal polymer conjugation site to which a polymer can be conjugated.

Pharmaceutical Compositions

Any of the peptides, fusion proteins and nucleic acids encoding the peptides or fusion proteins described herein can be incorporated into pharmaceutical compositions. Such compositions typically include one or more of the peptides (and/or nucleic acids encoding the peptides) and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. One or more peptides can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds (e.g., one or more chemotherapeutic agents) can also be incorporated into the compositions. Preferably, the composition comprises two or more (e.g., 2, 3, 4, 5, or 6) of the peptides described herein. The composition may also include an immunogenic peptide other than one disclosed herein, e.g., a peptide from WT1 or a derivative thereof, e.g., as described herein. Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

A pharmaceutical composition is generally formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the pharmaceutical composition must be sterile and should be fluid to the extent that easy syringability exists. It should be stable under the conditions of manufacture and storage and must be preserved against any contamination by microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating one or more of the peptides (or one or more the nucleic acids encoding the peptides) in the required amount in an appropriate solvent with one or a combination of ingredients enumerated above, as required, followed by filtered sterilization. Generally, dispersions are prepared by incorporating the peptide(s) (or fusion proteins or nucleic acid(s) encoding the peptide(s)) into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the one or more peptides (or fusion proteins) can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; a flavoring agent such as peppermint, methyl salicylate, or orange flavoring.

The powders and tablets can contain from 1% to 95% (w/w) of an individual peptide or a mixture of two or more peptides. In certain embodiments, the peptide can range from about 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the peptide (or nucleic acid) with encapsulating material as a carrier providing a capsule in which the peptide with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the peptides (or fusion proteins or nucleic acids) can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the peptides (or fusion proteins or nucleic acids) can be formulated into ointments, salves, gels, or creams as generally known in the art.

The peptides (or fusion proteins or nucleic acids) can also be prepared in the form of suppositories (e.g., with conventional suppository bases such as cocoa butter and other glycerides) or retention enemas for rectal delivery.

In one embodiment, the peptides (or fusion proteins or nucleic acids) can be prepared with carriers that will protect the peptides (fusion protein or nucleic acid) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to, e.g., APCs with monoclonal antibodies to APC-specific antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form, as used herein, refers to physically discrete units suited as unitary dosages for the subject to be treated; each unit containing a predetermined quantity of the peptides (or fusion protein or nucleic acids) calculated to produce the desired therapeutic effect in association with the required pharmaceutical carrier. Dosage units can also be accompanied by instructions for use.

The nucleic acid molecules encoding the peptides (or fusion protein) can be inserted into vectors and used as gene therapy vectors (as described above). Gene therapy vectors can be delivered to a subject by, for example, intravenous injection, local administration (see, e.g., U.S. Pat. No. 5,328,470) or by stereotactic injection (see, e.g., Chen, et al. (1994) Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system (see below under "Ex Vivo Methods").

Additional examples of gene delivery vehicles include, but are not limited to, liposomes, biocompatible polymers, including natural polymers and synthetic polymers; lipoproteins; polypeptides; polysaccharides; lipopolysaccharides; artificial viral envelopes; metal particles; bacteria; viruses such as baculovirus, adenovirus, and retrovirus; bacteriophage; cosmids; plasmids; fungal vectors and other recombination vehicles typically used in the art which have been described for expression in a variety of eukaryotic and prokaryotic hosts, and may be used for gene therapy as well as for simple protein expression.

Examples of viral vectors include retroviral vectors, adenovirus vectors, adeno-associated virus vectors, alphavirus vectors and the like. Liposomes that comprise a targeting moiety such as an antibody or fragment thereof can also be used to prepare pharmaceutical compositions of nucleic acids for delivery to a subject.

Any of the pharmaceutical compositions described herein can be included in a container, pack, or dispenser together with instructions for administration as described below.

MHC Molecule Multimer Compositions and Methods for Using the Compositions

The disclosure also features compositions comprising: (i) one or more of any of the peptides described above and (ii) a major histocompatibility complex (MHC) molecule multimer. The multimer contains two or more (e.g., three, four, five, six, seven, eight, nine, or 10 or more) entire MHC molecules or peptide-binding regions of an MHC molecule. The one or more peptides can be associated with (e.g., covalently or non-covalently bound to) the MHC molecule multimer.

An MHC molecule of the multimer can be an MHC class I molecule (e.g., an HLA-A molecule such as an HLA-A2 or an HLA-A24 molecule) or an MHC class II molecule. The MHC molecule can be a mammalian (e.g., a rodent, a non-human primate, a human, or any other mammal described herein) MHC molecule.

The two or more MHC molecules (or the peptide-binding regions of the MHC molecules) in the multimer can be from the same MHC molecule or from different MHC molecules. For example, an MHC molecule multimer can contain five MHC molecules, three of which are the same MHC molecules and two of which are different from the first three. In another example, each MHC molecule of the multimer is different. At least one of the MHC molecules can bind to at least one of the peptides.

In some embodiments, the above compositions can contain at least two (e.g., two, three, four, five, six, seven, eight, nine, 10, 11, or 15 or more) of any of the peptides described herein. The composition may also include an immunogenic peptide other than one disclosed herein, e.g., a peptide from WT1 or a derivative thereof. Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

The compositions can also be associated with a detectable label. For example, one or more of the MHC molecules of the multimer can be covalently or non-covalently bound to a detectable label. Suitable detectable labels (e.g., enzymes, fluorescent materials, luminescent materials, bioluminescent materials, or radionuclides) as well as methods for joining detectable labels to a peptide or an MHC molecule are described above.

An MHC multimer composition can be generated using a peptide described above as follows: a peptide that binds to an HLA molecule is refolded in the presence of the corresponding HLA heavy chain and $\beta_2$-microglobulin to generate a trimolecular complex. The complex is then biotinylated at the carboxyl terminal end of the heavy chain at a site that was previously engineered into the heavy chain. Multimer formation is then induced by the addition of streptavidin.

As T cell receptors are capable of recognizing a specific peptide-MHC complex on a target cell among a wide variety of other peptide-MHC complexes, the MHC multimer compositions described herein can be used to, e.g., detect antigen-specific T cells in a population of unrelated T cells (see below). For such assays, the multimers will generally be detectably labeled (see above).

For example, a multimeric MHC molecule/peptide complex can be used in an assay to assess peripheral blood mononuclear cells for the presence of antigen-specific CTL following exposure to an immunogen. The MHC multimer complex can be used to directly visualize antigen-specific CTL (see, e.g., Ogg et al., Science 279:2103-2106, 1998; and Altman et al., Science 174:94-96, 1996) and determine the frequency of the antigen-specific CTL population in a sample of peripheral blood mononuclear cells. In one example, a detectably-labeled streptavidin used to multimerize the MHC multimer can be used to label T cells that bind to the MHC molecule/peptide complexes of the multimer. To do this, cells treated with the multimer are exposed, e.g., to a label (e.g., a fluorophore conjugated to biotin). The cells can then be readily isolated or detected, e.g., using flow cytometry.

Applications

The peptides, fusion proteins (and pharmaceutical compositions thereof), MHC multimer containing compositions, kits, and articles of manufacture described herein can be used in a variety of methods. For example, the peptides described herein can be used to: (i) induce an immune response in a subject (e.g., a subject with a cancer); (ii) activate a T cell in culture (e.g., a central memory T cell and/or effector memory T cell); and/or (iii) treat or even prevent a cancer. Cancers include, e.g., lung cancer, liver cancer, bile duct cancer, stomach cancer, cervical cancer, nasopharyngeal cancer, breast cancer, colon cancer, pancreatic cancer, blood cell cancers, e.g., plasma cell cancers such as multiple myeloma and leaukemia such as AML or CML. The peptides described herein can also be used to treat precancerous conditions such as smoldering multiple myeloma. As described above, the MHC multimer containing compositions can be used to, e.g., detect antigen-specific T cells in a population of unrelated T cells.

While the utility of the peptides (or pharmaceutical compositions thereof), MHC multimer containing compositions, kits, or articles of manufacture is in no way limited to any of the particular embodiments described herein, exemplary methods in which these reagents can be used are provided below.

Methods for Inducing an Immune Response

The disclosure also features a variety of methods for inducing an immune response in a subject. The methods for inducing an immune response in a subject can include the step of administering to a subject one or more of any of peptides described herein or any of the pharmaceutical compositions described herein. The immune response can be a CD8+ T cell, a CD4+ T cell, a cytotoxic T lymphocyte (CTL), a $T_H1$ response, a $T_H2$ response, or a combination of both types of responses.

Any of the above methods can also be, e.g., methods for treating or preventing (prophylaxis against) a cancer (e.g., plasma cell disorder such as multiple myeloma or Waldenstrom's macroglobulinemia, or any other cancer expressing XBP1, CD138, or CS1) in a subject. When the terms "prevent," "preventing," or "prevention" are used herein in connection with a given treatment for a given condition, they mean that the treated subject does not develop a clinically observable level of the condition at all (e.g., the subject does not exhibit one or more symptoms of the condition or, in the case of a cancer, the subject does not develop a detectable level of the cancer), As used herein, the term "treat" "treatment," or "treating" a subject having a disorder, e.g., cancer, are used in connection with a given treatment for a given disorder, wherein at least one symptom of the disorder is cured, healed, alleviated, relieved, altered, remedied, ameliorated, or improved. Treating includes administering an amount of a composition effective to alleviate, relieve, alter, remedy, ameliorate, improve or affect the disorder or the symptoms of the disorder. The treatment may inhibit deterioration or worsening of a symptom of a disorder or may cause the condition to develop more slowly and/or to a lesser degree (e.g., fewer symptoms or lower numbers of cancer cells in the subject) in the subject than it would have absent the treatment. For example, a treatment will be said to have "treated" the condition if it is given during the condition, e.g., during an early diagnosis of a cancer (e.g., the detection of a few cancer cells in a sample from the subject) that would have been expected to produce a given manifestation of the condition (an advanced cancer), and results in the subject's experiencing fewer and/or milder symptoms of the condition than otherwise expected. A treatment can "treat" a cancer (e.g., a plasma cell disorder such as multiple myeloma or Waldenstrom's macroglobulinemia) when the subject displays only mild overt symptoms of the cancer.

In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer).

Generally, a peptide (or peptides) delivered to the subject will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily (see below).

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted reagent production cells). See, e.g., U.S. Pat. Nos. 4,407,957, 5,798,113 and 5,800,828, each incorporated herein by reference in their entirety.

In general, the dosage of a peptide or a nucleic acid required depends on the choice of the route of administration; the nature of the formulation; the nature or severity of the subject's illness; the immune status of the subject; the subject's size, weight, surface area, age, and sex; other drugs being administered; and the judgment of the attending medical professional.

Suitable dosages of peptide for inducing an immune response are in the range of 0.000001 to 10 mg of the reagent or antigenic/immunogenic composition per kg of the subject. Wide variations in the needed dosage are to be expected in view of the variety of reagents and the differing efficiencies of various routes of administration. For example, nasal or rectal administration may require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). For example, a peptide or peptides can be administered as an initial immunization and then administered one or more times subsequently as a booster immunization.

In order to optimize therapeutic efficacy (e.g., the efficacy of the one or more peptides or the nucleic acids encoding the peptides to induce an immune response in a subject), compositions containing the peptides or nucleic acids can be first administered at different dosing regimens. The unit dose and regimen depend on factors that include, e.g., the species of mammal, its immune status, the body weight of the mammal.

The frequency of dosing for a pharmaceutical composition (e.g., a pharmaceutical composition described herein) is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status.

In some embodiments, a pharmaceutical composition can be administered to a subject at least two (e.g., three, four, five, six, seven, eight, nine, 10, 11, 12, 15, or 20 or more) times. For example, a pharmaceutical composition can be administered to a subject once a month for three months; once a week for a month; every other week, once a year for three years, once a year for five years; once every five years; once every ten years; or once every three years for a lifetime.

In some embodiments, the reagent can be administered with an immune modulator such as a Toll Receptor ligand or an adjuvant (see below).

As defined herein, a "therapeutically effective amount" of a peptide or a nucleic acid encoding a peptide is an amount of the peptide or nucleic acid that is capable of producing an immune response in a treated subject. A therapeutically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A therapeutically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

As defined herein, a "prophylactically effective amount" of a peptide or nucleic acid encoding a peptide is an amount of the peptide or nucleic acid that is capable of producing an immune response against a cancer cell (e.g., a breast cancer cell, a colon cancer cell, a pancreatic cancer cell, a prostate cancer cell, a multiple myeloma cell or Waldenstrom's macroglobulinemia cell) in a treated subject, which immune response is capable of preventing the development of a cancer in a subject or is able to substantially reduce the chance of a subject developing or continue developing a cancer (see above). A prophylactically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A prophylactically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

The subject can be any animal capable of an immune response to an antigen such as, but not limited to, a mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. The subject can be one having, suspected of having, or at risk of developing a cancer such as multiple myeloma, Waldenstrom's macroglobulinemia, or any other type of cancer that expresses XBP1, CD138, or CS-1 (e.g., lung cancer, liver cancer, bile duct cancer, stomach cancer, cervical cancer, nasopharyngeal cancer, breast cancer, colon cancer, pancreatic cancer, leukemia, e.g., AML or CML). The subject can be one in remission from the cancer, e.g., the breast cancer, colon cancer, pancreatic cancer, prostate cancer, leukemia, e.g., AML or CML, multiple myeloma or Waldenstrom's macroglobulinemia.

The methods can also include the step of, prior to administering the one or more peptides (or nucleic acids) to the subject, determining whether one or more cancer cells of the subject's cancer (e.g., lung cancer, liver cancer, bile duct cancer, stomach cancer, cervical cancer, nasopharyngeal cancer, breast cancer, colon cancer, pancreactic cancer, prostate cancer, leukemia or a plasma cell disorder such as multiple myeloma or Waldenstrom's macroglobulinemia) express XBP1, CD138, or CS-1. Expression of these proteins includes both mRNA and protein expression. Methods for detecting protein and mRNA expression in a cell are known in the art and include, e.g., enzyme-linked immunosorbent assay (ELISA), western and dot-blotting techniques, or immunohistochemistry techniques for detecting protein and reverse transcription-polymerase chain reaction (RT-PCR) or northern-blotting techniques for detecting mRNA. (See Sambrook et al., supra).

The peptides or composition may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The additional treatment can be, e.g., surgery, one or more chemotherapeutic agents, one or more forms of ionizing radiation, and/or one or more immunomodulatory agents.

The one or more forms of ionizing radiation can be gamma-irradiation, X-irradiation, or beta-irradiation.

Exemplary classes of chemotherapeutic agents include, e.g., the following:

alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®).

anti-EGFR antibodies (e.g., cetuximab (Erbitux®) and panitumumab (Vectibix®).

anti-HER-2 antibodies (e.g., trastuzumab (Herceptin®).

antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®) and gemcitabine (Gemzar®). Preferred antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®).

vinca alkaloids: vinblastine (Velban®, Velsar®), vincristine (Vincasar®, Oncovin®), vindesine (Eldisine®), vinorelbine (Navelbine®).

platinum-based agents: carboplatin (Paraplat®, Paraplatin®), cisplatin (Platinol®), oxaliplatin (Eloxatin®).

anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®). Preferred anthracyclines include daunorubicin (Cerubidine®, Rubidomycin®) and doxorubicin (Adriamycin®).

topoisomerase inhibitors: topotecan (Hycamtin®), irinotecan (Camptosar®), etoposide (Toposar®, VePesid®), teniposide (Vumon®), lamellarin D, SN-38, camptothecin.

taxanes: paclitaxel (Taxol®), docetaxel (Taxotere®), larotaxel, cabazitaxel.

epothilones: ixabepilone, epothilone B, epothilone D, BMS310705, dehydelone, ZK-Epothilone (ZK-EPO).

poly ADP-ribose polymerase (PARP) inhibitors: (e.g., BSI 201, Olaparib (AZD-2281), ABT-888, AG014699, CEP 9722, MK 4827, KU-0059436 (AZD2281), LT-673, 3-aminobenzamide).

antibiotics: actinomycin (Cosmegen®), bleomycin (Blenoxane®), hydroxyurea (Droxia®, Hydrea®), mitomycin (Mitozytrex®, Mutamycin®).

immunomodulators: lenalidomide (Revlimid®), thalidomide (Thalomid®).

immune cell antibodies: alemtuzamab (Campath®), gemtuzumab (Myelotarg®), rituximab (Rituxan®), tositumomab (Bexxar®).

interferons (e.g., IFN-alpha (Alferon®, Roferon-A®, Intron®-A) or IFN-gamma (Actimmune®)).

interleukins: IL-1, IL-2 (Proleukin®), IL-24, IL-6 (Sigosix®), IL-12.

HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG").

angiogenesis inhibitors which include, without limitation A6 (Angstrom Pharmacueticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP 02) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514

(Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (Medlmmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

anti-androgens which include, without limitation nilutamide (Nilandron®) and bicalutamide (Caxodex®).

antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride.

anti-hypercalcaemia agents which include without limitation gallium (III) nitrate hydrate (Ganite®) and pamidronate disodium (Aredia®).

apoptosis inducers which include without limitation ethanol, 2-[[3-(2,3-dichlorophenoxy)propyl]amino]-(9Cl), gambogic acid, embelin and arsenic trioxide (Trisenox®).

Aurora kinase inhibitors which include without limitation binucleine 2.

Bruton's tyrosine kinase inhibitors which include without limitation terreic acid.

calcineurin inhibitors which include without limitation cypermethrin, deltamethrin, fenvalerate and tyrphostin 8.

CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide.

CD45 tyrosine phosphatase inhibitors which include without limitation phosphonic acid.

CDC25 phosphatase inhibitors which include without limitation 1,4-naphthalene dione, 2,3-bis[(2-hydroxyethyl) thio]-(9Cl).

CHK kinase inhibitors which include without limitation debromohymenialdisine.

cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid).

cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl).

cyclin dependent kinase inhibitors which include without limitation olomoucine and its derivatives, purvalanol B, roascovitine (Seliciclib®), indirubin, kenpaullone, purvalanol A and indirubin-3'-monooxime.

cysteine protease inhibitors which include without limitation 4-morpholinecarboxamide, N-[(1S)-3-fluoro-2-oxo-1-(2-phenylethyl)propyl]amino]-2-oxo-1-(phenylmethyl) ethyl]-(9Cl).

DNA intercalators which include without limitation plicamycin (Mithracin®) and daptomycin (Cubicin®).

DNA strand breakers which include without limitation bleomycin (Blenoxane®).

E3 ligase inhibitors which include without limitation N-((3,3,3-trifluoro-2-trifluoromethyl)propionyl)sulfanilamide.

EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

farnesyltransferase inhibitors which include without limitation A-hydroxyfarnesylphosphonic acid, butanoic acid, 2-[(2S)-2-[[(2S,3S)-2-[[(2R)-2-amino-3-mercaptopropyl] amino]-3-methylpentyl]oxy]-1-oxo-3-phenylpropyl] amino]-4-(methylsulfonyl)-1-methylethylester (2S)-(9Cl), and manumycin A.

Flk-1 kinase inhibitors which include without limitation 2-propenamide, 2-cyano-3-[4-hydroxy-3,5-bis(1-methylethyl)phenyl]-N-(3-phenylpropyl)-(2E)-(9Cl).

glycogen synthase kinase-3 (GSK3) inhibitors which include without limitation indirubin-3'-monooxime.

Heat Shock Protein 90 (Hsp90) chaperone modulators which include without limitation AUY922, STA-9090, ATI13387, MCP-3100, IPI-504, IPI-493, SNX-5422, Debio0932, HSP990, DS-2248, PU-H71, 17-DMAG (Alvespimycin), and XL888.

histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin and compounds disclosed in WO 02/22577.

I-kappa B-alpha kinase inhibitors (IKK) which include without limitation 2-propenenitrile, 3-[(4-methylphenyl) sulfonyl]-(2E)-(9Cl).

imidazotetrazinones which include without limitation temozolomide (Methazolastone®, Temodar® and its derivatives (e.g., as disclosed generically and specifically in U.S. Pat. No. 5,260,291) and Mitozolomide.

Insulin like growth factor pathway inhibitors such as IGF inhibitors or IGF receptor (IGFR1 or IGFR2) inhibitors include without limitation, small molecule inhibitors, e.g., OSI-906; anti-IGF antibodies or anti-IGFR antibodies, e.g., AVE-1642, MK-0646, IMC-A12 (cixutumab), R1507, CP-751,871 (Figitumumab).

insulin tyrosine kinase inhibitors which include without limitation hydroxyl-2-naphthalenylmethylphosphonic acid.

c-Jun-N-terminal kinase (JNK) inhibitors which include without limitation pyrazoleanthrone and epigallocatechin gallate.

mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl).

MDM2 inhibitors which include without limitation trans-4-iodo, 4'-boranyl-chalcone.

MEK inhibitors which include without limitation butanedinitrile, bis[amino[2-aminophenyl)thio]methylene]-(9Cl).

MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996.

mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD.

NGFR tyrosine kinase inhibitors which include without limitation tyrphostin AG 879.

p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxybenzoyl)amino]-4-methylphenyl]-(9Cl).

p56 tyrosine kinase inhibitors which include without limitation damnacanthal and tyrphostin 46.

PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854.

phosphatidylinositol 3-kinase inhibitors which include without limitation wortmannin, and quercetin dihydrate.

phosphatase inhibitors which include without limitation cantharidic acid, cantharidin, and L-leucinamide.

PKC inhibitors which include without limitation 1-H-pyrollo-2,5-dione,3-[1-[3-(dimethylamino)propyl]-1H-indol-3-yl]-4-(1H-indol-3-yl)-(9Cl), Bisindolylmaleimide IX, Sphinogosine, staurosporine, and Hypericin.

PKC delta kinase inhibitors which include without limitation rottlerin.polyamine synthesis inhibitors which include without limitation DMFO.

proteasome inhibitors which include, without limitation aclacinomycin A, gliotoxin and bortezomib (Velcade®).

protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid.

protein tyrosine kinase inhibitors which include, without limitation tyrphostin Ag 216, tyrphostin Ag 1288, tyrphostin Ag 1295, geldanamycin, genistein and 7H-pyrollo[2,3-d] pyrimidine derivatives;

PTP1B inhibitors which include without limitation L-leucinamide.

SRC family tyrosine kinase inhibitors which include without limitation PP1 and PP2.

Syk tyrosine kinase inhibitors which include without limitation piceatannol.

Janus (JAK-2 and/or JAK-3) tyrosine kinase inhibitors which include without limitation tyrphostin AG 490 and 2-naphthyl vinyl ketone.

retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®).

RNA polymerase II elongation inhibitors which include without limitation 5,6-dichloro-1-beta-D-ribofuranosylbenzimidazole.

serine/threonine kinase inhibitors which include without limitation 2-aminopurine.

sterol biosynthesis inhibitors which include without limitation squalene epoxidase and CYP2D6.VEGF pathway inhibitors which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632, AV-951 (tivozanib) and AZD2171 (also known as cediranib) (Recentin™).

For example, one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, thalidomide, lenalidomide, a proteosome inhibitor (e.g., bortezomib), an hsp90 inhibitor (e.g., tenespinmycin), transplatinum, 5-flurouracil, vincristin, vinblastin, methotrexate, or an analog of any of the aforementioned. Immunomodulatory agents include, e.g., a variety of chemokines and cytokines such as Interleukin 2 (IL-2), granulocyte/macrophage-colony stimulating factor (GM-CSF), and Interleukin 12 (IL-12).

In one embodiment, the additional therapy is one or more additional immunogenic peptide, e.g., one or more immunogenic peptide from WT1 or a derivative thereof. Exemplary WT1 immunogenic peptides include, but are not limited to, a WT1 class 1 epitope; a peptide comprising (or consisting of) RMFPNAPYL (SEQ ID NO: 538) (WT1 126-134); a peptide comprising (or consisting of) YMFPNAPYL (SEQ ID NO: 539); a peptide comprising (or consisting of) RSDELVRHHNMHQRNMTKL (SEQ ID NO: 540) (WT1 427-445); a peptide comprising (or consisting of) PGCNKRYFKLSHLQMHSRKHTG (SEQ ID NO: 541) (WT1 331-352); a peptide comprising (or consisting of) SGQARMFPNAPYLPSCLES (SEQ ID NO:

542) (WT1 122-140); and a peptide comprising (or consisting of) SGQAYMFPNAPYLPSCLES (SEQ ID NO: 543). Other WT1 immunogenic peptides are described in U.S. Pat. No. 7,598,221, the contents of which is incorporated herein by reference. Other immunogenic peptides include, but are not limited to, an immunogenic peptide from MUC1, an immunogenic peptide from gp100, an immunogenic peptide from TRP-2, an immunogenic peptide from MAG1, an immunogenic peptide from NY-ESO1, an immunogenic peptide from HER-2; and an immunogenic peptide from AIM2.

The subject can have, be suspected of having, or be at risk of developing a cancer such as lung cancer, liver cancer, bile duct cancer, stomach cancer, cervical cancer, nasopharyngeal cancer, breast cancer, colon cancer, pancreactic cancer, prostate cancer, leukemia, multiple myeloma or Waldenstrom's macroglobulinemia. A subject "suspected of having a cancer" is one having one or more symptoms of a cancer. Symptoms of cancer are well-known to those of skill in the art and generally include, without limitation, pain, weight loss, weakness, excessive fatigue, difficulty eating, loss of appetite, chronic cough, worsening breathlessness, coughing up blood, blood in the urine, blood in stool, nausea, vomiting, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, difficulty swallowing, and the like. Symptoms of multiple myeloma specifically include, e.g., bone pain (e.g., in the back or ribs), high levels of calcium in the blood, excessive thirst or urination, constipation, nausea, loss of appetite, confusion, weakness or numbness in the legs, weight loss, or repeated infections. Symptoms indicative of Waldenstrom's macroglobulinemia include, e.g., weakness, swollen lymph nodes, severe fatigue, nose bleeds, weight loss, neurological problems.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC), has been exposed to conditions, or is presently affected by conditions, that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, 4-aminobiphenyl, aromatic amines, benzene, benz{a}anthracene, benzo {a}pyrene, formaldehyde, hydrazine, Polonium-210 (Radon), urethane, or vinyl chloride). The subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. In addition, a subject can be "at risk of developing a cancer" when the subject suffers from an inflammation (e.g., chronic inflammation). A subject can be at risk of developing multiple myeloma if, e.g., the subject has monoclonal gammopathy of undetermined significance (MGUS). A subject can be at risk of developing any cancer described herein, for example, cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), head and neck, or multiple myeloma.

Multiple myeloma is a hematological cancer that affects approximately 45,000 people in United States each year. Multiple myeloma is characterized by a multifocal proliferation and clonal expansion of plasma cells within the bone marrow, which can result in skeletal dysfunction, serum monoclonal gammopathy, immunosuppression and end-organ sequelae.

Smoldering multiple myeloma (SMM) patients are at a high risk for progression to active multiple myeloma. While treatments including bone marrow transplant and chemotherapy are used to treat patients that develop active multiple myeloma, the prognosis of patients with these stage of the disease is often poor.

Smoldering multiple myeloma (SMM) is an asymptomatic, plasma cell proliferative disorder characterized by monoclonal plasma cell proliferation in the bone marrow and monoclonal proteins in the blood and/or urine without renal dysfunction, hypercalcemia, bone disease, or anemia. The diagnosis of SMM requires a serum monoclonal (M) protein level ≥3 g/dL and/or bone marrow clonal plasma cells (BMPC) >10%, and the absence of end-organ damage (i.e., hypercalcemia, renal insufficiency, anemia, or bone lesions [CRAM]). Although asymptomatic, SMM is associated with a high-risk of progression to symptomatic multiple myeloma (MM) or amyloidosis.

Currently, there is no active treatment for SMM. Instead, a "watchful" waiting approach is taken, with treatment initiated after progression to symptomatic disease. For most patients, progression is indicated by an increase in anemia (hemoglobin lower than 2 g/dL below the lower limit of normal or <10 g/dL) and/or skeletal involvement, including bone lesions and/or diffuse osteoporosis.

A subject having smoldering multiple myeloma is also a subject at risk for developing multiple myeloma. Smoldering multiple myeloma can be determined by increased levels of monoclonal protein, e.g., in the urine or blood of a subject. In addition, subjects having smoldering multiple myeloma can exhibit increased numbers of myeloma cells in the bone marrow. At present, it has been estimated that SMM accounts for approximately 15% of all newly diagnosed cases of MM. The median time to progression from diagnosis to symptomatic MM ranges from 2 to 3 years, and the annual risk of progression from SMM to symptomatic MM requiring treatment is estimated to be 10%. The risk of progression is contingent on 1) monoclonal protein levels ≥3 g/dL; 2) BMPC ≥10%; and 3) the presence of abnormal serum free light chain (FLC) ratio. As shown in Table 1, the median time to progression is notably shorter in patients meeting all 3 of these prognostic criteria (1.9 years) compared to those meeting only 1 of these criteria (10 years) or 2 of these criteria (5.1 years). Similarly, the proportion of patients progressing to symptomatic MM by 5 years is notably higher in those meeting all 3 prognostic criteria (76%) compared to those meeting only 1 or 2 of these criteria (25% and 51%, respectively).

TABLE 4

| SMM Prognosis | | | |
| --- | --- | --- | --- |
| Number of Risk Factors | Number of Patients (N) | Median Time to Progression (Years) | Progression at 5 Years (%) |
| 1 | 81 | 10 | 25 |
| 2 | 114 | 5.1 | 51 |
| 3 | 78 | 1.9 | 76 |

Source: Kyle RA, et al, 2010.

Recent data have demonstrated the importance of other prognostic criteria for SMM, including the presence of an aberrant phenotype of BMPC defined as a decrease in 1 or 2 of the uninvolved immunoglobulin (Ig) isotypes as well as whether M protein remains stable or progressively worsens over time. In this latter case, referred to as evolving SMM, patients with a progressive increase in serum M protein levels have shorter median time to progression (TTP) compared to those with a stable M protein of 1.3 versus 3.9 years, respectively.

In some embodiments, the method can also include determining if an immune response occurred in a subject after administering a peptide(s), nucleic acids or composition described herein to the subject. Suitable methods for determining whether an immune response occurred in a subject include use of immunoassays to detect, e.g., the presence of antibodies specific for a peptide in a biological sample from the subject. For example, after the administration of the peptide or composition to the subject, a biological sample (e.g., a blood sample) can be obtained from the subject and tested for the presence of antibodies specific for the peptide(s). An immune response can also be detected by assaying for the presence or amount of activated T cells in a sample. Such assays include, e.g., proliferation assays, limiting dilution assays, cytotoxicity assays (e.g., lympho-kine- or $^{51}$Cr-release assays)(as described above).

In some embodiments, the methods can also include the step of determining whether a subject has a cancer. Suitable methods for such a determination depend on the type of cancer to be detected in the subject, but are known in the art. Such methods can be qualitative or quantitative. For example, a medical practitioner can diagnose a subject as having multiple myeloma when the subject exhibits two or more (e.g., three, four, five, or six or more) symptoms of multiple myeloma such as any of those described herein. A subject can also be determined to have multiple myeloma by measuring the blood calcium level, the white or red blood cell count, or the amount of protein in the urine of a subject.

Ex Vivo Approaches. An ex vivo strategy for inducing an immune response in a subject can involve contacting suitable APCs (e.g., dendritic cells, monocytes, or macrophages) obtained from the subject with any of the peptides or compositions described herein. Alternatively, the cells can be transfected with a nucleic acid (e.g., an expression vector) encoding one or more of the peptides and optionally cultured for a period of time and under conditions that permit the expression of the peptides. The transfection method will depend on the type of cell and nucleic acid being transfected into the cell. (See above under "Nucleic Acids and Methods for Producing the Peptides" and also Sambrook et al., supra). Following the contacting or transfection, the cells are then returned to the subject.

The cells can be any of a wide range of types expressing MHC class I or II molecules. For example, the cells can include bone marrow cells, macrophages, monocytes, dendritic cells, T cells (e.g., T helper cells, CD4$^+$ cells, CD8$^+$ cells, or cytotoxic T cells), or B cells.

Ex vivo methods for stimulating an immune response can include contacting in vitro a T cell (e.g., in a population of lymphocytes obtained from a subject) with an antigen-presenting cell expressing an MHC molecule bound to one of the peptides described herein for an amount of time (and under conditions) that is sufficient to activate the T cell. Following the contacting, the activated T cell(s) are reintroduced into the subject from which the cells were obtained. Methods for generating an APC expressing an MHC molecule bound to one of the peptides described herein are set forth above in this section.

In some embodiments of any of the ex vivo methods, cells can be obtained from a subject of the same species other than the subject (allogeneic) can be contacted with the reagents (or immunogenic/antigenic compositions) and administered to the subject.

Methods for Producing an Antibody in a Subject

Methods of producing an antibody specific for an immunogen (e.g., one or more of any of the peptides described herein) are known in the art and detailed below. For example, antibodies or antibody fragments specific for a peptide described herein can be generated by immunization, e.g., using an animal, or by in vitro methods such as phage display. All or part of a peptide described herein can be used to generate an antibody or antibody fragment.

A peptide can be used to prepare antibodies by immunizing a suitable subject, (e.g., rabbit, goat, mouse, or other mammal such as a human) with the peptide. An appropriate immunogenic preparation can contain, for example, any of the reagents described herein. The preparation can further include an adjuvant, such as Freund's complete or incomplete adjuvant, alum, RIBI, or similar immunostimulatory agent. Adjuvants also include, e.g., cholera toxin (CT), *E. coli* heat labile toxin (LT), mutant CT (MCT) (Yamamoto et al. (1997) J. Exp. Med. 185:1203-1210) mutant *E. coli* heat labile toxin (MLT) (Di Tommaso et al. (1996) Infect. Immunity 64:974-979), a combination of carboxymethylcellulose, polyinosinic-polycytidylic acid, and poly-L-lysine double-stranded RNA (e.g., poly IC-LC, e.g., hiltonol), a water-and-oil emulsion (e.g., montanide), and proteins (e.g., a cytokine, a complement, GCSF, GM-CSF). MCT and MLT contain point mutations that substantially diminish toxicity without substantially compromising adjuvant activity relative to that of the parent molecules. Immunization of a suitable subject with an immunogenic peptide preparation (e.g., any of the reagents described herein) induces a polyclonal anti-peptide antibody response.

The term antibody as used herein refers to immunoglobulin molecules and immunologically active portions of immunoglobulin molecules (i.e., molecules that contain an antigen binding site that specifically binds to the peptide (e.g., a peptide described herein)). An antibody that specifically binds to a peptide described herein is an antibody that binds the peptide, but does not substantially bind other molecules in a sample. Examples of immunologically active portions of immunoglobulin molecules include, e.g., F(ab) fragments, F(ab')$_2$ fragments, or any other antibody fragments described herein (see below).

The anti-peptide antibody can be a monoclonal antibody or a preparation of polyclonal antibodies. The term monoclonal antibody, as used herein, refers to a population of antibody molecules that contain only one species of an antigen binding site capable of immunoreacting with the peptide. A monoclonal antibody composition thus typically displays a single binding affinity for a particular peptide with which it immunoreacts.

Polyclonal anti-peptide antibodies can be prepared as described above by immunizing a suitable subject with a peptide immunogen. The anti-peptide antibody titer in the immunized subject can be monitored over time by standard techniques, such as with an enzyme linked immunosorbent assay (ELISA) using immobilized peptide. If desired, the antibody molecules directed against the peptide can be isolated from the mammal (e.g., from the blood) and further purified by techniques such as protein A chromatography to obtain the IgG fraction. At an appropriate time after immunization, e.g., when the anti-peptide antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), or the EBV-hybridoma technique (Cole et al. (1985), Monoclonal Antibodies and Cancer Therapy, Alan R. Liss, Inc., pp. 77-96). Any of the many well known protocols used for fusing lymphocytes and immortalized cell lines can be applied for the purpose of generating an anti-peptide monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, New York (1980); and Lerner (1981) Yale J. Biol. Med., 54:387-402, the disclosures of each of which are incorporated by reference in their entirety).

As an alternative to preparing monoclonal antibody-secreting hybridomas, a monoclonal anti-peptide antibody can be identified and isolated by screening a recombinant combinatorial immunoglobulin library (e.g., an antibody phage display library) with a peptide described herein to isolate immunoglobulin library members that bind the peptide.

An anti-peptide antibody (e.g., a monoclonal antibody) can be used to isolate the peptide by techniques such as affinity chromatography or immunoprecipitation. Moreover, an anti-peptide antibody can be used to detect the peptide in screening assays described herein. An antibody can optionally be coupled to a detectable label such as any of those described herein or a first or second member of a binding pair (e.g., streptavidin/biotin or avidin/biotin), the second member of which can be conjugated to a detectable label.

Non-human antibodies to a target peptide (e.g., a peptide described herein) can also be produced in a non-human host (e.g., a rodent) and then humanized, e.g., as described in U.S. Pat. No. 6,602,503, EP 239 400, U.S. Pat. Nos. 5,693, 761, and 6,407,213, the disclosures of each of which are incorporated by reference in their entirety.

Methods for Selecting a Therapy

Methods for selecting a therapy for a subject with a cancer (e.g., a plasma cell disorder such as multiple myeloma and/or Waldenstrom's macroglobulinemia or any cancer in which XBP1, CD138, or CS1 are expressed (e.g., lung cancer, liver cancer, bile duct cancer, stomach cancer, cervical cancer, nasopharyngeal cancer, breast cancer, colon cancer, pancreatic cancer, leukemia such as AML or CML)) or with a precancerous condition (e.g., smoldering multiple myeloma) include the steps of: optionally, determining whether one or more cells (e.g., plasma cells) of a subject's cancer express XBP1; and if one or more cells express XBP1, selecting as a therapy for the subject a peptide or composition described herein e.g., a XBP1 peptide or composition comprising a XBP1 peptide described herein.

Methods for selecting a therapy for a subject with a cancer can include the steps of: optionally, determining whether one or more cells (e.g., plasma cells) of a subject's cancer express CD138; and if one or more cells express CD138, selecting as a therapy for the subject a peptide or composition described herein e.g., a CD138 peptide or composition comprising a CD138 peptide described herein.

Methods for selecting a therapy for a subject with a cancer can include the steps of: optionally, determining whether one or more cells (e.g., plasma cells) of a subject's cancer express CS-1; and if one or more cells express CS-1, selecting as a therapy for the subject a peptide or composition described herein, e.g., a CS-1 peptide or composition comprising a CS-1 peptide described herein.

It is understood that where one or more cells (e.g., plasma cells) of a subject's cancer express two or more of XBP1, CD138, and CS-1, a combination of suitable peptides can be delivered to the subject, e.g., via a composition described herein. For example, where one or more cells (e.g., plasma cells) of a subject's cancer are determined to express XBP1 and CD138, the methods for selecting a therapy can include selecting as a therapy for the subject: at least one XBP1 peptide and at least one CD138 peptide described herein, or a composition comprising such peptides.

Methods for determining whether one or more cells express XBP1, CD138, or CS-1 are known in the art and described above. For example, a biological sample (e.g., a blood sample or lymph node tissue sample) obtained from a subject can be tested using an XBP1-, CD138-, or CS-1-specific antibody made by a method described herein to detect the presence or amount of an XBP1, CD138, or CS-1 polypeptide expressed by a cell (or cell lysate). (See, e.g., the working Examples and Sambrook et al., supra). Methods for assaying a biological sample for the presence or amount of a polypeptide include, e.g., ELISA, immunohistochemistry, flow cytometry, western-blotting, or dot-blotting assays.

In some embodiments, any of the methods described herein can also include the step of providing a biological sample from a subject and/or obtaining a biological sample from a subject. Suitable biological samples for the methods described herein include any biological fluid, cell, tissue, or fraction thereof, which includes analyte proteins of interest (e.g., XBP1, CD138, or CS-1 proteins). A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a cell-containing biological fluid such as urine, blood, plasma, serum, saliva, semen, sputum, cerebral spinal fluid, tears, mucus or an aspirate (e.g., a lung or breast nipple aspirate), or such a sample absorbed onto a paper or polymer substrate. A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of sample types from a subject such as a combination of a tissue and biological fluid.

The biological samples can be obtained from a subject, e.g., a subject having, suspected of having, or at risk of developing, a cancer (e.g., lung cancer, liver cancer, bile duct cancer, stomach cancer, cervical cancer, nasopharyngeal cancer, breast cancer, colon cancer, pancreatic cancer, prostate cancer, leukemia (e.g., AML or CML), multiple myeloma and/or Waldenstrom's macroglobulinemia). Any suitable methods for obtaining the biological samples can be employed, although exemplary methods include, e.g., phle-botomy, swab (e.g., buccal swab), aspiration, or fine needle aspirate biopsy procedure. Non-limiting examples of tissues susceptible to fine needle aspiration include lymph node, lung, thyroid, breast, and liver. Samples can also be col-lected, e.g., by microdissection (e.g., laser capture micro-dissection (LCM) or laser microdissection (LMD)), bladder wash, smear (PAP smear), or ductal lavage.

After detecting a cancer (e.g., lung cancer, liver cancer, bile duct cancer, stomach cancer, cervical cancer, nasopha-ryngeal cancer, breast cancer, colon cancer, pancreatic can-cer, prostate cancer, leukemia, multiple myeloma and/or Waldenstrom's macroglobulinemia) or a precancerous con-dition, e.g., smoldering multiple myeloma, in a subject, e.g., using a method described above, a medical practitioner (e.g., a doctor) can select an appropriate therapeutic modality for the subject (e.g., a therapy comprising one or more of the peptides described herein) by, e.g.: (i) writing a prescription for a medicament; (ii) giving (but not necessarily adminis-tering) a medicament to a subject (e.g., handing a sample of a prescription medication to a patient while the patient is at the physician's office); (iii) communication (verbal, written (other than a prescription), or electronic (email, an electronic post to a secure site)) to the patient of the suggested or recommended therapeutic modality (e.g., a therapy compris-ing one or more of the peptides described herein); or (iv) identifying a suitable therapeutic modality for a subject and disseminating the information to other medical personnel, e.g., by way of patient record. The latter (iv) can be useful in a case where, e.g., more than one therapy or therapeutic agent are to be administered to a patient by different medical practitioners.

After detecting the presence or amount of XBP1, CD138, or CS-1 in a subject (using any of the methods above); and/or selecting a therapy for the subject, a medical practi-tioner (e.g., a doctor) can administer the appropriate thera-peutic modality to the subject. Methods for administering a therapy comprising one or more of the peptides described herein as detailed above.

In addition, a medical practitioner can also select, pre-scribe and/or administer one or more additional therapeutic agents to treat a cancer or one or more medicaments to treat side-effects of an anti-cancer agent. Suitable chemothera-peutic agents for treating multiple myeloma and/or Walden-strom's macroglobulinemia include, e.g., melphalan, cyclo-phosphamide, vincristine, doxorubicin, prednisone, dexamethasone, proteosome inhibitors (e.g., bortezomib), thalidomide, or lenalidomide.

Side effects of anti-cancer agents include, e.g., anemia, gastrointestinal symptoms (e.g., nausea, vomiting, diarrhea), leukopenia (decreased number of white blood cells, which may cause infection), temporary hair loss, or thrombocy-topenia (decreased number of platelets, which may cause bleeding). Thus, a doctor can prescribe or administer to a subject a chemotherapeutic agent such as vincristine along with an anti-anemia medicament such as epoetin alpha (e.g., Procrit® or Epogen®).

Kits and Articles of Manufacture

The disclosure also features a variety of kits. The kits can include, e.g., one or more (e.g., one, two, three, four, five, six, seven, eight, nine, or 10 or more) of any of the peptides or compositions (or expression vectors containing nucleic acid sequences encoding one or more peptides) described herein; and instructions for administering the peptide or composition to a subject. The kit can include one or more pharmaceutically acceptable carriers and/or one or more immune stimulating agents and/or one or more immune modulating agents. The immune stimulating agents can be, e.g., a T helper epitope, an altered peptide ligand, or an adjuvant. In one embodiment, the immune stimulating agent can be a combination of carboxymethylcellulose, polyinos-inic-polycytidylic acid, and poly-L-lysine double-stranded RNA (e.g., poly IC-LC, e.g., hiltonol); a water-and-oil emulsion (e.g., montanide); or a protein (e.g., a cytokine, a complement, GCSF, GM-CSF). In one embodiment, the immune modulating agent is a protein, e.g., an antibody which activates the immune system (e.g., an anti-CTLA4 antibody, e.g., ipilimumab or tremelimumab, an anti-PD-1 antibody, an anti-PDL-1 antibody); a small molecule adju-vant (e.g., thalidomide or a thalidomide derivative, e.g., lenalidomide).

The kits can also contain one or more therapeutic agents, diagnostic agents, or prophylactic agents. The one or more therapeutic, diagnostic, or prophylactic agents include, but are not limited to: (i) an agent that modulates inflammatory responses (e.g., aspirin, indomethacin, ibuprofen, naproxen, steroids, cromolyn sodium, or theophylline); (ii) an agent that affects renal and/or cardiovascular function (e.g., furo-semide, thiazide, amiloride, spironolactone, captopril, enal-april, lisinopril, diltiazem, nifedipine, verapamil, digoxin, isordil, dobutamine, lidocaine, quinidine, adenosine, digi-talis, mevastatin, lovastatin, simvastatin, or mevalonate); (iii) drugs that affect gastrointestinal function (e.g., omepra-zole or sucralfate); (iv) antibiotics (e.g., tetracycline, clin-damycin, amphotericin B, quinine, methicillin, vancomycin, penicillin G, amoxicillin, gentamicin, erythromycin, cipro-floxacin, doxycycline, streptomycin, gentamicin, tobramy-cin, chloramphenicol, isoniazid, fluconazole, or amanta-dine); (v) anti-cancer agents (e.g., cyclophosphamide, methotrexate, fluorouracil, cytarabine, mercaptopurine, vin-blastine, vincristine, doxorubicin, bleomycin, mitomycin C, hydroxyurea, prednisone, tamoxifen, cisplatin, or decarba-zine); (vi) immunomodulatory agents (e.g., interleukins, interferons (e.g., interferon gamma (IFN-γ), granulocyte macrophage-colony stimulating factor (GM-CSF), tumor necrosis factor alpha (TNFα), tumor necrosis factor beta (TNFβ), cyclosporine, FK506, azathioprine, steroids); (ix) drugs acting on the blood and/or the blood-forming organs (e.g., interleukins, G-CSF, GM-CSF, erythropoietin, hepa-rin, warfarin, or coumarin); or (vii) hormones (e.g., growth hormone (GH), prolactin, luteinizing hormone, TSH, ACTH, insulin, FSH, CG, somatostatin, estrogens, andro-gens, progesterone, gonadotropin-releasing hormone (GnRH), thyroxine, triiodothyronine); hormone antagonists; agents affecting calcification and bone turnover (e.g., cal-cium, phosphate, parathyroid hormone (PTH), vitamin D, bisphosphonates, calcitonin, fluoride).

Also featured are articles of manufacture that include: a container; and a composition contained within the container, wherein the composition comprises an active ingredient for inducing an immune response in a mammal (e.g., a human), wherein the active ingredient comprises one or more (e.g., two, three, four, five, six, seven, eight, nine, or 10 or more) of any of the peptides described herein, and wherein the container has a label indicating that the composition is for use in inducing an immune response in a mammal (e.g., any of the mammals described herein). The label can further indicate that the composition is to be administered to a mammal having, suspected of having, or at risk of devel-oping, a cancer, e.g., lung cancer, liver cancer, bile duct cancer, stomach cancer, cervical cancer, nasopharyngeal cancer, breast cancer, colon cancer, pancreatic cancer, prostate cancer, multiple myeloma, smoldering multiple myeloma and/or Waldenstrom's macroglobulinemia. The composition of the article of manufacture can be dried or lyophilized and can include, e.g., one or more solutions (and/or instructions) for solubilizing a dried or lyophilized composition.

The articles of manufacture can also include instructions for administering the composition to the mammal (e.g., as described above).

The following examples are intended to illustrate, not limit, the invention.

EXAMPLES

Example 1: Materials and Methods

Cell lines. The multiple myeloma cell lines: McCAR, MM1S and U266, were obtained from the American Type Culture Collection (ATCC; Manassas, VA). The human acute myeloid leukemia (AML) cell line, ML-2, was kindly provided by Dr. Y. Matsuo, Fujisaki Cell Center, Okayama, Japan. The T2 cell line, which is a human B and T cell hybrid expressing HLA-A2.1 molecules (Zweerink et al., (1993) J Immunol. 150(5):1763-71), was provided by Dr. J. Molldrem (University of Texas M. D. Anderson Cancer Center, Houston, TX) and was used as a source of antigen presenting cells (APCs). K562-A*0201 cells were provided by Karen Anderson (Dana Farber Cancer Institute, Boston, MA) and used in immune monitoring assays to present individual peptides to the CTL. Various cancer cells including LnCap, VCap, MB231, MCF7, BT474, LS180, SW480, WiDRr, OCI, U937, HEL, UT7, HL60, Nomo1, and THP1 were obtained from the ATCC. All cell lines were cultured in RPMI-1640 medium (Gibco-Life Technologies, Rockville, MD) supplemented with 10% fetal calf serum (FCS; Bio-Whittaker, Walkersville, MD), 100 IU/ml penicillin and 100 μg/ml streptomycin (Gibco-Life Technologies).

Reagents. Mouse anti-human CD80 or CD83 monoclonal antibodies (mAb) conjugated with phycoerythrin (PE) were purchased from Immunotech (Hialeigha, FL). Mouse anti-human CD3, CD4, CD8, CCR7, CD45RO, CD69, CD107α, IFN-γ, and HLA-A2 mAbs conjugated with FITC, PE, PerCP, PerCP-Cy5.5, APC, Pacific Blue, APC-H7 or PE-Cy7 were purchased from Becton Dickinson (BD)/Pharmingen or BD/Biosciences (San Diego, CA). Recombinant human IL-2, IL-4, IFN-α and TNF-α were purchased from R&D Systems (Minneapolis, MN), and GM-CSF was obtained from Immunex (Seattle, WA).

Synthetic peptides. Influenza virus protein matrix peptide$_{58-66}$ (GILGFVFTL; SEQ ID NO:25) and MAGE-3 peptide (FLWGPRALV; SEQ ID NO:26) were used as control HLA-A2-binding peptides. Six native non-spliced XBP1 peptides: XBP1$_{118-126}$ (LLREKTHGL; SEQ ID NO:1); XBP1$_{185-193}$ (NISPWILAV (SEQ ID NO:2)); XBP1$_{190-198}$ (ILAVLTLQI (SEQ ID NO:3)); XBP1$_{193-201}$ (VLTLQIQSL (SEQ ID NO:4)); XBP1$_{111-119}$ (KLLLENQLL (SEQ ID NO:5)); XBP1$_{94-102}$ (RMSELEQQV (SEQ ID NO:27)); three native spliced XBP1 peptides including SP XBP1$_{197-205}$ (GILDNLDPV (SEQ ID NO:7)); SP XBP1$_{194-202}$ (ILLGILDNL (SEQ ID NO:8)); SP XBP1$_{368-376}$ (ELFPQLISV (SEQ ID NO:9)); heteroclitic XBP1 (YISPWILAV (SEQ ID NO:6)); and heteroclitic spliced XBP1 (YILDNLDPV (SEQ ID NO: 24)); and YLFPQLISV (SEQ ID NO:10)) peptides were designed and examined as potential HLA-A2-binding peptides. As used herein, "heteroclitic" (e.g., a heteroclitic peptide) refers to a form of a peptide in which one or more amino acids have been modified from a wild-type or original sequence in order to produce a peptide that is more immunogenic than the corresponding wild-type peptide. For example, in the exemplary heteroclitic peptides described immediately above, the bolded amino acids indicate the amino acids that are modified from the wild-type sequence of XBP1.

Four native CD138 peptides: CD138$_{256-264}$ (VIAGGLVGL (SEQ ID NO:11)); CD138$_{260-268}$ (GLVGLIFAV (SEQ ID NO:12)); CD138$_{5-13}$ (ALWLWLCAL (SEQ ID NO:13)); and CD138$_{7-15}$ (WLWLCALAL (SEQ ID NO:14)) were designed and examined as potential HLA-A2-binding peptides.

Four native CS1 peptides: CS1-P1: CS1$_{236-245}$ (LLLSLFVLGL (SEQ ID NO:15)); CS1-P2: CS1$_{239-247}$ (SLFVLGLFL (SEQ ID NO:16)); CS1-P3: CS1$_{232-240}$ (LLVPLLLSL (SEQ ID NO:17)); and CS1-P4: CS1$_{9-17}$ (TLIYILWQL (SEQ ID NO:18)) were designed (using three different databases RANKPEP, BIMAS and NetMHC) and examined as potential HLA-A2-binding peptides. (See, e.g., Reche et al. (2002) Human Immunology 63:710-709).

XBP-1 and CD138 peptides were synthesized (Biosynthesis, Lewisville, TX) by standard FMOC (9-fluorenylm-ethyl-oxycarbonyl) chemistry, purified to >85% using reverse-phase chromatography and validated by mass-spectrometry for molecular weight. CS1 peptides were synthesized by New England Peptides LLC with greater than 95% purity.

Heteroclitic XBP1 US$_{185-193}$ (YISPWILAV) (SEQ ID NO: 6), heteroclitic XBP1 SP$_{368-376}$ (YLFPQLISV) (SEQ ID NO: 10), native CD138$_{260-268}$ (GLVGLIFAV) (SEQ ID NO: 12), and native CS1$_{239-247}$ (SLFVLGLFL) (SEQ ID NO: 16) peptides were derived from XBP1 unspliced (US), XBP1 spliced (SP), CD138 and CS1 antigens, respectively. Influenza virus matrix protein$_{58-66}$ (GILGFVFTL) (SEQ ID NO: 25) and CMV pp65 (NLVPMVATV) (SEQ ID NO: 28) were selected as HLA-A2-specific control peptides. All peptides were synthesized by standard fmoc (9-fluorenylm-ethyl-oxycarbonyl) chemistry, purified to >90% using reverse-phase chromatography, and validated by mass-spectrometry for molecular weight (Biosynthesis, Lewisville, TX). Lyophilized peptides were dissolved in DMSO (Sigma, St. Louis, MO), diluted in AIM-V medium (Gibco-Life Technologies), and stored at −140° C.

Peptide binding assay. A cocktail of four HLA-A2 peptides, heteroclitic XBP1 US185-193, heteroclitic XBP1 SP$_{368-376}$, CD138260-268 and CS1$_{239-247}$, was evaluated for binding affinity using the T2 cell line. In the assay, T2 cells were washed three times, resuspended in serum-free AIM-V medium (Gibco-Life Technologies) to a final concentration of $1×10^6$ cells/ml, and transferred into a 48-well tissue culture plate. The cells were pulsed with a cocktail of the four peptides at total peptide concentrations ranging from 0-50 μg/ml plus 3 μg/ml human β2-microglobulin (Sigma, St Louis, MO), and incubated at 37° C., 5% $CO_2$ in humidified air. Following overnight incubation, cells were washed, stained with mouse anti-human HLA-A2-FITC mAb for 15 minutes at 4° C., and analyzed using a FACSCanto™ II flow cytometer (Becton Dickinson, San Jose, CA).

Peptide stability assay. The multipeptide cocktail was examined for HLA-A2 stability over time. After overnight incubation of T2 cells pulsed with the multipeptide cocktail (25 μg/ml; 6.25 μg/ml/peptide), the cells were washed to remove unbound peptide and incubated with 10 μg/ml Brefeldin A (Sigma) at 37° C. and 5% $CO_2$ for 1 hour to block cell surface expression of newly synthesized HLA-A2 molecules. Peptide/HLA-A2 complex stability was measured at 0, 2, 4, 6 and 14 hours post-BFA treatment by staining cells with mouse anti-human HLA-A2-FITC mAb and analyzing by flow cytometry.

Generation of monocyte-derived mature dendritic cells. Peripheral blood mononuclear cells (PBMC) were isolated by standard density gradient centrifugation over Ficoll-Paque™ Plus (Amersham Pharmacia Biotech AB, Uppsala Sweden) from leukopaks obtained from HLA-A2$^+$ normal individuals. To generate dendritic cells (DC), monocytes isolated as the adherent cell fraction were cultured for 7 days in the presence of 1,000 U/ml GM-CSF and 1,000 U/ml IL-4 in RPMI-1640 medium (Gibco-Life Technologies) supplemented with 10% FCS. Fresh media plus GM-CSF and IL-4 was added to the cultures every other day. Mature DC (mDC) were obtained by adding 1,000 U/ml IFN-α plus 10 ng/ml TNF-α along with fresh GM-CSF and IL-4 in 10% FCS-RPMI on day 7 and incubating for an additional three days.

Isolation of CD3$^+$ T cells. CD3$^+$ T cells were obtained by negative selection from the non-adherent cell fraction using the EasySep® magnet and Robosep® from StemCell Technologies (Vancouver, Canada). In brief, T cell enrichment was accomplished by depletion of non-CD3 T cells including B cells, monocytes, NK cells, erythroid cells, platelets and basophils by labeling in bispecific tetrameric antibody complexes which are directed against CD14, CD16, CD19, CD20, CD36, CD56, CD66b, CD123, and glycophorin A. After the removal of magnetically labeled unwanted cells, the enriched CD3$^+$ T cells were washed and examined by flow cytometry.

Isolation of Primary CD138$^+$ cells from Bone Marrow Mononuclear Cells of MM patients. Bone marrow mononuclear cells (BMMC) were isolated by standard density gradient centrifugation over Ficoll-Paque™ Plus from bone marrow cells obtained from MM patients. CD138$^+$ MM cells were isolated from BMMC using RoboSep® CD138 positive immunomagnetic selection technology (StemCell Technologies).

Induction of peptide-specific CTL. CTL specific for individual peptides (peptide-specific CTL) or multiple peptides (MP-CTL) were generated ex vivo by repeated stimulation of CD3$^+$ T lymphocytes obtained from normal HLA-A2$^+$ or HLA-A24+ donors (see FIG. 25). In brief, APC (mDC or T2 cells) were pulsed overnight at 37° C. and 5% CO$_2$ in humidified air with either individual peptides or a cocktail of heteroclitic XBP1 US$_{185-193}$, heteroclitic XBP1 SP$_{368-376}$, CD138$_{260-268}$ and CS1$_{239-247}$ peptides (25 μg/ml total peptide). The loaded APC were harvested, washed, irradiated at 20 Gy, and resuspended in AIM-V medium supplemented with 10% human AB serum (Gemni Bio Products, West Sacramento, CA). Irradiated mp-pulsed mDC were used to prime autologous CD3$^+$ T cells at a 1:20 APC/mp-to-CD3$^+$ T cell ratio in AIM-V medium supplemented with 10% human AB serum. The cultures were restimulated every seven days with irradiated APC/mp for a total of 4 cycles to generate CTL specific to the mp. IL-2 (50 U/ml) was added to the cultures two days after the second stimulation and replenished until the culture is completed.

Phenotypic analysis of the XBP1-CTL, CD138-CTL, or target cells. One week after the fourth stimulation, MP-CTL and control T cells were evaluated for total CD3$^+$CD8$^+$ T cells or naïve, effector memory, and activated CD3$^+$CD8$^+$ T cells by staining them with CD3-PacBlue, CD8-APC-H7, CCR7-PeCy7, CD45RO-PE and/or CD69-PerCP mAbs at 4° C. for 30 minutes. After staining, the cells were washed, fixed in 2% paraformaldehyde-PBS, and analyzed by flow cytometry.

Western blotting. Approximately 100 μg protein lysate from each cell line (U266, McCAR, ML-2, and MM1S) was suspended in Laemmli's sample buffer (0.1 M Tris-HCl buffer, pH 6.8, containing 1% sodium dodecyl sulfate (SDS), 0.05% β-mercaptoethanol, 10% glycerol and 0.001% bromophenol blue), boiled for two minutes and subjected to 8-16% gradient sodium dodecyl sulfate-polyacrylamide gel electrophoresis (SDS-PAGE) for two hours (Xcell Surelock Mini Cell, Invitrogen, Carlsbad, CA) at 80 V. A protein ladder (a mixture of proteins of known molecular weight) was used as a size marker in the gel to determine the molecular weight of the peptides (Invitrogen, Carlsbad, CA). Gels were electroblotted onto nitrocellulose membranes (Trans-Blot, 0.2 micron transfer membrane, Bio-Rad Laboratories, CA) at 40 V for two hours in a Tris-glycine buffer. Transfer of the proteins onto the nitrocellulose membrane was confirmed by Ponceau S staining. Incubation of the membrane with mouse anti-human XBP1 antibody or an anti-human CD138 antibody was performed for one hour in phosphate buffered saline and Tween 20 (PBST) containing 1% BSA with constant rocking. The membrane was washed three times with PBST and incubated in anti-mouse IgG-horseradish peroxidase conjugates for one hour in PBST containing 3% non-fat dry milk. After washing, specific proteins were detected using enhanced chemiluminescence, according to the instructions provided in the product manual (Amersham Life Sciences Inc., Arlington Heights, IL).

IFN-γ ELISA. IFN-γ release by XBP1-CTL, CD138-CTL, or CS1-CTL following co-culture with multiple myeloma (MM) cells (McCAR, MM1S), acute myelogenous leukemia (AML) cells (ML-2), or T2 cells (above) was measured using a human IFN-γ ELISA kit from BD Biosciences (San Diego, CA) (see FIG. 27). Briefly, dilutions of purified IFN-γ as standards or CTL supernates were transferred into wells of a 96-well plate pre-coated with a monoclonal anti-human IFN-γ capture antibody and incubated for 2 hours at room temperature. After several washes, a buffer containing a detection antibody and avidin-horseradish peroxidase conjugate was added to each well and incubated for one hour at room temperature. The wells were washed and then to each well was added a horseradish peroxidase substrate solution and incubated at room temperature for 30 minutes. Stop solution was added to each well and the absorbance was determined at 450 nm was determined with a PerkinElmer Wallac Victor2 counter (PerkinElmer, Wellesley, MA). The amount of cytokine present in the CTL culture supernatant was calculated based on the IFN-γ standard curve.

Cell proliferation by Carboxy Fluorescein Succinimidyl Ester (CFSE) tracking. CTL proliferation was measured after co-culture with multiple myeloma (MM) cells (McCAR, MM1S), acute myelogenous leukemia (AML) cells (ML-2), or T2 cells (above) (see FIGS. 27 and 32). Individual XBP1-CTL, CD138-CTL, CS1-CTL or multi-peptide generated CTL were washed twice in PBS (Gibco-BRL) and resuspended in RPMI-1640 culture medium at a concentration of 1×10$^6$ cells/ml. CFSE (Molecular Probes, Eugene, OR) in the form of a 5 mM stock solution in DMSO was added to the CTL to give a final concentration of 5 μM and incubated for 10 minutes at 37° C. in a CO$_2$ incubator protected from light. After incubation, a volume of ice-cold PBS (containing 2% FCS) equivalent to five-times the volume of the CTL cells was added to the cells to quench the reaction. Cells were incubated for 5 minutes on ice, centrifuged and resuspended in fresh PBS (containing 2% FCS) after a total of three washings. CFSE-labeled T cells were adjusted to a concentration of $2 \times 10^6$ cells/ml with RPMI culture medium, stimulated with $2 \times 10^5$ cells/ml primary multiple myeloma cells, MM cell lines, various cancer cell lines or K562-A2 cells presenting individual peptides. The stimulated CFSE-labeled cells were examined by flow cytometry.

Cytotoxicity assay. The cytotoxic activities of individual XBP1-CTL, CD138-CTL, CS1-CTL or multi-peptide generated CTL were measured by a calcein release assay as described by, e.g., Roden et al. (1999) J. Immunol Methods 226:29-41. Briefly, target cells ($3 \times 10^5$ cells) including T2, U266 cells, McCAR cells, ML-2 cells, MM1S cell lines or primary multiple myeloma cells were incubated in serum-free culture medium containing 10 mM calcein-AM (Molecular Probes) for 30 minutes at 37° C., washed three times in cold PBS with 5% FCS, and incubated with effector cells ($5 \times 10^3$ cells/well) at various effector:target cell ratios in 96-well U-bottom microtiter plates (triplicate wells/sample). Plates were incubated for 3 hours at 37° C. and 5% $CO_2$. After incubation, the cells were pelleted by centrifugation at 1,000 rpm for 5 minutes and 100 μl of the supernatant was transferred to the wells of 96-well flat-bottomed microtiter plates (Nunc) and the calcein-release was measured as the amount of fluorescence released from the cells (using a VICTOR$^2$-1420 multilabel counter (PerkinElmer, Boston, MA)). Maximum calcein release was obtained from detergent-released target cell counts and spontaneous release from target cell counts in the absence of effector cells. Cellular cytotoxicity was calculated as follows: % Specific Lysis=[(experimental release–spontaneous release)÷(maximum release–spontaneous release)]×100.

CD107α degranulation assay. CD107α degranulation was measured after co-culture with multiple myeloma (MM) cells (McCAR, MM1S), acute myelogenous leukemia (AML) cells (ML-2), or T2 cells (above) (see FIGS. 27 and 30). The CD107α degranulation assay, a measure of cytotoxic activity, was performed as described by Betts et al. (2003) and Mittendorf et al. (2005) with minor modifications as detailed below. Primary multiple myeloma cells, MM cell lines, various cancer cell lines or K562-A2 cells pulsed with individual peptide were co-cultured at various effector:target ratios with CTL. A 10 μl aliquot of each of CD107α and CD107b (both conjugated to the detectable label FITC) was added to each well at the same time of adding the CD138-CTL. The plate containing the cells was centrifuged for 5 minutes at 1000 rpm and incubated at 37° C. for one hour. Following incubation, Brefeldin A and Monensin was added to each well and the cells were incubated at 37° C. for an additional four hours. The cells were collected and washed and stained with fluorochrome conjugated anti-human MABs The cells were washed and analyzed by flow cytometry.

CD107α Upregulation and Intracellular IFN-γ Production. CD107α upregulation and IFN-γ production were measured after co-culture with multiple myeloma (MM) cells (McCAR, MM1S), acute myelogenous leukemia (AML) cells (ML-2), or T2 cells (above) (see FIGS. 27 and 30). CD107α degranulation and IFN-γ producing CD8$^+$ CTL were determined by cell surface marker and intracellular cytokine staining by flow cytometry. Briefly, $1 \times 10^6$ responder cells (MP-CTL, Control T cells) were stimulated with $1 \times 10^6$ stimulator cells (HLA-A2$^+$ McCAR or U266 MM cell lines or K562-A*0201 cells pulsed with respective peptide). CD107α mAb was added to the cultures, and cells were placed into a 37° C., 5% $CO_2$ incubator. After 1 hour incubation, CD28/CD49d mAb (BD) and protein transport inhibitors Brefeldin A (BD) and Monensin (BD) were added to the cell cultures and incubated for an additional 5 hours. As a baseline control, MP-CTL were cultured in media with CD28/CD49d mAb, Brefeldin A and Monensin alone, without further stimulation. After incubation, the cells were harvested, washed, and surface stained with CD3-PacBlue and CD8-APC-H7, CCR7-PeCy7, CD45RO-PE and/or CD69-PerCP anti-human mAbs for 30 minutes. Cells were then permeabilized, fixed using Cytofix/Cytoperm (BD), and stained with anti-IFN-γ FITC mAb for 45 minutes to detect intracellular cytokine production. Lastly, cells were washed with Perm/Wash solution (BD), fixed in 2% paraformaldehyde, and acquired by flow cytometry.

IL-2 production Assay. CD107α degranulation and IL-2 producing CD3+CD8+ CTL were identified by cell surface marker and intracellular cytokine staining by flow cytometry. Briefly, the peptide-specific CTL or control T cells were stimulated with each specific stimulator in the presence of CD107a mAb. After 1 hour incubation, CD28/CD49d mAb (BD), as well as protein transport inhibitors Brefeldin A and Monensin, were added to the cultures and incubated for an additional 5 hours. As a baseline control, the CTL were cultured in media with CD28/CD49d mAb, Brefeldin A, and Monensin alone. After incubation, cells were stained with CD3-PacBlue and CD8-APC-H7 anti-human mAbs, followed by fixation/permeabilization and stained with anti-IL-2 APC anti-human mAb to detect intracellular cytokine production. After the staining, cells were washed with Perm/Wash solution three times, fixed in 2% paraformaldehyde, and analyzed by flow cytometry.

Statistical Analysis. Results are presented as mean±SE. Groups were compared using unpaired Student's t-test. Differences were considered significant when p<0.05.

Example 2: A Multipeptide (MP) Cocktail of XBP1 Unspliced, XBP1 Spliced, CD138 and CS1-Specific Peptides Displays High HLA-A2 Binding Affinity and Stability The four immunogenic peptides, heteroclitic XBP1 US$_{185\text{-}193}$ (YISPWILAV, SEQ ID NO: 6), heteroclitic XBP1 SP$_{368\text{-}376}$ (YLFPQLISV, SEQ ID NO: 10), native CD138$_{260\text{-}268}$ (GLVGLIFAV, SEQ ID NO: 12), and native CS1$_{239\text{-}247}$ (SLFVLGLFL, SEQ ID NO: 16) (Table 1), have been individually demonstrated to induce immune response. Here we have evaluated them as a MP cocktail. The HLA-A2-specific binding and stability of the MP cocktail was evaluated by measuring the upregulation of HLA-A2 molecules on T2 cells by flow cytometry (27). The peptide binding assay demonstrated an increase in the HLA-A2 mean fluorescence intensity (MFI) on T2 cells in a dose-dependent manner (0-50 μg/ml), reaching a plateau at a total peptide concentration of 25 μg/ml (6.25 μg/peptide/ml; MFI: 10,787.33±2,371.71) similar to the highest total peptide concentration, 50 μg/ml (MFI: 10,889.33±2,888.48) (FIG. 1a). Therefore, a MP concentration of 25 μg/ml (6.25 μg/peptide/ml) was selected for evaluation of HLA-A2 binding stability.

In the peptide binding stability assay, T2 cells were pulsed overnight with 25 μg/ml of the MP cocktail, washed to remove unbound peptides, and then treated with Brefeldin A (BFA) to block cell surface expression of newly synthesized HLA-A2 molecules. T2 cells were then evaluated for their HLA-A2 MFI at 0, 2, 4, 6 or 14 hrs post-BFA treatments. Flow cytometry analysis demonstrated that the stability of MP cocktail was highly maintained up to 6 hrs post-BFA treatment (MFI: 0 hr=9,726.00±1,373.24, 2 hr=9,132.33±1, 435.51, 4 hr: 9,125.33±1,130.62, 6 hr: 8,818.67±413.50) (FIG. 1*b*). At 14 hr post-BFA treatment, the HLA-A2-specific affinity of MP cocktail was lower, but was greater (MFI: 6,793.67±1,617.01) than the affinity of the control influenza virus matrix protein (IVMP)$_{58\_66}$ peptide (MFI: 4,921.33±1,428.16). Based on these results, we confirmed a high level of HLA-A2-specific affinity and stability of the MP cocktail and proceeded to further evaluate the cocktail for its immunogenicity and ability to induce MM-specific CTL.

TABLE 4

Native and heteroclitic epitopes evaluated as a
multipeptide for targeting MM

| TAA | Identification | Type | Sequence |
|---|---|---|---|
| XBP1-unspliced | XBP1$_{185-193}$ | Hetero-clitic | YISPWILAV (SEQ ID NO: 6) |
| XBP1-spliced | XBP1-SP$_{368-376}$ | Hetero-clitic | YLFPQLISV (SEQ ID NO: 10) |
| CD138 | CD138$_{260-268}$ | Native | GLVGLIFAV (SEQ ID NO: 12) |
| CS1 | CS1$_{239-247}$ | Native | SLFVLGLFL (SEQ ID NO: 16) |

Example 3: Multipeptide-Specific CTL Display a
Distinct Phenotype Representing Specific T Cell
Subtypes The MP-CTL were generated by stimulating HLA-A2$^+$ normal donor's T cells weekly with APC pulsed with the MP cocktail (25 μg/ml total; 6.25 μg/ml/peptide). One week after the fourth stimulation, the resulting MP-CTL were evaluated for their phenotype and functional activity. Flow cytometry analyses showed that the MP-CTL contained a higher proportion of CD3$^+$CD8$^+$ T cells (donor 1: 86%, donor 2: 74%) compared to control T cell cultures (donor 1: 25%, donor 2: 25%; FIG. 2). We also observed distinct phenotypic changes in the CD3$^+$CD8$^+$ T cell subset within the MP-CTL. The frequency of effector memory T cells (EM: CD45RO$^+$ CCR7$^-$/CD3$^+$CD8$^+$) was increased (Donor 1: Control 5% vs. MP-CTL 44%, Donor 2: Control 4% vs. MP-CTL 35%), associated with a corresponding decrease in naïve T cells (CD45RO$^-$CCR7$^+$/CD3$^+$CD8$^+$) (Donor 1: Control 74% vs. MP-CTL 8%, Donor 2: Control 60% vs. MP-CTL 6%). In addition, we observed an increase in the frequency of activated CD69$^+$/CD3$^+$CD8$^+$ T cells within the MP-CTL as compared to the control T cell cultures (Donor 1: Control 3% vs. MP-CTL 39%, Donor 2: Control 5% vs. MP-CTL 13%; FIG. 2). Thus, these results demonstrate that repeated stimulation of CD3$^+$ T cells with the MP cocktail specific to XBP1, CD138 or CS1 results in distinct phenotypic changes and expansion of the CD3$^+$/CD8$^+$ T cell subsets characteristic of antigen-specific CTL.

Example 4: Multipeptide-Specific CTL Include a
High Proportion of CD8$^+$ CTL Producing IFN-γ in
Response to HLA-A2$^+$ MM Cells MP-CTL were analyzed for their ability to produce intracellular IFN-γ upon stimulation with the HLA-A2$^+$ MM cell lines by flow cytometry. Both EM (CD45RO$^+$CCR7$^-$) and activated (CD69$^+$) CD3$^+$CD8$^+$ T cells within the MP-CTL produced IFN-γ in response to HLA-A2$^+$ MM cell lines (FIG. 3). The frequency of IFN-γ producing cells was increased upon stimulation with either McCAR cells [Donor 1: Control vs. MP-CTL-0% vs. 4.7% EM cells, 0.8% vs. 6.1% activated cells; Donor 2: 0.2% vs. 2.7% EM cells, 1% vs. 3.9% activated cells] or U266 cells [Donor 1: Control vs. MP-CTL-0% vs. 8% EM cells, 0% vs. 11.2% activated cells; Donor 2: 0.4% vs. 2.9% EM cells, 1.3% vs. 3.0% activated cells]. The naïve (CD45RO$^-$CCR7$^+$) CD3$^+$CD8$^+$ T cells within the MP-CTL showed a minimum level of IFN-γ-production when stimulated with the MM cell lines (data not shown).

Example 5: Multipeptide-Specific CTL Show Cell
Proliferation in Response to HLA-A2$^+$ MM Cells The function of the MP-CTL was analyzed using a CFSE-proliferation assay. MP-CTL proliferation was measured on day 5 as a decrease in fluorescence of the CFSE-labeled MP-CTL (Q1-gated cells) following stimulation with HLA-A2$^+$ MM primary cells or cell lines (FIG. 4). The MP-CTL showed a high level of cell proliferation in response to CD138$^+$ primary cells obtained from three different HLA-A2$^+$ MM patients (proliferating cells: 33%, 29% or 41%). In addition, the MP-CTL demonstrated a high level of cell proliferation in response to HLA-A2$^+$ MM cell lines including McCAR (proliferating cells: 57%) and U266 (proliferating cells: 49%). MP-CTL cultured in media alone displayed a low level (5%) of proliferation. Taken together, these data demonstrate the functional activity of MP-CTL through their ability to proliferate when stimulated with either HLA-A2$^+$ primary MM cells or MM cell lines.

Example 6: Multipeptide-Specific CTL Induce
Specific Lysis of HLA-A2$^+$ MM Cells We evaluated the cytotoxic activity of MP-CTL using a 4-hour calcein-release assay. The MP-CTL generated from different HLA-A2$^+$ donors' CD3$^+$ T cells were evaluated for their cytotoxic activity against HLA-A2$^+$ MM primary cells or cell lines (FIG. 5). The HLA-A2$^+$ primary MM cells were effectively lysed by the MP-CTL ([Donor A MP-CTL; Patient #1: 6-29%, Patient #2: 0-49%], [Donor B MP-CTL; Patient #1: 0-17%, Patient #2: 0-15%). In addition, MP-CTL demonstrated a high level of cytotoxic activity against the U266 cells (Donor A MP-CTL: 0-85%, Donor B MP-CTL: 2-44%) and McCAR cells (Donor A MP-CTL: 0-13%, Donor B MP-CTL: 0-79%) at the various Effector:Target cell ratios. Compared to the MP-CTL, control CD3$^+$ T cells from the same donors showed a significantly lower level of cytotoxicity against HLA-A2$^+$ MM primary cells or cell lines. In addition, the MP-CTL did not lyse antigen mismatched or MHC mismatched tumor cells including a HLA-A2$^+$ breast cancer cell line (MCF-7), HLA-A2$^-$ MM cell line (MM1S) or HLA-A2$^-$ primary cells from three different MM patients (data not shown). Taken together, these data confirm the HLA-A2-restricted and antigen-specific cytotoxic activity of MP-CTL.

Example 7: Multipeptide-Specific CTL Generate
Individual Immune Responses to Each Relevant
Peptide MP-CTL were analyzed for their ability to degranulate (CD107α expression) and produce intracellular IFN-γ in response to each relevant peptide including heteroclitic XBP1 US$_{185-193}$ (YISPWILAV) (SEQ ID NO: 6), heteroclitic XBP1 $SP_{368-376}$ (YLFPQLISV) (SEQ ID NO: 10), native $CD138_{260-268}$ (GLVGLIFAV) (SEQ ID NO: 12), and native $CS1_{239-247}$ (SLFVLGLFL) (SEQ ID NO: 16). The analyses were performed by measuring the specific MP-CTL responses to K562-A*0201 cells pulsed with the respective peptide. As controls, we used no peptide-pulsed K562-A*0201 cells or K562-A*0201 cells pulsed with an irrelevant HLA-A2-specific CMV pp65 (NLVPMVATV) (SEQ ID NO: 28) peptide. FIG. 6*a* shows a representative flow cytometric analysis of the peptide-specific response from Donor A MP-CTL. The MP-CTL showed a high proportion of $CD107\alpha^{+}IFN\gamma^{+}$/CD3+CD8$^{+}$ T cells (gated Q2) in response to XBP1 US (2.7%), CD138 (1.7%), and CS1 (12.5%) peptides, but not to XBP1 SP (0.2%) peptide. No response was observed to the irrelevant CMV pp65 peptide (0.2%) or no peptide (0.2%) controls. Further analyses were performed using MP-CTL generated from three additional HLA-A2$^{+}$ donors (Donor B, Donor C, Donor D) for their CD107$\alpha$ degranulation or IFN-$\gamma$ production in response to K562-A*0201 cells presenting each individual peptide (FIG. 6*b*). Specific responses were detected in the MP-CTL generated from each of these donors against all the relevant peptides, but not to irrelevant CMV pp65 peptide. However, variations were detected in the level of specific response in degranulation and IFN-$\gamma$ production to each relevant peptide among the CTL generated from different individuals. Therefore, these studies indicate that the MP cocktail including XBP1 US, XBP1 SP, CD138, and CS1 epitopes can induce response to respective peptides with the specific CTL capable of targeting multiple antigens on MM cells.

Example 8: XBP1 Expression in Cancer Cell Lines

Various cancer cell lines were analyzed for the expression of unspliced and spliced XBP1 antigens by flow cytometry. The relative expression levels are indicated with plus or minus signs and also with numbers indicating number of plus signs (FIG. 7).

Example 9: Proliferation of XBP1-CTL in Response to HLA-A2+ Breast Cancer Cells The proliferation of XBP1-CTL in response to stimulator cells from breast cancer cell lines was analyzed using a CFSE-proliferation assay. XBP1-CTL proliferation was measured on days 6 and 7 as a decrease in fluorescence of the CFSE-labeled MP-CTL (P3-gated cells) following stimulation with the HLA-A2$^{+}$ breast cancer cell line MCF-7, HLA-A2$^{-}$ breast cancer cell line BT434, HLA-A2$^{+}$ prostate cancer cell line LnCap, HLA-A2$^{-}$ prostate cancer cell line VCap and the NK-sensitive CML K562, or no cells. The XBP1-CTL showed a high level of cell proliferation in response to the HLA-A2$^{+}$ breast cancer cells at days 6 (FIG. 8*a*) and 7 (FIG. 8*b*), but not other cancer cell lines which were served as controls.

Example 10: IFN-$\gamma$ Production and Cell Activation of XBP1-CTL in Response to HLA-A2$^{+}$ Breast Cancer Cells XBP1-CTL, were analyzed by flow cytometry for IFN-$\gamma$ expression and CD69 upregulation in CD8+ T cells in response to breast cancer cell lines (MB231, MCF-7, BT434) and prostate cancer cell lines (LnCAP, VCap). IFN-$\gamma$ expression and activation (CD69) of XBP1-CTL were increased upon stimulation with HLA-A2+ breast cancer cells including MB231 and MCF-7, but not other cancer cell lines which were served as controls (FIG. 9).

Example 11: Degranulation (CD107$\alpha$) of XBP1-CTL in Response to HLA-A2+ Breast Cancer Cell Lines XBP1-CTL were analyzed for their ability to degranulate in response to breast cancer cell lines (MB231, MCF-7, BT434) and prostate cancer cell lines (LnCAP. VCap). CD107$\alpha$ upregulation were analyzed, as a measure of cytotoxic activity, in gated CD8+ T cells by flow cytometry. A significant level of degranulation (CD107$\alpha$ upregulation) was detected in response to HLA-A2+ breast cancer cells including MB231 and MCF-7, but not other cancer cell lines which were served as controls (FIG. 10).

Figure 11:
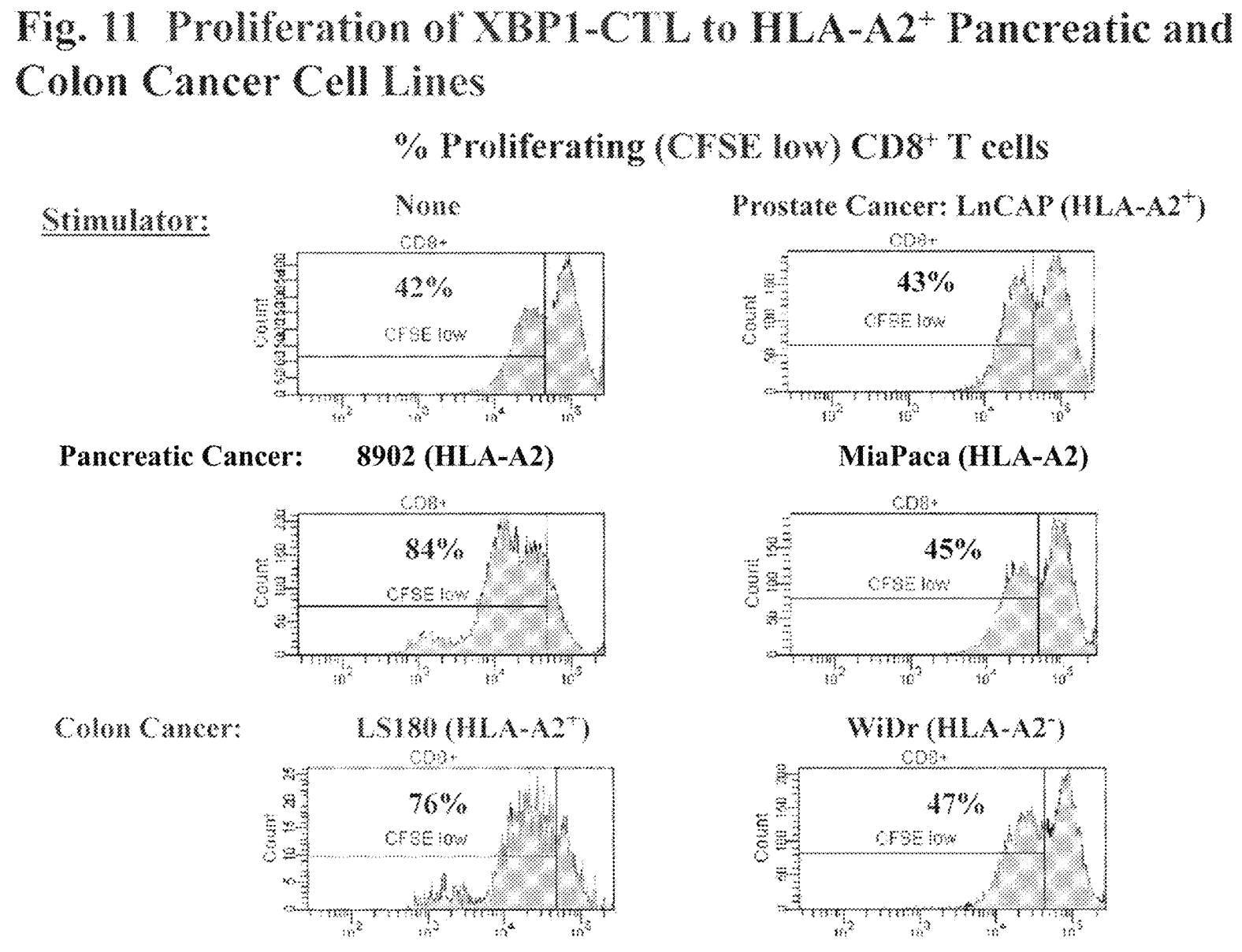

Example 12: Proliferation of XBP1-CTL in Response to HLA-A2+ Pancreatic and Colon Cancer Cell Lines The proliferation of XBP1-CTL in response to pancreatic and colon cancer cell lines was performed using a CFSE-based assay. XBP1-CTL proliferation was measured on day 6 as a decrease in fluorescence of the CFSE-labeled XBP1-CTL following stimulation with the HLA-A2$^{+}$ prostate cancer cell line (LnCap), the HLA-A2$^{+}$ pancreatic cancer cell line (8902), the HLA-A2$^{-}$ pancreatic cancer cell line (MiaPaca), the HLA-A2$^{+}$ colon cancer cell line (LS180), and the HLA-A2$^{-}$ colon cancer cell line (WiDr), or a no-cell control. The XBP1-CTL showed higher levels of cell proliferation in response to the HLA-A2$^{+}$ pancreatic cell line 8902 and HLA-A2$^{+}$ colon cancer cell line LS180 (FIG. 11).

Example 13: IFN-$\gamma$ Production and Degranulation of XBP1-CTL in Response to HLA-A2+ Pancreatic and Colon Cancer Cell Lines XBP1-CTL were analyzed for their ability to degranulate and produce IFN-$\gamma$ in response to pancreatic or colon cancer cell lines. XBP1-CTL were incubated with the HLA-A2+ pancreatic cancer cell lines (Pan1 and PL45), HLA-A2– pancreatic cancer cell line (MiaPaca), the HLA-A2+ colon cancer cell lines (LS180 and SW480), the HLA-A2– prostate cancer cell line (WiDr), or a no-cell control. CD107$\alpha$ and IFN-$\gamma$ production were analyzed by flow cytometry. CD107$\alpha$ upregulation and IFN-$\gamma$ production by XBP1-CTL were increased in stimulation with HLA-A2+ pancreatic cancer cells and HLA-A2+ colon cancer cells, not with other control cancer cells and showed the response in antigen-specific and HLA-A2 restricted manner (FIG. 12).

In addition, a significantly higher level of XBP1 gene expression was found in the primary tumor cells from breast cancer or colon cancer patients as compared to cells from healthy donors as shown by searching the canEvolve (http://www.canevolve.org/AnalysisResults/AnalysisResults.html) and Oncomine (http://www.webcitation.org/getfile?fileid=bcbe297e4085b19933cca759a88e0e2b9fac3b1e) public databases as shown below.

| canEvolve | | | | | | | |
| --- | --- | --- | --- | --- | --- | --- | --- |
| | | # Samples | | | | Exp. Status | Fold |
| Series | Tumor Type | Total | Normal | Patient | p value | in patients | change |
| TCGA-Colon | Colon Adenocarcinoma | 179 | 24 | 155 | 1.69E−12 | Upregulated | 1.60 |
| TCGA-BRCA | Breast Cancer | 599 | 63 | 536 | 3.70E−04 | Upregulated | 1.64 |

| Oncomine | | | | | | | |
| --- | --- | --- | --- | --- | --- | --- | --- |
| | | # Samples | | | | Exp. Status | Fold |
| Series | Tumor Type | Total | Normal | Patient | p value | in patients | change |
| TCGA-Colon | Colon Adenocarcinoma | 161 | | | | | |
| #1. | Mucinous Adenocarcinoma | | 19 | 22 | 1.92E−06 | Upregulated | 1.91 |
| #2. | Adenocarcinoma | | 19 | 101 | 0.016 | Upregulated | 1.23 |
| TCGA-BRCA | Breast cancer | 593 | | | | | |
| #1. | Invasive lobular | | 61 | 36 | 3.45E−07 | Upregulated | 2.63 |
| #2. | Invasive Ductal | | 61 | 392 | 6.19E−05 | Upregulated | 1.77 |
| #3. | Mixed lobular and Ductal | | 61 | 7 | 1.67E−04 | Upregulated | 3.67 |
| #4. | Intraductal Cribriform | | 61 | 3 | 2.86E−04 | Upregulated | 2.71 |
| #5. | Invasive Ductal & Lobular | | 61 | 3 | 0.003 | Upregulated | 3.04 |
| #6. | Invasive carcinoma | | 61 | 76 | 0.007 | Upregulated | 1.54 |

Example 14: CD138 and CS1 Expression in Cancer Cell Lines

Various cancer cell lines were analyzed for CD138 and CS1 antigen expression by flow cytometry. The relative CD138 and CS-1 expression levels for the various cancer cell lines are indicated with plus or minus signs and also with numbers indicating the expression levels of CD138 (FIG. 13) and CS1 (FIG. 14).

Example 15: Percentage of CD8+ CTL in T Cells from Smoldering Multiple Myeloma Patients by Stimulation with XBP1/CD138/CS1 Peptides Multipeptide-specific CTL (MP-CTL) generated from T cells obtained from four HLA-A2+ smoldering multiple myeloma patients were analyzed for specific T cells by flow cytometry. The MP-CTL generated from each patient's T cells show an increased percentage of CD3+CD8+ CTLs and decreased percentage of CD3+CD4+ Th cells (FIG. 15).

Example 16: Proliferation of MP-CTL from Smoldering Multiple Myeloma Patients Proliferation of MP-CTL generated from two smoldering multiple myeloma patients in response to various MM cell lines was analyzed using a CFSE-based assay. Cell proliferation was measured on days 5, 6 and 7 as a decrease in fluorescence of the CFSE-labeled MP-CTL (P3-gated) in stimulation with the HLA-A2$^+$ cell line (McCAR), the HLA-A2$^-$ cell lines (MM15, RPMI), NK sensitive cell line (K562), or without stimulation. MP-CTL generated from T cells of both SMM patients showed a high level of cell proliferation in response to the HLA-A2$^+$ multiple myeloma cell line McCAR, not to HLA-A2− cell lines nor NK sensitive cell line, demonstrating HLA-A2 restricted MP-CTL activities against multiple myeloma cells (FIGS. 16a, b).

Example 17: IFN-γ Production by MP-CTL Generated from Smoldering Multiple Myeloma Patients IFN-γ production of MP-CTL generated from four smoldering multiple myeloma patients was analyzed in response to various MM cell lines. The production was analyzed by flow cytometry following stimulation with an HLA-A2+ cell line (McCAR, U266), the HLA-A2− cell lines (MM1S, RPMI), the NK sensitive cell line (K562) or without any stimulation. The MP-CTL generated from all four patients showed an increase in IFN-γ production in an HLA-A2-restricted manner upon the stimulation with HLA-A2+ multiple myeloma cell lines (FIGS. 17a, b).

Example 18: Degranulation (CD107α) of MP-CTL Generated from Smoldering Multiple Myeloma Patients to Myeloma Cell Lines MP-CTL generated from four smolder multiple myeloma patients were analyzed for degranulation as a measure of cytotoxic activity in response to various HLA-A2+ and HLA-A2-cancer cell lines. The analyses were performed by measuring the MP-CTL specific responses to U266, McCAR, MM1S, RPMI, K562 cells, or no stimulator cells. CD107α upregulation was analyzed in gated CD8$^+$ T cells by flow cytometry. The MP-CTL generated from a SMM patient showed an increased level of CD107α degranulation in response to HLA-A2$^+$ MM cell lines, U266 and McCAR (FIG. 18$a$). The HLA-A2 restricted degranulation response to multiple myeloma cells was confirmed using the MP-CTL generated from four SMM patients (FIG. 18$b$).

Example 19: Percentage of IFN-γ+ CD107α+ Double Positive Cells Among the CD3+ CD8+ CD137+ Subset from MP-CTL Generated from Smoldering Multiple Myeloma Patients The CD3+ CD8+ CD137+ subset of MP-CTL generated from smoldering multiple myeloma patients were analyzed for their ability to degranulate (CD107α expression) and for IFN-γ production in response to K562-A2 cells presenting individual peptides. CD107α and/or IFN-γ expression was analyzed within the CD3+ CD8+ CD137+ subset using flow cytometry. MP-CTL generated from three SMM patients demonstrated increased levels of peptide-specific IFN-γ production and/or CD107α degranulation (FIGS. 19$a$-$d$).

Example 20: Phenotypic Characterization of MP-CTL Generated from Smoldering Multiple Myeloma Patients MP-CTL generated by a total four multipeptide stimulation were analyzed for native, central memory (CM), effector memory (EM) and terminal effector (TE) CD8+ T subsets by flow cytometry. MP-CTL generated from four SMM patients show an increased percentage of EM and TE CD8+ cells (FIG. 20$a$). The MP-CTL from SMM patient #2 and SMM patient #4 were received an additional three rounds of multipeptide stimulation (a total seven cycles of stimulation) and were analyzed by flow cytometry. Additional three cycles of MP stimulation resulted in a further expansion of the EM subset (cycle 4 vs. cycle 7) (FIG. 20$b$). In further experiments, the EM and TE subsets were evaluated from the MP-CTL generated from three SMM patients for IFN-γ production and CD107α upregulation in response to various cancer cell lines. Compared to TE, EM cells within the MP-CTL from all three patients show a higher percentage of IFN-γ+ CD107α+ double positive cell in response to HLA-A2+MM cell line McCAR (FIG. 20$c$). In addition, compared to native (CD45RO$^-$CCR7$^+$) CD8$^+$ T cells, memory (CD45RO$^+$) type of CD8$^+$ T cells showed a higher expression of CD69 activation marker within the MP-CTL generated from four smoldering multiple myeloma patients against HLA-A2$^+$ multiple myeloma cell line U266, confirming higher anti-tumor activities of MP-CTL by memory subsets (FIG. 20$d$).

Example 21. Peptides from Unspliced XBP1, Spliced XBP1, CD138, and CS1 Bind HLA-A24 with High Affinity The full length sequences of non-spliced or spliced XBP1 protein (see above) were analyzed using the search software SYFPEITHI (A database of MHC ligands and Peptide Motifs, Institute for Cell Biology, Department of Immunology, Heidlberg) to predict peptides specific to HLA-A24 followed by the BIMAS program to select peptides with extended half-time disassociation rates. The following peptides from non-spliced XBP1 were selected as potential HLA-A24-binding peptides: peptide 1 (SEQ ID NO: 33), peptide 2 (SEQ ID NO: 5), peptide 3 (SEQ ID NO: 34), peptide 4 (SEQ ID NO: 35), peptide 5 (SEQ ID NO: 36), peptide 6 (SEQ ID NO: 37), and peptide 7 (SEQ ID NO: 29). The following peptides from spliced XBP1 were selected as potential HLA-A24-binding peptides: peptide 1 (SEQ ID NO: 30), peptide 2 (SEQ ID NO: 38), peptide 3 (SEQ ID NO: 39), and peptide 4 (SEQ ID NO: 5). The following peptides from CD138 were selected as potential HLA-A24-binding peptides: peptide 1 (SEQ ID NO: 31), peptide 2 (SEQ ID NO: 40), peptide 3 (SEQ ID NO: 41), peptide 4 (SEQ ID NO: 42), peptide 5 (SEQ ID NO: 43), peptide 6 (SEQ ID NO: 44), and peptide 7 (SEQ ID NO: 45). The following peptides from CS1 were selected as potential HLA-A24-binding peptides: peptide 1 (SEQ ID NO: 46), peptide 2 (SEQ ID NO: 47), peptide 3 (SEQ ID NO: 48), peptide 4 (SEQ ID NO: 49), peptide 5 (SEQ ID NO: 32), and peptide 6 (SEQ ID NO: 50). The HLA-A24 affinity of these native XBP1 peptides and HIV envelope protein$_{583\text{-}591}$ (SEQ ID NO: 537), which is known to be a HLA-A24-binding peptide, was assessed using the T2 peptide-binding assay at a peptide concentration of 1 mg/ml. The specific affinity of the peptides was evaluated as HLA-A24-mean fluorescence intensity (MFI), which is a function of HLA-A24 upregulation on T2 cells following peptide binding to HLA-A24. Among the tested peptides, the following peptides displayed binding affinities for HLA-A24 comparable to or higher than that of HIV envelope protein$_{583\text{-}591}$ (SEQ ID NO: 537): peptides 4 and 7 from non-spliced XBP1, peptide 1 from spliced XBP1, peptides 1, 3, and 4 from CD138, and peptides 3 and 5 from CS1 (FIG. 21). The HLA-A24 affinities of the high-affinity peptides were then analyzed in the T2 peptide-binding assay using lower peptide concentrations (FIGS. 22-24). Based on these data, the following four peptides, including one peptide from each protein, were selected for further investigation: peptide 7 from non-spliced XBP1 (XBP1$_{186\text{-}194}$, sequence: ISP-WILAVL, SEQ ID NO: 29), peptide 1 from spliced XBP1 (SP XBP1224-232, sequence: VYPEGPSSL, SEQ ID NO: 30), peptide 3 from CD138 (CD138$_{265\text{-}273}$, sequence: IFAVCLVGF, SEQ ID NO: 31), and peptide 5 from CS1 (CS1$_{240\text{-}248}$, sequence: LFVLGLFLW, SEQ ID NO: 32).

Example 22: Percentage of CD8+ CTL in T Cells from Two Donors by Stimulation with XBP1, CD138, and CS1 Peptides CTL from two donor patients were analyzed for specific T cells by flow cytometry. The peptide-specific CTL generated from each patient's T cells show an increased percentage of CD8+ CTL (FIG. 26).

Example 23: IFN-γ Production and Cell Activation of Peptide-Specific CTL in Response to HLA-A24+ Multiple Myeloma Cells Peptide-specific CTL were analyzed by flow cytometry for expression of IFN-γ and CD8 in response to HLA-A24+ (KMS) and HLA-A24− (OMP1 and U266) multiple myeloma cell lines. IFN-γ expression of peptide-specific CTL was increased upon stimulation with HLA-A24+ but not with HLA-A24− multiple myeloma cells (FIGS. 28 and 29).

Example 24: IFN-γ Production and Degranulation of Peptide-Specific CTL in Response to HLA-A24+ Multiple Myeloma Cell Lines Peptide-specific CTL were analyzed for their ability to degranulate and produce IFN-γ in response to multiple myeloma cell lines. Peptide-specific CTL were incubated with the HLA-A24+(KMS11) and HLA-A24– (OMP1) multiple myeloma cell lines. CD107α and IFN-γ production were analyzed by flow cytometry. CD107α upregulation and IFN-γ production by peptide-specific CTL were increased by stimulation with HLA-A24+ but not with HLA-A24– multiple myeloma cells (FIG. 31).

Example 25: Proliferation of Peptide-Specific CTL in Response to HLA-A24+ Multiple Myeloma Cells The proliferation of peptide-specific CTL in response to stimulation from multiple myeloma cells was analyzed using a CFSE-proliferation assay. Peptide-specific CTL proliferation was measured on days 6 and 8 as a decrease in fluorescence of the CFSE-labeled MP-CTL (P3-gated cells) following either stimulation with the HLA-A24$^+$ multiple myeloma cell line KMS11 or the HLA-A24$^-$ multiple myeloma cell line OMP1 or no stimulation. The peptide-specific CTL showed a high level of cell proliferation at days 6 (FIG. 33a) and 8 (FIG. 33b) in response to the HLA-A24$^+$ multiple myeloma cells but not the HLA-A24$^-$ multiple myeloma cells.

Example 26: IL-2 Production by Peptide-Specific CTL in Response to HLA-A24+ Multiple Myeloma Cells IL-2 production by peptide-specific CTL in response to stimulation from multiple myeloma cells was analyzed by flow cytometry. IL-2 production by peptide-specific CTL proliferation was measured following either stimulation with the HLA-A24$^+$ multiple myeloma cell line KMS11 or the HLA-A24$^-$ multiple myeloma cell lines OMP1 and U266 or no stimulation. The peptide-specific CTL showed a high level of IL-2 production in response to the HLA-A24$^+$ multiple myeloma cells but not the HLA-A24$^-$ multiple myeloma cells (FIG. 34).

Example 27: IFN-γ Production and Cell Activation of Peptide-Specific CTL in Response to HLA-A24$^+$ Colon Cancer Cells Peptide-specific CTL from two donors were analyzed by flow cytometry for expression of IFN-γ and CD8 in response to HLA-A24$^+$ (SW480) and HLA-A24– (WiDr and LS180) colon cancer cell lines. CD8 and IFN-γ expression were analyzed by flow cytometry. IFN-γ expression of peptide-specific CTL was increased upon stimulation with HLA-A24+ but not with HLA-A24– colon cancer cells (FIGS. 35 and 37).

Figure 38:
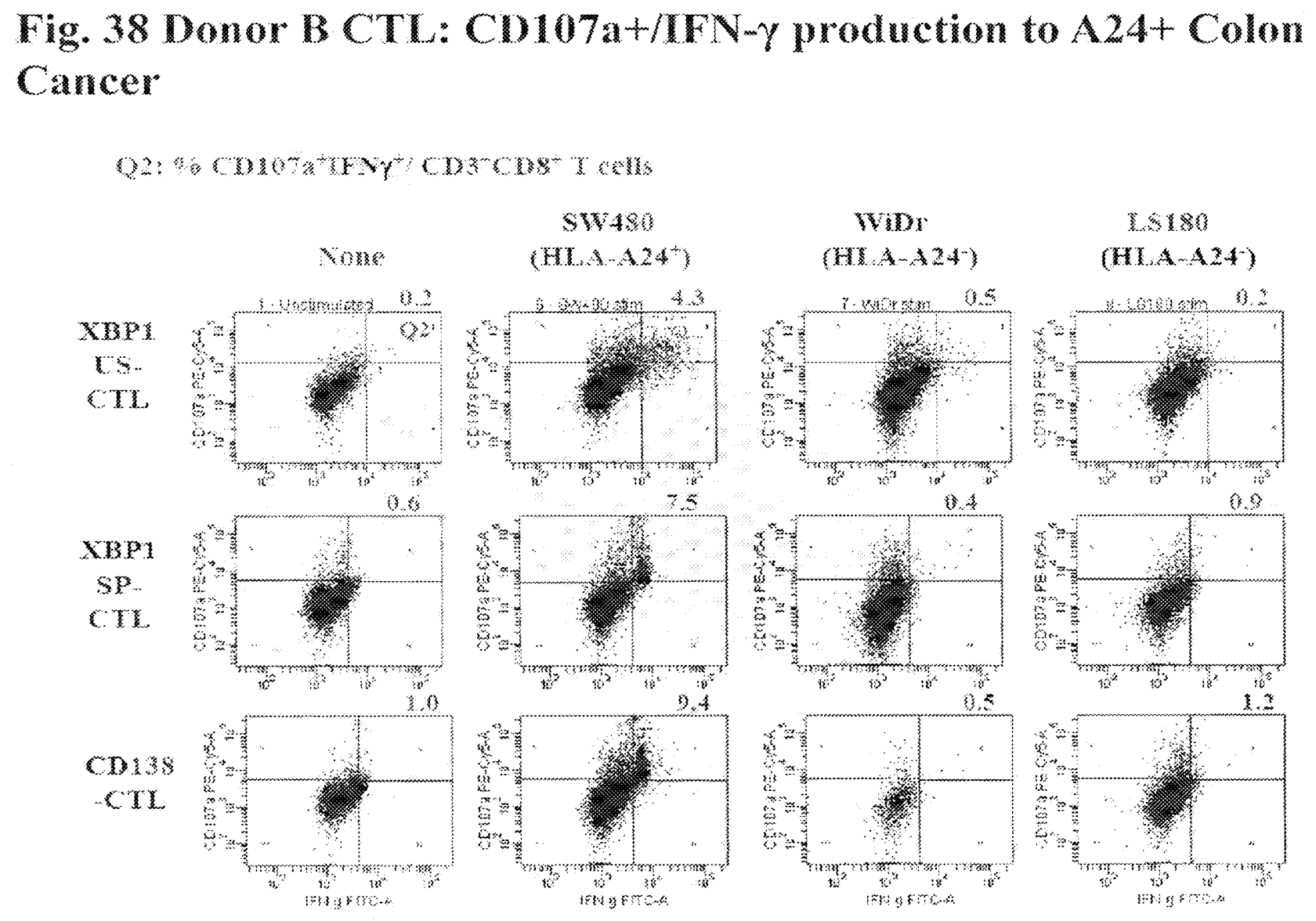

Example 28: IFN-γ Production and Degranulation of Peptide-Specific CTL in Response to HLA-A24+ Colon Cancer Cells Peptide-specific CTL were analyzed for their ability to degranulate and produce IFN-γ in response to HLA-A24+ (SW480) and HLA-A24– (WiDr and LS180) colon cancer cell lines. CD107α and IFN-γ production were analyzed by flow cytometry. CD107α upregulation and IFN-γ production by peptide-specific CTL were increased by stimulation with HLA-A24+ but not with HLA-A24– colon cancer cells (FIGS. 36 and 38).

Example 29: Degranulation and Production of IFN-γ and IL-2 in CD138-CTL in Response to Varying Amounts of HLA-A24+ Colon Cancer Cells CD138-CTL were analyzed for their ability to degranulate and produce IFN-γ and IL-2 in response to HLA-A24+ (SW480) and HLA-A24– (LS180) colon cancer cells at 5:1, 1:1, and 1:5 ratios of CTL to tumor cells. Degranulation, IFN-γ production, and IL-2 production displayed a substantial increase at higher ratios of CTL to tumor cells upon stimulation with HLA-A24+ colon cancer cells (FIG. 39a) but not with HLA-A24– colon cancer cells (FIG. 39b).

Example 30: Cell Activation, IFN-γ Production and Degranulation of HLA-A24-Specific CD138 Peptide-Specific CTL in Response to HLA-A24+ Colon Cancer and Multiple Myeloma Cells Peptide-specific CTL from two donors were analyzed for CD8 expression, degranulation, and produce IFN-γ production in response to HLA-A24+ colon cancer (SW480) and multiple myeloma (KMS11) cell lines. Spliced XBP1-CTL and CD138-CTL from both donors showed increased activation, IFN-γ production, and degranulation in response to colon cancer cells (FIGS. 40 and 41). Unspliced XBP1-CTL from Donor A showed increased activation, IFN-γ production, and degranulation in response to colon cancer cells, whereas these effects were stronger in response to multiple myeloma cells in unspliced XBP1-CTL from the Donor B (FIGS. 40 and 41).

Example 31: IFN-γ Production and Cell Activation of Peptide-Specific CD138-CTL in Response to HLA-A24+ Pancreatic Cancer Cells Peptide-specific CTL from Donor B were analyzed by flow cytometry for expression of IFN-γ and CD8 in response to HLA-A24+(8902 and PL45) and HLA-A24– (MiaPaca) colon cancer cell lines. CD8 and IFN-γ expression were analyzed by flow cytometry. IFN-γ expression of peptide-specific CTL was increased upon stimulation with HLA-A24$^+$ but not with HLA-A24– pancreatic cancer cells (FIG. 42).

Example 32: Degranulation and Production of IFN-γ and IL-2 in CD138-CTL in Response to Varying Amounts of HLA-A24+ Pancreatic Cancer Cells CD138-CTL were analyzed for their ability to degranulate and produce IFN-γ and IL-2 in response to HLA-A24+ (Panc1) pancreatic cancer cells at 1:1 and 1:5 ratios of CTL to tumor cells. Degranulation, IFN-γ production, and IL-2 production were higher at a 1:1 ratio of CTL to tumor cells (FIG. 43).

Example 33: Induction of Functionally Active Memory Cells with Heteroclitic Unspliced XBP1$_{184-192}$ (YISPWILAV) (SEQ ID NO: 6) and Heteroclitic Spliced XBP1 SP$_{196-204}$ (YLFPQLISV) (SEQ ID NO: 10) Peptides Cytotoxic T lymphocytes (CTL) induced with a cocktail of heteroclitic unspliced XBP1$_{184-192}$ (YISPWILAV) (SEQ ID NO: 6) and heteroclitic spliced XBP1 SP$_{196-204}$ (YLFPQLISV) (SEQ ID NO: 10) peptides contain both central memory (CM) and effector memory (EM) CD8$^+$ T cells (FIGS. 44, 45 and 46), which can recognize and target the specific XBP1 antigens on tumor cells. XBP1 peptides-specific CTL (XBP1-CTL) demonstrate a high level of cell proliferation, within the memory CTL subsets in response to breast (MB231; FIG. 47), colon (LS180; FIG. 48) or pancreatic (Panc1; FIG. 49) cancer cell lines. Overall, effector memory CTL had a higher level of cell proliferation as compared to central memory CTL (FIGS. 47, 48 and 49) in response to the different tumor cell lines. In contrast, central memory CTL induced a higher level of IFN-γ production, IL-2 production and cytotoxic activities as compared to effector memory CTL in response to HLA-A2$^+$ breast (MB231, MCF7), colon (LS180, SW480) and pancreatic (Panc1, PL45) cancer cell lines (FIGS. 50, 51, 52, 53, 54, 55). T-bet and Eomes are critical transcriptional regulators found in effector and memory T cells, which have roles relating to anti-tumor activities. XBP1-CTL memory cells displayed a high level of both T-bet (FIGS. 56, 57, 58) and Eomes expression (FIGS. 62, 63, 64). In response to breast, colon and pancreatic cancer lines, the T-bet$^+$ (FIGS. 59, 60, 61) and Eome$^+$ (FIGS. 65, 66, 67) cells display a high level of IFN-γ production. Memory cells within the XBP1-CTL were evaluated for upregulation of Granzyme B (indicator of anti-tumor cytotoxic activity) against breast, colon and pancreatic cancer lines. Compared to non-memory cells, memory cells showed a higher level of granzyme upregulation (FIG. 68). In addition, the granzyme$^+$ XPB1-CTL also produced IFN-γ in response to breast cancer, colon or pancreatic cancer cells (FIGS. 69, 70, 71). Therefore, the CTL induced with a cocktail of heteroclitic unspliced XBP1$_{184-192}$ (YISPWILAV) (SEQ ID NO: 6) and heteroclitic spliced XBP1 SP$_{196-204}$ (YLFPQLISV) (SEQ ID NO: 10) peptides contain both central memory and effector memory CD8$^+$ T cells, and those memory cells of the XBP1-CTL showed anti-tumor activities against breast cancer, colon cancer and pancreatic cancer cells.

Example 34: Lenalidomide Treatment Increases the Total Number and Function of Memory Cell Subsets within XBP1-CTL The number of memory CD8+ T cells is increased within the XBP1 peptide-specific CTL following treatment with Lenalidomide (at 5 uM for 5 days) (FIG. 72). This observation corresponds with a decrease in total non-memory CD8$^+$ T cells within the XBP1-CTL. A consistent increase or some increase of the frequency of central memory CD8$^+$ T cells or central memory CD3$^+$CD8$^+$ T cells, respectively, is detected after treatment with Lenalidomide (FIG. 73). In addition, critical markers for T cell activation and other immunological functions (i.e., CD40L, CD69, CD38) are increased on XBP1-CTL upon treatment with Lenalidomide (FIG. 74). The total CD3$^+$CD8$^+$ T cells, central memory CD3$^+$CD8$^+$ T cells and effector memory CD3$^+$CD8$^+$ T cells of XBP1-CTL display increased levels of T-bet expression/IFN-γ production and Eomes expression/IFN-g production in response to breast (MB231; FIGS. 75, 76), pancreatic (Panc1; FIG. 77, 78) or colon (SW480; FIGS. 79, 80) cancer cells by treatment with Lenalidomide. Memory XBP1-CTL treated with Lenalidomide have increased polyfunctional immune responses (cytotoxicity and IFN-γ production) against breast (MB231; FIG. 81), pancreatic (Panc1; FIG. 82) or colon (SW480; FIG. 83) cancer cells as compared to the XBP1 CTL alone. Therefore, these results provide evidence that anti-activities of CTL induced with a cocktail of heteroclitic unspliced XBP1$_{184-192}$ (YISPWILAV) (SEQ ID NO: 6) and heteroclitic spliced XBP1 SP$_{196-204}$ (YLFPQLISV) (SEQ ID NO: 10) peptides were enhanced by the treatment of CTL with Lenalidomide.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An immunogenic, HLA-A24-binding pharmaceutical composition comprising:
   (i) a non-spliced XBP1 peptide consisting of the amino acid sequence of SEQ ID NO: 29,
   (ii) a spliced XBP1 peptide consisting of the amino acid sequence of SEQ ID NO: 30,
   (iii) a CD138 peptide consisting of the amino acid sequence of SEQ ID NO: 31,
   (iv) a CS-1 peptide consisting of the amino acid sequence of SEQ ID NO: 32,
   one or more immune stimulating agents or immune modulating agents, and
   a pharmaceutically acceptable carrier.

2. The pharmaceutical composition of claim 1, wherein the immune stimulating agent is selected from an adjuvant comprising carboxymethylcellulose, polyinosinic-polycytidylic acid, and poly-L-lysine double-stranded RNA; an adjuvant comprising a water-and-oil emulsion; and an adjuvant comprising a protein.

3. The pharmaceutical composition of claim 1, wherein the immune modulating agent is selected from an antibody which activates the immune system, anti-PD-1 antibody, anti-PDL-1 antibody, and a small molecule adjuvant.

4. A kit comprising the pharmaceutical composition of claim 1, and instructions for administering the composition to a subject.

5. An article of manufacture comprising: a container and the pharmaceutical composition of claim 1 contained within the container.

6. A method for inducing an immune response in a subject, the method comprising delivering to a subject the pharmaceutical composition of claim 1.

7. The method of claim 6, wherein the subject is a human.

8. The method of claim 6, wherein the subject has breast cancer, colon cancer, pancreatic cancer, leukemia, multiple myeloma or Waldenstrom's macroglobulinemia.

9. A method for treating breast cancer, colon cancer, pancreatic cancer, leukemia, multiple myeloma or Waldenstrom's macroglobulinemia, the method comprising: administering to a subject the pharmaceutical composition of claim 1, wherein the subject has breast cancer, colon cancer, pancreatic cancer, leukemia, multiple myeloma or Waldenstrom's macroglobulinemia.

10. A method for treating smoldering multiple myeloma, the method comprising: administering to a subject the pharmaceutical composition of claim 1, wherein the subject has smoldering multiple myeloma.

11. A method of treating breast cancer in a subject, the method comprising administering a pharmaceutical composition comprising:
   (i) a non-spliced XBP1 peptide of 35 amino acids or less in length comprising the amino acid sequence of SEQ ID NO: 29,

(ii) a spliced XBP1 peptide of 35 amino acids or less in length and comprising the amino acid sequence of SEQ ID NO: 30, (iii) a CD138 peptide of 35 amino acids or less in length and comprising the amino acid sequence of SEQ ID NO: 31, (iv) a CS-1 peptide of 35 amino acids or less in length comprising the amino acid (iv) sequence of SEQ ID NO: 32, and a pharmaceutically acceptable carrier, to thereby treat the subject having breast cancer.

12. A method of treating colon cancer in a subject, the method comprising administering a pharmaceutical composition comprising:

(i) a non-spliced XBP1 peptide of 35 amino acids or less in length comprising the amino acid sequence of SEQ ID NO: 29, (ii) a spliced XBP1 peptide of 35 amino acids or less in length and comprising the amino acid sequence of SEQ ID NO: 30, (iii) a CD138 peptide of 35 amino acids or less in length and comprising the amino acid sequence of SEQ ID NO: 31, (iv) a CS-1 peptide of 35 amino acids or less in length comprising the amino acid sequence of SEQ ID NO: 32, and a pharmaceutically acceptable carrier, to thereby treat the subject having colon cancer.

13. A method of treating pancreatic cancer in a subject, the method comprising administering a pharmaceutical composition comprising:

(i) a non-spliced XBP1 peptide of 35 amino acids or less in length comprising the amino acid sequence of SEQ ID NO: 29, (ii) a spliced XBP1 peptide of 35 amino acids or less in length and comprising the amino acid sequence of SEQ ID NO: 30, (iii) a CD138 peptide of 35 amino acids or less in length and comprising the amino acid sequence of SEQ ID NO: 31, (iv) a CS-1 peptide of 35 amino acids or less in length comprising the amino acid (iv) sequence of SEQ ID NO: 32, and a pharmaceutically acceptable carrier, to thereby treat the subject having pancreatic cancer.

14. A method of treating leukemia in a subject, the method comprising administering the pharmaceutical composition of claim 1, to thereby treat the subject having leukemia.

15. The method of claim 11, wherein the breast cancer comprises estrogen receptor positive breast cancer, estrogen receptor negative breast cancer, HER-2 positive breast cancer, HER-2 negative breast cancer, triple negative breast cancer, or inflammatory breast cancer.

16. The pharmaceutical composition of claim 1, wherein any of (i)-(iv) have a binding affinity for HLA-A24 that is the same as, or higher than, the binding affinity of HIV envelope protein$_{583-591}$ peptide (SEQ ID NO: 537) to HLA-A24.

* * * * *